(12) United States Patent
Hahn et al.

(10) Patent No.: US 8,987,256 B2
(45) Date of Patent: Mar. 24, 2015

(54) OXO-HETEROCYCLIC SUBSTITUTED CARBOXYLIC ACID DERIVATIVES AND THE USE THEREOF

(75) Inventors: Michael Hahn, Langenfeld (DE); Eva-Maria Becker, Wuppertal (DE); Andreas Knorr, Erkrath (DE); Dirk Schneider, Wuppertal (DE); Johannes-Peter Stasch, Solingen (DE); Karl-Heinz Schlemmer, Wuppertal (DE); Frank Wunder, Wuppertal (DE); Friederike Stoll, Düsseldorf (DE); Stefan Heitmeier, Wülfrath (DE); Klaus Münter, Wülfrath (DE); Nils Griebenow, Dormagen (DE); Thomas Lampe, Düsseldorf (DE); Sherif El Sheikh, Essen (DE); Volkhart Min-Jian Li, Velbert (DE)

(73) Assignee: Bayer Intellectual Property GmbH, Monheim (DE)

( * ) Notice: Subject to any disclaimer, the term of this patent is extended or adjusted under 35 U.S.C. 154(b) by 643 days.

(21) Appl. No.: 12/937,995

(22) PCT Filed: Apr. 6, 2009

(86) PCT No.: PCT/EP2009/002510
§ 371 (c)(1),
(2), (4) Date: Oct. 14, 2010

(87) PCT Pub. No.: WO2009/127338
PCT Pub. Date: Oct. 22, 2009

(65) Prior Publication Data
US 2011/0034450 A1  Feb. 10, 2011

(30) Foreign Application Priority Data
Apr. 14, 2008 (DE) .................. 10 2008 018 675

(51) Int. Cl.
| | |
|---|---|
| A61K 31/5395 | (2006.01) |
| A61K 31/502 | (2006.01) |
| A61K 31/4245 | (2006.01) |
| A61K 31/53 | (2006.01) |
| C07D 237/32 | (2006.01) |
| C07D 273/04 | (2006.01) |
| C07D 271/113 | (2006.01) |
| C07D 253/075 | (2006.01) |
| C07D 209/46 | (2006.01) |
| C07D 209/48 | (2006.01) |
| C07D 213/64 | (2006.01) |
| C07D 215/227 | (2006.01) |
| C07D 231/56 | (2006.01) |
| C07D 233/32 | (2006.01) |
| C07D 237/14 | (2006.01) |
| C07D 239/88 | (2006.01) |
| C07D 253/08 | (2006.01) |
| C07D 261/20 | (2006.01) |

(Continued)

(52) U.S. Cl.
CPC ............ *C07D 237/32* (2013.01); *C07D 209/46* (2013.01); *C07D 209/48* (2013.01); *C07D 211/76* (2013.01); *C07D 213/64* (2013.01); *C07D 215/227* (2013.01); *C07D 231/56* (2013.01); *C07D 233/32* (2013.01); *C07D 237/14* (2013.01); *C07D 239/88* (2013.01); *C07D 253/075* (2013.01); *C07D 253/08* (2013.01); *C07D 261/20* (2013.01); *C07D 263/20* (2013.01); *C07D 271/113* (2013.01); *C07D 273/04* (2013.01); *C07D 275/06* (2013.01); *C07D 277/34* (2013.01); *C07D 417/12* (2013.01)
USPC ........ 514/229.2; 514/242; 514/248; 514/327; 514/364; 514/369; 514/376; 544/182; 544/237; 544/68; 546/221; 548/144; 548/187; 548/229

(58) Field of Classification Search
USPC .............. 514/229.2, 242, 248, 327, 364, 369, 514/376; 544/182, 237, 68; 546/221; 548/144, 187, 229
See application file for complete search history.

(56) References Cited

U.S. PATENT DOCUMENTS

| | | | |
|---|---|---|---|
| 5,041,453 | A | 8/1991 | Huang et al. |
| 5,811,429 | A | 9/1998 | Connell et al. |

(Continued)

FOREIGN PATENT DOCUMENTS

| | | |
|---|---|---|
| EP | 0608709 A1 | 8/1994 |
| EP | 1229010 A1 | 8/2002 |

(Continued)

OTHER PUBLICATIONS

Evgenov, et al.:"NO-Independent Stimulators and Activators of Soluble Guanylate Cyclase: Discovery and Theraputic Potential," Nature Reviews, Sep. 2006, 5(9): 755-768.

(Continued)

*Primary Examiner* — Kendra D Carter
*Assistant Examiner* — Jason A Deck
(74) *Attorney, Agent, or Firm* — Buchanan, Ingersoll & Rooney PC

(57) ABSTRACT

The present application relates to novel carboxylic acid derivatives having an oxo-substituted azaheterocyclic partial structure, processes for their preparation, their use for the treatment and/or prophylaxis of diseases, and their use for producing medicaments for the treatment and/or prophylaxis of diseases, especially for the treatment and/or prevention of cardiovascular disorders.

10 Claims, No Drawings

(51) Int. Cl.

| | |
|---|---|
| *C07D 263/20* | (2006.01) |
| *C07D 275/06* | (2006.01) |
| *C07D 417/12* | (2006.01) |
| *A61K 31/421* | (2006.01) |
| *A61K 31/451* | (2006.01) |
| *A61K 31/426* | (2006.01) |
| *C07D 263/22* | (2006.01) |
| *C07D 211/76* | (2006.01) |
| *C07D 401/12* | (2006.01) |
| *C07D 405/12* | (2006.01) |
| *C07D 277/34* | (2006.01) |
| *A61P 7/02* | (2006.01) |
| *A61P 9/12* | (2006.01) |
| *A61P 3/00* | (2006.01) |
| *A61P 9/04* | (2006.01) |
| *A61P 9/10* | (2006.01) |

(56) References Cited

U.S. PATENT DOCUMENTS

| | | | |
|---|---|---|---|
| 5,935,984 | A | 8/1999 | Goldmann et al. |
| 6,835,752 | B2 | 12/2004 | Tani et al. |
| 6,884,821 | B1 | 4/2005 | Shinoda et al. |
| 7,005,440 | B1 | 2/2006 | Jayyosi et al. |
| 7,238,716 | B2 | 7/2007 | Momose et al. |
| 7,241,785 | B2 | 7/2007 | Momose et al. |
| 7,244,861 | B2 | 7/2007 | Matsuura et al. |
| 7,368,578 | B2 | 5/2008 | Momose et al. |
| 7,371,777 | B2 | 5/2008 | Clark et al. |
| 2011/0130445 | A1 | 6/2011 | Lampe et al. |
| 2012/0028971 | A1 | 2/2012 | Lampe et al. |

FOREIGN PATENT DOCUMENTS

| | | |
|---|---|---|
| EP | 1285908 A1 | 2/2003 |
| WO | 96/30036 A1 | 10/1996 |
| WO | 00/64888 A1 | 11/2000 |

OTHER PUBLICATIONS

Stasch, et al.:"NO-and Haem-independent Activation of Soluble Guanylyl Cyclase: Molecular Basis and Cardiovascular Implications of a New Pharmacological Principle," British Journal of Pharmacology, 2002, 136:773-783.

Stasch, et al.:"Targeting the Heme-Oxidized Nitric Oxide Receptor for Selective Vasodilation of Diseased Blood Vessels," J. Clin. Invest., Sep. 2006, 116(9): 2552-2561.

U.S. Appl. No. 13/312,230, filed Dec. 7, 2010.

U.S. Appl. No. 13/431,934, filed Mar. 27, 2012.

OXO-HETEROCYCLIC SUBSTITUTED CARBOXYLIC ACID DERIVATIVES AND THE USE THEREOF

The present application relates to novel carboxylic acid derivatives having an oxo-substituted azaheterocyclic partial structure, processes for their preparation, their use for the treatment and/or prophylaxis of diseases, and their use for producing medicaments for the treatment and/or prophylaxis of diseases, especially for the treatment and/or prevention of cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyze the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. The latter is of central importance for the mechanism of activation. NO is able to bind to the iron atom of heme and thus markedly increase the activity of the enzyme. Heme-free preparations cannot, by contrast, be stimulated by NO. Carbon monoxide (CO) is also able to attach to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, thromboses, stroke and myocardial infarction.

A possible way of treating such disorders which is independent of NO and aims at influencing the cGMP signaling pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of heme. Besides the side effects, the development of tolerance is one of the crucial disadvantages of this mode of treatment [O. V. Evgenov et al., *Nature Rev. Drug Disc.* 5 (2006), 755].

Substances which directly stimulate soluble guanylate cyclase, i.e. without previous release of NO, have been identified in recent years. The indazole derivative YC-1 was the first NO-independent but heme-dependent sGC stimulator described [Evgenov et al., ibid.]. Based on YC-1, further substances were discovered which are more potent than YC-1 and show no relevant inhibition of phosphodiesterases (PDE). This led to the identification of the pyrazolopyridine derivatives BAY 41-2272, BAY 41-8543 and BAY 63-2521. Together with the recently published structurally different substances CMF-1571 and A-350619, these compounds form the new class of the sGC stimulators [Evgenov et al., ibid.]. A common characteristic of this substance class is an NO-independent and selective activation of the heme-containing sGC. In addition, the sGC stimulators in combination with NO have a synergistic effect on sGC activation based on a stabilization of the nitrosyl-heme complex. The exact binding site of the sGC stimulators at the sGC is still being debated. If the heme group is removed from the soluble guanylate cyclase, the enzyme still has a detectable catalytic basal activity, i.e. cGMP is still being formed. The remaining catalytic basal activity of the heme-free enzyme cannot be stimulated by any of the stimulators mentioned above [Evgenov et al., ibid.].

In addition, NO- and heme-independent sGC activators, with BAY 58-2667 as prototype of this class, have been identified. Common characteristics of these substances are that in combination with NO they only have an additive effect on enzyme activation, and that the activation of the oxidized or heme-free enzyme is markedly higher than that of the heme-containing enzyme [Evgenov et al., ibid.; J. P. Stasch et al., *Br. J. Pharmacol.* 136 (2002), 773; J. P. Stasch et al., *J. Clin. Invest.* 116 (2006), 2552]. Spectroscopic studies show that BAY 58-2667 displaces the oxidized heme group which, as a result of the weakening of the iron-histidine bond, is attached only weakly to the sGC. It has also been shown that the characteristic sGC heme binding motif Tyr-x-Ser-x-Arg is absolutely essential both for the interaction of the negatively charged propionic acids of the heme group and for the action of BAY 58-2667. Against this background, it is assumed that the binding site of BAY 58-2667 at the sGC is identical to the binding site of the heme group [J. P. Stasch et al., *J. Clin. Invest.* 116 (2006), 2552].

The compounds described in the present invention are now likewise capable of activating the heme-free form of soluble guanylate cyclase. This is also confirmed by the fact that these novel activators firstly have no synergistic action with NO at the heme-containing enzyme and that secondly their action cannot be blocked by the heme-dependent inhibitor of soluble guanylate cyclase, 1H-1,2,4-oxadiazolo[4,3-a]quinoxalin-1-one (ODQ), but is even potentiated by this inhibitor [cf. O. V. Evgenov et al., *Nature Rev. Drug Disc.* 5 (2006), 755; J. P. Stasch et al., *J. Clin. Invest.* 116 (2006), 2552].

WO 00/64876 and WO 00/64888 claim di- and triarylacid derivatives as PPAR ligands for the treatment of diabetes, hyperlipidemia, atherosclerosis and hypertension. Other multicyclic carboxylic acid derivatives are described in EP 1 357 115-A1, EP 1 394 154-A1 and EP 1 541 564-A1 as PPAR and/or RXR ligands for the treatment of diabetes, hyperlipidemia, obesity and hypertension. Furthermore, multicyclic acid derivatives are known from WO 91/19475 as leukotriene antagonists with anti-inflammatory and anti-allergic properties. EP 1 229 010-A1 discloses certain diarylamide derivatives for the treatment of atherosclerosis and restenosis. Furthermore, EP 0 779 279-A1 and EP 0 802 192-A1 describe various phenyl-acetamide derivatives having an azaheterocyclic partial structure as apolipoprotein B inhibitors for the treatment of atherosclerosis and coronary heart diseases, and EP 0 608 709-A1 discloses 2-oxoquinolinylmethyl-substituted phenylacetamides as angiotensin II antagonists for the treatment of arterial hypertension and atherosclerosis.

It was an object of the present invention to provide novel compounds which act as activators of soluble guanylate cyclase in the manner described above and can be used as such in particular for the treatment and prevention of cardiovascular disorders.

Structurally, the compounds of the present invention are distinguished by a terminal carboxylic acid grouping attached in the manner shown below to an oxo-substituted azaheterocycle as head group.

The present invention provides compounds of the general formula (I)

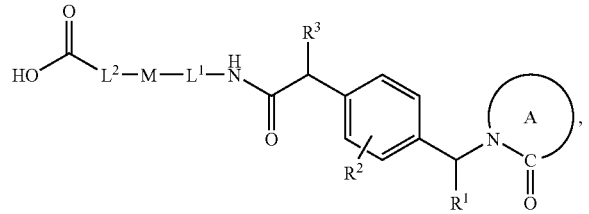

in which
ring A represents a 5- to 7-membered saturated or partially unsaturated oxo-substituted azaheterocycle attached via nitrogen,
which (i) may contain one or two further heteroatoms from the group consisting of N, O and S as ring members,
which (ii) is substituted by a radical selected from the group consisting of fluorine, chlorine, $(C_1-C_6)$-alkyl, trifluoromethyl, $(C_3-C_7)$-cycloalkyl, 4- to 7-membered heterocyclyl and phenyl or is benzo-fused,
where the phenyl substituent and the fused phenyl ring for their part may be substituted up to two times by identical or different radicals selected from the group consisting of halogen, cyano, $(C_1-C_4)$-alkyl, $(C_2-C_4)$-alkenyl, trifluoromethyl, $(C_1-C_4)$-alkoxy and trifluoromethoxy, and
which (iii) may additionally be substituted up to two times by identical or different further radicals selected from the group consisting of fluorine, $(C_1-C_6)$-alkyl, trifluoromethyl, oxo, $(C_3-C_7)$-cycloalkyl, 4- to 7-membered heterocyclyl and phenyl,
where phenyl for its part may be substituted up to two times by identical or different radicals selected from the group consisting of halogen, cyano, $(C_1-C_4)$-alkyl, $(C_2-C_4)$-alkenyl, trifluoromethyl, $(C_1-C_4)$-alkoxy and trifluoromethoxy,
$R^1$ represents hydrogen, $(C_1-C_4)$-alkyl or cyclopropyl,
$R^2$ represents hydrogen, halogen, cyano, $(C_1-C_4)$-alkyl or trifluoromethyl,
$R^3$ represents $(C_3-C_6)$-alkyl or $(C_3-C_6)$-alkenyl, each of which may be substituted by cyano, $(C_1-C_4)$-alkoxy or trifluoromethoxy and up to six times by fluorine,
or
represents $(C_3-C_7)$-cycloalkyl or $(C_3-C_7)$-cycloalkenyl, each of which may be substituted up to two times by identical or different radicals from the group consisting of $(C_1-C_4)$-alkyl, trifluoromethyl and $(C_1-C_4)$-alkoxy and also up to four times by fluorine,
or
represents oxetanyl, tetrahydrofuranyl or tetrahydropyranyl,
$L^1$ represents a bond or represents methylene, ethane-1,2-diyl or propane-1,3-diyl, each of which may be substituted up to two times by identical or different radicals from the group consisting of $(C_1-C_4)$-alkyl,
$L^2$ represents a bond or represents methylene, ethane-1,2-diyl, propane-1,3-diyl, ethene-1,2-diyl or propene-1,3-diyl, each of which may be substituted up to two times by identical or different radicals from the group consisting of $(C_1-C_4)$-alkyl,
or
represents a group of the formula

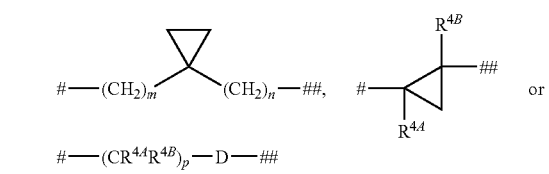

in which
# denotes the point of attachment to the carboxylic acid grouping,
## denotes the point of attachment to group M,
m represents the number 0 or 1,
n represents the number 0, 1 or 2,
p represents the number 1 or 2,
D represents O or S
and
$R^{4A}$ and $R^{4B}$ independently of one another represent hydrogen or $(C_1-C_4)$-alkyl,
where in the case that the group —$CR^{4A}R^{4B}$— appears twice, the individual meanings of $R^{4A}$ and $R^{4B}$ may in each case be identical or different,
M represents phenylene or 5- or 6-membered heteroarylene having up to two ring heteroatoms from the group consisting of N, O and S, where phenylene and heteroarylene may each be substituted up to two times by identical or different radicals selected from the group consisting of halogen, cyano, $(C_1-C_4)$-alkyl, trifluoromethyl, hydroxyl, $(C_1-C_4)$-alkoxy and trifluoromethoxy,
or
represents cyclopropane-1,2-diyl, cyclobutane-1,2-diyl, cyclobutane-1,3-diyl, cyclopentane-1,2-diyl, cyclopentane-1,3-diyl, cyclohexane-1,2-diyl, cyclohexane-1,3-diyl or cyclohexane-1,4-diyl, each of which may be substituted up to two times by identical or different radicals selected from the group consisting of fluorine, $(C_1-C_4)$-alkyl, trifluoromethyl and $(C_1-C_4)$-alkoxy,
or
$L^2$ and M are attached to one another and together form a group of the formula

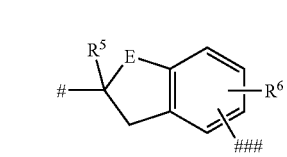

in which
# denotes the point of attachment to the carboxylic acid grouping,
### denotes the point of attachment to group $L^1$,
E represents O, S, $CH_2$ or $CH_2CH_2$,
$R^5$ represents hydrogen, $(C_1-C_4)$-alkyl or trifluoromethyl
and
$R^6$ represents hydrogen, halogen, $(C_1-C_4)$-alkyl, trifluoromethyl, $(C_1-C_4)$-alkoxy or trifluoromethoxy,
or a salt, solvate or solvate of a salt thereof.

Compounds according to the invention are the compounds of the formula (I) and their salts, solvates and solvates of the salts, the compounds included in the formula (I) of the formulae mentioned in the following and their salts, solvates and solvates of the salts, and the compounds included in the formula (I) and mentioned in the following as embodiment examples and their salts, solvates and solvates of the salts, where the compounds included in the formula (I) and mentioned in the following are not already salts, solvates and solvates of the salts.

The compounds according to the invention can exist in stereoisomeric forms (enantiomers, diastereomers), depending on their structure. The invention therefore includes the enantiomers or diastereomers and their particular mixtures. The stereoisomerically uniform constituents can be isolated from such mixtures of enantiomers and/or diastereomers in a known manner.

Where the compounds according to the invention can occur in tautomeric forms, the present invention includes all the tautomeric forms.

Preferred salts in the context of the present invention are physiologically acceptable salts of the compounds according to the invention. Salts which are not themselves suitable for pharmaceutical uses but can be used, for example, for isolation or purification of the compounds according to the invention are also included.

Physiologically acceptable salts of the compounds according to the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid, and benzoic acid.

Physiologically acceptable salts of the compounds according to the invention also include salts of conventional bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are designated as those forms of the compounds according to the invention which form a complex in the solid or liquid state by coordination with solvent molecules. Hydrates are a specific form of solvates, in which the coordination takes place with water. Hydrates are preferred solvates in the context of the present invention. The present invention moreover also includes prodrugs of the compounds according to the invention. The term "prodrugs" here designates compounds which themselves can be biologically active or inactive, but are converted (for example metabolically or hydrolytically) into compounds according to the invention during their dwell time in the body.

The present invention comprises in particular hydrolyzable ester derivatives of the carboxylic acids of the formula (I) according to the invention. These are to be understood as meaning esters which can be hydrolyzed to the free carboxylic acids, as the compounds that are mainly active biologically, in physiological media, under the conditions of the biological tests described later and in particular in vivo by enzymatic or chemical routes. $(C_1-C_4)$-alkyl esters, in which the alkyl group can be straight-chain or branched, are preferred as such esters. Particular preference is given to methyl, ethyl or tert-butyl esters.

In the context of the present invention, the substituents have the following meaning, unless specified otherwise:

$(C_1-C_6)$-Alkyl and $(C_1-C_4)$-alkyl in the context of the invention represent a straight-chain or branched alkyl radical having 1 to 6 or, respectively, 1 to 4 carbon atoms. A straight-chain or branched alkyl radical having 1 to 4 carbon atoms is preferred. The following may be mentioned by way of example and by way of preference: methyl, ethyl, n-propyl, isopropyl, n-butyl, iso-butyl, sec-butyl, tert-butyl, n-pentyl, 2-pentyl, 3-pentyl, n-hexyl, 2-hexyl and 3-hexyl.

$(C_3-C_6)$-Alkyl in the context of the invention represents a straight-chain or branched alkyl radical having 3 to 6 carbon atoms. A branched alkyl radical having 3 to 5 carbon atoms is preferred. There may be mentioned by way of example and preferably: n-propyl, isopropyl, n-butyl, isobutyl, sec-butyl, tert-butyl, n-pentyl, 2-pentyl, 3-pentyl, n-hexyl, 2-hexyl and 3-hexyl.

$(C_3-C_6)$-Alkenyl and $(C_2-C_4)$-alkenyl in the context of the invention represent a straight-chain or branched alkenyl radical having a double bond and 3 to 6 and 2 to 4 carbon atoms, respectively. A branched alkenyl radical having 3 to 5 carbon atoms or a straight-chain alkenyl radical having 2 or 3 carbon atoms is preferred. The following may be mentioned by way of example and by way of preference: vinyl, allyl, isopropenyl, n-but-2-en-1-yl, 2-methylprop-2-en-1-yl and n-but-3-en-1-yl.

$(C_1-C_4)$-Alkoxy in the context of the invention represents a straight-chain or branched alkoxy radical having 1 to 4 carbon atoms. The following may be mentioned by way of example and by way of preference: methoxy, ethoxy, n-propoxy, isopropoxy, n-butoxy and tert-butoxy.

$(C_3-C_7)$-Cycloalkyl and $(C_3-C_6)$-cycloalkyl in the context of the invention represent a monocyclic saturated cycloalkyl group having 3 to 7 and 3 to 6 carbon atoms, respectively. A cycloalkyl radical having 3 to 6 carbon atoms is preferred. The following may be mentioned by way of example and by way of preference: cyclopropyl, cyclobutyl, cyclopentyl, cyclohexyl and cycloheptyl.

$(C_3-C_7)$-Cycloalkenyl and $(C_4-C_6)$-cycloalkenyl in the context of the invention represent a monocyclic cycloalkyl group having 3 to 7 and 4 to 6 ring carbon atoms, respectively, and a ring double bond. A cycloalkenyl radical having 4 to 6, particularly preferably 5 or 6, carbon atoms is preferred. The following may be mentioned by way of example and by way of preference: cyclopropenyl, cyclobutenyl, cyclopentenyl, cyclohexenyl and cycloheptenyl.

4- to 7-membered heterocyclyl and 4- to 6-membered heterocyclyl in the context of the invention represent a monocyclic saturated heterocycle having a total of 4 to 7 and 4 to 6 ring atoms, respectively, which contains one or two ring heteroatoms from the group consisting of N, O and S and is attached via a ring carbon atom or, if appropriate, via a ring nitrogen atom. Preference is given to 4- to 6-membered heterocyclyl having one or two ring heteroatoms from the group consisting of N and O. The following may be mentioned by way of example: azetidinyl, oxetanyl, pyrrolidinyl, pyrazolidinyl, tetrahydrofuranyl, piperidinyl, piperazinyl, tetrahydropyranyl, morpholinyl, thiomorpholinyl, hexahydroazepinyl and hexahydro-1,4-diazepinyl. Preference is given to azetidinyl, oxetanyl, pyrrolidinyl, tetrahydrofuranyl, piperidinyl, piperazinyl, tetrahydropyranyl and morpholinyl.

5- or 6-membered heteroarylene in the context of the invention represents a divalent aromatic heterocycle (heteroaromatic) having a total of 5 or 6 ring atoms which contains one or two ring heteroatoms from the group consisting of N, O and S and is attached via ring carbon atoms and/or, if appropriate, via a ring nitrogen atom. The following may be mentioned by way of example: furyl, pyrrolyl, thienyl, pyrazolyl, imidazolyl, thiazolyl, oxazolyl, isoxazolyl, isothiazolyl, pyridyl, pyrimidinyl, pyridazinyl and pyrazinyl. Preference is given to furyl, thienyl, thiazolyl, oxazolyl, isoxazolyl, pyridyl and pyrimidinyl.

Halogen in the context of the invention includes fluorine, chlorine, bromine and iodine. Chlorine, fluorine and bromine are preferred, with fluorine and chlorine being particularly preferred.

An oxo substituent in the context of the invention represents an oxygen atom, which is bonded to a carbon atom via a double bond.

If radicals in the compounds according to the invention are substituted, the radicals can be mono- or polysubstituted, unless specified otherwise. In the context of the present invention, for all the radicals which occur several times, the meanings thereof are independent of each other. Substitution by one or by two or three identical or different substituents is preferred. Substitution by one or by two substituents is particularly preferred.

The present invention provides in particular compounds of the formula (I) in which
ring A represents an oxo-substituted azaheterocycle of the formula

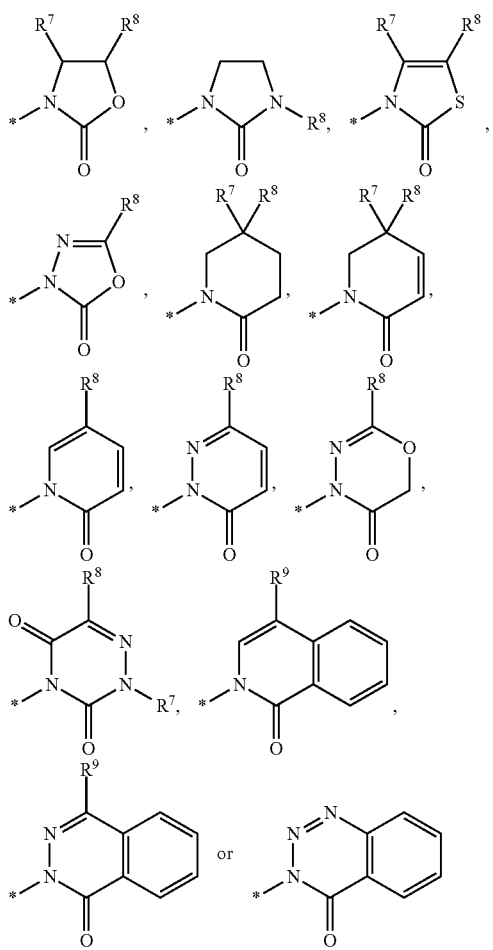

in which
* denotes the point of attachment to the remainder of the molecule,
$R^7$ represents hydrogen, $(C_1-C_6)$-alkyl or $(C_3-C_6)$-cycloalkyl,
$R^8$ represents $(C_1-C_6)$-alkyl, trifluoromethyl, $(C_3-C_6)$-cycloalkyl, 4- to 6-membered heterocyclyl or phenyl, where phenyl for its part may be substituted up to two times by identical or different radicals selected from the group consisting of fluorine, chlorine, bromine, cyano, $(C_1-C_4)$-alkyl, vinyl, trifluoromethyl, $(C_1-C_4)$-alkoxy and trifluoromethoxy, and
$R^9$ represents hydrogen or has the meaning of $R^8$ given above,
or a salt, solvate or solvate of a salt thereof.

The present invention also provides in particular compounds of the formula (I) in which
ring A represents an oxo-substituted azaheterocycle of the formula

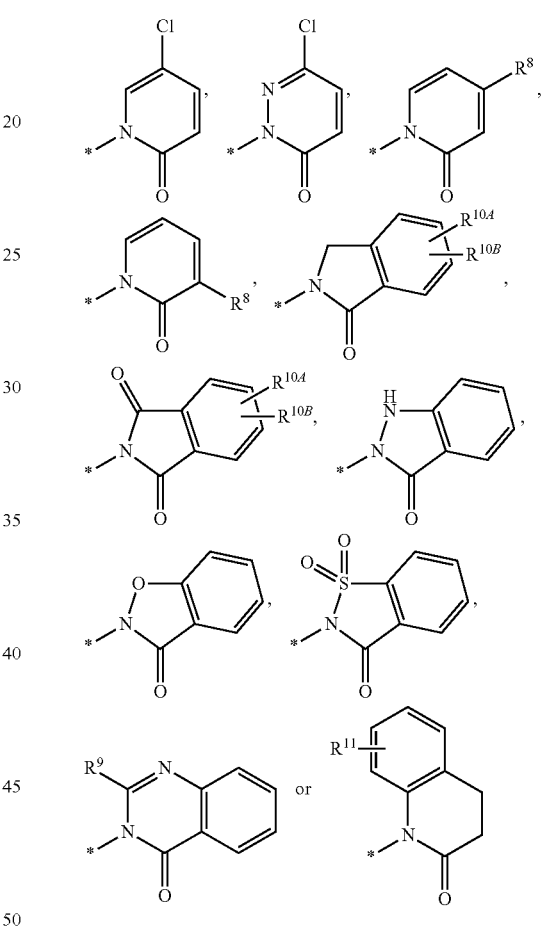

in which
* denotes the point of attachment to the remainder of the molecule,
$R^8$ represents $(C_1-C_6)$-alkyl, trifluoromethyl, $(C_3-C_6)$-cycloalkyl, 4- to 6-membered heterocyclyl or phenyl, where phenyl for its part may be substituted up to two times by identical or different radicals selected from the group consisting of fluorine, chlorine, bromine, cyano, $(C_1-C_4)$-alkyl, vinyl, trifluoromethyl, $(C_1-C_4)$-alkoxy and trifluoromethoxy,
$R^9$ represents hydrogen or has the meaning of $R^8$ given above,
$R^{10A}$ and $R^{10B}$ independently of one another represent hydrogen, fluorine or chlorine
and
$R^{11}$ represents hydrogen, fluorine or chlorine,
or a salt, solvate or solvate of a salt thereof.

In the context of the present invention, preference is given to compounds of the formula (I) in which
ring A represents an oxo-substituted azaheterocycle of the formula

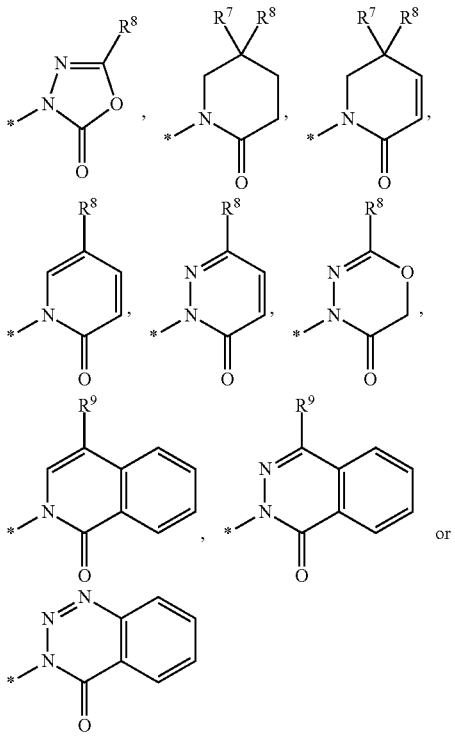

in which
* denotes the point of attachment to the remainder of the molecule,
$R^7$ represents hydrogen or $(C_1-C_4)$-alkyl,
$R^8$ represents $(C_1-C_6)$-alkyl, trifluoromethyl, $(C_3-C_6)$-cycloalkyl or phenyl, where phenyl for its part may be substituted up to two times by identical or different radicals selected from the group consisting of fluorine, chlorine, cyano, $(C_1-C_4)$-alkyl, trifluoromethyl, $(C_1-C_4)$-alkoxy and trifluoromethoxy,
and
$R^9$ represents hydrogen or has the meaning of $R^8$ given above,
$R^1$ represents hydrogen or $(C_1-C_4)$-alkyl,
$R^2$ represents hydrogen, fluorine, chlorine or trifluoromethyl,
$R^3$ represents $(C_3-C_6)$-alkyl or $(C_3-C_6)$-alkenyl, each of which may be substituted by cyano, methoxy, ethoxy or trifluoromethoxy and up to six times by fluorine,
or
represents $(C_3-C_6)$-cycloalkyl or $(C_4-C_6)$-cycloalkenyl, each of which may be substituted up to two times by identical or different radicals from the group consisting of $(C_1-C_4)$-alkyl and trifluoromethyl and also up to four times by fluorine,
or
represents oxetanyl,
$L^1$ represents a bond or represents methylene, ethane-1,2-diyl or propane-1,3-diyl, each of which may be substituted up to two times by methyl,
$L^2$ represents a bond or represents methylene, ethane-1,2-diyl, propane-1,3-diyl or ethene-1,2-diyl, each of which may be substituted up to two times by methyl,
or
represents a group of the formula

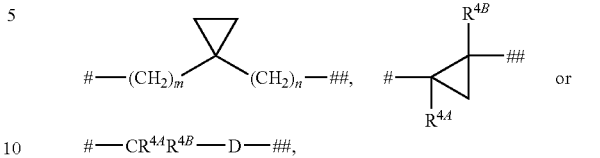

$$\text{\#}\!-\!CR^{4A}R^{4B}\!-\!D\!-\!\text{\#\#},$$

in which
# denotes the point of attachment to the carboxylic acid grouping,
## denotes the point of attachment to group M,
m represents the number 0 or 1,
n represents the number 0, 1 or 2,
D represents O or S
and
$R^{4A}$ and $R^{4B}$ independently of one another represent hydrogen or methyl,
M represents phenylene or 5- or 6-membered heteroarylene having up to two ring heteroatoms from the group consisting of N, O and S, where phenylene and heteroarylene may each be substituted up to two times by identical or different radicals selected from the group consisting of fluorine, chlorine, $(C_1-C_4)$-alkyl, trifluoromethyl, methoxy and trifluoromethoxy,
or
represents cyclopentane-1,3-diyl, cyclohexane-1,3-diyl or cyclohexane-1,4-diyl, each of which may be substituted up to two times by identical or different radicals selected from the group consisting of fluorine, methyl and trifluoromethyl,
or
$L^2$ and M are attached to one another and together form a group of the formula

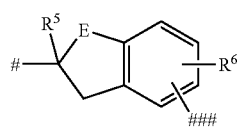

in which
# denotes the point of attachment to the carboxylic acid grouping,
### denotes the point of attachment to group $L^1$,
E represents $CH_2$ or $CH_2CH_2$,
$R^5$ represents hydrogen, methyl or trifluoromethyl
and
$R^6$ represents hydrogen, fluorine, chlorine, methyl, trifluoromethyl, methoxy or trifluoromethoxy,
or a salt, solvate or solvate of a salt thereof.

In the context of the present invention, preference is also given to compounds of the formula (I) in which
ring A represents an oxo-substituted azaheterocycle of the formula

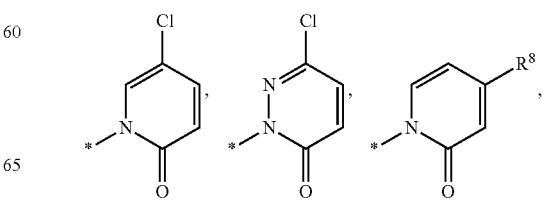

-continued

[chemical structures]

in which
* denotes the point of attachment to the remainder of the molecule,
$R^8$ represents $(C_1-C_6)$-alkyl, trifluoromethyl, $(C_3-C_6)$-cycloalkyl or phenyl, where phenyl for its part may be substituted up to two times by identical or different radicals selected from the group consisting of fluorine, chlorine, cyano, $(C_1-C_4)$-alkyl, trifluoromethyl, $(C_1-C_4)$-alkoxy and trifluoromethoxy,
$R^9$ represents hydrogen or has the meaning of $R^8$ given above
and
$R^{10A}$ and $R^{10B}$ independently of one another represent hydrogen, fluorine or chlorine,
$R^1$ represents hydrogen or $(C_1-C_4)$-alkyl,
$R^2$ represents hydrogen, fluorine, chlorine or trifluoromethyl,
$R^3$ represents $(C_3-C_6)$-alkyl or $(C_3-C_6)$-alkenyl, each of which may be substituted by cyano, methoxy, ethoxy or trifluoromethoxy and up to six times by fluorine,
or
represents $(C_3-C_6)$-cycloalkyl or $(C_4-C_6)$-cycloalkenyl, each of which may be substituted up to two times by identical or different radicals from the group consisting of $(C_1-C_4)$-alkyl and trifluoromethyl and also up to four times by fluorine,
or
represents oxetanyl,
$L^1$ represents a bond or represents methylene, ethane-1,2-diyl or propane-1,3-diyl, each of which may be substituted up to two times by methyl,
$L^2$ represents a bond or represents methylene, ethane-1,2-diyl, propane-1,3-diyl or ethene-1,2-diyl, each of which may be substituted up to two times by methyl,
or
represents a group of the formula

[chemical structures: #—(CH₂)ₘ—◁—(CH₂)ₙ—##, #—△(R⁴ᴬ,R⁴ᴮ)—##, or #—CR⁴ᴬR⁴ᴮ—D—##]

in which
# denotes the point of attachment to the carboxylic acid grouping,
## denotes the point of attachment to group M,
m represents the number 0 or 1,
n represents the number 0, 1 or 2,
D represents O or S
and
$R^{4A}$ and $R^{4B}$ independently of one another represent hydrogen or methyl,
M represents phenylene or 5- or 6-membered heteroarylene having up to two ring heteroatoms from the group consisting of N, O and S, where phenylene and heteroarylene may each be substituted up to two times by identical or different radicals selected from the group consisting of fluorine, chlorine, $(C_1-C_4)$-alkyl, trifluoromethyl, methoxy and trifluoromethoxy,
or
represents cyclopentane-1,3-diyl, cyclohexane-1,3-diyl or cyclohexane-1,4-diyl, each of which may be substituted up to two times by identical or different radicals selected from the group consisting of fluorine, methyl and trifluoromethyl,
or
$L^2$ and M are attached to one another and together form a group of the formula

[chemical structure]

in which
# denotes the point of attachment to the carboxylic acid grouping,
### denotes the point of attachment to group $L^1$,
E represents $CH_2$ or $CH_2CH_2$,
$R^5$ represents hydrogen, methyl or trifluoromethyl
and
$R^6$ represents hydrogen, fluorine, chlorine, methyl, trifluoromethyl, methoxy or trifluoromethoxy,
or a salt, solvate or solvate of a salt thereof.

In the context of the present invention, particular preference is given to compounds of the formula (I) in which
ring A represents an oxo-substituted azaheterocycle of the formula

[chemical structures]

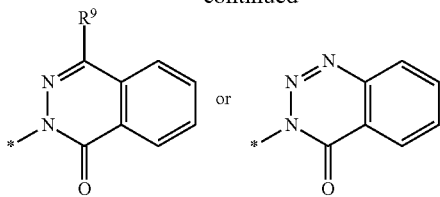 or 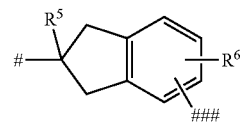

in which
* denotes the point of attachment to the remainder of the molecule,
$R^8$ represents trifluoromethyl, $(C_3-C_6)$-cycloalkyl or phenyl, where phenyl for its part may be substituted up to two times by identical or different radicals selected from the group consisting of fluorine, chlorine, cyano, methyl, trifluoromethyl, methoxy and trifluoromethoxy,
and
$R^9$ represents hydrogen or has the meaning of $R^8$ given above,
$R^1$ represents hydrogen or methyl,
$R^2$ represents hydrogen, fluorine or chlorine,
$R^3$ represents $(C_3-C_6)$-alkyl or $(C_3-C_6)$-alkenyl, each of which may be substituted up to six times by fluorine,
or
represents $(C_3-C_6)$-cycloalkyl, cyclopentenyl or cyclohexenyl, each of which may be substituted up to two times by identical or different radicals from the group consisting of methyl, ethyl and trifluoromethyl and also up to four times by fluorine,
$L^1$ represents a bond or represents methylene or ethane-1,2-diyl,
$L^2$ represents a bond or represents methylene, ethane-1,2-diyl, propane-1,3-diyl or ethene-1,2-diyl, each of which may be substituted up to two times by methyl,
or
represents a group of the formula

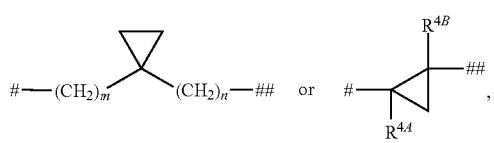

in which
# denotes the point of attachment to the carboxylic acid grouping,
## denotes the point of attachment to group M,
m represents the number 0 or 1,
n represents the number 1 or 2,
and
$R^{4A}$ and $R^{4B}$ independently of one another represent hydrogen or methyl,
M represents phenylene, pyridylene, furylene, thienylene, thiazolylene or isoxazolylene, each of which may be substituted up to two times by identical or different radicals selected from the group consisting of fluorine, chlorine, methyl and trifluoromethyl,
or
represents cyclopentane-1,3-diyl, cyclohexane-1,3-diyl or cyclohexane-1,4-diyl, each of which may be substituted up to two times by identical or different radicals from the group consisting of fluorine and methyl,
or
$L^2$ and M are attached to one another and together form a group of the formula

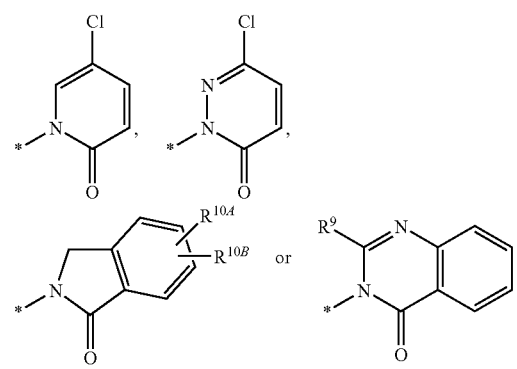

in which
# denotes the point of attachment to the carboxylic acid grouping,
### denotes the point of attachment to group $L^1$,
$R^5$ represents hydrogen, methyl or trifluoromethyl
and
$R^6$ represents hydrogen, fluorine or chlorine,
or a salt, solvate or solvate of a salt thereof.

In the context of the present invention, particular preference is also given to compounds of the formula (I) in which ring A represents an oxo-substituted azaheterocycle of the formula in which
* denotes the point of attachment to the remainder of the molecule,
$R^9$ represents hydrogen, methyl or trifluoromethyl
and
$R^{10A}$ and $R^{10B}$ independently of one another represent hydrogen or fluorine,
$R^1$ represents hydrogen or methyl,
$R^2$ represents hydrogen, fluorine or chlorine,
$R^3$ represents $(C_3-C_6)$-alkyl or $(C_3-C_6)$-alkenyl, each of which may be substituted up to six times by fluorine,
or
represents $(C_3-C_6)$-cycloalkyl, cyclopentenyl or cyclohexenyl, each of which may be substituted up to two times by identical or different radicals from the group consisting of methyl, ethyl and trifluoromethyl and also up to four times by fluorine,
$L^1$ represents a bond or represents methylene or ethane-1,2-diyl,
$L^2$ represents a bond or represents methylene, ethane-1,2-diyl, propane-1,3-diyl or ethene-1,2-diyl, each of which may be substituted up to two times by methyl, or
represents a group of the formula

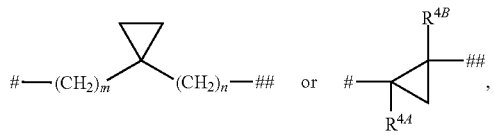

in which
\# denotes the point of attachment to the carboxylic acid grouping,
\#\# denotes the point of attachment to group M,
m represents the number 0 or 1,
n represents the number 1 or 2,
and
$R^{4A}$ and $R^{4B}$ independently of one another represent hydrogen or methyl,
M represents phenylene, pyridylene, furylene, thienylene, thiazolylene or isoxazolylene, each of which may be substituted up to two times by identical or different radicals selected from the group consisting of fluorine, chlorine, methyl and trifluoromethyl,
or
represents cyclopentane-1,3-diyl, cyclohexane-1,3-diyl or cyclohexane-1,4-diyl, each of which may be substituted up to two times by identical or different radicals from the group consisting of fluorine and methyl,
or
$L^2$ and M are attached to one another and together form a group of the formula

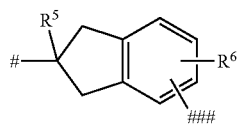

in which
\# denotes the point of attachment to the carboxylic acid grouping,
\#\#\# denotes the point of attachment to group $L^1$,
$R^5$ represents hydrogen, methyl or trifluoromethyl
and
$R^6$ represents hydrogen, fluorine or chlorine or a salt, solvate or solvate of a salt thereof.

In the context of the present invention, very particular preference is given to compounds of the formula (I) in which ring A represents an oxo-substituted azaheterocycle of the formula

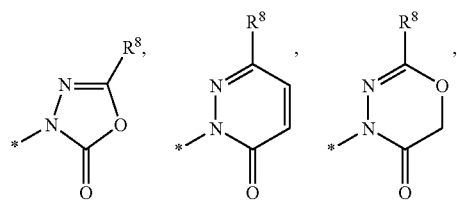

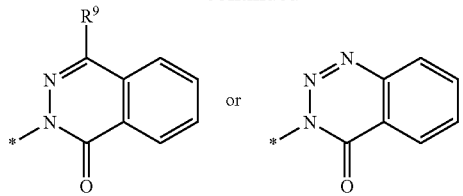

in which
\* denotes the point of attachment to the remainder of the molecule,
$R^8$ represents trifluoromethyl or phenyl which may be substituted up to two times by identical or different radicals selected from the group consisting of fluorine, chlorine, methyl and trifluoromethyl
and
$R^9$ represents hydrogen or has the meaning of $R^8$ given above,
$R^1$ represents hydrogen,
$R^2$ represents hydrogen,
$R^3$ represents propan-2-yl, butan-2-yl, pentan-2-yl, 1,1,1-trifluoropropan-2-yl, 1,1,1-trifluorobutan-2-yl, 4,4,4-trifluorobutan-2-yl, 4,4,4-trifluoro-2-methylbutan-1-yl, cyclopentyl or 3,3-difluorocyclopentyl,
$L^1$ represents a bond or represents methylene,
$L^2$ represents a bond, represents methylene or ethane-1,2-diyl, each of which may be substituted up to two times by methyl, or represents ethene-1,2-diyl
or
represents a group of the formula

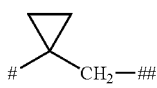

in which
\# denotes the point of attachment to the carboxylic acid grouping
and
\#\# denotes the point of attachment to group M,
M represents 1,3-phenylene or 1,4-phenylene, each of which may be substituted up to two times by identical or different radicals from the group consisting of fluorine, chlorine, methyl and trifluoromethyl, or represents cyclohexane-1,3-diyl or cyclohexane-1,4-diyl,
or
$L^2$ and M are attached to one another and together form a group of the formula

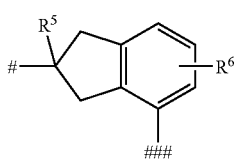

in which
\# denotes the point of attachment to the carboxylic acid grouping,
\#\#\# denotes the point of attachment to group $L^1$,
$R^5$ represents hydrogen or methyl
and
$R^6$ represents hydrogen or fluorine,
or a salt, solvate or solvate of a salt thereof.

In the context of the present invention, very particular preference is also given to compounds of the formula (I) in which
ring A represents an oxo-substituted azaheterocycle of the formula

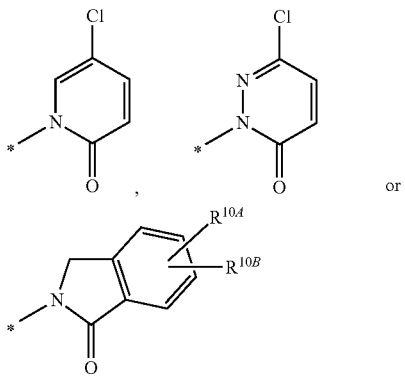

in which
* denotes the point of attachment to the remainder of the molecule
and
$R^{10A}$ and $R^{10B}$ independently of one another represent hydrogen or fluorine,
$R^1$ represents hydrogen,
$R^2$ represents hydrogen,
$R^3$ represents propan-2-yl, butan-2-yl, pentan-2-yl, 1,1,1-trifluoropropan-2-yl, 1,1,1-trifluorobutan-2-yl, 4,4,4-trifluorobutan-2-yl, 4,4,4-trifluoro-2-methylbutan-1-yl, cyclopentyl or 3,3-difluorocyclopentyl,
$L^1$ represents a bond,
$L^2$ represents methylene or ethane-1,2-diyl, each of which may be substituted up to two times by methyl, or represents ethene-1,2-diyl
or
represents a group of the formula

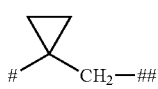

in which
# denotes the point of attachment to the carboxylic acid grouping
and
## denotes the point of attachment to group M,
M represents 1,3-phenylene or 1,4-phenylene, each of which may be substituted up to two times by identical or different radicals from the group consisting of fluorine, chlorine, methyl and trifluoromethyl,
or
$L^2$ and M are attached to one another and together form a group of the formula

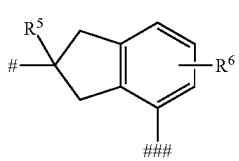

in which
# denotes the point of attachment to the carboxylic acid grouping,
### denotes the point of attachment to group $L^1$,
$R^5$ represents hydrogen or methyl
and
$R^6$ represents hydrogen or fluorine,
or a salt, solvate or solvate of a salt thereof.

The definitions of radicals indicated specifically in the respective combinations or preferred combinations of radicals are replaced as desired irrespective of the particular combinations indicated for the radicals also by definitions of radicals of other combinations.

Combinations of two or more of the abovementioned preferred ranges are very particularly preferred.

The invention further relates to a process for preparing the compounds of the formula (I) according to the invention, characterized in that initially a compound of the formula (II)

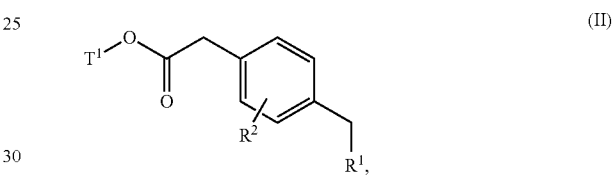

(II)

in which $R^1$ and $R^2$ have the meanings given above
and
$T^1$ represents $(C_1-C_4)$-alkyl,
is converted in an inert solvent in the presence of a base with a compound of the formula (III)

$$R^3—X \qquad (III),$$

in which $R^3$ has the meaning given above
and
X represents a leaving group such as, for example, halogen, mesylate, tosylate or triflate, into a compound of the formula (IV)

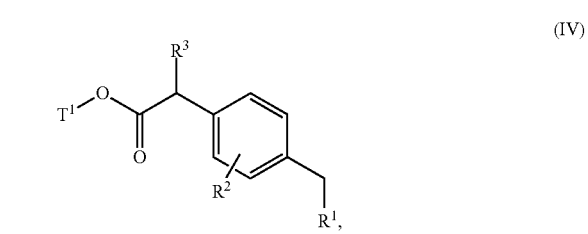

(IV)

in which $R^1$, $R^2$, $R^3$ and $T^1$ each have the meanings given above,
this is then brominated in an inert solvent with elemental bromine or with N-bromosuccinimide to give a compound of the formula (V)

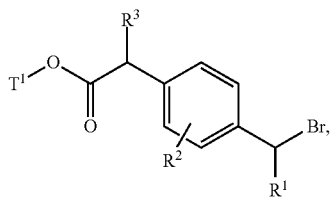

in which R¹, R², R³ and T¹ each have the meanings given above, then reacted in an inert solvent in the presence of a base with a compound of the formula (VI)

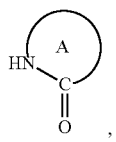

in which ring A represents an oxo-substituted azaheterocycle, as defined above, to give a compound of the formula (VII)

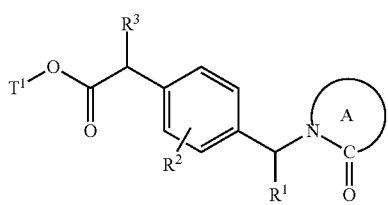

in which ring A, R¹, R², R³ and T¹ each have the meanings given above, the ester radical T¹ in (VII) is then removed under basic or acidic conditions, the resulting carboxylic acid of the formula (VIII)

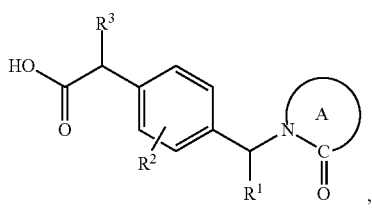

in which ring A, R¹, R² and R³ each have the meanings given above, is then coupled in an inert solvent in the presence of a condensing agent or via the intermediate of the corresponding carbonyl chloride in the presence of a base with an amine of the formula (IX)

in which L¹, L² and M have the meanings given above and

T² represents (C₁-C₄)-alkyl, to give a compound of the formula (X)

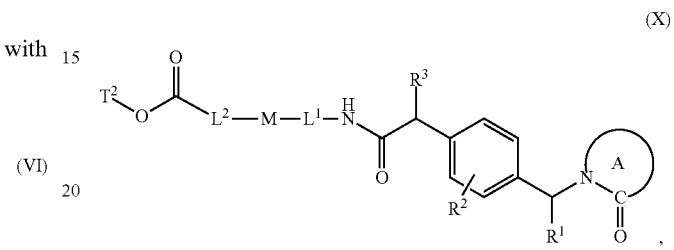

in which ring A, R¹, R², R³, L¹, L², M and T² each have the meanings given above, and the ester radical T² in (X) is then removed by further basic or acidic solvolysis to give the carboxylic acid of the formula (I)

and the compounds of the formula (I) are separated where appropriate by methods known to the skilled person into their enantiomers and/or diastereomers, and/or where appropriate reacted with the appropriate (i) solvents and/or (ii) bases or acids to give the solvates, salts and/or solvates of the salts thereof.

In the reaction sequence described above, it may be expedient where appropriate to reverse the order of individual transformations. Thus, it is possible, for example, to convert the compound of the formula (V-A) [T¹ in (V)=tert-butyl]

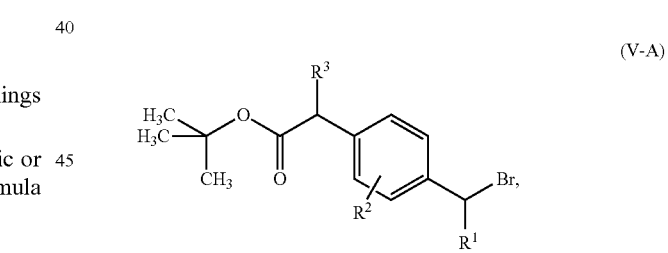

in which R¹, R² and R³ have the meanings given above, initially by treatment with an acid into a carboxylic acid of the formula (XI)

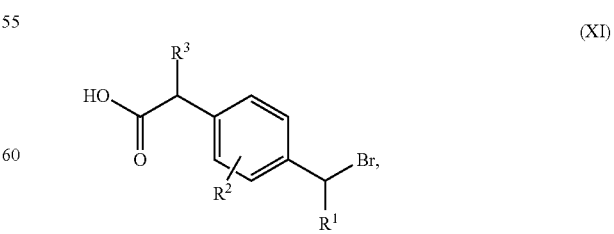

in which R¹, R² and R³ have the meanings given above, and then to couple this compound in an inert solvent in the presence of a condensing agent or via the intermediate of the corresponding carbonyl chloride in the presence of a base with an amine of the formula (IX)

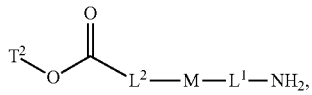  (IX)

in which $L^1$, $L^2$ and M have the meanings given above and
$T^2$ represents $(C_1\text{-}C_4)$-alkyl,
to give a compound of the formula (XII)

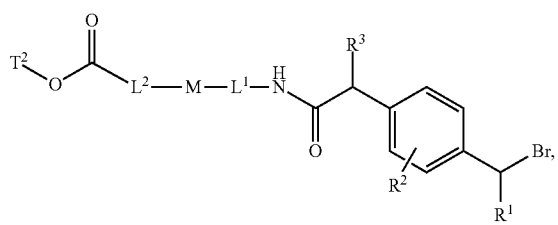  (XII)

in which $R^1$, $R^2$, $R^3$, $L^1$, $L^2$, M and $T^2$ each have the meanings given above,
which is then reacted in an inert solvent in the presence of a base with a compound of the formula (VI)

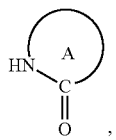  (VI)

in which ring A represents an oxo-substituted azaheterocycle, as described above,
to give the compound of the formula (X)

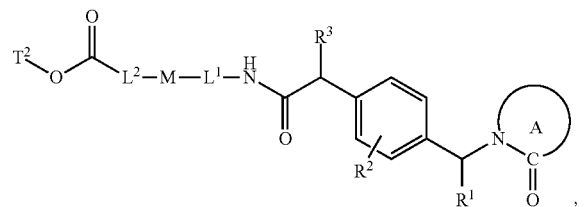  (X)

in which ring A, $R^1$, $R^2$, $R^3$, $L^1$, $L^2$, M and $T^2$ each have the meanings given above,
and converted by removal of the ester radical $T^2$ in (X) into the carboxylic acid of the formula (I).

Separation of the compounds of the invention into the corresponding enantiomers and/or diastereomers can take place where appropriate, depending on expediency, even at the stage of the compounds (VII), (VIII) or (X), which are then reacted further in separated form in accordance with the abovedescribed process sequences. Such a fractionation of the stereoisomers can be carried out by conventional methods known to the skilled person; chromatographic methods or separation via diastereomeric salts are preferably used.

Inert solvents for the process step (II)+(III)→(IV) are, for example, ethers such as diethyl ether, methyl tert-butyl ether, dioxane, tetrahydrofuran, glycol dimethyl ether or diethylene glycol dimethyl ether, hydrocarbons such as benzene, toluene, xylene, hexane, cyclohexane or mineral oil fractions, or dipolar aprotic solvents such as dimethylformamide (DMF), dimethyl sulfoxide (DMSO), N,N'-dimethylpropyleneurea (DMPU) or N-methylpyrrolidone (NMP). It is also possible to use mixtures of the solvents mentioned. Preference is given to using tetrahydrofuran, dimethylformamide or mixtures of these.

Suitable bases for the process step (II)+(III)→(IV) are customary strong inorganic or organic bases. These include in particular alkali metal alkoxides such as sodium methoxide or potassium methoxide, sodium ethoxide or potassium ethoxide or sodium tert-butoxide or potassium tert-butoxide, alkali metal hydrides such as sodium hydride or potassium hydride, or amides such as lithium bis(trimethylsilyl)amide, sodium bis(trimethylsilyl)amide or potassium bis(trimethylsilyl)amide or lithium diisopropylamide. Preference is given to using potassium tert-butoxide, sodium hydride or lithium diisopropylamide.

The reaction (II)+(III)→(IV) is generally carried out in a temperature range of from −100° C. to +30° C., preferably at from −78° C. to 0° C.

The bromination in process step (IV)→(V) is preferably carried out in a halogenated hydrocarbon as solvent, in particular in dichloromethane or carbon tetrachloride, in a temperature range of from +40° C. to +100° C. Suitable brominating agents are elemental bromine in the presence of light and also in particular N-bromosuccinimide (NBS) with addition of α,α'-azobis(isobutyronitrile) (AIBN) or dibenzoyl peroxide as initiator [cf., for example, R. R. Kurtz, D. J. Houser, *J. Org. Chem.* 46, 202 (1981); Z.-J. Yao et al., *Tetrahedron* 55, 2865 (1999)].

Inert solvents for the process steps (V)+(VI)→(VII) and (XII)+(VI)→(X) are, for example, ethers such as diethyl ether, methyl tert-butyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, chlorobenzene or chlorotoluene, or other solvents such as dimethylformamide (DMF), dimethyl sulfoxide (DMSO), N,N'-dimethylpropyleneurea (DMPU), N-methylpyrrolidone (NMP), acetonitrile or pyridine. It is also possible to use mixtures of the solvents mentioned. Preference is given to using tetrahydrofuran, dimethylformamide or mixtures of these.

Suitable bases for these reactions are the customary inorganic or organic bases. These include in particular alkali metal hydroxides such as, for example, lithium hydroxide, sodium hydroxide or potassium hydroxide, alkali metal carbonates such as lithium carbonate, sodium carbonate, potassium carbonate or cesium carbonate, alkali metal alkoxides such as sodium methoxide or potassium methoxide, sodium ethoxide or potassium ethoxide or sodium tert-butoxide or potassium tert-butoxide, alkali metal hydrides such as sodium hydride or potassium hydride, or amides such as lithium bis(trimethylsilyl)amide, sodium bis(trimethyl-silyl)amide or potassium bis(trimethylsilyl)amide or lithium diisopropylamide. Preference is given to using cesium carbonate or sodium hydride.

The reactions (V)+(VI)→(VII) and (XII)+(VI)→(X) are generally carried out in a temperature range of from −20° C. to +120° C., preferably in the range from 0° C. to +80° C.

The removal of the ester group T¹ or T² in the process steps (VII)→(VIII), (X)→(I) and (V-A)→(XI) is carried out by customary methods by treating the esters in inert solvents with acids or bases, where in the latter case the salts initially formed are converted by treatment with acid into the free carboxylic acids. In the case of the tert-butyl esters, the ester hydrolysis is preferably carried out using acids.

Suitable inert solvents for these reactions are water or the organic solvents customary for an ester hydrolysis. These preferably include alcohols such as methanol, ethanol, n-propanol, isopropanol, n-butanol or tert-butanol, or ethers such as diethyl ether, tetrahydrofuran, dioxane or glycol dimethyl ether, or other solvents such as acetone, dichloromethane, dimethylformamide or dimethyl sulfoxide. It is also possible to use mixtures of the solvents mentioned. In the case of a basic ester hydrolysis, preference is given to using mixtures of water with dioxane, tetrahydrofuran, methanol and/or ethanol. In the case of the reaction with trifluoroacetic acid, preference is given to using dichloromethane, and in the case of the reaction with hydrogen chloride, preference is given to using tetrahydrofuran, diethyl ether, dioxane or water.

Suitable bases are the customary inorganic bases. These include in particular alkali metal or alkaline earth metal hydroxides such as, for example, lithium hydroxide, sodium hydroxide, potassium hydroxide or barium hydroxide, or alkali metal or alkaline earth metal carbonates such as sodium carbonate, potassium carbonate or calcium carbonate. Preference is given to lithium hydroxide, sodium hydroxide or potassium hydroxide.

Suitable acids for the ester hydrolysis are in general sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid or mixtures thereof, if appropriate with addition of water. Preference is given to hydrogen chloride or trifluoroacetic acid in the case of the tert-butyl esters and hydrochloric acid in the case of the methyl esters.

The ester hydrolysis is generally carried out in a temperature range of from −20° C. to +100° C., preferably at from 0° C. to +60° C.

Inert solvents for the process steps (VIII)+(IX)→(X) and (XI)+(IX)→(XII) [amide coupling] are, for example, ethers such as diethyl ether, tert-butyl methyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, acetonitrile, ethyl acetate, pyridine, dimethyl sulfoxide (DMSO), dimethylformamide (DMF), N,N'-dimethylpropyleneurea (DMPU) or N-methylpyrrolidinone (NMP). It is also possible to use mixtures of the solvents mentioned. Preference is given to dichloromethane, tetrahydrofuran, dimethylformamide or mixtures of these solvents.

Suitable condensing agents for these coupling reactions are, for example, carbodiimides such as N,N'-diethyl-, N,N'-dipropyl-, N,N'-diisopropyl-, N,N'-dicyclohexylcarbodiimide (DCC) or N-(3-dimethylaminoisopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium 3-sulfate or 2-tert-butyl-5-methylisoxazolium perchlorate, acylamino compounds such as 2-ethoxy-1-ethoxycarbonyl-1,2-dihydroquinoline, or isobutyl chloroformate, propanephosphonic anhydride, diethyl cyanophosphonate, bis(2-oxo-3-oxa-zo- lidinyl)phosphoryl chloride, benzotriazol-1-yloxy-tris(dimethylamino)phosphonium hexafluorophosphate, benzotriazol-1-yloxy-tris(pyrrolidino)phosphonium hexafluorophosphate (PyBOP), O-(benzotriazol-1-yl)-N,N,N'N'-tetramethyluronium tetrafluoroborate (TBTU), O-(benzotriazol-1-yl)-N,N,N'N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), if appropriate in combination with further auxiliaries such as 1-hydroxybenzotriazole (HOBt) or N-hydroxysuccinimide (HOSu), and as bases alkali metal carbonates, for example sodium carbonate or potassium carbonate, or organic bases such as triethylamine, N-methylmorpholine, N-methylpiperidine, N,N-diisopropylethylamine, pyridine or 4-N,N-dimethylaminopyridine. Preference is given to using O-(7-azabenzotriazol-1-yl)-N,N,N',N'-tetramethyluronium hexafluorophosphate (HATU) or O-(benzotriazol-1-yl)-N,N,N'N'-tetramethyluronium tetrafluoroborate (TBTU), in each case in combination with pyridine or N,N-diisopropylethylamine, or N-(3-dimethylaminoisopropyl)-N'-ethylcarbodiimide hydrochloride (EDC) in combination with 1-hydroxybenzotriazole (HOBt) and triethylamine.

The couplings (VIII)+(IX)→(X) and (XI)+(IX)→(XII) are generally carried out in a temperature range of from 0° C. to +60° C., preferably at from +10° C. to +40° C.

When a carbonyl chloride corresponding to the compound (VIII) or (XI) is used, the coupling with the amine component (IX) is carried out in the presence of a customary organic auxiliary base such as triethylamine, N-methylmorpholine, N-methylpiperidine, N,N-diisopropylethylamine, pyridine, 4-N,N-dimethylaminopyridine, 1,8-diazabicyclo[5.4.0]undec-7-ene (DBU) or 1,5-diazabicyclo[4.3.0]non-5-ene (DBN). Preference is given to using triethylamine or N,N-diisopropylethylamine.

The reaction of (IX) with the carbonyl chloride is generally carried out in a temperature range of from −20° C. to +60° C., preferably in the range from 0° C. to +40° C.

For their part, the preparation of the carbonyl chlorides is carried out in a customary manner by treating the carboxylic acids (VIII) or (XI) with thionyl chloride.

The reactions mentioned can be carried out at atmospheric, at elevated or at reduced pressure (for example from 0.5 to 5 bar). In general, they are in each case carried out at atmospheric pressure.

The intermediates of the formula (IV) can also be prepared by other routes—as alternatives to the alkylation process (II)+(III)→(IV) described above. Thus, compounds of the formula (IV) are also obtainable, for example, by palladium-catalyzed arylation of carboxylic esters of the formula (XIII)

(XIII)

in which R³ and T¹ have the meanings given above, with phenyl bromides or iodides of the formula (XIV)

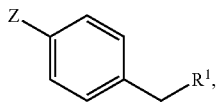
(XIV)

in which R¹ has the meaning given above
and
Z represents bromine or iodine,
or they can be obtained by a Friedel-Crafts acylation of toluene derivatives of the formula (XV)

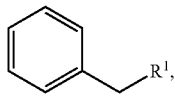
(XV)

in which R¹ has the meaning given above,
with carbonyl chlorides of the formula (XVI)

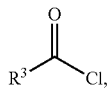
(XVI)

in which R³ has the meaning given above,
to give phenylketones of the formula (XVII)

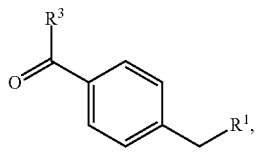
(XVII)

in which R¹ and R³ have the meanings given above;
the compounds of the formula (XVII) can then be converted in a multistep reaction sequence known from the literature into the phenylacetate derivatives of the formula (IV) (see Reaction Schemes 3 and 4 below).

If R³ represents an optionally substituted cyclopentyl or cyclohexyl radical, corresponding compounds of the formula (IV) can also be prepared by the Michael addition of a phenylacetic ester of the formula (XVIII)

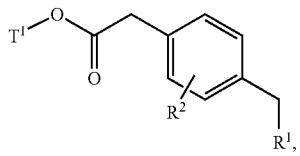
(XVIII)

in which R¹, R² and T¹ each have the meanings given above, to 2-cyclopenten-1-one and 2-cyclohexen-1-one, respectively, and subsequent transformation of the keto group (see Reaction Scheme 5 below).

The compounds of the formulae (II), (III), (VI), (IX), (XIII), (XIV), (XV), (XVI) and (XVIII) are commercially available, described as such in the literature or can be prepared analogously to processes known from the literature (cf. also Reaction Scheme 6 below).

The preparation of the compounds of the invention can be illustrated in an exemplary manner by the following synthesis schemes:

Scheme 1

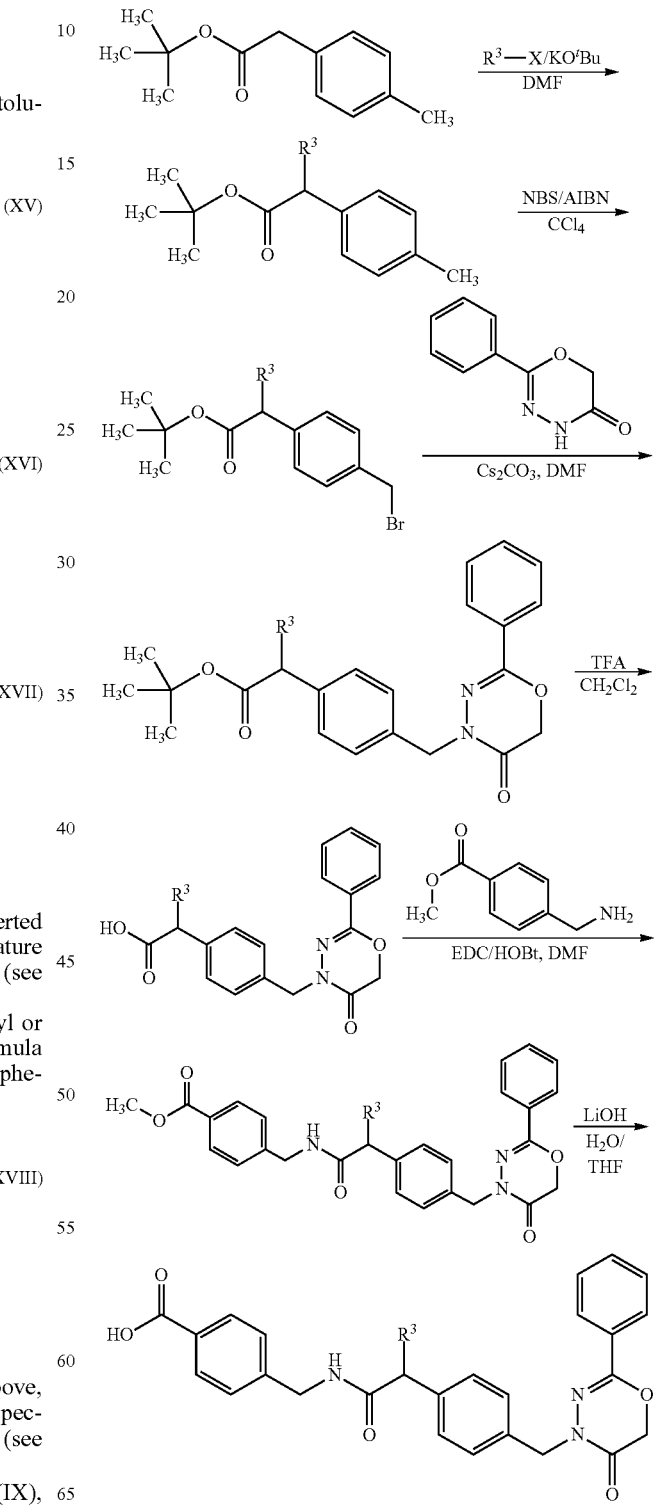

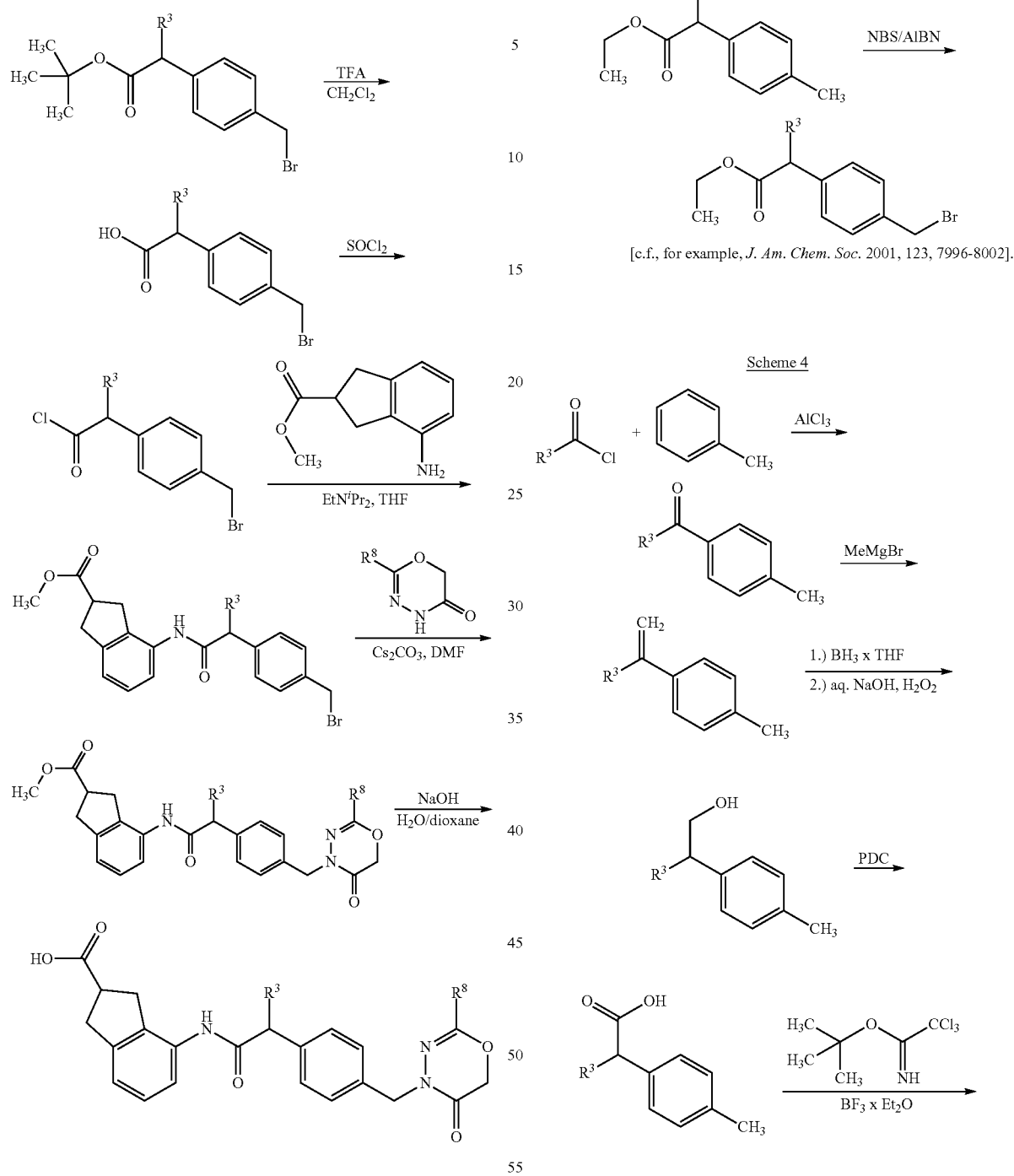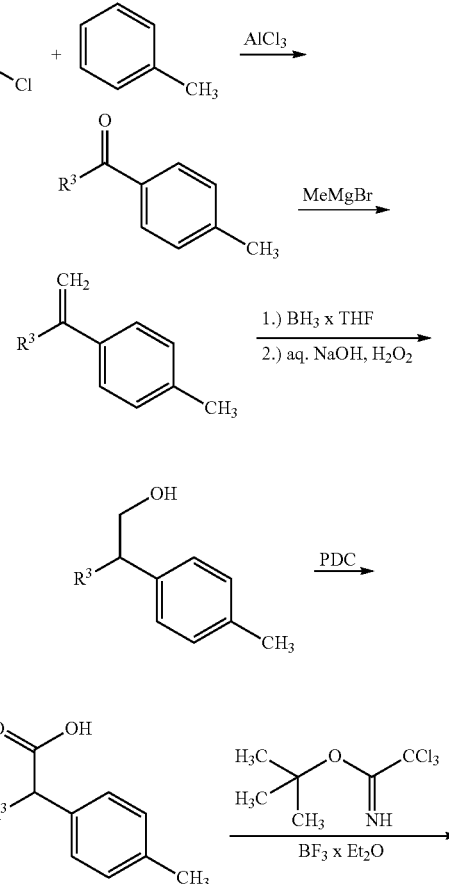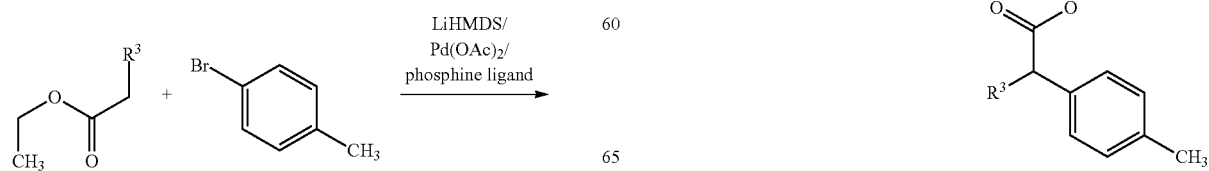

Scheme 5

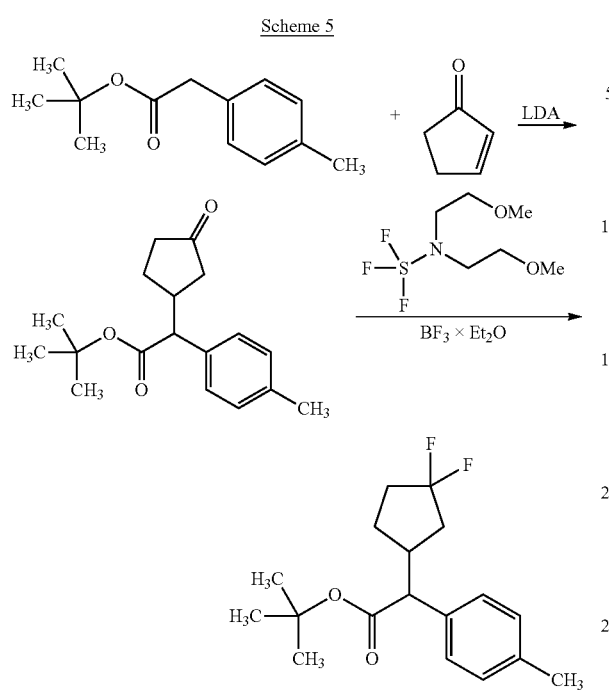

[cf., for example, J. Org. Chem. 2001, 66 (20), 6775-6786].

Scheme 6

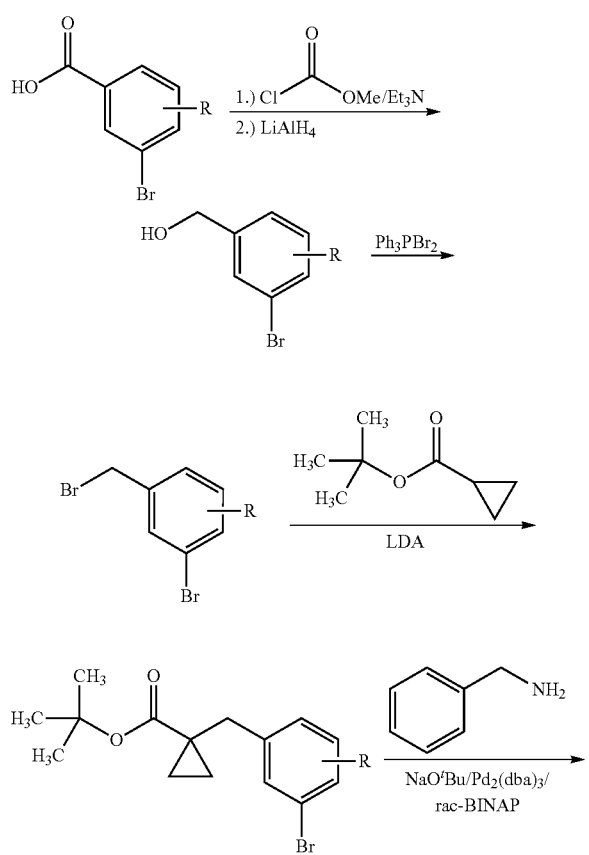

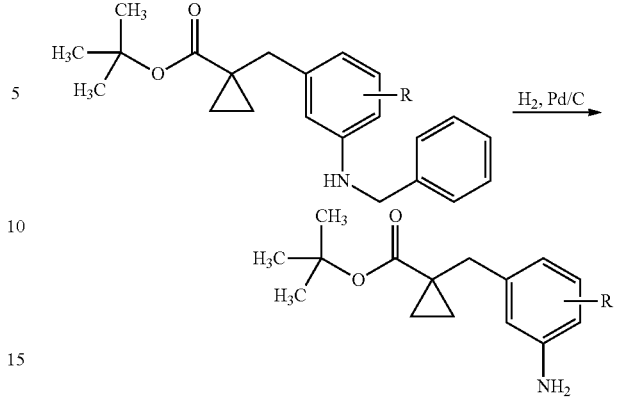

The compounds according to the invention have valuable pharmacological properties and can be used for the prevention and treatment of disorders in humans and animals.

The compounds according to the invention are potent activators of soluble guanylate cyclase. They lead to vasorelaxation, inhibition of platelet aggregation and lowering of blood pressure and increase of coronary blood flow. These effects are mediated via direct heme-independent activation of soluble guanylate cyclase and an increase of intracellular cGMP.

The compounds according to the invention can therefore be employed in medicaments for the treatment of cardiovascular disorders such as, for example, for the treatment of high blood pressure and heart failure, stable and unstable angina pectoris, pulmonary hypertension, renal hypertension, peripheral and cardiac vascular disorders, arrhythmias, for the treatment of thromboembolic disorders and ischemias such as myocardial infarction, stroke, transistory and ischemic attacks, disturbances of peripheral blood flow, prevention of restenoses as after thrombolysis therapies, percutaneous transluminal angioplasties (PTAs), percutaneous transluminal coronary angioplasties (PTCAs), bypass and for the treatment of arteriosclerosis, asthmatic disorders and diseases of the urogenital system such as, for example, prostate hypertrophy, erectile dysfunction, female sexual dysfunction, and incontinence, osteoporosis, glaucoma, and gastroparesis.

The compounds according to the invention can additionally be used for the treatment of primary and secondary Raynaud's phenomenon, of microcirculation impairments, claudication, peripheral and autonomic neuropathies, diabetic microangiopathies, diabetic retinopathy, diabetic ulcers on the extremities, CREST syndrome, erythematosis, onychomycosis and rheumatic disorders.

In addition, the compounds according to the invention can be used for preventing ischemia- and/or reperfusion-related damage to organs or tissues and also as additives for perfusion and preservation solutions of organs, organ parts, tissues or tissue parts of human or animal origin in particular for surgical interventions or in the field of transplantation medicine.

The compounds according to the invention are furthermore suitable for the treatment of respiratory distress syndromes and chronic obstructive airway disorders (COPD), of acute and chronic renal failure and for promoting wound healing.

The compounds described in the present invention also represent active ingredients for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory loss, vascular dementia, craniocerebral trauma, stroke, dementia occurring after strokes (post-stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff's psychosis. They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraine. They are also suitable for the prophylaxis and control of the sequelae of cerebral infarctions (Apoplexia cerebri) such as stroke, cerebral ischemias and craniocerebral trauma. The compounds according to the invention can likewise be employed for controlling states of pain.

In addition, the compounds according to the invention have an anti-inflammatory effect and can therefore be employed as anti-inflammatory agents.

The present invention further relates to the use of the compounds according to the invention for the treatment and/or prevention of disorders, especially of the aforementioned disorders.

The present invention further relates to the use of the compounds according to the invention for producing a medicament for the treatment and/or prevention of disorders, especially of the aforementioned disorders.

The present invention further relates to the use of the compounds according to the invention in a method for the treatment and/or prevention of disorders, especially of the aforementioned disorders.

The present invention further relates to a method for the treatment and/or prevention of disorders, especially of the aforementioned disorders, by using an effective amount of at least one of the compounds according to the invention.

The compounds according to the invention can be employed alone or, if required, in combination with other active ingredients. The present invention further relates to medicaments comprising at least one of the compounds according to the invention and one or more further active ingredients, in particular for the treatment and/or prevention of the aforementioned disorders. Examples of suitable combination active ingredients which may be preferably mentioned are:

organic nitrates and NO donors such as, for example, sodium nitroprusside, nitroglycerin, isosorbide mononitrate, isosorbide dinitrate, molsidomine or SIN-1, and inhaled NO; compounds which inhibit the breakdown of cyclic guanosine monophosphate (cGMP), such as, for example, inhibitors of phosphodiesterases (PDE) 1, 2 and/or 5, in particular PDE 5 inhibitors such as sildenafil, vardenafil and tadalafil;
NO-independent but heme-dependent stimulators of guanylate cyclase, such as, in particular, the compounds described in WO 00/06568, WO 00/06569, WO 02/42301 and WO 03/095451;

agents having antithrombotic activity, for example and preferably from the group of platelet aggregation inhibitors, of anticoagulants or of profibrinolytic substances;
active ingredients which lower blood pressure, for example and preferably from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics; and/or
active ingredients which modify lipid metabolism, for example and preferably from the group of thyroid receptor agonists, cholesterol synthesis inhibitors such as, for example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

Agents having antithrombotic activity preferably mean compounds from the group of platelet aggregation inhibitors, of anticoagulants or of profibrinolytic substances.

In a preferred embodiment of the invention, the compounds according to the invention are administered in combination with a platelet aggregation inhibitor such as, for example and preferably, aspirin, clopidogrel, ticlopidin or dipyridamole.

In a preferred embodiment of the invention, the compounds according to the invention are administered in combination with a thrombin inhibitor such as, for example and preferably, ximelagatran, melagatran, bivalirudin or clexane.

In a preferred embodiment of the invention, the compounds according to the invention are administered in combination with a GPIIb/IIIa antagonist such as, for example and preferably, tirofiban or abciximab.

In a preferred embodiment of the invention, the compounds according to the invention are administered in combination with a factor Xa inhibitor such as, for example and preferably, rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist such as, for example and preferably, coumarin.

Agents which lower blood pressure preferably mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics.

In a preferred embodiment of the invention, the compounds according to the invention are administered in combination with a calcium antagonist such as, for example and preferably, nifedipine, amlodipine, verapamil or diltiazem.

In a preferred embodiment of the invention, the compounds according to the invention are administered in combination with an alpha-1-receptor blocker such as, for example and preferably, prazosin.

In a preferred embodiment of the invention, the compounds according to the invention are administered in combination with a beta-receptor blocker such as, for example and preferably, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist such as, for example and preferably, losartan, candesartan, valsartan, telmisartan or embursatan.

In a preferred embodiment of the invention, the compounds according to the invention are administered in combination with an ACE inhibitor such as, for example and preferably, enalapril, captopril, lisinopril, ramipril, delapril, fosinopril, quinopril, perindopril or trandopril.

In a preferred embodiment of the invention, the compounds according to the invention are administered in combination with an endothelin antagonist such as, for example and preferably, bosentan, darusentan, ambrisentan or sitaxsentan.

In a preferred embodiment of the invention, the compounds according to the invention are administered in combination with a renin inhibitor such as, for example and preferably, aliskiren, SPP-600 or SPP-800.

In a preferred embodiment of the invention, the compounds according to the invention are administered in combination with a mineralocorticoid receptor antagonist such as, for example and preferably, spironolactone or eplerenone.

In a preferred embodiment of the invention, the compounds according to the invention are administered in combination with a diuretic such as, for example and preferably, furosemide. Agents which modify lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and of lipoprotein (a) antagonists.

In a preferred embodiment of the invention, the compounds according to the invention are administered in combination with a CETP inhibitor such as, for example and preferably, torcetrapib (CP-529 414), JJT-705 or CETP vaccine (Avant).

In a preferred embodiment of the invention, the compounds according to the invention are administered in combination with a thyroid receptor agonist such as, for example and preferably, D-thyroxine, 3,5,3'-triiodothyronine (T3), CGS 23425 or axitirome (CGS 26214). In a preferred embodiment of the invention, the compounds according to the invention are administered in combination with an HMG-CoA reductase inhibitor from the class of statins such as, for example and preferably, lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor such as, for example and preferably, BMS-188494 or TAK-475.

In a preferred embodiment of the invention, the compounds according to the invention are administered in combination with an ACAT inhibitor such as, for example and preferably, avasimibe, melinamide, pactimibe, eflucimibe or SMP-797.

In a preferred embodiment of the invention, the compounds according to the invention are administered in combination with an MTP inhibitor such as, for example and preferably, implitapide, BMS-201038, R-103757 or JTT-130.

In a preferred embodiment of the invention, the compounds according to the invention are administered in combination with a PPAR-gamma agonist such as, for example and preferably, pioglitazone or rosiglitazone.

In a preferred embodiment of the invention, the compounds according to the invention are administered in combination with a PPAR-delta agonist such as, for example and preferably, GW 501516 or BAY 68-5042.

In a preferred embodiment of the invention, the compounds according to the invention are administered in combination with a cholesterol absorption inhibitor such as, for example and preferably, ezetimibe, tiqueside or pamaqueside.

In a preferred embodiment of the invention, the compounds according to the invention are administered in combination with a lipase inhibitor such as, for example and preferably, orlistat.

In a preferred embodiment of the invention, the compounds according to the invention are administered in combination with a polymeric bile acid adsorbent such as, for example and preferably, cholestyramine, colestipol, colesolvam, Cholesta-Gel or colestimide.

In a preferred embodiment of the invention, the compounds according to the invention are administered in combination with a bile acid reabsorption inhibitor such as, for example and preferably, ASBT (=IBAT) inhibitors such as, for example, AZD-7806, S-8921, AK-105, BAR1-1741, SC-435 or SC-635.

In a preferred embodiment of the invention, the compounds according to the invention are administered in combination with a lipoprotein (a) antagonist such as, for example and preferably, gemcabene calcium (CI-1027) or nicotinic acid.

The present invention further relates to medicaments which comprise at least one compound according to the invention, normally together with one or more inert, non-toxic, pharmaceutically suitable excipients, and to the use thereof for the aforementioned purposes.

The compounds according to the invention can act systemically and/or locally. For this purpose, they can be administered in a suitable way such as, for example, by the oral, parenteral, pulmonary, nasal, sublingual, lingual, buccal, rectal, dermal, transdermal, conjunctival, otic routes or as implant or stent.

The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilisates or sterile powders.

Suitable for the other administration routes are, for example, pharmaceutical forms for inhalation (inter alia powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral or parenteral administration is preferred, especially oral and intravenous administration. The compounds according to the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and masking flavors and/or odors.

It has generally proved advantageous to administer on parenteral administration amounts of about 0.001 to 1 mg/kg, preferably about 0.01 to 0.5 mg/kg, of body weight to achieve effective results, and on oral administration the dosage is about 0.01 to 100 mg/kg, preferably about 0.01 to 20 mg/kg, and very particularly preferably 0.1 to 10 mg/kg, of body weight.

It may nevertheless be necessary where appropriate to deviate from the stated amounts, in particular as a function of the body weight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data for the liquid/liquid solutions are in each case based on volume.

A. EXAMPLES

Abbreviations and Acronyms:
abs. absolute
Ac acetyl
AIBN 2,2'-azobis(2-methylpropionitrile)
aq. aqueous, aqueous solution
ATP adenosine 5'-triphosphate
BINAP 2,2'-bis(diphenylphosphino)-1,1'-binaphthyl
Boc tert-butoxycarbonyl
Brij® polyethylene glycol dodecyl ether
BSA bovine serum albumin
Bu butyl
c concentration
CI chemical ionization (in MS)
d day(s)
dba dibenzylideneacetone
DBU 1,8-diazabicyclo[5.4.0]undec-7-ene
DCI direct chemical ionization (in MS)
de diastereomeric excess
DIBAH diisobutylaluminum hydride
DIEA diisopropylethylamine
DMF dimethylformamide
DMSO dimethyl sulfoxide
DTT dithiothreitol
EDC N'-(3-dimethylaminopropyl)-N-ethylcarbodiimide hydrochloride
ee enantiomeric excess
EI electron impact ionization (in MS)
ent enantiomerically pure, enantiomer
eq. equivalent(s)
ESI electrospray ionization (in MS)
Et ethyl
Ex. Example
GC gas chromatography
GTP guanosine 5'-triphosphate
h hour(s)
HATU O-(7-azabenzotriazol-1-yl)-N,N,N'N'-tetramethyluronium hexafluorophosphate
HOBt 1-hydroxy-M-benzotriazole hydrate
HPLC high pressure, high performance liquid chromatography
$^i$Pr isopropyl
KO$^t$Bu potassium tert-butoxide
LC-MS liquid chromatography-coupled mass spectrometry
LDA lithium diisopropylamide
LiHDMS lithium hexamethyldisilazide[lithium bis(trimethylsilyl)amide]
Me methyl
min minute(s)
MS mass spectroscopy
NBS N-bromosuccinimide
NMR nuclear magnetic resonance spectrometry
PDC pyridinium dichromate
Ph phenyl
Pr propyl
rac racemic, racemate
$R_f$ retention index (in TLC)
RP reversed phase (in HPLC)
RT room temperature
$R_t$ retention time (in HPLC)
$^t$Bu tert-butyl
TBTU O-(benzotriazol-1-yl)-N,N,N'N'-tetramethyluronium tetrafluoroborate
TCTU O-(1H-6-chlorobenzotriazol-1-yl)-1,1,3,3-tetramethyluronium tetrafluoroborate
TEA triethanolamine
TFA trifluoroacetic acid
THF tetrahydrofuran
TLC thin-layer chromatography
tog. together
UV ultraviolet spectroscopy
v/v volume to volume ratio (of a solution)
LC/MS Methods:
Method 1 (LC-MS)
 MS instrument type: Micromass ZQ; HPLC instrument type: HP 1100 Series; UV DAD; column: Phenomenex Synergi 2µ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.
Method 2 (LC-MS)
 MS instrument type: Micromass ZQ; HPLC instrument type: Waters Alliance 2795; column: Phenomenex Synergi 2µ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 3 (LC-MS)

Instrument: Micromass Platform LCZ with HPLC Agilent Series 1100; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 4 (LC-MS)

Instrument: Micromass Quattro LCZ with HPLC Agilent Series 1100; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.

Method 5 (LC-MS)

Instrument: Micromass Platform LCZ with HPLC Agilent Series 1100; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 6 (LC-MS)

MS instrument type: Micromass ZQ; HPLC instrument type: Waters Alliance 2795; column: Merck Chromolith SpeedROD RP-18e 100 mm×4.6 mm; mobile phase A: water+500 μl 50% strength formic acid/l, mobile phase B: acetonitrile+500 μl 50% strength formic acid/l; gradient: 0.0 min 10% B→7.0 min 95% B→9.0 min 95% B; flow rate: 0.0 min 1.0 ml/min→7.0 min 2.0 ml/min→9.0 min 2.0 ml/min; oven: 35° C.; UV detection: 210 nm.

Method 7 (LC-MS)

MS instrument type: Micromass ZQ; HPLC instrument type: HP 1100 Series; UV DAD; column: Phenomenex Gemini 3μ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 8 (LC-MS)

Instrument: Micromass Quattro LCZ with HPLC Agilent Series 1100; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 208-400 nm.

Method 9 (LC-MS)

MS instrument type: Waters ZQ; HPLC instrument type: Waters Alliance 2795; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 210 nm.

Method 10 (LC-MS)

MS instrument type: Micromass ZQ; HPLC instrument type: Waters Alliance 2795; column: Phenomenex Synergi 2.5μ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 11 (LC-MS)

Instrument: Micromass Quattro Premier with Waters HPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

Method 12 (LC-MS)

MS instrument type: Waters Micromass Quattro Micro; HPLC instrument type: Agilent 1100 Series; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 13 (LC-MS)

MS instrument type: Waters ZQ; HPLC instrument type: Agilent 1100 Series; UV DAD; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.1 min 100% A (flow rate 2.5 ml/min); oven: 55° C.; flow rate: 2 ml/min; UV detection: 210 nm.

Method 14 (LC-MS)

MS instrument: Waters ZQ 2000; HPLC instrument: Agilent 1100, 2-column configuration; autosampler: HTC PAL; column: YMC-ODS-AQ, 50 mm×4.6 mm, 3.0 μm; mobile phase A: water+0.1% formic acid, mobile phase B: acetonitrile+0.1% formic acid; gradient: 0.0 min 100% A→0.2 min 95% A→1.8 min 25% A→1.9 min 10% A→2.0 min 5% A→3.2 min 5% A→3.21 min 100% A→3.35 min 100% A; oven: 40° C.; flow rate: 3.0 ml/min; UV detection: 210 nm.

Method 15 (LC-MS)

Instrument: Waters Acquity SQD HPLC System; column: Waters Acquity HPLC HSS T3 1.8μ, 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; flow rate: 0.40 ml/min; oven: 50° C.; UV detection: 210-400 nm.

GC/MS Methods:

Method 1 (GC-MS)

Instrument: Micromass GCT, GC 6890; column: Restek RTX-35MS, 30 m×250 μm×0.25 μm; constant helium flow rate: 0.88 ml/min; oven: 60° C.; inlet: 250° C.; gradient: 60° C. (maintain for 0.30 min), 50° C./min→120° C., 16° C./min→250° C., 30° C./min→300° C. (maintain for 1.7 min).

Method 2 (GC-MS)

Instrument: Micromass GCT, GC 6890; column: Restek RTX-35MS, 30 m×250 μm×0.25 μm; constant helium flow rate: 0.88 ml/min; oven: 60° C.; inlet: 250° C.; gradient: 60° C. (maintain for 0.30 min), 50° C./min→120° C., 16° C./min→250° C., 30° C./min→300° C. (maintain for 8.7 min).

Method 3 (GC-MS)

Instrument: Micromass GCT, GC 6890; column: Restek RTX-35, 15 m×200 μm×0.33 μm; constant helium flow rate: 0.88 ml/min; oven: 70° C.; inlet: 250° C.; gradient: 70° C., 30° C./min→310° C. (maintain for 3 min).

HPLC Methods:
Method 1 (HPLC)

Instrument: HP 1100 with DAD detection; column: Kromasil 100 RP-18, 60 mm×2.1 mm, 3.5 µm; mobile phase A: 5 ml of HClO$_4$ (70% strength)/l of water, mobile phase B: acetonitrile; gradient: 0 min 2% B→0.5 min 2% B→4.5 min 90% B→9 min 90% B→9.2 min 2% B→10 min 2% B; flow rate: 0.75 ml/min; column temperature: 30° C.; UV detection: 210 nm.

Method 2 (HPLC)

Instrument: HP 1100 with DAD detection; column: Kromasil 100 RP-18, 60 mm×2.1 mm, 3.5 µm; mobile phase A: 5 ml of HClO$_4$ (70% strength)/l of water, mobile phase B: acetonitrile; gradient: 0 min 2% B→0.5 min 2% B→4.5 min 90% B→15 min 90% B→15.2 min 2% B→16 min 2% B; flow rate: 0.75 ml/min; column temperature: 30° C.; UV detection: 210 nm.

Starting Materials and Intermediates

Example 1A tert-Butyl 5,5,5-trifluoro-2-(4-methylphenyl)pentanoate

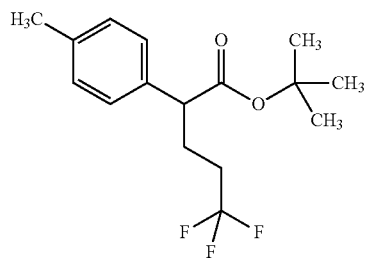 [SMILES: Cc1ccc(C(CCC(F)(F)F)C(=O)OC(C)(C)C)cc1]

Under exclusion of oxygen, 0.88 ml (6.3 mmol) of diisopropylamine was initially charged in 20 ml of THF, the mixture was cooled to −78° C. and 2.52 ml (6.3 mmol) of a 2.5 M solution of n-butyllithium in hexane were added slowly. The reaction solution was then warmed to −10° C. and stirred at this temperature for 10 min. The reaction solution was then once more cooled to −78° C., and 1 g (4.85 mmol) of tert-butyl(4-methylphenyl)acetate, dissolved in 10 ml of THF, was added slowly. The reaction solution was then slowly warmed to −30° C. and subsequently once more cooled to −78° C. After this temperature had been reached, 0.62 ml (5.82 mmol) of 3-bromo-1,1,1-trifluoropropane was slowly added dropwise. After the addition had ended, the solution was slowly warmed to room temperature and stirred overnight. After TLC check (mobile phase cyclohexane/ethyl acetate 10:1), saturated ammonium chloride solution was added and the mixture was taken up in ethyl acetate. The aqueous phase was extracted twice with ethyl acetate. The combined organic phases were dried over sodium sulfate. After filtration, the solvent was removed under reduced pressure. The crude product was purified chromatographically on silica gel (mobile phase cyclohexane/ethyl acetate 10:1). This gave 542 mg (1.79 mmol, 37% of theory) of a yellowish oil.

GC-MS (method 3): R$_t$=4.41 min; m/z=246 (M–C$_4$H$_9$+H)$^+$.

Example 2A tert-Butyl 3-methyl-2-(4-methylphenyl)pentanoate

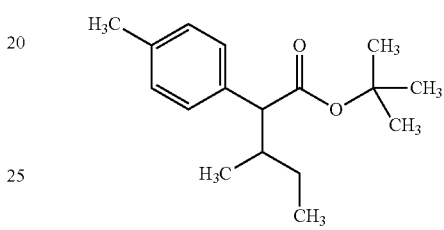

Under argon, 19.58 g (174.5 mmol) of potassium tert-butoxide were initially charged in 200 ml of DMF, the mixture was cooled to 0° C., 30 g (145.4 mmol) of tert-butyl(4-methylphenyl)acetate, dissolved in 50 ml of DMF, were added slowly and the mixture was then stirred at 0° C. for 30 min. 18.95 ml (174.5 mmol) of 2-bromobutane were then slowly added dropwise, and the solution was stirred at 0° C. for another 4 h. 200 ml of water and 200 ml of diethyl ether were then added to the reaction solution. The aqueous phase was extracted twice with diethyl ether. The combined organic phases were dried over magnesium sulfate. After filtration, the solvent was removed under reduced pressure. The crude product was purified chromatographically on silica gel (mobile phase cyclohexane/ethyl acetate 20:1). This gave 15.5 g (59.1 mmol, 40.6% of theory) of a colorless liquid.

$^1$H-NMR (400 MHz, DMSO-d$_6$, δ/ppm): 7.17 (2H, d), 7.11 (2H, d), 3.11 (1H, d), 2.27 (3H, s), 2.04-1.90 (1H, m), 1.55-1.42 (1H, m), 1.35 (9H, s), 1.24-1.10 (1H, m), 0.99-0.86 (3H, m), 0.77-0.51 (3H, m).

GC-MS (method 3): R$_t$=5.04 min; m/z=206 (M–C$_4$H$_9$+H)$^+$.

The compounds listed in the table below were obtained in a manner analogous to Example 2A:

| Example | Name/Structure | Analytical data |
|---|---|---|
| 3A | tert-butyl 3-methyl-2-(4-methylphenyl)butanoate | $^1$H-NMR (400 MHz, DMSO-d$_6$, δ/ppm): 7.17 (2H, d), 7.11 (2H, d), 3.00 (1H, d), 2.28 (3H, s), 2.21-2.07 (1H, m), 1.35 (9H, s), 0.97 (3H, d), 0.61 (3H, d). GC-MS (method 3): R$_t$ = 4.70 min; m/z = 192 (M – C$_4$H$_9$ + H)$^+$. |

-continued

| Example | Name/Structure | Analytical data |
|---|---|---|
| 4A | tert-butyl cyclopentyl(4-methylphenyl)acetate 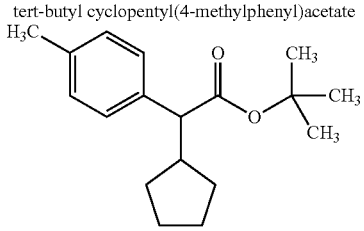 | $^1$H-NMR (400 MHz, DMSO-d$_6$, δ/ppm): 7.19 (2H, d), 7.11 (2H, d), 3.12 (1H, d), 2.45-2.29 (1H, m), 2.27 (3H, s), 1.89-1.71 (1H, m), 1.67-1.45 (3H, m), 1.44-1.15 (3H, m), 1.36 (9H, s), 1.02-0.84 (1H, m). MS (DCI): m/z = 292 (M + NH$_4$)$^+$; GC-MS (method 3): R$_t$ = 5.89 min; m/z = 218 (M − C$_4$H$_9$ + H)$^+$. |
| 5A | tert-butyl 4-cyano-3-methyl-2-(4-methylphenyl)butanoate 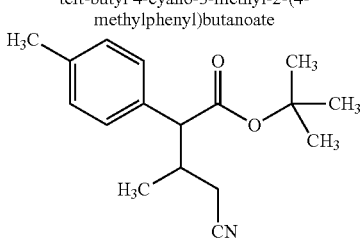 | $^1$H-NMR (400 MHz, DMSO-d$_6$, δ/ppm): 7.17 (4H, d), 3.31-3.18 (1H, m), 2.69-2.49 (1H, m), 2.48-2.34 (1H, m), 2.29 (3H, s), 2.08-1.98 (1H, m), 1.34 (9H, s), 1.11 (2H, d), 0.75 (1H, d). LC-MS (method 10): R$_t$ = 2.35 and 2.38 min; m/z = 274 (M + H)$^+$. |
| 6A | tert-butyl 3-methyl-2-(4-methylphenyl)-hexanoate 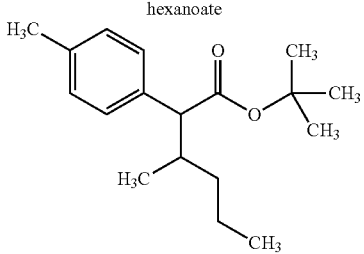 | MS (DCI): m/z = 294 (M + NH$_4$)$^+$; GC-MS (method 3): R$_t$ = 5.30 min; m/z = 220 (M − C$_4$H$_9$ + H)$^+$. |
| 7A | tert-butyl 4-methoxy-3-methyl-2-(4-methyl-phenyl)butanoate 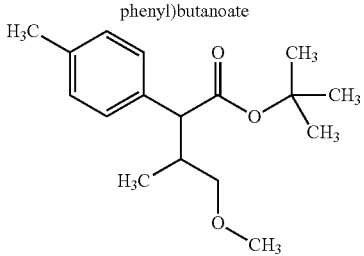 | MS (DCI): m/z = 279 (M + H)$^+$; GC-MS (method 3): R$_t$ = 5.34 and 5.37 min; m/z = 222 (M − C$_4$H$_9$ + H)$^+$. |

Example 8A tert-Butyl 2-[4-(bromomethyl)phenyl]-5,5,5-trifluoropentanoate

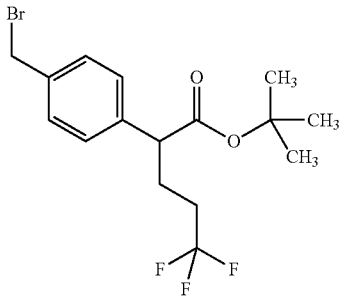 [SMILES: CC(C)(C)OC(=O)C(CCC(F)(F)F)c1ccc(CBr)cc1]

540 mg (1.79 mmol) of tert-butyl 5,5,5-trifluoro-2-(4-methylphenyl)pentanoate, 333.8 mg (1.78 mmol) of N-bromosuccinimide and 14.7 mg (0.09 mmol) of 2,2'-azobis-2-methylpropanenitrile in 10 ml of carbon tetrachloride were stirred under reflux for 2 h. After the reaction had gone to completion, the succinimide was filtered off and the filter residue was washed with dichloromethane. The filtrate was concentrated under reduced pressure. The crude product was purified chromatographically on silica gel (mobile phase cyclohexane/ethyl acetate 10:1). This gave 659 mg (1.72 mmol, 97% of theory) of a yellowish oil.

GC-MS (method 3): $R_t$=5.91 min; m/z=301 (M−Br)$^+$.

Example 9A tert-Butyl 2-[4-(bromomethyl)phenyl]-3-methylpentanoate

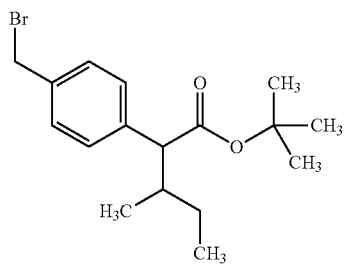 [SMILES: CCC(C)C(C(=O)OC(C)(C)C)c1ccc(CBr)cc1]

15 g (59.1 mmol) of tert-butyl 3-methyl-2-(4-methylphenyl)pentanoate, 11 g (62 mmol) of N-bromosuccinimide and 97 mg (0.59 mmol) of 2,2'-azobis-2-methylpropanenitrile in 150 ml of dichloromethane were stirred under reflux for 2 h. After the reaction had gone to completion, the solvent was removed under reduced pressure. The crude product was purified chromatographically on silica gel (mobile phase cyclohexane/ethyl acetate 20:1). This gave 16.22 g (47.5 mmol, 80% of theory) of a colorless oil.

GC-MS (method 3): $R_t$=6.41 min; m/z=261 (M−Br)$^+$.
MS (DCI): m/z=358/360 (M+NH$_4$)$^+$.

The compounds listed in the table below were obtained in an analogous manner:

| Example | Name/Structure | Analytical data |
|---|---|---|
| 10A | tert-butyl [4-(bromomethyl)phenyl](cyclopentyl)acetate | $^1$H-NMR (400 MHz, DMSO-d$_6$, δ/ppm): 7.39 (2H, d), 7.30 (2H, d), 4.68 (2H, s), 3.21 (1H, d), 2.45-2.31 (1H, m), 1.89-1.74 (1H, m), 1.69-1.45 (3H, m), 1.44-1.16 (3H, m), 1.35 (9H, s), 1.02-0.88 (1H, m). MS (DCI): m/z = 370/372 (M + NH$_4$)$^+$. |
| 11A | tert-butyl 2-[4-(bromomethyl)phenyl]-3-methylbutanoate | $^1$H-NMR (400 MHz, DMSO-d$_6$, δ/ppm): 7.40 (2H, d), 7.29 (2H, d), 4.68 (2H, s), 2.99 (1H, d), 2.23-2.08 (1H, m), 1.36 (9H, s), 0.98 (3H, d), 0.60 (3H, d). GC-MS (method 3): $R_t$ = 6.22 min; m/z = 247 (M − Br)$^+$. |

-continued

| Example | Name/Structure | Analytical data |
|---|---|---|
| 12A | tert-butyl 2-[4-(bromomethyl)phenyl]-4-cyano-3-methylbutanoate | $^1$H-NMR (400 MHz, DMSO-$d_6$, δ/ppm): 7.67-7.26 (4H, m), 4.70 (2H, s), 3.45-3.26 (1H, m), 2.60-2.22 (1H, m), 2.11-1.99 (1H, m), 1.40 and 1.37 (tog. 9H, 2s), 1.15 (2H, d), 0.77 (1H, d). MS (DCI): m/z = 351/353 (M)$^+$, 369/371 (M + NH$_4$)$^+$. |
| 13A | tert-butyl 2-[4-(bromomethyl)phenyl]-3-methylhexanoate | MS (DCI): m/z = 372/374 (M + NH$_4$)$^+$. |
| 14A | tert-butyl 2-[4-(bromomethyl)phenyl]-4-methoxy-3-methylbutanoate | MS (DCI): m/z = 357/359 (M +H)$^+$, 318/320 (M − C$_4$H$_8$ + NH$_4$)$^+$, 301/303 (M − C$_4$H$_8$)$^+$. |

Example 15A

N'-(2-Chloroacetyl)benzenecarbohydrazide

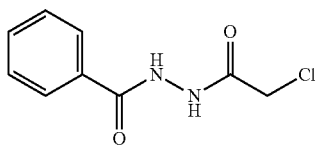 [SMILES: O=C(CCl)NNC(=O)c1ccccc1]

A suspension of 500 g (3.67 mol) of benzenecarbohydrazide in 3.75 liters of THF was heated at reflux, where the benzenecarbohydrazide went into solution. 497.7 g (4.41 mol) of chloroacetyl chloride, dissolved in 125 ml of THF, were added dropwise to this solution, and the solution was stirred under reflux for 30 min. After the reaction had gone to completion (monitored by TLC, mobile phase dichloromethane/methanol 9:1), 22.5 liters of water and 10 liters of ethyl acetate were added to the reaction mixture, and the pH was adjusted to pH 7 using solid sodium bicarbonate. The aqueous phase was extracted once with 2.5 liters of ethyl acetate. The combined organic phases were dried and the solution was then concentrated to dryness under reduced pressure. The white solid obtained was dissolved in a 1:1 mixture of dichloromethane and methanol and applied to 3 kg of silica gel. The product was chromatographed on two portions of silica gel (in each case 8 kg) initially with 50 liters of dichloromethane/ethyl acetate 7:3 and then with 125 liters of dichloromethane/ethyl acetate 1:1 as mobile phase. Concentration of the product fractions gave 424 g (1.99 mol, 54% of theory) of the title compound as a white solid.

$^1$H-NMR (400 MHz, DMSO-$d_6$, δ/ppm): 10.56-10.32 (2H, broad), 7.88 (2H, d), 7.58 (1H, t), 7.50 (2H, t), 4.21 (2H, s).
MS (DCI): m/z=213 (M+H)$^+$, 230 (M+NH$_4$)$^+$.

Example 16A

2-Phenyl-4H-1,3,4-oxadiazin-5(6H)-one

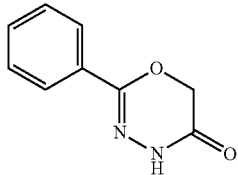 [SMILES: O=C1COC(c2ccccc2)=NN1]

812 g (3.82 mol) of N'-(2-chloroacetyl)benzenecarbohydrazide were dissolved in 13 liters of dry DMF, and 384.95 g (4.58 mol) of sodium bicarbonate were added. The reaction solution was then heated to 100° C. and stirred at this temperature overnight. After the reaction had gone to completion (monitored by TLC, mobile phase dichloromethane/ethyl acetate 9:1), the reaction solution was cooled to room temperature, poured into 65 liters of water and extracted three times with in each case 17.5 liters of ethyl acetate. The combined organic phases were washed with 13.8 liters of saturated aqueous sodium bicarbonate solution, dried and concentrated to dryness under reduced pressure. The solid obtained was dissolved in a 9:1 mixture of dichloromethane and methanol and applied to 17 kg of silica gel. The product was chromatographed on two portions of silica gel (in each case 8 kg) using 260 liters of dichloromethane/ethyl acetate 9:1 as mobile phase. The combined product fractions were concentrated, and the solid obtained was triturated with 3 liters of diethyl ether. Filtration gave 247 g (1.40 mol, 35% of theory) of the title compound as a white solid.

$^1$H-NMR (400 MHz, DMSO-$d_6$, δ/ppm): 11.04 (1H, s), 7.78 (2H, d), 7.53-7.41 (3H, m), 4.79 (2H, s).

MS (DCI): m/z=177 (M+H)$^+$.

The compounds listed in the table below were obtained in an analogous manner:

Example 19A

N'-(Chloroacetyl)-2,2-dimethylpropanehydrazide

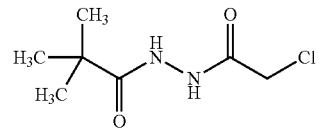

5.8 g (49.929 mmol) of 2,2-dimethylpropanehydrazide were dissolved in 600 ml of dry ethyl acetate and heated to reflux. 6.767 g (59.915 mmol) of chloroacetyl chloride, dissolved in 45 ml of dry ethyl acetate, were added dropwise to the solution. The mixture was stirred under reflux for 30 min. After cooling, the reaction mixture was concentrated on a rotary evaporator and the residue was dried under high vacuum. This gave 10.14 g of the title compound. The crude product was reacted further without further purification.

Example 20A 2-tert-Butyl-4H-1,3,4-oxadiazin-5(6H)-one

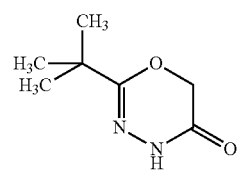

8.34 g (43.29 mmol) of N'-(chloroacetyl)-2,2-dimethylpropanehydrazide were dissolved in 800 ml of dry DMF, and 4.24 g (50.52 mmol) of sodium bicarbonate were added. The

| Example | Name/Structure | Analytical data |
|---|---|---|
| 17A | 2-(2-chlorophenyl)-4H-1,3,4-oxadiazin-5(6H)-one | LC-MS (method 2): $R_t$ = 1.49 min; m/z = 211 (M + H)$^+$. |
| 18A | 2-(2-methoxyphenyl)-4H-1,3,4-oxadiazin-5(6H)-one | LC-MS (method 7): $R_t$ = 1.54 min; m/z = 207 (M + H)$^+$. | reaction mixture was heated at 100° C. overnight. After cooling, the solvent was removed on a rotary evaporator, water was added to the residue and the mixture was acidified with 1 N hydrochloric acid. The mixture was extracted three times with ethyl acetate, and the combined organic phases were washed with water, dried over sodium sulfate and concentrated on a rotary evaporator. This gave 5.05 g of the target compound. The crude product was reacted further without further purification.

GC-MS (method 3): $R_t$=3.81 min; m/z=156 (M)$^+$.

The compounds listed in the table below were obtained in an analogous manner:

| Example | Name/Structure | Analytical data |
| --- | --- | --- |
| 21A | 2-(propan-2-yl)-4H-1,3,4-oxadiazin-5(6H)-one | GC-MS (method 3): $R_t$ = 3.72 min; m/z = 142 (M)$^+$. |
| 22A | 2-(2-methylpropyl)-4H-1,3,4-oxadiazin-5(6H)-one | GC-MS (method 3): $R_t$ = 4.14 min; m/z = 156 (M)$^+$. |

Example 23A

5-Methyl-2-oxohexan-3-yl thiocyanate

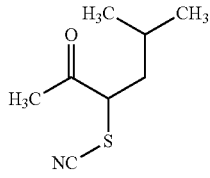

17.91 g (120.5 mmol) of 3-chloro-5-methylhexan-2-one were dissolved in 120 ml of methyl ethyl ketone, 10.0 g (123.4 mmol) of sodium thiocyanate were added and the reaction mixture was heated under reflux for 1 h. After cooling, the reaction mixture was filtered, the residue was washed with methyl ethyl ketone and the combined filtrates were concentrated on a rotary evaporator. The oily residue was taken up in about 400 ml of dichloromethane and washed three times with in each case 100 ml of water. The organic phase was dried over sodium sulfate and the solvent was removed on a rotary evaporator. This gave 20.07 g of the crude product, which was reacted further as such.

LC-MS (method 13): $R_t$=1.99 min; m/z=171 (M)$^+$.

Example 24A

4-Methyl-5-(2-methylpropyl)-1,3-thiazol-2(3H)-one

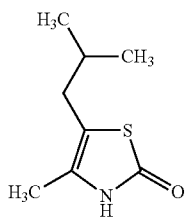

25 ml of 85% strength phosphoric acid were added to 20.07 g (117.26 mmol) of 5-methyl-2-oxohexan-3-yl thiocyanate, and the mixture was heated to 95° C. over a period of 1 h. At a temperature of 95-100° C., the mixture was stirred for another 0.5 h. After cooling, the reaction mixture was added to 40 ml of water and extracted repeatedly with tert-butyl methyl ether. The combined organic phases were washed with water, dried over sodium sulfate and concentrated on a rotary evaporator. This gave 18.11 g of the target compound, which was reacted further without further purification.

GC-MS (method 3): $R_t$=5.80 min; m/z=171 (M)$^+$.

Example 25A tert-Butyl cyclopentyl{4-[(5-oxo-2-phenyl-5,6-dihydro-4H-1,3,4-oxadiazin-4-yl)methyl]phenyl}acetate

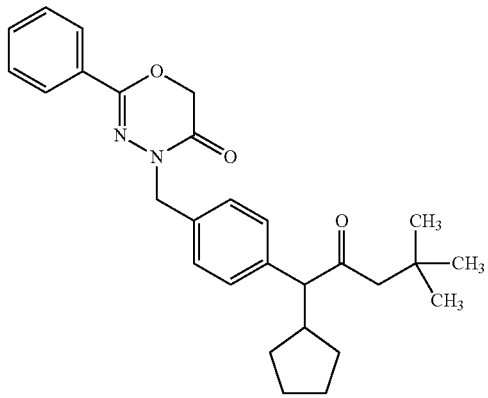 [SMILES: CC(C)(C)CC(=O)C(c1ccc(CN2N=C(c3ccccc3)OCC2=O)cc1)C1CCCC1]

Preparation Method 1:

9.9 g (28.0 mmol) of tert-butyl[4-(bromomethyl)phenyl](cyclopentyl)acetate, 5.92 g (33.6 mmol) of 2-phenyl-4H-1,3,4-oxadiazin-5(6H)-one and 13.70 g (42.03 mmol) of cesium carbonate were stirred in 100 ml of DMF at 60° C. for 12 h. After cooling, the reaction mixture was poured onto ice-water and extracted with diethyl ether. The organic phase was dried over magnesium sulfate and concentrated to dryness under reduced pressure. The crude product was purified chromatographically on silica gel (mobile phase cyclohexane/ethyl acetate 20:1). This gave 6.6 g (14.7 mmol, 52% of theory) of the title compound.

Preparation Method 2:

8.16 g (23.1 mmol) of tert-butyl[4-(bromomethyl)phenyl](cyclopentyl)acetate, 3.7 g (21 mmol) of 2-phenyl-4H-1,3,4-oxadiazin-5(6H)-one and 7.53 g (23.1 mmol) of cesium carbonate were stirred in 147 ml of DMF at room temperature for 12 h. The reaction solution was then stirred with saturated aqueous sodium bicarbonate solution and extracted twice with ethyl acetate. The combined organic phases were dried over magnesium sulfate and concentrated to dryness under reduced pressure. The crude product obtained was purified chromatographically on silica gel (mobile phase cyclohexane/ethyl acetate 5:1). This gave 6.51 g (14.5 mmol, 69% of theory) of the title compound.

$^1$H-NMR (400 MHz, DMSO-$d_6$, δ/ppm): 7.76 (2H, d), 7.55-7.42 (3H, m), 7.31 (4H, s), 4.94 (2H, s), 4.87 (2H, s), 3.19 (1H, d), 2.45-2.31 (1H, m), 1.88-1.74 (1H, m), 1.69-1.46 (3H, m), 1.45-1.15 (3H, m), 1.34 (9H, s), 1.03-0.89 (1H, m).

LC-MS (method 7): $R_t$=3.27 min; m/z=449 (M+H)$^+$.

The compounds listed in the table below were obtained in an analogous manner:

| Example | Name/Structure | Analytical data |
|---|---|---|
| 26A | 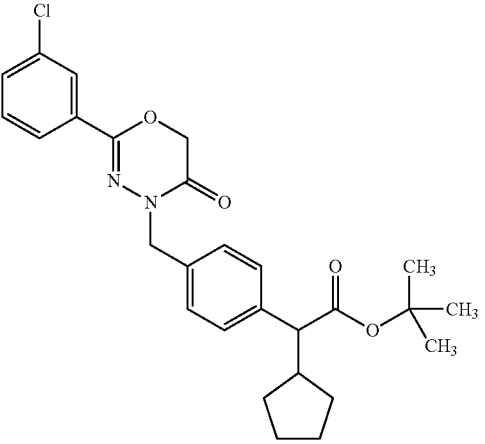<br>tert-butyl (4-{[2-(3-chlorophenyl)-5-oxo-5,6-dihydro-4H-1,3,4-oxadiazin-4-yl]methyl}phenyl)(cyclopentyl)acetate | LC-MS (method 7):<br>$R_t$ = 3.59 min;<br>m/z = 483 (M)$^+$. |
| 27A | 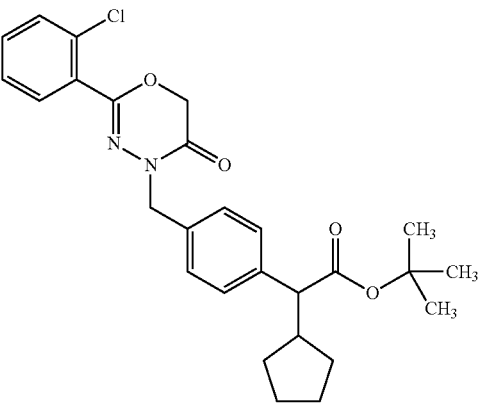<br>tert-butyl (4-{[2-(2-chlorophenyl)-5-oxo-5,6-dihydro-4H-1,3,4-oxadiazin-4-yl]methyl}phenyl)(cyclopentyl)acetate | LC-MS (method 7):<br>$R_t$ = 3.28 min;<br>m/z = 483 (M)$^+$. |

| Example | Name/Structure | Analytical data |
|---|---|---|
| 28A | 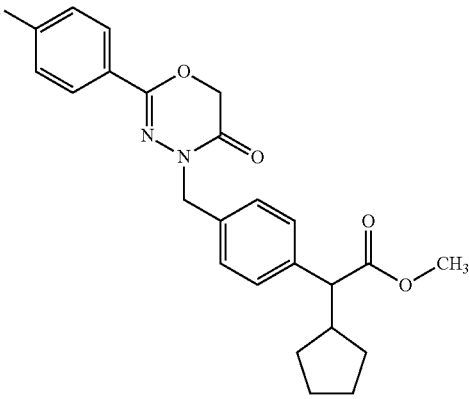  methyl (4-{[2-(4-chlorophenyl)-5-oxo-5,6-dihydro-4H-1,3,4-oxadiazin-4-yl]methyl}phenyl)(cyclopentyl)acetate | LC-MS (method 7): $R_t$ = 3.29 min; m/z = 441 $(M + H)^+$. |
| 29A | 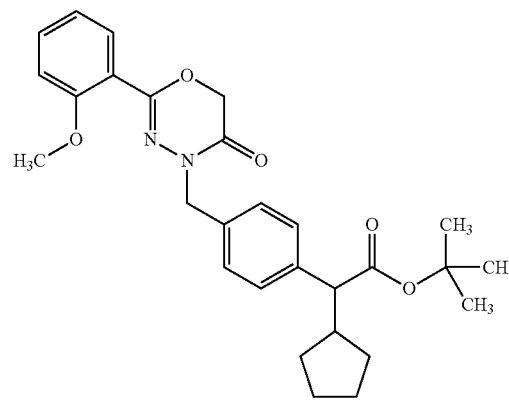  tert-butyl cyclopentyl(4-{[2-(2-methoxyphenyl)-5-oxo-5,6-dihydro-4H-1,3,4-oxadiazin-4-yl]methyl}-phenyl)acetate | LC-MS (method 2): $R_t$ = 3.09 min; m/z = 479 $(M + H)^+$. |
| 30A | 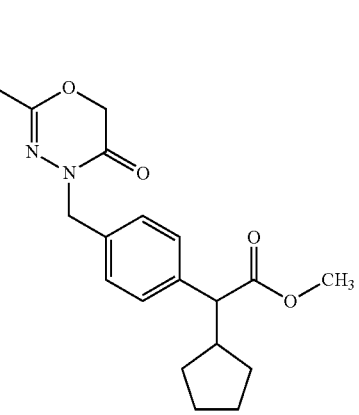  methyl cyclopentyl(4-{[2-(4-fluorophenyl)-5-oxo-5,6-dihydro-4H-1,3,4-oxadiazin-4-yl]methyl}phenyl)acetate | LC-MS (method 7): $R_t$ = 3.16 min; m/z = 425 $(M + H)^+$. |

-continued

| Example | Name/Structure | Analytical data |
|---|---|---|
| 31A | 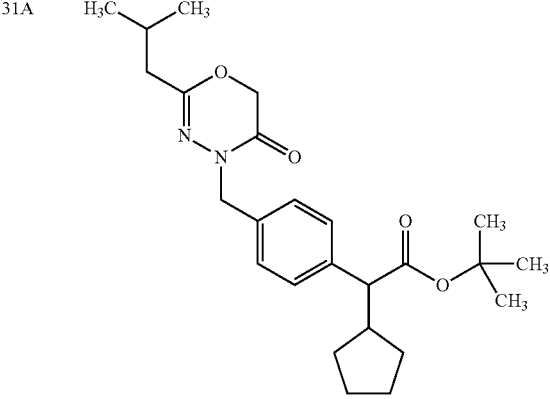<br>tert-butyl cyclopentyl(4-{[2-(2-methylpropyl)-5-oxo-5,6-dihydro-4H-1,3,4-oxadiazin-4-yl]methyl}-phenyl)acetate | LC-MS (method 10):<br>$R_t$ = 2.92 min;<br>m/z = 429<br>$(M + H)^+$. |
| 32A | 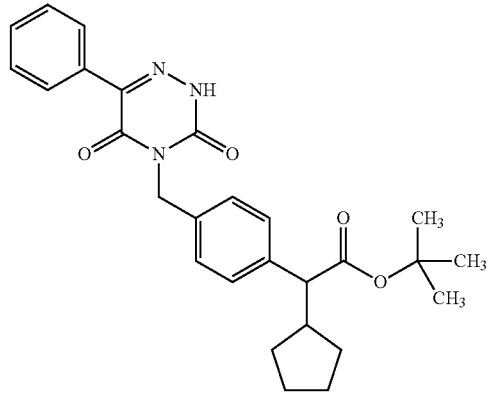<br>tert-butyl cyclopentyl{4-{[3,5-dioxo-6-phenyl-2,5-dihydro-1,2,4-triazin-4(3H)-yl)methyl]phenyl}acetate | LC-MS (method 2):<br>$R_t$ = 3.04 min;<br>m/z = 406<br>$(M - C_4H_8 + H)^+$. |
| 33A | 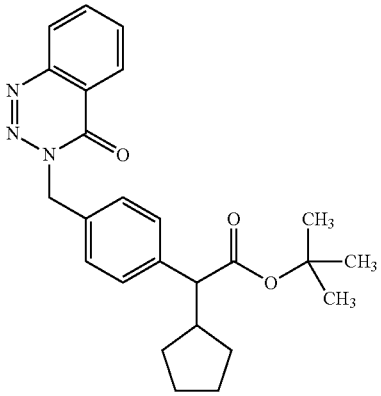<br>tert-butyl cyclopentyl{4-[(4-oxo-1,2,3-benzotriazin-3(4H)-yl)methyl]phenyl}acetate | $^1$H-NMR (400 MHz, DMSO-$d_6$, δ/ppm): 8.29-8.11 (2H, m), 8.10 (1H, t), 7.95 (1H, t), 7.37-7.28 (4H, m), 5.58 (2H, s), 3.19 (1H, d), 2.43-2.26 (1H, m), 1.87-1.74 (1H, m), 1.67-1.45 (3H, m), 1.44-1.30 (1H, m), 1.35 (9H, s), 1.30-1.16 (2H, m), 0.99-0.87 (1H, m).<br>LC-MS (method 10):<br>$R_t$ = 2.73 min; m/z = 420 $(M + H)^+$, 442 $(M + Na)^+$. |

| Example | Name/Structure | Analytical data |
|---|---|---|
| 34A | 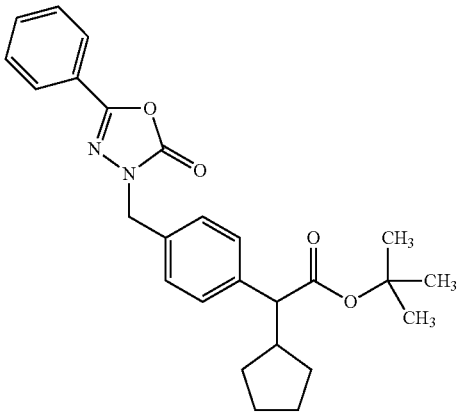<br>tert-butyl cyclopentyl{4-[(2-oxo-5-phenyl-1,3,4-oxadiazol-3(2H)-yl)methyl]phenyl}acetate | LC-MS (method 7):<br>$R_t$ = 3.27 min;<br>m/z = 452<br>$(M + NH_4)^+$. |
| 35A | 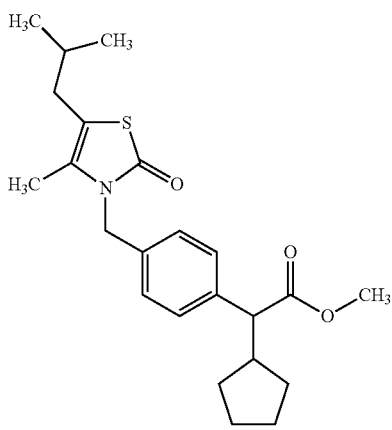<br>methyl cyclopentyl(4-{[4-methyl-5-(2-methylpropyl)-2-oxo-1,3-thiazol-3(2H)-yl]methyl}phenyl)acetate | LC-MS (method 13):<br>$R_t$ = 2.99 min;<br>m/z = 402<br>$(M + H)^+$. |
| 36A | 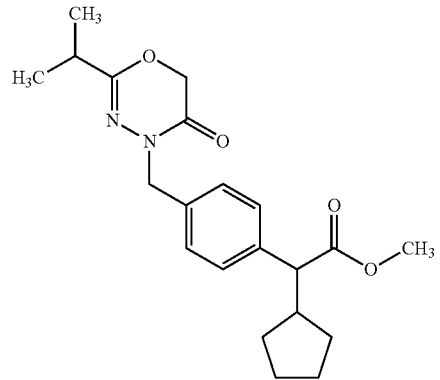<br>methyl cyclopentyl(4-{[5-oxo-2-(propan-2-yl)-5,6-dihydro-4H-1,3,4-oxadiazin-4-yl]methyl}phenyl)-acetate | LC-MS (method 7):<br>$R_t$ = 2.86 min;<br>m/z = 373<br>$(M + H)^+$. |

-continued

| Example | Name/Structure | Analytical data |
|---|---|---|
| 37A | 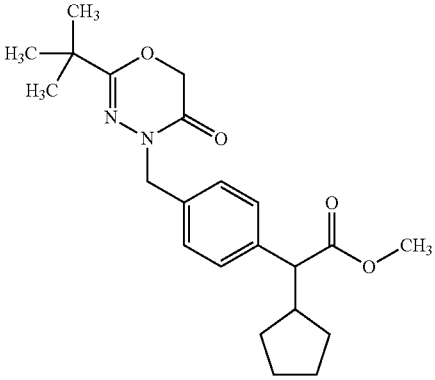<br>methyl {4-[(2-tert-butyl-5-oxo-5,6-dihydro-4H-1,3,4-oxadiazin-4-yl)methyl]phenyl}-(cyclopentyl)acetate | LC-MS (method 7):<br>$R_t$ = 3.02 min;<br>m/z = 387<br>$(M + H)^+$. |
| 38A | 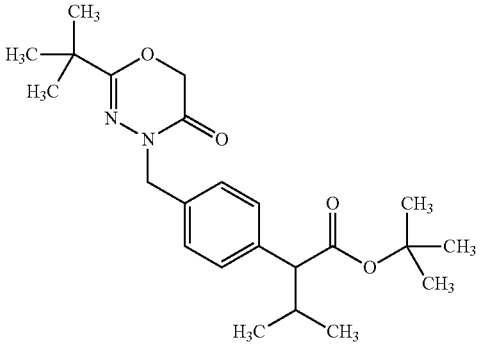<br>tert-butyl 2-{4-[(2-tert-butyl-5-oxo-5,6-dihydro-4H-1,3,4-oxadiazin-4-yl)methyl]phenyl}-3-methylbutanoate | LC-MS (method 11):<br>$R_t$ = 1.69 min;<br>m/z = 403<br>$(M + H)^+$. |
| 39A | 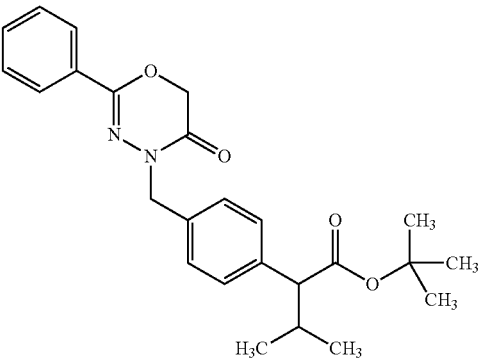<br>tert-butyl 3-methyl-2-{4-[(5-oxo-2-phenyl-5,6-dihydro-4H-1,3,4-oxadiazin-4-yl)methyl]phenyl}butanoate | LC-MS (method 10):<br>$R_t$ = 2.76 min;<br>m/z = 423<br>$(M + H)^+$. |

| Example | Name/Structure | Analytical data |
|---|---|---|
| 40A | 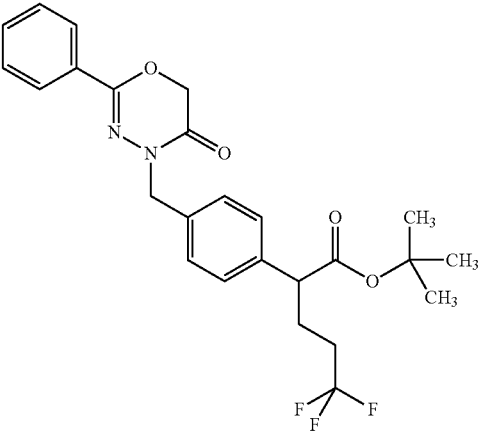<br>tert-butyl 5,5,5-trifluoro-2-{4-[(5-oxo-2-phenyl-5,6-dihydro-4H-1,3,4-oxadiazin-4-yl)methyl]phenyl}-pentanoate | LC-MS (method 10):<br>$R_t$ = 2.69 min;<br>m/z = 477<br>$(M + H)^+$. |
| 41A | 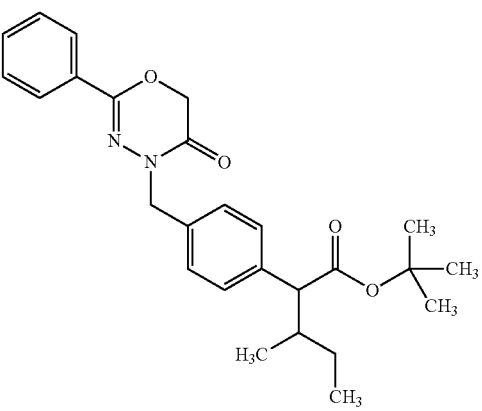<br>tert-butyl 3-methyl-2-{4-[(5-oxo-2-phenyl-5,6-dihydro-4H-1,3,4-oxadiazin-4-yl)methyl]phenyl}pentanoate | LC-MS (method 7):<br>$R_t$ = 3.24 min;<br>m/z = 437<br>$(M + H)^+$. |
| 42A | 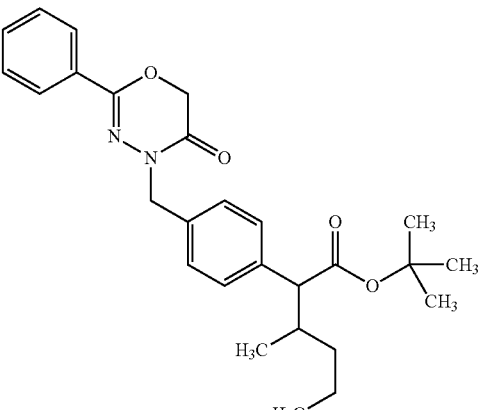<br>tert-butyl 3-methyl-2-{4-[(5-oxo-2-phenyl-5,6-dihydro-4H-1,3,4-oxadiazin-4-yl)methyl]phenyl}hexanoate | LC-MS (method 11):<br>$R_t$ = 1.76 min;<br>m/z = 473<br>$(M + Na)^+$. |

-continued

| Example | Name/Structure | Analytical data |
|---|---|---|
| 43A | 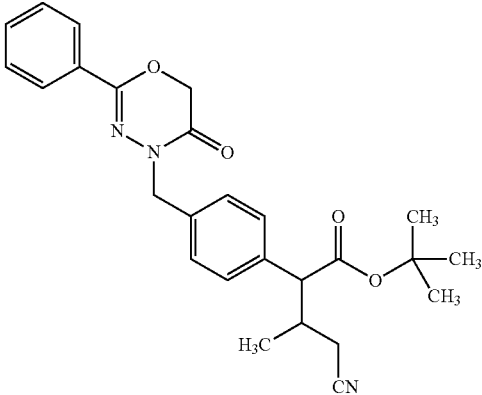  tert-butyl 4-cyano-3-methyl-2-{4-[(5-oxo-2-phenyl-5,6-dihydro-4H-1,3,4-oxadiazin-4-yl)methyl]phenyl}butanoate | LC-MS (method 11): $R_t$ = 1.46 min; m/z = 448 (M + H)+. |
| 44A | 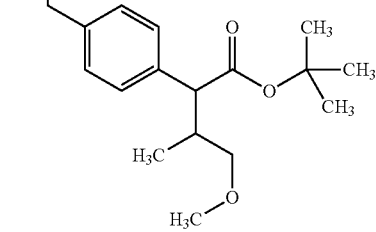  tert-butyl 4-methoxy-3-methyl-2-{4-[(5-oxo-2-phenyl-5,6-dihydro-4H-1,3,4-oxadiazin-4-yl)methyl]phenyl}butanoate | LC-MS (method 10): $R_t$ = 2.62 min; m/z = 475 (M + Na)+. |

Example 45A tert-Butyl(4-{[4-(4-chlorophenyl)-1-oxophthalazin-2(1H)-yl]methyl}phenyl)(cyclopentyl)acetate

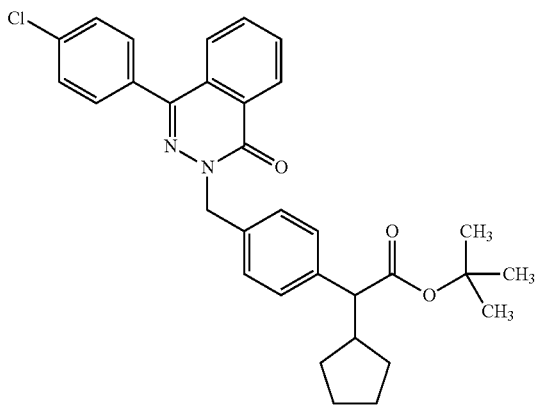 [SMILES: CC(C)(C)OC(=O)C(c1ccc(Cn2nc(-c3ccc(Cl)cc3)c3ccccc3c2=O)cc1)C1CCCC1]

At 0° C., 54 mg (2.14 mmol) of sodium hydride were added a little at a time to a solution of 500 mg (1.95 mmol) of 4-(4-chlorophenyl)phthalazin-1(2H)-one [CAS Reg. No. 51334-86-2] in 7.6 ml of THF. After the evolution of gas had ended, 688 mg (1.95 mmol) of tert-butyl[4-(bromomethyl)phenyl](cyclopentyl)acetate, dissolved in 4.5 ml of DMF, were slowly added dropwise at 0° C., and the reaction solution was then stirred at room temperature overnight. Water was then added carefully to the reaction mixture. The reaction mixture was extracted three times with ethyl acetate, and the combined organic phases were washed with saturated sodium chloride solution and dried over sodium sulfate. After filtration, the solvent was removed to dryness under reduced pressure. The crude product obtained was purified by flash chromatography on silica gel (mobile phase: initially cyclohexane/ethyl acetate 3:1, then ethyl acetate). This gave 630 mg (93% pure, 1.11 mmol, 57% of theory) of a colorless solid.

$^1$H-NMR (400 MHz, DMSO-$d_6$, δ/ppm): 8.43-8.35 (1H, m), 7.98-7.88 (2H, m), 7.74-7.68 (1H, m), 7.57-7.49 (4H, m), 7.37-7.25 (4H, m), 5.37 (2H, s), 3.18 (1H, d), 2.42-2.29 (1H, m), 1.86-1.72 (1H, m), 1.68-1.45 (3H, m), 1.44-1.30 (1H, m), 1.38 (9H, s), 1.29-1.15 (2H, m), 1.00-0.86 (1H, m).

LC-MS (method 2): $R_t$=3.45 min; m/z=529 (M+H)+.

The compounds listed in the table below were obtained in an analogous manner:

| Example | Name/Structure | Analytical data |
|---|---|---|
| 46A | 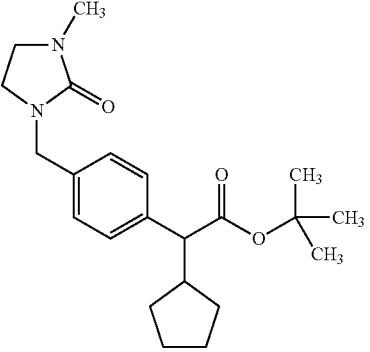<br>tert-butyl cyclopentyl{4-[(3-methyl-2-oxo-imidazolidin-1-yl)methyl]phenyl}acetate | $^1$H-NMR (400 MHz, DMSO-$d_6$, δ/ppm): 7.28 (2H, d), 7.16 (2H, d), 4.23 (2H, s), 3.24 (2H, t), 3.17 (1H, d), 3.12 (2H, t), 2.44-2.30 (1H, m), 1.87-1.74 (1H, m), 1.67-1.45 (3H, m), 1.44-1.31 (1H, m), 1.35 (9H, s), 1.30-1.17 (2H, m), 1.01-0.90 (1H, m).<br>MS (DCI): m/z = 373 (M + H)$^+$. |
| 47A | 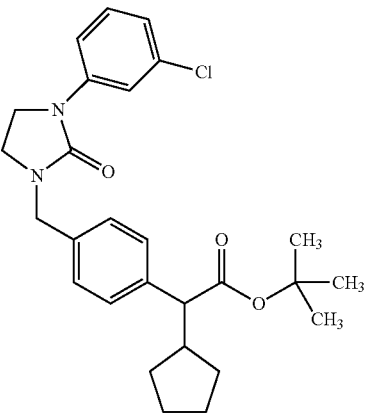<br>tert-butyl (4-{[3-(3-chlorophenyl)-2-oxo-imidazolidin-1-yl]methyl}phenyl)(cyclopentyl)acetate | $^1$H-NMR (400 MHz, DMSO-$d_6$, δ/ppm): 7.81 (1H, t), 7.44 (1H, d), 7.35 (1H, d), 7.31 (2H, d), 7.24 (2H, d), 7.05 (1H, d), 4.37 (2H, s), 3.83 (2H, t), 3.37 (2H, t), 3.19 (1H, d), 2.45-2.31 (1H, m), 1.88-1.76 (1H, m), 1.69-1.46 (3H, m), 1.45-1.32 (1H, m), 1.36 (9H, s), 1.31-1.17 (2H, m), 1.01-0.90 (1H, m).<br>LC-MS (method 11): $R_t$ = 1.75 min; m/z = 413 (M − $C_4H_8$)$^+$. |
| 48A | 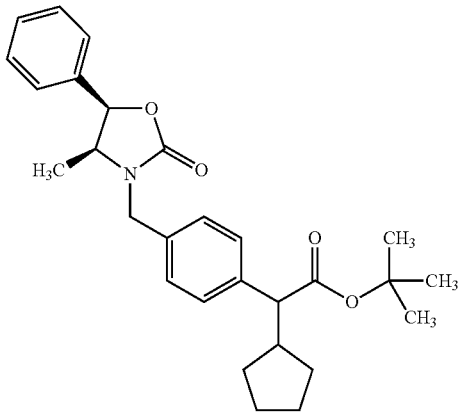<br>tert-butyl cyclopentyl(4-{[(4-{[(4S,5R)-4-methyl-2-oxo-5-phenyl-1,3-oxazolidin-3-yl]methyl}phenyl)acetate | LC-MS (method 2):<br>$R_t$ = 3.14 min;<br>m/z = 899 (2M + H)$^+$. |

| Example | Name/Structure | Analytical data |
|---|---|---|
| 49A | 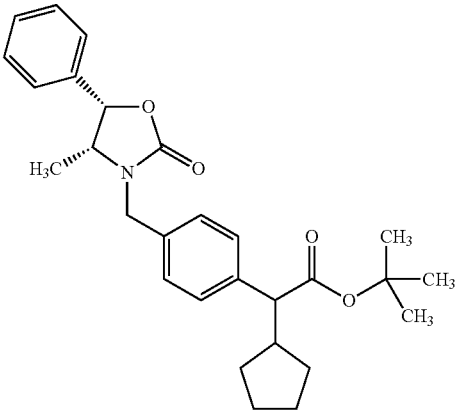

tert-butyl cyclopentyl(4-{[(4R,5S)-4-methyl-2-oxo-5-phenyl-1,3-oxazolidin-3-yl]methyl}phenyl)acetate | LC-MS (method 2):<br>$R_t$ = 3.14 min;<br>m/z = 899<br>$(2M + H)^+$. |
| 50A | 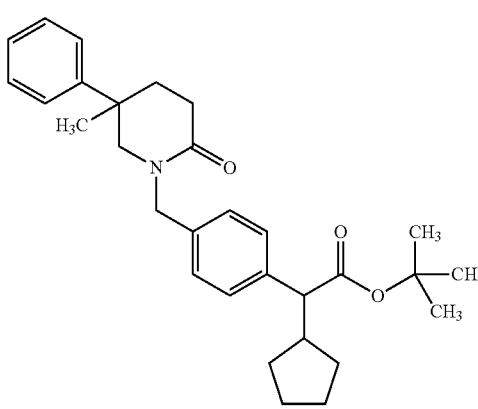

tert-butyl cyclopentyl{4-[(5-methyl-2-oxo-5-phenylpiperidin-1-yl)methyl]phenyl}acetate | LC-MS (method 7):<br>$R_t$ = 3.35 min;<br>m/z = 923<br>$(2M + H)^+$. |

Example 51A rac-Cyclopentyl{4-[(5-oxo-2-phenyl-5,6-dihydro-4H-1,3,4-oxadiazin-4-yl)methyl]phenyl}-acetic acid

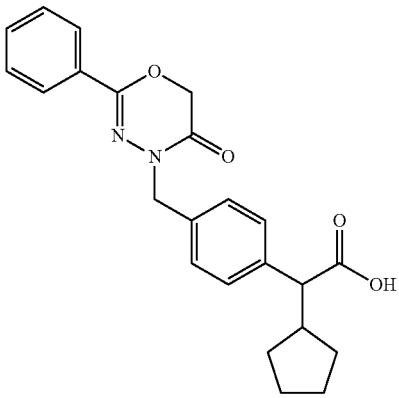 [SMILES: O=C(O)C(c1ccc(CN2N=C(c3ccccc3)OCC2=O)cc1)C1CCCC1]

At room temperature, 22.67 ml (294.3 mmol) of trifluoroacetic acid were added slowly to a solution of 6.6 g (14.7 mmol) of tert-butyl cyclopentyl{4-[(5-oxo-2-phenyl-5,6-dihydro-4H-1,3,4-oxadiazin-4-yl)methyl]phenyl}acetate in 90 ml of dichloromethane, and the mixture was stirred overnight. The solvent was then removed under reduced pressure, and the residue was taken up in 100 ml of ethyl acetate and extracted with 50 ml of water. The organic phase was dried over magnesium sulfate. After filtration, the solvent was removed under reduced pressure. This gave 4.8 g (12.23 mmol, 83% of theory) of a colorless solid.

$^1$H-NMR (400 MHz, DMSO-$d_6$, δ/ppm): 12.35-12.15 (1H, broad s), 7.78 (2H, d), 7.54-7.40 (3H, m), 7.29 (4H, s), 4.91 (2H, s), 4.83 (2H, s), 3.22 (1H, d), 2.48-2.35 (1H, m), 1.89-1.76 (1H, m), 1.68-1.46 (3H, m), 1.45-1.32 (1H, m), 1.32-1.14 (2H, m), 1.01-0.89 (1H, m).

LC-MS (method 7): $R_t$=2.75 min; m/z=393 $(M+H)^+$.

The compounds listed in the table below were obtained in an analogous manner:

| Example | Name/Structure | Analytical data |
|---|---|---|
| 52A | 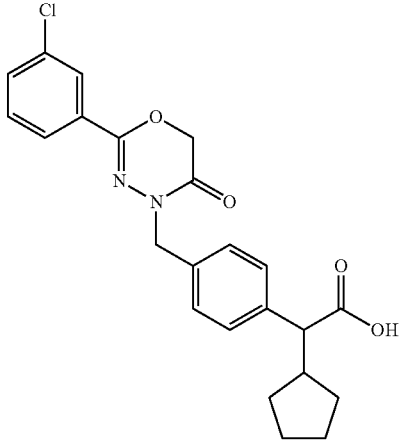<br>(4-{[2-(3-chlorophenyl)-5-oxo-5,6-dihydro-4H-1,3,4-oxadiazin-4-yl]methyl}phenyl)(cyclopentyl)acetic acid | LC-MS (method 7):<br>$R_t$ = 2.78 min;<br>m/z = 427<br>$(M + H)^+$. |
| 53A | 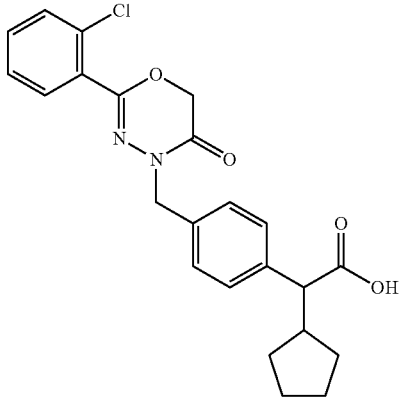<br>(4-{[2-(2-chlorophenyl)-5-oxo-5,6-dihydro-4H-1,3,4-oxadiazin-4-yl]methyl}phenyl)(cyclopentyl)acetic acid | LC-MS (method 7):<br>$R_t$ = 2.74 min;<br>m/z = 427<br>$(M + H)^+$. |
| 54A | 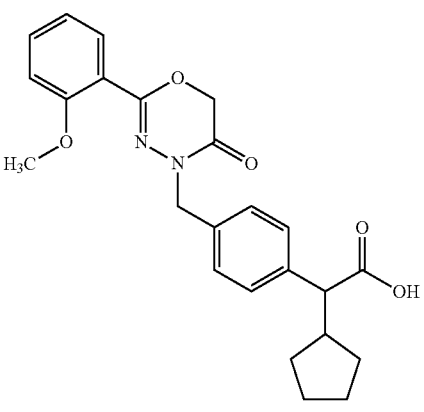<br>cyclopentyl(4-{[2-(2-methoxyphenyl)-5-oxo-5,6-dihydro-4H-1,3,4-oxadiazin-4-yl]methyl}phenyl)-acetic acid | LC-MS (method 7):<br>$R_t$ = 2.66 min;<br>m/z = 423<br>$(M + H)^+$. |

-continued

| Example | Name/Structure | Analytical data |
|---|---|---|
| 55A | 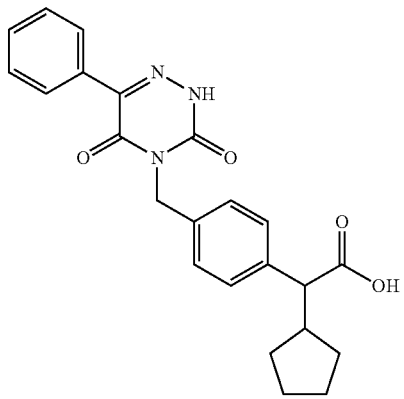<br>cyclopentyl{4-[(3,5-dioxo-6-phenyl-2,5-dihydro-1,2,4-triazin-4(3H)-yl)methyl]phenyl}acetic acid | LC-MS (method 2):<br>Rt = 2.28 min;<br>m/z = 811<br>$(2M + H)^+$. |
| 56A | 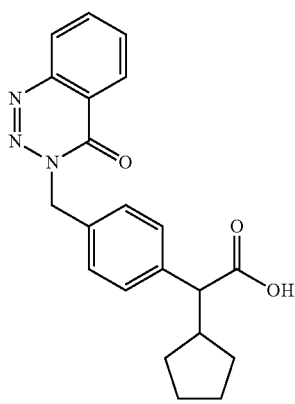<br>cyclopentyl{4-[(4-oxo-1,2,3-benzotriazin-3(4H)-yl)methyl]phenyl}acetic acid | $^1$H-NMR (400 MHz, DMSO-$d_6$, δ/ppm): 12.6-11.8 (1H, broad s), 8.28-8.21 (2H, m), 8.10 (1H, t), 7.94 (1H, t), 7.36-7.28 (4H, m), 5.57 (2H, s), 3.21 (1H, d), 2.48-2.35 (1H, m), 1.87-1.77 (1H, m), 1.66-1.45 (3H, m), 1.45-1.33 (1H, m), 1.31-1.16 (2H, m), 0.98-0.86 (1H, m).<br>LC-MS (method 7):<br>$R_t$ = 2.45 min;<br>m/z = 364<br>$(M + H)^+$. |
| 57A | 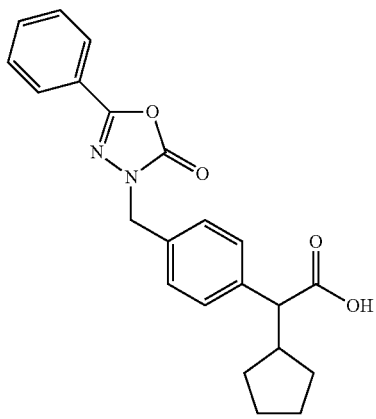<br>cyclopentyl{4-[(2-oxo-5-phenyl-1,3,4-oxadiazol-3(2H)-yl)methyl]phenyl}acetic acid | $^1$H-NMR (400 MHz, DMSO-$d_6$, δ/ppm): 12.6-11.9 (1H, broad s), 7.78 (2H, d), 7.62-7.48 (3H, m), 7.39-7.25 (4H, m), 4.95 (2H, s), 3.24 (1H, d), 2.48-2.36 (1H, m), 1.90-1.76 (1H, m), 1.67-1.47 (3H, m), 1.47-1.35 (1H, m), 1.33-1.17 (2H, m), 1.02-0.88 (1H, m).<br>LC-MS (method 7):<br>$R_t$ = 2.64 min;<br>m/z = 379<br>$(M + H)^+$. |

| Example | Name/Structure | Analytical data |
|---|---|---|
| 58A | 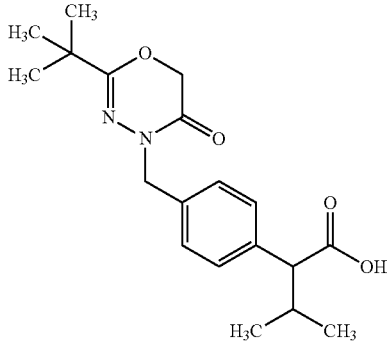

2-{4-[(2-tert-butyl-5-oxo-5,6-dihydro-4H-1,3,4-oxadiazin-4-yl)methyl]phenyl}-3-methylbutanoic acid | LC-MS (method 7): $R_t$ = 2.53 min; m/z = 347 $(M + H)^+$. |
| 59A | 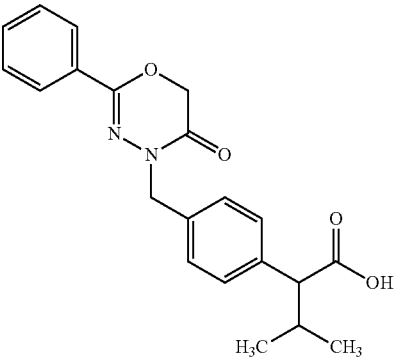

3-methyl-2-{4-[(5-oxo-2-phenyl-5,6-dihydro-4H-1,3,4-oxadiazin-4-yl)methyl]phenyl}butanoic acid | $^1$H-NMR (400 MHz, DMSO-$d_6$, δ/ppm): 12.28 (1H, s), 7.76 (2H, d), 7.54-7.40 (3H, m), 7.38-7.24 (4H, m), 4.91 (2H, s), 4.86 (2H, s), 3.09 (1H, d), 2.26-2.11 (1H, m), 0.98 (3H, d), 0.61 (3H, d). LC-MS (method 7): $R_t$ = 2.60 min; m/z = 367 $(M + H)^+$. |
| 60A | 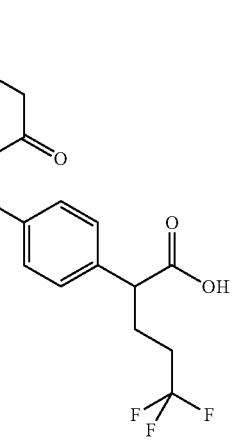

5,5,5-trifluoro-2-{4-[(5-oxo-2-phenyl-5,6-dihydro-4H-1,3,4-oxadiazin-4-yl)methyl]phenyl}pentanoic acid | $^1$H-NMR (400 MHz, DMSO-$d_6$, δ/ppm): 13.0-12.0 (1H, broad s), 7.77 (2H, d), 7.55-7.41 (3H, m), 7.35 (2H, d), 7.26 (2H, d), 4.92 (2H, s), 4.87 (2H, s), 3.67-3.53 (1H, m), 2.31-1.95 (3H, m), 1.89-1.74 (1H, m). LC-MS (method 7): Rt = 2.47 min; m/z = 421 $(M + H)^+$. |

-continued

| Example | Name/Structure | Analytical data |
|---|---|---|
| 61A | 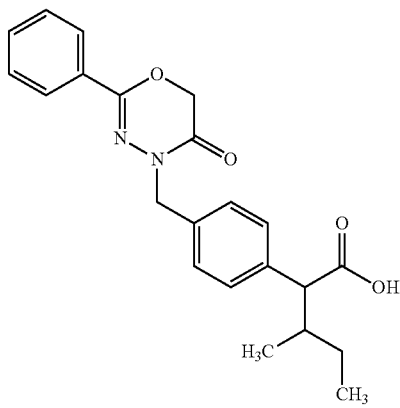<br>3-methyl-2-{4-[(5-oxo-2-phenyl-5,6-dihydro-4H-1,3,4-oxadiazin-4-yl)methyl]phenyl}pentanoic acid | LC-MS (method 10):<br>$R_t$ = 2.15 min;<br>m/z = 381<br>$(M + H)^+$. |
| 62A | 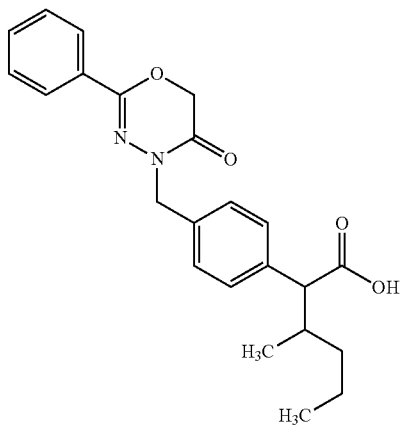<br>3-methyl-2-{4-[(5-oxo-2-phenyl-5,6-dihydro-4H-1,3,4-oxadiazin-4-yl)methyl]phenyl}hexanoic acid | LC-MS (method 12):<br>$R_t$ = 2.52 min;<br>m/z = 395<br>$(M + H)^+$. |
| 63A | 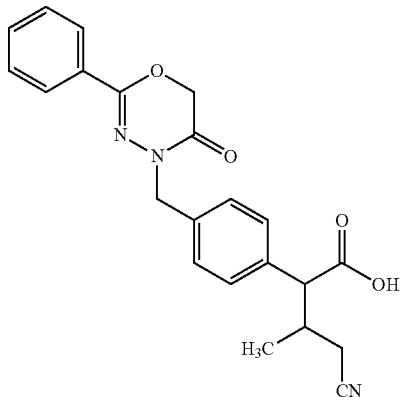<br>4-cyano-3-methyl-2-{4-[(5-oxo-2-phenyl-5,6-dihydro-4H-1,3,4-oxadiazin-4-yl)methyl]phenyl}butanoic acid | LC-MS (method 11):<br>$R_t$ = 1.13 min;<br>m/z = 392<br>$(M + H)^+$. |

-continued

| Example | Name/Structure | Analytical data |
|---|---|---|
| 64A | 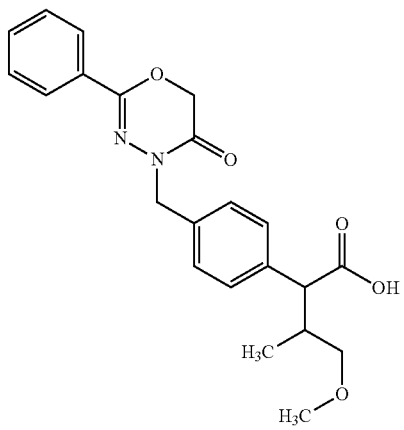<br>4-methoxy-3-methyl-2-{4-[(5-oxo-2-phenyl-5,6-dihydro-4H-1,3,4-oxadiazin-4-yl)methyl]phenyl}-butanoic acid | LC-MS (method 7): $R_t$ = 2.26 min; m/z = 397 $(M + H)^+$. |
| 65A | 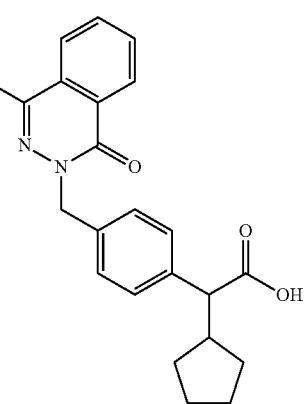<br>(4-{[4-(4-chlorophenyl)-1-oxophthalazin-2(1H)-yl]methyl}phenyl)(cyclopentyl)acetic acid | LC-MS (method 2): $R_t$ = 2.89 min; m/z = 473 $(M + H)^+$. |
| 66A | 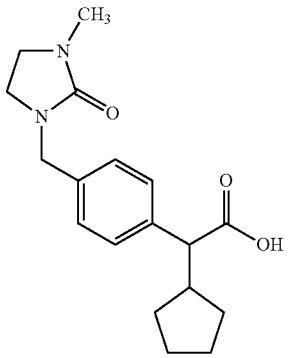<br>cyclopentyl{4-[(3-methyl-2-oxoimidazolidin-1-yl)methyl]phenyl}acetic acid | $^1$H-NMR (400 MHz, DMSO-$d_6$, δ/ppm): 12.23 (1H, s), 7.28 (2H, d), 7.18 (2H, d), 4.22 (2H, s), 3.28-3.17 (3H, m), 3.11 (2H, t), 2.47-2.35 (1H, m), 1.89-1.77 (1H, m), 1.69-1.48 (3H, m), 1.48-1.34 (1H, m), 1.33-1.15 (2H, m), 1.00-0.88 (1H, m).<br>MS (DC1): m/z = 317 $(M + H)^+$. |

| Example | Name/Structure | Analytical data |
|---|---|---|
| 67A | 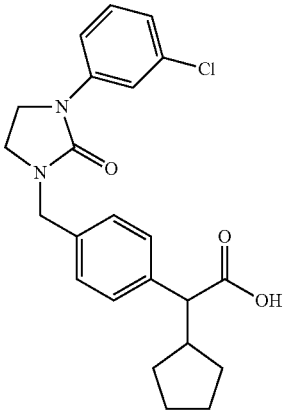<br>(4-{[3-(3-chlorophenyl)-2-oxoimidazolidin-1-yl]-methyl}phenyl)(cyclopentyl) acetic acid | $^1$H-NMR (400 MHz, DMSO-d$_6$, δ/ppm): 12.5-11.9 (1H, broad s), 7.81 (1H, s), 7.44 (1H, d), 7.38-7.28 (3H, m), 7.25 (2H, d), 7.04 (1H, d), 4.37 (2H, s), 3.81 (2H, t), 3.37 (2H, t), 3.22 (1H, d), 2.48-2.37 (1H, m), 1.89-1.76 (1H, m), 1.68-1.47 (3H, m), 1.47-1.34 (1H, m), 1.33-1.15 (2H, m), 1.01-0.88 (1H, m). LC-MS (method 7): R$_t$ = 2.72 min; m/z = 429/431 (M + NH$_4$)$^+$. |
| 68A | 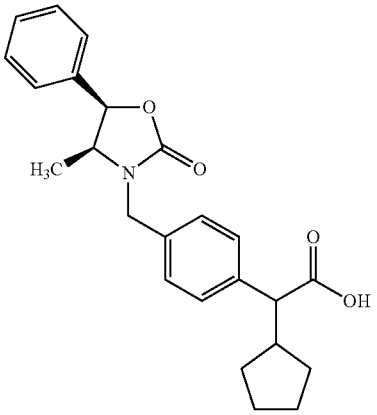<br>cyclopentyl(4-{[(4S,5R)-4-methyl-2-oxo-5-phenyl-1,3-oxazolidin-3-yl]methyl}phenyl) acetic acid | LC-MS (method 2): R$_t$ = 2.38 min; m/z = 787 (2M + H)$^+$. |
| 69A | 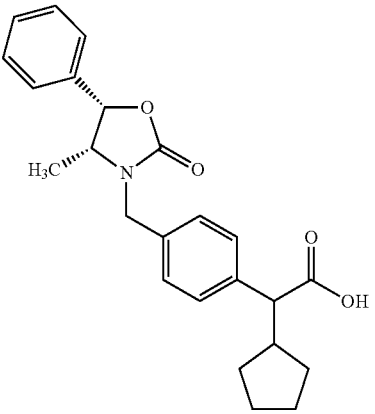<br>cyclopentyl(4-{[(4R,5S)-4-methyl-2-oxo-5-phenyl-1,3-oxazolidin-3-yl]methyl}phenyl) acetic acid | LC-MS (method 2): R$_t$ = 2.38 min; m/z = 787 (2M + H)$^+$. |

| Example | Name/Structure | Analytical data |
|---|---|---|
| 70A | 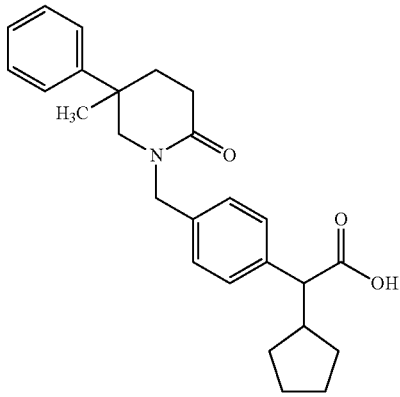<br>cyclopentyl{4-[(5-methyl-2-oxo-5-phenylpiperidin-1-yl)methyl]phenyl} acetic acid | LC-MS (method 7):<br>$R_t$ = 2.66 min;<br>m/z = 406<br>$(M + H)^+$. |

Example 71A

Cyclopentyl(4-{[4-methyl-5-(2-methylpropyl)-2-oxo-1,3-thiazol-3(2H)-yl]methyl}phenyl)-acetic acid

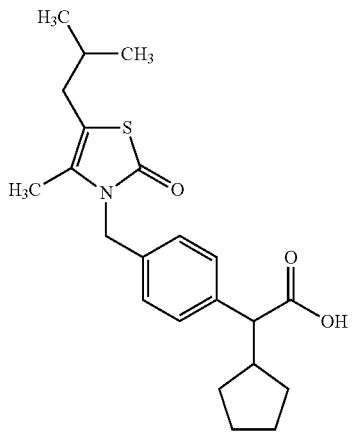 [SMILES: Cc1c(CC(C)C)sc(=O)n1Cc1ccc(C(C(=O)O)C2CCCC2)cc1]

1.01 g (2.515 mmol) of methyl cyclopentyl(4-{[4-methyl-5-(2-methylpropyl)-2-oxo-1,3-thiazol-3(2H)-yl]methyl}phenyl)acetate were dissolved in 30 ml of THF, and 10 ml of methanol and 10 ml of 1 N aqueous sodium hydroxide solution were added. The reaction solution was stirred at room temperature for 2 days. A further 5 ml of 1 N aqueous sodium hydroxide solution were then added, and the mixture was stirred at RT for another 2 days. 20 ml of 1 N hydrochloric acid were then added, and the reaction mixture was extracted three times with ethyl acetate. The combined organic phases were dried over sodium sulfate and the solvent was removed on a rotary evaporator. This gave 956 mg (2.47 mmol, 98% of theory) of the target compound.

LC-MS (method 7): $R_t$=2.95 min; m/z=775.4 $(2M+H)^+$.

Example 72A (4-{[2-(4-Chlorophenyl)-5-oxo-5,6-dihydro-4H-1,3,4-oxadiazin-4-yl]methyl}phenyl)(cyclopentyl)acetic acid

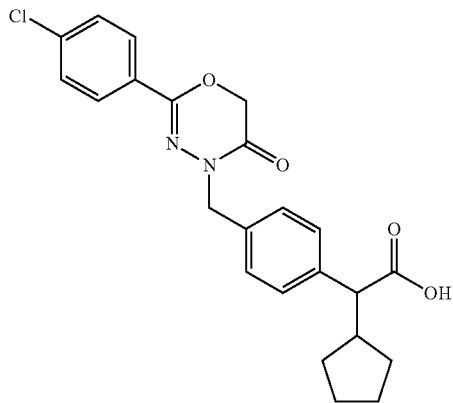 [SMILES: O=C(O)C(c1ccc(CN2N=C(c3ccc(Cl)cc3)OCC2=O)cc1)C1CCCC1]

86 mg (2.04 mmol) of lithium hydroxide monohydrate were added to a solution of 450 mg (1.02 mmol) of methyl (4-{[2-(4-chlorophenyl)-5-oxo-5,6-dihydro-4H-1,3,4-oxadiazin-4-yl]methyl}phenyl)(cyclopentyl)acetate in 10 ml of dioxane and 10 ml of water, and the mixture was stirred at 80° C. for 12 h. After removal of the dioxane under reduced pressure, the aqueous phase was adjusted to pH 2 using 1 M hydrochloric acid, which resulted in the flocculation of the product. The solution was filtered and the filter residue was dried under reduced pressure. This gave 373 mg (0.87 mmol, 86% of theory) of the title compound as a white solid.

LC-MS (method 13): $R_t$=2.67 min; m/z=427 $(M+H)^+$.

The compounds listed in the table below were obtained in a manner analogous to Examples 71A and 72A:

| Example | Name/Structure | Analytical data |
| --- | --- | --- |
| 73A | cyclopentyl(4-{[5-oxo-2-(propan-2-yl)-5,6-dihydro-4H-1,3,4-oxadiazin-4-yl]methyl}phenyl)acetic acid | LC-MS (method 7): $R_t$ = 2.52 min; m/z = 359 (M + H)$^+$. |
| 74A | {4-[(2-tert-butyl-5-oxo-5,6-dihydro-4H-1,3,4-oxadiazin-4-yl)methyl]phenyl}(cyclopentyl)acetic acid | LC-MS (method 7): $R_t$ = 2.70 min; m/z = 373 (M + H)$^+$. |
| 75A | cyclopentyl(4-{[2-(4-fluorophenyl)-5-oxo-5,6-dihydro-4H-1,3,4-oxadiazin-4-yl]methyl}phenyl)acetic acid | LC-MS (method 13): $R_t$ = 2.53 min; m/z = 411 (M + H)$^+$. |

Example 76A and Example 77A ent-Cyclopentyl{4-[(5-oxo-2-phenyl-5,6-dihydro-4H-1,3,4-oxadiazin-4-yl)methyl]phenyl}-acetic acid (enantiomers 1 and 2)

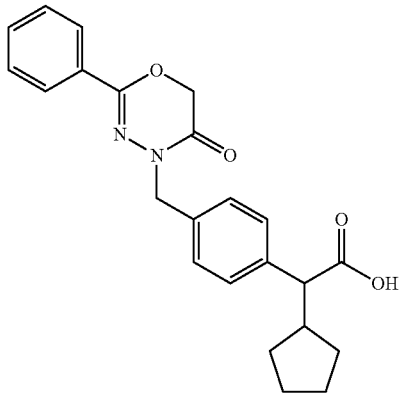 [SMILES: O=C(O)C(c1ccc(CN2N=C(c3ccccc3)OCC2=O)cc1)C1CCCC1]

75 g (191.1 mmol) of racemic cyclopentyl{4-[(5-oxo-2-phenyl-5,6-dihydro-4H-1,3,4-oxadiazin-4-yl)methyl]phenyl}acetic acid (Example 51A) were separated into the enantiomers by preparative HPLC on a chiral phase [column: chiral silica gel phase based on the selector poly(N-methacryloyl-L-isoleucine-3-pentylamide), 430 mm×40 mm; mobile phase: isohexane/ethyl acetate 1:1 (v/v); flow rate: 50 ml/min; temperature: 24° C.; UV detection: 270 nm]:

Example 76A

Enantiomer 1

Yield: 35 g

LC-MS (method 7): $R_t$=2.75 min; m/z=393 (M+H)$^+$ $R_t$ 5.73 min; purity >99%; >99% ee

[column: chiral silica gel phase based on the selector poly(N-methacryloyl-L-isoleucine-3-pentylamide), 250 mm×4.6 mm; mobile phase: isohexane/ethyl acetate 1:1 (v/v); flow rate: 2 ml/min; temperature: 24° C.; UV detection: 270 nm].

Example 77A

Enantiomer 2

Yield: 32 g $^1$H-NMR (400 MHz, DMSO-d$_6$, δ/ppm): 12.35-12.15 (1H, broad s), 7.78 (2H, d), 7.54-7.40 (3H, m), 7.29 (4H, s), 4.91 (2H, s), 4.83 (2H, s), 3.22 (1H, d), 2.48-2.35 (1H, m), 1.89-1.76 (1H, m), 1.68-1.46 (3H, m), 1.45-1.32 (1H, m), 1.32-1.14 (2H, m), 1.01-0.89 (1H, m).

LC-MS (method 7): $R_t$=2.75 min; m/z=393 (M+H)$^+$ $R_t$ 6.86 min; purity >99%; >99% ee

[column: chiral silica gel phase based on the selector poly(N-methacryloyl-L-isoleucine-3-pentylamide), 250 mm×4.6 mm; mobile phase: isohexane/ethyl acetate 1:1 (v/v); flow rate: 2 ml/min; temperature: 24° C.; UV detection: 270 nm].

Example 78A and Example 79A ent-3-Methyl-2-{4-[(5-oxo-2-phenyl-5,6-dihydro-4H-1,3,4-oxadiazin-4-yl)methyl]phenyl}-butanoic acid (enantiomers 1 and 2)

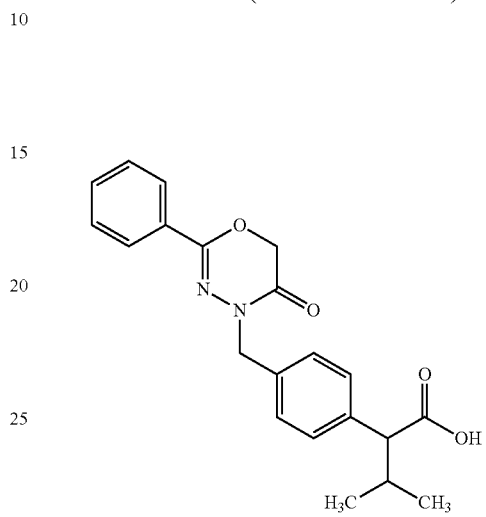

3 g (8.19 mmol) of racemic 3-methyl-2-{4-[(5-oxo-2-phenyl-5,6-dihydro-4H-1,3,4-oxadiazin-4-yl)methyl]phenyl}butanoic acid (Example 59A) were separated into the enantiomers by preparative HPLC on a chiral phase [column: Daicel Chiralpak AD-H, 5 μm, 250 mm×20 mm; mobile phase: isohexane/(isopropanol+0.2% trifluoroacetic acid+1% water) 50:50 (v/v); flow rate: 15 ml/min; temperature: 40° C.; UV detection: 220 nm]:

Example 78A

Enantiomer 1

$R_t$ 4.58 min; purity >99%; >99% ee (column: see above)

Yield: 1.23 g

LC-MS (method 11): $R_t$=1.26 min; m/z=367 (M+H)$^+$.

Example 79A

Enantiomer 2

$R_t$ 7.34 min; purity >99%; >99% ee (column: see above)

Yield: 1.32 g $^1$H-NMR (400 MHz, DMSO-d$_6$, δ/ppm): 12.5-12.0 (1H, broad s), 7.77 (2H, d), 7.55-7.40 (3H, m), 7.38-7.23 (4H, m), 4.91 (2H, s), 4.85 (2H, s), 3.09 (1H, d), 2.27-2.11 (1H, m), 0.99 (3H, d), 0.61 (3H, d).

LC-MS (method 11): $R_t$=1.25 min; m/z=367 (M+H)$^+$.

Example 80A rac-Cyclopentyl{4-[(5-oxo-2-phenyl-5,6-dihydro-4H-1,3,4-oxadiazin-4-yl)methyl]phenyl}-acetyl chloride

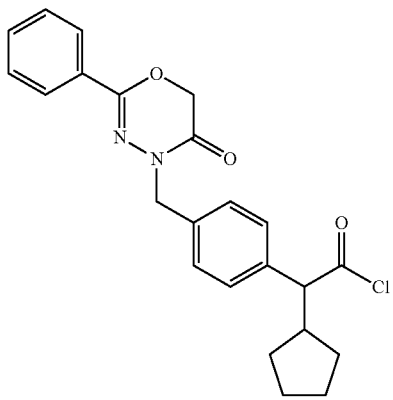 [SMILES: O=C(Cl)C(c1ccc(CN2N=C(c3ccccc3)OCC2=O)cc1)C1CCCC1]

At room temperature, 8.9 g (22.68 mmol) of rac-cyclopentyl{-4-[(5-oxo-2-phenyl-5,6-dihydro-4H-1,3,4-oxadiazin-4-yl)methyl]phenyl}acetic acid were stirred with 63.6 ml (871.5 mmol) of thionyl chloride for 2 h. The reaction solution was then warmed to 50° C. and stirred for a further 2 h. After the reaction had gone to completion, the reaction solution was freed from the thionyl chloride under reduced pressure. This gave 7.7 g (18.74 mmol, 82% of theory) of the title compound as a colorless oil, which was used without further purification in subsequent reactions.

$^1$H-NMR (400 MHz, DMSO-$d_6$, δ/ppm): 7.76 (2H, d), 7.58-7.36 (3H, m), 7.30 (4H, s), 4.91 (2H, s), 4.82 (2H, s), 3.21 (1H, d), 2.48-2.29 (1H, m), 1.89-1.76 (1H, m), 1.68-1.45 (3H, m), 1.45-1.32 (1H, m), 1.32-1.15 (2H, m), 1.01-0.87 (1H, m).

MS (ESI): m/z=411 (M+H)$^+$.

The compounds listed in the table below were obtained in an analogous manner:

| Example | Name/Structure | Analytical data |
|---|---|---|
| 81A | ent-cyclopentyl{4-[(5-oxo-2-phenyl-5,6-dihydro-4H-1,3,4-oxadiazin-4-yl)methyl]phenyl}acetyl chloride (enantiomer 1; from Example 77A) 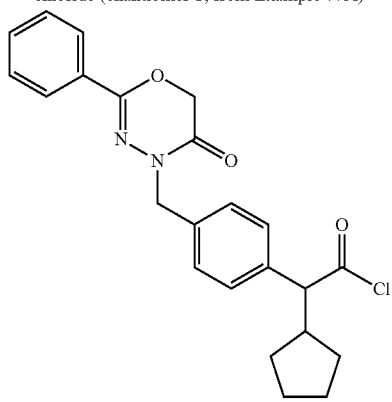 | see Example 80A |
| 82A | cyclopentyl(4-{[5-oxo-2-(propan-2-yl)-5,6-dihydro-4H-1,3,4-oxadiazin-4-yl]methyl}phenyl)acetyl chloride 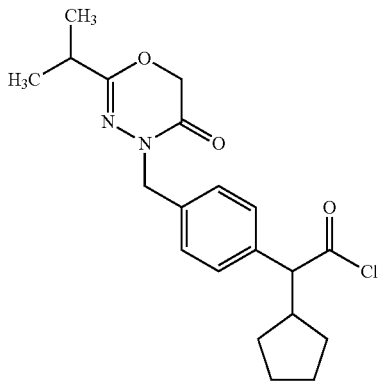 [SMILES: CC(C)C1=NN(Cc2ccc(C(C(=O)Cl)C3CCCC3)cc2)C(=O)CO1] | |
| 83A | {4-[(2-tert-butyl-5-oxo-5,6-dihydro-4H-1,3,4-oxadiazin-4-yl)methyl]phenyl}(cyclopentyl)acetyl chloride 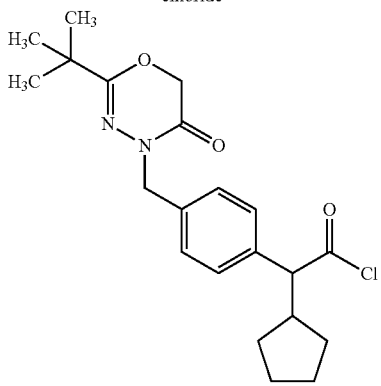 | |
| 84A | cyclopentyl(4-{[4-methyl-5-(2-methylpropyl)-2-oxo-1,3-thiazol-3(2H)-yl]methyl}phenyl)acetyl chloride 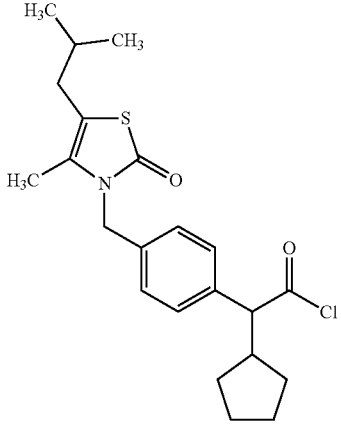 [SMILES: Cc1c(CC(C)C)sc(=O)n1Cc1ccc(C(C(=O)Cl)C2CCCC2)cc1] | LC-MS (method 11): $R_t$ = 1.45 min; m/z = 388 (M − Cl + H$_2$O)$^+$. |

Example 85A

Dimethyl 4-nitro-1,3-dihydro-2H-indene-2,2-dicarboxylate

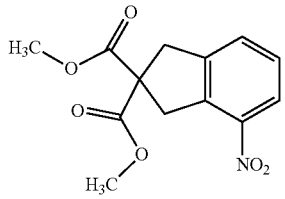

A solution of 126.79 g (0.96 mol) of dimethyl malonate, 296.5 g (0.96 mol) of 1,2-bis-(bromomethyl)-3-nitrobenzene and 530.5 g (3.84 mol) of potassium carbonate in 5.9 liters of acetonitrile was stirred under reflux overnight (monitored by TLC: mobile phase petroleum ether/dichloromethane 7:3 to identify the starting material 1,2-bis(bromomethyl)-3-nitrobenzene, dichloromethane/petroleum ether 7:3 to identify the product). After cooling to room temperature and filtration, the solvent was removed to dryness under reduced pressure. The residue was taken up in 2 liters of ethyl acetate and washed once with 500 ml of saturated sodium chloride solution and dried over sodium sulfate. After filtration, the solvent was removed to dryness under reduced pressure. The crude product obtained was purified by flash chromatography on 10 kg of silica gel (mobile phase dichloromethane/petroleum ether 7:3→9:1). This gave 191 g (0.63 mol, purity 93%, 66% of theory) of a colorless solid.

$^1$H-NMR (400 MHz, CDCl$_3$, δ/ppm): 8.04 (1H, d), 7.51 (1H, d), 7.37 (1H, t), 4.11 (2H, s), 3.78 (6H, s), 3.68 (2H, s).

MS (DCI, NH$_3$): m/z=297 (M+NH$_4$)$^+$.

Example 86A

4-Nitro-2,3-dihydro-1H-indene-2-carboxylic acid

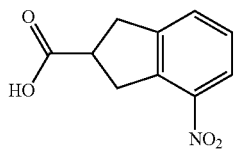 [SMILES: O=C(O)C1Cc2cccc([N+](=O)[O-])c2C1]

At room temperature, 1520 ml of 2 N aqueous sodium hydroxide solution were added to a solution of 190 g (0.68 mol) of dimethyl 4-nitro-1,3-dihydro-2H-indene-2,2-dicarboxylate in 1520 ml of dioxane, and the mixture was then stirred at 50° C. for two hours. After complete conversion (monitored by TLC: mobile phase dichloromethane/petroleum ether 8:2), the reaction solution was slowly adjusted to pH 1 using concentrated hydrochloric acid and stirred under reflux overnight. 3.4 liters of water were then added, and the reaction solution was extracted three times with in each case 3.4 liters of ethyl acetate. The combined organic phases were washed with saturated sodium chloride solution and dried over sodium sulfate. After filtration, the solvent was removed to dryness under reduced pressure. The crude product obtained was purified by flash chromatography on 5 kg of silica gel (mobile phase dichloromethane/methanol 95:5). This gave 75 g (0.35 mol, 97% pure, 51% of theory) of a colorless solid.

$^1$H-NMR (400 MHz, DMSO-d$_6$, δ/ppm): 12.6-12.35 (1H, broad s), 7.99 (1H, d), 7.67 (1H, d), 7.46 (1H, t), 3.68-3.47 (3H, m), 3.44-3.17 (2H, m).

MS (DCI, NH$_3$): m/z=225 (M+NH$_4$)$^+$.

Example 87A

Methyl 4-nitro-2,3-dihydro-1H-indene-2-carboxylate

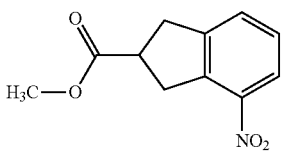 [SMILES: COC(=O)C1Cc2cccc([N+](=O)[O-])c2C1]

At −10° C., 52.8 ml (0.72 mol) of thionyl chloride were slowly added dropwise to 538 ml of methanol, and the mixture was stirred at this temperature for 10 min. 75 g (0.36 mol) of 4-nitro-2,3-dihydro-1H-indene-2-carboxylic acid were then added in one portion, and the mixture was stirred at room temperature for three hours. After the reaction had ended (monitored by TLC: mobile phase dichloromethane/methanol 95:5), the solvent was removed under reduced pressure. The residue obtained was dissolved in ethyl acetate, washed once with saturated sodium bicarbonate solution and dried over sodium sulfate. After filtration, the solvent was removed to dryness under reduced pressure. The crude product obtained was purified by flash chromatography on 2.2 kg of silica gel (mobile phase petroleum ether/ethyl acetate 8:2). This gave 75 g (0.34 mol, 94% of theory) of a colorless solid.

$^1$H-NMR (400 MHz, DMSO-d$_6$, δ/ppm): 7.99 (1H, d), 7.67 (1H, d), 7.47 (1H, t), 3.74-3.43 (3H, m), 3.65 (3H, s), 3.38-3.18 (2H, m).

MS (DCI, NH$_3$): m/z=239 (M+NH$_4$)$^+$.

Example 88A rac-Methyl 4-amino-2,3-dihydro-1H-indene-2-carboxylate

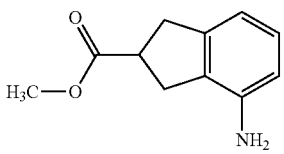

At room temperature, 3 g of palladium on carbon (10%) were added to a solution of 82 g (0.37 mol) of methyl 4-nitro-2,3-dihydro-1H-indene-2-carboxylate in 800 ml of ethyl acetate, and the mixture was hydrogenated under atmospheric pressure for 22 hours. After the reaction had gone to completion (monitored by TLC: mobile phase dichloromethane/methanol 95:5), the reaction solution was filtered through kieselguhr and the filtrate was concentrated under reduced pressure. This gave 67.5 g (0.35 mol, 95% of theory) of a colorless solid.

$^1$H-NMR (400 MHz, DMSO-d$_6$, δ/ppm): 6.83 (1H, t), 6.39 (2H, t), 4.88 (2H, s), 3.64 (3H, s), 3.38-3.27 (1H, m), 3.12-2.80 (4H, m).

MS (DCI, NH$_3$): m/z=209 (M+NH$_4$)$^+$, 192 (M+H)$^+$.

Example 89A and Example 90A ent-Methyl 4-amino-2,3-dihydro-1H-indene-2-carboxylate (enantiomers 1 and 2)

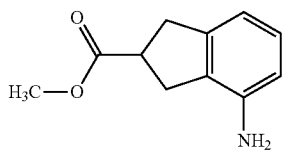

67.5 g (0.35 mmol) of racemic methyl 4-amino-2,3-dihydro-1H-indene-2-carboxylate (Example 88A) were separated into the enantiomers by preparative HPLC on a chiral phase [column: Daicel Chiralpak OJ-H, 250 mm×20 mm; mobile phase: isohexane/isopropanol/methanol 70:18:12 (v/v); flow rate: 25 ml/min; temperature: 24° C.; UV detection: 260 nm]:

Example 89A

Enantiomer 1

$R_t$ 11.76 min; purity >99%; >99.5% ee (column: see above)
Yield: 23.1 g
$^1$H-NMR (400 MHz, DMSO-$d_6$, δ/ppm): 6.83 (1H, t), 6.39 (2H, t), 4.88 (2H, s), 3.64 (3H, s), 3.38-3.27 (1H, m), 3.12-2.80 (4H, m).
MS (DCI, $NH_3$): m/z=209 $(M+NH_4)^+$, 192 $(M+H)^+$.

Example 90A

Enantiomer 2

$R_t$ 12.65 min; purity >99%; >99% ee (column: see above)
Yield: 30 g.

Example 91A

Ethyl 4-methoxy-2-methyl-2,3-dihydro-1H-indene-2-carboxylate

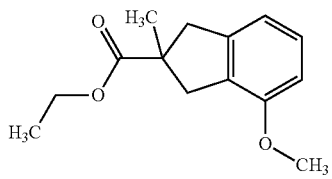

At −78° C., 2.7 ml of a 2.5 M solution of n-butyllithium in hexane were added to a solution of 0.95 ml of diisopropylamine (6.75 mmol) in 30 ml of THF, and the mixture was then briefly warmed to −10° C. The mixture was once more cooled to −78° C., 1.24 g (5.63 mmol) of ethyl 4-methoxy-2,3-dihydro-1H-indene-2-carboxylate [Beilstein Reg. No. 8980172], dissolved in 10 ml of THF, were added dropwise, and the solution was stirred for another hour. 0.46 ml (7.32 mmol) of iodomethane was then added dropwise to the reaction solution, and the reaction mixture was stirred at −78° C. for a further 2 hours. After the reaction had gone to completion, saturated aqueous ammonium chloride solution was added quickly to the reaction mixture. After phase separation, the aqueous phase was extracted three times with ethyl acetate and the combined organic phases were dried over magnesium sulfate. After filtration, the solvent was removed to dryness under reduced pressure. The crude product obtained was purified by flash chromatography on silica gel (mobile phase cyclohexane/ethyl acetate 10:1). This gave 1.19 g (5.08 mmol, 90% of theory) of a colorless solid.
LC-MS (method 7): $R_t$=2.60 min; m/z=235 $(M+H)^+$.

Example 92A

Methyl 4-hydroxy-2-methyl-2,3-dihydro-1H-indene-2-carboxylate

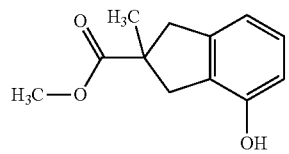

At 0° C., 15.2 ml (15.24 mmol) of a 1 M solution of boron tribromide in dichloromethane were added to a solution of 1.19 g (5.08 mmol) of ethyl 4-methoxy-2-methyl-2,3-dihydro-1H-indene-2-carboxylate in 20 ml of dichloromethane. Stirring at 0° C. was continued for one hour. 16 ml of methanol were then added, and the reaction mixture was stirred overnight. 10 ml of water and 10 ml of dichloromethane were then added. After phase separation, the aqueous phase was extracted three times with dichloromethane and the combined organic phases were dried over magnesium sulfate. After filtration, the solvent was evaporated to dryness under reduced pressure. This gave 897 mg (4.35 mmol, 86% of theory) of a colorless oil.
LC-MS (method 12): $R_t$=1.83 min; m/z=207 $(M+H)^+$.

Example 93A

Methyl 2-methyl-4-{[(trifluoromethyl)sulfonyl]oxy}-2,3-dihydro-1H-indene-2-carboxylate

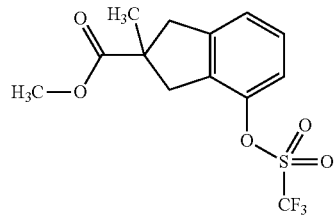 [SMILES: COC(=O)C1(C)Cc2cccc(OS(=O)(=O)C(F)(F)F)c2C1]

At −15° C., 1.5 ml (8.7 mmol) of trifluoromethanesulfonic anhydride were slowly added dropwise to a solution of 897 mg (4.35 mmol) of methyl 4-hydroxy-2-methyl-2,3-dihydro-1H-indene-2-carboxylate in 20 ml of pyridine. After warming to room temperature, the reaction mixture was stirred for another 2 h. 20 ml of water were then added and, after phase separation, the aqueous phase was extracted three times with ethyl acetate. The combined organic phases were washed with saturated sodium chloride solution and dried over sodium sulfate. After filtration, the solvent was removed to dryness under reduced pressure. The crude product obtained was purified by flash chromatography on silica gel (mobile phase cyclohexane/ethyl acetate 10:1). This gave 1100 mg (3.25 mmol, 75% of theory) of a colorless oil.

LC-MS (method 7): $R_t$=2.76 min; m/z=339 (M+H)$^+$.

Example 94A

Methyl 4-(benzylamino)-2-methyl-2,3-dihydro-1H-indene-2-carboxylate

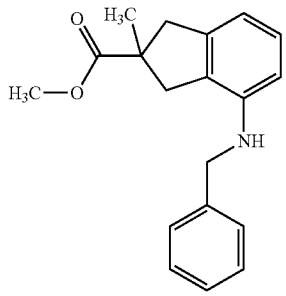 [SMILES: COC(=O)C1(C)Cc2cccc(NCc3ccccc3)c2C1]

Under argon, a solution of 1 g (2.96 mmol) of methyl 2-methyl-4-{[(trifluoromethyl)sulfonyl]oxy}-2,3-dihydro-1H-indene-2-carboxylate, 290 μl (2.66 mmol) of benzylamine, 2.41 g (7.29 mmol) of cesium carbonate, 56 mg (0.12 mmol) of 2-dicyclohexylphosphino-2',4',6'-triisopropylbiphenyl and 54 mg (0.059 mmol) of tris(dibenzylideneaceton) dipalladium in 50 ml of dioxane was stirred at a bath temperature of 100° C. overnight. After cooling to room temperature, the reaction mixture was filtered through kieselguhr and the residue was washed repeatedly with dioxane. The combined filtrates were concentrated to dryness under reduced pressure. The crude product obtained was purified by flash chromatography on silica gel (mobile phase cyclohexane/ethyl acetate 20:1→4:1→1:1). This gave 769 mg (2.42 mmol, 93% content, 82% of theory) of a colorless solid.

LC-MS (method 7): $R_t$=2.77 min; m/z=296 (M+H)$^+$.

Example 95A

Methyl 4-amino-2-methyl-2,3-dihydro-1H-indene-2-carboxylate

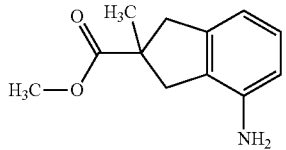

At room temperature, 50 mg of palladium on carbon (10%) were added to a solution of 860 mg (2.91 mmol) of methyl 4-(benzylamino)-2-methyl-2,3-dihydro-1H-indene-2-carboxylate in 84 ml of methanol, and the mixture was hydrogenated under atmospheric pressure overnight. After the reaction had gone to completion, the reaction solution was filtered through kieselguhr and the filtrate was concentrated under reduced pressure. The crude product obtained was purified by flash chromatography on silica gel (mobile phase cyclohex-ane/ethyl acetate 10:1→1:1). This gave 483 mg (2.35 mol, 81% of theory) of a colorless solid.

LC-MS (method 11): $R_t$=0.81 min; m/z=206 (M+H)$^+$.

Example 96A tert-Butyl 3-(3-amino-2-methylphenyl)propanoate

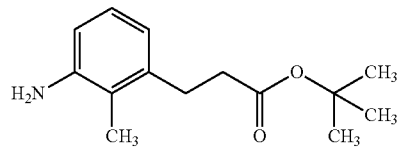 [SMILES: Cc1c(N)cccc1CCC(=O)OC(C)(C)C]

Under argon, 201 ml (1.39 mol) of tert-butyl prop-2-enoate were added dropwise to a solution of 100 g (463 mmol) of 1-bromo-2-methyl-3-nitrobenzene, 322 ml (2.31 mol) of triethylamine, 28.18 g (92.58 mmol) of tri-2-tolylphosphine and 10.39 g (46.29 mmol) of palladium(II) acetate in 2 liters of DMF, and the mixture was then stirred at 125° C. for 36 h. After cooling to room temperature, the reaction mixture was stirred with saturated aqueous ammonium chloride solution and the organic phase was separated off. The aqueous phase was extracted three times with tert-butyl methyl ether, and the combined organic phases were washed with saturated sodium chloride solution and dried over sodium sulfate. After filtration, the solvent was removed to dryness under reduced pressure. The residue obtained was purified by flash chromatography on silica gel (mobile phase petroleum ether/ethyl acetate 9:1). This gave 89 g (338 mmol, 73% of theory) of the intermediate tert-butyl(2E)-3-(2-methyl-3-nitrophenyl)prop-2-enoate as a colorless solid. 88 g (334 mmol) of this solid were dissolved in 2 liters of ethanol, 7 g of palladium on carbon (10%) were added at room temperature and the mixture was hydrogenated at atmosperic pressure for 18 h. After the reaction had gone to completion, the reaction solution was filtered through kieselguhr and the filtrate obtained was concentrated under reduced pressure. This gave 61.3 g (260.5 mmol, 78% of theory) of the title compound as a colorless solid.

$^1$H-NMR (400 MHz, DMSO-d$_6$, δ/ppm): 6.77 (1H, t), 6.47 (1H, d), 6.36 (1H, d), 4.72 (2H, s), 2.14 (2H, t), 2.36 (2H, t), 1.95 (3H, s), 1.39 (9H, s).

LC-MS (method 7): $R_t$=1.84 min; m/z=236 (M+H)$^+$.

Example 97A

Ethyl 3-(3-amino-2-methylphenyl)propanoate

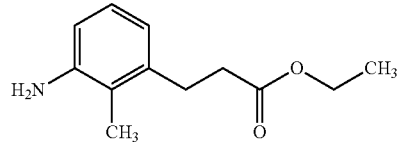

Under argon, 10.844 g (108 mmol) of ethyl prop-2-enoate were added dropwise to a solution of 7.8 g (36.1 mmol) of 1-bromo-2-methyl-3-nitrobenzene, 25 ml (180.5 mmol) of triethylamine, 2.197 g (7.22 mmol) of tri-2-tolylphosphine and 810 mg (3.6 mmol) of palladium(II) acetate in 200 ml of DMF, and the mixture was then stirred at 125° C. for 36 h.

After cooling to room temperature, the reaction mixture was stirred with saturated aqueous ammonium chloride solution and the organic phase was separated off. The aqueous phase was extracted three times with tert-butyl methyl ether, and the combined organic phases were washed with saturated sodium chloride solution and dried over sodium sulfate. After filtration, the solvent was removed to dryness under reduced pressure. The residue obtained was purified by flash chromatography on silica gel (mobile phase petroleum ether/ethyl acetate 3:1). This gave 6.6 g (27.2 mmol, content 97%, 75% of theory) of the intermediate ethyl (2E)-3-(2-methyl-3-nitrophenyl)prop-2-enoate as a colorless solid. 6.6 g (27.2 mmol, content 97%) of this solid were dissolved in 200 ml of ethanol, 500 mg of palladium on carbon (10%) were added at room temperature and the mixture was hydrogenated under atmospheric pressure overnight. After the reaction had gone to completion, the reaction solution was filtered through kieselguhr and the filtrate obtained was concentrated under reduced pressure. This gave 5.47 g (26.38 mmol, content 97%, 97% of theory) of the title compound as a colorless solid.

LC-MS (method 10): $R_t$=1.07 min; m/z=208 (M+H)$^+$.

Example 98A

Methyl 3-(trans-4-aminocyclohexyl)propanoate hydrochloride

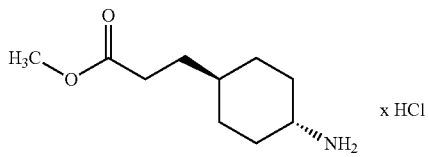

At −5° C., 2.9 ml (40.5 mmol) of thionyl chloride were slowly added dropwise to 100 ml of methanol, and the mixture was stirred at this temperature for 10 min. 5 g (18.4 mmol) of 3-{trans-4-[(tert-butoxycarbonyl)amino]cyclohexyl}propanoic acid were then added in one portion, and the reaction mixture was stirred at room temperature overnight. After the reaction had gone to completion, the solvent was evaporated under reduced pressure. This gave 3.97 g (17.9 mmol, 97% of theory) of a colorless solid.

$^1$H-NMR (400 MHz, DMSO-d$_6$, δ/ppm): 8.18 (3H, broad s), 3.59 (3H, s), 2.96-2.79 (1H, m), 2.31 (2H, t), 2.03-1.89 (2H, m), 1.81-1.68 (2H, m), 1.49-1.21 (4H, m), 1.21-1.08 (1H, m), 1.00-0.85 (2H, m).

MS (ES): m/z=186 (M+H—HCl)$^+$.

Example 99A

Methyl 3-(cis-4-aminocyclohexyl)propanoate hydrochloride

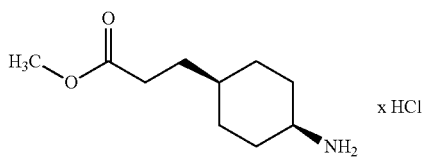

At −5° C., 2.9 ml (40.5 mmol) of thionyl chloride were slowly added dropwise to 100 ml of methanol, and the mixture was stirred at this temperature for 10 min. 5 g (18.4 mmol) of 3-{cis-4-[(tert-butoxycarbonyl)amino]cyclohexyl}propanoic acid were then added in one portion, and the reaction mixture was stirred at room temperature overnight. After the reaction had gone to completion, the solvent was evaporated under reduced pressure. This gave 3.95 g (17.8 mmol, 96.7% of theory) of a colorless solid.

$^1$H-NMR (400 MHz, DMSO-d$_6$, δ/ppm): 8.05 (3H, broad s), 3.59 (3H, s), 3.21-3.05 (1H, m), 2.39-2.24 (2H, m), 1.74-1.31 (11H, m).

MS (ES): m/z=186 (M+H—HCl)$^+$.

Example 100A

Methyl 3-(3-aminocyclohexyl)propanoate hydrochloride

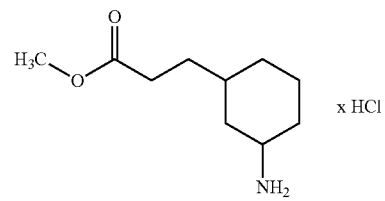

At −5° C., 1.9 ml (25.7 mmol) of thionyl chloride were slowly added dropwise to 50 ml of methanol, and the mixture was stirred at this temperature for 10 min. 2 g (11.7 mmol) of 3-(3-aminocyclohexyl)propanoic acid were then added in one portion, and the reaction mixture was stirred at room temperature overnight. After the reaction had gone to completion, the solvent was evaporated under reduced pressure. This gave 2.46 g (11.1 mmol, 95% of theory) of a colorless solid.

$^1$H-NMR (400 MHz, DMSO-d$_6$, δ/ppm): 8.05 (3H, broad s), 3.59 (3H, s), 3.01-2.84 (1H, m), 2.39-2.22 (2H, m), 2.01-1.82 (1H, m), 1.80-1.59 (2H, m), 1.59-1.40 (3H, m), 1.40-1.08 (3H, m), 1.01-0.85 (1H, m), 0.85-0.65 (1H, m).

GC-MS (method 3): $R_t$=4.75 min; m/z=185 (M−HCl)$^+$.

Example 101A

Ethyl 5-(aminomethyl)isoxazole-3-carboxylate hydrochloride

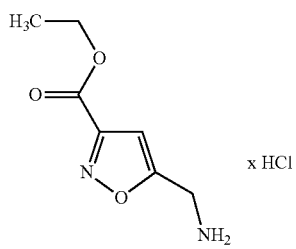

360 mg (1.3 mmol) of ethyl 5-{[(tert-butoxycarbonyl)amino]methyl} isoxazole-3-carboxylate were stirred overnight in 3.3 ml of a 4 M solution of hydrogen chloride in dioxane at room temperature. After the reaction had ended, the solvent was evaporated under reduced pressure. This gave 258 mg (1.25 mmol, 94% of theory) of a yellowish solid.

LC-MS (method 12): $R_t$=0.49 min; m/z=171 (M+H—HCl)$^+$.

Example 102A

Methyl 2-[(3-aminophenyl)sulfanyl]-2-methylpropanoate

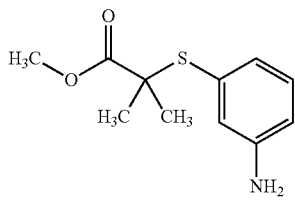

At room temperature, 1.36 ml (10.5 mmol) of methyl 2-bromo-2-methylpropanoate were added slowly to a solution of 1.2 g (9.6 mmol) of 3-aminobenzenethiol and 1.046 g (12.5 mmol) of sodium bicarbonate in 6 ml of DMF, and the mixture was stirred overnight. After the reaction had ended, the reaction mixture was added to water. The reaction mixture was extracted three times with diethyl ether, and the combined organic phases were washed with saturated sodium chloride solution and dried over magnesium sulfate. After filtration, the solvent was removed to dryness under reduced pressure. This gave 1.45 g (6.4 mmol, 67% of theory) of a colorless solid.

LC-MS (method 11): $R_t$=0.96 min; m/z=226 (M+H)$^+$.

Example 103A

Methyl 2-methyl-2-(2-methyl-3-nitrophenoxy)propanoate

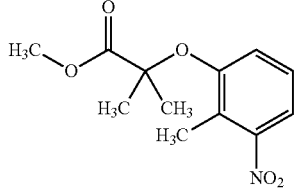

2.00 g (13.06 mmol) of 2-methyl-3-nitrophenol were dissolved in 40 ml of DMF, and 3.55 g (19.59 mmol) of methyl 2-bromo-2-methylpropanoate and 4.68 g (14.37 mmol) of cesium carbonate were added. The reaction mixture was stirred at 100° C. for 2 d, and a further 1.77 g (9.80 mmol) of methyl 2-bromo-2-methylpropanoate were then added. The mixture was stirred at 100° C. for another 1 d, a further 1.77 g (9.80 mmol) of methyl 2-bromo-2-methylpropanoate were then added and the mixture was stirred at 100° C. for another 1 d. After cooling, saturated aqueous sodium bicarbonate solution was added and the mixture was extracted repeatedly with ethyl acetate. The combined organic phases were washed with saturated aqueous sodium bicarbonate solution, dried over sodium sulfate and concentrated on a rotary evaporator. The residue was purified by preparative HPLC. This gave 1.33 g (39% of theory) of the target compound.

$^1$H-NMR (300 MHz, CDCl$_3$, δ/ppm): 1.58 (s, 6H), 2.27 (s, 3H), 3.75 (s, 3H), 6.95 (d, 1H), 7.35 (t, 1H), 7.60 (d, 1H).

Example 104A

Methyl 2-(3-amino-2-methylphenoxy)-2-methylpropanoate hydrochloride

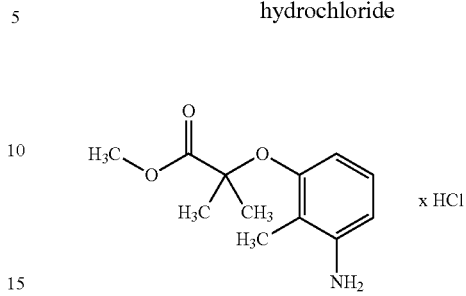

1.33 g (5.25 mmol) of methyl 2-methyl-2-(2-methyl-3-nitrophenoxy)propanoate were dissolved in 60 ml of ethanol, and 1 ml of concentrated hydrochloric acid and 0.30 g of palladium on carbon (10%) were added. Under an atmosphere of hydrogen, the mixture was hydrogenated at atmospheric pressure and room temperature for 3 h. The reaction mixture was then filtered through Tonsil. The filter residue was washed with ethanol and the collected filtrates were concentrated under reduced pressure. This gave 1.39 g (89% of theory) of the target compound.

LC-MS (method 11): $R_t$=0.80 min; m/z=225 (M−Cl+H)$^+$.

Example 105A

Methyl 4-[(cyclopentyl{4-[(5-oxo-2-phenyl-5,6-dihydro-4H-1,3,4-oxadiazin-4-yl)methyl]phenyl}acetyl)amino]-2,3-dihydro-1H-indene-2-carboxylate

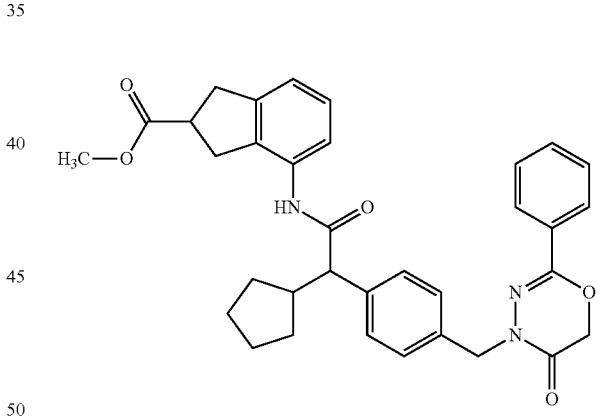

337 mg (0.821 mmol) of cyclopentyl{4-[(5-oxo-2-phenyl-5,6-dihydro-4H-1,3,4-oxadiazin-4-yl)methyl]phenyl}acetyl chloride (enantiomer 1; Example 81A) were dissolved in 8 ml of dichloromethane, and 83 mg (0.821 mmol) of triethylamine were added. 157 mg (0.821 mmol) of methyl 4-amino-2,3-dihydro-1H-indene-2-carboxylate (enantiomer 1; Example 89A), dissolved in 2 ml of dichloromethane, were added to the mixture. The mixture was stirred at room temperature overnight. Water was then added, and the reaction solution was extracted with dichloromethane. The combined organic phases were dried over sodium sulfate and concentrated on a rotary evaporator. The residue was purified by chromatography on silica gel (mobile phase cyclohexane/ethyl acetate 3:1→1:1). This gave 182 mg (0.32 mmol, 39% of theory) of the title compound.

LC-MS (method 10): $R_t$=2.50 min; m/z=566 (M+H)$^+$.

The compounds listed in the table below were obtained in an analogous manner:

| Example | Name/Structure/Starting materials | Analytical data |
| --- | --- | --- |
| 106A | methyl 4-{[cyclopentyl(4-{[4-methyl-5-(2-methylpropyl)-2-oxo-1,3-thiazol-3(2H)-yl]methyl}phenyl)acetyl]amino}-2,3-dihydro-1H-indene-2-carboxylate<br>(from Ex. 84A and Ex. 88A) | LC-MS (method 10): $R_t$ = 2.68 min; m/z = 561 (M + H)$^+$. |
| 107A | methyl 4-{[cyclopentyl(4-{[5-oxo-2-(propan-2-yl)-5,6-dihydro-4H-1,3,4-oxadiazin-4-yl]methyl}phenyl)-acetyl]amino}-2,3-dihydro-1H-indene-2-carboxylate<br>(from Ex. 82A and Ex. 89A) | LC-MS (method 10): $R_t$ = 2.42 and 2.47 min; m/z = 532 (M + H)$^+$ (isomers 1 and 2). |
| 108A | methyl 4-{[{4-[(2-tert-butyl-5-oxo-5,6-dihydro-4H-1,3,4-oxadiazin-4-yl)methyl]phenyl}(cyclopentyl)acetyl]-amino}-2,3-dihydro-1H-indene-2-carboxylate<br>(from Ex. 83A and Ex. 89A) | LC-MS (method 11): $R_t$ = 1.53 min; m/z = 546 (M + H)$^+$. |

| Example | Name/Structure/Starting materials | Analytical data |
|---|---|---|
| 109A | methyl (2E)-3-{2-[(cyclopentyl{4-[(5-oxo-2-phenyl-5,6-dihydro-4H-1,3,4-oxadiazin-4-yl)methyl]phenyl}-acetyl)amino]phenyl}prop-2-enoate<br>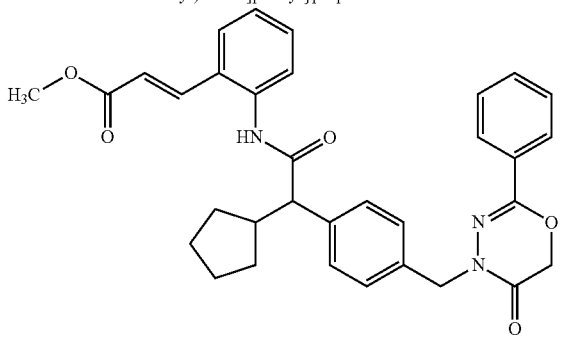<br>(from Ex. 81A and methyl (2E)-3-(2-aminophenyl)-prop-2-enoate [CAS Reg. No. 1664-62-6]) | LC-MS (method 10):<br>$R_t$ = 2.41 min; m/z = 552 (M + H)$^+$. |
| 110A | methyl {3-[(cyclopentyl{4-[(5-oxo-2-phenyl-5,6-dihydro-4H-1,3,4-oxadiazin-4-yl)methyl]phenyl}-acetyl)amino]phenyl}acetate<br>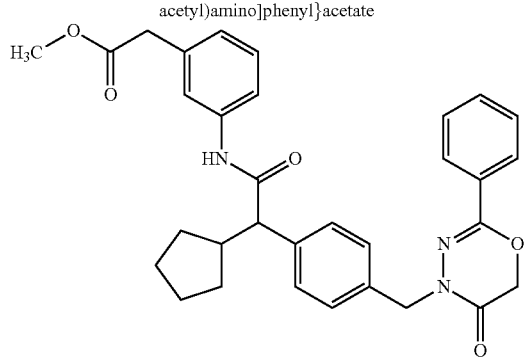<br>(from Ex. 81A and methyl (3-aminophenyl)acetate hydrochloride [CAS Reg. No. 150319-83-8]) | LC-MS (method 10):<br>$R_t$ = 2.43 min; m/z = 540 (M + H)$^+$. |
| 111A | ethyl (2E)-3-{4-[(cyclopentyl{4-[(5-oxo-2-phenyl-5,6-dihydro-4H-1,3,4-oxadiazin-4-yl)methyl]phenyl}-acetyl)amino]phenyl}prop-2-enoate<br>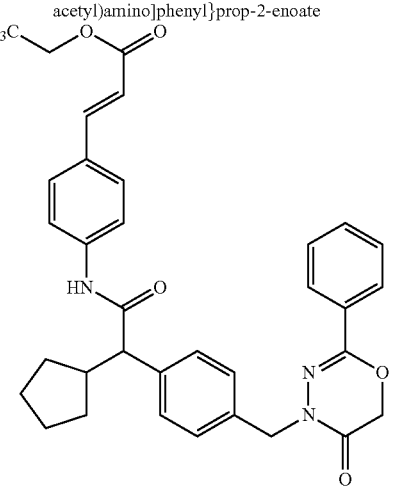<br>(from Ex. 81A and ethyl (2E)-3-(4-aminophenyl)-prop-2-enoate [CAS Reg. No. 5048-82-8]) | LC-MS (method 12):<br>$R_t$ = 2.89 min; m/z = 566 (M + H)$^+$. |

Example 112A

Methyl 4-({[(4-{[4-(4-chlorophenyl)-1-oxoph-thalazin-2(1H)-yl]methyl}phenyl)(cyclo-pentyl)acetyl]amino}methyl)benzenecarboxylate

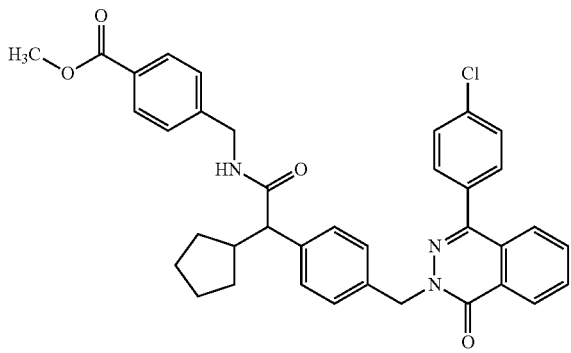

60 mg (0.127 mmol) of (4-{[4-(4-chlorophenyl)-1-oxoph-thalazin-2(1H)-yl]methyl}phenyl)(cyclopentyl)acetic acid (Example 65A) were dissolved in 0.6 ml of dichloromethane, and 26 mg (0.127 mmol) of methyl 4-(aminomethyl)benzenecarboxylate hydrochloride, 19 mg (0.140 mmol) of 1-hydroxy-1H-benzotriazole hydrate, 28 mg (0.146 mmol) of 1-(3-dimethylaminopropyl)-3-ethylcarbodiimide hydrochloride and 28 mg (0.273 mmol) of triethylamine were added in succession. The reaction mixture was stirred at room temperature overnight. 1 N hydrochloric acid was then added, and the mixture was extracted with ethyl acetate. The combined organic phases were dried over sodium sulfate and concentrated on a rotary evaporator. The residue was purified by preparative HPLC. This gave 36 mg (46% of theory) of the title compound.

LC-MS (method 7): $R_t$=3.27 min; m/z=620 (M+H)$^+$.

The compounds listed in the table below were obtained in an analogous manner:

| Example | Name/Structure/Starting materials | Analytical data |
|---|---|---|
| 113A | methyl 4-{[(cyclopentyl{4-[(5-oxo-2-phenyl-5,6-dihydro-4H-1,3,4-oxadiazin-4-yl)methyl]phenyl}-acetyl)amino]methyl}benzenecarboxylate<br><br>(from Ex. 51A and methyl 4-(aminomethyl)-benzenecarboxylate hydrochloride) | LC-MS (method 2): $R_t$ = 2.84 min; m/z = 540 (M + H)$^+$. |
| 114A | methyl 4-{[(cyclopentyl{4-[(2-oxo-5-phenyl-1,3,4-oxadiazol-3(2H)-yl)methyl]phenyl}acetyl)amino]-methyl}benzenecarboxylate<br><br>(from Ex. 57A and methyl 4-(aminomethyl)-benzenecarboxylate hydrochloride) | LC-MS (method 2): $R_t$ = 2.71 min; m/z = 526 (M + H)$^+$. |

| Example | Name/Structure/Starting materials | Analytical data |
|---|---|---|
| 115A | methyl 4-({[cyclopentyl(4-{[(4R,5S)-4-methyl-2-oxo-5-phenyl-1,3-oxazolidin-3-yl]methyl}phenyl)acetyl]-amino}methyl)benzenecarboxylate<br>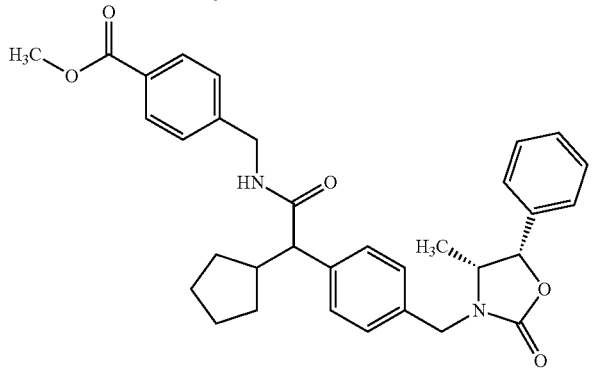 [SMILES: COC(=O)c1ccc(CNC(=O)C(c2ccc(CN3C(=O)O[C@@H](c4ccccc4)[C@H]3C)cc2)C2CCCC2)cc1]<br>(from Ex. 69A and methyl 4-(aminomethyl)-benzenecarboxylate hydrochloride) | LC-MS (method 2):<br>$R_t$ = 2.76 min; m/z = 541 (M + H)$^+$. |
| 116A | methyl 4-({[cyclopentyl(4-{[(4S,5R)-4-methyl-2-oxo-5-phenyl-1,3-oxazolidin-3-yl]methyl}phenyl)acetyl]-amino}methyl)benzenecarboxylate<br>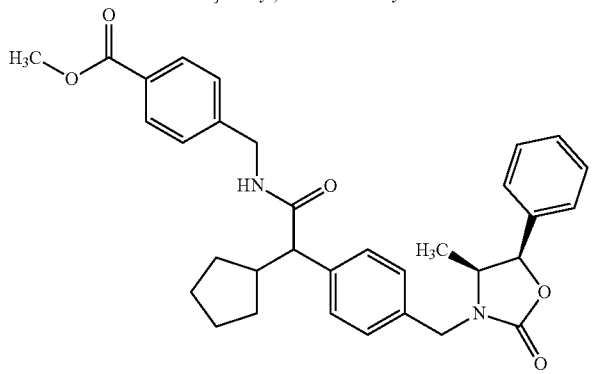<br>(from Ex. 68A and methyl 4-(aminomethyl)-benzenecarboxylate hydrochloride) | LC-MS (method 2):<br>$R_t$ = 2.76 min; m/z = 541 (M + H)$^+$. |
| 117A | methyl 4-{[(cyclopentyl{4-[(3,5-dioxo-6-phenyl-2,5-dihydro-1,2,4-triazin-4(3H)-yl)methyl]phenyl}acetyl)-amino]methyl}benzenecarboxylate<br>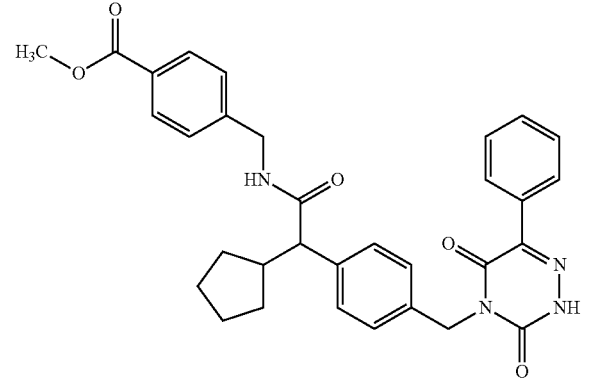 [SMILES: COC(=O)c1ccc(CNC(=O)C(c2ccc(Cn3c(=O)[nH]nc(-c4ccccc4)c3=O)cc2)C2CCCC2)cc1]<br>(from Ex. 55A and methyl 4-(aminomethyl)-benzenecarboxylate hydrochloride) | LC-MS (method 2):<br>$R_t$ = 2.67 min; m/z = 553 (M + H)$^+$. |

| Example | Name/Structure/Starting materials | Analytical data |
|---|---|---|
| 118A | methyl 4-{[(cyclopentyl{4-[(5-methyl-2-oxo-5-phenylpiperidin-1-yl)methyl]phenyl}acetyl)amino]-methyl}benzenecarboxylate<br>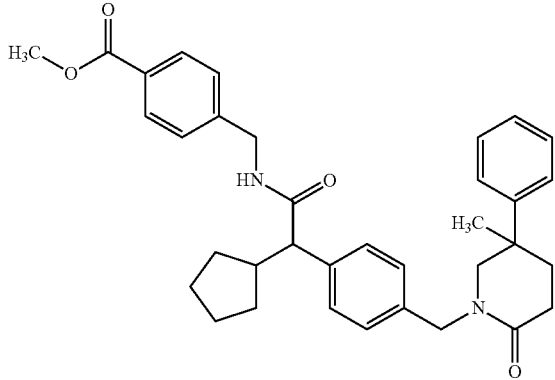 [SMILES: COC(=O)c1ccc(CNC(=O)C(c2ccc(CN3CC(C)(c4ccccc4)CCC3=O)cc2)C2CCCC2)cc1]<br>(from Ex. 70A and methyl 4-(aminomethyl)-benzenecarboxylate hydrochloride) | LC-MS (method 2):<br>$R_t$ = 2.69 min; m/z = 553 (M + H)$^+$. |
| 119A | methyl (4-{[(cyclopentyl{4-[(5-oxo-2-phenyl-5,6-dihydro-4H-1,3,4-oxadiazin-4-yl)methyl]phenyl}acetyl)amino]-methyl}phenyl)acetate<br>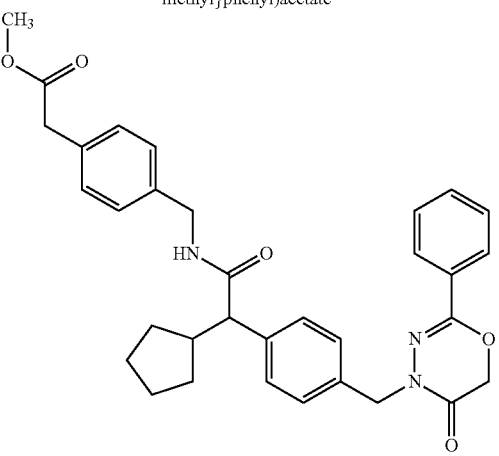<br>(from Ex. 51A and methyl [4-(aminomethyl)-phenyl]acetate hydrochloride [CAS Reg. No. 99075-26-9]) | LC-MS (method 2):<br>$R_t$ = 2.77 min; m/z = 554 (M + H)$^+$. |
| 120A | methyl 4-({[(4-{[2-(3-chlorophenyl)-5-oxo-5,6-dihydro-4H-1,3,4-oxadiazin-4-yl]methyl}phenyl)(cyclopentyl)acetyl]-amino}methyl)benzenecarboxylate<br>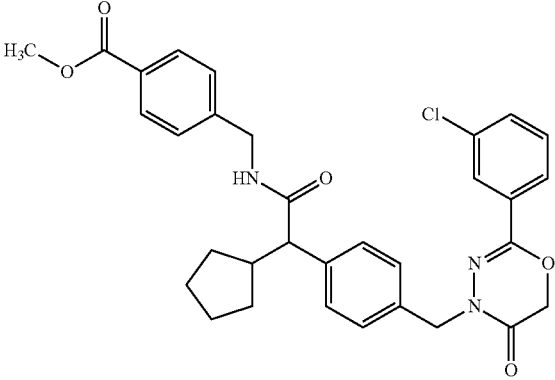 [SMILES: COC(=O)c1ccc(CNC(=O)C(c2ccc(CN3N=C(c4cccc(Cl)c4)OCC3=O)cc2)C2CCCC2)cc1]<br>(from Ex. 52A and methyl 4-(aminomethyl)-benzenecarboxylate hydrochloride) | LC-MS (method 2):<br>$R_t$ = 2.87 min; m/z = 574 (M + H)$^+$. |

| Example | Name/Structure/Starting materials | Analytical data |
|---|---|---|
| 121A | methyl 6-({[(4-{[4-(4-chlorophenyl)-1-oxophthalazin-2(1H)-yl]methyl}phenyl)(cyclopentyl)acetyl]amino}-methyl)pyridine-3-carboxylate 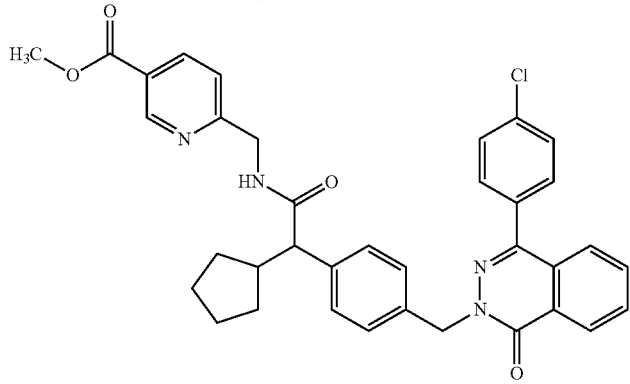 [SMILES: COC(=O)c1ccc(CNC(=O)C(c2ccc(Cn3nc(-c4ccc(Cl)cc4)c4ccccc4c3=O)cc2)C2CCCC2)nc1] (from Ex. 65A and methyl 6-(aminomethyl)pyridine-3-carboxylate hydrochloride [Beilstein Reg. No. 7701946]) | LC-MS (method 2): $R_t$ = 2.97 min; m/z = 621 (M + H)$^+$. |
| 122A | methyl 4-({[(4-{[2-(2-chlorophenyl)-5-oxo-5,6-dihydro-4H-1,3,4-oxadiazin-4-yl]methyl}phenyl)(cyclopentyl)acetyl]-amino}methyl)benzenecarboxylate 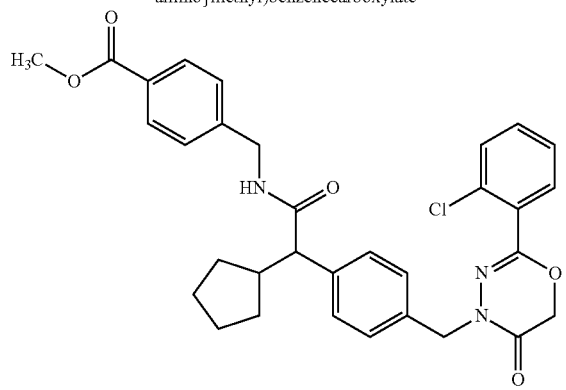 (from 53A and methyl 4-(aminomethyl)-benzenecarboxylate hydrochloride) | LC-MS (method 7): $R_t$ = 2.95 min; m/z = 574 (M + H)$^+$. |
| 123A | ethyl 5-({[(4-{[4-(4-chlorophenyl)-1-oxophthalazin-2(1H)-yl]methyl}phenyl)(cyclopentyl)acetyl]amino}methyl)-furan-2-carboxylate 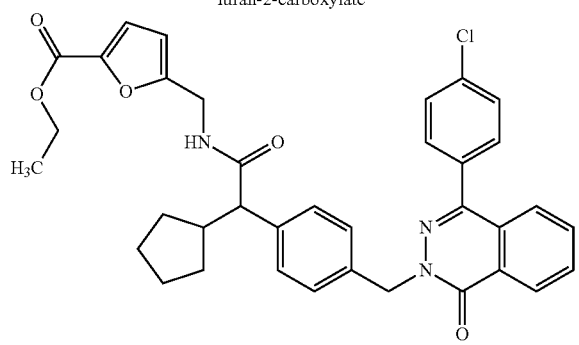 (from Ex. 65A and ethyl 5-(aminomethyl)furan-2-carboxylate [CAS Reg. No. 18707-63-6]) | LC-MS (method 9): $R_t$ = 4.74 min; m/z = 624 (M + H)$^+$. |

| Example | Name/Structure/Starting materials | Analytical data |
|---|---|---|
| 124A | methyl 4-({[(4-{[2-(4-chlorophenyl)-5-oxo-5,6-dihydro-4H-1,3,4-oxadiazin-4-yl]methyl}phenyl)(cyclopentyl)acetyl]-amino}methyl)benzenecarboxylate<br>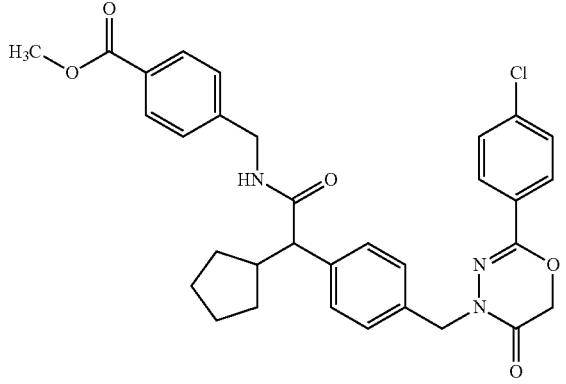 [SMILES: COC(=O)c1ccc(CNC(=O)C(c2ccc(CN3N=C(c4ccc(Cl)cc4)OCC3=O)cc2)C2CCCC2)cc1]<br>(from Ex. 72A and methyl 4-(aminomethyl)-benzenecarboxylate hydrochloride) | LC-MS (method 9):<br>$R_t$ = 4.29 min; m/z = 574 (M + H)$^+$. |
| 125A | methyl 4-({[cyclopentyl(4-{[2-(2-methoxyphenyl)-5-oxo-5,6-dihydro-4H-1,3,4-oxadiazin-4-yl]methyl}phenyl)acetyl]-amino}methyl)benzenecarboxylate<br>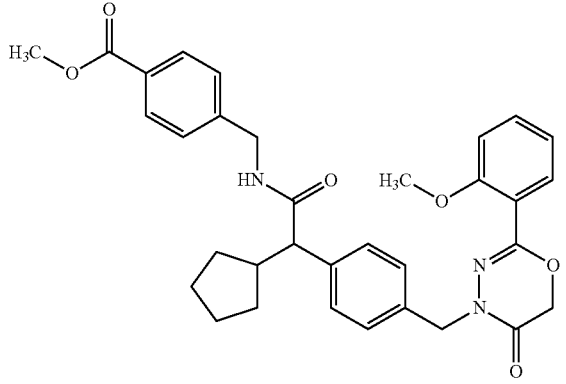 [SMILES: COC(=O)c1ccc(CNC(=O)C(c2ccc(CN3N=C(c4ccccc4OC)OCC3=O)cc2)C2CCCC2)cc1]<br>(from Ex. 54A and methyl 4-(aminomethyl)-benzenecarboxylate hydrochloride) | LC-MS (method 7):<br>$R_t$ = 2.78 min; m/z = 570 (M + H)$^+$. |
| 126A | ethyl 4-{[(cyclopentyl{4-[(5-oxo-2-phenyl-5,6-dihydro-4H-1,3,4-oxadiazin-4-yl)methyl]phenyl}-acetyl)amino]methyl}cyclohexanecarboxylate<br>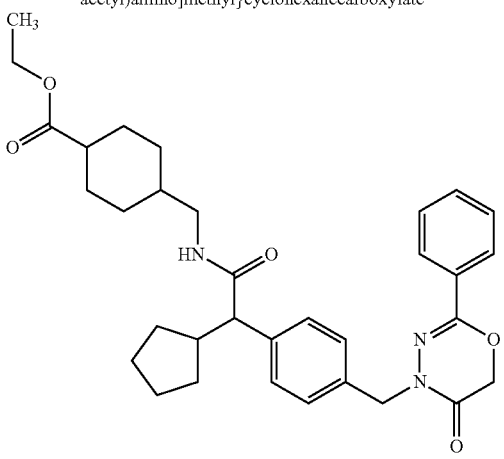<br>(from Ex. 51A and ethyl 4-(aminomethyl)-cyclohexanecarboxylate hydrochloride (cis/trans mixture) [Beilstein Reg. No. 10814930]) | LC-MS (method 11):<br>$R_t$ = 1.49 min; m/z = 560 (M + H)$^+$. |

Examples 127A-130A

Ethyl 4-{[(cyclopentyl{4-[(5-oxo-2-phenyl-5,6-dihydro-4H-1,3,4-oxadiazin-4-yl)methyl]phenyl}acetyl)amino]methyl}cyclohexanecarboxylate (isomers 1-4)

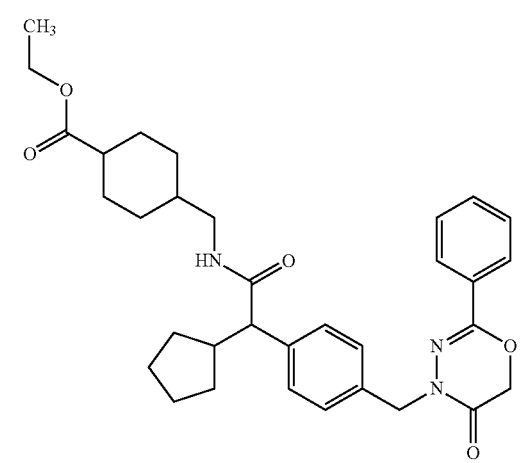 [SMILES: CCOC(=O)C1CCC(CNC(=O)C(c2ccc(CN3N=C(c4ccccc4)OCC3=O)cc2)C2CCCC2)CC1]

297.5 mg of the compound from Example 126A were initially separated by preparative HPLC into the two racemic cis and trans diastereomers [yield: 63 mg diastereomer 1, 171 mg diastereomer 2; column: Sunfire C18 OBD, 5 μm, 250 mm×20 mm; mobile phase: water/acetonitrile 30:70 (v/v); flow rate: 25 ml/min; temperature: 24° C.; UV detection: 210 nm]. These were then separated by preparative HPLC on a chiral phase into the respective enantiomers [column: Daicel Chiralpak AD-H, 250 mm×20 mm; mobile phase: ethanol/isohexane 30:70 (v/v); flow rate: 1.0 ml/min; temperature: 30° C.; UV detection: 220 nm]:

Example 127A

Diastereomer 1, Enantiomer 1

Yield: 31 mg
$R_t$ 5.63 min; purity >98.5%; >99.0% ee (Daicel column: see above)

Example 128A

Diastereomer 1, Enantiomer 2

Yield: 25 mg
$R_t$ 6.00 min; purity >99.0%; >99.0% ee (Daicel column: see above)

Example 129A

Diastereomer 2, Enantiomer 1

Yield: 77 mg
$R_t$ 5.81 min; purity >99.0%; >99.0% ee (Daicel column: see above)

Example 130A

Diastereomer 2, Enantiomer 2

Yield: 91 mg
$R_t$ 7.01 min; purity >99.8%; >99.0% ee (Daicel column: see above).

Example 131A

Methyl 4-[(cyclopentyl{4-[(5-oxo-2-phenyl-5,6-dihydro-4H-1,3,4-oxadiazin-4-yl)methyl]phenyl}acetyl)amino]-2-methyl-2,3-dihydro-1H-indene-2-carboxylate

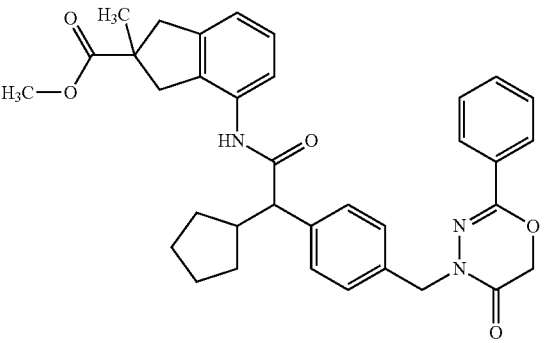 [SMILES: COC(=O)C1(C)Cc2cccc(NC(=O)C(c3ccc(CN4N=C(c5ccccc5)OCC4=O)cc3)C3CCCC3)c2C1]

A solution of 200 mg (0.97 mmol) of cyclopentyl{4-[(5-oxo-2-phenyl-5,6-dihydro-4H-1,3,4-oxadiazin-4-yl)methyl]phenyl}acetic acid (enantiomer 2, Example 77A), 459 mg (1.2 mmol) of methyl 4-amino-2-methyl-2,3-dihydro-1H-indene-2-carboxylate (Example 95A), 556 mg (1.46 mmol) of O-(7-azabenzotriazol-1-yl)-N,N,N'N'-tetramethyluronium hexafluorophosphate (HATU) and 5 ml of pyridine in 20 ml of DMF was stirred at room temperature overnight. After the reaction had ended, the reaction mixture was poured onto ice-water, the phases were separated and the aqueous phase was extracted three times with tert-butyl methyl ether. The combined organic phases were dried over sodium sulfate, and after filtration the solvent was removed to dryness under reduced pressure. The crude product obtained was purified by preparative HPLC. This gave 448 mg (0.77 mmol, 79% of theory) of a colorless oil.

LC-MS (method 11): $R_t$=1.54 min; m/z=580 (M+H)$^+$.

The compounds listed in the table below were obtained in an analogous manner:

| Example | Name/Structure/Starting materials | Analytical data |
|---|---|---|
| 132A | methyl 4-{[(4-{[2-(4-chlorophenyl)-5-oxo-5,6-dihydro-4H-1,3,4-oxadiazin-4-yl]methyl}phenyl)-(cyclopentyl)acetyl]amino}-2,3-dihydro-1H-indene-2-carboxylate<br />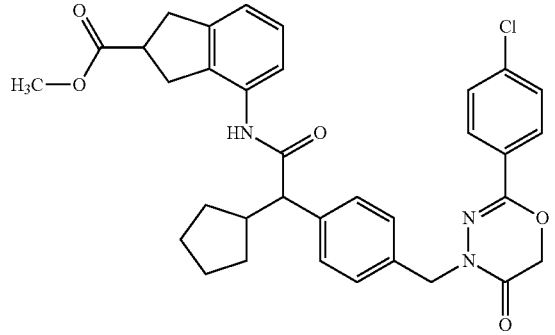 [SMILES: COC(=O)C1Cc2cccc(NC(=O)C(c3ccc(CN4N=C(c5ccc(Cl)cc5)OCC4=O)cc3)C3CCCC3)c2C1]<br />(from Ex. 72A and Ex. 88A) | $^1$H-NMR (400 MHz, DMSO-$d_6$, δ/ppm): 9.47 (1H, s), 7.76 (2H, d), 7.51 (2H, d), 7.40 (2H, d), 7.35-7.26 (3H, m), 7.05 (1H, t), 6.95 (1H, d), 4.91 (2H, s), 4.85 (2H, s), 3.62 (3H, s), 3.51 (1H, d), 3.39-3.25 (1H, m), 3.20-2.92 (4H, m), 2.61-2.41 (1H, m), 1.88-1.71 (1H, m), 1.71-1.25 (6H, m), 1.04-0.90 (1H, m).<br />LC-MS (method 10): $R_t$ = 2.65 min; m/z = 600 (M)$^+$. |
| 133A | methyl 4-{[(4-{[2-(4-fluorophenyl)-5-oxo-5,6-dihydro-4H-1,3,4-oxadiazin-4-yl]methyl}phenyl)(cyclopentyl)acetyl]amino}-2,3-dihydro-1H-indene-2-carboxylate<br />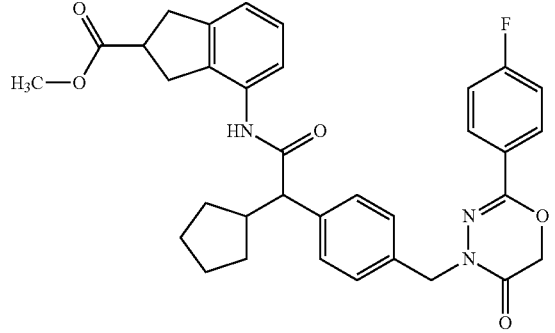 [SMILES: COC(=O)C1Cc2cccc(NC(=O)C(c3ccc(CN4N=C(c5ccc(F)cc5)OCC4=O)cc3)C3CCCC3)c2C1]<br />(from Ex. 75A and Ex. 88A) | LC-MS (method 13): $R_t$ = 2.79 min; m/z = 584 (M + H)$^+$. |
| 134A | methyl 4-[(3-methyl-2-{4-[(5-oxo-2-phenyl-5,6-dihydro-4H-1,3,4-oxadiazin-4-yl)methyl]phenyl}-butanoyl)amino]-2,3-dihydro-1H-indene-2-carboxylate<br />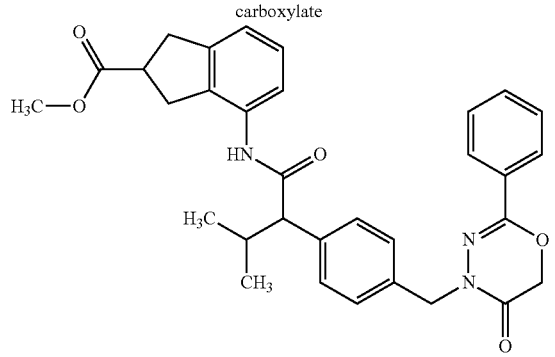<br />(from Ex. 59A and Ex. 88A) | $^1$H-NMR (400 MHz, DMSO-$d_6$, δ/ppm): 9.49 (1H, s), 7.76 (2H, d), 7.53-7.26 (8H, m), 7.05 (1H, t), 6.95 (1H, d), 4.91 (2H, s), 4.86 (2H, s), 3.62 (3H, s), 3.42-3.27 (2H, m), 3.21-2.92 (4H, m), 2.39-2.21 (1H, m), 1.02 (3H, d), 0.65 (3H, d).<br />LC-MS (method 11): $R_t$ = 1.45 min; m/z = 540 (M + H)$^+$. |

| Example | Name/Structure/Starting materials | Analytical data |
|---|---|---|
| 135A | ethyl (2E)-3-{3-[(3-methyl-2-{4-[(5-oxo-2-phenyl-5,6-dihydro-4H-1,3,4-oxadiazin-4-yl)methyl]-phenyl}butanoyl)amino]phenyl}prop-2-enoate<br>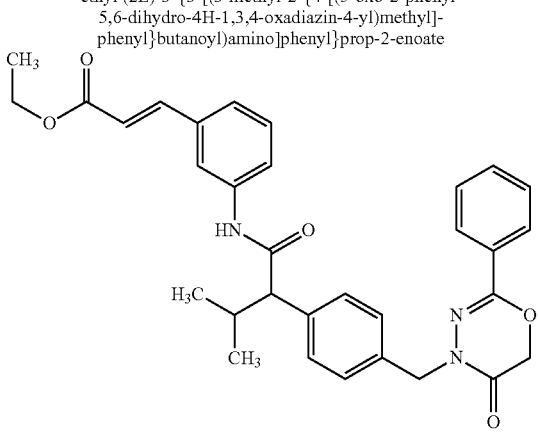<br>(from Ex. 79A and ethyl (2E)-3-(3-aminophenyl)-prop-2-enoate [CAS Reg. No. 6328-01-4]) | LC-MS (method 11):<br>$R_t$ = 1.51 min; m/z = 540 (M + H)$^+$. |
| 136A | methyl 2-methyl-4-[(3-methyl-2-{4-[(5-oxo-2-phenyl-5,6-dihydro-4H-1,3,4-oxadiazin-4-yl)methyl]phenyl}butanoyl)amino]-2,3-dihydro-1H-indene-2-carboxylate<br>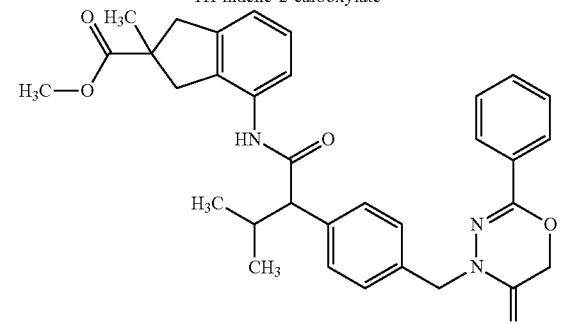<br>(from Ex. 79A and Ex. 95A) | LC-MS (method 7):<br>$R_t$ = 2.97 min; m/z = 554 (M + H)$^+$. |
| 137A | methyl ({3-[(3-methyl-2-{4-[(5-oxo-2-phenyl-5,6-dihydro-4H-1,3,4-oxadiazin-4-yl)methyl]phenyl}-butanoyl)amino]phenyl}sulfanyl)acetate<br>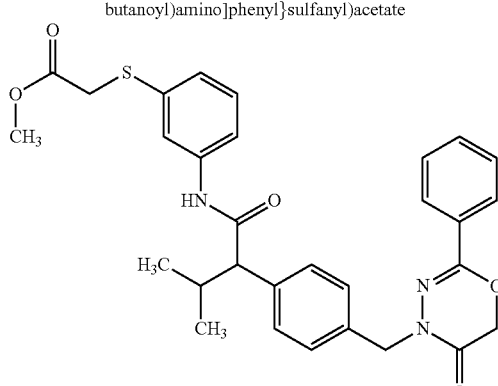<br>(from Ex. 79A and methyl [(3-aminophenyl)-sulfanyl]acetate [CAS Reg. No. 933371-82-5]) | $^1$H-NMR (400 MHz, DMSO-$d_6$, δ/ppm): 10.12 (1H, s), 7.75 (2H, d), 7.63 (1H, s), 7.54-7.28 (8H, m), 7.20 (1H, t), 6.99 (1H, d), 4.89 (2H, s), 4.84 (2H, s), 3.84 (2H, s), 3.59 (3H, s), 3.21 (1H, d), 2.40-2.24 (1H, m), 1.00 (3H, d), 0.68 (3H, d).<br>LC-MS (method 7):<br>$R_t$ = 2.88 min; m/z = 546 (M + H)$^+$. |

-continued

| Example | Name/Structure/Starting materials | Analytical data |
|---|---|---|
| 138A | methyl ({3-[(cyclopentyl{4-[(5-oxo-2-phenyl-5,6-dihydro-4H-1,3,4-oxadiazin-4-yl)methyl]phenyl}-acetyl)amino]phenyl}sulfanyl)acetate<br><br>(from Ex. 77A and methyl [(3-aminophenyl)-sulfanyl]acetate [CAS Reg. No. 933371-82-5]) | $^1$H-NMR (400 MHz, DMSO-d$_6$, δ/ppm): 10.08 (1H, s), 7.74 (2H, d), 7.61 (1H, s), 7.52-7.26 (8H, m), 7.19 (1H, t), 6.98 (1H, d), 4.88 (2H, s), 4.83 (2H, s), 3.83 (2H, s), 3.58 (3H, s), 3.31 (1H, d), 2.61-2.45 (1H, m), 1.83-1.69 (1H, m), 1.68-1.15 (6H, m), 1.03-0.85 (1H, m).<br>LC-MS (method 7):<br>R$_t$ = 3.02 min; m/z = 572 (M + H)$^+$. |
| 139A | ethylo 5-{[(cyclopentyl{4-[(5-oxo-2-phenyl-5,6-dihydro-4H-1,3,4-oxadiazin-4-yl)methyl]phenyl}-acetyl)amino]methyl}isoxazole-3-carboxylate<br><br>(from Ex. 77A and Ex. 101A) | LC-MS (method 7):<br>R$_t$ = 2.81 min; m/z = 545 (M + H)$^+$. |
| 140A | methyl 2-methyl-2-({3-[(3-methyl-2-{4-[(5-oxo-2-phenyl-5,6-dihydro-4H-1,3,4-oxadiazin-4-yl)methyl]-phenyl}butanol)amino]phenyl}sulfanyl)propanoate<br><br>(from Ex. 79A and Ex. 102A) | LC-MS (method 7):<br>R$_t$ = 3.01 min; m/z = 574 (M + H)$^+$. |

-continued

| Example | Name/Structure/Starting materials | Analytical data |
|---|---|---|
| 141A | methyl 2-({3-[(cyclopentyl{4-[(5-oxo-2-phenyl-5,6-dihydro-4H-1,3,4-oxadiazin-4-yl)methyl]phenyl}acetyl)amino]phenyl}sulfanyl)-2-methylpropanoate<br>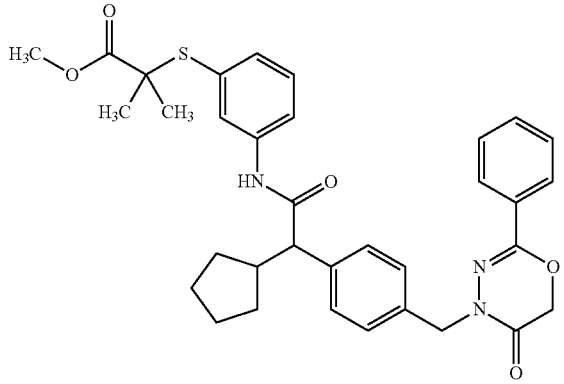<br>(from Ex. 77A and Ex. 102A) | LC-MS (method 7):<br>$R_t$ = 3.12 min; m/z = 600 (M + H)$^+$. |
| 142A | methyl 3-{3-[(3-methyl-2-{4-[(5-oxo-2-phenyl-5,6-dihydro-4H-1,3,4-oxadiazin-4-yl)methyl]phenyl}-butanoyl)amino]cyclohexyl}propanoate<br>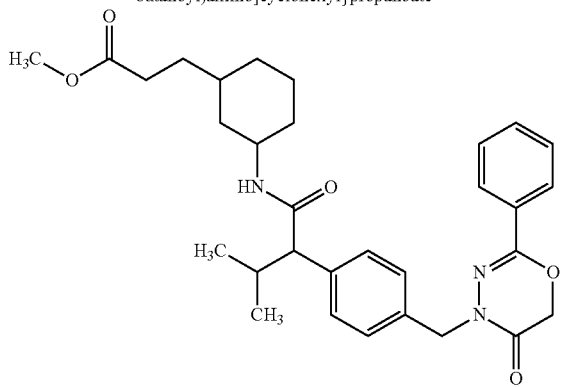<br>(from Ex. 79A and Ex. 100A) | LC-MS (method 7):<br>$R_t$ = 2.78 min; m/z = 534 (M + H)$^+$. |
| 143A | methyl 4-[(5,5,5-trifluoro-2-{4-[(5-oxo-2-phenyl-5,6-dihydro-4H-1,3,4-oxadiazin-4-yl)methyl]phenyl}pentanoyl)amino]-2,3-dihydro-1H-indene-2-carboxylate<br>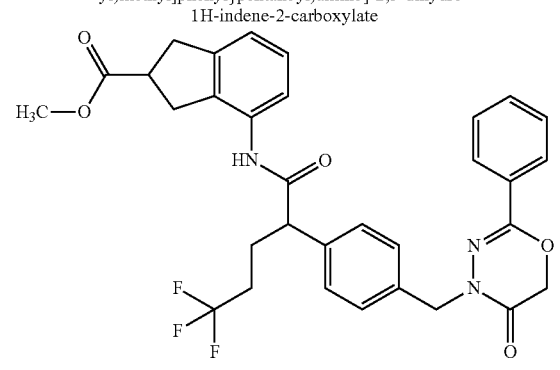<br>(from Ex. 60A and Ex. 89A) | LC-MS (method 10):<br>$R_t$ = 2.44 min; m/z = 594 (M + H)$^+$. |

| Example | Name/Structure/Starting materials | Analytical data |
|---|---|---|
| 144A | methyl 3-{trans-4-[(3-methyl-2-{4-[(5-oxo-2-phenyl-5,6-dihydro-4H-1,3,4-oxadiazin-4-yl)methyl]phenyl}butanoyl)amino]cyclohexyl}propanoate<br>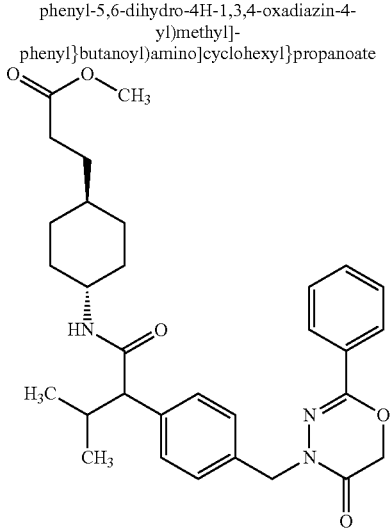<br>(from Ex. 79A and Ex. 98A) | $^1$H-NMR (400 MHz, DMSO-d$_6$, δ/ppm): 7.83 (1H, d), 7.76 (2H, d), 7.53-7.40 (3H, m), 7.32-7.22 (4H, m), 4.90 (2H, s), 4.84 (2H, s), 3.56 (3H, s), 3.41-3.28 (1H, m), 2.93 (1H, d), 2.27 (2H, t), 2.22-2.11 (1H, m), 1.87-1.75 (1H, m), 1.72-1.49 (2H, m), 1.44-1.31 (2H, m), 1.31-1.18 (2H, m), 1.18-0.95 (2H, m), 0.95-0.77 (2H, m), 0.91 (3H, d), 0.59 (3H, d).<br>LC-MS (method 11): R$_t$ = 1.41 min; m/z = 534 (M + H)$^+$. |
| 145A | methyl 3-{cis-4-[(3-methyl-2-{4-[(5-oxo-2-phenyl-5,6-dihydro-4H-1,3,4-oxadiazin-4-yl)methyl]phenyl}butanoyl)amino]cyclohexyl}propanoate<br>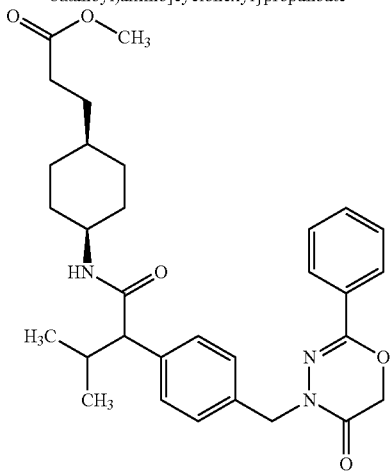<br>(from Ex. 79A and Ex. 99A) | $^1$H-NMR (400 MHz, DMSO-d$_6$, δ/ppm): 7.95 (1H, s), 7.75 (2H, d), 7.54-7.40 (3H, m), 7.35-7.21 (4H, m), 4.91 (2H, s), 4.84 (2H, s), 3.74-3.62 (1H, m), 3.57 (3H, s), 3.11 (1H, d), 2.28 (2H, t), 2.22-2.11 (1H, m), 1.61-1.19 (11H, m), 0.91 (3H, d), 0.61 (3H, d).<br>LC-MS (method 7): R$_t$ = 2.78 min; m/z = 534 (M + H)$^+$. |

| Example | Name/Structure/Starting materials | Analytical data |
| --- | --- | --- |
| 146A | ethyl 3-{3-[(3-methyl-2-{4-[(5-oxo-2-phenyl-5,6-dihydro-4H-1,3,4-oxadiazin-4-yl)methyl]phenyl}-pentanoyl)amino]phenyl}propanoate<br><br>(from Ex. 61A and ethyl 3-(3-aminophenyl)propanoate) | LC-MS (method 10):<br>$R_t$ = 2.54 min; m/z = 556 (M + H)$^+$. |
| 147A | methyl 4-[(3-methyl-2-{4-[(5-oxo-2-phenyl-5,6-dihydro-4H-1,3,4-oxadiazin-4-yl)methyl]phenyl}-pentanoyl)amino]-2,3-dihydro-1H-indene-2-carboxylate<br><br>(from Ex. 61A and Ex. 89A) | LC-MS (method 10):<br>$R_t$ = 2.45 min; m/z = 554 (M + H)$^+$. |
| 148A | methyl 3-{trans-4-[(cyclopentyl{4-[(5-oxo-2-phenyl-5,6-dihydro-4H-1,3,4-oxadiazin-4-yl)methyl]phenyl}-acetyl)amino]cyclohexyl}propanoate<br><br>(from Ex. 77A and Ex. 98A) | $^1$H-NMR (400 MHz, DMSO-$d_6$, δ/ppm): 7.80 (1H, d), 7.76 (2H, d), 7.54-7.41 (3H, m), 7.28 (4H, q), 4.91 (2H, s), 4.83 (2H, s), 3.56 (3H, s), 3.41-3.31 (1H, m), 3.08 (1H, d), 2.55-2.39 (1H, m), 2.27 (2H, t), 1.86-1.75 (1H, m), 1.75-0.78 (18H, m).<br>LC-MS (method 7):<br>$R_t$ = 2.90 min; m/z = 560 (M + H)$^+$. |

-continued

| Example | Name/Structure/Starting materials | Analytical data |
| --- | --- | --- |
| 149A | methyl 3-{cis-4-[(cyclopentyl{4-[(5-oxo-2-phenyl-5,6-dihydro-4H-1,3,4-oxadiazin-4-yl)methyl]phenyl}-acetyl)amino]cyclohexyl}propanoate<br><br>(from Ex. 77A and Ex. 99A) | $^1$H-NMR (400 MHz, DMSO-d$_6$, δ/ppm): 7.82-7.69 (3H, m), 7.54-7.40 (3H, m), 7.33 (2H, d), 7.26 (2H, d), 4.91 (2H, s), 4.84 (2H, s), 3.74-3.61 (1H, m), 3.57 (3H, s), 3.26 (1H, d), 2.55-2.39 (1H, m), 2.28 (2H, t), 1.73-1.10 (16H, m), 0.99-0.78 (3H, m).<br>LC-MS (method 7):<br>R$_t$ = 2.90 min; m/z = 560 (M + H)$^+$. |
| 150A | ethyl 4-{[(3-methyl-2-{4-[(5-oxo-2-phenyl-5,6-dihydro-4H-1,3,4-oxadiazin-4-yl)methyl]phenyl}-pentanoyl)amino]methyl}cyclohexanecarboxylate<br><br>(from Ex. 61A and ethyl 4-(aminomethyl)-cyclohexanecarboxylate (mixture of isomers; Beilstein Reg. No. 10777142)) | LC-MS (method 10):<br>R$_t$ = 2.45 min; m/z = 548 (M + H)$^+$. |
| 151A | ethyl 3-{2-methyl-3-[(3-methyl-2-{4-[(5-oxo-2-phenyl-5,6-dihydro-4H-1,3,4-oxadiazin-4-yl)methyl]phenyl}-pentanoyl)amino]phenyl}propanoate<br><br>(from Ex. 61A and Ex. 97A) | LC-MS (method 10):<br>R$_t$ = 2.49 min; m/z = 570 (M + H)$^+$. |

| Example | Name/Structure/Starting materials | Analytical data |
|---------|-----------------------------------|-----------------|
| 152A | methyl (1S,3S)-3-[(cyclopentyl{4-[(5-oxo-2-phenyl-5,6-dihydro-4H-1,3,4-oxadiazin-4-yl)methyl]phenyl}-acetyl)amino]cyclopentanecarboxylate<br><br>(from Ex. 77A and methyl (1S,3S)-3-amino-cyclopentanecarboxylate hydrochloride [CAS Reg. No. 222530-45-2]) | $^1$H-NMR (400 MHz, DMSO-$d_6$, δ/ppm): 8.00 (1H, d), 7.78 (2H, d), 7.54-7.39 (3H, m), 7.37-7.20 (4H, m), 4.91 (2H, s), 4.84 (2H, s), 4.05-3.91 (1H, m), 3.55 (3H, s), 3.08 (1H, d), 2.94-2.81 (1H, m), 2.60-2.39 (1H, m), 1.99-1.78 (3H, m), 1.75-1.10 (10H, m), 0.96-0.81 (1H, m).<br>LC-MS (method 7):<br>$R_t$ = 2.68 min; m/z = 518 (M + H)$^+$. |
| 153A | methyl (1S,3R)-3-[(cyclopentyl{4-[(5-oxo-2-phenyl-5,6-dihydro-4H-1,3,4-oxadiazin-4-yl)methyl]phenyl}-acetyl)amino]cyclopentanecarboxylate<br><br>(from Ex. 77A and methyl (1S,3R)-3-amino-cyclopentanecarboxylate hydrochloride [CAS Reg. No. 180323-49-3]) | $^1$H-NMR (400 MHz, DMSO-$d_6$, δ/ppm): 8.01 (1H, d), 7.77 (2H, d), 7.54-7.41 (3H, m), 7.29 (4H, q), 4.91 (2H, s), 4.83 (2H, s), 3.98-3.85 (1H, m), 3.59 (3H, s), 3.10 (1H, d), 2.84-2.70 (1H, m), 2.58-2.39 (1H, m), 2.23-2.10 (1H, m), 1.84-1.11 (12H, m), 0.96-0.81 (1H, m).<br>LC-MS (method 7):<br>$R_t$ = 2.69 min; m/z = 518 (M + H)$^+$. |

| Example | Name/Structure/Starting materials | Analytical data |
|---|---|---|
| 154A | methyl (1R,3R)-3-[cyclopentyl{4-[(5-oxo-2-phenyl-5,6-dihydro-4H-1,3,4-oxadiazin-4-yl)methyl]phenyl}-acetyl)amino]cyclopentanecarboxylate<br />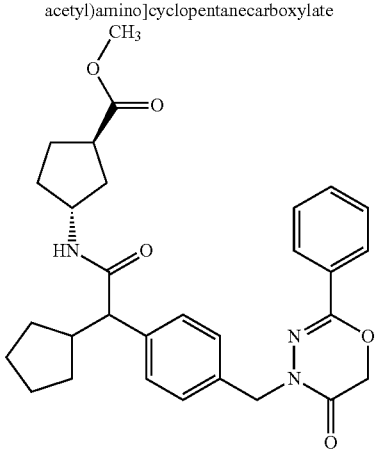<br />(from Ex. 77A and methyl (1R,3R)-3-amino-cyclopentanecarboxylate hydrochloride [CAS Reg. No. 489446-79-9]) | $^1$H-NMR (400 MHz, DMSO-d$_6$, δ/ppm): 7.99 (1H, d), 7.76 (2H, d), 7.55-7.41 (3H, m), 7.28 (4H, q), 4.91 (2H, s), 4.84 (2H, s), 4.04-3.92 (1H, m), 3.58 (3H, s), 3.09 (1H, d), 2.95-2.82 (1H, m), 2.58-2.39 (1H, m), 2.01-1.85 (2H, m), 1.84-1.12 (11H, m), 0.95-0.82 (1H, m).<br />LC-MS (method 7): R$_t$ = 2.66 min; m/z = 518 (M + H)$^+$. |
| 155A | methyl (1R,3S)-3-[cyclopentyl{4-[(5-oxo-2-phenyl-5,6-dihydro-4H-1,3,4-oxadiazin-4-yl)methyl]phenyl}-acetyl)amino]cyclopentanecarboxylate<br />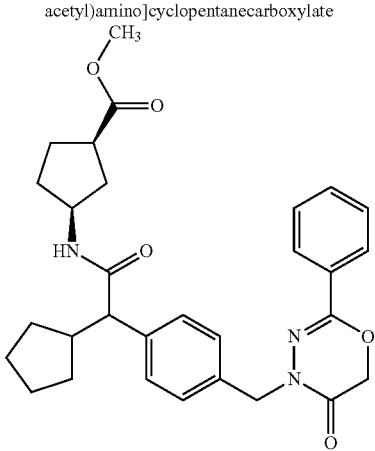<br />(from Ex. 77A and methyl (1R,3S)-3-amino-cyclopentanecarboxylate hydrochloride [CAS Reg. No. 180196-56-9]) | LC-MS (method 11): R$_t$ = 1.39 min; m/z = 518 (M + H)$^+$. |

| Example | Name/Structure/Starting materials | Analytical data |
|---|---|---|
| 156A | tert-butyl 3-{3-[(cyclopentyl{4-[(4-oxo-1,2,3-benzotriazin-3(4H)-yl)methyl]phenyl}acetyl)-amino]phenyl}propanoate<br><br>(from Ex. 56A and tert-butyl 3-(3-aminophenyl)-propanoate [Beilstein Reg. No. 10341419]) | LC-MS (method 7):<br>$R_t$ = 3.14 min; m/z = 565 $(M - H)^-$. |
| 157A | tert-butyl 3-{3-[(cyclopentyl{4-[(2-oxo-5-phenyl-1,3,4-oxadiazol-3(2H)-yl)methyl]phenyl}acetyl)-amino]phenyl}propanoate<br><br>(from Ex. 57A and tert-butyl 3-(3-aminophenyl)-propanoate [Beilstein Reg. No. 10341419]) | LC-MS (method 7):<br>$R_t$ = 3.24 min; m/z = 580 $(M - H)^-$. |
| 158A | methyl trans-4-[(cyclopentyl{4-[(5-oxo-2-phenyl-5,6-dihydro-4H-1,3,4-oxadiazin-4-yl)methyl]phenyl}-acetyl)amino]cyclohexanecarboxylate<br><br>(from Ex. 77A and methyl trans-4-amino-cyclohexanecarboxylate hydrochloride [CAS Reg. No. 61367-07-5]) | $^1$H-NMR (400 MHz, DMSO-$d_6$, δ/ppm): 7.85 (1H, d), 7.76 (2H, d), 7.53-7.40 (3H, m), 7.29 (4H, q), 4.91 (2H, s), 4.83 (2H, s), 3.68-3.55 (1H, m), 3.59 (3H, s), 3.20 (1H, d), 2.48-2.39 (1H, m), 1.88-1.73 (2H, m), 1.73-1.35 (10H, m), 1.35-1.12 (4H, m), 0.99-0.82 (1H, m).<br>LC-MS (method 7):<br>$R_t$ = 2.76 min; m/z = 532 $(M + H)^+$. |

| Example | Name/Structure/Starting materials | Analytical data |
|---|---|---|
| 159A | methyl cis-4-[(cyclopentyl{4-[(5-oxo-2-phenyl-5,6-dihydro-4H-1,3,4-oxadiazin-4-yl)methyl]phenyl}-acetyl)amino]cyclohexanecarboxylate<br>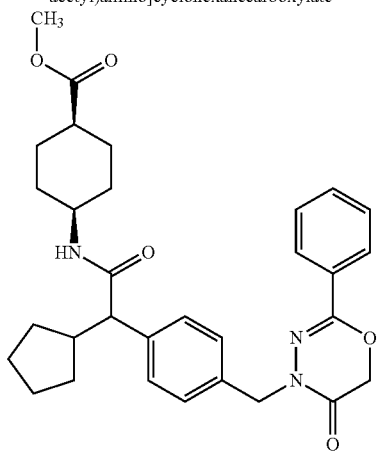<br>(from Ex. 77A and methyl cis-4-aminocyclohexanecarboxylate hydrochloride [CAS Reg. No. 61367-16-6]) | $^1$H-NMR (400 MHz, DMSO-$d_6$, δ/ppm): 7.85 (1H, d), 7.76 (2H, d), 7.54-7.41 (3H, m), 7.28 (4H, q), 4.91 (2H, s), 4.83 (2H, s), 3.56 (3H, s), 3.42-3.55 (1H, m), 3.09 (1H, d), 2.57-2.39 (1H, m), 2.29-2.16 (1H, m), 1.94-1.78 (3H, m), 1.77-1.01 (12H, m), 0.95-0.82 (1H, m).<br>LC-MS (method 7):<br>$R_t$ = 2.73 min; m/z = 532 $(M + H)^+$. |
| 160A | methyl 2-methyl-4-[(3-methyl-2-{4-[(5-oxo-2-phenyl-5,6-dihydro-4H-1,3,4-oxadiazin-4-yl)methyl]phenyl}pentanoyl)amino]-2,3-dihydro-1H-indene-2-carboxylate<br>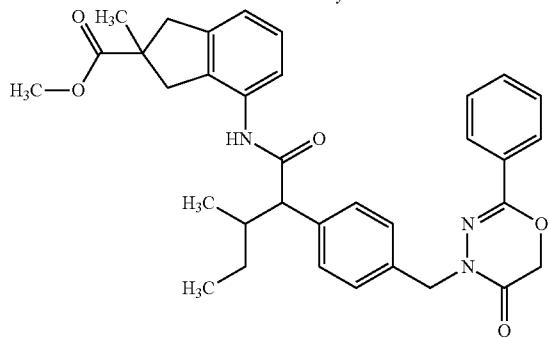<br>(from Ex. 61A and Ex. 95A) | LC-MS (method 11):<br>$R_t$ = 1.53 min; m/z = 568 $(M + H)^+$. |

| Example | Name/Structure/Starting materials | Analytical data |
|---|---|---|
| 161A | tert-butyl 3-(3-{[(4-{[3-(3-chlorophenyl)-2-oxo-imidazolidin-1-yl]methyl}phenyl)(cyclopentyl)-acetyl]amino}-2-methylphenyl)propanoate<br>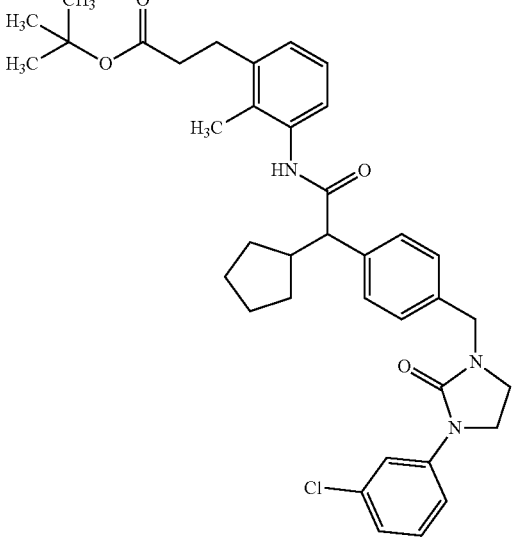<br>(from Ex. 67A and Ex. 96A) | LC-MS (method 10):<br>$R_t$ = 2.83 min; m/z = 648<br>$(M + NH_4)^+$. |
| 162A | tert-butyl 3-{3-[(cyclopentyl{4-[(3-methyl-2-oxo-imidazolidin-1-yl)methyl]phenyl}acetyl)amino]-2-methylphenyl}propanoate<br>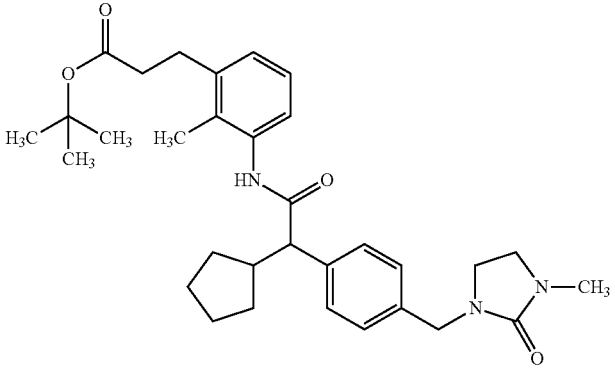 [SMILES: Cc1c(CCC(=O)OC(C)(C)C)cccc1NC(=O)C(c1ccc(CN2CCN(C)C2=O)cc1)C1CCCC1]<br>(from Ex. 66A and Ex. 96A) | LC-MS (method 11):<br>$R_t$ = 1.43 min; m/z = 551<br>$(M + NH_4)^+$. |
| 163A | tert-butyl 3-{2-methyl-3-[(3-methyl-2-{4-[(5-oxo-2-phenyl-5,6-dihydro-4H-1,3,4-oxadiazin-4-yl)methyl]-phenyl}hexanoyl)amino]phenyl}propanoate<br>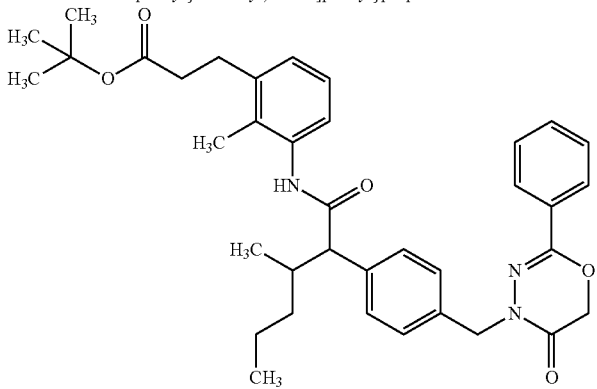<br>(from Ex. 62A and Ex. 96A) | LC-MS (method 11):<br>$R_t$ = 1.68 min; m/z = 634<br>$(M + Na)^+$, 610 $(M - H)^-$. |

| Example | Name/Structure/Starting materials | Analytical data |
|---|---|---|
| 164A | ethyl 3-{3-[(3-methyl-2-{4-[(5-oxo-2-phenyl-5,6-dihydro-4H-1,3,4-oxadiazin-4-yl)methyl]phenyl}-hexanoyl)amino]phenyl}propanoate<br>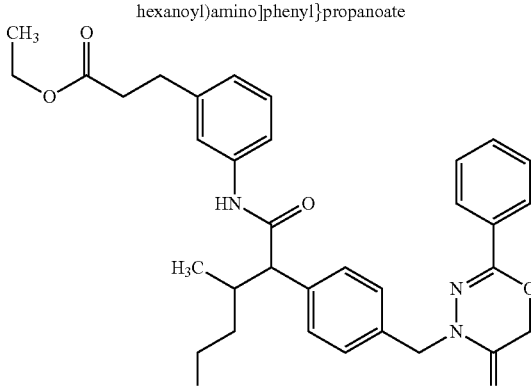<br>(from Ex. 62A and ethyl 3-(3-aminophenyl)propanoate) | LC-MS (method 7):<br>$R_t$ = 3.04 min; m/z = 570 (M + H)$^+$. |
| 165A | methyl 4-[(3-methyl-2-{4-[(5-oxo-2-phenyl-5,6-dihydro-4H-1,3,4-oxadiazin-4-yl)methyl]phenyl}-hexanoyl)amino]-2,3-dihydro-1H-indene-2-carboxylate<br>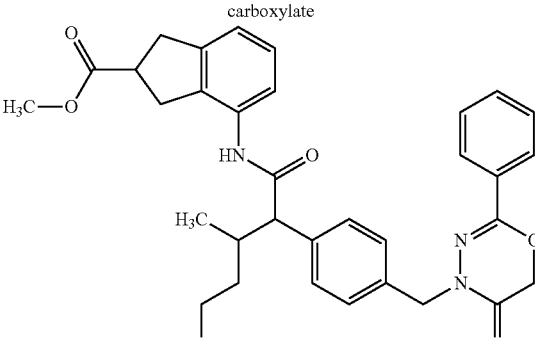<br>(from Ex. 62A and Ex. 89A) | LC-MS (method 7):<br>$R_t$ = 2.96 min; m/z = 568 (M + H)$^+$. |
| 166A | tert-butyl 3-{3-[(cyclopentyl{4-[(4-oxo-1,2,3-benzotriazin-3(4H)-yl)methyl]phenyl}acetyl)amino]-2-methylphenyl}propanoate<br>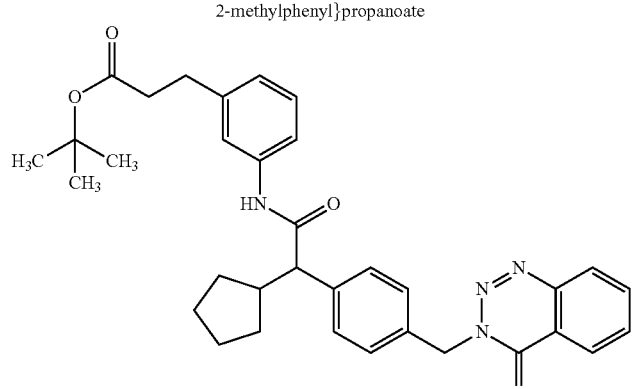<br>(from Ex. 56A and Ex. 96A) | $^1$H-NMR (400 MHz, DMSO-d$_6$, δ/ppm): 9.46 (1H, d), 8.28-8.21 (2H, m), 8.10 (1H, t), 7.95 (1H, t), 7.40 (2H, d), 7.33 (2H, d), 7.04-6.92 (3H, m), 5.57 (2H, s), 3.45 (1H, d), 2.77 (2H, t), 2.61-2.48 (1H, m), 2.41 (2H, t), 1.98 (3H, s), 1.89-1.75 (1H, m), 1.74-1.40 (4H, m), 1.40-1.28 (2H, m), 1.36 (9H, s), 1.02-0.88 (1H, m).<br>LC-MS (method 11):<br>$R_t$ = 1.57 min; m/z = 603 (M + Na)$^+$. |

| Example | Name/Structure/Starting materials | Analytical data |
|---------|-----------------------------------|-----------------|
| 167A | tert-butyl 3-{3-[(cyclopentyl{4-[(2-oxo-5-phenyl-1,3,4-oxadiazin-3(2H)-yl)methyl]phenyl}acetyl)amino]-2-methylphenyl}propanoate<br><br>(from Ex. 57A and Ex. 96A) | LC-MS (method 10):<br>$R_t$ = 2.77 min; m/z = 613 $(M + NH_4)^+$. |
| 168A | tert-butyl 3-(3-{[(4-{[3-(3-chlorophenyl)-2-oxo-imidazolidin-1-yl]methyl}phenyl)(cyclopentyl)-acetyl]amino}phenyl)propanoate<br><br>(from Ex. 67A and tert-butyl 3-(3-aminophenyl)-propanoate) | LC-MS (method 10):<br>$R_t$ = 2.86 min; m/z = 634 $(M + NH_4)^+$. |

| Example | Name/Structure/Starting materials | Analytical data |
|---|---|---|
| 169A | tert-butyl 3-{3-[(cyclopentyl{4-[(3-methyl-2-oxo-imidazolidin-1-yl)methyl]phenyl}acetyl)amino]-phenyl}propanoate<br />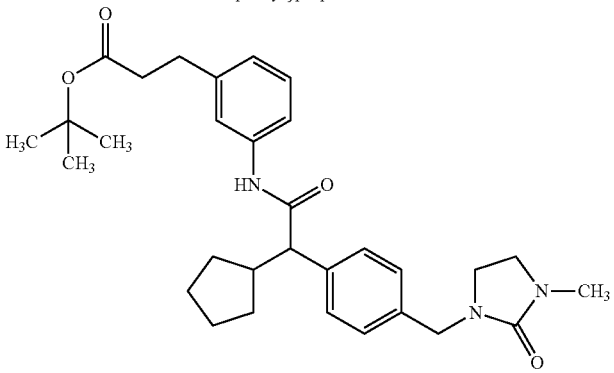<br />(from Ex. 66A and tert-butyl 3-(3-aminophenyl)-propanoate) | LC-MS (method 11):<br />$R_t$ = 1.44 min; m/z = 518 (M − H)⁻. |
| 170A | tert-butyl 3-{3-[(4-methoxy-3-methyl-2-{4-[(5-oxo-2-phenyl-5,6-dihydro-4H-1,3,4-oxadiazin-4-yl)methyl]phenyl}butanoyl)amino]-2-methylphenyl}propanoate<br />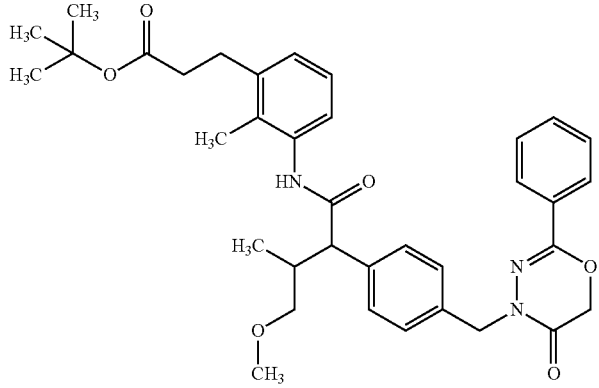 [SMILES: COCC(C)C(C(=O)Nc1cccc(CCC(=O)OC(C)(C)C)c1C)c1ccc(CN2N=C(c3ccccc3)OCC2=O)cc1]<br />(from Ex. 64A and Ex. 96A) | LC-MS (method 7):<br />$R_t$ = 2.94 min; m/z = 614 (M + H)⁺. |
| 171A | tert-butyl 3-{3-[(4-cyano-3-methyl-2-{4-[(5-oxo-2-phenyl-5,6-dihydro-4H-1,3,4-oxadiazin-4-yl)methyl]phenyl}butanoyl)amino]-2-methylphenyl}propanoate<br />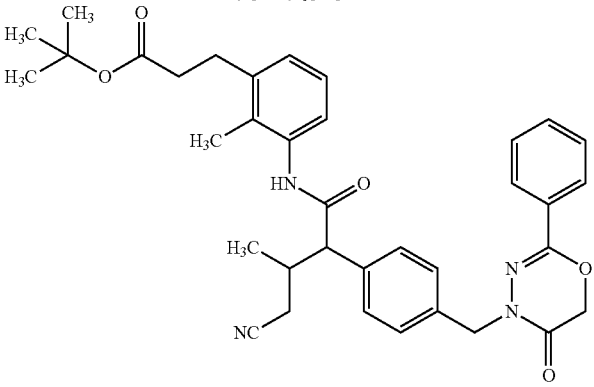<br />(from Ex. 63A and Ex. 96A) | LC-MS (method 7):<br />$R_t$ = 2.47 min; m/z = 626 (M + NH₄)⁺. |

| Example | Name/Structure/Starting materials | Analytical data |
|---|---|---|
| 172A | methyl 3-{3-[(4-cyano-3-methyl-2-{4-[(5-oxo-2-phenyl-5,6-dihydro-4H-1,3,4-oxadiazin-4-yl)methyl]phenyl}butanoyl)amino]phenyl}propanoate<br>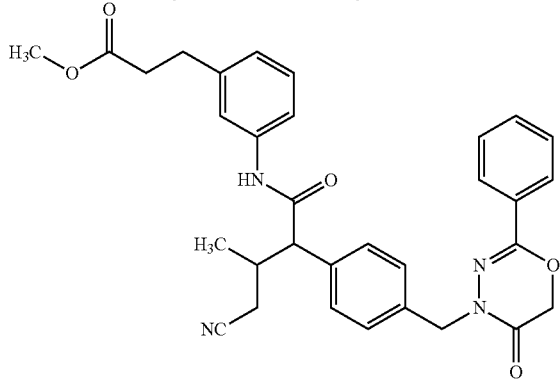 [SMILES: COC(=O)CCc1cccc(NC(=O)C(c2ccc(CN3N=C(c4ccccc4)OCC3=O)cc2)C(C)CC#N)c1]<br>(from Ex. 63A and methyl 3-(3-aminophenyl)-propanoate) | LC-MS (method 7):<br>$R_t$ = 2.58 min; m/z = 553 (M + H)$^+$. |
| 173A | methyl 4-[(4-cyano-3-methyl-2-{4-[(5-oxo-2-phenyl-5,6-dihydro-4H-1,3,4-oxadiazin-4-yl)methyl]phenyl}butanoyl)amino]-2,3-dihydro-1H-indene-2-carboxylate<br>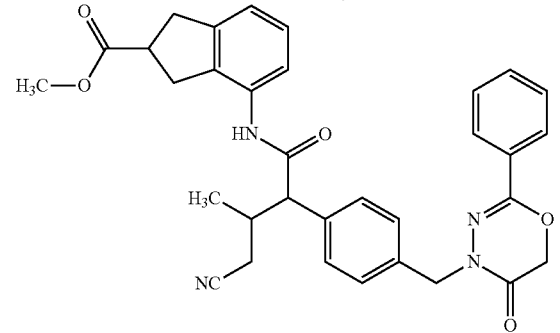 [SMILES: COC(=O)C1Cc2cccc(NC(=O)C(c3ccc(CN4N=C(c5ccccc5)OCC4=O)cc3)C(C)CC#N)c2C1]<br>(from Ex. 63A and Ex. 89A) | LC-MS (method 7):<br>$R_t$ = 2.59 min; m/z = 565 (M + H)$^+$. |
| 174A | ethyl (2E)-3-{3-[(cyclopentyl{4-[(5-oxo-2-phenyl-5,6-dihydro-4H-1,3,4-oxadiazin-4-yl)methyl]phenyl}acetyl)amino]phenyl}prop-2-enoate<br>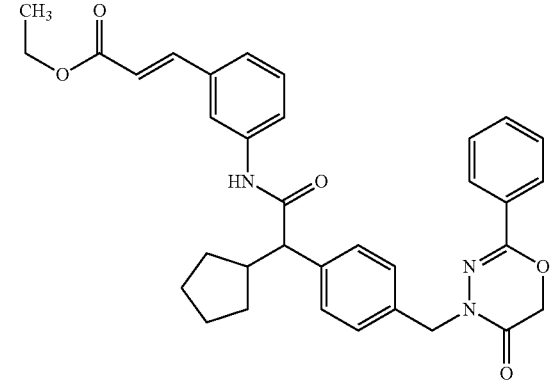 [SMILES: CCOC(=O)/C=C/c1cccc(NC(=O)C(c2ccc(CN3N=C(c4ccccc4)OCC3=O)cc2)C2CCCC2)c1]<br>(from Ex. 77A and ethyl (2E)-3-(3-aminophenyl)-prop-2-enoate) | LC-MS (method 11):<br>$R_t$ = 2.58 min; m/z = 566 (M + H)$^+$. |

-continued

| Example | Name/Structure/Starting materials | Analytical data |
|---|---|---|
| 175A | tert-butyl-3-{3-[(cyclopentyl{4-[(5-oxo-2-phenyl-5,6-dihydro-4H-1,3,4-oxadiazin-4-yl)methyl]phenyl}acetyl)amino]-2-methylphenyl}propanoate<br><br>(from Ex. 77A and Ex. 96A) | $^1$H-NMR (400 MHz, DMSO-d$_6$, δ/ppm): 9.46 (1H, d), 7.78 (2H, d), 7.55-7.38 (5H, m), 7.31 (2H, d), 7.05-6.91 (3H, m), 4.92 (2H, s), 4.86 (2H, s), 3.45 (1H, d), 2.76 (2H, t), 2.61-2.46 (1H, m), 2.40 (2H, t), 1.96 (3H, s), 1.89-1.76 (1H, m), 1.75-1.28 (6H, m), 1.35 (9H, s), 1.06-0.81 (1H, m).<br>LC-MS (method 10): R$_t$ = 2.79 min; m/z = 632 (M + Na)$^+$. |
| 176A | ethyl (2E)-3-{4-[(3-methyl-2-{4-[(5-oxo-2-phenyl-5,6-dihydro-4H-1,3,4-oxadiazin-4-yl)methyl]phenyl}butanoyl)amino]phenyl}prop-2-enoate<br><br>(from Ex. 79A and ethyl (2E)-3-(4-aminophenyl)-prop-2-enoate) | LC-MS (method 11): R$_t$ = 1.50 min; m/z = 540 (M + H)$^+$. |
| 177A | methyl 2-{3-[(cyclopentyl{4-[(5-oxo-2-phenyl-5,6-dihydro-4H-1,3,4-oxadiazin-4-yl)methyl]phenyl}-acetyl)amino]-2-methylphenoxy}-2-methylpropanoate<br><br>(from Ex. 77A and Ex. 104A) | LC-MS (method 7): R$_t$ = 3.05 min; m/z = 598 (M + H)$^+$. |

| Example | Name/Structure/Starting materials | Analytical data |
|---|---|---|
| 178A | ethyl (2E)-3-{3-[(2-{4-[(2-tert-butyl-5-oxo-5,6-dihydro-4H-1,3,4-oxadiazin-4-yl)methyl]phenyl}-3-methylbutanoyl)amino]phenyl}prop-2-enoate<br>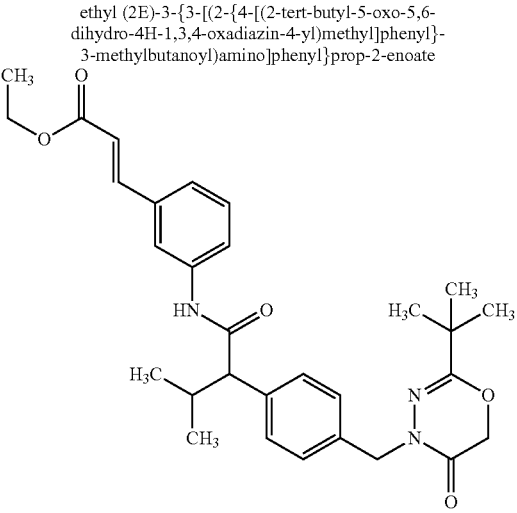<br>(from Ex. 58A and ethyl (2E)-3-(3-aminophenyl)-prop-2-enoate) | LC-MS (method 7):<br>$R_t$ = 3.08 min; m/z = 520 (M + H)$^+$. |
| 179A | ethyl 4-{3-[(cyclopentyl{4-[(5-oxo-2-phenyl-5,6-dihydro-4H-1,3,4-oxadiazin-4-yl)methyl]phenyl}-acetyl)amino]phenyl}butanoate<br>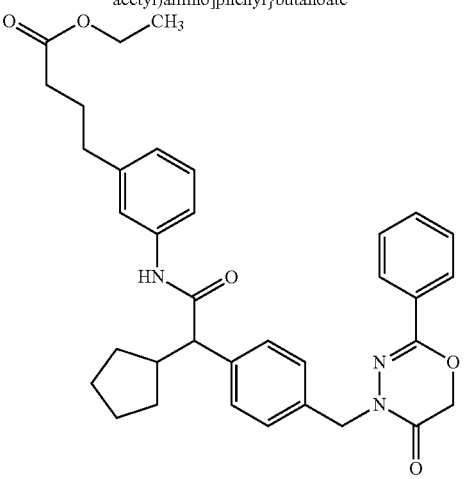<br>(from Ex. 77A and ethyl 4-(3-aminophenyl)butanoate [Beilstein Reg.No. 1043134]) | LC-MS (method 7):<br>$R_t$ = 3.16 min; m/z = 582 (M + H)$^+$. |

-continued

| Example | Name/Structure/Starting materials | Analytical data |
|---|---|---|
| 180A | ethyl 3-{3-[(cyclopentyl{4-[(5-oxo-2-phenyl-5,6-dihydro-4H-1,3,4-oxadiazin-4-yl)methyl]phenyl}-acetyl)amino]phenyl}propanoate<br><br>(from Ex. 77A and ethyl 3-(3-aminophenyl)propanoate) | LC-MS (method 7):<br>$R_t$ = 3.03 min; m/z = 568 $(M + H)^+$. |
| 181A | methyl 2-{3-[(cyclopentyl{4-[(5-oxo-2-phenyl-5,6-dihydro-4H-1,3,4-oxadiazin-4-yl)methyl]phenyl}-acetyl)amino]phenyl}-2-methylpropanoate<br><br>(from Ex. 77A and methyl 2-(3-aminophenyl)-2-methylpropanoate) | LC-MS (method 11):<br>$R_t$ = 1.55 min; m/z = 568 $(M + H)^+$. |

Example 182A

[4-(Bromomethyl)phenyl](cyclopentyl)acetic acid

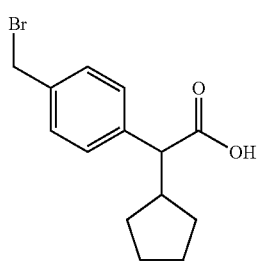 [SMILES: O=C(O)C(c1ccc(CBr)cc1)C1CCCC1]

1.635 ml (2.420 g, 21.228 mmol) of trifluoroacetic acid were added to a solution of 500 mg (1.415 mmol) of tert-butyl [4-(bromomethyl)phenyl](cyclopentyl)acetate (Example 10A) in 5 ml of dichloromethane. The mixture was stirred at room temperature for 2 h. Saturated aqueous sodium bicarbonate solution was then added, and the mixture was extracted with ethyl acetate. The combined organic phases were dried over sodium sulfate and concentrated under reduced pressure. This gave 364 mg (87% of theory) of the title compound.

LC-MS (method 10): $R_t$=2.09 min; m/z=295 $(M-H)^-$.

Example 183A

[4-(Bromomethyl)phenyl](cyclopentyl)acetyl chloride

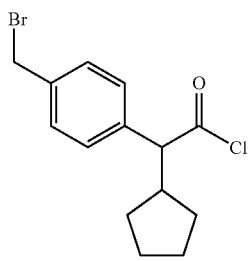 [SMILES: O=C(Cl)C(c1ccc(CBr)cc1)C1CCCC1]

246 mg (0.766 mmol) of [4-(bromomethyl)phenyl](cyclopentyl)acetic acid were dissolved in 5 ml of thionyl chloride, and the mixture was stirred at room temperature for 1 h and then at 50° C. for 1 h. The mixture was then concentrated under reduced pressure. This gave 253 mg of the title compound, which was reacted without further purification in the next step.

Example 184A

Methyl 4-({[4-(bromomethyl)phenyl](cyclopentyl)acetyl}amino)-2,3-dihydro-1H-indene-2-carboxylate

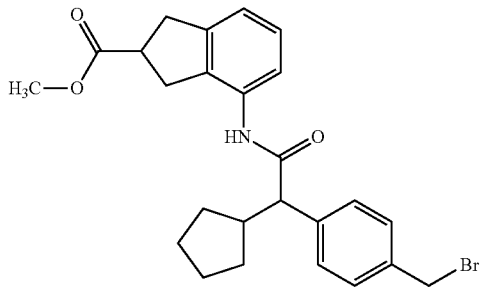 [SMILES: COC(=O)C1Cc2cccc(NC(=O)C(c3ccc(CBr)cc3)C3CCCC3)c2C1]

235 mg (1.228 mmol) of methyl 4-amino-2,3-dihydro-1H-indene-2-carboxylate (racemic; Example 88A) were dissolved in 10 ml of THF, and 428 mg (4.911 mmol) of N,N-diisopropylethylamine and 388 mg (1.228 mmol) of [4-(bromomethyl)phenyl](cyclopentyl)acetyl chloride were added at 0° C. The mixture was stirred at 0° C. for 30 min. Saturated aqueous sodium bicarbonate solution was then added, and the mixture was extracted with ethyl acetate. The combined organic phases were dried over sodium sulfate and concentrated on a rotary evaporator. This gave 577 mg of the title compound.

LC-MS (method 13): $R_t$=2.72 min; m/z=470 (M+H)$^+$.

Example 185A

Methyl 4-{[cyclopentyl(4-{[2-(2-methylpropyl)-5-oxo-5,6-dihydro-4H-1,3,4-oxadiazin-4-yl]methyl}phenyl)acetyl]amino}-2,3-dihydro-1H-indene-2-carboxylate

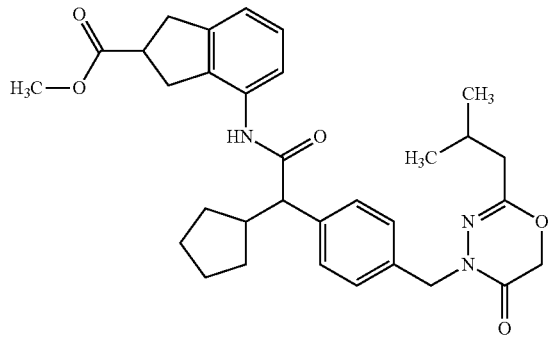 [SMILES: COC(=O)C1Cc2cccc(NC(=O)C(c3ccc(CN4N=C(CC(C)C)OCC4=O)cc3)C3CCCC3)c2C1]

100 mg (0.213 mmol) of methyl 4-({[4-(bromomethyl)phenyl](cyclopentyl)acetyl}amino)-2,3-dihydro-1H-indene-2-carboxylate were dissolved in 3.5 ml of DMF, and 55 mg (0.213 mmol) of 2-(2-methylpropyl)-4H-1,3,4-oxadiazin-5(6H)-one (Example 22A) and 76 mg (0.234 mmol) of cesium carbonate were added. The reaction mixture was stirred at room temperature for 3 d. The reaction mixture was then concentrated under reduced pressure, and the residue was purified by preparative HPLC. This gave 8 mg (8% of theory) of the title compound.

LC-MS (method 7): $R_t$=3.07 min; m/z=546 (M−H)$^−$.

Example 186A

Ethyl 3-{4-[(3-methyl-2-{4-[(5-oxo-2-phenyl-5,6-dihydro-4H-1,3,4-oxadiazin-4-yl)methyl]phenyl}butanoyl)amino]phenyl}propanoate

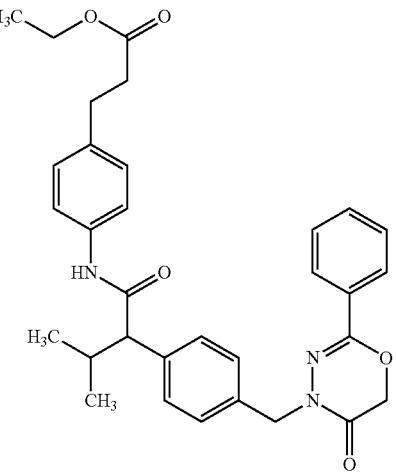

41 mg (0.076 mmol) of ethyl (2E)-3-{4-[(3-methyl-2-{4-[(5-oxo-2-phenyl-5,6-dihydro-4H-1,3,4-oxadiazin-4-yl)methyl]phenyl}butanoyl)amino]phenyl}prop-2-enoate (Example 176A) were dissolved in 17 ml of ethanol, and 75 mg of palladium on carbon (10%) were added. Under an atmosphere of hydrogen, the mixture was hydrogenated at atmospheric pressure for 2 h. The reaction mixture was then filtered through Celite, and the filtrate was concentrated under reduced pressure. This gave 39 mg (95% of theory) of the title compound.

LC-MS (method 10): $R_t$=2.46 min; m/z=542 (M+H)$^+$.

Example 187A

Methyl 3-{3-[(cyclopentyl{4-[(5-oxo-2-phenyl-5,6-dihydro-4H-1,3,4-oxadiazin-4-yl)methyl]phenyl}acetyl)amino]cyclohexyl}propanoate

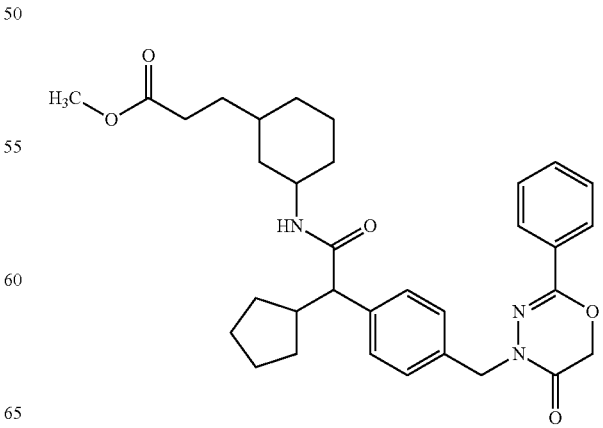

A solution of 590 mg (1.5 mmol) of cyclopentyl{4-[(5-oxo-2-phenyl-5,6-dihydro-4H-1,3,4-oxadiazin-4-yl)methyl]phenyl}acetic acid (enantiomer 2; Example 77A), 400 mg (1.8 mmol) of methyl 3-(3-aminocyclohexyl)propanoate hydrochloride (mixture of isomers), 1.05 ml (6.0 mmol) of N,N-diisopropylethylamine and 857 mg (2.26 mmol) of O-(7-azabenzotriazol-1-yl)-N,N,N',N'-tetramethyluronium hexafluorophosphate (HATU) in 13 ml of DMF was stirred at room temperature overnight. After the reaction had ended, the reaction mixture was poured onto ice-water, whereupon the target compound precipitated in the form of white crystals. After filtration, the crystals obtained were washed three times with water and then dried overnight at 40° C. in a vacuum drying cabinet. This gave 830 mg (1.58 mol, 98% of theory) of the title compound as a mixture of diastereomers.

LC-MS (method 7): $R_t$=2.90 and 2.92 min; m/z=560 (M+H)$^+$.

Examples 188A-191A

Methyl 3-{3-[(cyclopentyl{4-[(5-oxo-2-phenyl-5,6-dihydro-4H-1,3,4-oxadiazin-4-yl)methyl]phenyl}acetyl)amino]cyclohexyl}propanoate (isomers 1-4)

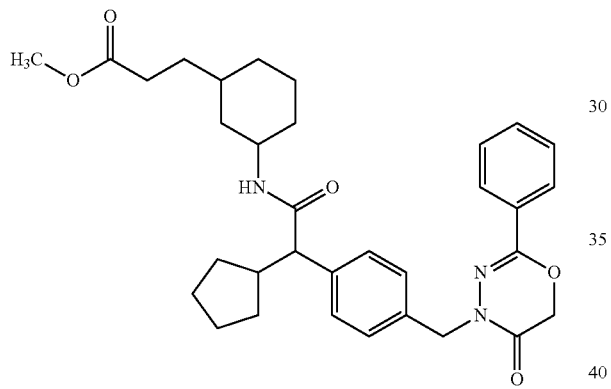

830 mg (1.58 mmol) of the methyl 3-{3-[(cyclopentyl{4-[(5-oxo-2-phenyl-5,6-dihydro-4H-1,3,4-oxadiazin-4-yl)methyl]phenyl}acetyl)amino]cyclohexyl}propanoate obtained as a mixture of diastereomers (Example 187A) were separated further by preparative HPLC on a chiral phase [column: Daicel Chiralpak AD-H, 5 μm, 250 mm×20 mm; mobile phase: isohexane/ethanol 60:40 (v/v); flow rate: 15 ml/min; temperature: 40° C.; UV detection: 220 nm]. This gave four diastereomers in isomerically pure form as colorless solids (see Examples 188A-191A).

Example 188A

Diastereomer 1

$R_t$ 6.63 min; purity >95%; >99% ee (column: see above)
Yield: 36 mg
LC-MS (method 11): $R_t$=1.50 min; m/z=560 (M+H)$^+$.

Example 189A

Diastereomer 2

$R_t$ 6.98 min; purity >99%; >96% ee (column: see above)
Yield: 36 mg
LC-MS (method 11): $R_t$=1.49 min; m/z=560 (M+H)$^+$.

Example 190A

Diastereomer 3

$R_t$ 7.39 min; purity >99%; >99% ee (column: see above)
Yield: 295 mg
LC-MS (method 7): $R_t$=2.89 min; m/z=560 (M+H)$^+$.

Example 191A

Diastereomer 4

$R_t$ 8.48 min; purity >99%; >99% ee
Yield: 307 mg
LC-MS (method 7): $R_t$=2.92 min; m/z=560 (M+H)$^+$.

Example 192A

Methyl (2E)-3-{2-[(3-methyl-2-{4-[(5-oxo-2-phenyl-5,6-dihydro-4H-1,3,4-oxadiazin-4-yl)-methyl]phenyl}butanoyl)amino]phenyl}prop-2-enoate

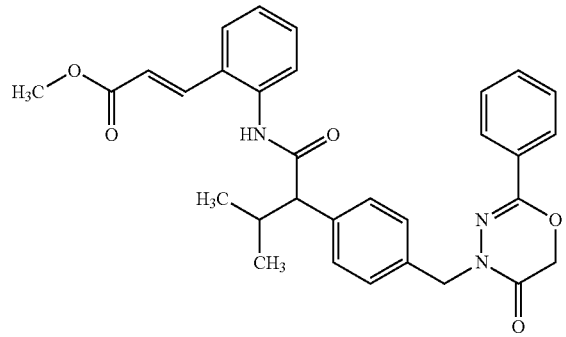 [SMILES: COC(=O)/C=C/c1ccccc1NC(=O)C(c1ccc(CN2N=C(c3ccccc3)OCC2=O)cc1)C(C)C]

A solution of 50 mg (0.14 mmol) of 3-methyl 2-{4-[(5-oxo-2-phenyl-5,6-dihydro-4H-1,3,4-oxadiazin-4-yl)methyl]phenyl}butanoic acid (enantiomer 2; Example 79A), 20 mg (0.11 mmol) of methyl (2E)-3-(2-aminophenyl)prop-2-enoate, 1.5 ml of pyridine and 65 mg (0.17 mmol) of O-(7-azabenzotriazol-1-yl)-N,N,N'N'-tetramethyluronium hexafluorophosphate (HATU) in 5 ml of DMF was stirred at room temperature overnight. After the reaction had ended, the reaction mixture was poured onto ice-water, the phases were separated and the aqueous phase was extracted three times with tert-butyl methyl ether. The combined organic phases were dried over sodium sulfate, and after filtration the solvent was removed to dryness under reduced pressure. The crude product obtained was purified by preparative HPLC. This gave 7 mg (0.01 mmol, 9.8% of theory) of a colorless oil.

LC-MS (method 11): $R_t$=1.38 min; m/z=526 (M+H)$^+$.

Example 193A

Ethyl 3-{3-[(3-methyl-2-{4-[(5-oxo-2-phenyl-5,6-dihydro-4H-1,3,4-oxadiazin-4-yl)methyl]-phenyl}butanoyl)amino]phenyl}propanoate

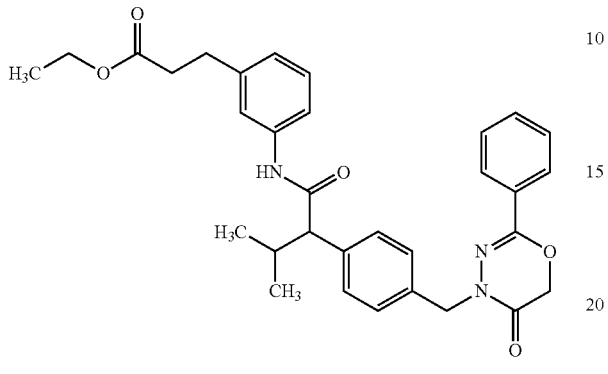

130 mg (0.24 mmol) of ethyl (2E)-3-{3-[(3-methyl-2-{4-[(5-oxo-2-phenyl-5,6-dihydro-4H-1,3,4-oxadiazin-4-yl)methyl]phenyl}butanoyl)amino]phenyl}prop-2-enoate (Example 135A) were dissolved in 10 ml of ethanol, and 10 mg of palladium on carbon (10%) were added. Under an atmosphere of hydrogen, the mixture was hydrogenated at atmospheric pressure overnight. The reaction mixture was then filtered through Celite and the filtrate was concentrated under reduced pressure. This gave 118 mg (0.22 mmol, 90% of theory) of the title compound.

LC-MS (method 11): $R_t$=1.48 min; m/z=542 (M+H)$^+$.

Example 194A tert-Butyl(+/−)-{4-[(acetyloxy)methyl]phenyl}(cyclopentyl)acetate

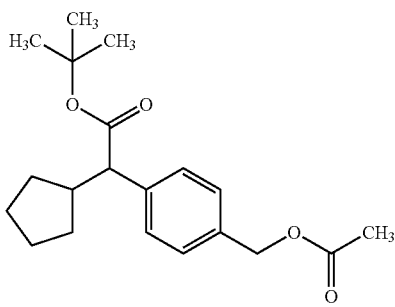 [SMILES: CC(=O)OCc1ccc(C(C(=O)OC(C)(C)C)C2CCCC2)cc1]

20.0 g (75% pure, 42.5 mmol) of tert-butyl(+/−)-[4-(bromomethyl)phenyl](cyclopentyl)acetate were added to a suspension of 16.3 g (84.9 mmol) of cesium acetate in 80 ml of DMF. The resulting mixture was heated at 50° C. for 1.5 h. After cooling, the mixture was diluted with ethyl acetate, washed successively with water and saturated sodium chloride solution, dried over magnesium sulfate and concentrated under reduced pressure. The crude product was purified by chromatography on silica gel (mobile phase cyclohexane/ethyl acetate 40:1→about 10:1). This gave 11.7 g (76.4% of theory) of the title compound.

GC-MS (method 3): $R_t$=7.16 min; no ionization.
MS (DCI): m/z=350 (M+NH$_4$)$^+$.
$^1$H-NMR (400 MHz, DMSO-d$_6$): δ=7.35-7.29 (m, 4H), 5.07 (s, 2H), 3.21 (d, 1H), 2.45-2.37 (m, 1H), 2.07 (s, 3H), 1.98-1.88 (m, 1H), 1.65-1.38 (m, about 4H), 1.37 (s, 9H), 1.30-1.18 (m, 2H), 1.01-0.92 (m, 1H).

Example 195A (+/−)-{4-[(Acetyloxy)methyl]phenyl}(cyclopentyl)acetic acid

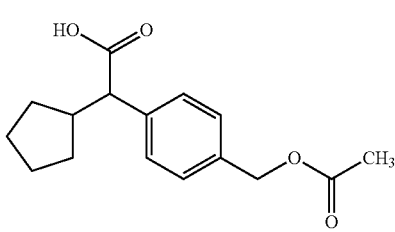 [SMILES: CC(=O)OCc1ccc(C(C(=O)O)C2CCCC2)cc1]

13.27 g (37.2 mmol, 95% pure) of tert-butyl(+/−)-{4-[(acetyloxy)methyl]phenyl}(cyclopentyl)acetate were dissolved in 117 ml of dichloromethane, the mixture was cooled to 0° C. and 58.4 ml of trifluoroacetic acid were added. The reaction mixture was initially stirred at 0° C. for 1.5 h and then at RT for a further 1.5 h. The mixture was then concentrated under reduced pressure and the residue was dried under high vacuum. The residue was taken up in 50 ml of dichloromethane, and the solution was washed four times with water. The organic phase was dried over magnesium sulfate and concentrated under reduced pressure. Drying under high vacuum gave 11.41 g of the title compound which were used without further purification for the next reaction.

LC-MS (method 10): $R_t$=1.88 min; m/z=275 (M−H)$^-$.
$^1$H-NMR (400 MHz, DMSO-d$_6$): δ=7.35-7.28 (m, 4H), 5.03 (s, 2H), 3.24 (d, 1H), 2.48-2.40 (m, 1H), 2.05 (s, 3H), 1.90-1.80 (m, 1H), 1.65-1.20 (m, about 6H), 0.98-0.90 (m, 1H).

Example 196A tert-Butyl(+/−)-3-(3-{[{4-[(acetyloxy)methyl]phenyl}(cyclopentyl)acetyl]amino}-2-methyl-phenyl)propanoate

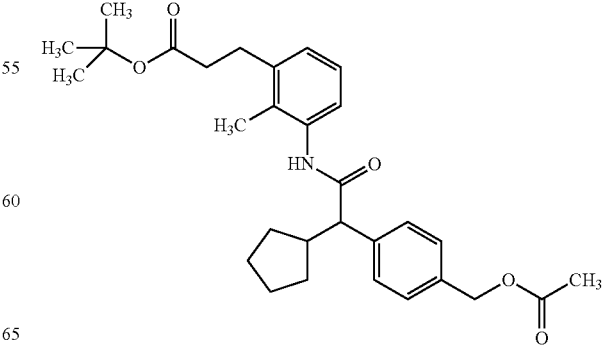

11.41 g (90% pure, 37.16 mmol) of (+/−)-{4-[(acetyloxy)methyl]phenyl}(cyclopentyl)acetic acid were dissolved in a mixture of 71.8 ml of DMF and 22.5 ml of pyridine, and 15.54 g (40.88 mmol) of 1-[bis(dimethylamino)methylene]-5-chloro-3-oxy-1H-benzotriazol-1-ium tetrafluoroborate and 8.75 g (37.16 mmol) of tert-butyl 3-(3-amino-2-methylphenyl)propanoate were added. The reaction mixture was stirred at RT overnight and then concentrated under high vacuum. The residue was taken up in 100 ml of ethyl acetate and washed successively with 10% strength aqueous citric acid, saturated sodium bisulfate solution and saturated sodium chloride solution. The organic phase was dried over magnesium sulfate and concentrated under reduced pressure. The crude product was purified by chromatography on silica gel (mobile phase cyclohexane/ethyl acetate 10:1→3:1). This gave 16.36 g (89.2% of theory) of the title compound.

LC-MS (method 11): $R_t$=1.52 min; m/z=511 (M+NH$_4$)$^+$.

$^1$H-NMR (400 MHz, DMSO-d$_6$): δ=9.98 (s, 1H), 7.42 (d, 2H), 7.32 (d, 2H), 7.05-6.96 (m, 3H), 5.05 (s, 2H), 3.48 (d, 1H), 2.70 (t, 2H), 2.64-2.55 (m, 1H), 2.42 (t, 2H), 2.08 (s, 3H), 2.02 (s, 3H), 1.90-1.80 (m, 1H), 1.72-1.45 (m, about 5H), 1.38 (s, 9H), 1.02-0.95 (m, 1H).

Example 197A tert-Butyl(+/−)-3-[3-({cyclopentyl[4-(hydroxymethyl)phenyl]acetyl}amino)-2-methylphenyl]propanoate

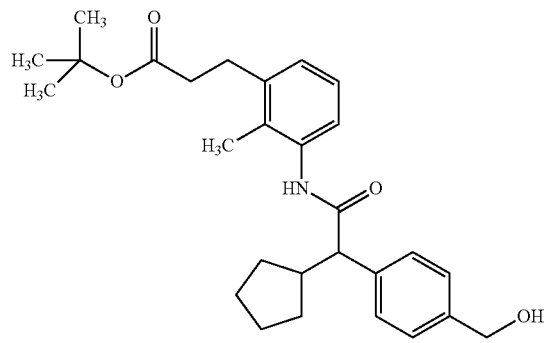 [SMILES: Cc1c(CCC(=O)OC(C)(C)C)cccc1NC(=O)C(c1ccc(CO)cc1)C1CCCC1]

16.0 g (32.41 mmol) of tert-butyl(+/−)-3-(3-{[{4-[(acetyloxy)methyl]phenyl}(cyclopentyl)-acetyl]amino}-2-methylphenyl)propanoate were dissolved in 300 ml of a 2 M solution of ammonia in methanol and initially stirred at 30-40° C. for 2 h and then overnight at RT. The solution was then concentrated under reduced pressure and the residue was purified by chromatography on silica gel (mobile phase dichloromethane/methanol 100:1). This gave 13.6 g (93.1% of theory) of the title compound.

LC-MS (method 11): $R_t$=1.37 min; m/z=452 (M+H)$^+$.

$^1$H-NMR (400 MHz, DMSO-d$_6$): δ=9.95 (s, 1H), 7.37 (d, 2H), 7.27 (d, 2H), 7.05-6.96 (m, 3H), 5.13 (t, 1H), 4.47 (d, 2H), 3.45 (d, 1H), 2.79 (t, 2H), 2.62-2.52 (m, 1H), 2.42 (t, 2H), 2.01 (s, 3H), 1.90-1.80 (m, 1H), 1.73-1.40 (m, 4H), 1.38 (s, 9H), 1.02-0.95 (m, 1H).

Example 198A tert-butyl(+/−)-3-[3-({[4-(bromomethyl)phenyl](cyclopentyl)acetyl}amino)-2-methylphenyl]propanoate

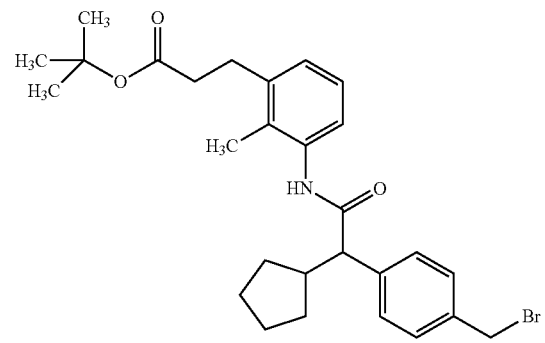 [SMILES: Cc1c(CCC(=O)OC(C)(C)C)cccc1NC(=O)C(c1ccc(CBr)cc1)C1CCCC1]

6.0 g (13.29 mmol) of tert-butyl(+/−)-3-[3-({cyclopentyl[4-(hydroxymethyl)phenyl]acetyl}amino)-2-methylphenyl]propanoate were dissolved in 375 ml of dry THF, and 9.25 g (27.9 mmol) of carbon tetrabromide were added. Over a period of 1.5 h, 9.06 g (34.54 mmol) of triphenylphosphine were then added in small portions. The reaction mixture was stirred at RT for 5 h, and the solid was then filtered off and the filtrate was concentrated. The residue was purified by chromatography on silica gel (mobile phase cyclohexane/ethyl acetate 5:1→1:1). This gave 7.22 g (about 100% of theory, purity about 95%) of the title compound.

LC-MS (method 7): $R_t$=3.07 min; m/z=514/516 (M+H)$^+$.

$^1$H-NMR (400 MHz, DMSO-d$_6$): δ=9.99 (s, 1H), 7.42-7.38 (m, 4H), 7.05-6.95 (m, 3H), 4.70 (d, 2H), 3.48 (d, 1H), 3.30-3.25 (m, about 1H), 2.70 (t, 2H), 2.64-2.53 (m, 1H), 2.41 (t, 2H), 2.01 (s, 3H), 1.90-1.80 (m, 1H), 1.73-1.40 (m, 4H), 1.35 (s, 9H), 1.02-0.93 (m, 1H).

Example 199A (1R,2S,5R)-5-Methyl-2-(propan-2-yl)cyclohexyl(4-methylphenyl)acetate

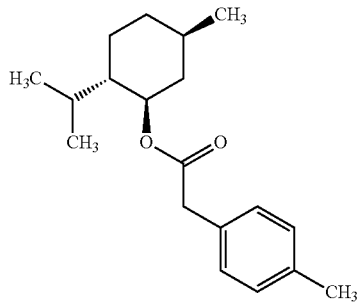

303.7 g (2022.46 mmol) of (4-methylphenyl)acetic acid and 301 g (1926.2 mmol) of (1R,2S,5R)-5-methyl-2-(propan-2-yl)cyclohexanol were initially charged in 933 ml of toluene, 2.5 ml (38.5 mmol) of methanesulfonic acid were added and the mixture was heated at reflux on a water separator overnight. The reaction solution was then allowed to cool, and a mixture of 30 ml of 45% strength aqueous sodium hydroxide solution and 400 ml of water was added. After 30 min the phases were separated. The organic phase was dried over sodium sulfate, filtered and concentrated on a rotary evaporator. This gave 569.5 g (97% of theory) of the title compound.

$^1$H-NMR (500 MHz, DMSO-d$_6$): δ=7.12 (s, 4H), 4.56 (td, 1H), 3.57 (s, 2H), 2.50 (br. s, 1H), 2.27 (s, 3H), 1.84 (d, 1H), 1.77-1.70 (m, 1H), 1.66-1.57 (m, 2H), 1.48-1.37 (m, 1H), 1.32 (t, 1H), 1.10-0.89 (m, 2H), 0.86 (d, 3H), 0.81 (d, 3H), 0.65 (d, 3H).

Example 200A (1R,2S,5R)-5-Methyl-2-(propan-2-yl)cyclohexyl (2S)-cyclopentyl(4-methylphenyl)ethanoate

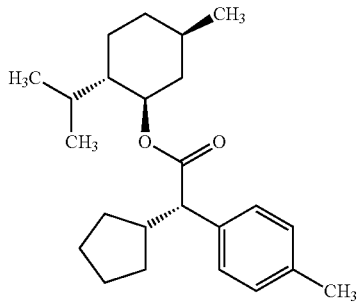 [SMILES: Cc1ccc([C@@H](C(=O)O[C@@H]2C[C@H](C)CC[C@H]2C(C)C)C2CCCC2)cc1]

Under argon, 442.73 g (3945.5 mmol) of potassium tert-butoxide were initially charged in 1230 ml of DMF at −10° C., and 569 g (1972.7 mmol) of (1R,2S,5R)-5-methyl-2-(propan-2-yl)cyclohexyl-(4-methylphenyl)acetate were added a little at a time. 352.81 g (2367.8 mmol) of bromocyclopentane were then added dropwise, the reaction temperature being maintained between −5° C. and −10° C. After 90 min at −10° C., 1.6 liters of water were added and the mixture was stirred at RT for 15 min. 1.2 liters of ethyl acetate were then added, the mixture was stirred for a further 15 min and the phases were then separated. The organic phase was dried over sodium sulfate, filtered and concentrated on a rotary evaporator. The crude product was recrystallized from 2 liters of methanol at 50° C. This gave 423.0 g (60% of theory) of the title compound.

$^1$H-NMR (400 MHz, DMSO-d$_6$): δ=7.19 (d, 2H), 7.11 (d, 2H), 4.55 (td, 1H), 3.26 (d, 1H), 2.27 (s, 3H), 1.83-1.73 (m, 2H), 1.68-1.24 (m, 11H), 1.23-1.13 (m, 1H), 1.04-0.94 (m, 2H), 0.88-0.77 (m, 8H), 0.66 (d, 3H).

Example 201A (1R,2S,5R)-5-Methyl-2-(propan-2-yl)cyclohexyl (2S)-[4-(bromomethyl)phenyl](cyclopentyl)ethanoate

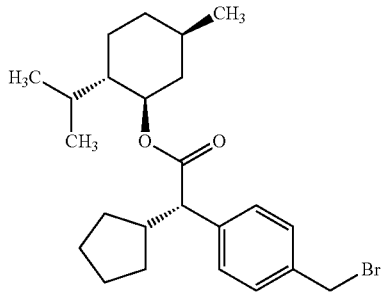 [SMILES: CC(C)[C@@H]1CC[C@@H](C)C[C@H]1OC(=O)[C@H](c1ccc(CBr)cc1)C1CCCC1]

The title compound can be prepared according to U.S. Pat. No. 5,714,494 by bromination of (1R,2S,5R)-5-methyl-2-(propan-2-yl)cyclohexyl(2S)-cyclopentyl(4-methylphenyl)ethanoate in boiling carbon tetrachloride using N-bromosuccinimide in the presence of 2,2'-azobis(2-methylpropionitrile).

GC-MS (method 3): R$_t$=9.15 min; no ionization.
LC-MS (method 12): R$_t$=3.54 min; no ionization.
MS (DCI): m/z=452/454 (M+NH$_4$)$^+$.

Example 202A (2S)-Cyclopentyl-(4-methylphenyl)acetic acid

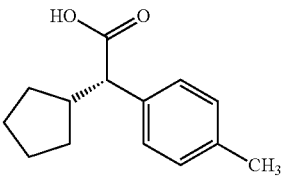 [SMILES: Cc1ccc([C@@H](C(=O)O)C2CCCC2)cc1]

50.0 g (0.140 mol) of (1R,2S,5R)-5-methyl-2-(propan-2-yl)cyclohexyl(2S)-cyclopentyl(4-methylphenyl)ethanoate were stirred under reflux for 16 h in 500 ml of trifluoroacetic acid. The trifluoroacetic acid was then removed on a rotary evaporator and the residue was taken up in 500 ml each of water and ethyl acetate. After extraction, the organic phase was washed with saturated sodium chloride solution, dried over sodium sulfate and concentrated. The residue was taken up in 1.5 liters of water, adjusted to pH 10 with aqueous sodium hydroxide solution and washed twice with in each case 300 ml of tert-butyl methyl ether. The aqueous phase was then adjusted to pH 4 using concentrated hydrochloric acid and extracted twice with in each case 300 ml of ethyl acetate. The combined ethyl acetate extracts were dried over sodium sulfate, filtered and concentrated on a rotary evaporator. This gave 27.4 g (89% of theory) of the title compound.

LC-MS (method 11): R$_t$=1.28 min; m/z=217 (M−H)$^-$.
$^1$H-NMR (400 MHz, DMSO-d$_6$): δ=7.19 (d, 2H), 7.13-7.08 (m, 2H), 3.16 (d, 1H), 2.41 (dt, 1H), 2.26 (s, 3H), 1.87-1.76 (m, 1H), 1.66-1.14 (m, 6H), 1.00-0.87 (m, 1H).

Example 203A tert-Butyl(2S)-cyclopentyl-(4-methylphenyl)acetate

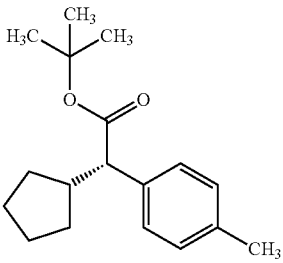 [SMILES: Cc1ccc([C@@H](C(=O)OC(C)(C)C)C2CCCC2)cc1]

160 g (732.9 mmol) of (2S)-cyclopentyl-(4-methylphenyl)acetic acid were initially charged in 480 ml of dichloromethane, and 2.1 ml of sulfuric acid and 172 ml (1722.4 mmol) of condensed 2-methylprop-1-ene were added at 10° C. The mixture was stirred at RT overnight. If required, the addition of sulfuric acid and 2-methylprop-1-ene was repeated until all the starting material had been consumed. After the reaction had ended, 21 g of potassium carbonate were added and the mixture was stirred for another 2-3 h (evolution of gas). The mixture was then diluted with 700 ml of water and extracted with ethyl acetate. The organic phase was dried over sodium sulfate, filtered and concentrated on a rotary evaporator. The crude product was purified by chromatography on silica gel (mobile phase cyclohexane/ethyl acetate 4:1). This gave 172 g (85% of theory) of the title compound.

$^1$H-NMR (400 MHz, DMSO-$d_6$): δ=7.19 (d, 2H), 7.11 (d, 2H), 3.13 (d, 1H), 2.44-2.31 (m, 1H), 2.27 (s, 3H), 1.86-1.76 (m, 1H), 1.68-1.36 (m, 4H), 1.34 (s, 9H), 1.31-1.17 (m, 2H), 1.00-0.89 (m, 1H).

Example 204A tert-Butyl(2S)-[4-(bromomethyl)phenyl](cyclopentyl)acetate

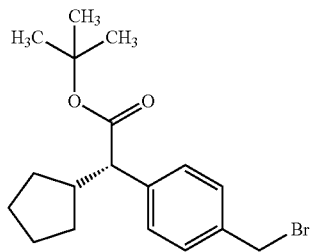 [SMILES: CC(C)(C)OC(=O)[C@H](c1ccc(CBr)cc1)C1CCCC1]

3.0 g (10.93 mmol) of tert-butyl(2S)-cyclopentyl-(4-methylphenyl)acetate were heated to reflux in 20 ml of chloroform, and 90 mg (0.55 mmol) of 2,2'-azobis(2-methylpropanenitrile) and 2.72 g (15.31 mmol) of N-bromosuccinimide were then added in 5 portions every 30 min. The mixture was stirred under reflux for 6 h and then cooled to RT and concentrated on a rotary evaporator. The residue was purified by chromatography on 120 ml of silica gel (mobile phase cyclohexane/ethyl acetate 4:1). This gave 2.8 g (72% of theory) of the title compound.

$^1$H-NMR (400 MHz, DMSO-$d_6$): δ=7.39 (d, 2H), 7.31 (d, 2H), 4.68 (s, 2H), 2.45-2.32 (m, 1H), 1.89-1.77 (m, 1H), 1.69-1.38 (m, 5H), 1.37-1.32 (m, 9H), 1.30-1.16 (m, 2H), 1.00-0.92 (m, 1H).

Example 205A

Ethyl 4,4,4-trifluoro-3-methyl-2-(4-methylphenyl)butanoate

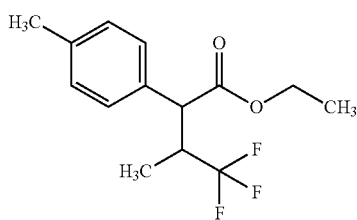 [SMILES: CCOC(=O)C(c1ccc(C)cc1)C(C)C(F)(F)F]

Under argon, 196.9 mg (0.88 mmol) of palladium(II) acetate and 724.8 mg (1.84 mmol) of 2-dicyclohexylphosphino-2'-(N,N-dimethylamino)biphenyl were initially charged in 50 ml of anhydrous toluene. 43.8 ml (43.8 mmol) of a 1 M solution of lithium hexamethyldisilazide in THF were then added slowly to the reaction solution, and the mixture was stirred at room temperature for 10 min. The reaction solution was then cooled to −10° C., 7 g (38.0 mmol) of ethyl 4,4,4-trifluoro-3-methylbutanoate were added slowly and the mixture was stirred at −10° C. for 10 min. 5 g (29.2 mmol) of 4-bromotoluene, dissolved in 50 ml of toluene, were then added dropwise, and the reaction solution was warmed first to room temperature and then to 80° C. The mixture was stirred at this temperature for 2 h and then cooled to room temperature and stirred overnight. After the reaction had ended (monitored by TLC; mobile phase cyclohexane/dichloromethane 2:1), the reaction mixture was filtered through kieselguhr, the residue was washed repeatedly with ethyl acetate and dichloromethane and the combined filtrates were concentrated under reduced pressure. The crude product obtained was purified chromatographically on silica gel (mobile phase petroleum ether/dichloromethane 4:1→3:1). This gave 3.91 g (14.3 mmol, 48.8% of theory) of the title compound as a colorless liquid.

$^1$H-NMR (400 MHz, DMSO-$d_6$, δ/ppm): 7.26 (2H, d), 7.20-7.12 (2H, m), 4.17-3.95 (2H, m), 3.74 (0.25H, d), 3.66 (0.75H, d), 3.35-3.07 (1H, m), 2.29 (2.25H, s), 2.28 (0.75H, s), 1.17 (0.75H, d), 1.11 (3H, t), 0.76 (2.25H, d) (mixture of diastereomers).

GC-MS (method 3): $R_t$=4.20 min; m/z=275 (M+H)$^+$ (diastereomer 1); $R_t$=4.23 min; m/z=275 (M+H)$^+$ (diastereomer 2).

The compound listed in the table below was obtained in an analogous manner:

| Example | Name/Structure | Analytical data |
|---|---|---|
| 206A | ethyl 2-(4-methylphenyl)-3-(trifluoromethyl)pentanoate<br>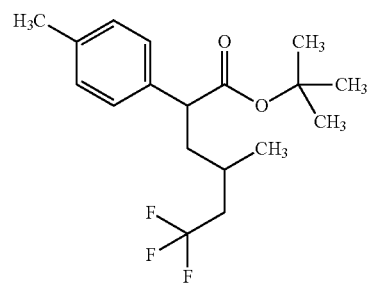<br>(from 4-bromotoluene and ethyl 3-(trifluoromethyl)pentanoate [CAS Reg. No. 400-25-9]) | GC-MS (method 3):<br>$R_t$ = 4.57 min;<br>m/z = 288 (M + H)$^+$. |

Example 207A tert-Butyl 6,6,6-trifluoro-4-methyl-2-(4-methylphenyl)hexanoate

Under exclusion of oxygen, 0.44 ml (3.2 mmol) of diisopropylamine was initially charged in 4 ml of THF, the mixture was cooled to −78° C. and 1.28 ml (3.2 mmol) of a 2.5 M solution of n-butyllithium in hexane were added slowly. The reaction solution was then warmed to −10° C. and stirred at this temperature for 10 min. The reaction solution was then once more cooled to −78° C., and 500 mg (2.32 mmol) of tert-butyl(4-methylphenyl)acetate, dissolved in 6 ml of THF, were added slowly. The reaction solution was then slowly warmed to −30° C. and then once more cooled to −78° C. Once this temperature had been reached, 596 mg (2.91 mmol) of 5-bromo-1,1,1-trifluoro-3-methylpentane were slowly added dropwise. After the addition had ended, the solution was slowly warmed to room temperature and stirred overnight. After TLC check (mobile phase cyclohexane/ethyl acetate 10:1), saturated ammonium chloride solution was added and the mixture was taken up in ethyl acetate. The aqueous phase was extracted twice with ethyl acetate. The combined organic phases were dried over sodium sulfate. After filtration, the solvent was removed under reduced pressure. The crude product was purified chromatographically on silica gel (mobile phase cyclohexane/ethyl acetate 20:1). This gave 490 mg (1.48 mmol, 61% of theory) of a yellowish oil.

GC-MS (method 3): $R_t$=4.89 min; m/z=274 (M+H)$^+$.

Example 208A 4,4,4-Trifluoro-2-methyl-1-(4-methylphenyl)butan-1-one

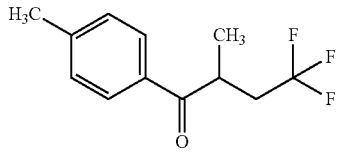 [SMILES: Cc1ccc(C(=O)C(C)CC(F)(F)F)cc1]

At 0° C., 16.44 g (123.3 mmol) of aluminum chloride were added a little at a time to 12.6 ml (118.6 mmol) of toluene and 20.9 g (119.7 mmol) of 4,4,4-trifluoro-2-methylbutanoyl chloride in 300 ml of 1,2-dichloroethane, and the mixture was stirred at 0° C. for one hour. The reaction mixture was then slowly warmed to room temperature and stirred at this temperature for three hours. The reaction mixture was then slowly added to 300 ml of ice-cooled 18.5% strength hydrochloric acid, and the organic phase was then removed. The aqueous phase was extracted three more times with dichloromethane. The combined organic phases were dried over sodium sulfate and filtered, and the solvent was removed under reduced pressure. The crude product was purified chromatographically on silica gel (mobile phase cyclohexane/ethyl acetate 4:1). This gave 19.96 g (18.7 mmol, 73% of theory) of the title compound.

LC-MS (method 11): $R_t$=1.35 min; m/z=228 (M−H)$^−$.

$^1$H-NMR (400 MHz, DMSO-d$_6$): δ=7.92 (d, 2H), 7.36 (d, 2H), 3.82-3.98 (m, 1H), 2.70-2.92 (m, 1H), 2.40-2.49 (m, 1H), 2.36-2.40 (m, 3H), 1.18 (d, 3H).

Example 209A

1-Methyl-4-(5,5,5-trifluoro-3-methylpent-1-en-2-yl)benzene

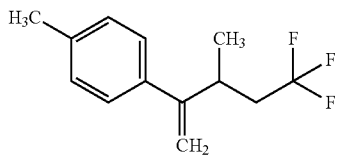 [SMILES: C=C(c1ccc(C)cc1)C(C)CC(F)(F)F]

Under argon, 1.45 ml (4.34 mmol) of a 3 M solution of methylmagnesium iodide in diethyl ether were initially charged in 10 ml of diethyl ether, and 1000 mg (4.34 mmol) of 4,4,4-trifluoro-2-methyl-1-(4-methylphenyl)butan-1-one, dissolved in 5 ml of diethyl ether, were added slowly at 0 C. The reaction mixture was then slowly warmed to room temperature and stirred overnight. The reaction solution was then slowly added to 15 ml of 1 M hydrochloric acid and diluted with diethyl ether. After removal of the organic phase, the aqueous phase was extracted three more times with diethyl ether. The combined organic phases were dried over magnesium sulfate and filtered, and the solvent was removed under reduced pressure. The crude product was purified chromatographically on silica gel (mobile phase cyclohexane/ethyl acetate 50:1). This gave 710 mg (3.11 mmol, 71% of theory) of the title compound as a colorless oil.

GC-MS (method 3): $R_t$=3.23 min; m/z=228 (M)$^+$.

Example 210A 5,5,5-Trifluoro-3-methyl-2-(4-methylphenyl)pentan-1-ol

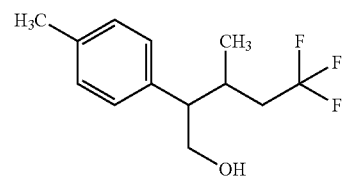 [SMILES: Cc1ccc(C(CO)C(C)CC(F)(F)F)cc1]

Under argon, 9.4 g (41.2 mmol) of 1-methyl-4-(5,5,5-trifluoro-3-methylpent-1-en-2-yl)benzene were dissolved in 130 ml of THF, 57.6 ml of a 1 M borane/THF complex solution were added and the mixture was stirred at room temperature for 24 h. With vigorous stirring, initially 79 ml of water, then 24 ml of 6 M aqueous sodium hydroxide solution and finally 14.5 ml (475 mmol) of 30% strength aqueous hydrogen peroxide solution were added. Subsequently, the reaction solution was added to 200 ml of saturated sodium chloride solution, the organic phase was separated off and the aqueous phase was extracted three more times with diethyl ether. The combined organic phases were dried over magnesium sulfate and filtered, and the solvent was removed under reduced pressure. The crude product was purified chromatographically on silica gel (mobile phase cyclohexane/ethyl acetate 4:1→2:1). This gave 5 g (20.3 mmol, 49% of theory) of the title compound as a colorless oil.

GC-MS (method 3): $R_t$=4.45 min; m/z=246 (M)$^+$ (diastereomer 1); $R_t$=4.54 min; m/z=246 (M)$^+$ (diastereomer 2).

Example 211A 5,5,5-Trifluoro-3-methyl-2-(4-methylphenyl)pentanoic acid

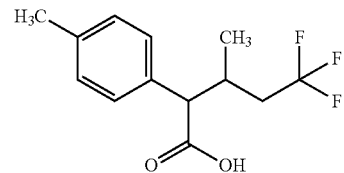 [SMILES: Cc1ccc(C(C(=O)O)C(C)CC(F)(F)F)cc1]

26.7 g (71.1 mmol) of pyridinium dichromate were added to 5 g (20.3 mmol) of 5,5,5-trifluoro-3-methyl-2-(4-methylphenyl)pentan-1-ol in 83 ml of DMF, and the mixture was stirred at room temperature for 12 hours. The reaction mixture was subsequently added to 100 ml of water, the organic phase was separated off and the aqueous phase was extracted six more times with diethyl ether. The combined organic phases were extracted five times with 0.5 M aqueous sodium hydroxide solution. The combined aqueous-basic phases were then acidified to about pH 3 with 3 M hydrochloric acid and extracted six times with ethyl acetate. The combined ethyl acetate phases were dried over magnesium sulfate and filtered, and the solvent was removed under reduced pressure. This gave 3.79 g (14.56 mmol, 71% of theory) of the title compound as a colorless oil.

LC-MS (method 15): $R_t$=1.09 min; m/z=259 (M–H)⁻ (diastereomer 1); $R_t$=1.12 min; m/z=259 (M–H)⁻ (diastereomer 2).

Example 212A tert-Butyl 5,5,5-trifluoro-3-methyl-2-(4-methylphenyl)pentanoate

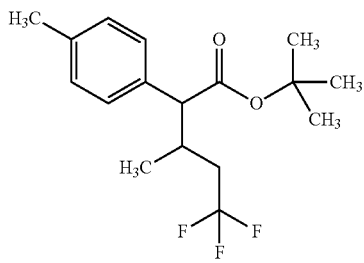 [SMILES: Cc1ccc(C(C(=O)OC(C)(C)C)C(C)CC(F)(F)F)cc1]

Under argon, 3.79 g (14.5 mmol) of 5,5,5-trifluoro-3-methyl-2-(4-methylphenyl)pentanoic acid were dissolved in 60 ml of THF at room temperature, and 27 µl (0.22 mmol) of a 1 M boron trifluoride/diethyl ether complex solution were added. 3.828 g (17.48 mmol) of tert-butyl 2,2,2-trichloroethanimidoate were then metered in a little at a time, and the mixture was stirred at room temperature overnight. After the reaction had gone to completion (monitored by TLC; mobile phase cyclohexane/ethyl acetate 2:1), 2 g of solid sodium bicarbonate were added with vigorous stirring of the reaction solution. The reaction mixture was then filtered, and the solvent was removed under reduced pressure. The crude product was purified chromatographically on silica gel (mobile phase cyclohexane/ethyl acetate 5:1). This gave 3.25 g (10.27 mmol, 71% of theory) of the title compound as a colorless oil.

MS (DCI): m/z=334 (M+NH₄)⁺.

GC-MS (method 3): $R_t$=4.49 min; m/z=260 (M–C₄H₈)⁺ (diastereomer 1); $R_t$=4.52 min; m/z=260 (M–C₄H₈)⁺ (diastereomer 2).

Example 213A tert-Butyl(4-methylphenyl)(3-oxocyclopentyl)acetate

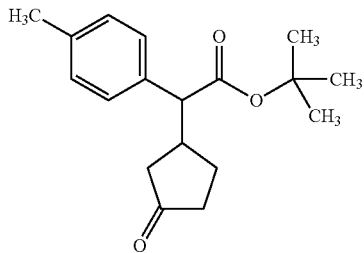 [SMILES: Cc1ccc(C(C(=O)OC(C)(C)C)C2CCC(=O)C2)cc1]

Under argon, 4.4 ml (31.5 mmol) of diisopropylamine were initially charged in 50 ml of THF, the mixture was cooled to –30° C. and 13.7 ml (31.5 mmol) of a 2.3 M solution of n-butyllithium in hexane were added slowly. The reaction solution was then warmed to –20° C., 5 g (24.3 mmol) of tert-butyl(4-methylphenyl)acetate, dissolved in 30 ml of THF, were added slowly, and the mixture was stirred at this temperature for 2 hours. The reaction solution was then cooled to –78° C., and 2.2 ml (25.7 mmol) of 2-cyclopenten-1-one, dissolved in 20 ml of THF, were added slowly. After the addition had ended, the solution was stirred at this temperature for another hour. After TLC check (mobile phase cyclohexane/ethyl acetate 9:1), saturated ammonium chloride solution was added and the mixture was taken up in ethyl acetate. The aqueous phase was extracted twice with ethyl acetate. The combined organic phases were dried over sodium sulfate. After filtration, the solvent was removed under reduced pressure. The crude product was purified chromatographically on silica gel (mobile phase cyclohexane/ethyl acetate 9:1). This gave 3020 mg (10.47 mmol, 43% of theory) of the title compound as a colorless oil.

MS (DCI): m/z=306 (M+NH₄)⁺.

¹H-NMR (500 MHz, DMSO-d₆): δ=7.20 (t, 2H), 7.14 (t, 2H), 3.38 (t, 1H), 2.66-2.80 (m, 1H), 2.30-2.39 (m, 1H), 2.28 (d, 3H), 1.92-2.23 (m, 3H), 1.72-1.79 (m, 1H), 1.51-1.66 (m, 1H), 1.35 (d, 9H).

Example 214A tert-Butyl(3,3-difluorocyclopentyl)(4-methylphenyl)acetate

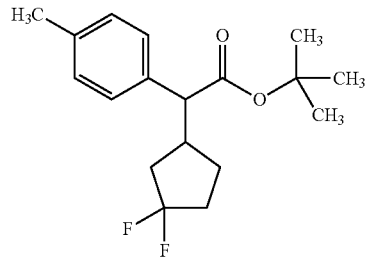 [SMILES: Cc1ccc(C(C(=O)OC(C)(C)C)C2CCC(F)(F)C2)cc1]

Under argon, 4.8 ml (4.85 mmol) of a 50% strength solution of 1,1'-[(trifluoro-λ⁴-sulfanyl)-imino]bis(2-methoxyethane) (Deoxo-Fluor) in THF, dissolved in 5 ml of toluene, were initially charged, the mixture was cooled to 5° C., 22 µl (0.17 mmol) of a 1 M boron trifluoride/diethyl ether complex solution were added slowly and the mixture was stirred at 5° C. for two hours. 1 g (3.45 mmol) of tert-butyl(4-methylphenyl)(3-oxocyclopentyl)acetate, dissolved in 5 ml of toluene, was then added slowly to the reaction solution, and the mixture was then warmed to 55° C. and stirred at this temperature for 24 hours. The reaction mixture was then added to a mixture, cooled to 0° C., of 5 ml of toluene and 10 ml of 2 M aqueous sodium hydroxide solution. The organic phase was separated off, and the aqueous phase was extracted two more times with ethyl acetate. The combined organic phases were dried over sodium sulfate. After filtration, the solvent was removed under reduced pressure. The crude product was purified chromatographically on silica gel (mobile phase cyclohexane/ethyl acetate 7:1). This gave 701 mg (2.26 mmol, 65% of theory) of the title compound as a colorless oil.

MS (DCI): m/z=328 (M+NH₄)⁺.

GC-MS (method 3): $R_t$=5.64 min; m/z=254 (M–C₄H₈)⁺ (diastereomer 1); $R_t$=5.66 min; m/z=254 (M–C₄H₈)⁺ (diastereomer 2).

Example 215A

Ethyl 2-[4-(bromomethyl)phenyl]-4,4,4-trifluoro-3-methylbutanoate

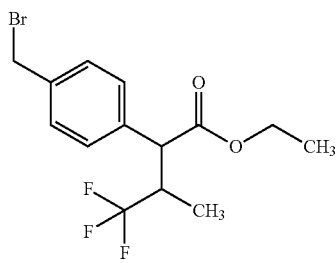 [SMILES: CCOC(=O)C(c1ccc(CBr)cc1)C(C)C(F)(F)F]

2.25 g (8.2 mmol) of ethyl 4,4,4-trifluoro-3-methyl-2-(4-methylphenyl)butanoate, 1.53 g (8.6 mmol) of N-bromosuccinimide and 67 mg (0.41 mmol) of 2,2'-azobis(2-methylpropanenitrile) in 36 ml of trichloromethane were stirred under reflux overnight. After the reaction had gone to completion, the succinimide was filtered off and the filter residue was washed with dichloromethane. The filtrate was concentrated under reduced pressure. The crude product was purified chromatographically on silica gel (mobile phase cyclohexane/ethyl acetate 40:1). This gave 2.667 g (7.5 mmol, 92% of theory) of a yellowish oil.

GC-MS (method 3): $R_t$=5.72 min; m/z=373 (M–Br)$^+$ (diastereomer 1); $R_t$=5.74 min; m/z=373 (M–Br)$^+$ (diastereomer 2).

The compounds listed in the table below were obtained in an analogous manner:

| Example | Name/Structure | Analytical data |
|---|---|---|
| 216A | ![structure] tert-butyl 2-[4-(bromomethyl)phenyl]-6,6,6-trifluoro-4-methylhexanoate | GC-MS (method 3): diastereomer 1 $R_t$ = 6.27 min, m/z = 274 (M—Br—C$_4$H$_8$)$^+$; diastereomer 2 $R_t$ = 6.30 min, m/z = 274 (M—Br—C$_4$H$_8$)$^+$. |
| 217A | ![structure] tert-butyl 2-[4-(bromomethyl)phenyl]-5,5,5-trifluoro-3-methylpentanoate | GC-MS (method 3): diastereomer 1 $R_t$ = 5.96 min, m/z = 259 (M—Br—C$_4$H$_8$)$^+$; diastereomer 2 $R_t$ = 6.00 min, m/z = 259 (M—Br—C$_4$H$_8$)$^+$. MS (DCI): m/z = 412/414 (M + NH$_4$)$^+$. |
| 218A | ![structure] ethyl 2-[4-(bromomethyl)phenyl]-3-(trifluoromethyl)pentanoate | GC-MS (method 3): diastereomer 1 $R_t$ = 6.01 min, m/z = 287 (M—Br)$^+$; diastereomer 2 $R_t$ = 6.04 min, m/z = 287 (M—Br)$^+$. |

| Example | Name/Structure | Analytical data |
|---|---|---|
| 219A | 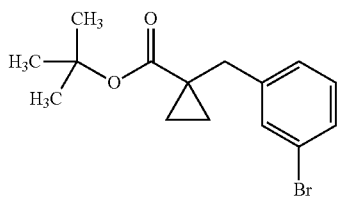 [SMILES: CC(C)(C)OC(=O)C1(Cc2cccc(Br)c2)CC1]<br>tert-butyl [4-(bromomethyl)phenyl](3,3-difluoro-cyclopentyl)acetate | GC-MS (method 3):<br>diastereomer 1<br>$R_t$ = 5.64 min, m/z = 331/333<br>$(M-C_4H_9)^+$, 254 $(M-Br-C_4H_8 + H)^+$;<br>diastereomer 2<br>$R_t$ = 5.66 min, m/z = 331/333<br>$(M-C_4H_9)^+$, 254 $(M-Br-C_4H_8 + H)^+$. |

Example 220A tert-Butyl 1-(3-bromobenzyl)cyclopropanecarboxylate

Under argon, 14.8 ml (105.48 mmol) of diisopropylamine were initially charged in 66 ml of dry THF, and the mixture was cooled to −40° C. 42.2 ml (105.48 mmol) of n-butyllithium solution (2.5 M in hexane) were slowly added dropwise, and the mixture was stirred for 30 min. The reaction solution was then cooled to −78° C., and a solution of 10.0 g (70.32 mmol) of tert-butyl cyclopropanecarboxylate in 17 ml of THF were added. After 4 h of stirring at −78° C., a solution of 19.34 g (77.36 mmol) of 3-bromobenzyl bromide in 17 ml of THF was added. Slowly, the reaction mixture was warmed to RT overnight, ammonium chloride solution was then added carefully and the mixture was extracted three times with ethyl acetate. The combined organic phases were washed with saturated sodium chloride solution, dried over magnesium sulfate and concentrated under reduced pressure. The crude product was purified by chromatography on 750 g of silica gel (mobile phase cyclohexane/dichloromethane 50:1, then 5:1). This gave 13.3 g (60.7% of theory) of the title compound.

GC-MS (method 3): $R_t$=5.94 min; m/z=256 $(M-C_4H_8)^+$.

$^1$H-NMR (400 MHz, DMSO-$d_6$): δ=7.46 (s, 1H), 7.38 (m, 1H), 7.25 (m, 2H), 2.82 (s, 2H), 1.28 (s, 9H), 1.08 (q, 2H), 0.87 (q, 2H).

Example 221A tert-Butyl 1-[3-(benzylamino)benzyl]cyclopropanecarboxylate

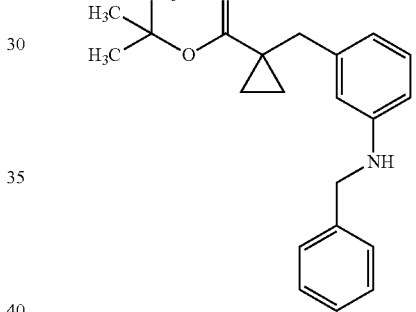

Under argon and dry conditions, 13.3 g (42.73 mmol) of tert-butyl 1-(3-bromobenzyl)-cyclopropanecarboxylate, 5.6 ml (51.28 mmol) of benzylamine, 1.96 g (2.14 mmol) of tris-(dibenzylideneacetone)dipalladium, 4.93 g (51.28 mmol) of sodium tert-butoxide and 1.06 g (1.71 mmol) of (+/−)-2,2'-bis(diphenylphosphino)-1,1'-binaphthyl were suspended in 50 ml of toluene. The reaction mixture was stirred at 110° C. for 1.5 h. The mixture was then filtered off with suction through kieselguhr, the residue was washed with toluene and the filtrate was concentrated. The residue of the filtrate was taken up in ethyl acetate and extracted twice with ammonium chloride solution. The organic phase was dried over magnesium sulfate and concentrated under reduced pressure. The crude product was purified by chromatography on silica gel (mobile phase cyclohexane/ethyl acetate 20:1). This gave 6.98 g (48.4% of theory) of the title compound.

LC-MS (method 12): $R_t$=2.75 min; m/z=338 $(M+H)^+$.

$^1$H-NMR (400 MHz, DMSO-$d_6$): δ=7.35-7.26 (m, 4H), 7.20 (t, 1H), 6.91 (t, 1H), 6.45 (s, 1H), 6.38 (m, 2H), 6.12 (t, 1H), 4.23 (d, 2H), 2.69 (s, 2H), 1.28 (s, 9H), 0.99 (q, 2H), 0.69 (q, 2H).

Example 222A tert-Butyl 1-(3-aminobenzyl)cyclopropanecarboxylate

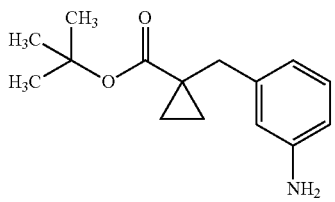

6.98 g (22.43 mmol) of tert-butyl 1-[3-(benzylamino)benzyl]cyclopropanecarboxylate were dissolved in 50 ml of ethanol and 50 ml of THF, and 0.48 g (0.45 mmol) of palladium (10% on carbon) were added. At RT, the mixture was stirred under an atmosphere of hydrogen at atmospheric pressure for 2 h. The reaction mixture was then filtered off with suction through kieselguhr, the residue was washed with THF and the filtrate was concentrated. The crude product was purified by chromatography on silica gel (mobile phase cyclohexane/ethyl acetate 10:1). This gave 3.66 g (65.9% of theory) of the title compound.

LC-MS (method 7): $R_t$=1.84 min; m/z=192 (M+H)$^+$.
$^1$H-NMR (400 MHz, DMSO-d$_6$): δ=6.88 (t, 1H), 6.42 (s, 1H), 6.37 (dd, 2H), 4.89 (d, 2H), 2.69 (s, 2H), 1.31 (s, 9H), 1.03 (q, 2H), 0.75 (q, 2H).

Example 223A tert-Butyl 1-(2-methyl-3-nitrobenzyl)cyclopropane carboxylate

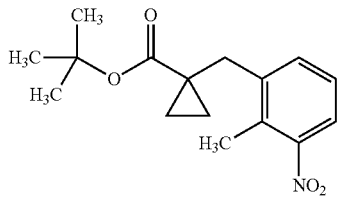

Under argon, 1.28 ml (9.15 mmol) of diisopropylamine were initially charged in 6 ml of dry THF, and the mixture was cooled to −40° C. 4.26 ml (9.15 mmol) of n-butyllithium solution (2.5 M in hexane) were slowly added dropwise, and the mixture was stirred for 30 min. The reaction solution was then cooled to −78° C., and a solution of 1.30 g (9.15 mmol) of tert-butyl cyclopropanecarboxylic acid in 2 ml of THF was added. After 4 h of stirring at −78° C., a solution of 2.00 g (8.69 mmol) of 1-(bromomethyl)-2-methyl-3-nitrobenzene in 2 ml of THF was added. Slowly, the reaction mixture was warmed to RT overnight. Ammonium chloride solution was then added carefully, and the mixture was extracted three times with ethyl acetate. The combined organic phases were washed with saturated sodium chloride solution, dried over magnesium sulfate and concentrated under reduced pressure. The crude product was purified by chromatography on silica gel (mobile phase cyclohexane/dichloromethane 50:1, then 5:1). This gave 0.78 g (29.3% of theory) of the title compound.

$^1$H-NMR (400 MHz, DMSO-d$_6$): δ=7.61 (d, 1H), 7.54 (d, 1H), 7.39 (t, 1H), 2.96 (s, 2H), 2.26 (s, 3H), 1.26 (s, 9H), 1.20 (q, 2H), 0.79 (q, 2H).

Example 224A tert-Butyl 1-(3-amino-2-methylbenzyl)cyclopropanecarboxylate

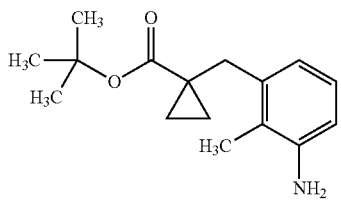 [SMILES: Cc1c(CC2(C(=O)OC(C)(C)C)CC2)cccc1[N+](=O)[O-]]

765 mg (2.63 mmol) of tert-butyl 1-(2-methyl-3-nitrobenzyl)cyclopropanecarboxylate were dissolved in 5 ml of ethanol, and 139.7 mg (0.13 mmol) of palladium (10% on carbon) were added. At RT, the mixture was hydrogenated at atmospheric pressure for 2 h. The reaction mixture was filtered off with suction through kieselguhr, the residue was washed with THF and the filtrate was concentrated. This gave 680 mg (99.1% of theory) of the title compound.

LC-MS (method 7): $R_t$=1.96 min; m/z=262 (M+H)$^+$.
$^1$H-NMR (400 MHz, DMSO-d$_6$): δ=6.77 (t, 1H), 6.47 (d, 1H), 6.40 (d, 2H), 4.69 (s, 2H), 2.88 (s, 2H), 1.91 (s, 3H), 1.31 (s, 9H), 1.03 (q, 2H), 0.55 (q, 2H).

Example 225A tert-Butyl(2E)-3-(4-fluoro-3-nitrophenyl)prop-2-enoate

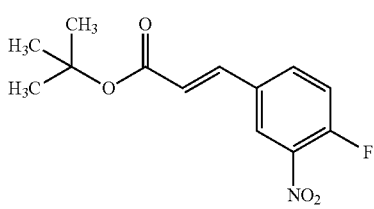 [SMILES: CC(C)(C)OC(=O)/C=C/c1ccc(F)c([N+](=O)[O-])c1]

Under argon, 130.1 mg (3.25 mmol) of sodium hydride were initially charged in 2 ml of toluene and 2 ml of THF. The mixture was cooled to 0° C., and 857.7 mg (3.40 mmol) of tert-butyl (diethoxyphosphoryl)acetate were added slowly. The mixture was stirred for another 30 min, and 500 mg (2.96 mmol) of 4-fluoro-3-nitrobenzaldehyde were then added. The reaction mixture was slowly warmed to RT and stirred for 3 h. The reaction mixture was then added to water and extracted three times with ethyl acetate. The organic phase was concentrated under reduced pressure and the residue purified by chromatography on silica gel (mobile phase cyclohexane/ethyl acetate 30:1→10:1). This gave 543 mg (69% of theory) of the title compound.

LC-MS (method 12): $R_t$=2.41 min; m/z=212 (M−C$_4$H$_8$+H)$^+$.
$^1$H-NMR (400 MHz, DMSO-d$_6$): δ=8.51 (dd, 1H), 8.19 (ddd, 1H), 7.69-7.59 (m, 2H), 6.70 (d, 1H), 1.49 (s, 9H).

Example 226A tert-butyl 3-(3-amino-4-fluorophenyl)propanoate

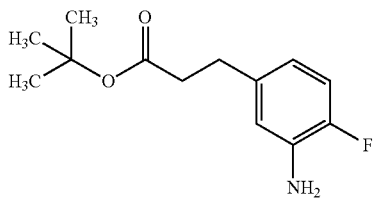 [SMILES: CC(C)(C)OC(=O)CCc1ccc(F)c(N)c1]

535 mg (2.00 mmol) of tert-butyl(2E)-3-(4-fluoro-3-nitrophenyl)prop-2-enoate were dissolved in 1 ml of ethanol and 1 ml of THF, and 21.3 mg of palladium (10% on carbon) were added. At RT, the mixture was hydrogenated under a hydrogen atmosphere at atmospheric pressure overnight. The reaction mixture was filtered off with suction through kieselguhr, the residue was washed with THF and the filtrate was concentrated. This gave 479 mg (100% of theory) of the title compound.

LC-MS (method 15): $R_t$=1.06 min; m/z=184 (M−$C_4H_8$)$^+$.
$^1$H-NMR (400 MHz, DMSO-$d_6$): δ=6.84 (dd, 1H), 6.58 (dd, 1H), 6.36-6.29 (m, 1H), 5.00 (s, 2H), 2.64 (t, 2H), 2.42 (t, 2H), 1.36 (s, 9H).

Example 227A

3-Bromo-2-fluoroaniline

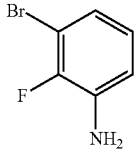

Under argon, 1.0 g (4.54 mmol) of 3-bromo-2-fluoronitrobenzene was initially charged in 5 ml of dioxane, and 4.3 g (22.72 mmol) of tin(II) chloride and a few drops of 1 N hydrochloric acid were added. After 2 h of stirring, the reaction mixture was concentrated on a rotary evaporator and the residue was taken up in ethyl acetate. The organic phase was washed with 1 N aqueous sodium hydroxide solution, water and saturated sodium chloride solution and then dried over magnesium sulfate and concentrated. This gave 826 mg (95% of theory) of the title compound.

LC-MS (method 15): $R_t$=0.89 min; m/z=190 (M+H)$^+$.
$^1$H-NMR (400 MHz, DMSO-$d_6$): δ=6.83-6.70 (m, 3H), 5.43 (s, 2H).

Example 228A tert-Butyl(2E)-3-(3-amino-2-fluorophenyl)prop-2-enoate

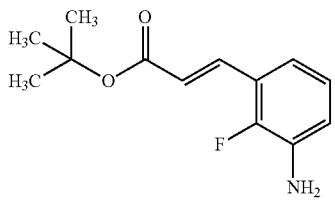 [SMILES: CC(C)(C)OC(=O)/C=C/c1cccc(N)c1F]

400 mg (2.10 mmol) of 3-bromo-2-fluoroaniline, 809.42 mg (6.32 mmol) of tert-butyl acrylate and 1.47 ml (10.53 mmol) of triethylamine were initially charged in 2.4 ml of DMF. The reaction vessel was evacuated three times and in each case vented with argon. 47.26 mg (0.21 mmol) of palladium(II) acetate and 128.14 mg (0.42 mmol) of tri-2-tolylphosphine were then added, and the reaction vessel was evacuated two more times and again vented with argon. The mixture was stirred at 145° C. overnight. The reaction mixture was then cooled, added to saturated ammonium chloride solution and extracted three times with ethyl acetate. The combined organic phases were dried over magnesium sulfate and concentrated. The crude product was purified by preparative RP-HPLC (mobile phase: acetonitrile/water gradient). This gave 210 mg (42% of theory) of the title compound.

LC-MS (method 11): $R_t$=1.27 min; m/z=238 (M+H)$^+$.
$^1$H-NMR (400 MHz, DMSO-$d_6$): δ=7.59 (d, 1H), 6.94-6.87 (m, 2H), 6.85-6.77 (m, 1H), 6.45 (d, 1H), 5.27 (s, 2H), 1.52-1.43 (m, 9H).

Example 229A tert-Butyl 3-(3-amino-2-fluorophenyl)propanoate

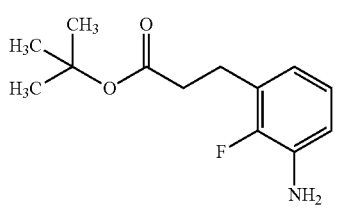 [SMILES: CC(C)(C)OC(=O)CCc1cccc(N)c1F]

210 mg (0.88 mmol) of tert-butyl(2E)-3-(3-amino-2-fluorophenyl)prop-2-enoate were dissolved in 0.44 ml of ethanol and 0.20 ml of THF, and 9.4 mg of palladium (10% on carbon) were added. At RT, the mixture was hydrogenated under an atmosphere of hydrogen at atmospheric pressure overnight. The reaction mixture was filtered off with suction through kieselguhr, the residue was washed with THF and the filtrate was concentrated. The crude product was purified on a Biotage column (mobile phase cyclohexane/ethyl acetate 10:1). This gave 116 mg (54% of theory) of the title compound.

LC-MS (method 15): $R_t$=1.07 min; m/z=184 (M−$C_4H_8$)$^+$.
$^1$H-NMR (400 MHz, DMSO-$d_6$): δ=6.75 (t, 1H), 6.60 (t, 1H), 6.38 (t, 1H), 5.01 (br. s, 2H), 2.74 (t, 2H), 2.48-2.42 (m, 2H), 1.36 (s, 9H).

General Procedure 1: Preparation of Benzyl Alcohols from Benzoic Acids

At RT, 1.3 eq. of triethylamine and then 1.2 eq. of methyl chloroformate were added to a 0.5 M solution of the benzoic acid in question in toluene, and the mixture was stirred at RT overnight. The resulting suspension was then filtered through Celite and the residue was washed with toluene. The filtrate was concentrated, and the residue of the filtrate was dissolved in THF (1.5 ml/mmol) and then added dropwise to a suspension, cooled to −78° C., of 1.2 eq. of lithium aluminum hydride in THF (1 ml/mmol). After 1.5 h at −78° C., the reaction mixture was warmed to RT, and stirring was continued overnight. The resulting suspension was poured into 5% strength aqueous sodium hydroxide solution (5 ml/mmol), and the mixture was filtered through Celite and the filter cake was washed with ethyl acetate. The filtrate was extracted repeatedly with ethyl acetate. The combined organic phases were washed with saturated sodium chloride solution, dried over magnesium sulfate and concentrated under reduced pressure.

The following compounds were prepared according to this procedure:

| Example | Name/Structure | Analytical data |
|---|---|---|
| 230A | 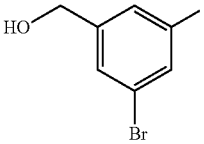<br>(3-bromo-5-fluorophenyl) methanol | LC-MS (method 11):<br>$R_t$ = 0.96 min; m/z = 187 [M − $H_2O$]$^+$. |
| 231A | 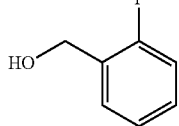<br>(5-bromo-2-fluorophenyl) methanol | LC-MS (method 12):<br>$R_t$ = 1.61 min; m/z = 187 [M − $H_2O$]$^+$. |
| 232A | 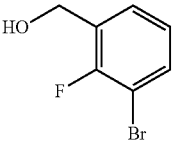<br>(3-bromo-2-fluorophenyl) methanol | LC-MS (method 15):<br>$R_t$ = 0.81 min; m/z = 187 [M − $H_2O$]$^+$.<br>$^1$H-NMR (400 MHz, DMSO-$d_6$): δ = 7.54-7.66 (m, 1H), 7.47 (t, 1H), 7.16 (t, 1H), 5.39 (t, 1H), 4.56 (d, 2H). |

General Procedure 2: Preparation of Benzyl Bromides from Benzyl Alcohols

Method 2A: The benzyl alcohol in question was initially charged in DMF (2 ml/mmol), and 2 eq. of carbon tetrabromide were added. 2 eq. of triphenylphosphin were then added a little at a time over a period of 30 min, and the mixture was stirred at RT overnight. The reaction mixture was then poured into water and extracted with tert-butyl methyl ether. The organic phases were dried over magnesium sulfate and concentrated. The crude product was then purified by flash chromatography on silica gel (mobile phase cyclohexane).

Method 2B: The benzyl alcohol in question was initially charged in dichloromethane (2 ml/mmol), 1.2 eq. of triphenylphosphine dibromide were added and the mixture was stirred at RT overnight. The reaction mixture was then washed with water, and the organic phase was dried over magnesium sulfate and concentrated. The crude product was purified by flash chromatography on silica gel (mobile phase cyclohexane).

The following compounds were prepared according to General procedure 2A or 2B:

| Example | Name/Structure | Method | Analytical data |
|---|---|---|---|
| 233A | 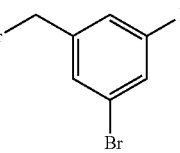<br>1-bromo-3-(bromomethyl)-5-fluorobenzene | 2A | LC-MS (method 15):<br>$R_t$ = 1.17 min; m/z = 289 [M + $NH_4$]$^+$. |
| 234A | <br>2-bromo-4-(bromomethyl)-1-fluorobenzene | 2B | GC-MS (method 3):<br>$R_t$ = 4.53 min; m/z = 268 [M]$^+$.<br>$^1$H-NMR (400 MHz, DMSO-$d_6$): δ = 7.84 (dd, 1H), 7.42-7.59 (m, 1H), 7.33-7.42 (m, 1H), 4.71 (s, 2H). |
| 235A | 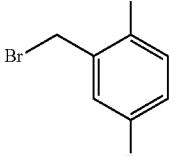<br>4-bromo-2-(bromomethyl)-1-fluorobenzene | 2B | GC-MS (method 3):<br>$R_t$ = 4.32 min; m/z = 268 [M]$^+$.<br>$^1$H-NMR (400 MHz, DMSO-$d_6$): δ = 7.80 (dd, 1H), 7.60 (ddd, 1H), 7.19-7.30 (m, 1H), 4.62-4.73 (m, 2H). |
| 236A | 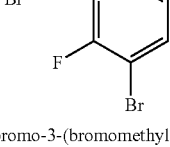<br>1-bromo-3-(bromomethyl)-2-fluorobenzene | 2B | GC-MS (method 3):<br>$R_t$ = 4.32 min; m/z = 268 [M]$^+$.<br>$^1$H-NMR (400 MHz, DMSO-$d_6$): δ = 7.66-7.78 (m, 1H), 7.49-7.63 (m, 1H), 7.18 (t, 1H), 4.73 (s, 2H). |

General Procedure 3: Alkylation of Benzyl Bromides with Ester Enolates

Under argon, a 0.3 M solution of diisopropylamine in THF was cooled to −40° C., and 1 eq. of n-butyllithium was added. After 30 min, the solution was cooled to −78° C., and 0.8 eq. of a solution of the carboxylic ester in question in THF (0.7 M) was added. The reaction mixture was stirred at −78° C. for 4 h, and 0.75 eq. of the benzyl bromide in question in THF (0.6 M) was then added. The reaction mixture was stirred overnight, during which time it was warmed to RT. Saturated ammonium chloride solution was then added. The mixture was extracted with ethyl acetate, and the organic phase was dried over magnesium sulfate and concentrated. The crude product obtained in this manner was purified by flash chromatography on silica gel (typical mobile phase mixture: cyclohexane/ethyl acetate 15:1→10:1).

The following compounds were prepared according to General procedure 3:

| Example | Name/Structure | Analytical data |
|---|---|---|
| 237A | 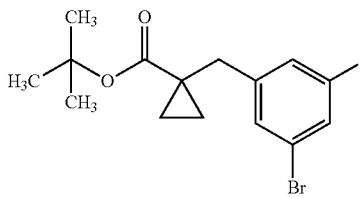<br>tert-butyl 1-(3-bromo-5-fluorobenzyl)-cyclopropanecarboxylate | GC-MS (method 3): $R_t$ = 5.64 min; m/z = 272/274 [M − $C_4H_9$]$^+$.<br>$^1$H-NMR (400 MHz, DMSO-$d_6$): δ = 7.37 (dd, 1H), 7.33 (s, 1H), 7.13 (d, 1H), 2.84 (s, 2H), 1.25-1.32 (m, 9H), 1.06-1.14 (m, 2H), 0.89-0.93 (m, 2H). |
| 238A | 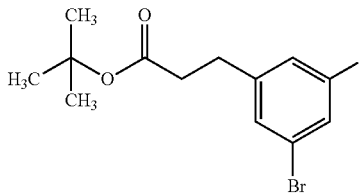<br>tert-butyl 3-(3-bromo-5-fluorophenyl)propanoate | GC-MS (method 3): $R_t$ = 5.24 min; m/z = 246/248 [M − $C_4H_9$]$^+$.<br>$^1$H-NMR (400 MHz, DMSO-$d_6$): δ = 7.33-7.40 (m, 1H), 7.32 (s, 1H), 7.15 (d, 1H), 2.82 (t, 2H), 2.52-2.58 (m, 2H), 1.35 (s, 9H). |
| 239A | 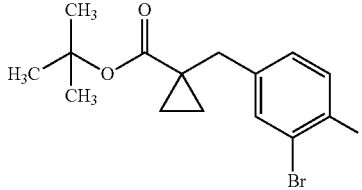<br>tert-butyl 1-(3-bromo-5-fluorobenzyl)-cyclopropanecarboxylate | GC-MS (method 3): $R_t$ = 5.85 min; m/z = 272/274 [M − $C_4H_9$]$^+$.<br>$^1$H-NMR (400 MHz, DMSO-$d_6$): δ = 7.52-7.62 (m, 1H), 7.22-7.36 (m, 2H), 2.81 (s, 2H), 1.29 (s, 9H), 1.05-1.10 (m, 2H), 0.86-0.91 (m, 2H). |
| 240A | 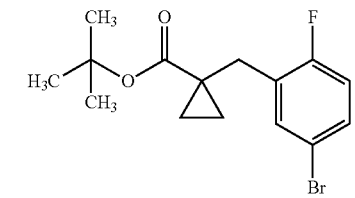<br>tert-butyl 1-(5-bromo-2-fluorobenzyl)-cyclopropanecarboxylate | GC-MS (method 3): $R_t$ = 5.72 min; m/z = 272/274 [M − $C_4H_9$]$^+$.<br>$^1$H-NMR (400 MHz, DMSO-$d_6$): δ = 7.52 (dd, 1H), 7.39-7.49 (m, 1H), 7.07-7.21 (m, 1H), 2.86 (s, 2H), 1.29 (s, 9H), 1.10-1.15 (m, 2H), 0.84-0.91 (m, 2H). |
| 241A | 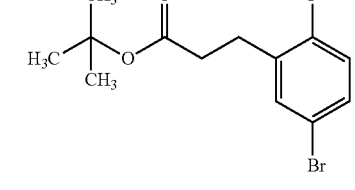<br>tert-butyl 3-(5-bromo-2-fluorophenyl)propanoate | GC-MS (method 3): $R_t$ = 5.32 min; m/z = 246/248 [M − $C_4H_9$]$^+$. |

| Example | Name/Structure | Analytical data |
|---|---|---|
| 242A | tert-butyl 1-(3-bromo-2-fluorobenzyl)-cyclopropanecarboxylate | ¹H-NMR (400 MHz, DMSO-d₆): δ = 7.50-7.59 (m, 1H), 7.39 (t, 1H), 7.11 (t, 1H), 2.91 (s, 2H), 1.22-1.29 (m, 9H), 1.10-1.16 (m, 2H), 0.84-0.91 (m, 2H). |

General Procedure 4: Buchwald-Hartwig Reaction of Phenyl Bromides to N-Benzylphenyl-Amines Under an atmosphere of argon, 1.2 eq. of sodium tert-butoxide were suspended in toluene (1.5 ml/mmol), 1 eq. of the phenyl bromide in question, 1.2 eq. of benzylamine, 0.05 eq. of tris(dibenzylideneacetone)dipalladium and 0.04 eq. of rac-2,2'-bis(diphenylphosphino)-1,1'-binaphthyl were added and the mixture was heated at 110° C. for 2 h. After cooling to RT, saturated ammonium chloride solution and ethyl acetate were added, and the reaction mixture was filtered through Celite. The organic phase was washed in each case once with saturated ammonium chloride solution and saturated sodium chloride solution, then dried over magnesium sulfate and concentrated. The crude product obtained in this manner was purified by flash chromatography on silica gel (typical mobile phase mixture: cyclohexane/ethyl acetate 50:1).

The following compounds were prepared according to General procedure 4:

| Example | Name/Structure | Analytical data |
|---|---|---|
| 243A | tert-butyl 1-[3-(benzylamino)-5-fluorobenzyl]-cyclopropanecarboxylate | LC-MS (method 11): $R_t$ = 1.60 min; m/z = 356 [M + H]⁺. ¹H-NMR (400 MHz, DMSO-d₆): δ = 7.28-7.37 (m, 4H), 7.16-7.28 (m, 1H), 6.50 (t, 1H), 6.31 (s, 1H), 6.04-6.20 (m, 2H), 4.23 (d, 2H), 2.68 (s, 2H), 1.22-1.32 (m, 9H), 0.97-1.06 (m, 2H), 0.67-0.79 (m, 2H). |
| 244A | tert-butyl 3-[3-(benzylamino)-5-fluorophenyl]-propanoate | LC-MS (method 15): $R_t$ = 1.35 min; m/z = 330 [M + H]⁺. ¹H-NMR (400 MHz, DMSO-d₆): δ = 7.26-7.40 (m, 4H), 7.18-7.26 (m, 1H), 6.48 (t, 1H), 6.29 (s, 1H), 6.07-6.20 (m, 2H), 4.24 (d, 2H), 2.64 (t, 2H), 2.43 (t, 2H), 1.36 (s, 9H). |
| 245A | tert-butyl 1-[3-(benzylamino)-4-fluorobenzyl]-cyclopropanecarboxylate | LC-MS (method 11): $R_t$ = 1.63 min; m/z = 356 [M + H]⁺. ¹H-NMR (400 MHz, DMSO-d₆): δ = 7.27-7.39 (m, 4H), 7.22 (d, 1H), 6.88 (dd, 1H), 6.43 (dd, 1H), 6.31-6.38 (m, 1H), 6.02-6.13 (m, 1H), 4.30 (d, 2H), 2.64 (s, 2H), 1.25 (s, 9H), 0.89-0.96 (m, 2H), 0.55-0.63 (m, 2H). |

-continued

| Example | Name/Structure | Analytical data |
|---|---|---|
| 246A | tert-butyl 3-[5-(benzylamino)-2-fluorophenyl]-propanoate | LC-MS (method 15): $R_t$ = 1.34 min; m/z = 330 $[M + H]^+$<br>$^1$H-NMR (400 MHz, DMSO-$d_6$): δ = 7.26-7.46 (m, 4H), 7.16-7.26 (m, 1H), 6.80 (t, 1H), 6.47 (dd, 1H), 6.37 (dt, 1H), 6.04 (t, 1H), 4.21 (d, 2H), 2.69 (t, 2H), 2.42 (t, 2H), 1.36 (s, 9H). |
| 247A | tert-butyl 1-[5-(benzylamino)-2-fluorobenzyl]-cyclopropanecarboxylate | LC-MS (method 11): $R_t$ = 1.60 min; m/z = 356 $[M + H]^+$.<br>$^1$H-NMR (400 MHz, DMSO-$d_6$): δ = 7.18-7.35 (m, 5H), 6.75-6.87 (m, 1H), 6.52 (dd, 1H), 6.37 (dt, 1H), 6.11 (t, 1H), 4.19 (d, 2H), 2.76 (s, 2H), 1.29 (s, 9H), 0.92-1.04 (m, 2H), 0.60-0.72 (m, 2H). |
| 248A | tert-butyl 1-[3-(benzylamino)-2-fluorobenzyl]-cyclopropanecarboxylate | LC-MS (method 11): $R_t$ = 1.66 min; m/z = 356 $[M + H]^+$.<br>$^1$H NMR (400 MHz, DMSO-$d_6$): δ = 7.25-7.41 (m, 4H), 7.13-7.25 (m, 1H), 6.75 (t, 1H), 6.48 (t, 1H), 6.39 (t, 1H), 6.02-6.16 (m, 1H), 4.32 (d, 2H), 2.85 (s, 2H), 1.29 (s, 9H), 1.03-1.12 (m, 2H), 0.70-0.83 (m, 2H). |

General Procedure 5: Hydrogenation of N-Benzylphenylamines to Phenylamines

The N-benzylphenylamine in question was dissolved in a 1:1 mixture of ethanol and THF (5 ml/mmol), 10% palladium on activated carbon (35 mg/mmol) was added and the mixture was stirred overnight at RT and a hydrogen pressure of 1 bar. The reaction mixture was then filtered through Celite, the residue was washed with ethanol and the filtrate was concentrated. The crude product obtained in this manner was purified by flash chromatography on silica gel (typical mobile phase mixture: cyclohexane/ethyl acetate 3:1).

The following compounds were prepared according to General procedure 5:

| Example | Name/Structure | Analytical data |
|---|---|---|
| 249A | tert-butyl 1-(3-amino-5-fluorobenzyl)-cyclopropanecarboxylate | LC-MS (method 15): $R_t$ = 1.14 min; m/z = 266 $[M + H]^+$. $^1$H-NMR (400 MHz, DMSO-$d_6$): δ = 6.25 (s, 1H), 6.11 (d, 1H), 6.14 (d, 1H), 5.28 (s, 2H), 2.68 (s, 2H), 1.30 (s, 9H), 1.01-1.11 (m, 2H), 0.71-0.85 (m, 2H). |

| Example | Name /Structure | Analytical data |
|---|---|---|
| 250A | tert-butyl 3-(3-amino-5-fluorophenyl)propanoate | GC-MS (method 3): $R_t$ = 5.89 min; m/z = 239 [M]$^+$. $^1$H-NMR (400 MHz, DMSO-d$_6$): δ = 6.20 (s, 1H), 6.05-6.17 (m, 2H), 5.30 (s, 2H), 2.63 (t, 2H), 2.43 (t, 2H), 1.37 (s, 9H). |
| 251A | tert-butyl 1-(3-amino-4-fluorobenzyl)-cyclopropanecarboxylate | LC-MS (method 15): $R_t$ = 1.14 min; m/z = 266 [M + H]$^+$. $^1$H-NMR (400 MHz, DMSO-d$_6$): δ = 6.84 (dd, 1H), 6.63 (dd, 1H), 6.36 (ddd, 1H), 4.98 (s, 2H), 2.68 (s, 2H), 1.25-1.35 (m, 9H), 0.96-1.09 (m, 2H), 0.69-0.83 (m, 2H). |
| 252A | tert-butyl 3-(5-amino-2-fluorophenyl)propanoate | LC-MS (method 15): $R_t$ = 1.14 min; m/z = 240 [M + H]$^+$. $^1$H-NMR (400 MHz, DMSO-d$_6$): δ = 6.76 (dd, 1H), 6.29-6.50 (m, 2H), 4.85 (br. s, 2H), 2.68 (t, 2H), 2.42 (t, 2H), 1.36 (s, 9H). |
| 253A | tert-butyl 1-(3-amino-2-fluorobenzyl)-cyclopropanecarboxylate | LC-MS (method 15): $R_t$ = 1.14 min; m/z = 266 [M + H]$^+$. $^1$H-NMR (400 MHz, DMSO-d$_6$): δ = 6.68-6.87 (m, 1H), 6.51-6.66 (m, 1H), 6.39-6.51 (m, 1H), 4.98 (s, 2H), 2.83 (s, 2H), 1.25-1.38 (m, 9H), 1.01-1.13 (m, 2H), 0.68-0.84 (m, 2H). |
| 254A | tert-butyl 1-(5-amino-2-fluorobenzyl)-cyclopropanecarboxylate | GC-MS (method 3): $R_t$ = 6.16 min; m/z = 265 [M]$^+$. |

Example 255A

Methyl 2,2-dimethyl-3-(3-nitrophenyl)propanoate

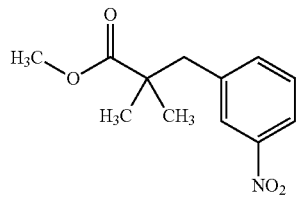 [SMILES: COC(=O)C(C)(C)Cc1cccc([N+](=O)[O-])c1]

Under argon, 11.7 ml (83.32 mmol) of diisopropylamine were dissolved in 200 ml of THF and cooled to −78° C. 33.3 ml (83.32 mmol) of a 2.5 M solution of n-butyllithium in hexane were added dropwise to this solution. The reaction solution was then warmed to −10° C. and stirred at this temperature for 10 min. The reaction solution was then once more cooled to −78° C., and 8.4 ml (72.9 mmol) of methyl 2-methylpropanoate were added slowly. The mixture was then stirred at −78° C. for 30 min. 15 g (69.4 mmol) of 1-(bromomethyl)-3-nitrobenzene, dissolved in 150 ml of THF, were then slowly added dropwise. After the addition had ended, the solution was slowly warmed to room temperature and stirred overnight. After TLC check (mobile phase: toluene/ethyl acetate 10:1), saturated ammonium chloride solution was added and the reaction mixture was taken up in ethyl acetate. The aqueous phase was extracted three times with ethyl acetate. The combined organic phases were dried over sodium sulfate. After filtration, the solvent was removed under reduced pressure. The crude product was purified chromatographically on silica gel (mobile phase toluene/ethyl acetate 20:1). This gave 12.2 g (51.4 mmol, 74% of theory) of the title compound.

$^1$H-NMR (400 MHz, DMSO-$d_6$): δ=8.11 (d, 1H), 7.96 (s, 1H), 7.54-7.63 (m, 2H), 2.97 (s, 3H), 2.54 (s, 2H), 1.14 (s, 6H).

Example 256A

Methyl 3-(3-aminophenyl)-2,2-dimethylpropanoate

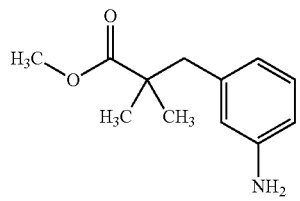

At room temperature, 1 g of palladium on carbon (10%) was added to a solution of 12 g (51.42 mmol) of methyl 2,2-dimethyl-3-(3-nitrophenyl)propanoate in 200 ml of ethanol, and the mixture was hydrogenated under atmospheric pressure for 12 hours. After the reaction had gone to completion (monitored by TLC; mobile phase cyclohexane/ethyl acetate 1:1), the reaction solution was filtered through kieselguhr and the filtrate was concentrated under reduced pressure. The crude product was purified chromatographically on silica gel (mobile phase cyclohexane/ethyl acetate 4:1→1:1). This gave 9.2 g (44.39 mmol, 86% of theory) of the title compound.

LC-MS (method 10): $R_t$=1.10 min; m/z=208 (M+H)$^+$.

$^1$H-NMR (400 MHz, DMSO-$d_6$): δ=6.88 (t, 1H), 6.39 (d, 1H), 6.27 (s, 1H), 6.20 (d, 1H), 4.93 (s, 2H), 2.62 (s, 3H), 1.99 (s, 2H), 1.09 (s, 6H).

Example 257A

2-Chloro-3-nitrobenzaldehyde

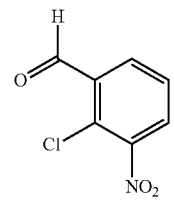 [SMILES: O=Cc1cccc([N+](=O)[O-])c1Cl]

8.43 g (39.09 mmol) of pyridinium chlorochromate (PCC) were added to a solution of 6.11 g (32.57 mmol) of (2-chloro-3-nitrophenyl)methanol in 120 ml of dichloromethane, and the mixture was stirred at room temperature for 12 hours. After complete conversion, the solvent was evaporated to dryness under reduced pressure. The residue obtained was purified chromatographically on silica gel (mobile phase dichloromethane/methanol 20:1). This gave 4.82 g (25.97 mmol, 79.7% of theory) of the title compound.

GC-MS (method 3): $R_t$=5.09 min; m/z=186 (M+H)$^+$.

$^1$H-NMR (400 MHz, DMSO-$d_6$): δ=10.35 (s, 1H), 8.33 (dd, 1H), 8.13 (dd, 1H), 7.77 (t, 1H).

Example 258A tert-Butyl(2E)-3-(2-chloro-3-nitrophenyl)prop-2-enoate

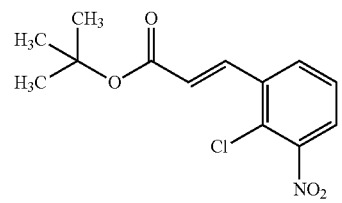 [SMILES: CC(C)(C)OC(=O)/C=C/c1cccc([N+](=O)[O-])c1Cl]

Under argon, 98 mg (2.46 mmol, 60% pure) of sodium hydride were suspended in 2 ml of toluene and 2 ml of THF, and the suspension was cooled to 0° C. 0.6 ml (2.57 mmol) of tert-butyl (diethoxyphosphoryl)acetate was then slowly added dropwise, and the mixture was stirred at 0° C. for 30 min. 415 mg (2.24 mmol) of 2-chloro-3-nitrobenzaldehyde were then added to the reaction mixture, and the reaction mixture was then warmed to room temperature. The mixture was stirred at room temperature for 2 hours, and 5 ml of water were then added. After removal of the organic phase, the aqueous phase was extracted three more times with ethyl acetate. The combined organic phases were dried over sodium sulfate. After filtration, the solvent was removed under reduced pressure. The crude product was purified chromatographically on silica gel (mobile phase cyclohexane/ethyl acetate 10:1). This gave 429 mg (1.51 mmol, 59% of theory) of the title compound.

MS (DCI): m/z=301 (M+NH$_4$)$^+$.

$^1$H-NMR (400 MHz, DMSO-$d_6$): δ=8.23 (d, 1H), 8.07 (d, 1H), 7.84 (d, 1H), 7.62 (t, 1H), 6.73 (d, 1H), 1.50 (s, 9H).

Example 259A tert-Butyl 3-(3-amino-2-chlorophenyl)propanoate

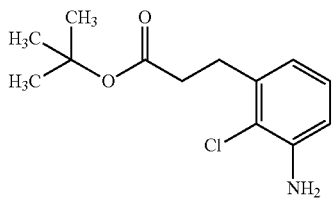

At room temperature, 50 mg of platinum on carbon (5%) were added to a solution of 200 mg (0.71 mmol) of tert-butyl (2E)-3-(2-chloro-3-nitrophenyl)prop-2-enoate in 10 ml of ethyl acetate, and the mixture was hydrogenated at atmospheric pressure for 12 hours. After the reaction had gone to completion (monitored by TLC; mobile phase cyclohexane/ethyl acetate 1:1), the reaction solution was filtered through kieselguhr and the filtrate was concentrated under reduced pressure. The crude product was purified by preparative HPLC. This gave 115 mg (0.62 mmol, 64% of theory) of the title compound.

GC-MS (method 3): $R_t$=6.42 min; m/z=256 (M+H)$^+$.

Example 260A tert-Butyl(2E)-3-(4-chloro-3-nitrophenyl)prop-2-enoate

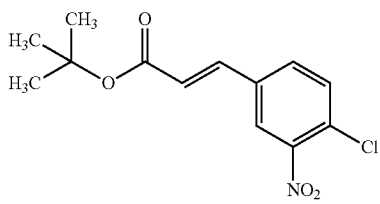 [SMILES: CC(C)(C)OC(=O)/C=C/c1ccc(Cl)c([N+](=O)[O-])c1]

Under argon, 1.19 g (29.64 mmol, 60% pure) of sodium hydride were suspended in 25 ml of toluene and 25 ml of THF, and the suspension was cooled to 0° C. 7.28 ml (30.99 mmol) of tert-butyl(diethoxyphosphoryl)acetate were then slowly added dropwise, and the mixture was stirred at 0° C. for 30 min. 5 g (26.94 mmol) of 4-chloro-3-nitrobenzaldehyde were then added to the reaction mixture, and the reaction mixture was then warmed to room temperature. The mixture was stirred at room temperature for 2 hours, and 50 ml of water were then added. After removal of the organic phase, the aqueous phase was extracted three more times with ethyl acetate. The combined organic phases were dried over sodium sulfate. After filtration, the solvent was removed under reduced pressure. The crude product was purified chromatographically on silica gel (mobile phase cyclohexane/ethyl acetate 9:1). This gave 6.77 g (23.86 mmol, 77% of theory) of the title compound.

MS (DCI): m/z=301 (M+NH$_4$)$^+$.

$^1$H-NMR (400 MHz, DMSO-d$_6$): δ=8.46 (d, 1H), 8.07 (dd, 1H), 7.71 (d, 1H), 7.51 (d, 1H), 6.75 (d, 1H), 1.49 (s, 9H).

Example 261A tert-Butyl 3-(3-amino-4-chlorophenyl)propanoate

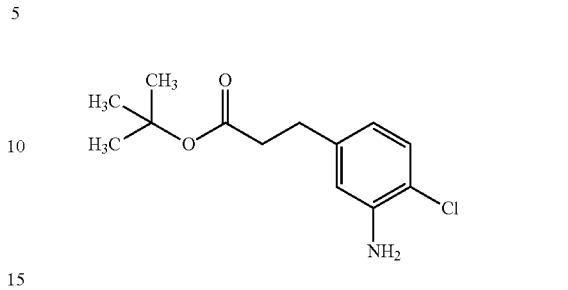

At room temperature, 500 mg of palladium on carbon (10%) were added to a solution of 6.74 g (23.76 mmol) of tert-butyl(2E)-3-(4-chloro-3-nitrophenyl)prop-2-enoate in 200 ml of ethanol and 20 ml of THF, and the mixture was hydrogenated under atmospheric pressure for 12 hours. After the reaction had gone to completion (monitored by TLC; mobile phase cyclohexane/ethyl acetate 1:1), the reaction solution was filtered through kieselguhr and the filtrate was concentrated under reduced pressure. The crude product was purified chromatographically on silica gel (mobile phase cyclohexane/ethyl acetate 4:1→2:1). This gave 1.40 g (5.47 mmol, 23% of theory) of the title compound.

LC-MS (method 15): $R_t$=1.14 min; m/z=256 (M+H)$^+$.

$^1$H-NMR (400 MHz, DMSO-d$_6$): δ=7.08 (d, 1H), 6.62 (s, 1H), 6.39 (dd, 1H), 5.22 (s, 2H), 2.66 (t, 2H), 2.45 (t, 2H), 1.37 (s, 9H).

Example 262A

6-Phenylpyridazin-3(2H)-one

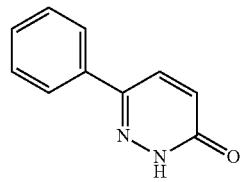 [SMILES: O=c1ccc(-c2ccccc2)n[nH]1]

19.6 g (162.95 mmol) of 1-phenylethanone and 5 g (54.32 mmol) of oxoacetate monohydrate were stirred at 100° C. for 2 hours. The reaction solution was then cooled to 40° C., and 20 ml of water and 4 ml of ammonia were added. The mixture was then twice extracted with 50 ml of dichloromethane. 2.64 ml (53.32 mmol) of hydrazine monohydrate were then added to the aqueous phase obtained, and the mixture was stirred at 100° C. for 2 hours. After the reaction, the reaction solution was cooled to room temperature. The precipitated crystals were filtered off with suction, washed with water and dried in a vacuum drying cabinet at 50° C. overnight. This gave 4.3 g (24.97 mmol, 15% of theory) of the title compound as colorless crystals.

LC-MS (method 7): $R_t$=1.39 min; m/z=173 (M+H)$^+$.

$^1$H-NMR (400 MHz, DMSO-d$_6$, δ/ppm): 13.2 (s, 1H), 8.04 (d, 1H), 7.86 (d, 2H), 7.53-7.41 (m, 3H), 7.00 (d, 1H).

Example 263A 6-(Trifluoromethyl)-4,5-dihydropyridazin-3(2H)-one

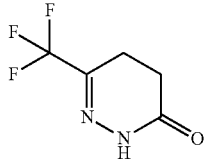

8.44 g (26.1 mmol) of tert-butyl 3-[5-oxo-4-(propan-2-yl)-2-(trifluoromethyl)-2,5-dihydro-1,3-oxazol-2-yl]propanoate [CAS Reg. No. 87341-14-8] and 13.44 g (130.5 mmol) of hydrazine hydrochloride were stirred in 100 ml of glacial acetic acid at 118° C. for 2 hours. The reaction solution was then evaporated to dryness under reduced pressure. The residue obtained was taken up in 100 ml of water and made basic using potassium carbonate. The basic solution was subsequently extracted three times with dichloromethane. The combined organic phases were dried over magnesium sulfate, filtered and concentrated to dryness. The crude product was purified chromatographically on silica gel (mobile phase dichloromethane/methanol 50:1→10:1). This gave 2.65 g (15.95 mmol, 61% of theory) of the title compound.

$^1$H-NMR (400 MHz, DMSO-$d_6$): δ=11.33 (br. s, 1H), 2.76 (t, 2H), 2.52 (t, 2H).

GC-MS (method 3): $R_t$=2.76 min; m/z=166 (M)$^+$.

Example 264A 6-(Trifluoromethyl)pyridazin-3(2H)-one

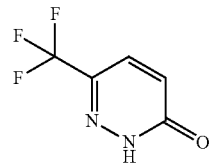 [SMILES: O=c1ccc(C(F)(F)F)n[nH]1]

2.6 g (15.65 mmol) of 6-(trifluoromethyl)-4,5-dihydropyridazin-3(2H)-one were dissolved in 20 ml of glacial acetic acid, and the mixture was heated to 100° C. 0.81 ml (15.65 mmol) of bromine was then slowly added dropwise to the solution, and the mixture was stirred at 100° C. for 4 hours. After cooling of the reaction solution, the solvent was removed under reduced pressure and the residue obtained was purified chromatographically on silica gel (mobile phase dichloromethane/methanol 50:1→20:1). This gave 1.34 g (8.15 mmol, 52% of theory) of the title compound.

$^1$H-NMR (400 MHz, DMSO-$d_6$): δ=13.73 (br. s, 1H), 7.81 (d, 1H), 7.11 (d, 1H).

GC-MS (method 3): $R_t$=2.92 min; m/z=164 (M)$^+$.

MS (DCI): m/z=182 (M+NH$_4$)$^+$.

The compounds listed in the table below were obtained in a manner analogous to Example 25A:

| Example | Name/Structure/Starting materials | Analytical data |
|---|---|---|
| 265A | ethyl 4,4,4-trifluoro-3-methyl-2-{4-[(5-oxo-2-phenyl-5,6-dihydro-4H-1,3,4-oxadiazin-4-yl)methyl]phenyl}butanoate<br>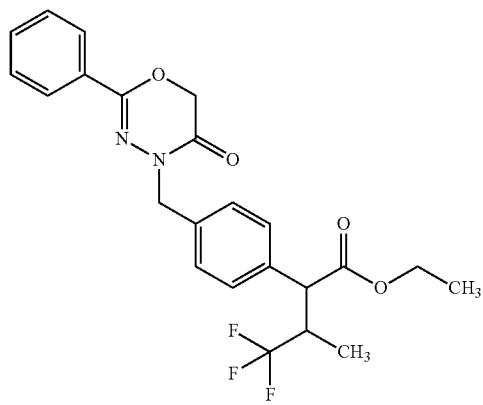<br>(from ethyl 2-[4-(bromomethyl)phenyl]-4,4,4-trifluoro-3-methylbutanoate and 2-phenyl-4H-1,3,4-oxadiazin-5(6H)-one) | GC-MS (method 3):<br>$R_t$ = 9.98 min; m/z = 449 (M + H)$^+$. |

| Example | Name/Structure/Starting materials | Analytical data |
|---|---|---|
| 266A | ethyl 4,4,4-trifluoro-3-methyl-2-{4-[(6-oxo-3-phenylpyridazin-1(6H)-yl)methyl]phenyl}butanoate<br>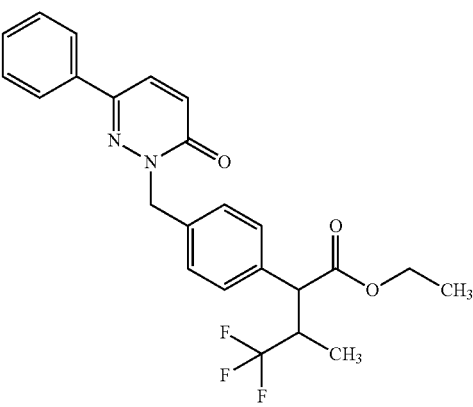<br>(from ethyl 2-[4-(bromomethyl)phenyl]-4,4,4-trifluoro-3-methylbutanoate and 6-phenylpyridazin-3(2H)-one) | LC-MS (method 7): $R_t$ = 2.78 min; m/z = 445 (M + H)$^+$. |
| 267A | tert-butyl 6,6,6-trifluoro-4-methyl-2-{4-[(5-oxo-2-phenyl-5,6-dihydro-4H-1,3,4-oxadiazin-4-yl)methyl]phenyl}hexanoate<br>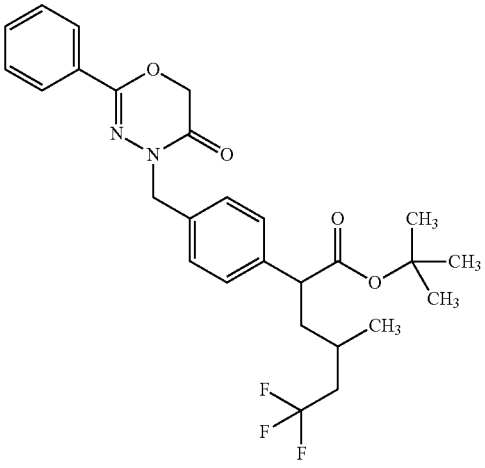<br>(from tert-butyl 2-[4-(bromomethyl)phenyl]-6,6,6-trifluoro-4-methylhexanoate and 2-phenyl-4H-1,3,4-oxadiazin-5(6H)-one) | LC-MS (method 10): $R_t$ = 2.85 min; m/z = 505 (M + H)$^+$. |

| Example | Name/Structure/Starting materials | Analytical data |
|---|---|---|
| 268A | tert-butyl cyclopentyl{4-[(6-oxo-3-phenylpyridazin-1(6H)-yl)methyl]phenyl}acetate<br>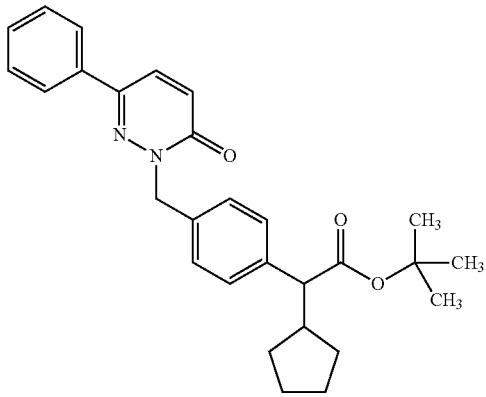 [SMILES: CC(C)(C)OC(=O)C(c1ccc(Cn2nc(-c3ccccc3)ccc2=O)cc1)C1CCCC1]<br>(from Example 10A and 6-phenylpyridazin-3(2H)-one) | LC-MS (method 11):<br>$R_t$ = 1.70 min; m/z = 445 (M + H)$^+$. |
| 269A | tert-butyl 5,5,5-trifluoro-3-methyl-2-{4-[(5-oxo-2-phenyl-5,6-dihydro-4H-1,3,4-oxadiazin-4-yl)-methyl]phenyl}pentanoate<br>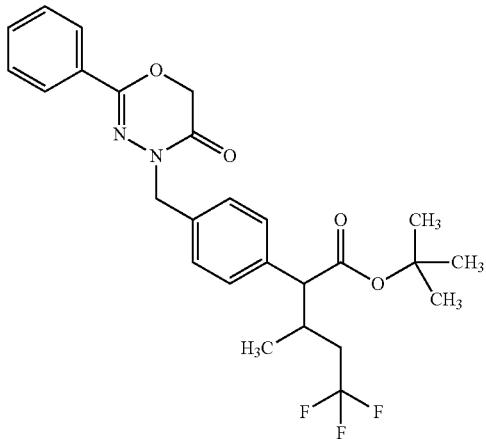<br>(from tert-butyl 2-[4-(bromomethyl)phenyl]-5,5,5-trifluoro-3-methylpentanoate and 2-phenyl-4H-1,3,4-oxadiazin-5(6H)-one) | LC-MS (method 11):<br>$R_t$ = 1.63 min; m/z = 491 (M + H)$^+$. |

| Example | Name/Structure/Starting materials | Analytical data |
|---|---|---|
| 270A | ethyl 2-{4-[(5-oxo-2-phenyl-5,6-dihydro-4H-1,3,4-oxadiazin-4-yl)methyl]phenyl}-3-(trifluoromethyl)-pentanoate<br>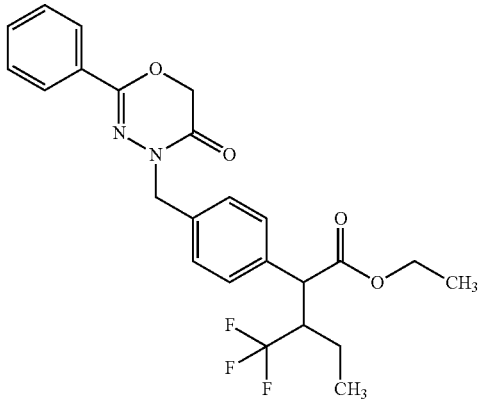<br>(from ethyl 2-[4-(bromomethyl)phenyl]-3-(trifluoromethyl)pentanoate and 2-phenyl-4H-1,3,4-oxadiazin-5(6H)-one) | LC-MS (method 12):<br>$R_t$ = 2.77 min; m/z = 463 (M + H)$^+$. |
| 271A | tert-butyl cyclopentyl{4-[(3-methyl-6-oxopyridazin-1(6H)-yl)methyl]phenyl}acetate<br>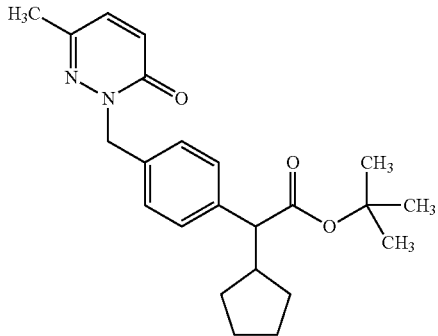<br>(from Example 10A and 6-methylpyridazin-3(2H)-one) | LC-MS (method 12):<br>$R_t$ = 2.65 min; m/z = 327 (M – $C_4H_8$ + H)$^+$. |
| 272A | tert-butyl cyclopentyl(4-{[6-oxo-3-(trifluoromethyl)-pyridazin-1(6H)-yl]methyl}phenyl)acetate<br>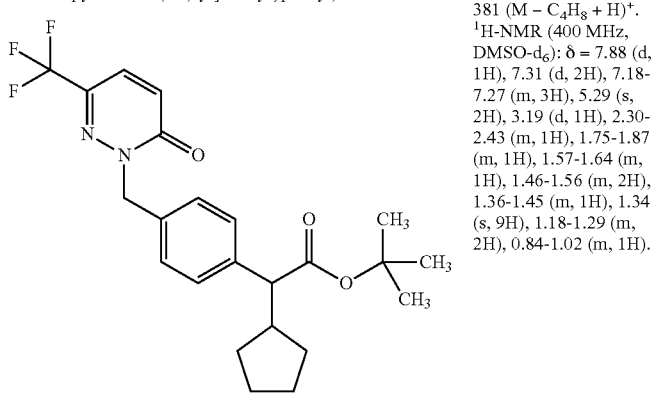<br>(from Example 10A and 6-(trifluoromethyl)pyridazin-3(2H)-one) | LC-MS (method 15):<br>$R_t$ = 1.45 min; m/z = 381 (M – $C_4H_8$ + H)$^+$.<br>$^1$H-NMR (400 MHz, DMSO-$d_6$): δ = 7.88 (d, 1H), 7.31 (d, 2H), 7.18-7.27 (m, 3H), 5.29 (s, 2H), 3.19 (d, 1H), 2.30-2.43 (m, 1H), 1.75-1.87 (m, 1H), 1.57-1.64 (m, 1H), 1.46-1.56 (m, 2H), 1.36-1.45 (m, 1H), 1.34 (s, 9H), 1.18-1.29 (m, 2H), 0.84-1.02 (m, 1H). |

| Example | Name/Structure/Starting materials | Analytical data |
|---|---|---|
| 273A | tert-butyl cyclopentyl{4-[(5-methyl-6-oxopyridazin-1(6H)-yl)methyl]phenyl}acetate<br><br>(from Example 10A and 4-methylpyridazin-3(2H)-one) | LC-MS (method 15): $R_t$ = 1.42 min; m/z = 382 (M + H)$^+$.<br>$^1$H-NMR (500 MHz, DMSO-d$_6$): δ = 7.65 (d, 1H), 7.25-7.34 (m, 3H), 7.17-7.24 (m, 2H), 6.16 (t, 1H), 5.08 (s, 2H), 3.17 (d, 1H), 2.33-2.42 (m, 1H), 2.00 (s, 3H), 1.76-1.86 (m, 1H), 1.60 (d, 1H), 1.46-1.56 (m, 2H), 1.37-1.46 (m, 1H), 1.34 (s, 9H), 1.18-1.29 (m, 2H), 0.89-0.99 (m, 1H). |
| 274A | tert-butyl cyclopentyl(4-{[6-oxo-4-(trifluoromethyl)-pyridazin-1(6H)-yl]methyl}phenyl)acetate<br><br>(from Example 10A and 5-(trifluoromethyl)pyridazin-3(2H)-one) | LC-MS (method 15): $R_t$ = 1.39 min; m/z = 380 (M − C$_4$H$_8$ + H)$^+$.<br>$^1$H-NMR (500 MHz, DMSO-d$_6$): δ = 8.10 (d, 1H), 7.30 (d, 2H), 7.24 (d, 2H), 6.82 (s, 1H), 6.53 (d, 1H), 5.13 (s, 2H), 3.18 (d, 1H), 2.29-2.42 (m, 1H), 1.77-1.85 (m, 1H), 1.60 (d, 1H), 1.48-1.56 (m, 2H), 1.37-1.44 (m, 1H), 1.34 (s, 9H), 1.24 (d, 2H), 0.93 (dd, 1H). |
| 275A | tert-butyl (3,3-difluorocyclopentyl){4-[(5-oxo-2-phenyl-5,6-dihydro-4H-1,3,4-oxadiazin-4-yl)methyl]phenyl}acetate<br><br>(from tert-butyl [4-(bromomethyl)phenyl](3,3-difluorocyclopentyl)acetate and 2-phenyl-4H-1,3,4-oxadiazin-5(6H)-one) | LC-MS (method 15): $R_t$ = 1.40 min; m/z = 485 (M + H)$^+$. |

| Example | Name/Structure/Starting materials | Analytical data |
|---|---|---|
| 276A | tert-butyl cyclopentyl{4-[(4-methyl-6-oxopyridazin-1(6H)-yl)methyl]phenyl}acetate<br><br>(from Example 10A and 5-methylpyridazin-3(2H)-one) | LC-MS (method 15): $R_t$ = 1.30 min; m/z = 326 (M − $C_4H_8$ + H)$^+$.<br>$^1$H-NMR (500 MHz, DMSO-$d_6$): δ = 7.66 (d, 1H), 7.28 (d, 2H), 7.18 (d, 2H), 6.23 (s, 1H), 6.10 (d, 1H), 5.02 (s, 2H), 3.16 (d, 1H), 2.33-2.41 (m, 1H), 2.12 (s, 3H), 1.75-1.84 (m, 1H), 1.45-1.67 (m, 3H), 1.36-1.44 (m, 1H), 1.34 (s, 9H), 1.17-1.28 (m, 2H), 0.85-0.97 (m, 1H). |
| 277A | ethyl 4,4,4-trifluoro-3-methyl-2-(4-{[6-oxo-3-(trifluoromethyl)pyridazin-1(6H)-yl]methyl}phenyl)butanoate<br><br>(from ethyl 2-[4-(bromomethyl)phenyl]-3-(trifluoromethyl)pentanoate and 6-(trifluoromethyl)pyridazin-3(2H)-one) | LC-MS (method 11): $R_t$ = 1.45 min; m/z = 437 (M + H)$^+$. |
| 278A | tert-butyl cyclopentyl(4-{[6-oxo-5-(trifluoromethyl)-pyridazin-1(6H)-yl]methyl}phenyl)acetate<br><br>(from Example 10A and 4-(trifluoromethyl)pyridazin-3(2H)-one) | LC-MS (method 15): $R_t$ = 1.37 min; m/z = 380 (M − $C_4H_8$ + H)$^+$. |

-continued

| Example | Name/Structure/Starting materials | Analytical data |
|---|---|---|
| 279A | tert-butyl {4-[(3-chloro-6-oxopyridazin-1(6H)-yl)-methyl]phenyl}(cyclopentyl)acetate<br><br>(from Example 10A and 6-chloropyridazin-3(2H)-one) | LC-MS (method 11):<br>$R_t$ = 1.56 min; m/z<br>347 $(M - C_4H_8 + H)^+$. |

Example 280A and Example 281A tert-Butyl cyclopentyl{4-[(6-oxo-3-phenylpyridazin-1(6H)-yl)methyl]phenyl}acetate (enantiomers 1 and 2)

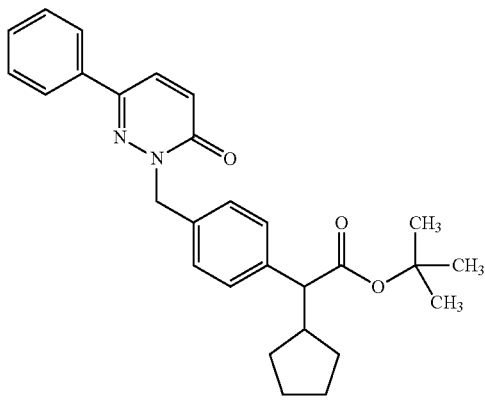

7.42 g (16.69 mmol) of the racemic tert-butyl cyclopentyl{4-[(6-oxo-3-phenylpyridazin-1(6H)-yl)methyl]phenyl}acetate were separated into the enantiomers by preparative HPLC on a chiral phase [column: Daicel Chiralpak AS-H, 5 μm, 250 mm×20 mm; mobile phase: isohexane/isopropanol 75:25 (v/v); flow rate: 15 ml/min; UV detection: 220 nm; temperature: 30° C.]:

Example 280A

Enantiomer 1

Yield: 4.1 g $R_t$ 5.28 min; purity >99%; >99% ee

[column: Daicel Chiralpak AS-H, 5 μm, 250 mm×4.6 mm; mobile phase: isohexane/isopropanol 75:25 (v/v); flow rate: 1 ml/min; UV detection: 220 nm; temperature: 40° C.].

Example 281A

Enantiomer 2

Yield: 2.8 g $R_t$ 5.84 min; purity >98%; >96% ee

[column: Daicel Chiralpak AS-H, 5 μm, 250 mm×4.6 mm; mobile phase: isohexane/isopropanol 75:25 (v/v); flow rate: 1 ml/min; UV detection: 220 nm; temperature: 40° C.].

Example 282A tert-Butyl cyclopentyl{4-[(1,3-dioxo-1,3-dihydro-2H-isoindol-2-yl)methyl]phenyl}acetate

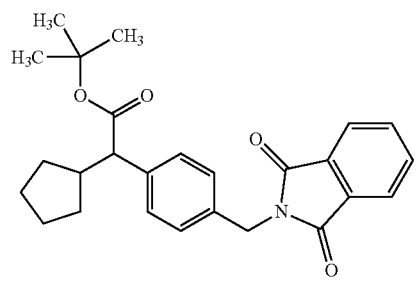 [SMILES: CC(C)(C)OC(=O)C(c1ccc(CN2C(=O)c3ccccc3C2=O)cc1)C1CCCC1]

Under argon, 6.49 g (35 mmol) of potassium phthalimide were initially charged in 60 ml of DMF, 15 g (31.8 mmol) of tert-butyl(+/−)-2-(4-(bromomethyl)phenyl)-2-cyclopentylacetate were added and the mixture was stirred at 80° C. overnight. A further 0.5 equivalent of potassium phthalimide was then added, and the mixture was stirred at 80° C. for another 6 h. The reaction mixture was then filtered, and the filtrate was concentrated under reduced pressure. The residue was triturated with ethanol and the solid was filtered off with suction, washed with ethanol and dried under high vacuum. This gave 8.5 g (about 96% pure, 61% of theory) of the target compound.

LC-MS (method 10): $R_t$=2.87 min; m/z=364 $(M-C_4H_8+H)^+$.

$^1$H-NMR (400 MHz, DMSO-d$_6$): δ=7.9-7.85 (m, 4H), 7.29-7.24 (m, 4H), 4.75 (s, 1H), 3.17 (d, 1H), 2.4-2.3 (m, 1H), 1.80 (ddd, 1H), 1.66-1.37 (m, 4H), 1.34 (s, 9H), 1.28-1.17 (m, 2H), 1.06 (t, 1H), 0.93 (m, 1H).

Example 283A (+/−)-2-Cyclopentyl-2-(4-((1,3-dioxoisoindolin-2-yl)methyl)phenyl)acetic acid

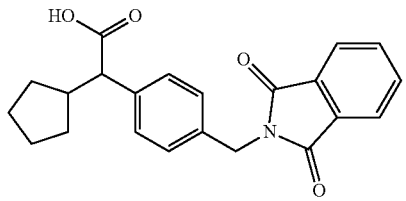 [SMILES: O=C(O)C(c1ccc(CN2C(=O)c3ccccc3C2=O)cc1)C1CCCC1]

8.5 g (20.26 mmol) of tert-butyl(+/−)-2-cyclopentyl-2-(4-((1,3-dioxoisoindolin-2-yl)methyl)-phenyl)acetate were initially charged in 95 ml of dichloromethane, 31.2 ml (405.2 mmol) of trifluoroacetic acid were added and the mixture was stirred at room temperature for 2 h. Water (250 ml) was then added, and the reaction mixture was extracted with dichloromethane. The organic phase was washed with water, dried over magnesium sulfate and concentrated. This gave 6.98 g (95% of theory) of the target compound.

LC-MS (method 11): R$_t$=1.28 min; m/z=364 (M+H)$^+$.

$^1$H-NMR (400 MHz, DMSO-d$_6$): δ=7.88 (m, 4H), 7.29-7.24 (m, 4H), 4.74 (s, 2H), 3.20 (d, 1H), 2.46-2.33 (m, 1H), 1.87-1.76 (m, 1H), 1.65-1.12 (m, 6H), 0.97-0.87 (m, 1H).

Example 284A tert-Butyl(+/−)-3-(3-(2-cyclopentyl-2-(4-((1,3-dioxoisoindolin-2-yl)methyl)phenyl)acetamido)-2-methylphenyl)propanoate

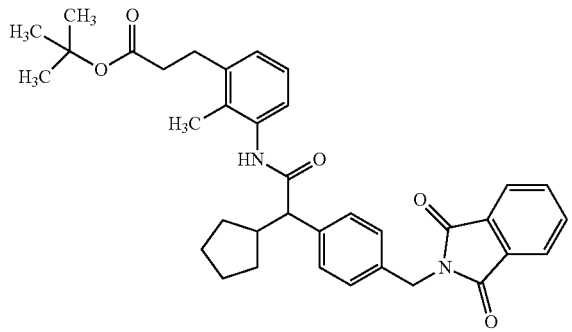 [SMILES: Cc1c(CCC(=O)OC(C)(C)C)cccc1NC(=O)C(c1ccc(CN2C(=O)c3ccccc3C2=O)cc1)C1CCCC1]

7.5 g (20.6 mmol) of (+/−)-2-cyclopentyl-2-(4-((1,3-dioxoisoindolin-2-yl)methyl)phenyl)acetic acid were dissolved in a mixture of 170 ml of DMF and 68 ml of pyridine, and 10.2 g (26.8 mmol) of TCTU were added. After 30 min of stirring at room temperature, 4.86 g (20.6 mmol) of tert-butyl 3-(3-amino-2-methylphenyl)propanoate were added. After stirring at room temperature overnight, the reaction mixture was concentrated and the residue pre-purified by flash chromatography on silica gel (mobile phase dichloromethane/methanol 100:1). The product obtained in this manner was triturated successively with ethanol and methanol, and the solid was filtered off with suction and dried under high vacuum. This gave 8.5 g (71% of theory) of the target compound.

LC-MS (method 10): R$_t$=2.71 min; m/z=581 (M+H)$^+$.

Example 285A (+/−)-tert-Butyl 3-[3-({[4-(aminomethyl)phenyl](cyclopentyl)acetyl}amino)-2-methyl-phenyl]propanoate

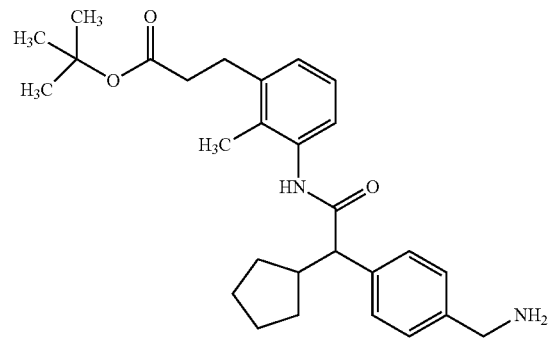 [SMILES: Cc1c(CCC(=O)OC(C)(C)C)cccc1NC(=O)C(c1ccc(CN)cc1)C1CCCC1]

8.5 g (14.6 mmol) of tert-butyl(+/−)-3-(3-(2-cyclopentyl-2-(4-((1,3-dioxoisoindolin-2-yl)methyl)phenyl)acetamido)-2-methylphenyl)propanoate were initially charged in 85 ml of ethanol, and 2.35 ml (48.3 mmol) of hydrazine hydrate were added. The reaction mixture was heated under reflux overnight. After cooling to room temperature, the precipitated solid was filtered off and washed with ethanol. The filtrate was concentrated, the residue was triturated with acetonitrile and the precipitated crystals were filtered off with suction and discarded. The mother liquor was concentrated and the residue was purified by flash chromatography on silica gel (mobile phase dichloromethane/methanol/aq. ammonia 100:5:1). This gave 4.51 g (68% of theory) of the target compound.

LC-MS (method 7): R$_t$=1.70 min; m/z=451 (M+H)$^+$.

$^1$H-NMR (400 MHz, DMSO-d$_6$): δ=9.44 (s, 1H), 7.31-7.39 (m, 2H), 7.24-7.30 (m, 2H), 6.93-7.07 (m, 3H), 3.68 (s, 2H), 3.43 (dd, 1H), 3.12-3.19 (m, 1H), 2.79 (t, 2H), 2.38-2.46 (m, 2H), 2.00 (s, 3H), 1.21-1.92 (m, 16H), 0.91-1.06 (m, 1H).

Example 286A (+/−)-tert-Butyl 3-{3-[(cyclopentyl{4-[(1-oxo-1,3-dihydro-2H-isoindol-2-yl)methyl]phenyl}-acetyl)amino]-2-methylphenyl}propanoate

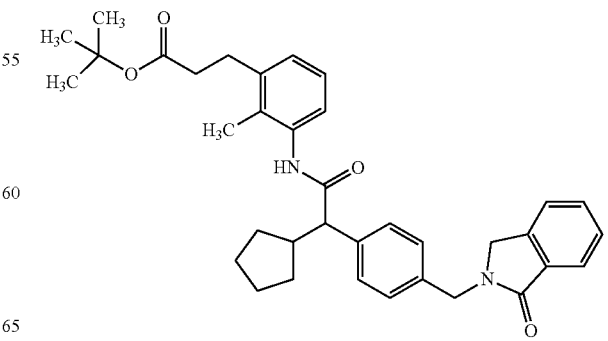

At RT, 50 mg (0.11 mmol) of (+/−)-tert-butyl 3-[3-({[4-(aminomethyl)phenyl](cyclopentyl)acetyl}amino)-2-methylphenyl]propanoate and 16.4 mg (0.12 mmol) of phthaldialdehyde were dissolved in 2.5 ml of glacial acetic acid, and the mixture was left to stand for 1 h. The reaction mixture was then poured into water and extracted with ethyl acetate. The organic phase was dried over magnesium sulfate and concentrated. The residue was purified by preparative RP-HPLC. This gave 53 mg (85% of theory) of the target compound.

LC-MS (method 10): $R_t$=2.54 min; m/z=567 (M+H)$^+$.

$^1$H-NMR (400 MHz, DMSO-d$_6$): δ=9.45 (s, 1H), 7.73 (d, 1H), 7.54-7.63 (m, 2H), 7.47-7.53 (m, 1H), 7.40 (d, 2H), 7.23 (d, 2H), 6.94-7.06 (m, 3H), 4.71 (s, 2H), 4.37 (s, 2H), 3.45 (d, 1H), 2.78 (t, 2H), 2.41 (t, 2H), 1.97 (s, 3H), 1.27-1.89 (m, 17H), 0.90-1.05 (m, 1H).

Example 287A tert-Butyl(+/−)-cyclopentyl{4-[(1-oxo-1,3-dihydro-2H-isoindol-2-yl)methyl]phenyl}acetate

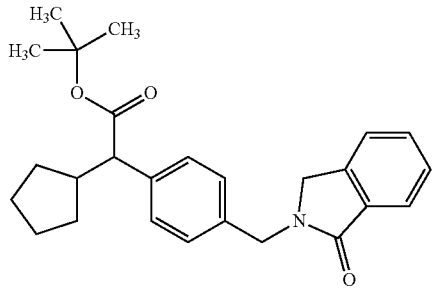

At 0° C., 611.3 mg (15.3 mmol, 60% pure) of sodium hydride were added to 2.035 g (15.3 mmol) of 1-oxoindoline in 12 ml of DMF. The mixture was stirred for 30 min, and 6.0 g (12.7 mmol) of tert-butyl(+/−)-[4-(bromomethyl)phenyl](cyclopentyl)acetate were then added at 0° C. The reaction mixture was stirred for a further 4 h, water was then added and the mixture was extracted twice with dichloromethane. The combined organic phases were washed with saturated sodium chloride solution, dried over magnesium sulfate and concentrated. The crude product was treated with diethyl ether in an ultrasonic bath and the solid was isolated by filtration. This gave 3.40 g (60.2% of theory) of the target compound.

LC-MS (method 11): $R_t$=1.57 min; m/z=350 (M−C$_4$H$_8$+H)$^+$.

$^1$H-NMR (400 MHz, DMSO-d$_6$): δ=7.72 (d, 1H), 7.60-7.50 (m, 3H), 7.30 (d, 2H), 7.21 (d, 2H), 4.71 (s, 2H), 4.38 (s, 2H), 3.18 (d, 1H), 2.35 (m, 1H), 1.85-1.37 (m, 5H), 1.34 (s, 9H), 1.20 (m, 2H), 0.91 (m, 1H).

Example 288A tert-Butyl(+)-(2S)-cyclopentyl{4-[(1-oxo-1,3-dihydro-2H-isoindol-2-yl)methyl]phenyl}acetate

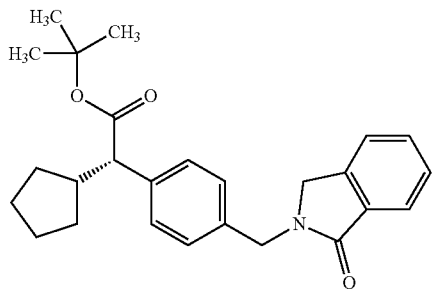 [SMILES: CC(C)(C)OC(=O)[C@H](c1ccc(CN2Cc3ccccc3C2=O)cc1)C1CCCC1]

The racemate obtained in Example 287A was separated into the enantiomers by preparative HPLC on a chiral phase [column: Daicel Chiralpak IA-H, 5 μm, 250 mm×20 mm; flow rate: 15 ml/min; UV detection: 220 nm; injection volume: 0.25 ml; temperature: 30° C.; mobile phase: 20% acetonitrile/80% methyl tert-butyl ether]. Starting with 3.40 g of racemate, 1.50 g of the (+)-enantiomer were obtained (the other enantiomer was not isolated in pure form).

LC-MS (method 11): $R_t$=1.58 min; m/z=350 (M−C$_4$H$_8$+H)$^+$.

$^1$H-NMR (400 MHz, DMSO-d$_6$): δ=7.73 (d, 1H), 7.58 (m, 2H), 7.50 (t, 1H), 7.30 (d, 2H), 7.22 (d, 2H), 4.71 (s, 2H), 4.38 (s, 2H), 3.18 (d, 1H), 2.36 (m, 1H), 1.80 (m, 1H), 1.66-1.36 (m, 4H), 1.34 (s, 9H), 1.24 (m, 2H), 0.95 (m, 1H).

[α]$_D^{20}$=+8.2°, c=0.38, chloroform.

Example 289A (+/−)-Cyclopentyl{4-[(1-oxo-1,3-dihydro-2H-isoindol-2-yl)methyl]phenyl}acetic acid

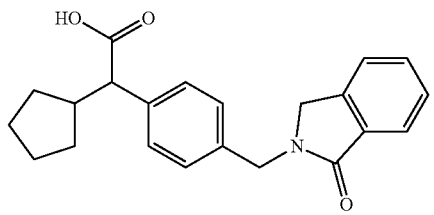 [SMILES: O=C(O)C(c1ccc(CN2Cc3ccccc3C2=O)cc1)C1CCCC1]

At RT, 695 mg (1.71 mmol) of tert-butyl(+/−)-cyclopentyl{4-[(1-oxo-1,3-dihydro-2H-isoindol-2-yl)methyl]phenyl}acetate were dissolved in 11 ml of a 4 N solution of hydrogen chloride in dioxane, and the mixture was stirred for 12 h. The reaction mixture was then frozen and freeze-dried under high vacuum. This gave 700 mg of product, which was not purified any further.

LC-MS (method 11): $R_t$=1.17 min; m/z=350 (M+H)$^+$.

$^1$H-NMR (400 MHz, DMSO-d$_6$): δ=12.21 (s, 1H), 7.73 (d, 1H), 7.62-7.47 (m, 3H), 7.30 (d, 2H), 7.22 (d, 2H), 4.70 (s, 2H), 4.37 (s, 2H), 3.21 (d, 1H), 2.42 (m, 1H), 1.89-1.17 (m, 7H), 0.94 (m, 1H).

Example 290A (+)-(2S)-Cyclopentyl{4-[(1-oxo-1,3-dihydro-2H-isoindol-2-yl)methyl]phenyl}acetic acid

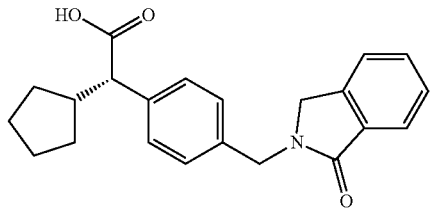 [SMILES: O=C(O)[C@H](c1ccc(CN2Cc3ccccc3C2=O)cc1)C1CCCC1]

At RT, 500 mg (1.23 mmol) of tert-butyl(+)-(2S)-cyclopentyl{4-[(1-oxo-1,3-dihydro-2H-isoindol-2-yl)methyl]phenyl}acetate were dissolved in 11 ml of a 4 N solution of hydrogen chloride in dioxane, and the mixture was stirred for 12 h. The reaction mixture was then frozen and freeze-dried under high vacuum. This gave 450 mg of product, which was not purified any further.

LC-MS (method 11): $R_t$=1.17 min; m/z=350 (M+H)$^+$.

$^1$H-NMR (400 MHz, DMSO-d$_6$): δ=7.72 (d, 1H), 7.57 (m, 2H), 7.50 (t, 1H), 7.30 (d, 2H), 7.22 (d, 2H), 4.71 (s, 2H), 4.37 (s, 2H), 3.21 (d, 1H), 2.42 (m, 1H), 1.82 (m, 1H), 1.66-1.16 (m, 6H), 0.93 (m, 1H).

$[α]_D^{20}$=+38.1°, c=0.585, chloroform.

Example 291A 5,6-Difluoro-1H-isoindole-1,3(2H)-dione

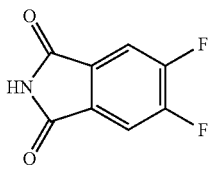 [SMILES: O=C1NC(=O)c2cc(F)c(F)cc21]

At 130° C., 1.0 g (5.4 mmol) of 4,5-difluorophthalic anhydride was stirred in 6 ml of formamide for 2 h. After cooling, the reaction mixture was then added to ice-cold water. The precipitated yellow solid was filtered off with suction, washed thoroughly with cold water and dried under high vacuum. This gave 744 mg of a white solid (74.8% of theory).

LC-MS (method 10): $R_t$=1.10 min; m/z=182 (M–H)$^-$.

$^1$H-NMR (400 MHz, DMSO-d$_6$): δ=11.58 (s, 1H), 8.01 (t, 2H).

Example 292A 5,6-Difluoro-3-hydroxy-2,3-dihydro-1H-isoindol-1-one

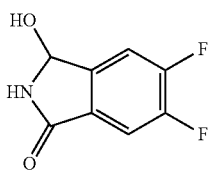 [SMILES: O=C1NC(O)c2cc(F)c(F)cc21]

740 mg (4.04 mmol) of 5,6-difluoro-1H-isoindole-1,3(2H)-dione were dissolved in 6.6 ml of ethanol, the mixture was cooled to 0° C. and 76.4 mg (2.02 mmol) of sodium borohydride were added a little at a time. After the addition had ended, the reaction mixture was slowly warmed to RT and stirred at RT for another 30 min before the reaction mixture was adjusted to neutral with 1 N hydrochloric acid. The mixture was concentrated to dryness under reduced pressure, and the residue was dried further under high vacuum. This gave 800.8 mg of crude product which was used without further purification for the next reaction.

LC-MS (method 15): $R_t$=0.51 min; m/z=184 (M–H)$^-$.

Example 293A 5,6-Difluoro-2,3-dihydro-1H-isoindol-1-one

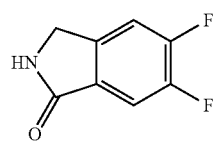

748 mg of 5,6-difluoro-3-hydroxy-2,3-dihydro-1H-isoindol-1-one (crude product, about 4.04 mmol) were initially charged in 50 ml of dichloromethane, 3.8 ml (48.5 mmol) of trifluoroacetic acid and 1.3 ml (8.08 mmol) of triethylsilane were added and the mixture was stirred overnight at RT. The reaction mixture was then concentrated, and the residue was dissolved in dichloromethane and washed with sodium bicarbonate solution. The crude product was purified by chromatography on silica gel (mobile phase cyclohexane/ethyl acetate 1:1 to 0:1). This gave 72 mg (10.6% of theory) of the target compound.

LC-MS (method 15): $R_t$=0.61 min; m/z=170 (M+H)$^+$.

$^1$H-NMR (400 MHz, DMSO-d$_6$): δ=8.74 (br. s, 1H), 7.76-7.64 (m, 2H), 4.36 (s, 2H).

Example 294A

4-Fluoro-1H-isoindole-1,3(2H)-dione

Under argon, 10.0 g (60.2 mmol) of 4-fluoro-2-benzofuran-1,3-dione were stirred at 130° C. in 50 ml of formamide for 1 h. The cooled reaction mixture was then added to ice-water. A solid precipitated out. This solid was filtered off with suction and washed with water. The product was dried under high vacuum. This gave 8.3 g (83% of theory) of the target compound.

LC-MS (method 11): $R_t$=0.57 min; m/z=166 (M+H)$^+$.

$^1$H-NMR (400 MHz, DMSO-d$_6$): δ=11.47 (br. s, 1H), 7.87 (td, 1H), 7.69-7.61 (m, 2H).

Example 295A

4-Fluoro-2,3-dihydro-1H-isoindol-1-one

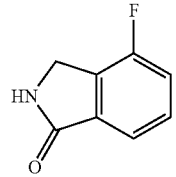

458 mg (12.1 mmol) of sodium borohydride were added a little at a time to a suspension, cooled to 0° C., of 4.0 g (24.2 mmol) of 4-fluoro-1H-isoindole-1,3(2H)-dione in 40 ml of ethanol. After the addition had ended, cooling was removed and the mixture was warmed to RT. After 20 min of stirring, a further 458 mg (12.1 mmol) of sodium borohydride were added at RT. After a further 30 min at RT, 1 N hydrochloric acid was added carefully to the reaction mixture and the pH was adjusted to neutral. The mixture was concentrated under reduced pressure and the residue was taken up in dichloromethane and filtered through Celite. The collected filtrate was concentrated under reduced pressure. This gave 4.05 g of 4-fluoro-3-hydroxy-2,3-dihydro-1H-isoindol-1-one, which was directly reacted further as crude product.

4.05 g (about 24.2 mmol) of 4-fluoro-3-hydroxy-2,3-dihydro-1H-isoindol-1-one were initially charged in 10 ml of dichloromethane, 22.4 ml (290.8 mmol) of trifluoroacetic acid and 7.7 ml (48.5 mmol) of triethylsilane were added and the mixture was stirred at RT overnight. The reaction mixture was then concentrated and the residue was dissolved in dichloromethane and washed with sodium bicarbonate solution. The crude product was purified by chromatography on silica gel (mobile phase cyclohexane/ethyl acetate 3:1 to 1:1). This gave 890 mg (24.2% of theory) of the target compound.

LC-MS (method 12): $R_t$=1.18 min; m/z=152 (M+H)$^+$.

$^1$H-NMR (400 MHz, DMSO-d$_6$): δ=8.77 (br. s, 1H), 7.58-7.51 (m, 2H), 7.49-7.40 (m, 1H), 4.46 (s, 2H).

Example 296A 4,7-Difluoro-1H-isoindole-1,3(2H)-dione

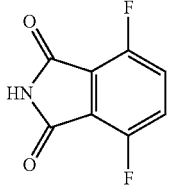

Under argon, 2.15 g (11.68 mmol) of 4,7-difluoro-2-benzofuran-1,3-dione were stirred in 15 ml of formamide at 130° C. for 5 h. The cooled reaction mixture was then added to ice-water. A solid precipitated out. This solid was filtered off with suction and washed with water. The product was dried under high vacuum. This gave 0.45 g (21% of theory) of the target compound.

LC-MS (method 15): $R_t$=0.56 min; m/z=184 (M+H)$^+$.

$^1$H-NMR (400 MHz, DMSO-d$_6$): δ=11.58 (br. s, 1H), 7.71 (t, 2H).

Example 297A tert-Butyl(+/−)-cyclopentyl{4-[(3-oxo-1,3-dihydro-2H-indazol-2-yl)methyl]phenyl}acetate

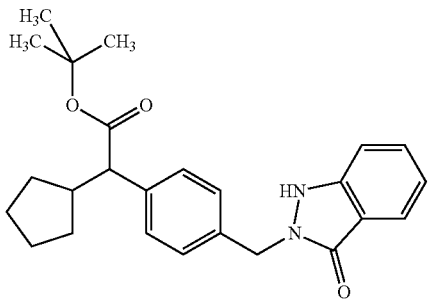 [SMILES: CC(C)(C)OC(=O)C(c1ccc(Cn2[nH]c3ccccc3c2=O)cc1)C1CCCC1]

At 0° C., 170.9 mg (1.27 mmol) of 1,2-dihydro-3H-indazol-3-one were added to 50.9 mg (1.27 mmol, 60% pure) of sodium hydride in 1.8 ml of DMF. The mixture was stirred for 30 min, and 500 mg (1.06 mmol) of tert-butyl(+/−)-[4-(bromomethyl)phenyl](cyclopentyl)acetate were then added at 0° C. The reaction mixture was stirred for a further 30 min, and water and ethyl acetate were then added. The organic phase was washed with saturated sodium chloride solution and dried over magnesium sulfate. The crude product was purified by preparative RP-HPLC (mobile phase: acetonitrile/water gradient). This gave 217 mg (50.3% of theory) of the target compound.

LC-MS (method 11): $R_t$=1.53 min; m/z=407 (M+H)$^+$.

$^1$H-NMR (400 MHz, DMSO-d$_6$): δ=10.67 (br. s, 1H), 7.62 (d, 1H), 7.53 (d, 1H), 7.32 (t, 1H), 7.24 (d, 2H), 7.12 (d, 2H), 6.99 (t, 1H), 5.33 (s, 2H), 3.14 (d, 1H), 2.40-2.29 (m, 1H), 1.84-1.72 (m, 1H), 1.65-1.35 (m, 5H), 1.33 (s, 9H), 1.26-1.15 (m, 2H).

Example 298A (+/−)-Cyclopentyl{4-[(3-oxo-1,3-dihydro-2H-indazol-2-yl)methyl]phenyl}acetic acid

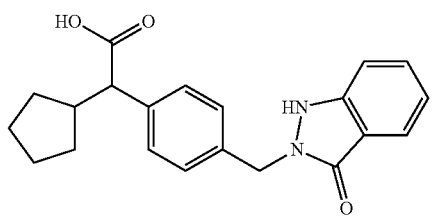 [SMILES: O=C(O)C(c1ccc(Cn2[nH]c3ccccc3c2=O)cc1)C1CCCC1]

71.0 mg (0.17 mmol) of tert-butyl(+/−)-cyclopentyl{4-[(3-oxo-1,3-dihydro-2H-indazol-2-yl)-methyl]phenyl}acetate were initially charged in 400 μl of dichloromethane, and 134 μl of trifluoroacetic acid were added. The mixture was stirred at RT for 2 h. The reaction mixture was then concentrated on a rotary evaporator, and the residue was dried under high vacuum. This gave 82 mg of crude product, which was used without further purification.

LC-MS (method 15): $R_t$=1.01 min; m/z=350 (M+H)$^+$.

$^1$H-NMR (400 MHz, DMSO-d$_6$): δ=7.62 (d, 1H), 7.53 (d, 1H), 7.32 (t, 1H), 7.24 (d, 2H), 7.12 (d, 2H), 6.99 (t, 1H), 5.33 (s, 2H), 3.17 (d, 1H), 2.45-2.35 (m, 1H), 1.86-1.75 (m, 1H), 1.63-1.46 (m, 4H), 1.44-1.33 (m, 1H), 1.29-1.15 (m, 2H), 0.96-0.85 (m, 1H).

Example 299A

Ethyl 4,4,4-trifluoro-3-methyl-2-{4-[(1-oxo-1,3-dihydro-2H-isoindol-2-yl)methyl]phenyl}-butanoate

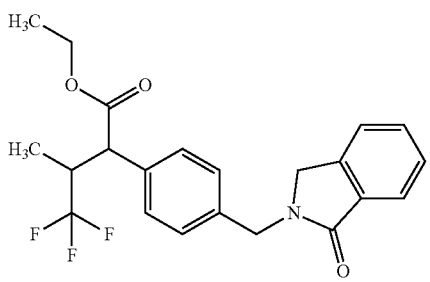 [SMILES: CCOC(=O)C(c1ccc(CN2Cc3ccccc3C2=O)cc1)C(C)C(F)(F)F]

At 0° C., 222.6 mg (1.67 mmol) of 2,3-dihydro-1H-isoindol-1-one were added to 66.9 mg (1.67 mmol, 60% pure) of sodium hydride in 2 ml of DMF. The mixture was stirred for 30 min, and 600 mg (1.39 mmol) of ethyl 2-[4-(bromomethyl)phenyl]-4,4,4-trifluoro-3-methylbutanoate were then added at 0° C. The reaction mixture was stirred for a further 2 h, and water and ethyl acetate were then added. The organic phase was washed with saturated sodium chloride solution and dried over magnesium sulfate. The crude product was purified by preparative RP-HPLC (mobile phase: acetonitrile/water gradient). This gave 108 mg (19% of theory) of the target compound.

LC-MS (method 12): $R_t$=2.42 min; m/z=406 (M+H)$^+$.

$^1$H-NMR (400 MHz, DMSO-d$_6$): δ=7.73 (d, 1H), 7.62-7.47 (m, 3H), 7.40-7.35 (m, 2H), 7.30-7.22 (m, 2H), 4.75-4.70 (m, 2H), 4.41-4.36 (m, 2H), 4.15-3.96 (m, 2H), 3.82-3.68 (m, 1H), 1.19-1.14 (m, 1H), 1.13-1.08 (m, 3H), 0.76 (d, 2H).

Example 300A 4,4,4-Trifluoro-3-methyl-2-{4-[(1-oxo-1,3-dihydro-2H-isoindol-2-yl)methyl]phenyl}butanoic acid

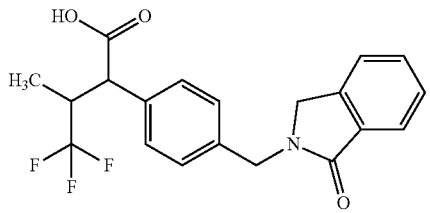 [SMILES: CC(C(C(=O)O)c1ccc(CN2Cc3ccccc3C2=O)cc1)C(F)(F)F]

Under argon, 270 mg (0.66 mmol) of ethyl 4,4,4-trifluoro-3-methyl-2-{4-[(1-oxo-1,3-dihydro-2H-isoindol-2-yl)methyl]phenyl}butanoate were dissolved in 1 ml each of THF, methanol and water, and 69.9 mg (1.66 mmol) of lithium hydroxide were added. The mixture was stirred at RT overnight. The reaction mixture was diluted with water and acidified with 1 N hydrochloric acid, and the resulting precipitate was filtered off with suction. The solid was washed with water until the washings remained neutral. This gave 222 mg (88.3% of theory) of the target compound.

LC-MS (method 12): $R_t$=2.05 min; m/z=378 (M+H)$^+$.

$^1$H-NMR (400 MHz, DMSO-d$_6$): δ=12.72 (br. s, 1H), 7.73 (d, 1H), 7.63-7.54 (m, 2H), 7.50 (t, 1H), 7.35 (d, 2H), 7.27 (d, 2H), 4.73 (s, 2H), 4.38 (s, 2H), 3.63-3.57 (m, 1H), 3.27-3.18 (m, 1H), 0.75 (d, 3H).

Example 301A tert-Butyl(+/−)-cyclopentyl{4-[(5,6-difluoro-1-oxo-1,3-dihydro-2H-isoindol-2-yl)methyl]-phenyl}acetate

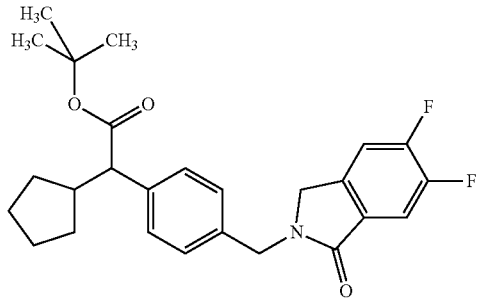 [SMILES: CC(C)(C)OC(=O)C(c1ccc(CN2Cc3cc(F)c(F)cc3C2=O)cc1)C1CCCC1]

At 0° C., 60 mg (0.355 mmol) of 5,6-difluoro-2,3-dihydro-1H-isoindol-1-one were added to 21.3 mg (0.53 mmol, 60% pure) of sodium hydride in 1 ml of DMF. The mixture was stirred for 30 min, and 125.3 mg (0.35 mmol) of tert-butyl (+/−)-[4-(bromomethyl)phenyl](cyclopentyl)acetate were then added at 0° C. The reaction mixture was stirred for a further 2 h, and water and ethyl acetate were then added. The organic phase was washed with saturated sodium chloride solution and dried over magnesium sulfate. The crude product was purified by chromatography on silica gel (mobile phase cyclohexane/ethyl acetate 10:1 to 2:1). This gave 30.0 mg (19.2% of theory) of the target compound.

LC-MS (method 10): $R_t$=2.75 min; m/z=442 (M+H)$^+$.

Example 302A (+/−)-Cyclopentyl{4-[(5,6-difluoro-1-oxo-1,3-dihydro-2H-isoindol-2-yl)methyl]phenyl}acetic acid

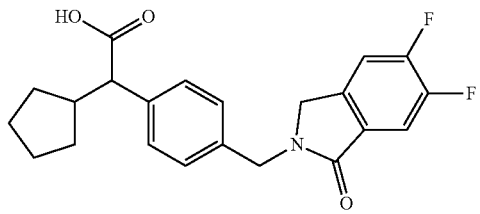 [SMILES: O=C(O)C(c1ccc(CN2Cc3cc(F)c(F)cc3C2=O)cc1)C1CCCC1]

27.0 mg (0.06 mmol) of tert-butyl(+/−)-cyclopentyl{4-[(5,6-difluoro-1-oxo-1,3-dihydro-2H-isoindol-2-yl)methyl]phenyl}acetate were initially charged in 200 μl of dichloromethane, and 94 μl of trifluoroacetic acid were added. The mixture was stirred at RT for 2 h. The reaction mixture was then concentrated on a rotary evaporator, and the residue was dried under high vacuum. This gave 23.5 mg (99.7% of theory) of the target compound.

LC-MS (method 15): $R_t$=1.09 min; m/z=386 (M+H)$^+$.

Example 303A tert-Butyl(+/−)-cyclopentyl{4-[(4,7-difluoro-1,3-dioxo-1,3-dihydro-2H-isoindol-2-yl)methyl]phenyl}acetate

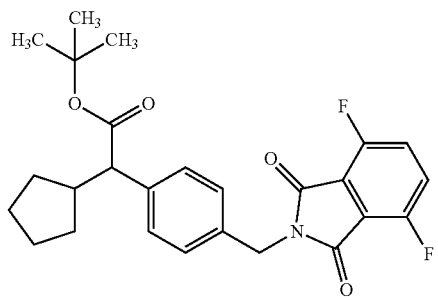 [SMILES: CC(C)(C)OC(=O)C(c1ccc(CN2C(=O)c3c(F)ccc(F)c3C2=O)cc1)C1CCCC1]

500 mg (2.71 mmol) of 4,7-difluoro-1H-isoindole-1,3(2H)-dione and 889.7 mg (2.71 mmol) of cesium carbonate were added to a solution of 964.7 mg (2.71 mmol) of tert-butyl(+/−)-[4-(bromomethyl)phenyl](cyclopentyl)acetate in 2 ml of DMF. The mixture was stirred at 60° C. for 2 h, and the reaction mixture was then added to ice-water. The mixture was extracted three times with ethyl acetate. The combined organic phases were washed with saturated sodium chloride solution and dried over magnesium sulfate. The crude product was purified by chromatography on silica gel (mobile phase cyclohexane/ethyl acetate 10:1 to 5:1). This gave 424 mg (34.1% of theory) of the target compound.

LC-MS (method 15): $R_t$=1.47 min; m/z=478 (M+Na)$^+$.

$^1$H-NMR (400 MHz, DMSO-d$_6$): δ=7.76 (t, 2H), 7.31-7.24 (m, 4H), 4.70 (s, 2H), 3.18 (d, 1H), 2.42-2.26 (m, 1H), 1.85-1.75 (m, 1H), 1.66-1.37 (m, 5H), 1.34 (s, 9H), 1.30-1.18 (m, 2H).

Example 304A tert-Butyl cyclopentyl{4-[(4,7-difluoro-1-hydroxy-3-oxo-1,3-dihydro-2H-isoindol-2-yl)methyl]phenyl}acetate

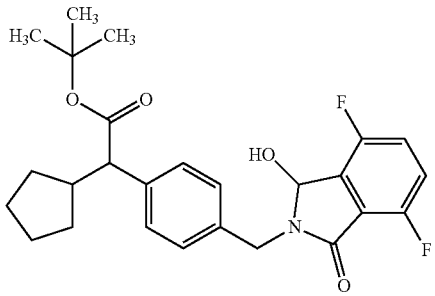 [SMILES: CC(C)(C)OC(=O)C(c1ccc(CN2C(=O)c3c(F)ccc(F)c3C2O)cc1)C1CCCC1]

A solution of 200.0 mg (0.44 mmol) of tert-butyl(+/−)-cyclopentyl{4-[(4,7-difluoro-1,3-dioxo-1,3-dihydro-2H-isoindol-2-yl)methyl]phenyl}acetate in 1 ml of ethanol was cooled to 0° C., and 18.3 mg (0.48 mmol) of sodium borohydride were added. 0.2 ml of dichloromethane was added, and the reaction mixture was warmed to RT. After 1 h of stirring, the mixture was concentrated and the residue was purified by chromatography on silica gel (mobile phase cyclohexane/ethyl acetate 6:1 to 4:1). This gave 182 mg (90.6% of theory) of the target compound.

LC-MS (method 11): $R_t$=1.49 min; m/z=458 (M+H)$^+$.

$^1$H-NMR (400 MHz, DMSO-d$_6$): δ=7.55-7.49 (m, 1H), 7.41 (td, 1H), 7.32-7.20 (m, 4H), 7.03 (dd, 1H), 5.91-5.82 (m, 1H), 4.80 (d, 1H), 4.34 (d, 1H), 3.18 (d, 1H), 2.43-2.32 (m, 1H), 1.86-1.76 (m, 1H), 1.67-1.46 (m, 3H), 1.45-1.37 (m, 1H), 1.35 (s, 9H), 1.31-1.18 (m, 2H), 0.95 (dd, 1H).

Example 305A (+/−)-Cyclopentyl{4-[(4,7-difluoro-1-oxo-1,3-dihydro-2H-isoindol-2-yl)methyl]phenyl}acetic acid

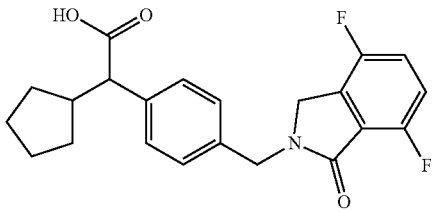 [SMILES: O=C(O)C(c1ccc(CN2Cc3c(F)ccc(F)c3C2=O)cc1)C1CCCC1]

90.0 mg (0.20 mmol) of tert-butyl cyclopentyl{4-[(4,7-difluoro-1-hydroxy-3-oxo-1,3-dihydro-2H-isoindol-2-yl)methyl]phenyl}acetate were initially charged in 1 ml of dichloromethane, and 300 μA of trifluoroacetic acid and 62 μl (0.39 mmol) of triethylsilane were added. The mixture was stirred at RT for 2 h. The reaction mixture was then concentrated on a rotary evaporator, the residue was taken up in ethyl acetate and the solution was washed with water and saturated sodium chloride solution. The organic phase was dried over magnesium sulfate and concentrated under reduced pressure. This gave 77.0 mg of the target compound.

LC-MS (method 11): $R_t$=1.21 min; m/z=386 (M+H)$^+$.

$^1$H-NMR (400 MHz, DMSO-d$_6$): δ=7.53-7.45 (m, 1H), 7.38-7.32 (m, 1H), 7.31 (d, 2H), 7.25 (d, 2H), 4.66 (s, 2H), 4.48 (s, 2H), 2.47-2.31 (m, 2H), 1.87-1.77 (m, 1H), 1.65-1.17 (m, 7H).

Example 306A tert-Butyl(+/−)-cyclopentyl{4-[(4-fluoro-1-oxo-1,3-dihydro-2H-isoindol-2-yl)methyl]-phenyl}acetate

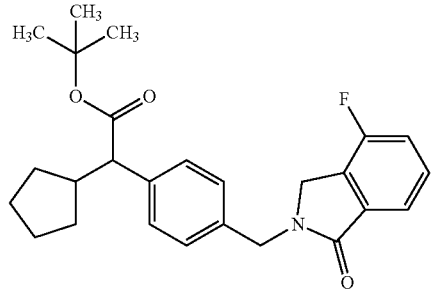 [SMILES: CC(C)(C)OC(=O)C(c1ccc(CN2Cc3c(F)cccc3C2=O)cc1)C1CCCC1]

At 0° C., 280 mg (1.85 mmol) of 4-fluoro-2,3-dihydro-1H-isoindol-1-one were added to a suspension of 96.3 mg (2.41 mmol, 60% pure) of sodium hydride in 1 ml of DMF. The mixture was stirred for 30 min, and 654.5 mg (1.85 mmol) of tert-butyl(+/−)-[4-(bromomethyl)phenyl](cyclopentyl)acetate were then added at 0° C. Stirring was continued for a further 2 h, and water and ethyl acetate were then added to the reaction mixture. The organic phase was washed with saturated sodium chloride solution and dried over magnesium sulfate. The crude product was purified by chromatography on silica gel (mobile phase cyclohexane/ethyl acetate 6:1 to 5:1). This gave 394 mg (50.2% of theory) of the target compound.

LC-MS (method 15): $R_t$=1.44 min; m/z=446 (M+Na)$^+$.

$^1$H-NMR (400 MHz, DMSO-d$_6$): δ=7.62-7.52 (m, 2H), 7.45 (dt, 1H), 7.30 (d, 2H), 7.24 (d, 2H), 4.71 (s, 2H), 4.49 (s, 2H), 3.18 (d, 1H), 2.42-2.32 (m, 1H), 1.80 (dd, 1H), 1.66-1.36 (m, 5H), 1.34 (s, 9H), 1.30-1.14 (m, 2H).

Example 307A (+/−)-Cyclopentyl{4-[(4-fluoro-1-oxo-1,3-dihydro-2H-isoindol-2-yl)methyl]phenyl}acetic acid

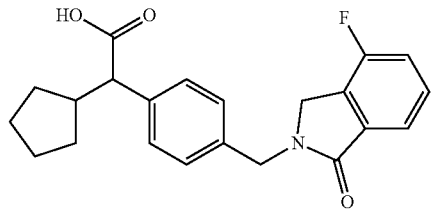 [SMILES: O=C(O)C(c1ccc(CN2Cc3c(F)cccc3C2=O)cc1)C1CCCC1]

150.0 mg (0.35 mmol) of tert-butyl(+/−)-cyclopentyl{4-[(4-fluoro-1-oxo-1,3-dihydro-2H-isoindol-2-yl)methyl]phenyl}acetate were initially charged in 300 µl of dichloromethane, and 515 µl of trifluoroacetic acid were added. The mixture was stirred at RT for 1 h. The reaction mixture was then concentrated on a rotary evaporator, and the residue was dried under high vacuum. Acetonitrile was added to the product, and the precipitated solid was triturated and then filtered off with suction. This gave 112.0 mg (86.1% of theory) of the target compound.

LC-MS (method 15): $R_t$=1.08 min; m/z=368 (M+H)$^+$.

$^1$H-NMR (400 MHz, DMSO-d$_6$): δ=12.25 (br. s, 1H) 7.62-7.54 (m, 2H), 7.44 (t, 1H), 7.30 (d, 2H), 7.25 (d, 2H), 4.71 (s, 2H), 4.51 (s, 2H), 3.21 (d, 1H), 2.48-2.40 (m, 1H), 1.98-1.80 (m, 1H), 1.66-1.48 (m, 3H), 1.45-1.38 (m, 1H), 1.32-1.18 (m, 2H), 0.99-0.90 (m, 1H).

Example 308A (−)-(1R,2S,5R)-5-Methyl-2-(propan-2-yl)cyclohexyl (2S)-{4-[(5-chloro-2-oxopyridin-1(2H)-yl)methyl]phenyl}(cyclopentyl)ethanoate

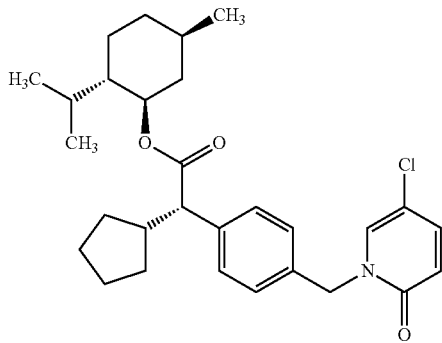 [SMILES: CC(C)[C@@H]1CC[C@@H](C)C[C@H]1OC(=O)[C@H](c1ccc(Cn2cc(Cl)ccc2=O)cc1)C1CCCC1]

At RT, 406.1 mg (3.14 mmol) of 5-chloropyridin-2(1H)-one were added to a suspension of 125.4 mg (3.14 mmol, 60% pure) of sodium hydride in 5 ml of DMF. The mixture was stirred for 30 min, and 1050 mg (2.41 mmol) of (1R,2S,5R)-5-methyl-2-(propan-2-yl)cyclohexyl (2S)-[4-(bromomethyl)phenyl](cyclopentyl)ethanoate were then added at RT. Stirring at RT was continued for a further 2 h, and the reaction mixture was then added to water. The precipitated solid was filtered off with suction and washed with water and isohexane. This gave 830 mg (71% of theory) of the target compound.

LC-MS (method 15): $R_t$=1.60 min; m/z=484 (M+H)$^+$.

$^1$H-NMR (400 MHz, DMSO-d$_6$): δ=8.10 (d, 1H), 7.49 (dd, 1H), 7.30 (d, 2H), 7.25 (d, 2H), 6.46 (d, 1H), 5.04 (s, 2H), 4.53 (td, 1H), 2.47-2.38 (m, 1H), 1.84-1.69 (m, 2H), 1.68-1.13 (m, 12H), 1.03-0.91 (m, 2H), 0.84-0.75 (m, 8H), 0.61 (d, 3H).

$[α]_D^{20}$=−27°, c=0.540, chloroform.

Example 309A (+)-(2S)-{4-[(5-Chloro-2-oxopyridin-1(2H)-yl)methyl]phenyl}(cyclopentyl)acetic acid

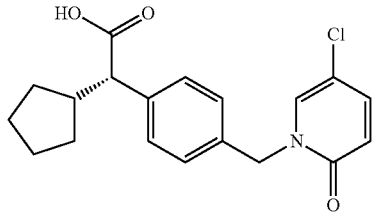 [SMILES: O=C(O)[C@H](c1ccc(Cn2cc(Cl)ccc2=O)cc1)C1CCCC1]

50 ml of trifluoroacetic acid were added to 800.0 mg (1.65 mmol) of (1R,2S,5R)-5-methyl-2-(propan-2-yl)cyclohexyl (2S)-{4-[(5-chloro-2-oxopyridin-1(2H)-yl)methyl]phenyl}-(cyclopentyl)ethanoate. The mixture was stirred under reflux for 48 h. The reaction mixture was then concentrated on a rotary evaporator, and the residue was dried under high vacuum. The crude product was purified by chromatography on silica gel (mobile phase cyclohexane/ethyl acetate 4:1→2:1→1:1). This gave 400 mg (70.0% of theory) of the target compound.

LC-MS (method 15): $R_t$=1.01 min; m/z=346 (M+H)$^+$.

$^1$H-NMR (400 MHz, DMSO-d$_6$): δ=12.25 (s, 1H), 8.11 (d, 1H), 7.49 (dd, 1H), 7.29 (d, 2H), 7.24 (d, 2H), 6.46 (d, 1H), 5.04 (s, 2H), 3.21 (d, 1H), 2.47-2.35 (m, 1H), 1.82 (dd, 1H), 1.66-1.17 (m, 6H), 1.00-0.88 (m, 1H).

$[α]_D^{20}$=+39.5°, c=0.505, chloroform.

Example 310A tert-Butyl(+/−)-cyclopentyl(4-{[2-oxo-5-(trifluoromethyl)pyridin-1(2H)-yl]methyl}phenyl)acetate

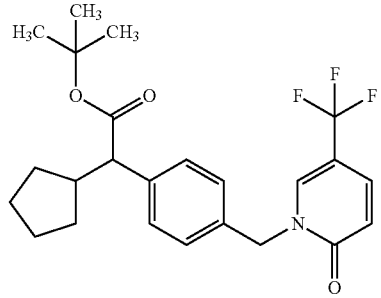 [SMILES: CC(C)(C)OC(=O)C(c1ccc(Cn2cc(C(F)(F)F)ccc2=O)cc1)C1CCCC1]

73.6 mg (1.84 mmol, 60% pure) of sodium hydride were added to 300 mg (1.84 mmol) of 5-(trifluoromethyl)pyridin-2(1H)-one in 2.5 ml of DMF. After 30 min of stirring, 500 mg (1.42 mmol) of tert-butyl(+/−)-[4-(bromomethyl)phenyl](cyclopentyl)acetate were added. After a further 2 h of stirring at RT, the reaction mixture was warmed to 40° C. for 1 h. Water and ethyl acetate were then added to the mixture, and the phases were separated. The organic phase was washed with saturated sodium chloride solution and dried over magnesium sulfate. The crude product was purified by chromatography on silica gel (mobile phase cyclohexane/ethyl acetate 6:1 to 4:1). This gave 522.0 mg (84.7% of theory) of the target compound.

LC-MS (method 11): $R_t$=1.62 min; m/z=380 (M+H—C$_4$H$_8$)$^+$.

$^1$H-NMR (400 MHz, DMSO-d$_6$): δ=8.54 (s, 1H), 7.70 (dd, 1H), 7.30 (d, 2H), 7.24 (d, 2H), 6.57 (d, 1H), 5.18-5.07 (m, 2H), 3.18 (d, 1H), 2.44-2.30 (m, 1H), 1.88-1.74 (m, 1H), 1.67-1.38 (m, 4H), 1.37-1.33 (m, 9H), 1.30-1.16 (m, 2H), 1.00-0.86 (m, 1H).

Example 311A

Cyclopentyl(4-{[2-oxo-5-(trifluoromethyl)pyridin-1(2H)-yl]methyl}phenyl)acetic acid

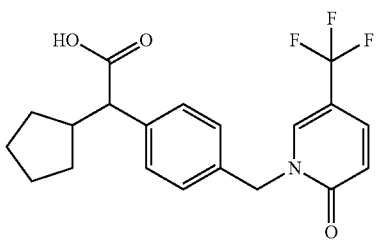 [SMILES: O=C(O)C(c1ccc(Cn2cc(C(F)(F)F)ccc2=O)cc1)C1CCCC1]

390 mg (0.90 mmol) of tert-butyl(+/−)-cyclopentyl(4-{[2-oxo-5-(trifluoromethyl)pyridin-1(2H)-yl]methyl}phenyl)ethanoate were initially charged in 2.7 ml of dichloromethane, and 690 µl of trifluoroacetic acid were added. The reaction mixture was stirred at RT for 2 h and then concentrated under reduced pressure, and the residue was dried under high vacuum. This gave 523 mg of product, which was used without further purification.

LC-MS (method 11): $R_t$=1.23 min; m/z=380 (M+H)$^+$.
$^1$H-NMR (400 MHz, DMSO-$d_6$): δ=8.56 (s, 1H), 7.69 (dd, 1H), 7.30 (d, 2H), 7.25 (d, 2H), 6.57 (d, 1H), 5.13 (s, 2H), 3.21 (d, 1H), 2.47-2.36 (m, 1H), 1.91-1.76 (m, 1H), 1.68-1.13 (m, 6H), 0.92 (dq, 1H).

Example 312A (−)-(1R,2S,5R)-5-Methyl-2-(propan-2-yl)cyclohexyl (2S)-cyclopentyl(4-{[2-oxo-5-(trifluoro-methyl)pyridin-1(2H)-yl]methyl}phenyl)ethanoate

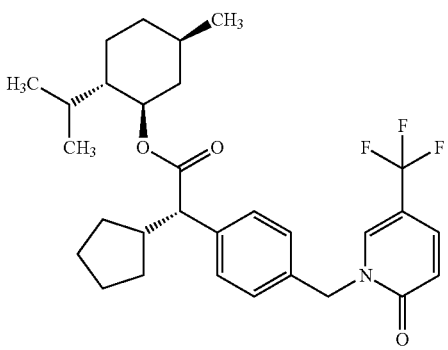 [SMILES: CC(C)[C@@H]1CC[C@@H](C)C[C@H]1OC(=O)[C@H](c1ccc(Cn2cc(C(F)(F)F)ccc2=O)cc1)C1CCCC1]

At RT, 973.8 mg (5.97 mmol) of 5-(trifluoromethyl)pyridin-2(1H)-one were added to 238.8 mg (5.97 mmol, 60% pure) of sodium hydride in 5 ml of DMF. The mixture was stirred for 30 min, and 2.0 g (4.59 mmol) of (1R,2S,5R)-5-methyl-2-(propan-2-yl)cyclohexyl(2S)-[4-(bromomethyl)phenyl](cyclopentyl)ethanoate were then added at RT. Stirring at RT was continued for 2 h. Water and ethyl acetate were then added to the reaction mixture. After phase separation, the organic phase was washed with saturated sodium chloride solution and dried over magnesium sulfate. The crude product was purified by chromatography on silica gel (mobile phase cyclohexane/ethyl acetate 5:1). This gave 2.0 g (85.0% of theory) of the target compound.

LC-MS (method 15): $R_t$=1.65 min; m/z=518 (M+H)$^+$.
$^1$H-NMR (400 MHz, DMSO-$d_6$): δ=8.52 (s, 1H), 7.69 (dd, 1H), 7.31 (d, 2H), 7.26 (d, 2H), 6.57 (d, 1H), 5.13 (s, 2H), 4.52 (td, 1H), 2.48-2.42 (m, 2H), 1.82-1.13 (m, 13H), 1.00-0.90 (m, 2H), 0.83-0.74 (m, 8H), 0.59 (d, 3H).
$[α]_D^{20}$=−21.2°, c=0.515, chloroform.

Example 313A (+)-(2S)-Cyclopentyl-(4-{[2-oxo-5-(trifluoromethyl)pyridin-1(2H)-yl]methyl}phenyl)acetic acid

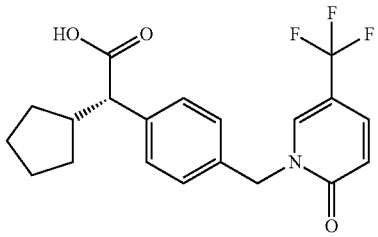 [SMILES: O=C(O)[C@H](c1ccc(Cn2cc(C(F)(F)F)ccc2=O)cc1)C1CCCC1]

50 ml of trifluoroacetic acid were added to 1.0 g (1.93 mmol) of (1R,2S,5R)-5-methyl-2-(propan-2-yl)cyclohexyl-(2S)-cyclopentyl(4-{[2-oxo-5-(trifluoromethyl)pyridin-1(2H)-yl]methyl}phenyl)ethanoate. The mixture was stirred under reflux for 48 h. The reaction mixture was then concentrated under reduced pressure and the residue was dried under high vacuum. The crude product was purified by chromatography on silica gel (mobile phase cyclohexane/ethyl acetate 4:1→2:1→1:1). This gave 670 mg (91.4% of theory) of the target compound.

LC-MS (method 15): $R_t$=1.07 min; m/z=380 (M+H)$^+$.
$^1$H-NMR (400 MHz, DMSO-$d_6$): δ=8.56 (s, 1H), 7.69 (dd, 1H), 7.30 (d, 2H), 7.25 (d, 2H), 6.57 (d, 1H), 5.13 (s, 2H), 3.21 (d, 1H), 2.47-2.36 (m, 1H), 1.87-1.77 (m, 1H), 1.67-1.15 (m, 7H), 0.99-0.88 (m, 1H).
$[α]_D^{20}$=+19.9°, c=0.530, chloroform.

Example 314A

Ethyl 4,4,4-trifluoro-2-{4-[(4-fluoro-1-oxo-1,3-dihydro-2H-isoindol-2-yl)methyl]phenyl}-3-methylbutanoate

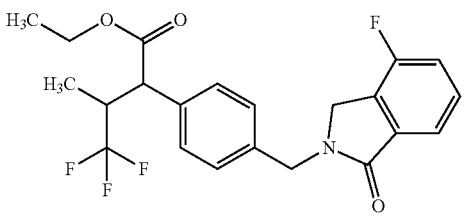 [SMILES: CCOC(=O)C(c1ccc(CN2Cc3c(F)cccc3C2=O)cc1)C(C)C(F)(F)F]

At 0° C., 645 mg (4.27 mmol) of 4-fluoro-2,3-dihydro-1H-isoindol-1-one were added to 170.7 mg (4.27 mmol, 60% pure) of sodium hydride in 4 ml of DMF. The mixture was stirred for 30 min, and 2.11 g (5.98 mmol) of ethyl 2-[4-(bromomethyl)phenyl]-4,4,4-trifluoro-3-methylbutanoate were then added at 0° C. The reaction mixture was stirred for a further 2 h, and water and ethyl acetate were then added. The organic phase was washed with saturated sodium chloride solution and dried over magnesium sulfate. The crude product was purified by chromatography on silica gel (mobile phase cyclohexane/ethyl acetate 40:1 to 3:1). This gave 856 mg (33.9% of theory) of the target compound.

LC-MS (method 15): R$_t$=1.24 min; m/z=424 (M+H)$^+$.

$^1$H-NMR (400 MHz, DMSO-d$_6$): δ=7.62-7.53 (m, 2H), 7.45 (t, 1H), 7.38 (d, 2H), 7.29 (d, 2H), 4.73 (s, 2H), 4.50 (s, 2H), 4.14-3.95 (m, 2H), 3.71 (d, 1H), 1.14-1.08 (m, 4H), 0.76 (d, 3H).

Example 315A 4,4,4-Trifluoro-2-{4-[(4-fluoro-1-oxo-1,3-dihydro-2H-isoindol-2-yl)methyl]phenyl}-3-methylbutanoic acid

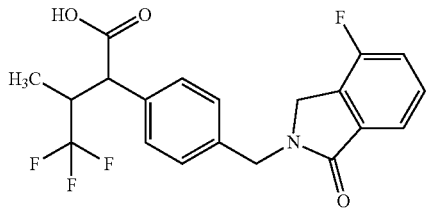 [SMILES: CC(C(C(=O)O)c1ccc(CN2Cc3c(F)cccc3C2=O)cc1)C(F)(F)F]

855 mg (2.02 mmol) of ethyl 4,4,4-trifluoro-2-{4-[(4-fluoro-1-oxo-1,3-dihydro-2H-isoindol-2-yl)methyl]phenyl}-3-methylbutanoate were dissolved in 5.7 ml each of THF, methanol and water, and 16.2 ml (40.39 mmol) of 10% strength aqueous sodium hydroxide solution were added. The mixture was stirred at RT overnight. The reaction mixture was then diluted with water, acidified with 1 N hydrochloric acid and extracted with ethyl acetate. The organic phase was dried over sodium sulfate and concentrated. The crude product was purified by preparative RP-HPLC (mobile phase: acetonitrile/water gradient). This gave 457.2 mg (58.2% of theory) of the target compound.

LC-MS (method 15): R$_t$=1.01 min; m/z=396 (M+H)$^+$.

$^1$H-NMR (400 MHz, DMSO-d$_6$): δ=12.72 (br. s, 1H), 7.62-7.54 (m, 2H), 7.48-7.41 (m, 1H), 7.36 (d, 2H), 7.29 (d, 2H), 4.73 (s, 2H), 4.50 (s, 2H), 3.61 (d, 1H), 3.28-3.19 (m, 1H), 0.76 (d, 3H).

Example 316A

Ethyl 4,4,4-trifluoro-3-methyl-2-(4-{[2-oxo-5-(trifluoromethyl)pyridin-1(2H)-yl]methyl}phenyl)butanoate (mixture of isomers)

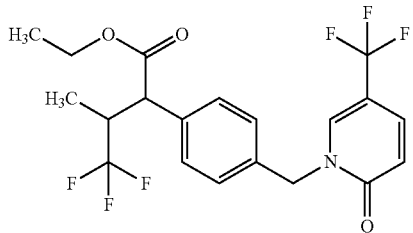 [SMILES: CCOC(=O)C(c1ccc(Cn2cc(C(F)(F)F)ccc2=O)cc1)C(C)C(F)(F)F]

1.80 g (11.04 mmol) of 5-(trifluoromethyl)pyridin-2(1H)-one were initially charged in 2.5 ml of DMF, and 0.44 g (11.04 mmol, 60% pure) of sodium hydride was added. The mixture was stirred for 30 min, and 3.0 g (8.49 mmol) of ethyl 2-[4-(bromomethyl)phenyl]-4,4,4-trifluoro-3-methylbutanoate were then added. After a further 2 h at RT, water was added and the reaction mixture was extracted with ethyl acetate. The organic phase was washed with saturated sodium chloride solution and dried over magnesium sulfate. The crude product was purified by chromatography on silica gel (mobile phase cyclohexane/ethyl acetate 10:1 to 4:1). This gave 2.89 g (78.2% of theory) of the target compound.

LC-MS (method 15): R$_t$=1.19 min; m/z=436 (M+H)$^+$.

$^1$H-NMR (400 MHz, DMSO-d$_6$): δ=8.61-8.54 (m, 1H), 7.70 (dd, 1H), 7.38 (d, 2H), 7.29 (d, 2H), 6.57 (d, 1H), 5.18-5.07 (m, 2H), 4.17-3.94 (m, 2H), 3.71 (d, 1H), 3.31-3.16 (m, 1H), 1.14-1.05 (m, 3H), 0.75 (d, 3H).

Example 317A 4,4,4-Trifluoro-3-methyl-2-(4-{[2-oxo-5-(trifluoromethyl)pyridin-1(2H)-yl]methyl}phenyl)-butanoic acid (mixture of isomers)

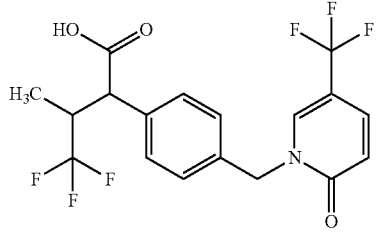 [SMILES: CC(C(C(=O)O)c1ccc(Cn2cc(C(F)(F)F)ccc2=O)cc1)C(F)(F)F]

2.80 g (6.43 mmol) of ethyl 4,4,4-trifluoro-3-methyl-2-(4-{[2-oxo-5-(trifluoromethyl)pyridin-1(2H)-yl]methyl}phenyl)butanoate were dissolved in 18.2 ml each of THF, methanol and water, and 51.5 ml (128.6 mmol) of 10% strength aqueous sodium hydroxide solution were added. The mixture was stirred at RT overnight. The reaction mixture was then diluted with water, acidified with 1 N hydrochloric acid and extracted with ethyl acetate. The organic phase was dried over sodium sulfate and concentrated. This gave 2.82 g of product, which was used without further purification.

LC-MS (method 15): R$_t$=1.02 min; m/z=408 (M+H)$^+$.

$^1$H-NMR (400 MHz, DMSO-d$_6$): δ=12.70 (br. s, 1H), 8.61-8.54 (m, 1H), 7.70 (dd, 1H), 7.35 (d, 2H), 7.28 (d, 2H), 6.57 (d, 1H), 5.15 (s, 2H), 3.61 (d, 1H), 3.29-3.18 (m, 1H), 0.75 (d, 3H).

The mixture of isomers obtained above was separated by preparative HPLC on a chiral phase [column: Daicel Chiralpak AD-H, 5 μm, 250 mm×20 mm; flow rate: 15 ml/min; UV detection: 220 nm; injection volume: 0.2 ml; temperature: 27° C.; mobile phase: 75% isohexane/25% ethanol (with 0.2% TFA and 1% water)]. Starting from 2810 mg of the mixture of isomers, 867 mg of enantiomer 1 and 776 mg of enantiomer 2 were isolated (see Examples 318A and 319A).

Example 318A

−)-(2R,3S)-4,4,4-Trifluoro-3-methyl-2-(4-{[2-oxo-5-(trifluoromethyl)pyridin-1(2H)-yl]methyl}-phenyl)butanoic acid (enantiomer 1

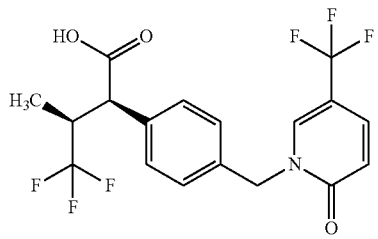 [SMILES: C[C@@H]([C@@H](C(=O)O)c1ccc(Cn2cc(C(F)(F)F)ccc2=O)cc1)C(F)(F)F]

$^{1}$H-NMR (400 MHz, DMSO-d$_{6}$): δ=8.57 (s, 1H), 7.70 (dd, 1H), 7.36 (d, 2H), 7.29 (d, 2H), 6.57 (d, 1H), 5.15 (s, 2H), 3.60 (d, 1H), 3.30-3.17 (m, 1H), 0.75 (d, 3H).
[α]$_D^{20}$=−45.9°, c=0.335, chloroform.

Example 319A (+)-(2S,3R)-4,4,4-Trifluoro-3-methyl-2-(4-{[2-oxo-5-(trifluoromethyl)pyridin-1(2H)-yl]methyl}phenyl)butanoic acid (enantiomer 2

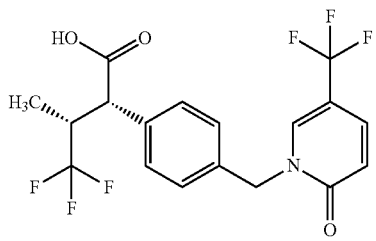 [SMILES: C[C@H]([C@H](C(=O)O)c1ccc(Cn2cc(C(F)(F)F)ccc2=O)cc1)C(F)(F)F]

LC-MS (method 15): R$_t$=1.02 min; m/z=408 (M+H)$^+$.
$^{1}$H-NMR (400 MHz, DMSO-d$_{6}$): δ=8.57 (s, 1H), 7.70 (dd, 1H), 7.35 (d, 2H), 7.29 (d, 2H), 6.57 (d, 1H), 5.15 (s, 2H), 3.60 (d, 1H), 3.31-3.18 (m, 1H), 0.75 (d, 3H).
[α]$_D^{20}$=+44.8°, c=0.400, chloroform.

Example 320A 4,4,4-Trifluoro-3-methyl-2-{4-[(5-oxo-2-phenyl-5,6-dihydro-4H-1,3,4-oxadiazin-4-yl)methyl]phenyl}butanoic acid

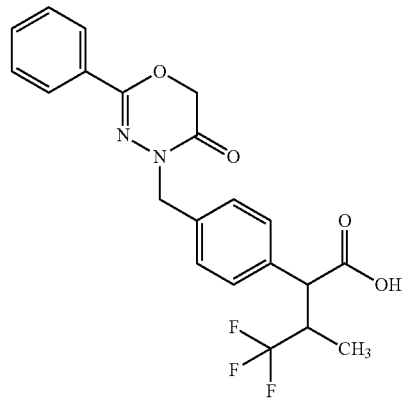 [SMILES: CC(C(C(=O)O)c1ccc(CN2N=C(c3ccccc3)OCC2=O)cc1)C(F)(F)F]

11.4 ml (11.4 mmol) of 1 N aqueous sodium hydroxide solution were added to a solution of 1283 mg (2.86 mmol) of ethyl 4,4,4-trifluoro-3-methyl-2-{4-[(5-oxo-2-phenyl-5,6-dihydro-4H-1,3,4-oxadiazin-4-yl)methyl]phenyl}butanoate in 10 ml of dioxane, and the mixture was stirred at 80° C. overnight. After the reaction had gone to completion, the dioxane was removed under reduced pressure and the solution that remained was diluted with water and then adjusted to pH 2 using 1 M hydrochloric acid. The precipitated solid was filtered off, washed with water and dried under reduced pressure at 45° C. overnight. This gave 1058 mg (2.52 mmol, 88% of theory) of the title compound as a mixture of isomers.

LC-MS (method 15): R$_t$=1.12 min; m/z=421 (M+H)$^+$ (diastereomer 1); R$_t$=1.13 min; m/z=421 (M+H)$^+$ (diastereomer 2).

The compounds listed in the table below were prepared analogously to Examples 51A, 72A and 320A:

| Example | Name/Structure/Starting material | Analytical data |
| --- | --- | --- |
| 321A | 6,6,6-trifluoro-4-methyl-2-{4-[(5-oxo-2-phenyl-5,6-dihydro-4H-1,3,4-oxadiazin-4-yl)methyl]phenyl}-hexanoic acid<br><br>(from tert-butyl 6,6,6-trifluoro-4-methyl-2-{4-[(5-oxo-2-phenyl-5,6-dihydro-4H-1,3,4-oxadiazin-4-yl)methyl]phenyl}hexanoate) | LC-MS (method 7): R$_t$ = 2.57 min; m/z = 449 (M + H)$^+$. |

| Example | Name/Structure/Starting material | Analytical data |
|---|---|---|
| 322A | 5,5,5-trifluoro-3-methyl-2-{4-[(5-oxo-2-phenyl-5,6-dihydro-4H-1,3,4-oxadiazin-4-yl)methyl]phenyl}-pentanoic acid 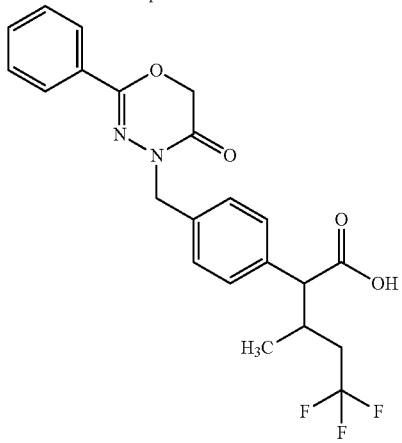 (from tert-butyl 5,5,5-trifluoro-3-methyl-2-{4-[(5-oxo-2-phenyl-5,6-dihydro-4H-1,3,4-oxadiazin-4-yl)methyl]phenyl}pentanoate) | LC-MS (method 15): $R_t$ = 1.15 min; m/z = 435 (M + H)$^+$. |
| 323A | {4-[(3-chloro-6-oxopyridazin-1(6H)-yl)methyl]-phenyl}(cyclopentyl)acetic acid 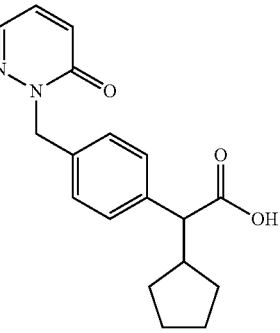 (from tert-butyl {4-[(3-chloro-6-oxopyridazin-1(6H)-yl)methyl]phenyl}(cyclopentyl)acetate) | LC-MS (method 11): $R_t$ = 1.41 min; m/z = 347 (M + H)$^+$. |
| 324A | 2-{4-[(5-oxo-2-phenyl-5,6-dihydro-4H-1,3,4-oxadiazin-4-yl)methyl]phenyl}-3-(trifluoromethyl)pentanoic acid 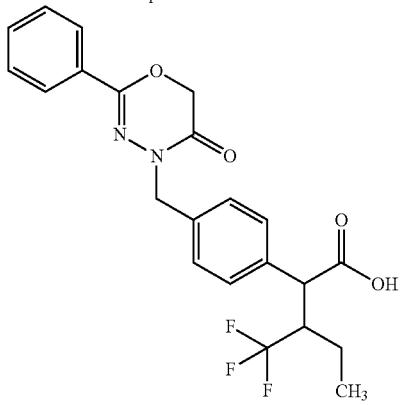 (from ethyl 2-{4-[(5-oxo-2-phenyl-5,6-dihydro-4H-1,3,4-oxadiazin-4-yl)methyl]phenyl}-3-(trifluoromethyl)pentanoate) | LC-MS (method 15): $R_t$ = 1.18 min; m/z = 435 (M + H)$^+$. |

| Example | Name/Structure/Starting material | Analytical data |
|---|---|---|
| 325A | cyclopentyl {4-[{3-methyl-6-oxopyridazin-1(6H)-yl)-methyl]phenyl}acetic acid<br>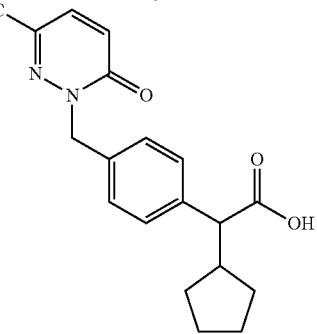<br>(from tert-butyl cyclopentyl {4-[(3-methyl-6-oxo-pyridazin-1(6H)-yl)methyl]phenyl}acetate) | LC-MS (method 12):<br>$R_t$ = 1.96 min; m/z = 327 (M + H)⁺. |
| 326A | cyclopentyl(4-{[6-oxo-3-(trifluoromethyl)pyridazin-1(6H)-yl]methyl}phenyl)acetic acid<br><br>(from tert-butyl cyclopentyl(4-{[6-oxo-3-(trifluoromethyl)pyridazin-1(6H)-yl]methyl}phenyl)acetate | LC-MS (method 12):<br>$R_t$ = 2.27 min; m/z = 381 (M + H)⁺.<br>¹H-NMR (400 MHz, DMSO-$d_6$): δ = 12.24 (br. s, 1H), 7.86 (d, 1H), 7.31 (d, 2H), 7.25 (d, 2H), 7.20 (d, 1H), 5.28 (s, 2H), 3.22 (d, 1H), 2.38-2.46 (m, 1H), 1.77-1.89 (m, 1H), 1.56-1.67 (m, 1H), 1.48-1.56 (m, 2H), 1.34-1.46 (m, 1H), 1.14-1.32 (m, 2H), 0.86-0.99 (m, 1H). |
| 327A | cyclopentyl {4-[(5-methyl-6-oxopyridazin-1(6H)-yl)-methyl]phenyl}acetic acid<br><br>(from tert-butyl cyclopentyl {4-[(5-methyl-6-oxo-pyridazin-1(6H)-yl)methyl]phenyl}acetate) | LC-MS (method 15):<br>$R_t$ = 0.98 min; m/z = 326 (M + H)⁺.<br>¹H-NMR (400 MHz, DMSO-$d_6$): δ = 12.24 (s, 1H), 7.64 (d, 1H), 7.26-7.35 (m, 3H), 7.21 (d, 2H), 6.15 (t, 1H), 5.07 (s, 2H), 3.20 (d, 1H), 2.35-2.47 (m, 1H), 2.00 (s, 3H), 1.82 (dd, 1H), 1.47-1.65 (m, 3H), 1.34-1.46 (m, 1H), 1.16-1.31 (m, 2H), 0.87-0.99 (m, 1H). |

-continued

| Example | Name/Structure/Starting material | Analytical data |
| --- | --- | --- |
| 328A | cyclopentyl(4-{[6-oxo-4-(trifluoromethyl)pyridazin-1(6H)-yl]methyl}phenyl)acetic acid<br><br>(from tert-butyl cyclopentyl(4-{[6-oxo-4-(trifluoromethyl)pyridazin-1(6H)-yl]methyl}phenyl)acetate) | LC-MS (method 11): $R_t$ = 1.21 min; m/z = 380 (M + H)$^+$.<br>$^1$H-NMR (400 MHz, DMSO-d$_6$): δ = 12.24 (s, 1H), 8.08 (d, 1H), 7.30 (d, 2H), 7.25 (d, 2H), 6.81 (s, 1H), 6.51 (dd, 1H), 5.13 (s, 2H), 3.21 (d, 1H), 2.36-2.47 (m, 1H), 1.82 (dd, 1H), 1.47-1.65 (m, 3H), 1.35-1.46 (m, 1H), 1.15-1.31 (m, 2H), 0.87-0.98 (m, 1H). |
| 329A | (3,3-difluorocyclopentyl) {4-[(5-oxo-2-phenyl-5,6-dihydro-4H-1,3,4-oxadiazin-4-yl)methyl]phenyl}-acetic acid<br><br>(from tert-butyl (3,3-difluorocyclopentyl){4-[(5-oxo-2-phenyl-5,6-dihydro-4H-1,3,4-oxadiazin-4-yl)methyl]phenyl}acetate) | LC-MS (method 11): $R_t$ = 1.28 min; m/z = 429 (M + H)$^+$. |
| 330A | cyclopentyl {4-[(4-methyl-6-oxopyridazin-1(6H)-yl)methyl]phenyl}acetic acid<br><br>(from tert-butyl cyclopentyl {4-[(4-methyl-6-oxo-pyridazin-1(6H)-yl)methyl]phenyl}acetate) | LC-MS (method 11): $R_t$ = 1.07 min; m/z = 326 (M + H)$^+$.<br>$^1$H-NMR (400 MHz, DMSO-d$_6$): δ = 7.64 (d, 1H), 7.27 (d, 2H), 7.19 (d, 2H), 6.23 (s, 1H), 6.09 (dd, 1H), 5.02 (s, 2H), 3.20 (d, 1H), 2.36-2.46 (m, 1H), 2.12 (s, 3H), 1.82 (dd, 1H), 1.57-1.70 (m, 1H), 1.47-1.56 (m, 2H), 1.35-1.45 (m, 1H), 1.19-1.30 (m, 2H), 0.92 (dd, 1H). |

| Example | Name/Structure/Starting material | Analytical data |
|---|---|---|
| 331A | 4,4,4-trifluoro-3-methyl-2-(4-{[6-oxo-3-(trifluoromethyl)pyridazin-1(6H)-yl]methyl}phenyl)butanoic acid<br><br>(from ethyl 4,4,4-trifluoro-3-methyl-2-(4-{[6-oxo-3-(trifluoromethyl)pyridazin-1(6H)-yl]methyl}-phenyl)butanoate) | LC-MS (method 11): $R_t$ = 1.21 min; m/z = 409 (M + H)$^+$.<br>$^1$H-NMR (400 MHz, DMSO-d$_6$): δ = 12.74 (br. s, 1H), 7.87 (d, 1H), 7.36 (d, 2H), 7.29 (d, 2H), 7.21 (d, 1H), 5.30 (s, 2H), 3.61 (d, 1H), 3.17-3.29 (m, 1H), 0.75 (d, 3H). |
| 332A | cyclopentyl(4-{[6-oxo-5-(trifluoromethyl)pyridazin-1(6H)-yl]methyl}phenyl)acetic acid<br><br>(from tert-butyl cyclopentyl(4-{[6-oxo-5-(trifluoromethyl)pyridazin-1(6H)-yl]methyl}phenyl)acetate) | LC-MS (method 11): $R_t$ = 1.39 min; m/z = 380 (M + H)$^+$.<br>$^1$H-NMR (400 MHz, DMSO-d$_6$): δ = 12.24 (br. s, 1H), 8.16 (d, 1H), 7.94 (d, 1H), 7.31 (d, 2H), 7.25 (d, 2H), 6.40 (t, 1H), 5.14 (s, 2H), 3.22 (d, 1H), 2.35-2.47 (m, 1H), 1.75-1.89 (m, 1H), 1.48-1.66 (m, 3H), 1.35-1.45 (m, 1H), 1.13-1.32 (m, 2H), 0.87-1.00 (m, 1H). |
| 333A | cyclopentyl {4-[(6-oxo-3-phenylpyridazin-1(6H)-yl)methyl]phenyl}acetic acid (enantiomer 2)<br><br>(from tert-butyl cyclopentyl {4-[(6-oxo-3-phenyl-pyridazin-1(6H)-yl)methyl]phenyl}acetate (enantiomer 2)) | LC-MS (method 10): $R_t$ = 2.11 min; m/z = 389 (M + H)$^+$.<br>$[α]_D^{20}$ = −21.0°, c = 0.265, methanol. |

-continued

| Example | Name/Structure/Starting material | Analytical data |
|---|---|---|
| 334A | cyclopentyl {4-[(6-oxo-3-phenylpyridazin-1(6H)-yl-methyl]phenyl}acetic acid (enantiomer 1)<br>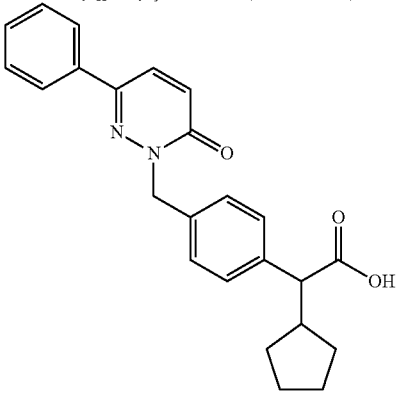<br>(from tert-butyl cyclopentyl {4-[(6-oxo-3-phenyl-pyridazin-1(6H)-yl)methyl]phenyl}acetate (enantiomer 1)) | LC-MS (method 10): $R_t$ = 2.11 min; m/z = 389 (M + H)$^+$. $[\alpha]_D^{20}$ = +37.3°, c = 0.315, methanol. $^1$H-NMR (400 MHz, DMSO-$d_6$): δ = 12.15-12.31 (br. s, 1H), 8.09 (d, 1H), 7.89 (d, 2H), 7.43-7.53 (m, 3H), 7.25-7.34 (m, 4H), 7.09 (d, 1H), 5.30 (s, 2H), 3.21 (d, 1H), 2.34-2.47 (m, 1H), 1.75-1.89 (m, 1H), 1.32-1.66 (m, 4H), 1.15-1.31 (m, 2H), 0.87-0.99 (m, 1H). |
| 335A | 4,4,4-trifluoro-3-methyl-2-{4-[(6-oxo-3-phenylpyridazin-1(6H)-yl)methyl]phenyl}butanoic acid<br>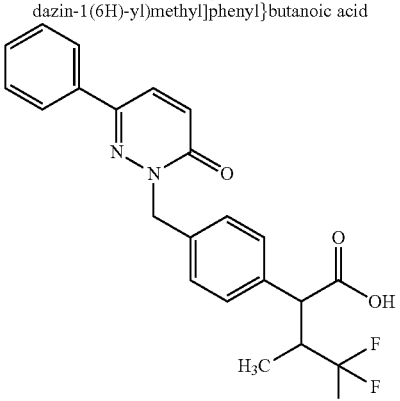<br>(from ethyl 4,4,4-trifluoro-3-methyl-2-{4-[(6-oxo-3-phenylpyridazin-1(6H)-yl)methyl]phenyl}butanoate) | LC-MS (method 11): $R_t$ = 1.27 min; m/z = 417 (M + H)$^+$. |

Examples 336A-339A 4,4,4-Trifluoro-3-methyl-2-{4-[(5-oxo-2-phenyl-5,6-dihydro-4H-1,3,4-oxadiazin-4-yl)methyl]phenyl}butanoic acid (isomers 1-4)

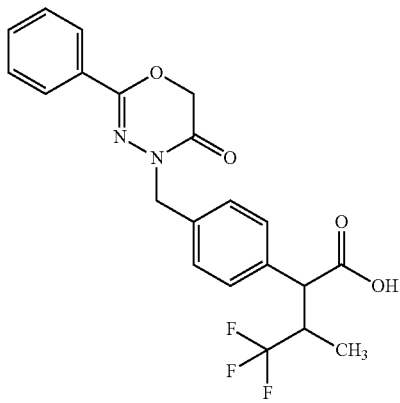 [SMILES: CC(C(C(=O)O)c1ccc(CN2N=C(c3ccccc3)OCC2=O)cc1)C(F)(F)F]

630 mg (1.50 mmol) of the mixture of isomers of 4,4,4-trifluoro-3-methyl-2-{4-[(5-oxo-2-phenyl-5,6-dihydro-4H-1,3,4-oxadiazin-4-yl)methyl]phenyl}butanoic acid were initially separated into the isomers by preparative HPLC on a chiral phase [column: Daicel Chiralpak AD-H, 5 μm, 250 mm×20 mm; mobile phase: isohexane/(isopropanol+0.2% trifluoroacetic acid+1% water) 75:25 (v/v); flow rate: 15 ml/min; UV detection: 220 nm; temperature: 30° C.]:

Example 336A

Isomer 1

Yield: 26 mg
$R_t$ 6.17 min; purity >99%; >99% ee
[column: Daicel Chiralpak AD-H, 5 μm, 250 mm×4.6 mm; mobile phase: isohexane/(isopropanol+0.2% trifluoroacetic acid+1% water) 75:25 (v/v); flow rate: 1 ml/min; UV detection: 220 nm; temperature: 25° C.].

Example 337A

Isomer 2

Yield: 35 mg
$R_t$ 6.57 min; purity >98%; >99% ee
[column: Daicel Chiralpak AD-H, 5 μm, 250 mm×4.6 mm; mobile phase: isohexane/(isopropanol+0.2% trifluoroacetic acid+1% water) 75:25 (v/v); flow rate: 1 ml/min; UV detection: 220 nm; temperature: 25° C.].

Example 338A

Isomer 3

Yield: 236 mg $R_t$ 8.03 min; purity >99%; >99% ee
[column: Daicel Chiralpak AD-H, 5 μm, 250 mm×4.6 mm; mobile phase: isohexane/(isopropanol+0.2% trifluoroacetic acid+1% water) 75:25 (v/v); flow rate: 1 ml/min; UV detection: 220 nm; temperature: 25° C.].

LC-MS (method 15): $R_t$=1.12 min; m/z=421 (M+H)⁺.

$^1$H-NMR (400 MHz, DMSO-d₆, δ/ppm): 12.60-12.81 (1H, br. s), 7.78 (2H, d), 7.41-7.53 (3H, m), 7.37 (4H, s), 4.93 (2H, s), 4.89 (2H, s), 3.61 (1H, d), 3.18-3.32 (1H, m), 0.77 (3H, d).
$[\alpha]_D^{20}$=+45.6°, c=0.565, methanol.

Example 339A

Isomer 4

Yield: 247 mg $R_t$ 9.17 min; purity >99%; >98% ee
[column: Daicel Chiralpak AD-H, 5 μm, 250 mm×4.6 mm; mobile phase: isohexane/(isopropanol+0.2% trifluoroacetic acid+1% water) 75:25 (v/v); flow rate: 1 ml/min; UV detection: 220 nm; temperature: 25° C.].
$[\alpha]_D^{20}$=−45.8°, c=0.305, methanol.

Examples 340A-343A

3-Methyl-2-{4-[(5-oxo-2-phenyl-5,6-dihydro-4H-1,3,4-oxadiazin-4-yl)methyl]phenyl}pentanoic acid (isomers 1-4)

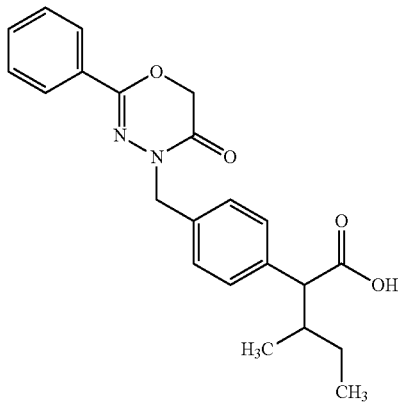 [SMILES: CCC(C)C(C(=O)O)c1ccc(CN2N=C(c3ccccc3)OCC2=O)cc1]

11.8 g (31.02 mmol) of the mixture of isomers of 3-methyl-2-{4-[(5-oxo-2-phenyl-5,6-dihydro-4H-1,3,4-oxadiazin-4-yl)methyl]phenyl}pentanoic acid were initially separated into the diastereomers by preparative HPLC on a chiral phase [column: chiral silica gel phase based on the selector poly(N-methacryloyl-D-valine-3-pentylamid), 500 mm×75 mm; mobile phase: isohexane/ethyl acetate 30:70 (v/v); flow rate: 200 ml/min; UV detection: 290 nm; temperature: 25° C.]. This gave 4.11 g and 5.2 g, respectively, of the two diastereomers.

Separation of Diastereomer 1:

4.11 g of the diastereomer 1 were separated into the enantiomers by preparative HPLC on a chiral phase (isomers 1 and 2) [column: Daicel Chiralpak AD-H, 5 μm, 250 mm×20 mm; mobile phase: isohexane/isopropanol 95:5 (v/v); flow rate: 25 ml/min; UV detection: 230 nm; temperature: 24° C.]:

Example 340A

Isomer 1

Yield: 865 mg $R_t$ 7.36 min; purity >91%; >93% ee
[column: Daicel Chiralpak AD-H, 5 μm, 250 mm×4 mm; mobile phase: isohexane/isopropanol 80:20 (v/v); flow rate: 1 ml/min; UV detection: 230 nm; temperature: 25° C.].

LC-MS (method 10): $R_t$=2.16 min; m/z=381 (M+H)⁺.

Example 341A

Isomer 2

Yield: 1662 mg $R_t$ 7.91 min; purity >99%; >97% ee
[column: Daicel Chiralpak AD-H, 5 μm, 250 mm×4 mm; mobile phase: isohexane/isopropanol 80:20 (v/v); flow rate: 1 ml/min; UV detection: 230 nm; temperature: 25° C.].

LC-MS (method 7): $R_t$=2.53 min; m/z=381 (M+H)⁺.

$^1$H-NMR (400 MHz, DMSO-d₆, δ/ppm): 12.35-12.15 (1H, br. s), 7.78 (2H, d), 7.54-7.40 (3H, m), 7.31 (4H, q), 4.92 (2H, s), 4.86 (2H, s), 3.19 (1H, d), 2.09-1.95 (1H, m), 1.59-1.43 (1H, m), 1.25-1.09 (1H, m), 0.89 (3H, t), 0.58 (3H, d).
$[\alpha]_D^{20}$=+21.7°, c=0.525, methanol.

Separation of Diastereomer 2:

5.2 g of the diastereomer 2 were separated into the enantiomers by preparative HPLC on a chiral phase (isomers 3 and 4) [column: Daicel Chiralcel OJ-H, 5 μm, 250 mm×20 mm; mobile phase: isohexane/isopropanol 95:5 (v/v); flow rate: 25 ml/min; UV detection: 230 nm; temperature: 24° C.]:

Example 342A

Isomer 3

Yield: 2970 mg $R_t$ 7.21 min; purity >94%; >99% ee
[column: Daicel Chiralcel OJ-H, 5 μm, 250 mm×4 mm; mobile phase: isohexane/isopropanol 80:20 (v/v); flow rate: 1 ml/min; UV detection: 230 nm; temperature: 25° C.].

LC-MS (method 7): $R_t$=2.53 min; m/z=381 (M+H)⁺.

Example 343A

Isomer 4

Yield: 1350 mg $R_t$ 7.77 min; purity >90%; >84% ee
[column: Daicel Chiralcel OJ-H, 5 μm, 250 mm×4 mm; mobile phase: isohexane/isopropanol 80:20 (v/v); flow rate: 1 ml/min; UV detection: 230 nm; temperature: 25° C.].

LC-MS (method 10): $R_t$=2.17 min; m/z=381 (M+H)⁺.

Example 344A and Example 345A 4,4,4-Trifluoro-3-methyl-2-{4-[(6-oxo-3-phenylpyridazin-1(6H)-yl)methyl]phenyl}butanoic acid (isomers 1 and 2)

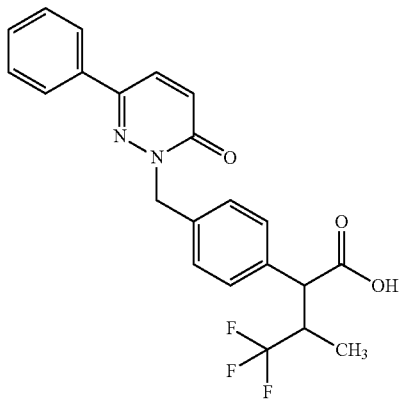 [SMILES: CC(C(C(=O)O)c1ccc(Cn2nc(-c3ccccc3)ccc2=O)cc1)C(F)(F)F]

715 mg (1.72 mmol) of the mixture of isomers of 4,4,4-trifluoro-3-methyl-2-{4-[(6-oxo-3-phenylpyridazin-1(6H)-yl)methyl]phenyl}butanoic acid were separated into the isomers by preparative HPLC on a chiral phase [column: chiral silica gel phase based on the selector poly(N-methacryloyl-L-isoleucine-3-pentylamide), 430 mm×40 mm; mobile phase: ethyl acetate; flow rate: 80 ml/min; UV detection: 265 nm; temperature: 26° C.]. Only the two enantiomers (isomers 1 and 2) of one diastereomer were isolated.

Example 344A

Isomer 1

Yield: 284 mg
$R_t$ 7.71 min; purity >99%; >99.5% ee; >99% de [column: chiral silica gel phase based on the selector poly (N-methacryloyl-L-isoleucine-3-pentylamide), 250 mm×4.6 mm; mobile phase: isohexane/ethyl acetate 20:80 (v/v); flow rate: 2 ml/min; UV detection: 265 nm; temperature: 25° C.].
LC-MS (method 15): $R_t$=1.10 min; m/z=417 (M+H)$^+$.
$[\alpha]_D^{20}$=−45.9°, c=0.48, methanol.

Example 345A

Isomer 2

Yield: 293 mg
$R_t$ 13.19 min; purity >99%; >99.5% ee; >88% de [column: chiral silica gel phase based on the selector poly (N-methacryloyl-L-isoleucine-3-pentylamide), 250 mm×4.6 mm; mobile phase: isohexane/ethyl acetate 20:80 (v/v); flow rate: 2 ml/min; UV detection: 265 nm; temperature: 25° C.].
LC-MS (method 15): $R_t$=1.10 min; m/z=417 (M+H)$^+$.
$^1$H-NMR (400 MHz, DMSO-d$_6$, δ/ppm): 12.72 (1H, br. s), 8.09 (1H, d), 7.79 (2H, d), 7.54-7.42 (3H, m), 7.36 (4H, s), 7.09 (1H, d), 5.33 (2H, s), 3.60 (1H, d), 3.30-3.16 (1H, m), 0.75 (3H, d).
$[\alpha]_D^{20}$=+48.0°, c=0.49, methanol.

The compounds listed in the table below were prepared analogously to Example 112A:

| Example | Name/Structure/Starting materials | Analytical data |
| --- | --- | --- |
| 346A | tert-butyl 3-{2-methyl-3-[(3-methyl-2-{4[(5-oxo-2-phenyl-5,6-dihydro-4H-1,3,4-oxadiazin-4-yl)methyl]-phenyl}butanoyl)amino]phenyl}propanoate<br><br>(from Ex. 79A and Ex. 96A) | $R_t$ = 2.33 min [column: Onyx Monolithic C18; mobile phase: acetonitrile/(water + 0.05% TFA) 1:1 (v/v); flow rate: 5 ml/min; UV detection: 214/254 nm; temperature: 40° C.]. |

| Example | Name/Structure/Starting materials | Analytical data |
|---|---|---|
| 347A | methyl 3-{3-[(cyclopentyl{4-[(5-oxo-2-phenyl-5,6-dihydro-4H-1,3,4-oxadiazin-4-yl)methyl]phenyl}-acetyl)amino]phenyl}-2,2-dimethylpropanoate<br>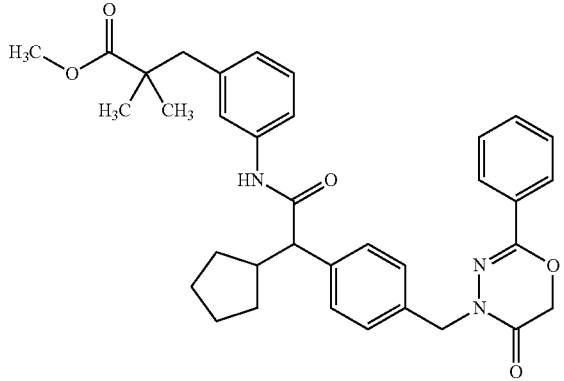 [SMILES: COC(=O)C(C)(C)Cc1cccc(NC(=O)C(c2ccc(CN3N=C(c4ccccc4)OCC3=O)cc2)C2CCCC2)c1]<br>(from Ex. 77A and methyl 3-(3-aminophenyl)-2,2-dimethylpropanoate) | LC-MS (method 7): $R_t$ = 3.06 min; m/z = 582 (M + H)⁺.<br>¹H-NMR (400 MHz, DMSO-$d_6$): δ = 9.97 (s, 1H), 7.76 (d, 2H), 7.28-7.52 (m, 9H), 7.13 (t, 1H), 6.72 (d, 1H), 4.90 (s, 2H), 4.84 (s, 2H), 3.37 (d, 1H), 3.32 (s, 2H), 2.71 (s, 2H), 1.72-1.83 (m, 1H), 1.13-1.67 (m, 7H), 1.08 (s, 6H), 0.90-1.02 (m, 1H). |
| 348A | methyl 3-{3-[(cyclopentyl{4-[(6-oxo-3-phenylpyridazin-1(6H)-yl)methyl]phenyl}acetyl)amino]phenyl}-2,2-dimethylpropanoate<br>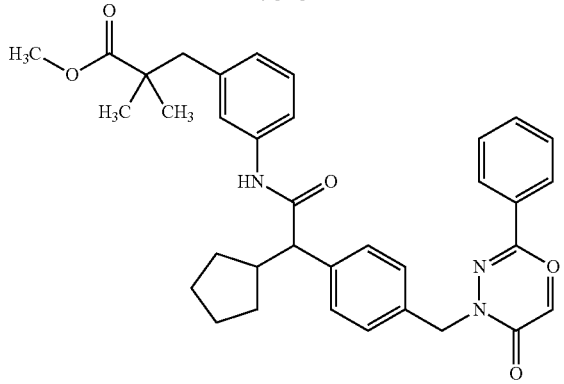<br>(from cyclopentyl-{4-[(6-oxo-3-phenylpyridazin-1(6H)-yl)methyl]phenyl}acetic acid and methyl 3-(3-aminophenyl)-2,2-dimethylpropanoate) | LC-MS (method 7): $R_t$ = 2.98 min; m/z = 578 (M + H)⁺.<br>¹H-NMR (400 MHz, DMSO-$d_6$): δ = 9.96 (s, 1H), 8.06 (d, 1H), 7.87 (d, 2H), 7.42-7.52 (m, 3H), 7.38 (d, 2H), 7.28-7.35 (m, 4H), 7.13 (t, 1H), 7.07 (d, 1H), 6.72 (d, 1H), 5.29 (s, 2H), 3.54 (s, 3H), 3.36 (d, 1H), 2.71 (s, 2H), 1.72-1.82 (m, 1H), 1.17-1.67 (m, 6H), 1.08 (s, 6H), 0.88-1.01 (m, 1H). |
| 349A | methyl 2,2-dimethyl-3-{3-[(3-methyl-2-{4-[(5-oxo-2-phenyl-5,6-dihydro-4H-1,3,4-oxdiazin-4-yl)methyl]-phenyl}butanoyl)amino]phenyl}propanoate<br>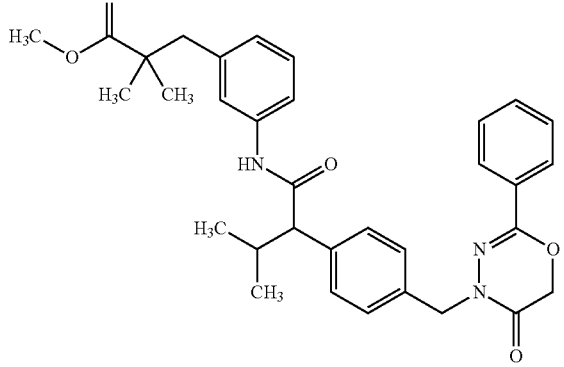<br>(from Ex. 79A and methyl 3-(3-aminophenyl)-2,2-dimethylpropanoate) | LC-MS (method 7): $R_t$ = 2.93 min; m/z = 556 (M + H)⁺.<br>¹H-NMR (400 MHz, DMSO-$d_6$): δ = 9.99 (s, 1H), 7.76 (d, 2H), 7.40-7.53 (m, 3H), 7.26-7.39 (m, 6H), 7.13 (t, 1H), 6.72 (d, 1H), 4.90 (s, 2H), 4.84 (s, 2H), 3.55 (s, 3H), 3.22 (d, 1H), 2.71 (s, 2H), 2.26-2.38 (m, 1H), 1.07 (s, 6H), 0.99 (d, 3H), 0.65 (d, 3H). |

| Example | Name/Structure/Starting materials | Analytical data |
|---|---|---|
| 350A | tert-butyl 3-{3-[(cyclopentyl{4-[(6-oxo-3-phenyl-pyridazin-1(6H)-yl)methyl]phenyl}acetyl)amino]-2-methylphenyl}propanoate<br><br>(from cyclopentyl-{4-[(6-oxo-3-phenylpyridazin-1(6H)-yl)methyl]phenyl}acetic acid and Ex. 96A) | LC-MS (method 7):<br>$R_t$ = 3.07 min; m/z = 606 (M + H)⁺.<br>¹H-NMR (400 MHz, DMSO-d₆): δ = 9.45 (s, 1H), 8.07 (d, 1H), 7.88 (d, 2H), 7.43-7.53 (m, 3H), 7.41 (d, 2H), 7.32 (d, 2H), 7.09 (d, 1H), 6.92-7.03 (m, 3H), 5.32 (s, 2H), 3.45 (d, 1H), 2.77 (t, 2H), 2.56-2.64 (m, 1H), 2.40 (t, 2H), 1.94-1.99 (m, 3H), 1.41-1.89 (m, 7H), 1.31-1.40 (m, 9H), 0.88-1.06 (m, 1H). |
| 351A | methyl 3-{2-methyl-3-[(6,6,6-trifluoro-4-methyl-2-{4-[(6-oxo-3-phenylpyridazin-1(6H)-yl)methyl]-phenyl}hexanoyl)amino]phenyl}propanoate<br><br>(from 6,6,6-trifluoro-4-methyl-2-{4-[(6-oxo-3-phenylpridazin-1(6H)-yl)methyl]phenyl}hexanoic acid and Ex. 97A) | LC-MS (method 10):<br>$R_t$ = 2.49 min; m/z = 624 (M + H)⁺. |
| 352A | methyl 2,2-dimethyl-3-{3-[(3-methyl-2-{4-[(5-oxo-2-phenyl-5,6-dihydro-4H-1,3,4-oxadiazin-4-yl)methyl]-phenyl}pentanoyl)amino]phenyl}propanoate<br><br>(from 3-methyl-2-{4-[(5-oxo-2-phenyl-5,6-dihydro-4H-1,3,4-oxadiazin-4-yl)methyl]phenyl}pentanoic acid (isomer 2) and methyl 3-(3-aminophenyl)-2,2-dimethylpropanoate) | LC-MS (method 7):<br>$R_t$ = 3.02 min; m/z = 570 (M + H)⁺.<br>¹H-NMR (400 MHz, DMSO-d₆): δ = 10.00 (s, 1H), 7.76 (d, 2H), 7.41-7.52 (m, 3H), 7.29-7.38 (m, 6H), 7.13 (t, 1H), 6.72 (d, 1H), 4.90 (s, 2H), 4.84 (s, 2H), 3.54 (s, 3H), 3.34 (d, 1H), 2.71 (s, 2H), 2.12-2.23 (m, 1H), 1.46-1.59 (m, 1H), 1.13-1.25 (m, 1H), 1.07 (s, 6H), 0.85-0.93 (m, 3H), 0.61 (d, 3H). |

| Example | Name/Structure/Starting materials | Analytical data |
|---|---|---|
| 353A | methyl 4-[(cyclopentyl{4-[(6-oxo-3-phenylpyridazin-1(6H)-yl)methyl]phenyl}acetyl)amino]-2,3-dihydro-1H-indene-2-carboxylate<br><br>(from cyclopentyl-{4-[(6-oxo-3-phenylpyridazin-1(6H)-yl)methyl]phenyl}acetic acid and Ex. 89A) | LC-MS (method 11): $R_t$ = 1.45 min; m/z = 562 (M + H)$^+$. |
| 354A | tert-butyl 3-{2-methyl-3-[4,4,4-trifluoro-3-methyl-2-{4-[(6-oxo-3-phenylpyridazin-1(6H)-yl)methyl]phenyl}butanoyl)amino]phenyl}propanoate<br><br>(from 4,4,4-trifluoro-3-methyl-2-{4-[(6-oxo-3-phenylpyridazin-1(6H)-yl)methyl]phenyl}butanoic acid and Ex. 96A) | LC-MS (method 10): $R_t$ = 2.62 min; m/z = 634 (M + H)$^+$. |
| 355A | tert-butyl 1-{3-[(cyclopentyl{4-[(6-oxo-3-phenyl-pyridazin-1(6H)-yl)methyl]phenyl}acetyl)amino]-benzyl}cyclopropanecarboxylate<br><br>(from cyclopentyl-{4-[(6-oxo-3-phenylpyridazin-1(6H)-yl)methyl]phenyl}acetic acid (enantiomer 1) and tert-butyl 1-(3-aminobenzyl)cyclopropanecarboxylate) | LC-MS (method 7): $R_t$ = 3.18 min; m/z = 616 (M − H)$^-$.<br>$^1$H-NMR (400 MHz, DMSO-$d_6$): δ = 9.93 (s, 1H), 8.06 (d, 1H), 7.87 (d, 2H), 7.47 (d, 4H), 7.38 (d, 2H), 7.27-7.35 (m, 3H), 7.13 (t, 1H), 7.07 (d, 1H), 6.87 (d, 1H), 5.29 (s, 2H), 3.37 (d, 1H), 2.75 (s, 2H), 1.74-1.82 (m, 1H), 1.58-1.68 (m, 1H), 1.50-1.58 (m, 2H), 1.41-1.49 (m, 1H), 1.33-1.39 (m, 1H), 1.17-1.30 (m, 11H), 1.01-1.06 (m, 2H), 0.92-1.00 (m, 1H), 0.76-0.81 (m, 2H). |

| Example | Name/Structure/Starting materials | Analytical data |
|---|---|---|
| 356A | tert-butyl 1-{3-[(4,4,4-trifluoro-3-methyl-2-{4-[(6-oxo-3-phenylpyridazin-1(6H)-yl)methyl]phenyl}-butanoyl)amino]benzyl}cyclopropanecarboxylate (isomer 1)<br>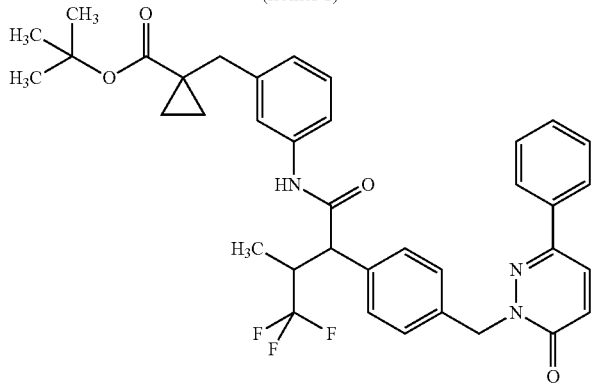<br>(from 4,4,4-trifluoro-3-methyl-2-{4-[(6-oxo-3-phenylpyridazin-1(6H)-yl)methyl]phenyl}butanoic acid (isomer 1) and tert-butyl 1-(3-aminobenzyl)cyclopropanecarboxylate) | LC-MS (method 11):<br>$R_t$ = 1.63 min; m/z = 644 (M − H)⁻. |
| 357A | tert-butyl 1-{3-[(4,4,4-trifluoro-3-methyl-2-{4-[(6-oxo-3-phenylpyridazin-1(6H)-yl)methyl]phenyl}-butanoyl)amino]benzyl}cyclopropanecarboxylate (isomer 2)<br>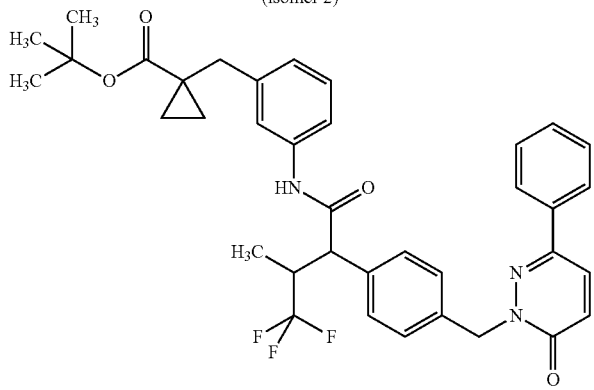<br>(from 4,4,4-trifluoro-3-methyl-2-{4-[(6-oxo-3-phenylpyridazin-1(6H)-yl)methyl]phenyl}butanoic acid (isomer 2) and tert-butyl 1-(3-aminobenzyl)cyclopropanecarboxylate) | LC-MS (method 11):<br>$R_t$ = 1.63 min; m/z = 644 (M − H)⁻. |

| Example | Name/Structure/Starting materials | Analytical data |
|---|---|---|
| 358A | tert-butyl 1-{3-[(5,5,5-trifluoro-3-methyl-2-{4-[(5-oxo-2-phenyl-5,6-dihydro-4H-1,3,4-oxadiazin-4-yl)-methyl]-phenyl}pentanoyl)amino]benzyl}cyclopropanecarboxylate<br />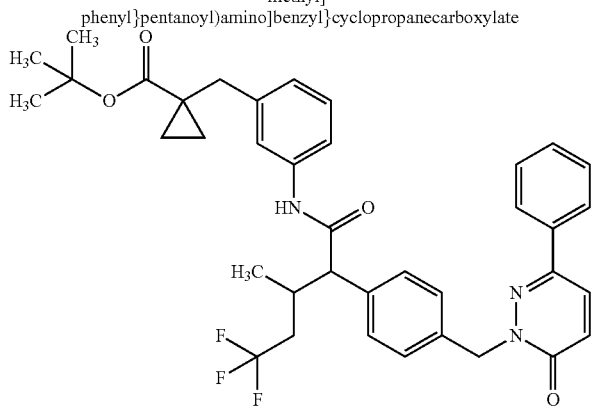<br />(from 5,5,5-trifluoro-3-methyl-2-{4-[(5-oxo-2-phenyl-5,6-dihydro-4H-1,3,4-oxadiazin-4-yl)methyl]phenyl}pentanoic acid and tert-butyl 1-(3-aminobenzyl)cyclopropanecarboxylate) | LC-MS (method 15): $R_t$ = 1.49 min; m/z = 662 (M – H)⁻. |
| 359A | tert-butyl 1-(3-{[{4-[(3-chloro-6-oxopyridazin-1(6H)-yl)methyl]phenyl}(cyclopentyl)acetyl]amino}-benzyl)cyclopropanecarboxylate<br />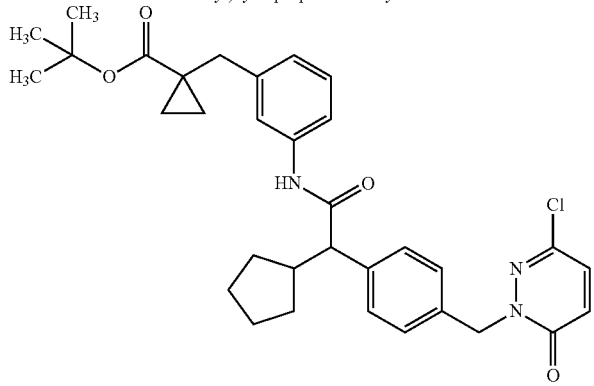<br />(from {4-[3-chloro-6-oxopyridazin-1(6H)-yl)-methyl]phenyl}(cyclopentyl)acetic acid and tert-butyl 1-(3-aminobenzyl)cyclopropanecarboxylate | LC-MS (method 15): $R_t$ = 1.41 min; m/z = 520 (M – $C_4H_8$)⁺. |

| Example | Name/Structure/Starting materials | Analytical data |
|---|---|---|
| 360A | tert-butyl 1-{3-[(4,4,4-trifluoro-3-methyl-2-{4-[(5-oxo-2-phenyl-5,6-dihydro-4H-1,3,4-oxadiazin-4-yl)-methyl]-phenyl}butanoyl)amino]benzyl}cyclopropanecarboxylate (isomer 1)<br>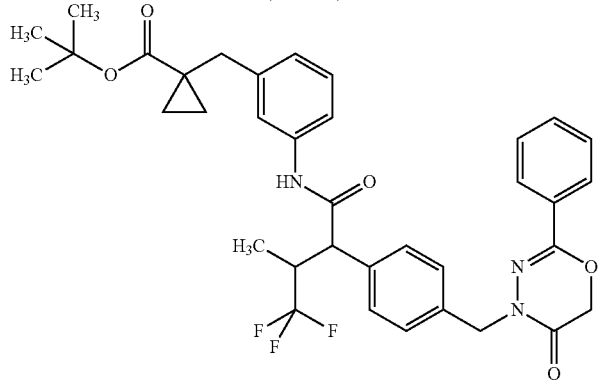<br>(from 4,4,4-trifluoro-3-methyl-2-{4-[(5-oxo-2-phenyl-5,6-dihydro-4H-1,3,4-oxadiazin-4-yl)methyl]phenyl}butanoic acid (isomer 1) and tert-butyl 1-(3-aminobenzyl)cyclopropanecarboxylate) | LC-MS (method 15): $R_t$ = 1.46 min; m/z = 594 (M − $C_4H_8$ + H)$^+$. |
| 361A | tert-butyl 1-{3-[(4,4,4-trifluoro-3-methyl-2-{4-[(5-oxo-2-phenyl-5,6-dihydro-4H-1,3,4-oxadiazin-4-yl)-methyl]-phenyl}butanoyl)amino]benzyl}cyclopropanecarboxylate (isomer 2)<br>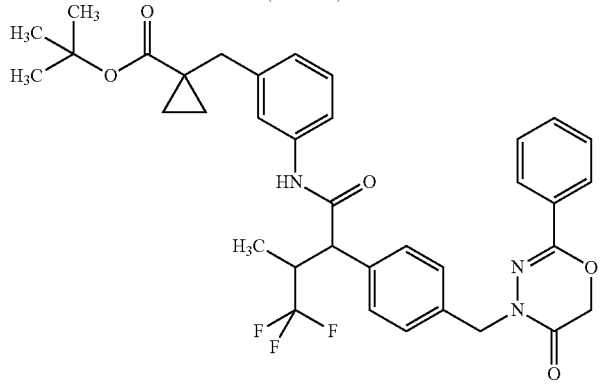<br>(from 4,4,4-trifluoro-3-methyl-2-{4-[(5-oxo-2-phenyl-5,6-dihydro-4H-1,3,4-oxadiazin-4-yl)methyl]phenyl}butanoic acid (isomer 2) and tert-butyl 1-(3-aminobenzyl)cyclopropanecarboxylate) | LC-MS (method 15): $R_t$ = 1.46 min; m/z = 594 (M − $C_4H_8$ + H)$^+$. |

| Example | Name/Structure/Starting materials | Analytical data |
|---|---|---|
| 362A | tert-butyl 1-{3-[(4,4,4-trifluoro-3-methyl-2-{4-[(5-oxo-2-phenyl-5,6-dihydro-4H-1,3,4-oxadiazin-4-yl)-methyl]-phenyl}butanoyl)amino]benzyl}cyclopropanecarboxylate (isomer 3)<br>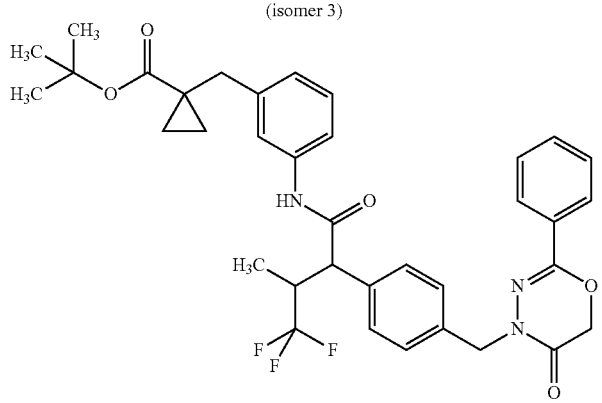<br>(from 4,4,4-trifluoro-3-methyl-2-{4-[(5-oxo-2-phenyl-5,6-dihydro-4H-1,3,4-oxadiazin-4-yl)methyl]phenyl}butanoic acid (isomer 3) and tert-butyl 1-(3-aminobenzyl)cyclopropanecarboxylate) | LC-MS (method 15): $R_t$ = 1.46 min; m/z = 648 (M − H)⁻. |
| 363A | tert-butyl 1-{3-[(4,4,4-trifluoro-3-methyl-2-{4-[(5-oxo-2-phenyl-5,6-dihydro-4H-1,3,4-oxadiazin-4-yl)-methyl]-phenyl}butanoyl)amino]benzyl}cyclopropanecarboxylate (isomer 4)<br>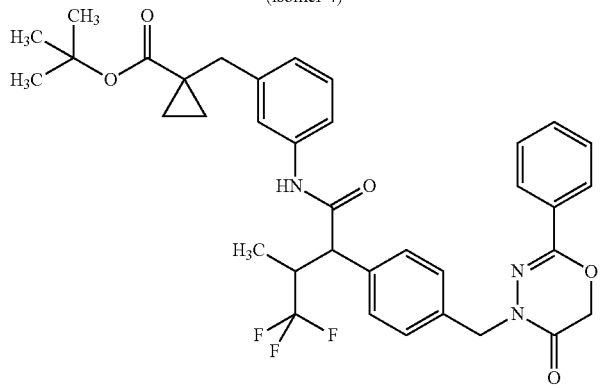<br>(from 4,4,4-trifluoro-3-methyl-2-{4-[(5-oxo-2-phenyl-5,6-dihydro-4H-1,3,4-oxadiazin-4-yl)methyl]phenyl}butanoic acid (isomer 4) and tert-butyl 1-(3-aminobenzyl)cyclopropanecarboxylate) | LC-MS (method 15): $R_t$ = 1.46 min; m/z = 648 (M − H)⁻. |

| Example | Name/Structure/Starting materials | Analytical data |
|---|---|---|
| 364A | tert-butyl 3-{2-methyl-3-[(4,4,4-trifluoro-3-methyl-2-{4-[(5-oxo-2-phenyl-5,6-dihydro-4H-1,3,4-oxadiazin-4-yl)-methyl]phenyl}butanoyl)amino]phenyl}propanoate<br>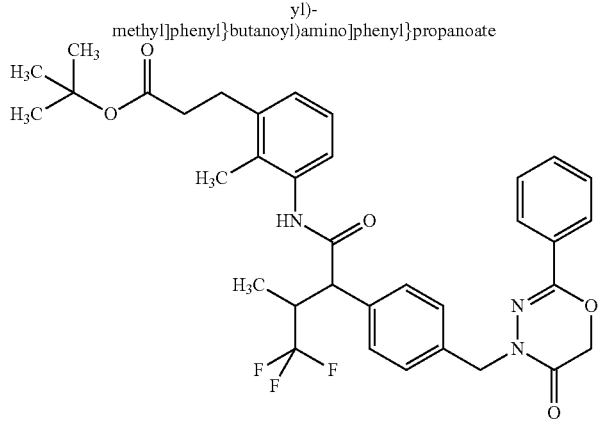<br>(from 4,4,4-trifluoro-3-methyl-2-{4-[(5-oxo-2-phenyl-5,6-dihydro-4H-1,3,4-oxadiazin-4-yl)methyl]phenyl}butanoic acid and Ex. 96A) | LC-MS (method 11): $R_t$ = 1.61 min; m/z = 636 (M − H)⁻. |
| 365A | methyl 3-{3-[(4,4,4-trifluoro-3-methyl-2-{4-[(5-oxo-2-phenyl-5,6-dihydro-4H-1,3,4-oxadiazin-4-yl)methyl]-phenyl}butanoyl)amino]phenyl}propanoate<br>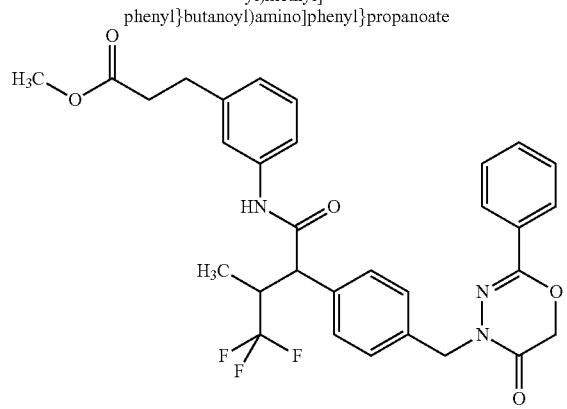<br>(from 4,4,4-trifluoro-3-methyl-2-{4-[(5-oxo-2-phenyl-5,6-dihydro-4H-1,3,4-oxadiazin-4-yl)methyl]phenyl}butanoic acid and methyl 3-(3-aminophenyl)propanoate) | LC-MS (method 11): $R_t$ = 1.47 min; m/z = 582 (M + H)⁺. |

-continued

| Example | Name/Structure/Starting materials | Analytical data |
|---|---|---|
| 366A | tert-butyl 1-(3-{[2-{4-[(5-oxo-2-phenyl-5,6-dihydro-4H-1,3,4-oxadiazin-4-yl)methyl]phenyl}-3-(trifluoromethyl)-pentanoyl]amino}benzyl)cyclopropanecarboxylate<br><br>(from 2-{4-[(5-oxo-2-phenyl-5,6-dihydro-4H-1,3,4-oxadiazin-4-yl)methyl]phenyl}-3-(trifluoromethyl)-pentanoic acid and tert-butyl 1-(3-aminobenzyl)cyclopropanecarboxylate) | LC-MS (method 15): $R_t$ = 1.49 min; m/z = 662 (M − H)⁻. |
| 367A | tert-butyl 1-{3-[(cyclopentyl{4-[(3-methyl-6-oxo-pyridazin-1(6H)-yl)methyl]phenyl}acetyl)amino]-benzyl}cyclopropanecarboxylate<br><br>(from cyclopentyl{4-[(3-methyl-6-oxopyridazin-1(6H)-yl)methyl]phenyl}acetic acid and tert-butyl 1-(3-aminobenzyl)cyclopropanecarboxylate) | LC-MS (method 11): $R_t$ = 1.54 min; m/z = 500 (M − $C_4H_8$ + H)⁺. ¹H-NMR (400 MHz, DMSO-d6): δ = 9.94 (s, 1H), 7.49 (s, 1H), 7.30-7.39 (m, 4H), 7.21 (d, 2H), 7.14 (t, 1H), 6.86-6.92 (m, 2H), 5.14 (s, 2H), 3.36 (d, 1H), 2.77 (s, 2H), 2.56-2.62 (m, 1H), 2.24 (s, 3H), 1.77 (dd, 1H), 1.30-1.67 (m, 5H), 1.16-1.29 (m, 1H), 1.24 (s, 9H), 1.03-1.07 (m, 2H), 0.96 (dt, 1H), 0.76-0.82 (m, 2H). |
| 368A | tert-butyl 1-(3-{[cyclopentyl(4-{[6-oxo-3-(trifluoromethyl)pyridazin-1(6H)-yl]methyl}phenyl)-acetyl]amino}benzyl)cyclopropanecarboxylate<br><br>(from cyclopentyl(4-{[6-oxo-3-(trifluoromethyl)pyridazin-1(6H)-yl]methyl}phenyl)acetic acid and tert-butyl 1-(3-aminobenzyl)cyclopropanecarboxylate) | LC-MS (method 15): $R_t$ = 1.45 min; m/z = 608 (M − H)⁻. ¹H-NMR (400 MHz, DMSO-d₆): δ = 9.95 (s, 1H), 7.85 (d, 1H), 7.49 (s, 1H), 7.39 (d, 2H), 7.34 (d, 1H), 7.25 (d, 2H), 7.18 (d, 1H), 7.14 (t, 1H), 6.88 (d, 1H), 5.27 (s, 2H), 3.37 (d, 1H), 2.77 (s, 2H), 2.56-2.64 (m, 1H), 1.71-1.84 (m, 1H), 1.29-1.69 (m, 6H), 1.23 (s, 9H), 1.02-1.07 (m, 2H), 0.89-1.01 (m, 1H), 0.76-0.82 (m, 2H). |

| Example | Name/Structure/Starting materials | Analytical data |
|---|---|---|
| 369A | methyl 3-(3-{[cyclopentyl(4-{[6-oxo-3-(trifluoromethyl)pyridazin-1(6H)-yl]methyl}phenyl)acetyl]amino}phenyl)propanoate<br>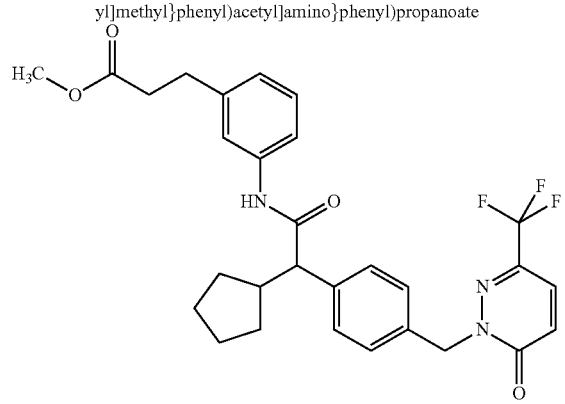<br>(from cyclopentyl(4-{[6-oxo-3-(trifluoromethyl)pyridazin-1(6H)-yl]methyl}phenyl)acetic acid and methyl 3-(3-aminoohenyl)propanoate) | LC-MS (method 11): $R_t$ = 1.45 min; m/z = 542 (M + H)⁺.<br>¹H-NMR (400 MHz, DMSO-d₆): δ = 9.98 (s, 1H), 7.84 (d, 1H), 7.36-7.44 (m, 4H), 7.26 (d, 2H), 7.12-7.21 (m, 2H), 6.86 (d, 1H), 5.27 (s, 2H), 3.56 (s, 3H), 3.37 (d, 1H), 2.74-2.82 (m, 2H), 2.54-2.62 (m, 3H), 1.72-1.82 (m, 1H), 1.60-1.70 (m, 1H), 1.50-1.59 (m, 2H), 1.41-1.50 (m, 1H), 1.31-1.38 (m, 1H), 1.22-1.28 (m, 1H), 0.90-1.00 (m, 1H). |
| 370A | tert-butyl 1-{3-[(cyclopentyl{4-[(3-methyl-2-oxo-pyridin-1(2H)-yl)methyl]phenyl}acetyl)amino]-benzyl}cyclopropanecarboxylate<br>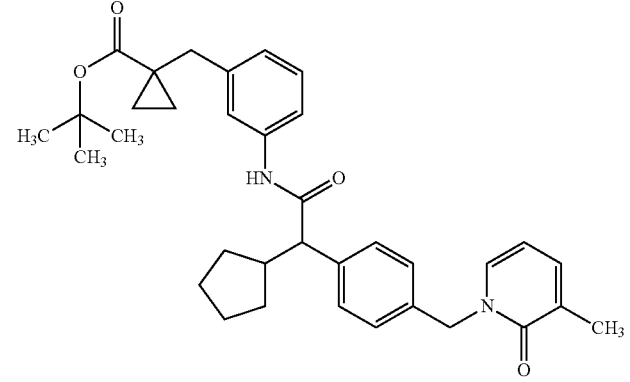 [SMILES: Cc1cccn(Cc2ccc(C(C(=O)Nc3cccc(CC4(C(=O)OC(C)(C)C)CC4)c3)C3CCCC3)cc2)c1=O]<br>(from cyclopentyl {4-[(3-methyl-2-oxopyridin-1(2H)-yl)methyl]phenyl}acetic acid and tert-butyl 1-(3-aminobenzyl)cyclopropanecarboxylate) | LC-MS (method 11): $R_t$ = 1.54 min; m/z = 553 (M − H)⁻. |
| 371A | tert-butyl 1-(3-{[cyclopentyl(4-{[2-oxo-4-(trifluoromethyl)pyridin-1(2H)-yl]methyl}phenyl)-acetyl]amino}benzyl)cyclopropanecarboxylate<br>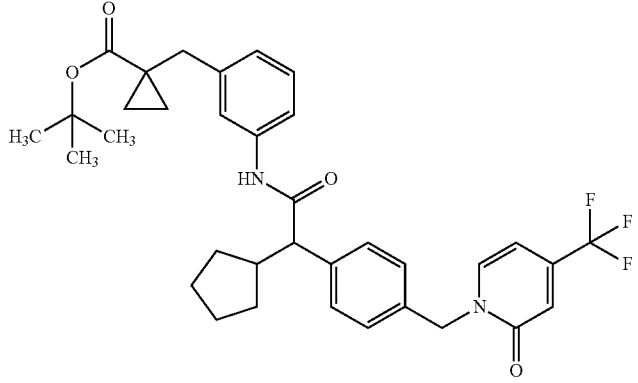 [SMILES: CC(C)(C)OC(=O)C1(Cc2cccc(NC(=O)C(c3ccc(Cn4ccc(C(F)(F)F)cc4=O)cc3)C3CCCC3)c2)CC1]<br>(from cyclopentyl(4-{[2-oxo-4-(trifluoromethyl)pyridin-1(2H)-yl]methyl}phenyl)acetic acid and tert-butyl 1-(3-aminobenzyl)cyclopropanecarboxylate) | LC-MS (method 11): $R_t$ = 1.62 min; m/z = 607 (M − H)⁻. |

| Example | Name/Structure/Starting materials | Analytical data |
|---|---|---|
| 372A | methyl 3-(3-{[(3,3-difluorocyclopentyl){4-[(5-oxo-2-phenyl-5,6-dihydro-4H-1,3,4-oxadiazin-4-yl)methyl]-phenyl}acetyl]amino}phenyl)propanoate<br />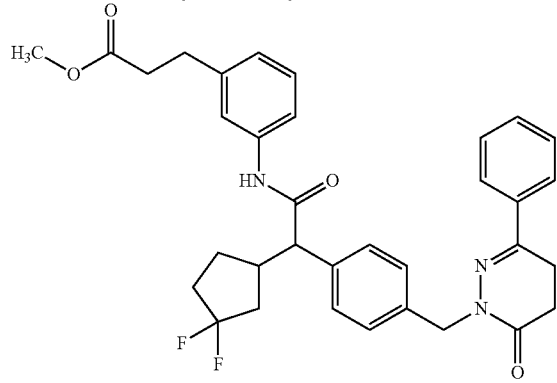 [SMILES: COC(=O)CCc1cccc(NC(=O)C(c2ccc(CN3N=C(c4ccccc4)CCC3=O)cc2)C2CCC(F)(F)C2)c1]<br />(from (3,3-difluorocyclopentyl){4-[(5-oxo-2-phenyl-5,6-dihydro-4H-1,3,4-oxadiazin-4-yl)methyl]phenyl}acetic acid and methyl 3-(3-aminophenyl)propanoate) | LC-MS (method 11):<br />$R_t$ = 1.46 min; m/z = 590 (M + H)⁺. |
| 373A | tert-butyl 1-(3-{[(3,3-difluorocyclopentyl){4-[(5-oxo-2-phenyl-5,6-dihydro-4H-1,3,4-oxadiazin-4-yl)-methyl]-phenyl}acetyl]amino}benzyl)cyclopropanecarboxylate<br />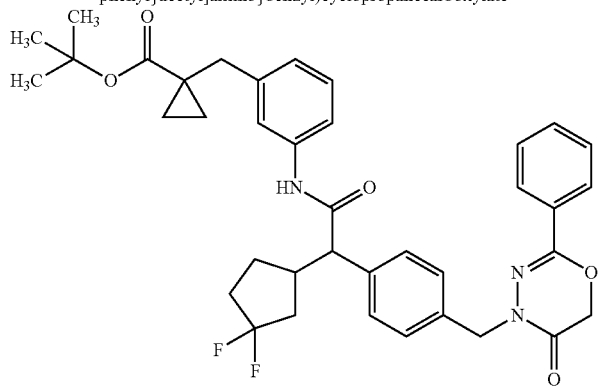<br />(from (3,3-difluorocyclopentyl){4-[(5-oxo-2-phenyl-5,6-dihydro-4H-1,3,4-oxadiazin-4-yl)methyl]phenyl}acetic acid and tert-butyl 1-(3-aminobenzyl)cyclopropanecarboxylate) | LC-MS (method 11):<br />$R_t$ = 1.66 min; m/z = 602 (M − $C_4H_8$ + H)⁺. |

-continued

| Example | Name/Structure/Starting materials | Analytical data |
|---|---|---|
| 374A | tert-butyl 1-{3-[(cyclopentyl{4-[(4-methyl-2-oxo-pyridin-1(2H)-yl)methyl]phenyl}acetyl)amino]-benzyl}cyclopropanecarboxylate<br><br>(from cyclopentyl{4-[(4-methyl-2-oxopyridin-1(2H)-yl)methyl]phenyl}acetic acid and tert-butyl 1-(3-aminobenzyl)cyclopropanecarboxylate) | LC-MS (method 15):<br>$R_t$ = 1.34 min; m/z = 555 (M + H)$^+$. |
| 375A | methyl 3-(3-{[4,4,4-trifluoro-3-methyl-2-(4-{[6-oxo-3-(trifluoromethyl)pyridazin-1(6H)-yl]methyl}phenyl)-butanoyl]amino}phenyl)propanoate<br><br>(from 4,4,4-trifluoro-3-methyl-2-(4-{[6-oxo-3-(trifluoromethyl)pyridazin-1(6H)-yl]methyl}phenyl)butanoic acid and methyl 3-(3-aminophenyl)propanoate) | LC-MS (method 11):<br>$R_t$ = 1.40 min; m/z = 570 (M + H)$^+$. |

| Example | Name/Structure/Starting materials | Analytical data |
|---|---|---|
| 376A | tert-butyl 1-(3-{[4,4,4-trifluoro-3-methyl-2-(4-{[6-oxo-3-(trifluoromethyl)pyridazin-1(6H)-yl]methyl}-phenyl)-butanoyl]amino}benzyl)cyclopropanecarboxylate<br>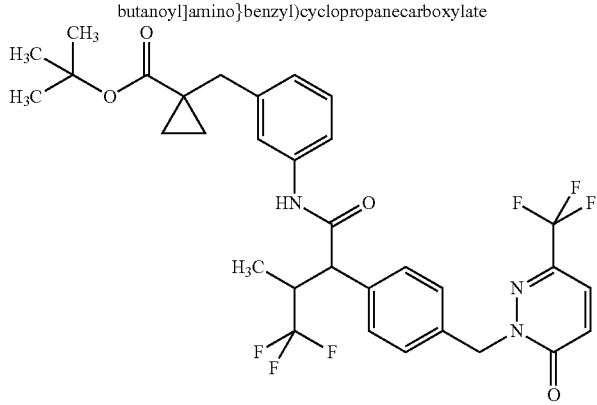<br>(from 4,4,4-trifluoro-3-methyl-2-(4-{[6-oxo-3-(trifluoromethyl)pyridazin-1(6H)-yl]methyl}phenyl)butanoic acid and tert-butyl 1-(3-aminobenzyl)cyclopropanecarboxylate) | LC-MS (method 11): $R_t$ = 1.61 min; m/z = 636 (M − H)⁻.<br>1H-NMR (400 MHz, DMSO-$d_6$): δ = 10.13 (s, 1H), 7.85 (d, 1H), 7.46 (s, 1H), 7.40 (d, 2H), 7.27-7.32 (m, 3H), 7.18 (d, 1H), 7.14 (t, 1H), 6.89 (d, 1H), 5.28 (s, 2H), 3.81 (d, 1H), 3.34-3.42 (m, 1H), 2.76 (s, 2H), 1.21 (s, 9H), 1.04 (q, 2H), 0.80 (q, 2H), 0.77 (d, 3H). |
| 377A | tert-butyl 1-(3-{[cyclopentyl(4-{[2-oxo-3-(trifluoromethyl)pyridin-1(2H)-yl]methyl}phenyl)-acetyl]amino}benzyl)cyclopropanecarboxylate<br>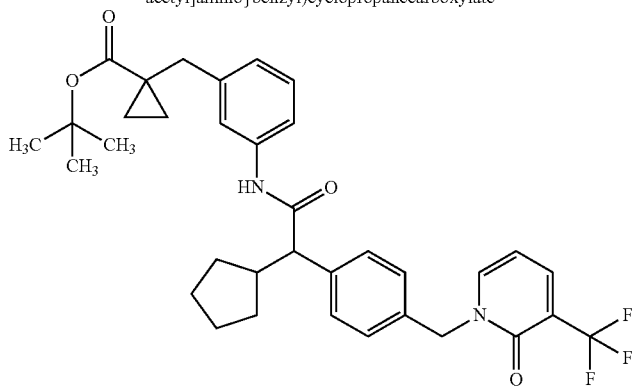<br>(from cyclopentyl(4-{[2-oxo-3-(trifluoromethyl)pyridin-1(2H)-yl]methyl}phenyl)acetic acid and tert-butyl 1-(3-aminobenzyl)cyclopropanecarboxylate) | LC-MS (method 15): $R_t$ = 1.39 min; m/z = 553 (M − $C_4H_8$ + H)⁺. |

| Example | Name/Structure/Starting materials | Analytical data |
|---|---|---|
| 378A | tert-butyl 3-{2-chloro-3-[(4,4,4-trifluoro-3-methyl-2-{4-[(5-oxo-2-phenyl-5,6-dihydro-4H-1,3,4-oxadiazin-4-yl)-methyl]phenyl}butanoyl)amino]phenyl}propanoate<br><br>(from 4,4,4-trifluoro-3-methyl-2-{4-[(5-oxo-2-phenyl-5,6-dihydro-4H-1,3,4-oxadiazin-4-yl)methyl]-phenyl}butanoic acid and tert-butyl 3-(3-amino-2-chlorophenyl)propanoate) | LC-MS (method 11): $R_t$ = 1.67 min; m/z = 657 (M − H)$^-$. |
| 379A | tert-butyl 3-{4-fluoro-3-[(4,4,4-trifluoro-3-methyl-2-{4-[(5-oxo-2-phenyl-5,6-dihydro-4H-1,3,4-oxadiazin-4-yl)-methyl]phenyl}butanoyl)amino]phenyl}propanoate<br><br>(from 4,4,4-trifluoro-3-methyl-2-{4-[(5-oxo-2-phenyl-5,6-dihydro-4H-1,3,4-oxadiazin-4-yl)methyl]-phenyl}butanoic acid (isomer 3) and tert-butyl 3-(3-amino-4-fluorophenyl)propanoate) | LC-MS (method 12): $R_t$ = 2.94 min; m/z = 640 (M − H)$^-$. |

| Example | Name/Structure/Starting materials | Analytical data |
|---|---|---|
| 380A | tert-butyl 1-{4-fluoro-3-[(4,4,4-trifluoro-3-methyl-2-{4-[(5-oxo-2-phenyl-5,6-dihydro-4H-1,3,4-oxadiazin-4-yl)-methyl]phenyl}butanoyl)amino]benzyl}cyclopropane carboxylate<br>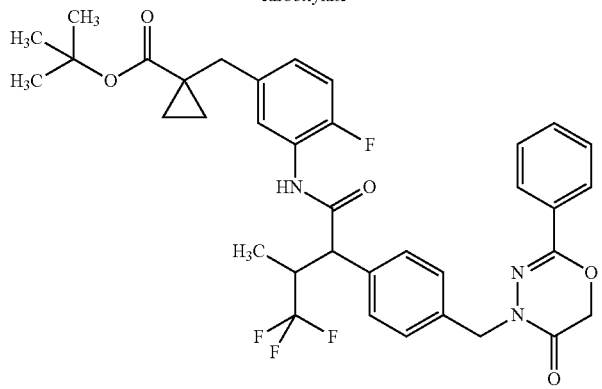<br>(from 4,4,4-trifluoro-3-methyl-2-{4-[(5-oxo-2-phenyl-5,6-dihydro-4H-1,3,4-oxadiazin-4-yl)methyl]-phenyl}butanoic acid (isomer 3) and tert-butyl 1-(3-amino-4-fluorobenzyl)cyclopropanecarboxylate) | LC-MS (method 12): $R_t$ = 3.03 min; m/z = 666 (M − H)⁻. |

The compound listed in the table below was obtained analogously to Example 105A:

| Example | Name/Structure/Starting materials | Analytical data |
|---|---|---|
| 381A | tert-butyl 3-{4-chloro-3-[(cyclopentyl{4-[(5-oxo-2-phenyl-5,6-dihydro-4H-1,3,4-oxadiazin-4-yl)-methyl]phenyl}acetyl)amino]phenyl}propanoate<br>(from Ex. 80A and tert-butyl 3-(3-amino-4-chlorophenyl)propanoate) | LC-MS (method 11): $R_t$ = 1.73 min; m/z = 629 (M − H)⁻ |

Example 382A and Example 383A

Methyl 3-{3-[(cyclopentyl{4-[(6-oxo-3-phenylpyridazin-1(6H)-yl)methyl]phenyl}-acetyl)amino]phenyl}-2,2-dimethylpropanoate (enantiomers 1 and 2)

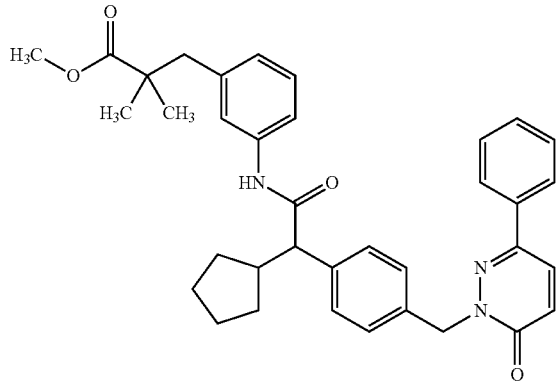 [SMILES: COC(=O)C(C)(C)Cc1cccc(NC(=O)C(c2ccc(Cn3nc(-c4ccccc4)ccc3=O)cc2)C2CCCC2)c1]

100 mg (0.17 mmol) of the racemate of methyl 3-{3-[(cyclopentyl{4-[(6-oxo-3-phenylpyridazin-1(6H)-yl)methyl]phenyl}acetyl)amino]phenyl}-2,2-dimethylpropanoate were separated into the enantiomers by preparative HPLC on a chiral phase [column: Daicel Chiralpak AS-H, 5 μm, 250 mm×20 mm; mobile phase: isohexane/isopropanol 75:25 (v/v); flow rate: 15 ml/min; UV detection: 220 nm; temperature: 40° C.]:

Example 382A
Enantiomer 1

Yield: 58 mg
$R_t$ 6.81 min; purity >99%; >99% ee
[column: Daicel Chiralpak AD-H, 5 μm, 250 mm×4.6 mm; mobile phase: isohexane/isopropanol 75:25 (v/v); flow rate: 1 ml/min; UV detection: 220 nm; temperature: 40° C.].

Example 383A
Enantiomer 2

Yield: 41 mg
$R_t$ 8.45 min; purity >98%; >98.5% ee
[column: Daicel Chiralpak AD-H, 5 μm, 250 mm×4.6 mm; mobile phase: isohexane/isopropanol 75:25 (v/v); flow rate: 1 ml/min; UV detection: 220 nm; temperature: 40° C.].

Example 384A and Example 385A tert-Butyl-3-{3-[(cyclopentyl{4-[(6-oxo-3-phenylpyridazin-1(6H)-yl)methyl]phenyl}acetyl)-amino]-2-methylphenyl}propanoate (enantiomers 1 and 2)

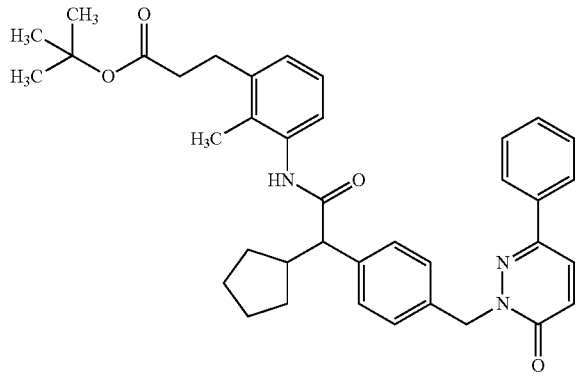 [SMILES: Cc1c(CCC(=O)OC(C)(C)C)cccc1NC(=O)C(c1ccc(Cn2nc(-c3ccccc3)ccc2=O)cc1)C1CCCC1]

920 mg (1.52 mmol) of the racemate of tert-butyl 3-{3-[(cyclopentyl{4-[(6-oxo-3-phenylpyridazin-1(6H)-yl)methyl]phenyl}acetyl)amino]-2-methylphenyl}propanoate were separated into the enantiomers by preparative HPLC on a chiral phase [column: Daicel Chiralpak IA, 5 μm, 250 mm×20 mm; mobile phase: tert-butyl methyl ether/acetonitrile/methanol 75:20:10 (v/v); flow rate: 15 ml/min; UV detection: 220 nm; temperature: 30° C.]:

Example 384A
Enantiomer 1

Yield: 345 mg
$R_t$ 4.76 min; purity >99%; >99% ee
[column: Daicel Chiralpak IA, 5 μm, 250 mm×4.6 mm; mobile phase: tert-butyl methyl ether/acetonitrile/methanol 75:20:10 (v/v); flow rate: 1 ml/min; UV detection: 220 nm; temperature: 25° C.].

Example 385A
Enantiomer 2

Yield: 478 mg
$R_t$ 6.43 min; purity >98%; >98% ee
[column: Daicel Chiralpak IA, 5 μm, 250 mm×4.6 mm; mobile phase: tert-butyl methyl ether/acetonitrile/methanol 75:20:10 (v/v); flow rate: 1 ml/min; UV detection: 220 nm; temperature: 25° C.].

Example 386A and Example 387A tert-Butyl 3-{3-[(cyclopentyl{4-[(2-oxo-5-phenyl-1,3,4-oxadiazol-3(2H)-yl)methyl]phenyl}-acetyl)amino]-2-methylphenyl}propanoate (enantiomers 1 and 2)

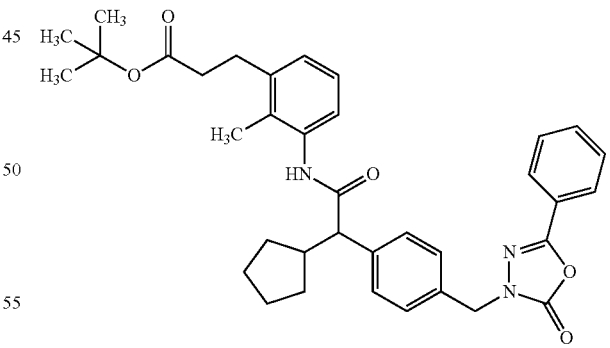

194 mg (0.32 mmol) of the racemate of tert-butyl 3-{3-[(cyclopentyl{4-[(2-oxo-5-phenyl-1,3,4-oxadiazol-3(2H)-yl)methyl]phenyl}acetyl)amino]-2-methylphenyl}propanoate (Example 167A) were separated into the enantiomers by preparative HPLC on a chiral phase [column: Daicel Chiralpak IA, 5 μm, 250 mm×20 mm; mobile phase: tert-butyl methyl ether/acetonitrile/methanol 75:20:10 (v/v); flow rate: 15 ml/min; UV detection: 220 nm; temperature: 27° C.]:

Example 386A

Enantiomer 1

Yield: 70 mg
$R_t$ 4.15 min; purity >99%; >99% ee
[column: Daicel Chiralpak IA, 5 μm, 250 mm×4.6 mm; mobile phase: tert-butyl methyl ether/acetonitrile/methanol 75:20:10 (v/v); flow rate: 1 ml/min; UV detection: 220 nm; temperature: 25° C.].

Example 387A

Enantiomer 2

Yield: 61 mg
$R_t$ 5.24 min; purity >99%; >97.5% ee
[column: Daicel Chiralpak IA, 5 μm, 250 mm×4.6 mm; mobile phase: tert-butyl methyl ether/acetonitrile/methanol 75:20:10 (v/v); flow rate: 1 ml/min; UV detection: 220 nm; temperature: 25° C.].

Example 388A and Example 389A tert-Butyl 1-(3-{[4,4,4-trifluoro-3-methyl-2-(4-{[6-oxo-3-(trifluoromethyl)pyridazin-1(6H)-yl]methyl}phenyl)butanoyl]amino}benzyl)cyclopropanecarboxylate (enantiomers 1 and 2)

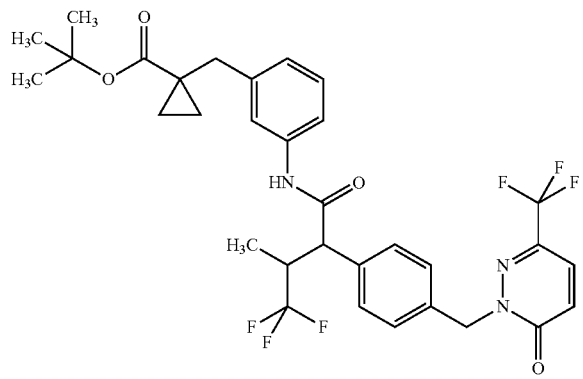 [SMILES: CC(C(C(=O)Nc1cccc(CC2(C(=O)OC(C)(C)C)CC2)c1)c1ccc(Cn2nc(C(F)(F)F)ccc2=O)cc1)C(F)(F)F]

150 mg (0.24 mmol) of the mixture of isomers of tert-butyl 1-(3-{[4,4,4-trifluoro-3-methyl-2-(4-{[6-oxo-3-(trifluoromethyl)pyridazin-1(6H)-yl]methyl}phenyl)butanoyl]amino}-benzyl)cyclopropanecarboxylate were separated further by preparative HPLC on a chiral phase [column: Daicel Chiralpak AD-H, 5 μm, 250 mm×20 mm; mobile phase: isohexane/ethanol 80:20 (v/v); flow rate: 15 ml/min; UV detection: 220 nm; temperature: 30° C.]. Only the enantiomers of the main diastereomer were isolated.

Example 388A

Enantiomer 1

Yield: 68 mg
$R_t$ 3.94 min; purity >95%; >99% ee
[column: Daicel Chiralpak AD-H, 5 μm, 250 mm×4.6 mm; mobile phase: isohexane/(ethanol+0.2% trifluoroacetic acid+1% water) 80:20 (v/v); flow rate: 1 ml/min; UV detection: 220 nm; temperature: 40° C.].

Example 389A

Enantiomer 2

Yield: 72 mg
$R_t$ 4.59 min; purity >96%; >98.8% ee
[column: Daicel Chiralpak AD-H, 5 μm, 250 mm×4.6 mm; mobile phase: isohexane/(ethanol+0.2% trifluoroacetic acid+1% water) 80:20 (v/v); flow rate: 1 ml/min; UV detection: 220 nm; temperature: 40° C.].

Example 390A tert-Butyl 3-{3-[(cyclopentyl{4-[(4-oxoquinazolin-3(4H)-yl)methyl]phenyl}acetyl)amino]-2-methylphenyl}propanoate

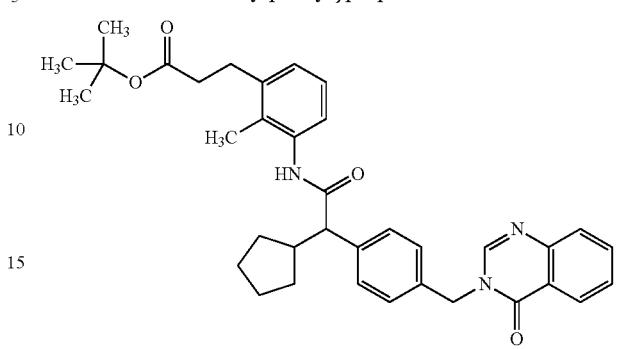

Preparation Method 8:
15 mg (0.39 mmol, content 60%) of sodium hydride were added to a solution of 34 mg (0.23 mmol) of quinazolin-4(3H)-one in 5 ml of DMF, and the mixture was stirred under an atmosphere of argon at 0° C. for 30 min. 100 mg (0.19 mmol) of tert-butyl 3-[3-({[4-(bromomethyl)phenyl](cyclopentyl)acetyl}amino)-2-methylphenyl]propanoate, dissolved in 1 ml of DMF, were then added to the reaction solution, and the latter was slowly warmed to room temperature. After the reaction had gone to completion (monitored by TLC; cyclohexane/ethyl acetate 2:1), 1 ml of saturated ammonium chloride solution was added and the reaction mixture was purified directly by preparative HPLC. This gave 28 mg (0.05 mmol, 25% of theory) of the racemic title compound.

LC-MS (method 10): $R_t$=2.51 min; m/z=580 (M+H)$^+$.
$^1$H-NMR (400 MHz, DMSO-d$_6$): δ=9.45 (s, 1H), 8.57 (s, 1H), 8.16 (d, 1H), 7.80-7.88 (m, 1H), 7.70 (d, 1H), 7.56 (t, 1H), 7.40 (d, 2H), 7.31 (d, 2H), 6.87-7.06 (m, 3H), 5.19 (s, 2H), 3.45 (d, 1H), 2.77 (t, 2H), 2.41 (t, 2H), 1.97 (s, 3H), 1.82 (dd, 1H), 1.29-1.72 (m, 14H), 0.79-1.03 (m, 1H).

Example 391A tert-Butyl 3-{3-[(cyclopentyl{4-[(4-methyl-1-oxophthalazin-2(1H)-yl)methyl]phenyl}acetyl)-amino]-2-methylphenyl}propanoate

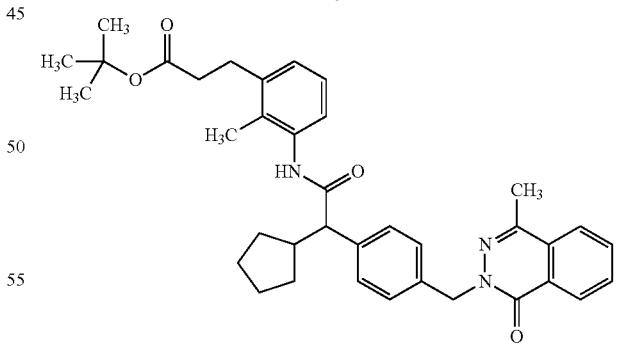

Preparation Method 9:
50 mg (0.097 mmol) of tert-butyl 3-[3-({[4-(bromomethyl)phenyl](cyclopentyl)acetyl}amino)-2-methylphenyl]propanoate, 19 mg (0.12 mmol) of 4-methylphthalazin-1(2H)-one and 47 mg (0.15 mmol) of cesium carbonate were stirred in 5 ml of DMF at 60° C. for 12 h. After cooling, the reaction mixture was purified directly by preparative HPLC. This gave 43 mg (0.07 mmol, 74% of theory) of the racemic title compound.

LC-MS (method 10): $R_t$=2.70 min; m/z=594 (M+H)$^+$.

The compounds listed in the table below were prepared in an analogous manner according to Preparation methods 8 and 9:

| Example | Name/Structure/Starting materials | Analytical data |
|---------|-----------------------------------|-----------------|
| 392A | tert-butyl 3-{3-[(cyclopentyl{4-[(1-oxoisoquinolin-2(1H)-yl)methyl]phenyl}acetyl)amino]-2-methylphenyl}propanoate 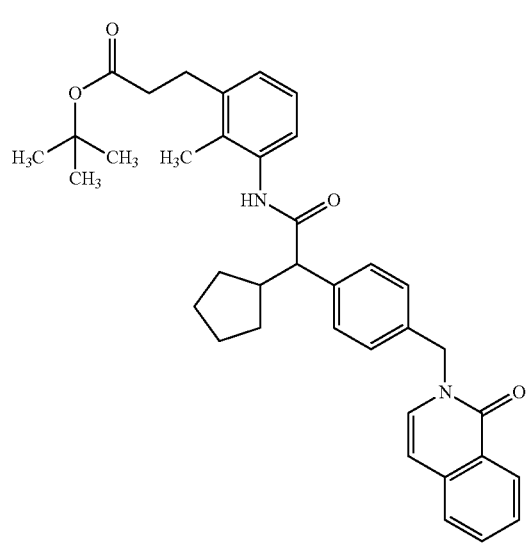 (from tert-butyl 3-[3-({[4-(bromomethyl)phenyl]-(cyclopentyl)acetyl}amino)-2-methylphenyl]propanoate and isoquinolin-1(2H)-one) | LC-MS (method 10): $R_t$ = 2.64 min; m/z = 579 (M + H)$^+$. |
| 393A | tert-butyl 3-{3-[(cyclopentyl{4-[(2-oxo-3,4-dihydroquinolin-1(2H)-yl)methyl]phenyl}acetyl)amino]-2-methylphenyl}propanoate 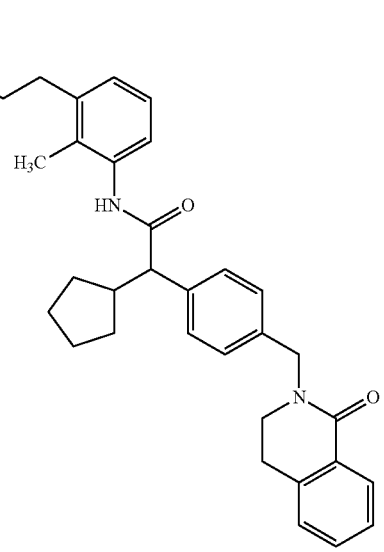 (from tert-butyl 3-[3-({[4-(bromomethyl)phenyl]-(cyclopentyl)acetyl}amino)-2-methylphenyl]propanoate and 3,4-dihydroquinolin-2(1H)-one) | LC-MS (method 7): $R_t$ = 3.02 min; m/z = 598 (M + NH$_4$)$^+$. |

| Example | Name/Structure/Starting materials | Analytical data |
|---|---|---|
| 394A | tert-butyl 3-{3-[(cyclopentyl{4-[(1-oxophthalazin-2(1H)-yl)methyl]phenyl}acetyl)amino]-2-methylphenyl}propanoate<br>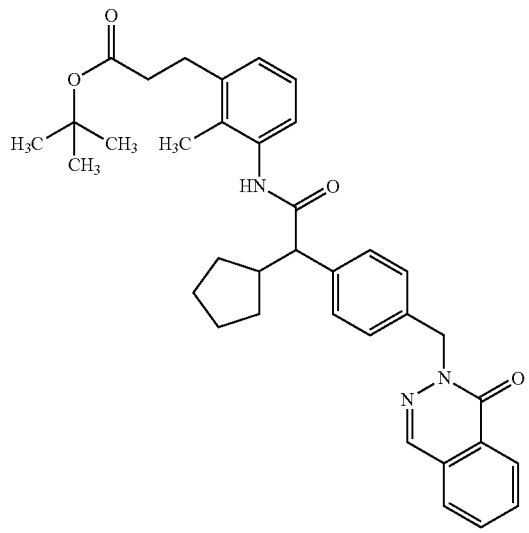<br>(from tert-butyl 3-[3-({[4-(bromomethyl)phenyl]-(cyclopentyl)acetyl}amino)-2-methylphenyl]propanoate and phthalazin-1(2H)-one) | LC-MS (method 10): $R_t$ = 2.63 min; m/z = 578 (M − H)⁻.<br>¹H-NMR (400 MHz, DMSO-d₆): δ = 9.45(s, 1H), 8.47(s, 1H), 8.29 (d, 1H), 7.93-8.01(m, 2H), 7.84-7.92(m, 1H), 7.38(d, 2H), 7.28(d, 2H), 6.92-7.05(m, 3H), 5.32(s, 2H), 3.45(d, 1H), 2.78(t, 2H), 2.34-2.42(m, 3H), 1.98(s, 3H), 1.77-1.88(m, 1H), 1.42-1.71(m, 4H), 1.30-1.40(m, 11H), 0.89-1.05(m, 1H). |
| 395A | tert-butyl 3-(3-{[{4-[(6-chloro-2-oxo-3,4-dihydroquinolin-1(2H)-yl)methyl]phenyl}(cyclopentyl)-acetyl]amino}-2-methylphenyl)propanoate<br>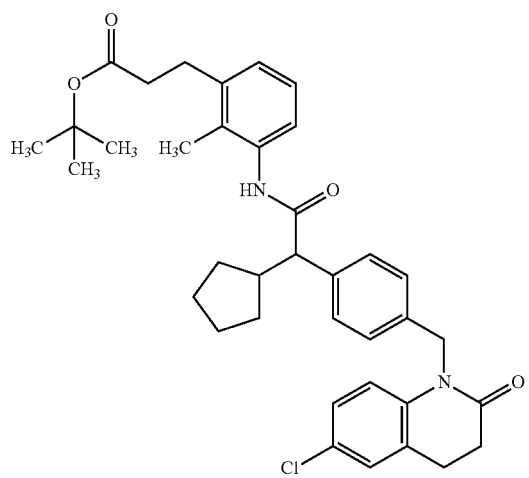<br>(from tert-butyl 3-[3-({[4-(bromomethyl)phenyl]-(cyclopentyl)acetyl}amino)-2-methylphenyl]propanoate and 6-chloro-3,4-dihydroquinolin-2(1H)-one) | LC-MS (method 11): $R_t$ = 1.64 min; m/z = 614 (M − H)⁻. |

| Example | Name/Structure/Starting materials | Analytical data |
|---|---|---|
| 396A | tert-butyl 3-(3-{[{4-[(3-chloro-6-oxopyridazin-1(6H)-yl)-methyl]phenyl}(cyclopentyl)acetyl]amino}-2-methylphenyl)propanoate<br>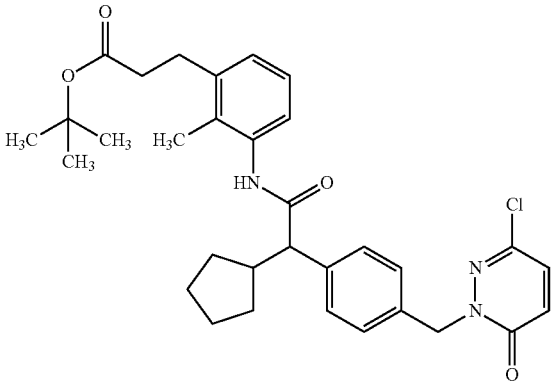<br>(from tert-butyl 3-[3-({[4-(bromomethyl)phenyl]-(cyclopentyl)acetyl}amino)-2-methylphenyl]propanoate and 6-chloropyridazin-3(2H)-one) | LC-MS (method 10): $R_t$ = 2.53 min; m/z = 562 (M − H)⁻.<br>¹H-NMR (400 MHz, DMSO-d₆): δ = 9.47(s, 1H), 7.57(d, 1H), 7.40 (d, 2H), 7.24(d, 2H), 7.09(d, 1H), 6.85-7.05 (m, 3H), 5.18(s, 2H), 3.46(d, 1H), 2.79(t, 2H), 2.41(t, 2H), 1.99 (s, 3H), 1.81-1.88(m, 1H), 1.61-1.74(m, 1H), 1.50-1.60(m, 2H), 1.46 (d, 1H), 1.33-1.42(m, 12H), 0.96(dd, 1H). |
| 397A | tert-butyl 3-{3-[(cyclopentyl{4-[(1,1-dioxido-3-oxo-1,2-benzisothiazol-2(3H)-yl)methyl]phenyl}acetyl)-amino]-2-methylphenyl}propanoate<br>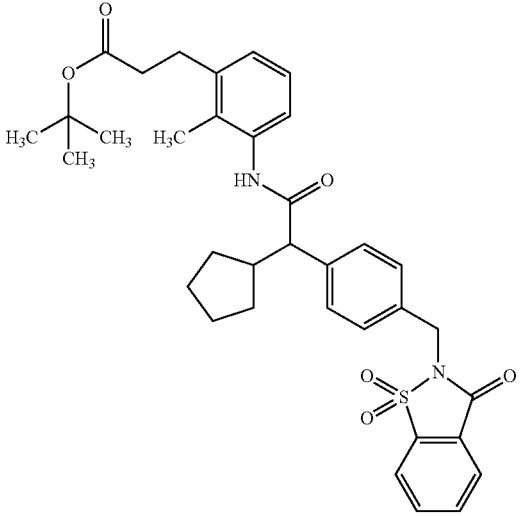<br>(from tert-butyl 3-[3-({[4-(bromomethyl)phenyl]-(cyclopentyl)acetyl}amino)-2-methylphenyl]propanoate and 1,2-benzisothiazol-3(2H)-one 1,1-dioxide) | LC-MS (method 10): $R_t$ = 2.65 min; m/z = 615 (M − H)⁻. |

| Example | Name/Structure/Starting materials | Analytical data |
|---------|-----------------------------------|-----------------|
| 398A | tert-butyl 3-{3-[(cyclopentyl{4-[(3-methyl-6-oxo-pyridazin-1(6H)-yl)methyl]phenyl}acetyl)amino]-2-methylphenyl}propanoate 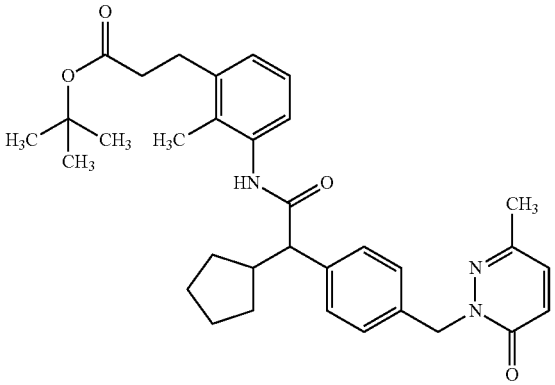 (from tert-butyl 3-[3-({[4-(bromomethyl)phenyl]-(cyclopentyl)acetyl}amino)-2-methylphenyl]propanoate and 6-methylpyridazin-3(2H)-one) | LC-MS (method 11): $R_t$ = 1.46 min; m/z = 542 (M − H)⁻. $^1$H-NMR (400 MHz, DMSO-$d_6$): δ = 9.46(s, 1H), 7.36(dd, 3H), 7.22 (d, 2H), 6.95-7.04(m, 3H), 6.91(d, 1H), 5.16 (s, 2H), 3.48-3.53(m, 1H), 3.45(d, 1H), 2.79 (t, 2H), 2.41(t, 2H), 2.26(s, 3H), 1.99(s, 3H), 1.83(dd, 1H), 1.62-1.71(m, 1H), 1.52-1.61(m, 2H), 1.41-1.50 (m, 1H), 1.36(m, 11H), 0.96(dd, 1H). |
| 399A | tert-butyl 3-{3-[(cyclopentyl{4-[(5-methyl-2-oxo-pyridin-1(2H)-yl)methyl]phenyl}acetyl)amino]-2-methylphenyl}propanoate 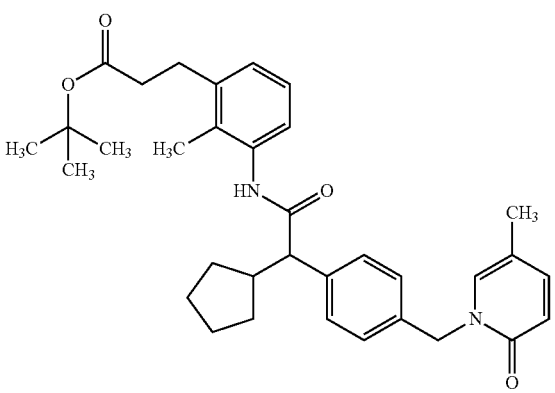 (from tert-butyl 3-[3-({[4-(bromomethyl)phenyl]-(cyclopentyl)acetyl}amino)-2-methylphenyl]propanoate and 5-methylpyridin-2(1H)-one) | LC-MS (method 15): $R_t$ = 1.27 min; m/z = 487 (M − $C_4H_8$ + H)⁺. $^1$H-NMR (400 MHz, DMSO-$d_6$): δ = 9.47(s, 1H), 7.56(s, 1H), 7.38 (d, 2H), 7.29(dd, 1H), 7.22(d, 2H), 6.94-7.05 (m, 3H), 6.37(d, 1H), 5.02(s, 2H), 3.45(d, 1H), 2.79(t, 2H), 2.56-2.65(m, 1H), 2.41(t, 2H), 2.00(s, 3H), 1.99 (s, 3H), 1.78-1.89(m, 1H), 1.62-1.74(m, 1H), 1.52-1.61(m, 2H), 1.42-1.52(m, 1H), 1.30-1.40 (m, 11H), 0.91-1.02(m, 1H). |

| Example | Name/Structure/Starting materials | Analytical data |
|---|---|---|
| 400A | tert-butyl 3-{3-[(cyclopentyl{4-[(3-oxo-1,2-benz-isoxazol-2(3H)-yl)methyl]phenyl}acetyl)amino]-2-methylphenyl}propanoate<br><br>(from tert-butyl 3-[3-({[4-(bromomethyl)phenyl]-(cyclopentyl)acetyl}amino)-2-methylphenyl]propanoate and 1,2-benzisoxazol-3(2H)-one [CAS Reg. No. 21725-69-9]) | LC-MS (method 11): $R_t$ = 1.54 min; m/z = 513 (M − $C_4H_8$ + H)$^+$. |
| 401A | tert-butyl 3-(3-{[cyclopentyl(4-{[6-oxo-3-(trifluoromethyl)pyridazin-1(6H)-yl]methyl}phenyl)acetyl]amino}-2-methylphenyl)propanoate<br><br>(from tert-butyl 3-[3-({[4-(bromomethyl)phenyl]-(cyclopentyl)acetyl}amino)-2-methylphenyl]propanoate and 6-(trifluoromethyl)pyridazin-3(2H)-one) | LC-MS (method 15): $R_t$ = 1.39 min; m/z = 542 (M − $C_4H_8$ + H)$^+$.<br>$^1$H-NMR (400 MHz, DMSO-$d_6$): δ = 9.45(s, 1H), 7.86(d, 1H), 7.41 (d, 2H), 7.26(d, 2H), 7.21(d, 1H), 6.93-7.05 (m, 3H), 5.75(s, 2H), 3.46(d, 1H), 2.78(t, 2H), 2.53-2.62(m, 1H), 2.41(t, 2H), 1.97(s, 3H), 1.79-1.89(m, 1H), 1.42-1.72(m, 4H), 1.33-1.39(m, 11H), 0.90-1.02(m, 1H). |

Example 402A tert-Butyl(+)-1-(3-{[(2S)-2-cyclopentyl-2-{4-[(5-oxo-2-phenyl-5,6-dihydro-4H-1,3,4-oxadiazin-4-yl)methyl]phenyl}acetyl]amino}benzyl)cyclopropanecarboxylate

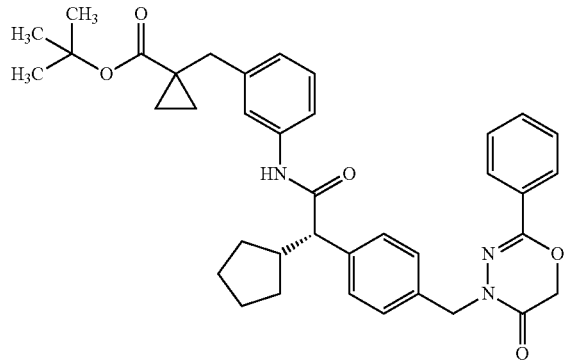

At 0° C., 873 µl (5.01 mmol) of DIEA and 595.0 mg (2.41 mmol) of tert-butyl 1-(3-aminobenzyl)cyclopropanecarboxylate were added to a solution of 786.8 mg (2.0 mmol) of (2S)-cyclopentyl{4-[(5-oxo-2-phenyl-5,6-dihydro-4H-1,3,4-oxadiazin-4-yl)methyl]phenyl}ethanoic acid and 325.1 mg (2.41 mmol) of 1-hydroxy-1H-benzotriazole hydrate in 4 ml of DMF. At 0° C., 838.5 mg (2.21 mmol) of HATU were added a little at a time to the resulting mixture. The reaction mixture was then slowly warmed to RT and stirred at RT for 3 h. The mixture was then added to water and extracted three times with ethyl acetate. The combined organic phases were dried over magnesium sulfate and concentrated under reduced pressure. The product was purified by chromatography on silica gel (mobile phase cyclohexane/ethyl acetate 4:1 to 3:1). This gave 827 mg (66.4% of theory) of the title compound.

LC-MS (method 10): $R_t$=2.92 min; m/z=566 (M–$C_4H_8$)$^+$.

$^1$H-NMR (400 MHz, DMSO-$d_6$): δ=9.95 (s, 1H), 7.77 (d, 2H), 7.54-7.36 (m, 6H), 7.37-7.26 (m, 3H), 7.14 (t, 1H), 6.88 (d, 1H), 4.90 (s, 2H), 4.84 (s, 2H), 3.38 (d, 1H), 2.76 (s, 2H), 2.65-2.56 (m, 1H), 1.85-1.71 (m, 1H), 1.70-1.30 (m, 5H), 1.34 (s, 9H), 1.05 (d, 2H), 1.03-0.91 (m, 1H), 0.91-0.81 (m, 1H), 0.79 (d, 2H).

$[α]_D^{20}$=+27.2°, c=0.455, chloroform.

Example 403A tert-Butyl(+)-1-(3-{[(2S)-2-cyclopentyl-2-{4-[(5-oxo-2-phenyl-5,6-dihydro-4H-1,3,4-oxadiazin-4-yl)methyl]phenyl}acetyl]amino}-2-methylbenzyl)cyclopropanecarboxylate

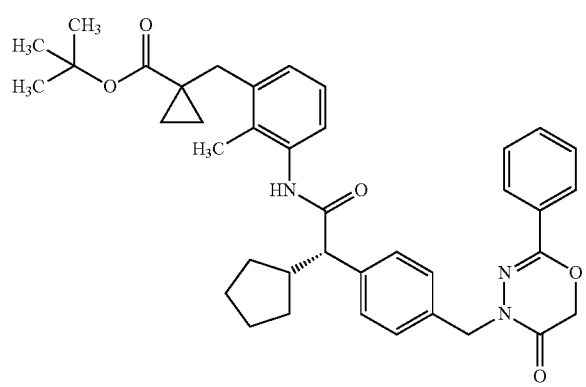 [SMILES: Cc1c(CC2(C(=O)OC(C)(C)C)CC2)cccc1NC(=O)[C@H](c1ccc(CN2N=C(c3ccccc3)OCC2=O)cc1)C1CCCC1]

At 0° C., 200 µl (1.15 mmol) of DIEA and 149.8 mg (0.57 mmol) of tert-butyl 1-(3-amino-2-methylbenzyl)cyclopropanecarboxylate were added to a solution of 150.0 mg (0.38 mmol) of (2S)-cyclopentyl{4-[(5-oxo-2-phenyl-5,6-dihydro-4H-1,3,4-oxadiazin-4-yl)methyl]phenyl}ethanoic acid and 62 mg (0.46 mmol) of 1-hydroxy-1H-benzotriazole hydrate in 500 µl of DMF. At 0° C., 174.4 mg (0.46 mmol) of HATU were added a little at a time to the resulting mixture. The reaction mixture was then slowly warmed to RT and stirred at RT for 3 h. The mixture was then added to water and extracted three times with ethyl acetate. The combined organic phases were dried over magnesium sulfate and concentrated under reduced pressure. The crude product was purified by preparative RP-HPLC (mobile phase: acetonitrile/water gradient). This gave 175 mg (72.0% of theory) of the title compound.

LC-MS (method 7): $R_t$=3.23 min; m/z=580 (M–$C_4H_8$)$^+$.

$^1$H-NMR (400 MHz, DMSO-$d_6$): δ=9.48 (s, 1H), 7.76 (d, 2H), 7.54-7.37 (m, 5H), 7.31 (d, 2H), 7.06-6.93 (m, 3H), 4.92 (s, 2H), 4.86 (s, 2H), 3.44 (d, 1H), 2.85 (s, 2H), 2.63-2.55 (m, 1H), 1.90 (s, 3H), 1.88-1.79 (m, 1H), 1.71-1.41 (m, 4H), 1.39 (s, 2H), 1.27 (s, 9H), 1.10 (d, 2H), 1.06-0.92 (m, 1H), 0.62 (q, 2H).

$[α]_D^{20}$=+15.6°, c=0.500, chloroform.

Example 404A tert-Butyl(+/−)-1-{3-[(Cyclopentyl{4-[(1-oxo-1,3-dihydro-2H-isoindol-2-yl)methyl]phenyl}-acetyl)amino]benzyl}cyclopropanecarboxylate

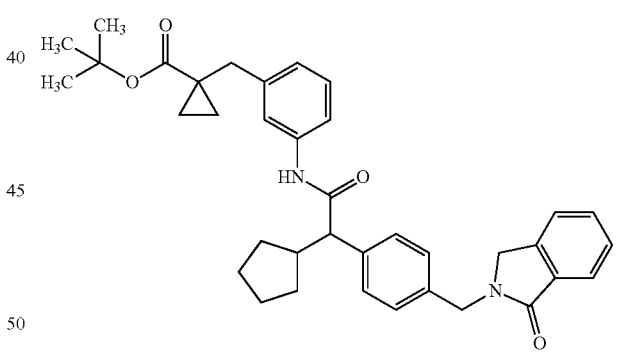

107.4 mg (0.31 mmol) of (+/−)-cyclopentyl{4-[(1-oxo-1,3-dihydro-2H-isoindol-2-yl)methyl]-phenyl}acetic acid were initially charged in 1 ml of DMF and 0.17 ml (2.15 mmol) of pyridine, 128.6 mg (0.34 mmol) of 1-[bis(dimethylamino)methylene]-5-chloro-3-oxy-1H-benzotriazol-1-ium tetrafluoroborate and 80 mg (0.31 mmol) of tert-butyl 1-(3-aminobenzyl)cyclopropanecarboxylate were added and the mixture was stirred at RT overnight. The reaction mixture was then diluted with a little acetonitrile and purified directly by preparative RP-HPLC (mobile phase: acetonitrile/water gradient). This gave 112 mg (50.4% of theory) of the title compound.

LC-MS (method 7): $R_t$=3.03 min; m/z=523 (M–$C_4H_8$+H)$^+$.

¹H-NMR (400 MHz, DMSO-d₆): δ=9.95 (s, 1H), 7.71 (d, 1H), 7.62-7.47 (m, 5H), 7.39 (d, 2H), 7.22 (d, 2H), 7.14 (t, 1H), 6.88 (d, 1H), 4.73-4.65 (s, 2H), 4.39-4.31 (s, 2H), 3.39 (d, 1H), 2.76 (s, 2H), 2.64-2.56 (m, 1H), 1.85-1.70 (m, 1H), 1.69-1.39 (m, 4H), 1.40-1.29 (m, 1H), 1.30-1.24 (m, 1H), 1.22 (s, 9H), 1.05 (q, 2H), 1.02-0.89 (m, 1H), 0.78 (q, 2H).

General Procedure 6: Coupling of a Carboxylic Acid with an Amine Under Hatu Activation At RT, 1.2 to 2.5 eq. of DIEA were added to a solution of 1 eq. of the carboxylic acid in question and 1.0 to 1.5 eq. of the amine in question in DMF (about 0.03 to 0.5 mol/l). The resulting mixture was cooled to 0° C., and about 1.2 eq. of HATU were added a little at a time. The reaction mixture was then slowly warmed to RT and stirred at RT for 1 h to 24 h. The target product could be obtained by preparative RP-HPLC (mobile phase: acetonitrile/water gradient) directly from the reaction mixture or after aqueous work-up and a further purification step. To this end, the reaction mixture was added to water and extracted three times with ethyl acetate. The combined organic phases were dried over magnesium sulfate and concentrated under reduced pressure. The crude product was purified by preparative RP-HPLC (mobile phase: acetonitrile/water gradient) or by chromatography on silica gel (mobile phase mixtures of cyclohexane/ethyl acetate or dichloromethane/methanol).

The following compounds were prepared according to General procedure 6:

| Example | Name/Structure | Analytical data |
|---|---|---|
| 405A | tert-butyl 1-(3-{[(2S)-2-cyclopentyl-2-{4-[(1-oxo-1,3-dihydro-2H-isoindol-2-yl)methyl]phenyl}acetyl]amino}-benzyl)cyclopropanecarboxylate | LC-MS (method 11): R$_t$ = 1.58 min; m/z = 523 (M - C$_4$H$_8$ + H)$^+$. ¹H-NMR (400 MHz, DMSO-d₆): δ = 9.95 (s, 1H), 7.72 (d, 1H), 7.62-7.44 (m, 4H), 7.39 (d, 2H), 7.35 (d, 1H), 7.22 (d, 2H), 7.14 (t, 1H), 6.88 (d, 1H), 4.69 (s, 2H), 4.35 (s, 2H), 3.40-3.35 (m, 1H), 2.76 (s, 2H), 2.63-2.55 (m, 1H), 1.81-1.71 (m, 1H), 1.68-1.41 (m, 4H), 1.40-1.31 (m, 1H), 1.30-1.24 (m, 1H), 1.22 (s, 9H), 1.05 (q, 2H), 1.01-0.90 (m, 1H), 0.79 (q, 2H). |
| 406A | tert-butyl 1-{3-[(cyclopentyl{4-[(3-oxo-1,3-dihydro-2H-indazol-2-yl)methyl]phenyl}acetyl)amino]benzyl}-cyclopropanecarboxylate | LC-MS (method 11): R$_t$ = 1.55 min; m/z = 524 (M - C$_4$H$_8$)$^+$. ¹H-NMR (400 MHz, CDCl₃): δ = 7.73 (d, 1H), 7.40-7.33 (m, 1H), 7.32-7.26 (m, 4H), 7.18 (dd, 3H), 7.11 (t, 1H), 7.05 (t, 1H), 6.93 (d, 1H), 5.29 (s, 2H), 5.24 (s, 2H), 3.08 (d, 1H), 2.84 (s, 2H), 2.65-2.54 (m, 1H), 2.04-1.93 (m, 1H), 1.64-1.34 (m, 7H), 1.30 (s, 9H), 1.18-1.14 (m, 2H), 0.71-0.66 (m, 2H). |

-continued

| Example | Name/Structure | Analytical data |
|---|---|---|
| 407A | tert-butyl 1-{3-[(cyclopentyl{4-[(5,6-difluoro-1-oxo-1,3-dihydro-2H-isoindol-2-yl)methyl]phenyl}acetyl)amino]-benzyl}cyclopropanecarboxylate | LC-MS (method 15): $R_t$ = 1.44 min; m/z = 559 $(M - C_4H_8)^+$. $^1$H-NMR (400 MHz, DMSO-$d_6$): δ = 9.94 (s, 1H), 7.75 (dd, 1H), 7.65 (dd, 1H), 7.49 (s, 1H), 7.39 (d, 2H), 7.35 (d, 1H), 7.22 (d, 2H), 7.14 (t, 1H), 6.88 (d, 1H), 4.68 (s, 2H), 4.32 (s, 2H), 3.37 (d, 1H), 2.77 (s, 1H), 2.64-2.54 (m, 2H), 1.83-1.72 (m, 1H), 1.68-1.31 (m, 4H), 1.23 (s, 9H), 1.07-1.02 (m, 1H), 1.01-0.90 (m, 1H), 0.82-0.75 (m, 1H). |
| 408A | tert-butyl 1-{3-[(cyclopentyl{4-[(4,7-difluoro-1-oxo-1,3-dihydro-2H-isoindol-2-yl)methyl]phenyl}acetyl)amino]-benzyl}cyclopropanecarboxylate | LC-MS (method 11): $R_t$ = 1.62 min; m/z = 559 $(M - C_4H_8)^+$. $^1$H-NMR (400 MHz, DMSO-$d_6$): δ = 9.95 (s, 1H), 7.51-7.44 (m, 2H), 7.40 (d, 2H), 7.36-7.31 (m, 2H), 7.25 (d, 2H), 7.14 (t, 1H), 6.88 (d, 1H), 4.65 (s, 2H), 4.46 (s, 2H), 3.38 (d, 1H), 2.76 (s, 2H), 2.63-2.56 (m, 1H), 1.82-1.73 (m, 1H), 1.67-1.28 (m, 7H), 1.22 (s, 9H), 1.07-1.03 (m, 2H), 0.81-0.77 (m, 2H). |
| 409A | tert-butyl 1-(3-{[cyclopentyl(4-{[2-oxo-5-(trifluoromethyl)pyridin-1(2H)-yl]methyl}phenyl)acetyl]amino}benzyl)-cyclopropanecarboxylate | LC-MS (method 15): $R_t$ = 1.41 min; m/z = 553 $(M - C_4H_8)^+$. $^1$H-NMR (400 MHz, DMSO-$d_6$): δ = 9.94 (s, 1H), 8.54 (br. s, 1H), 7.66 (s, 1H), 7.49 (s, 1H), 7.38 (d, 2H), 7.33 (d, 1H), 7.27 (d, 2H), 7.14 (t, 1H), 6.89 (d, 1H), 6.56 (d, 1H), 5.76 (s, 1H), 5.12 (s, 2H), 3.35 (d, 1H), 2.76 (s, 2H), 2.37 (s, 1H), 2.35-2.31 (m, 1H), 1.78 (br. s, 1H), 1.68-1.40 (m, 4H), 1.40-1.28 (m, 1H), 1.23 (s, 9H), 1.05 (br. s, 2H), 0.80 (br. s, 2H). |

-continued

| Example | Name/Structure | Analytical data |
|---|---|---|
| 410A | tert-butyl (+)-1-(3-{[(2S)-2-{4-[(5-chloro-2-oxopyridin-1(2H)-yl)methyl]phenyl}-2-cyclopentylacetyl]amino}benzyl)-cyclopropanecarboxylate | LC-MS (method 12): $R_t$ = 2.72 min; m/z = 519 $(M - C_4H_8)^+$. $^1$H-NMR (400 MHz, DMSO-$d_6$): δ = 9.94 (s, 1H), 8.09 (d, 1H), 7.51-7.44 (m, 2H), 7.37 (d, 2H), 7.34 (d, 1H), 7.25 (d, 2H), 7.14 (t, 1H), 6.88 (d, 1H), 6.44 (d, 1H), 5.02 (s, 2H), 3.37 (d, 1H), 2.77 (s, 1H), 1.82-1.72 (m, 1H), 1.69-1.27 (m, 8H), 1.24 (s, 9H), 1.07-1.02 (m, 2H), 0.99-0.91 (m, 1H), 0.82-0.78 (m, 2H). $[α]_D^{20}$ = +40.9°, c = 0.455, chloroform. |
| 411A | tert-butyl (+)-3-(3-{[(2S)-2-{4-[(5-chloro-2-oxopyridin-1(2H)-yl)methyl]phenyl}-2-cyclopentylacetyl]amino}phenyl)propanoate | LC-MS (method 15): $R_t$ = 1.31 min; m/z = 549 $(M + H)^+$. $^1$H-NMR (400 MHz, DMSO-$d_6$): δ = 9.96 (s, 1H), 8.09 (d, 1H), 7.47 (dd, 1H), 7.45 (s, 1H), 7.37 (d, 2H), 7.34 (d, 1H), 7.25 (d, 2H), 7.15 (t, 1H), 6.86 (d, 1H), 6.44 (d, 1H), 5.03 (s, 2H), 3.36 (d, 1H), 2.74 (t, 2H), 2.63-2.55 (m, 1H), 2.48-2.42 (m, 2H), 1.81-1.32 (m, 6H), 1.31 (s, 9H), 1.27-1.20 (m, 1H), 1.02-0.90 (m, 1H). $[α]_D^{20}$ = +44.4°, c = 0.490, chloroform. |
| 412A | tert-butyl (+)-3-(3-{[2S,3R)-4,4,4-trifluoro-3-methyl-2-(4-{[2-oxo-5-(trifluoromethyl)pyridin-1(2H)-yl]methyl}-phenyl)butanoyl]amino}phenyl)propanoate | LC-MS (method 11): $R_t$ = 1.51 min; m/z = 555 $(M - C_4H_8)^+$. $^1$H-NMR (400 MHz, CDCl$_3$): δ = 7.66 (br. s, 1H), 7.45 (dd, 1H), 7.39 (d, 2H), 7.35-7.28 (m, 3H), 7.24-7.16 (m, 2H), 7.11 (s, 1H), 6.94 (d, 1H), 6.67 (d, 1H), 5.14 (s, 2H), 3.57 (d, 1H), 3.45-3.30 (m, 1H), 2.85 (t, 2H), 2.50 (t, 2H), 1.40 (s, 9H), 0.90 (d, 3H). $[α]_D^{20}$ = +17.9°, c = 0.360, chloroform. |

| Example | Name/Structure | Analytical data |
|---|---|---|
| 413A | tert-butyl (-)-3-(3-{[2R,3S]-4,4,4-trifluoro-3-methyl-2-(4-{[2-oxo-5-(trifluoromethyl)pyridin-1(2H)-yl]methyl}-phenyl)butanoyl]amino}phenyl)propanoate 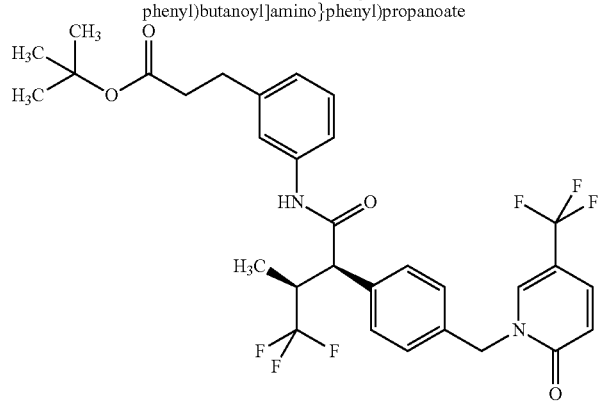 | LC-MS (method 11): $R_t$ = 1.51 min; m/z = 555 (M - $C_4H_8$)$^+$. $^1$H-NMR (400 MHz, CDCl$_3$): δ = 7.66 ( br. s, 1H), 7.45 (dd, 1H), 7.39 (d, 2H), 7.34-7.29 (m, 3H), 7.24-7.16 (m, 2H), 7.10 (s, 1H), 6.94 (d, 1H), 6.68 (d, 1H), 5.14 (s, 2H), 3.57 (d, 1H), 3.44-3.32 (m, 1H), 2.85 (t, 2H), 2.56-2.45 (m, 2H), 1.40 (s, 9H), 0.90 (d, 3H). [α]$_D^{20}$ = -74°, c = 0.220, chloroform. |
| 414A | tert-butyl (+)-1-(3-{[(2S)-2-cyclopentyl-2-(4-{[2-oxo-5-(trifluoromethyl)pyridin-1(2H)-yl]methyl}-phenyl)acetyl]-amino}benzyl)cyclopropanecarboxylate 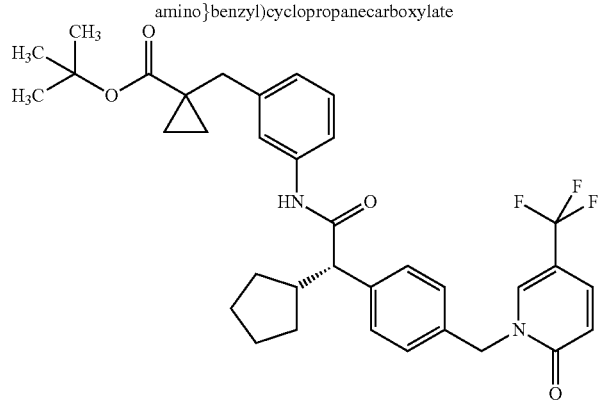 | LC-MS (method 15): $R_t$ = 1.40 min; m/z = 553 (M - $C_4H_8$)$^+$. $^1$H-NMR (400 MHz, DMSO-d$_6$): δ = 9.94 (s, 1H), 8.54 (s, 1H), 7.67 (dd, 1H), 7.49 (s, 1H), 7.38 (d, 2H), 7.33 (d, 1H), 7.26 (d, 2H), 7.14 (t, 1H), 6.88 (d, 1H), 6.55 (d, 1H), 5.12 (s, 2H), 3.37 (d, 1H), 2.76 (d, 2H), 2.63-2.55 (m, 1H), 1.82-1.71 (m, 1H), 1.68-1.29 (m, 6H), 1.23 (s, 9H), 1.08-1.03 (m, 2H), 1.00-0.89 (m, 1H), 0.83-0.75 (m, 2H). [α]$_D^{20}$ = +22.1°, c = 0.505, chloroform. |
| 415A | tert-butyl (+)-3-(3-{[(2S)-2-cyclopentyl-2-(4-{[2-oxo-5-(trifluoromethyl)pyridin-1(2H)-yl]methyl}phenyl)acetyl]-amino}phenyl)propanoate 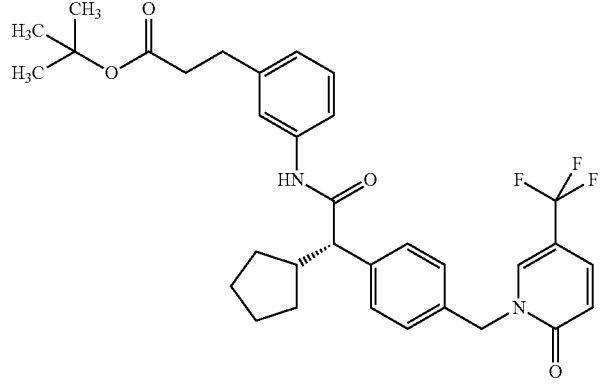 [SMILES: CC(C)(C)OC(=O)CCc1cccc(NC(=O)[C@H](c2ccc(Cn3cc(C(F)(F)F)ccc3=O)cc2)C2CCCC2)c1] | LC-MS (method 15): $R_t$ = 1.35 min; m/z = 527 (M - $C_4H_8$)$^+$. $^1$H-NMR (400 MHz, DMSO-d$_6$): δ = 9.97 (s, 1H), 8.54 (s, 1H), 7.67 (dd, 1H), 7.45 (s, 1H), 7.38 (d, 2H), 7.34 (d, 1H), 7.26 (d, 2H), 7.15 (t, 1H), 6.86 (d, 1H), 6.55 (d, 1H), 5.12 (s, 2H), 3.36 (d, 1H), 2.78-2.70 (m, 2H), 2.64-2.55 (m, 1H), 2.48-2.40 (m, 2H), 1.81-1.71 (m, 1H), 1.69-1.32 (m, 5H), 1.30 (s, 9H), 1.24 (dd, 1H), 0.88-0.99 (m, 1H). [α]$_D^{20}$ = +28.9°, c = 0.525, chloroform. |

Example 416A tert-Butyl(+/−)-1-{3-[(4,4,4-trifluoro-3-methyl-2-{4-[(1-oxo-1,3-dihydro-2H-isoindol-2-yl)-methyl]phenyl}butanoyl)amino]benzyl}cyclocarboxylate

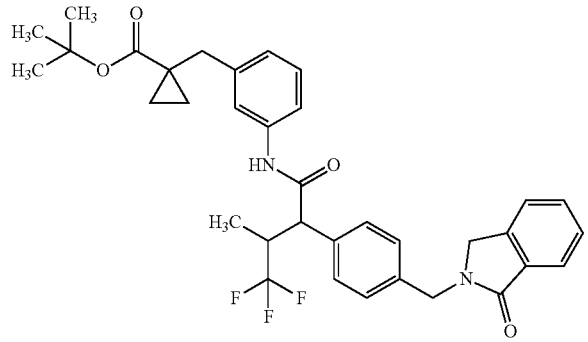 [SMILES: CC(C(C(=O)Nc1cccc(CC2(C(=O)OC(C)(C)C)CC2)c1)c1ccc(CN2Cc3ccccc3C2=O)cc1)C(F)(F)F]

202.5 mg (0.82 mmol) of tert-butyl 1-(3-aminobenzyl)cyclopropanecarboxylate were added to a solution of 206 mg (0.55 mmol) of 4,4,4-trifluoro-3-methyl-2-{4-[(1-oxo-1,3-dihydro-2H-isoindol-2-yl)methyl]phenyl}butanoic acid, 100.3 mg (0.66 mmol) of 1-hydroxy-1H-benzotriazole hydrate and 285 μl (1.64 mmol) of DIEA in 1 ml of DMF. At 0° C., a little at a time, 249.1 mg (0.66 mmol) of HATU were added to the resulting mixture. The reaction mixture was then slowly warmed to RT and stirred at RT for 2 h. The mixture was added to water and extracted three times with ethyl acetate. The combined organic phases were dried over magnesium sulfate and concentrated under reduced pressure. The crude product was purified by chromatography on silica gel (mobile phase cyclohexane/ethyl acetate 3:1). This gave 287 mg (87% of theory) of the title compound.

LC-MS (method 12): $R_t$=2.72 min; m/z=551 (M−C$_4$H$_8$)$^+$.

The mixture of isomers obtained above (mainly the racemate of a main diastereomer) was separated into the enantiomers by preparative HPLC on a chiral phase [column: Daicel Chiralpak AD-H, 5 μm, 250 mm×20 mm; flow rate: 18 ml/min; UV detection: 230 nm; injection volume: 0.5 ml; temperature: RT; mobile phase: 60% isohexane/40% ethanol]. Starting with 250 mg of the mixture of isomers, 115 mg of enantiomer 1 and 99 mg of enantiomer 2 were isolated (see Examples 417A and 418A).

Example 417A tert-Butyl(+)-1-{3-[(4,4,4-trifluoro-3-methyl-2-{4-[(1-oxo-1,3-dihydro-2H-isoindol-2-yl)methyl]phenyl}butanoyl)amino]benzyl}cyclocarboxylate (enantiomer 1)

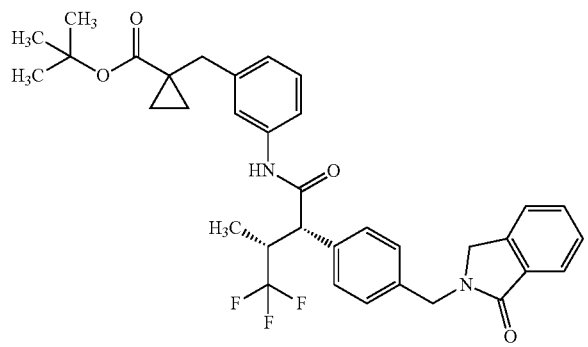 [SMILES: C[C@H]([C@H](C(=O)Nc1cccc(CC2(C(=O)OC(C)(C)C)CC2)c1)c1ccc(CN2Cc3ccccc3C2=O)cc1)C(F)(F)F]

LC-MS (method 7): $R_t$=2.94 min; m/z=551 (M−C$_4$H$_8$)$^+$.
$^1$H-NMR (500 MHz, DMSO-d$_6$): δ=10.11 (s, 1H), 7.71 (d, 1H), 7.60-7.44 (m, 4H), 7.40 (d, 2H), 7.31 (d, 1H), 7.26 (d, 2H), 7.14 (t, 1H), 6.89 (d, 1H), 4.71 (s, 2H), 4.35 (s, 2H), 3.81 (d, 1H), 2.76 (s, 2H), 1.20 (s, 10H), 1.09 (s, 1H), 1.04 (br. s, 3H), 0.90-0.82 (m, 1H), 0.78 (br. s, 2H).
[α]$_D^{20}$=+61°, c=0.265, chloroform.

Example 418A tert-Butyl(−)-1-{3-[(4,4,4-trifluoro-3-methyl-2-{4-[(1-oxo-1,3-dihydro-2H-isoindol-2-yl)-methyl]phenyl}butanoyl)amino]benzyl}cyclocarboxylate (enantiomer 2)

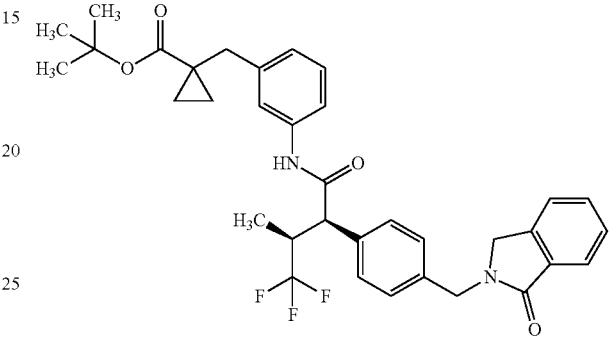

LC-MS (method 7): $R_t$=2.95 min; m/z=551 (M−C$_4$H$_8$)$^+$.
$^1$H-NMR (500 MHz, DMSO-d$_6$): δ=10.11 (s, 1H), 7.71 (d, 1H), 7.57 (d, 1H), 7.54-7.44 (m, 3H), 7.40 (d, 2H), 7.31 (d, 1H), 7.26 (d, 2H), 7.14 (t, 1H), 6.89 (d, 1H), 4.71 (s, 2H), 4.35 (s, 2H), 3.81 (d, 1H), 2.76 (s, 2H), 1.47-1.40 (m, 1H), 1.34-1.26 (m, 1H), 1.20 (s, 9H), 1.09 (s, 2H), 1.04 (br. s, 3H), 0.90-0.82 (m, 1H).
[α]$_D^{20}$=−61°, c=0.285, chloroform.

Example 419A tert-Butyl(+/−)-1-{3-[(cyclopentyl{4-[(4-fluoro-1-oxo-1,3-dihydro-2H-isoindol-2-yl)-methyl]phenyl}acetyl)amino]benzyl}cyclopropanecarboxylate

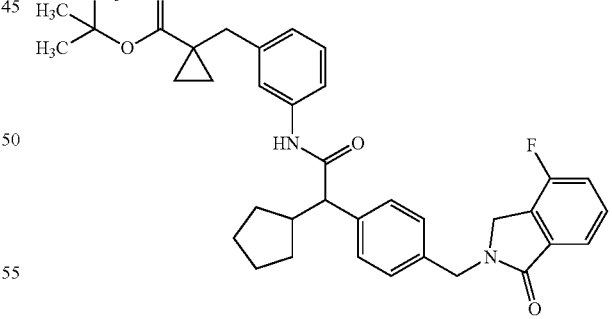

77.5 mg (0.31 mmol) of tert-butyl 1-(3-aminobenzyl)cyclopropanecarboxylate were added to a solution of 96 mg (0.26 mmol) of cyclopentyl{4-[(4-fluoro-1-oxo-1,3-dihydro-2H-isoindol-2-yl)methyl]phenyl}acetic acid in 1 ml of DMF. At 0° C., 136 μl (0.78 mmol) of DIEA and then, a little at a time, 119.2 mg (0.31 mmol) of HATU were added to the resulting mixture. The reaction mixture was then slowly warmed to RT and stirred at RT for 1 h. The reaction mixture was added to water and extracted three times with ethyl acetate. The combined organic phases were dried over magnesium sulfate and concentrated under reduced pressure. This gave 146 mg (93% of theory) of the title compound.

LC-MS (method 15): $R_t$=1.44 min; m/z=541 (M–$C_4H_8$)⁺.

¹H-NMR (400 MHz, DMSO-$d_6$): δ=9.95 (s, 1H), 7.62-7.53 (m, 2H), 7.50 (s, 1H), 7.47-7.42 (m, 1H), 7.39 (d, 2H), 7.34 (d, 1H), 7.24 (d, 2H), 7.14 (t, 1H), 6.88 (d, 1H), 4.69 (s, 2H), 4.46 (s, 2H), 3.37 (d, 1H), 2.76 (s, 2H), 1.82-1.72 (m, 1H), 1.68-1.24 (m, 7H), 1.22 (s, 9H), 1.09 (s, 1H), 1.07-1.02 (m, 2H), 0.81-0.76 (m, 2H).

The racemate obtained above was separated into the enantiomers by preparative HPLC on a chiral phase [column: Daicel Chiralpak AD-H, 5 µm, 250 mm×20 mm; flow rate: 15 ml/min; UV detection: 230 nm; injection volume: 0.5 ml; temperature: 30° C.; mobile phase: 65% isohexane/35% ethanol]. Starting with 109 mg of racemate, 53 mg of enantiomer 1 and 35 mg of enantiomer 2 were isolated (see Examples 420A and 421A).

Example 420A tert-Butyl(+)-1-{3-[(cyclopentyl{4-[(4-fluoro-1-oxo-1,3-dihydro-2H-isoindol-2-yl)methyl]-phenyl}acetyl)amino]benzyl}cyclopropanecarboxylate (enantiomer 1)

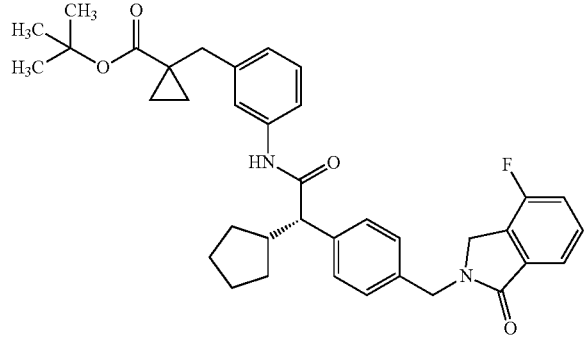

LC-MS (method 12): $R_t$=2.84 min; m/z=541 (M–$C_4H_8$)⁺.

¹H-NMR (400 MHz, CDCl₃): δ=7.68 (d, 1H), 7.50-7.42 (m, 1H), 7.38 (d, 2H), 7.32 (br. s, 2H), 7.27 (br. s, 2H), 7.17 (q, 2H), 7.09 (s, 1H), 6.96 (d, 1H), 4.77 (s, 2H), 4.31 (s, 2H), 3.11 (d, 1H), 2.87 (s, 2H), 2.66 (d, 1H), 2.02 (dd, 1H), 1.69-1.61 (m, 2H), 1.48 (td, 2H), 1.31 (s, 9H), 1.21-1.16 (m, 2H), 1.03 (d, 1H), 0.76-0.68 (m, 2H).

$[\alpha]_D^{20}$=+33°, c=0.205, chloroform.

Example 421A tert-Butyl(−)-1-{3-[(cyclopentyl{4-[(4-fluoro-1-oxo-1,3-dihydro-2H-isoindol-2-yl)methyl]-phenyl}acetyl)amino]benzyl}cyclopropanecarboxylate (enantiomer 2)

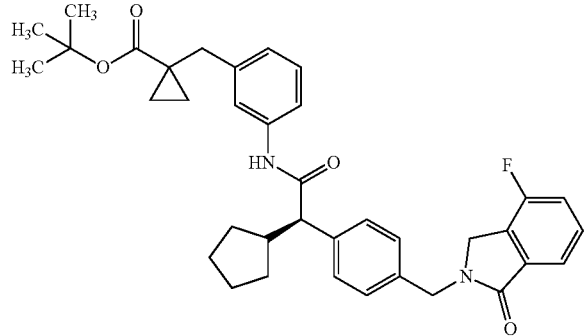 [SMILES: CC(C)(C)OC(=O)C1(Cc2cccc(NC(=O)[C@@H](c3ccc(CN4Cc5c(F)cccc5C4=O)cc3)C3CCCC3)c2)CC1]

LC-MS (method 12): $R_t$=2.84 min; m/z=541 (M–$C_4H_8$)⁺.

¹H-NMR (400 MHz, CDCl₃): δ=7.68 (d, 1H), 7.45 (td, 1H), 7.38 (d, 2H), 7.32 (br. s, 2H), 7.27 (br. s, 2H), 7.17 (q, 2H), 7.08 (s, 1H), 6.96 (d, 1H), 4.77 (s, 2H), 4.31 (s, 2H), 3.11 (d, 1H), 2.87 (s, 2H), 2.72-2.59 (m, 1H), 2.07-1.94 (m, 1H), 1.71-1.57 (m, 3H), 1.48 (td, 2H), 1.32 (s, 9H), 1.21-1.16 (m, 2H), 1.07-0.82 (m, 1H), 0.74-0.68 (m, 1H).

$[\alpha]_D^{20}$=−37°, c=0.270, chloroform.

Example 422A tert-Butyl 1-(3-{[4,4,4-trifluoro-2-{4-[(4-fluoro-1-oxo-1,3-dihydro-2H-isoindol-2-yl)methyl]phenyl}-3-methylbutanoyl]amino}benzyl)cyclopropanecarboxylate

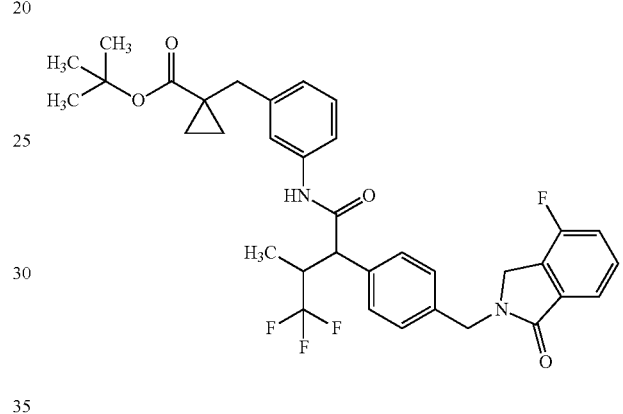

110.8 mg (0.41 mmol) of tert-butyl 1-(3-aminobenzyl)cyclopropanecarboxylate were added to a solution of 129.0 mg (0.33 mmol) of 4,4,4-trifluoro-2-{4-[(4-fluoro-1-oxo-1,3-dihydro-2H-isoindol-2-yl)methyl]phenyl}-3-methylbutanoic acid and 52.9 mg (0.39 mmol) of 1-hydroxy-1H-benzotriazole hydrate in 1 ml of DMF. At 0° C., 142 µl (0.82 mmol) of DIEA and then, a little at a time, 136.5 mg (0.36 mmol) of HATU were added to the resulting mixture. The reaction mixture was then slowly warmed to RT and stirred at RT for 2.5 h. The mixture was added to water and extracted three times with ethyl acetate. The combined organic phases were dried over magnesium sulfate and concentrated under reduced pressure. The crude product was purified by preparative RP-HPLC (mobile phase: acetonitrile/water gradient). This gave 97.4 mg (47.6% of theory) of the title compound.

LC-MS (method 15): $R_t$=1.39 min; m/z=623 (M–H)⁻.

The mixture of isomers obtained above (mainly the racemate of a main diastereomer) was separated into the enantiomers by preparative HPLC on a chiral phase [column: Daicel Chiralpak AD-H, 5 µm, 250 mm×20 mm; flow rate: 15 ml/min; UV detection: 220 nm; injection volume: 0.5 ml; temperature: 30° C.; mobile phase: 75% isohexane/25% isopropanol]. Starting with 94 mg of the mixture of isomers, 31 mg of enantiomer 1 and 32 mg of enantiomer 2 were isolated (see Examples 423A and 424A).

Example 423A tert-Butyl(+)-1-(3-{[(2S,3R)-4,4,4-trifluoro-2-{4-[(4-fluoro-1-oxo-1,3-dihydro-2H-isoindol-2-yl)methyl]phenyl}-3-methylbutanoyl]amino}benzyl)cyclopropanecarboxylate (enantiomer 1)

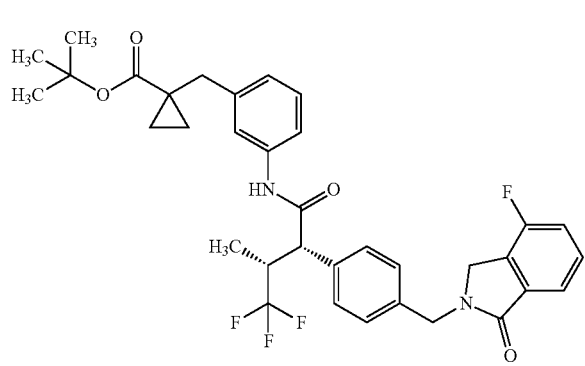 [SMILES: C[C@H]([C@H](C(=O)Nc1cccc(CC2(C(=O)OC(C)(C)C)CC2)c1)c1ccc(CN2Cc3c(F)cccc3C2=O)cc1)C(F)(F)F]

LC-MS (method 15): $R_t$=1.38 min; m/z=623 (M−H)⁻.

¹H-NMR (400 MHz, CDCl₃): δ=7.69 (d, 1H), 7.46 (td, 1H), 7.39-7.33 (m, 2H), 7.30 (d, 4H), 7.23-7.11 (m, 3H), 6.98 (d, 1H), 4.79 (s, 2H), 4.33 (s, 2H), 3.57 (d, 1H), 3.44-3.34 (m, 1H), 2.87 (s, 2H), 1.31 (s, 9H), 1.22-1.16 (m, 2H), 0.92-0.87 (m, 3H), 0.71 (d, 2H).

$[\alpha]_D^{20}$=+34°, c=0.230, chloroform.

Example 424A tert-Butyl(−)-1-(3-{[(2R,3S)-4,4,4-trifluoro-2-{4-[(4-fluoro-1-oxo-1,3-dihydro-2H-isoindol-2-yl)methyl]phenyl}-3-methylbutanoyl]amino}benzyl)cyclopropanecarboxylate (enantiomer 2)

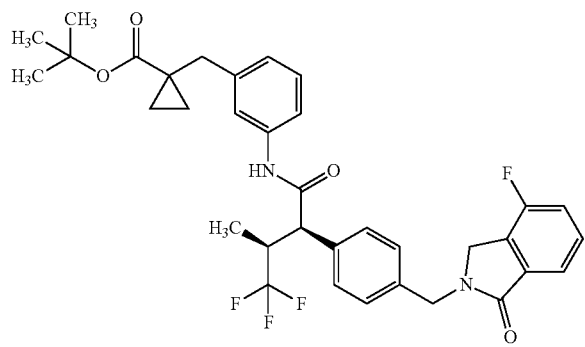 [SMILES: C[C@@H]([C@@H](C(=O)Nc1cccc(CC2(C(=O)OC(C)(C)C)CC2)c1)c1ccc(CN2Cc3c(F)cccc3C2=O)cc1)C(F)(F)F]

LC-MS (method 15): $R_t$=1.38 min; m/z=623 (M−H)⁻.

¹H-NMR (400 MHz, CDCl₃): δ=7.69 (d, 1H), 7.46 (td, 1H), 7.40-7.34 (m, 2H), 7.30 (d, 4H), 7.23-7.08 (m, 3H), 6.98 (d, 1H), 4.79 (s, 2H), 4.33 (s, 2H), 3.57 (d, 1H), 3.45-3.33 (m, 1H), 2.87 (s, 2H), 1.31 (s, 9H), 1.19 (d, 2H), 0.89 (d, 3H), 0.71 (d, 2H).

$[\alpha]_D^{20}$=−85°, c=0.235, chloroform.

Example 425A tert-Butyl(+)-3-(3-{[(2S)-2-cyclopentyl-2-{4-[(5-oxo-2-phenyl-5,6-dihydro-4H-1,3,4-oxadiazin-4-yl)methyl]phenyl}acetyl]amino}-4-fluorophenyl)propanoate

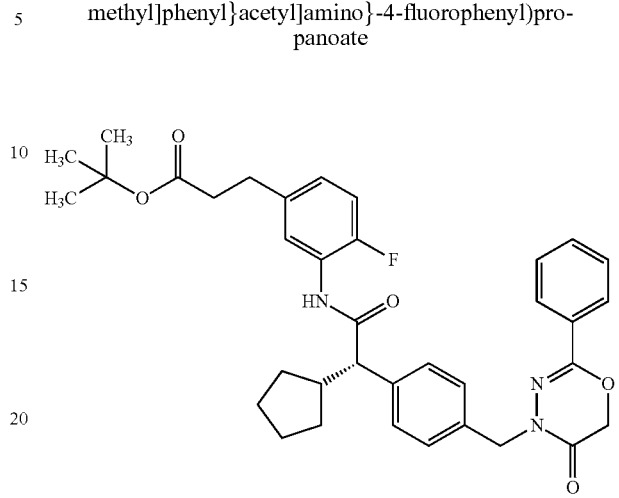

109.75 mg (0.46 mmol) of tert-butyl 3-(3-amino-4-fluorophenyl)propanoate were added to a solution of 150.0 mg (0.38 mmol) of (2S)-cyclopentyl{4-[(5-oxo-2-phenyl-5,6-dihydro-4H-1,3,4-oxadiazin-4-yl)methyl]phenyl}ethanoic acid and 70.2 mg (0.46 mmol) of 1-hydroxy-1H-benzotriazole hydrate in 1 ml of DMF. At 0° C., 200 µl (1.15 mmol) of DIEA and then, a little at a time, 174.4 mg (0.46 mmol) of HATU were added to the resulting mixture. The reaction mixture was then slowly warmed to RT and subsequently stirred at 60° C. for 4 h. The mixture was added to water and extracted three times with ethyl acetate. The combined organic phases were dried over magnesium sulfate and concentrated under reduced pressure. The crude product was purified by preparative RP-HPLC (mobile phase: acetonitrile/water gradient). This gave 104 mg (44.3% of theory) of the title compound.

LC-MS (method 11): $R_t$=1.68 min; m/z=612 (M−H)⁻.

¹H-NMR (400 MHz, DMSO-d₆): δ=9.77 (s, 1H), 7.76 (d, 2H), 7.65 (dd, 1H), 7.52-7.43 (m, 3H), 7.40 (d, 2H), 7.31 (d, 2H), 7.09 (dd, 1H), 6.98-6.90 (m, 1H), 4.94 (d, 1H), 4.90 (s, 2H), 4.85 (s, 2H), 3.60 (d, 1H), 2.72 (t, 2H), 2.43 (t, 2H), 1.82-1.31 (m, 7H), 1.29 (s, 9H), 1.01-0.92 (m, 1H).

$[\alpha]_D^{20}$=+61°, c=0.480, chloroform.

Example 426A tert-Butyl 3-{3-[(4,4,4-trifluoro-2-{4-[(4-fluoro-1-oxo-1,3-dihydro-2H-isoindol-2-yl)methyl]phenyl}-3-methylbutanoyl)amino]phenyl}propanoate

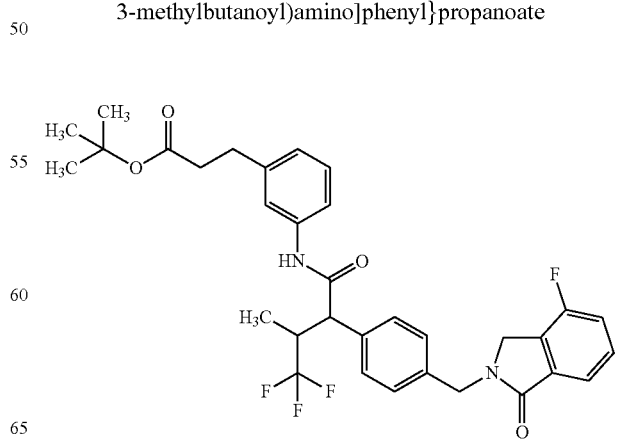

215.3 mg (0.89 mmol) of tert-butyl 3-(3-aminophenyl)propanoate were added to a solution of 280.0 mg (0.71 mmol) of 4,4,4-trifluoro-2-{4-[(4-fluoro-1-oxo-1,3-dihydro-2H-isoindol-2-yl)methyl]phenyl}-3-methylbutanoic acid and 114.8 mg (0.85 mmol) of 1-hydroxy-1H-benzotriazole hydrate in 1.4 ml of DMF. At 0° C., 308 µl (1.77 mmol) of DIEA and then, a little at a time, 296.2 mg (0.78 mmol) of HATU were added to the resulting mixture. The reaction mixture was then slowly warmed to RT and subsequently stirred at RT for 2.5 h. The mixture was added to water and extracted three times with ethyl acetate. The combined organic phases were dried over magnesium sulfate and concentrated under reduced pressure. The crude product was purified by preparative RP-HPLC (mobile phase: acetonitrile/water gradient). This gave 333 mg (78.6% of theory) of the title compound.

LC-MS (method 15): $R_t$=1.33 min; m/z=597 (M−H)⁻.

¹H-NMR (400 MHz, DMSO-$d_6$): δ=10.15 (s, 1H), 7.61-7.53 (m, 2H), 7.46-7.37 (m, 4H), 7.33 (d, 1H), 7.29 (d, 2H), 7.16 (t, 1H), 6.87 (d, 1H), 4.71 (s, 2H), 4.47 (s, 2H), 3.81 (d, 1H), 2.73 (t, 2H), 2.44 (t, 2H), 1.40-1.36 (m, 1H), 1.28 (s, 9H), 0.78 (d, 3H).

The mixture of isomers obtained above (mainly the racemate of a main diastereomer) was separated into the enantiomers by preparative HPLC on a chiral phase [column: Daicel Chiralpak AD-H, 5 µm, 250 mm×20 mm; flow rate: 15 ml/min; UV detection: 220 nm; injection volume: 0.25 ml; temperature: 40° C.; mobile phase: 70% isohexane/30% ethanol]. Starting with 333 mg of the mixture of isomers, 138 mg of enantiomer 1 and 134 mg of enantiomer 2 were isolated (see Examples 427A and 428A).

Example 427A tert-Butyl(+)-3-{3-[(4,4,4-trifluoro-2-{4-[(4-fluoro-1-oxo-1,3-dihydro-2H-isoindol-2-yl)methyl]phenyl}-3-methylbutanoyl)amino]phenyl}propanoate (enantiomer 1)

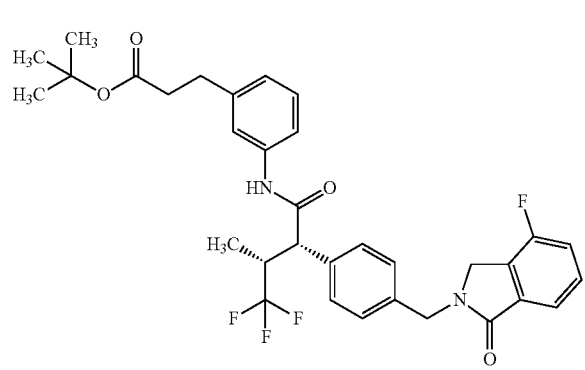 [SMILES: C[C@H]([C@H](C(=O)Nc1cccc(CCC(=O)OC(C)(C)C)c1)c1ccc(CN2Cc3c(F)cccc3C2=O)cc1)C(F)(F)F]

LC-MS (method 15): $R_t$=1.34 min; m/z=597 (M−H)⁻.

¹H-NMR (400 MHz, DMSO-$d_6$): δ=10.15 (s, 1H), 7.61-7.53 (m, 2H), 7.46-7.37 (m, 4H), 7.33 (d, 1H), 7.29 (d, 2H), 7.16 (t, 1H), 6.87 (d, 1H), 4.71 (s, 2H), 4.47 (s, 2H), 3.81 (d, 1H), 3.40-3.30 (m, 1H), 2.73 (t, 2H), 2.44 (t, 2H), 1.40-1.36 (m, 1H), 1.28 (s, 9H), 0.78 (d, 3H).

$[\alpha]_D^{20}$=+68.4°, c=0.605, chloroform.

Example 428A tert-Butyl(−)-3-{3-[(4,4,4-trifluoro-2-{4-[(4-fluoro-1-oxo-1,3-dihydro-2H-isoindol-2-yl)methyl]phenyl}-3-methylbutanoyl)amino]phenyl}propanoate (enantiomer 2)

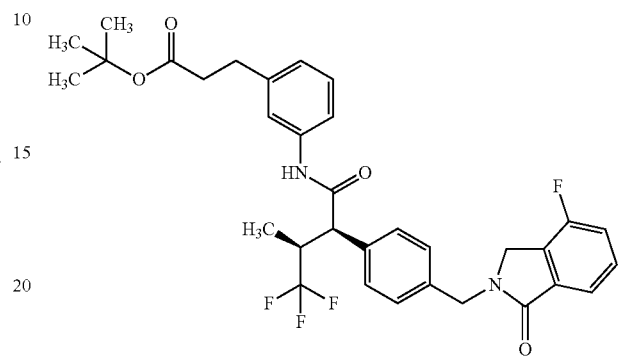

LC-MS (method 15): $R_t$=1.34 min; m/z=597 (M−H)⁻.

¹H-NMR (400 MHz, DMSO-$d_6$): δ=10.15 (s, 1H), 7.61-7.53 (m, 2H), 7.46-7.37 (m, 4H), 7.33 (d, 1H), 7.29 (d, 2H), 7.16 (t, 1H), 6.87 (d, 1H), 4.71 (s, 2H), 4.47 (s, 2H), 3.81 (d, 1H), 3.40-3.30 (m, 1H), 2.73 (t, 2H), 2.44 (t, 2H), 1.40-1.36 (m, 1H), 1.28 (s, 9H), 0.78 (d, 3H).

$[\alpha]_D^{20}$=−76.8°, c=0.485, chloroform.

Example 429A tert-Butyl(+)-3-(3-{[(2S)-2-cyclopentyl-2-{4-[(5-oxo-2-phenyl-5,6-dihydro-4H-1,3,4-oxadiazin-4-yl)methyl]phenyl}acetyl]amino}-2-fluorophenyl)propanoate

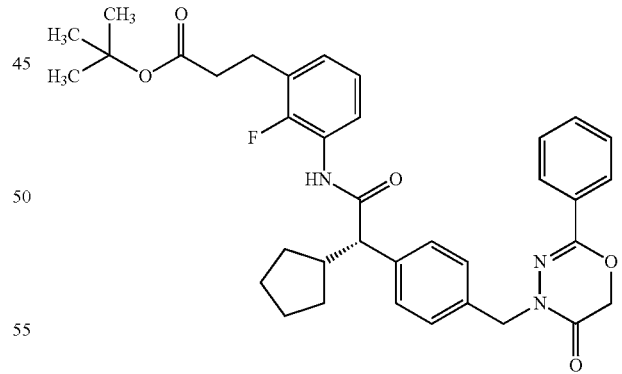

114.0 mg (0.77 mmol) of tert-butyl 3-(3-amino-2-fluorophenyl)propanoate and 193 µl (0.99 mmol) of DIEA were added to a solution of 155.8 mg (0.40 mmol) of (2S)-cyclopentyl{4-[(5-oxo-2-phenyl-5,6-dihydro-4H-1,3,4-oxadiazin-4-yl)methyl]phenyl}ethanoic acid in 1 ml of DMF. At 0° C., 181.1 mg (0.47 mmol) of HATU were added a little at a time to the resulting mixture. The reaction mixture was stirred at 0° C. for 30 min, then warmed to RT and subsequently stirred at 60° C. for 7 h. The reaction mixture was then added to saturated sodium carbonate solution and extracted three times with ethyl acetate. The combined organic phases were dried over magnesium sulfate and concentrated under reduced pressure. The reaction product was purified by preparative RP-HPLC (mobile phase: acetonitrile/water gradient). This gave 125.6 mg (51.6% of theory) of the title compound.

LC-MS (method 7): $R_t$=3.19 min; m/z=612 (M−H)⁻.

¹H-NMR (400 MHz, DMSO-$d_6$): δ=9.78 (s, 1H), 7.78 (d, 1H), 7.62 (m, 1H), 7.52-7.49 (m, 5H), 7.30 (d, 2H), 7.02-6.98 (m, 2H), 4.91 (s, 2H), 4.85 (s, 2H), 3.61 (d, 1H), 2.81 (t, 2H), 1.82-1.75 (m, 1H), 1.70-1.25 (m, 5H), 1.35 (s, 9H), 1.01-0.91 (m, 1H).

$[α]_D^{20}$=+6.5°, c=0.34, chloroform.

General Procedure 7: Coupling of Anilines with Aliphatic Carboxylic Acids

Method 7A: 1.3 eq. of HATU and 3 eq. of N,N-diisopropylethylamine were added to a 0.35 M solution of the carboxylic acid in question in DMF, and the mixture was stirred at RT for 30 min. 1.1 eq. of the aniline in question were then added. The reaction mixture was stirred at RT overnight and then purified directly by preparative RP-HPLC.

Method 7B: 1.3 eq. of TCTU were added to a 0.15 M solution of the carboxylic acid in question in DMF/pyridine (3:1 v/v), and the mixture was stirred at RT for 30 min. The aniline in question was then added, and the reaction mixture was stirred at RT overnight. The reaction mixture was then concentrated under reduced pressure, and the residue was purified by preparative RP-HPLC.

The following compounds were prepared according to General procedure 7A or 7B:

| Example | Structure | Method | Analytical data |
|---|---|---|---|
| 430A | 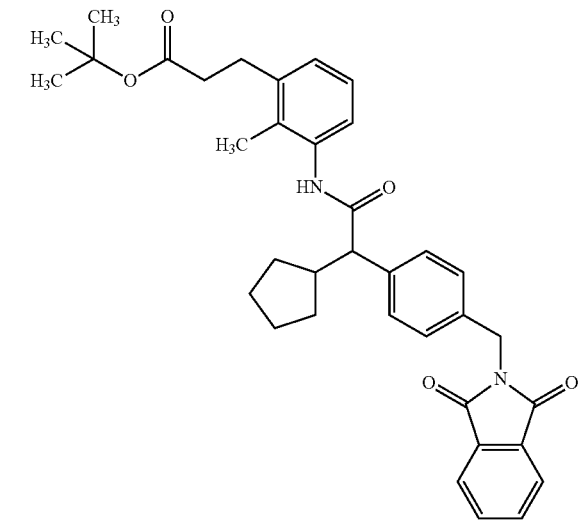 [SMILES: Cc1c(CCC(=O)OC(C)(C)C)cccc1NC(=O)C(c1ccc(CN2C(=O)c3ccccc3C2=O)cc1)C1CCCC1] | 7B | LC-MS (method 7): $R_t$ = 3.08 min; m/z = 599 [M + H]⁺. ¹H-NMR (400 MHz, DMSO-$d_6$): δ = 9.46 (s, 1H), 7.79-7.97 (m, 4H), 7.38 (d, 2H), 7.26 (d, 2H), 6.90-7.06 (m, 3H), 4.75 (s, 2H), 2.78 (t, 2H), 2.38-2.46 (m, 2H), 1.98 (s, 3H), 1.77-1.87 (m, 1H), 1.18-1.73 (m, 17H), 0.95 (dd, 1H). |
| 431A | 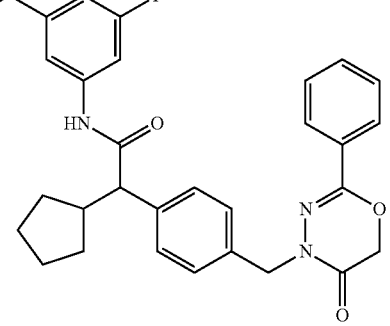 | 7A | LC-MS (method 15): $R_t$ = 1.50 min; m/z = 657 [M + NH₄]⁺. ¹H-NMR (400 MHz, DMSO-$d_6$): δ = 10.16 (s, 1H), 7.68-7.85 (m, 2H), 7.41-7.55 (m, 3H), 7.28-7.40 (m, 5H), 7.21 (s, 1H), 6.70 (d, 1H), 4.78-4.96 (m, 4H), 3.34-3.42 (m, 2H), 2.74-2.79 (m, 2H), 1.77 (m, 1H), 1.15-1.68 (m, 15H), 1.04-1.13 (m, 2H), 0.88-1.03 (m, 1H), 0.77-0.87 (m, 2H). |

-continued

| Example | Structure | Method | Analytical data |
|---|---|---|---|
| 432A | 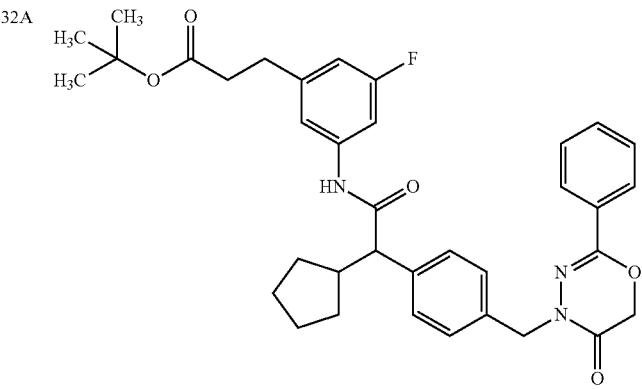 | 7A | LC-MS (method 15): $R_t$ = 1.46 min; m/z = 631 $[M + NH_4]^+$. $^1$H-NMR (400 MHz, DMSO-$d_6$): δ = 10.18 (s, 1H), 7.69-7.84 (m, 2H), 7.41-7.54 (m, 3H), 7.28-7.40 (m, 5H), 7.15 (s, 1H), 6.72 (d, 1H), 4.80-4.96 (m, 4H), 3.36 (d, 1H), 2.73 (t, 2H), 2.43-2.48 (m, 2H), 1.71-1.84 (m, 1H), 1.13-1.69 (m, 16H), 0.90-1.02 (m, 1H). |
| 433A | 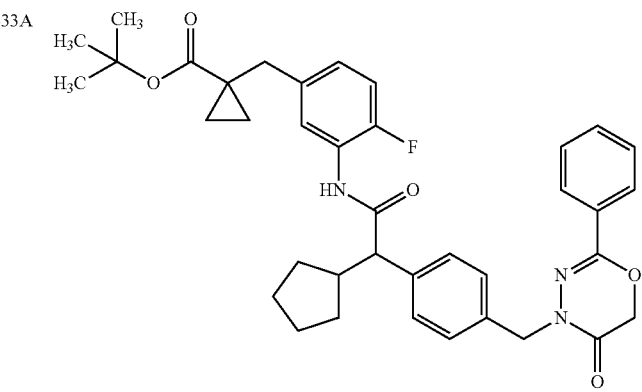 | 7A | LC-MS (method 11): $R_t$ = 1.50 min; m/z = 584 $[M - C_4H_9]^+$. $^1$H-NMR (400 MHz, DMSO-$d_6$): ( = 9.75 (s, 1H), 7.74-7.82 (m, 2H), 7.68 (dd, 1H), 7.35-7.53 (m, 5H), 7.25-7.34 (m, 2H), 7.09 (dd, 1H), 6.89-7.01 (m, 1H), 4.80-4.95 (m, 4H), 3.58 (d, 1H), 2.74 (d, 2H), 1.78 (dd, 1H), 1.16-1.71 (m, 16H), 0.99-1.05 (m, 2H), 0.97 (d, 1H), 0.71-0.82 (m, 2H). |
| 434A | EMBED ISISServer | 7A | LC-MS (method 11): $R_t$ = 1.68 min; m/z = 632 $[M + NH_4]^+$. $^1$H-NMR (400 MHz, DMSO-$d_6$): δ =10.02 (s, 1H), 7.76 (d, 2H), 7.41-7.60 (m, 4H), 7.29-7.41 (m, 5H), 7.02 (t, 1H), 4.80-4.92 (m, 4H), 2.70-2.80 (m, 2H), 2.40-2.47 (m, 2H), 1.71-1.81 (m, 1H), 1.14-1.70 (m, 16H), 0.86-1.04 (m, 1H). |
| 435A | 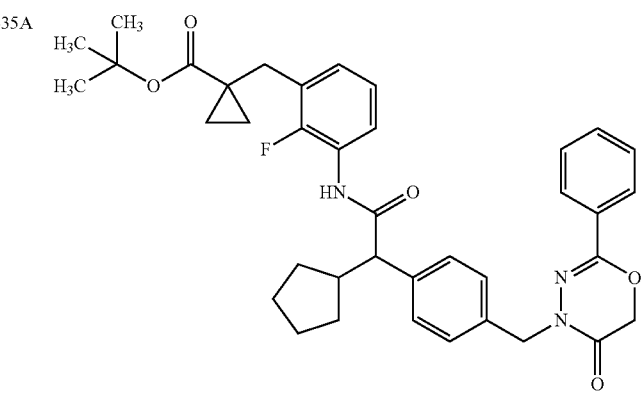 | 7A | LC-MS (method 12): $R_t$ = 3.13 min; m/z = 657 $[M + NH_4]^+$. $^1$H-NMR (400 MHz, DMSO-$d_6$): δ = 9.76 (s, 1H), 7.72-7.86 (m, 2H), 7.53-7.66 (m, 1H), 7.38-7.53 (m, 5H), 7.31 (d, 2H), 6.95-7.14 (m, 2H), 4.71-4.99 (m, 4H), 3.54-3.65 (m, 1H), 2.87 (br. s, 2H), 1.74-1.83 (m, 1H), 1.20-1.71 (m, 15H), 1.06-1.10 (m, 2H), 0.91-1.02 (m, 1H), 0.77-0.81 (m, 2H). |

| Example | Structure | Method | Analytical data |
|---|---|---|---|
| 436A | 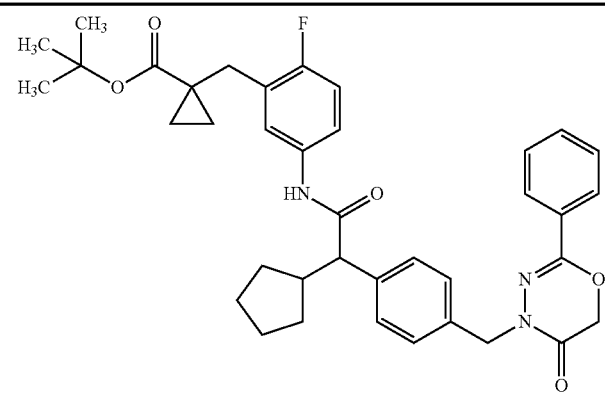 | 7A | LC-MS (method 12): $R_t$ = 3.13 min; m/z = 657 $[M + NH_4]^+$. <br> $^1$H-NMR (400 MHz, DMSO-$d_6$): δ = 10.01 (s, 1H), 7.73-7.79 (m, 2H), 7.58-7.64 (m, 1H), 7.34-7.53 (m, 7H), 7.28-7.33 (m, 2H), 6.97-7.04 (m, 1H), 4.81-4.94 (m, 4H), 2.78-2.84 (m, 2H), 1.70-1.84 (m, 1H), 1.17-1.68 (m, 15H), 1.05-1.12 (m, 2H), 0.90-1.03 (m, 1H), 0.73-0.84 (m, 2H). |

EXEMPLARY EMBODIMENTS

Example 1

4-({[(4-{[4-(4-Chlorophenyl)-1-oxophthalazin-2 (1H)-yl]methyl}phenyl)(cyclopentyl)acetyl]-amino}methyl)benzenecarboxylic acid (racemate)

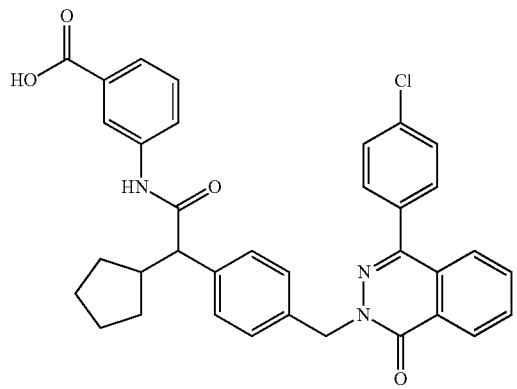 [SMILES: O=C(O)c1cccc(NC(=O)C(c2ccc(Cn3nc(-c4ccc(Cl)cc4)c4ccccc4c3=O)cc2)C2CCCC2)c1]

Preparation Method 1

270 mg (0.435 mmol) of methyl 4-({[(4-{[4-(4-chlorophenyl)-1-oxophthalazin-2(1H)-yl]methyl}phenyl)(cyclopentyl)acetyl]amino}methyl)benzenecarboxylate (Example 112A) were dissolved in 10 ml of dioxane/water (3:1 v/v), and 0.652 ml (0.652 mmol) of 1 N aqueous sodium hydroxide solution was added. The mixture was stirred at room temperature overnight. The reaction mixture was then acidified with 1 N hydrochloric acid and extracted repeatedly with ethyl acetate. The combined organic phases were dried over sodium sulfate and concentrated under reduced pressure. This gave 269 mg of the target compound.

LC-MS (method 7): $R_t$=3.03 min; m/z=606 (M+H)$^+$.

Example 2

2-Methyl-4-[(3-methyl-2-{4-[(5-oxo-2-phenyl-5,6-dihydro-4H-1,3,4-oxadiazin-4-yl)methyl]-phenyl}butanoyl)amino]-2,3-dihydro-1H-indene-2-carboxylic acid (mixture of diastereomers)

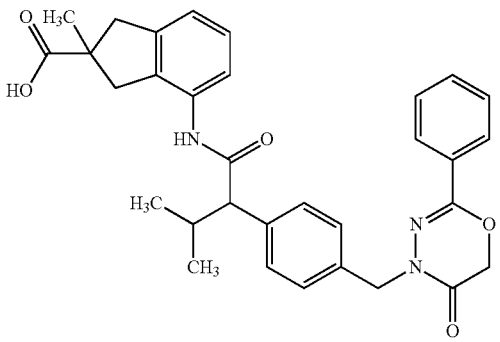 [SMILES: CC(C)C(C(=O)Nc1cccc2c1CC(C)(C(=O)O)C2)c1ccc(CN2N=C(c3ccccc3)OCC2=O)cc1]

Preparation Method 2

9.1 mg (0.22 mmol) of lithium hydroxide monohydrate were added to a solution of 60 mg (0.11 mmol) of methyl 2-methyl-4-[(3-methyl-2-{4-[(5-oxo-2-phenyl-5,6-dihydro-4H-1,3,4-oxadiazin-4-yl)methyl]phenyl}butanoyl) amino]-2,3-dihydro-1H-indene-2-carboxylate (Example 136A) in 2 ml of THF and 2 ml of water, and the mixture was stirred at 60° C. for 8 h. The reaction mixture was then adjusted to pH 4 with 1 M hydrochloric acid and concentrated to dryness under reduced pressure. The crude product obtained was purified by flash chromatography on silica gel (mobile phase cyclohexane/ethyl acetate 10:1→4:1→1:1 or dichloromethane/methanol 10:1). This gave 43 mg (0.08 mmol, 74% of theory) of the title compound.

$^1$H-NMR (400 MHz, DMSO-$d_6$, δ/ppm): 12.45-12.24 (1H, broad s), 9.46 (1H, d), 7.76 (2H, d), 7.52-7.26 (8H, m), 7.04 (1H, t), 6.94 (1H, d), 4.91 (2H, s), 4.86 (2H, s), 3.43-3.18 (3H, m), 2.79-2.57 (2H, m), 2.38-2.21 (1H, m), 1.23 (3H, s), 1.02 (3H, d), 0.65 (3H, d).

LC-MS (method 11): $R_t$=1.34 min; m/z=540 (M+H)$^+$.

Example 3

3-{3-[(4-Methoxy-3-methyl-2-{4-[(5-oxo-2-phenyl-5,6-dihydro-4H-1,3,4-oxadiazin-4-yl)-methyl]phenyl}butanoyl)amino]-2-methylphenyl}propanoic acid (mixture of diastereomers)

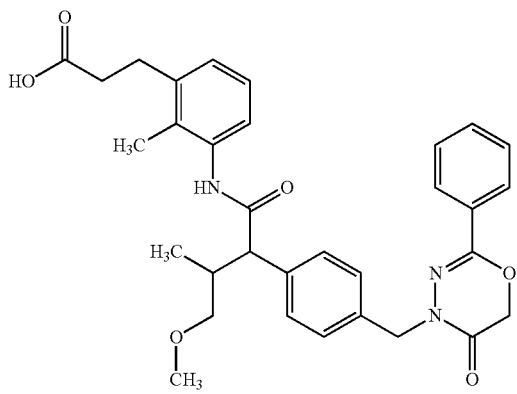

Preparation Method 3

0.27 ml (3.45 mmol) of trifluoroacetic acid was added dropwise to a solution of 106 mg (0.17 mmol) of tert-butyl 3-{3-[(4-methoxy-3-methyl-2-{4-[(5-oxo-2-phenyl-5,6-dihydro-4H-1,3,4-oxadiazin-4-yl)methyl]phenyl}butanoyl)amino]-2-methylphenyl}propanoate (Example 170A) in 2 ml of dichloromethane, and the mixture was stirred at room temperature for 3 h. The reaction solution was then concentrated to dryness under reduced pressure. The residue obtained was purified by preparative HPLC. This gave 66 mg (0.12 mmol, 68% of theory) of the title compound as a mixture of diastereomers.

LC-MS (method 11): diastereomer 1: $R_t$=1.23 min (28%), m/z=558 (M+H)$^+$; diastereomer 2: $R_t$=1.24 min (72%); m/z=558 (M+H)$^+$.

The compounds listed in the table below were obtained in an analogous manner:

| Example | Name/Structure<br>Preparation method/Starting material | Analytical data |
|---|---|---|
| 4 | 4-{[(cyclopentyl{4-[(2-oxo-5-phenyl-1,3,4-oxadiazol-3(2H)-yl)methyl]phenyl}acetyl)amino]methyl}-benzenecarboxylic acid (racemate)<br><br>preparation method 1 (from Ex. 114A) | LC-MS (method 2):<br>$R_t$ = 2.38 min; m/z = 512 (M + H)$^+$. |
| 5 | 4-{[(cyclopentyl{4-[(3,5-dioxo-6-phenyl-2,5-dihydro-1,2,4-triazin-4(3H)-yl)methyl]phenyl}acetyl)amino]methyl}benzenecarboxylic acid (racemate)<br><br>preparation method 1 (from Ex. 117A) | LC-MS (method 2):<br>$R_t$ = 2.22 min; m/z = 539 (M + H)$^+$. |

| Example | Name/Structure Preparation method/Starting material | Analytical data |
|---|---|---|
| 6 | 4-({[cyclopentyl(4-{[(4R,5S)-4-methyl-2-oxo-5-phenyl-1,3-oxazolidin-3-yl]methyl}phenyl)acetyl]-amino}methyl)benzenecarboxylic acid (racemate)<br>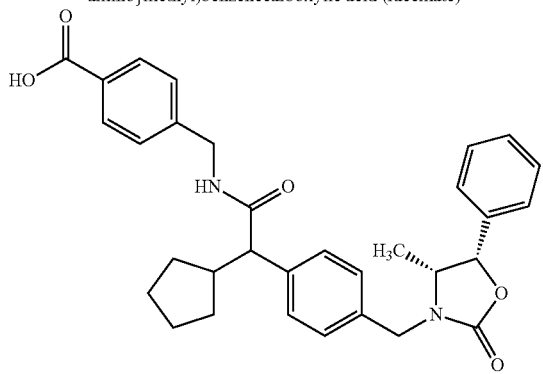<br>preparation method 1 (from Ex. 115A) | LC-MS (method 7):<br>$R_t$ = 2.55 min; m/z = 527 $(M + H)^+$. |
| 7 | 4-({[cyclopentyl(4-{[(4S,5R)-4-methyl-2-oxo-5-phenyl-1,3-oxazolidin-3-yl]methyl}phenyl)acetyl]-amino}methyl)benzenecarboxylic acid (racemate)<br>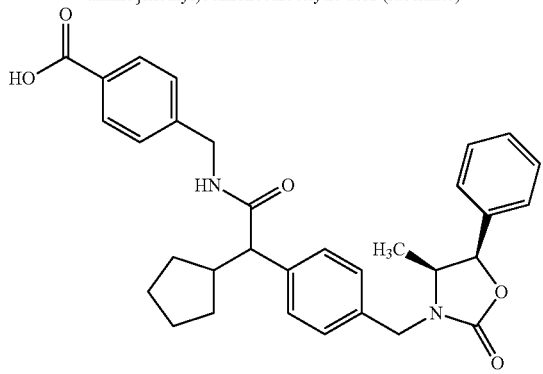<br>preparation method 1 (from Ex. 116A) | LC-MS (method 2):<br>$R_t$ = 2.31 min; m/z = 527 $(M + H)^+$. |
| 8 | 4-{[(cyclopentyl{4-[(5-methyl-2-oxo-5-phenyl-piperidin-1-yl)methyl]phenyl}acetyl)amino]-methyl}benzenecarboxylic acid (mixture of diastereomers)<br>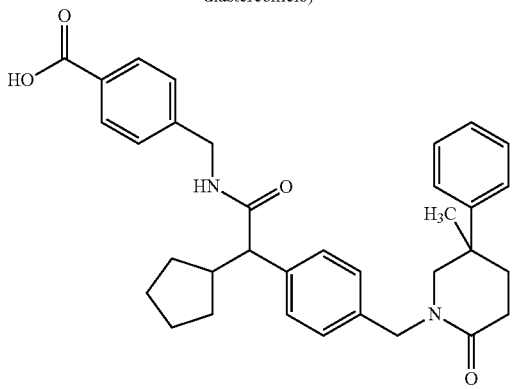<br>preparation method 1 (from Ex. 118A) | LC-MS (method 7):<br>$R_t$ = 2.50 min; m/z = 539 $(M + H)^+$. |

| Example | Name/Structure Preparation method/Starting material | Analytical data |
|---|---|---|
| 9 | 4-{[(cyclopentyl{4-[(5-oxo-2-phenyl-5,6-dihydro-4H-1,3,4-oxadiazin-4-yl)methyl]phenyl}acetyl)-amino]methyl}phenyl)acetic acid (racemate)<br />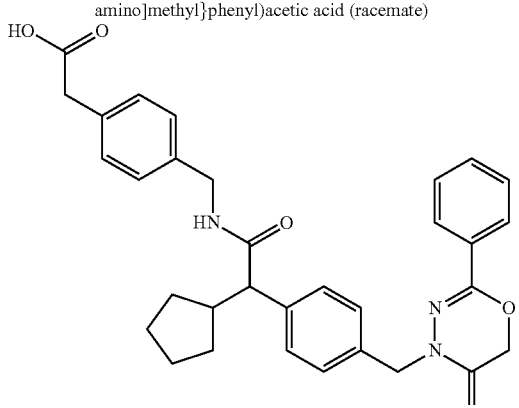<br />preparation method 1 (from Ex. 119A) | LC-MS (method 7):<br />$R_t$ = 2.53 min; m/z = 540 (M + H)$^+$. |
| 10 | 4-({[(4-{[2-(3-chlorophenyl)-5-oxo-5,6-dihydro-4H-1,3,4-oxadiazin-4-yl]methyl}phenyl)(cyclopentyl)-acetyl]amino}methyl)benzenecarboxylic acid (racemate)<br />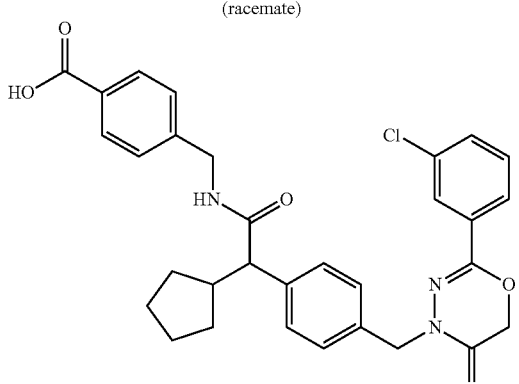<br />preparation method 1 (from Ex. 120A) | LC-MS (method 2):<br />$R_t$ = 2.57 min; m/z = 560 (M + H)$^+$. |
| 11 | 6-({[(4-{[4-(4-chlorophenyl)-1-oxophthalazin-2(1H)-yl]-methyl}phenyl)(cyclopentyl)acetyl]amino}methyl)-pyridine-3-carboxylic acid (racemate)<br />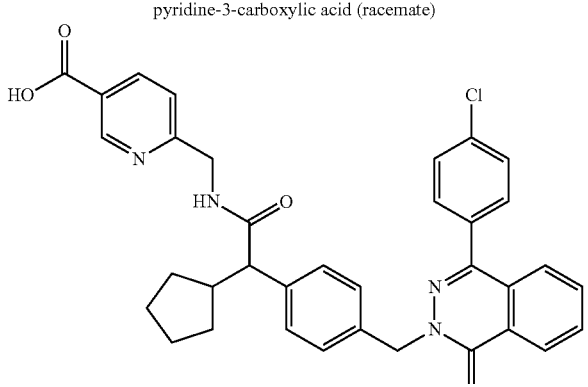<br />preparation method 1 (from Ex. 121A) | LC-MS (method 2):<br />$R_t$ = 2.60 min; m/z = 607 (M + H)$^+$. |

| Example | Name/Structure Preparation method/Starting material | Analytical data |
|---|---|---|
| 12 | 4-({[(4-{[2-(2-chlorophenyl)-5-oxo-5,6-dihydro-4H-1,3,4-oxadiazin-4-yl]methyl}phenyl)(cyclopentyl)-acetyl]amino}methyl)benzenecarboxylic acid (racemate)<br><br>preparation method 1 (from Ex. 122A) | LC-MS (method 2):<br>$R_t$ = 2.42 min; m/z = 560 $(M + H)^+$. |
| 13 | 5-({[(4-{[4-(4-chlorophenyl)-1-oxophthalazin-2(1H)-yl]-methyl}phenyl)(cyclopentyl)acetyl]amino}methyl)-furan-2-carboxylic acid (racemate)<br><br>preparation method 1 (from Ex. 123A) | LC-MS (method 9):<br>$R_t$ = 4.09 min; m/z = 596 $(M + H)^+$. |
| 14 | 4-({[(4-{[2-(4-chlorophenyl)-5-oxo-5,6-dihydro-4H-1,3,4-oxadiazin-4-yl]methyl}phenyl)(cyclopentyl)-acetyl]amino}methyl)benzenecarboxylic acid (racemate)<br><br>preparation method 1 (from Ex. 124A) | LC-MS (method 7):<br>$R_t$ = 2.90 min; m/z = 560 $(M + H)^+$. |

| Example | Name/Structure Preparation method/Starting material | Analytical data |
|---|---|---|
| 15 | 4-({[cyclopentyl(4-{[2-(2-methoxyphenyl)-5-oxo-5,6-dihydro-4H-1,3,4-oxadiazin-4-yl]methyl}-phenyl)acetyl]amino}methyl)benzenecarboxylic acid (racemate)<br><br>preparation method 1 (from Ex. 125A) | LC-MS (method 8):<br>$R_t$ = 3.57 min; m/z = 566 (M + H)$^+$. |
| 16 | 4-{[cyclopentyl(4-{[2-(2-methylpropyl)-5-oxo-5,6-dihydro-4H-1,3,4-oxadiazin-4-yl]methyl}phenyl)-acetyl]amino}-2,3-dihydro-1H-indene-2-carboxylic acid (mixture of diastereomers)<br><br>preparation method 1 (from Ex. 185A) | LC-MS (method 11):<br>$R_t$ = 1.38 min; m/z = 532 (M + H)$^+$. |
| 17 | 4-{[(4-{[2-(4-chlorophenyl)-5-oxo-5,6-dihydro-4H-1,3,4-oxadiazin-4-yl]methyl}phenyl)(cyclopentyl)-acetyl]amino}-2,3-dihydro-1H-indene-2-carboxylic acid (mixture of diastereomers)<br><br>preparation method 2 (from Ex. 132A) | LC-MS (method 7):<br>$R_t$ = 3.01 min; m/z = 586 (M + H)$^+$. |

-continued

| Example | Name/Structure Preparation method/Starting material | Analytical data |
|---|---|---|
| 18 | 4-{[(4-{[2-(4-fluorophenyl)-5-oxo-5,6-dihydro-4H-1,3,4-oxadiazin-4-yl]methyl}phenyl)(cyclopentyl)-acetyl]amino}-2,3-dihydro-1H-indene-2-carboxylic acid (mixture of diastereomers)<br>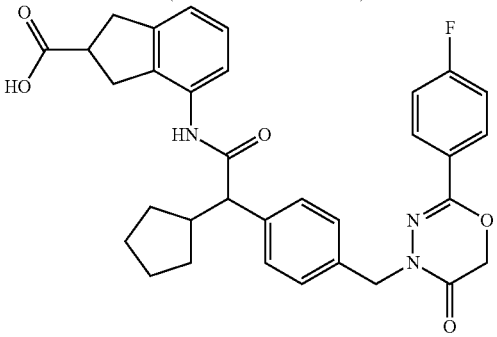<br>preparation method 2 (from Ex. 133A) | $^1$H-NMR (400 MHz, DMSO-$d_6$, δ/ppm): 12.35-12.18 (1H, broad s), 9.47 (1H, d), 7.85-7.75 (2H, m), 7.41 (2H, d), 7.36-7.22 (5H, m), 7.04 (1H, t), 6.96 (1H, d), 4.91 (2H, s), 4.85 (2H, s), 3.52 (1H, d), 3.28-3.15 (1H, m), 3.14-2.97 (4H, m), 2.61-2.46 (1H, m), 1.87-1.74 (1H, m), 1.73-1.21 (5H, m), 1.04-0.90 (1H, m). LC-MS (method 7): $R_t$ = 2.86 min; m/z = 570 $(M + H)^+$. |
| 19 | 4-{[cyclopentyl(4-{[4-methyl-5-(2-methylpropyl)-2-oxo-1,3-thiazol-3(2H)-yl]methyl}phenyl)acetyl]-amino}-2,3-dihydro-1H-indene-2-carboxylic acid (mixture of diastereomers)<br>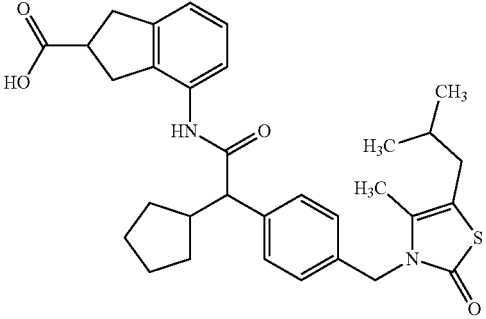 [SMILES: Cc1c(CC(C)C)sc(=O)n1Cc1ccc(C(C(=O)Nc2cccc3c2CC(C(=O)O)C3)C2CCCC2)cc1]<br>preparation method 1 (from Ex. 106A) | LC-MS (method 7): $R_t$ = 3.02 min; m/z = 547 $(M + H)^+$. |
| 20 | 4-{[cyclopentyl(4-{[5-oxo-2-(propan-2-yl)-5,6-dihydro-4H-1,3,4-oxadiazin-4-yl]methyl}phenyl)-acetyl]amino}-2,3-dihydro-1H-indene-2-carboxylic acid (mixture of diastereomers)<br>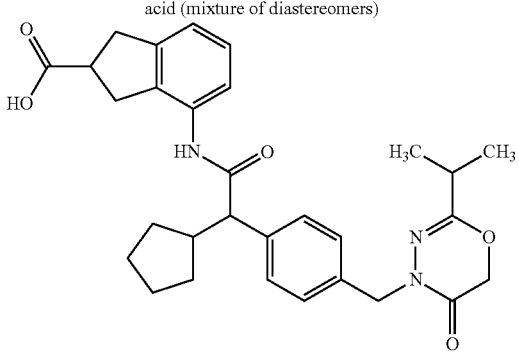<br>preparation method 1 (from Ex. 107A) | LC-MS (method 10): $R_t$ = 2.14 min; m/z = 518 $(M + H)^+$. |

| Example | Name/Structure Preparation method/Starting material | Analytical data |
|---|---|---|
| 21 | 3-{3-[(cyclopentyl{4-[(4-oxo-1,2,3-benzotriazin-3(4H)-yl)methyl]phenyl}acetyl)amino]phenyl}-propanoic acid (racemate)<br><br>preparation method 3 (from Ex. 156A) | $^1$H-NMR (400 MHz, DMSO-$d_6$, δ/ppm): 12.2-11.8 (1H, broad s), 9.98 (1H, d), 8.30-8.18 (2H, m), 8.09 (1H, t), 7.98-7.87 (1H, m), 7.43-7.28 (6H, m), 7.14 (1H, t), 6.86 (1H, d), 5.55 (2H, s), 3.38 (1H, d), 2.73 (2H, t), 2.61-2.46 (1H, m), 2.45 (2H, t), 1.83-1.70 (1H, m), 1.70-1.19 (6H, m), 1.01-0.88 (1H, m).<br>LC-MS (method 11): R$_t$ = 1.28 min; m/z = 511 (M + H)$^+$. |
| 22 | 3-{3-[(cyclopentyl{4-[2-oxo-5-phenyl-1,3,4-oxadiazol-3(2H)-yl)methyl]phenyl}acetyl)amino]-phenyl}propanoic acid (racemate)<br><br>preparation method 3 (from Ex. 157A) | $^1$H-NMR (400 MHz, DMSO-$d_6$, δ/ppm): 12.25-11.95 (1H, broad s), 10.00 (1H, d), 7.79 (2H, d), 7.62-7.48 (3H, m), 7.48-7.35 (4H, m), 7.32 (2H, d), 7.15 (1H, t), 6.88 (1H, d), 4.94 (2H, s), 3.39 (1H, d), 2.74 (2H, t), 2.65-2.42 (1H, m), 2.48 (2H, t), 1.88-1.71 (1H, m), 1.70-1.19 (6H, m), 1.07-0.89 (1H, m).<br>LC-MS (method 11): R$_t$ = 1.36 min; m/z = 526 (M + H)$^+$. |
| 23 | 3-{3-[(3-methyl-2-{4-[(5-oxo-2-phenyl-5,6-dihydro-4H-1,3,4-oxadiazin-4-yl)methyl]phenyl}hexanoyl)amino]-phenyl}propanoic acid (mixture of diastereomers)<br><br>preparation method 2 (from Ex. 164A) | LC-MS (method 7): R$_t$ = 2.70 min; m/z = 542 (M + H)$^+$. |

| Example | Name/Structure Preparation method/Starting material | Analytical data |
|---|---|---|
| 24 | 4-[(3-methyl-2-{4-[(5-oxo-2-phenyl-5,6-dihydro-4H-1,3,4-oxadiazin-4-yl)methyl]phenyl}hexanoyl)-amino]-2,3-dihydro-1H-indene-2-carboxylic acid (mixture of diastereomers)<br><br>preparation method 2 (from Ex. 165A) | LC-MS (method 11):<br>$R_t$ = 1.42 min; m/z = 554 (M + H)$^+$. |
| 25 | 3-{3-[(cyclopentyl{4-[(3-methyl-2-oxoimidazolidin-1-yl)methyl]phenyl}acetyl)amino]-2-methyl-phenyl}propanoic acid (racemate)<br><br>preparation method 3 (from Ex. 162A) | $^1$H-NMR (400 MHz, DMSO-d$_6$, δ/ppm): 12.3-11.9 (1H, broad s), 9.46 (1H, d), 7.38 (2H, d), 7.17 (2H, d), 7.08-6.95 (3H, m), 4.23 (2H, s), 3.45 (1H, d), 3.22 (2H, t), 3.11 (2H, t), 2.79 (2H, t), 2.66 (3H, s), 2.64-2.42 (1H, m), 2.43 (2H, t), 1.99 (3H, s), 1.90-1.79 (1H, m), 1.75-1.29 (6H, m), 1.05-0.91 (1H, m).<br>LC-MS (method 11):<br>$R_t$ = 1.12 min; m/z = 478 (M + H)$^+$. |
| 26 | 3-(3-{[(4-{[3-(3-chlorophenyl)-2-oxoimidazolidin-1-yl]methyl}phenyl)(cyclopentyl)acetyl]amino}-2-methylphenyl)propanoic acid (racemate)<br><br>preparation method 3 (from Ex. 161A) | $^1$H-NMR (400 MHz, DMSO-d$_6$, δ/ppm): 12.3-11.9 (1H, broad s), 9.47 (1H, d), 7.82 (1H, s), 7.49-7.39 (3H, m), 7.34 (1H, t), 7.26 (2H, d), 7.08-6.94 (4H, m), 4.38 (2H, s), 3.82 (2H, t), 3.47 (1H, d), 3.37 (2H, t), 2.80 (2H, t), 2.65-2.48 (1H, m), 2.43 (2H, t), 2.00 (3H, s), 1.91-1.78 (1H, m), 1.75-1.28 (6H, m), 1.05-0.91 (1H, m).<br>LC-MS (method 10):<br>$R_t$ = 2.28 min; m/z = 574 (M + H)$^+$. |

| Example | Name/Structure Preparation method/Starting material | Analytical data |
|---|---|---|
| 27 | 3-(3-{[(4-{[3-(3-chlorophenyl)-2-oxoimidazolidin-1-yl]-methyl}phenyl)(cyclopentyl)acetyl]amino}phenyl)-propanoic acid (racemate)<br><br>preparation method 3 (from Ex. 168A) | $^1$H-NMR (400 MHz, DMSO-$d_6$, δ/ppm): 12.2-12.0 (1H, broad s), 10.00 (1H, d), 7.81 (1H, s), 7.49-7.38 (5H, m), 7.32 (1H, t), 7.24 (2H, d), 7.16 (1H, t), 7.03 (1H, d), 6.88 (1H, d), 4.36 (2H, s), 3.80 (2H, t), 3.41-3.29 (3H, m), 2.75 (2H, t), 2.69-2.52 (1H, m), 2.65-2.48 (2H, t), 1.86-1.71 (1H, m), 1.69-1.20 (6H, m), 1.03-0.90 (1H, m).<br>LC-MS (method 10): $R_t$ = 2.33 min; m/z = 560 (M + H)$^+$. |
| 28 | 3-{3-[(cyclopentyl{4-[(3-methyl-2-oxoimidazolidin-1-yl)methyl]phenyl}acetyl)amino]phenyl}propanoic acid (racemate)<br><br>preparation method 3 (from Ex. 169A) | LC-MS (method 10): $R_t$ = 1.77 min; m/z = 464 (M + H)$^+$. |

| Example | Name/Structure Preparation method/Starting material | Analytical data |
|---|---|---|
| 29 | 3-{3-[(cyclopentyl{4-[(4-oxo-1,2,3-benzotriazin-3(4H)-yl)methyl]phenyl}acetyl)amino]-2-methylphenyl}propanoic acid (racemate)<br>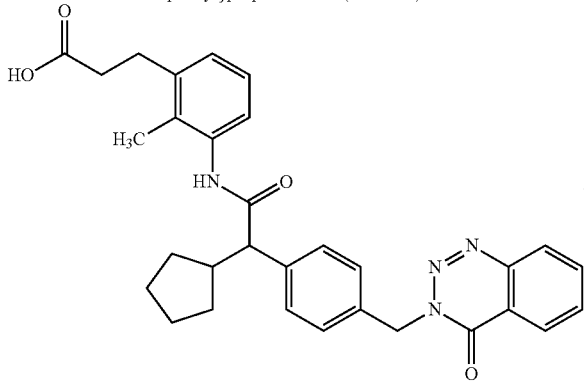 [SMILES: Cc1c(CCC(=O)O)cccc1NC(=O)C(c1ccc(Cn2nnc3ccccc3c2=O)cc1)C1CCCC1]<br>preparation method 3 (from Ex. 166A) | $^1$H-NMR (400 MHz, DMSO-$d_6$, δ/ppm): 12.13-(1H, s), 9.46 (1H, d), 8.31-8.19 (2H, m), 8.10 (1H, t), 7.95 (1H, t), 7.40 (2H, d), 7.33 (2H, d), 7.07-6.94 (3H, m), 5.57 (2H, s), 3.45 (1H, d), 2.78 (2H, t), 2.59-2.46 (1H, m), 2.42 (2H, t), 1.97 (3H, s), 1.88-1.75 (1H, m), 1.71-1.25 (6H, m), 1.01-0.89 (1H, m).<br>LC-MS (method 10): $R_t$ = 2.05 min; m/z = 525 (M + H)$^+$. |
| 30 | 3-{3-[(cyclopentyl{4-[(2-oxo-5-phenyl-1,3,4-oxadiazol-3(2H)-yl)methyl]phenyl}acetyl)amino]-2-methylphenyl}propanoic acid (racemate)<br>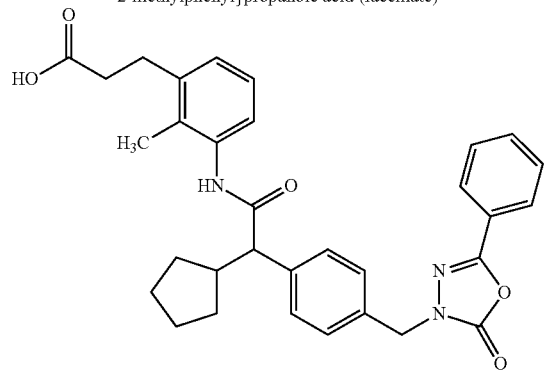<br>preparation method 3 (from Ex. 167A) | $^1$H-NMR (400 MHz, DMSO-$d_6$, δ/ppm): 12.3-11.8 (1H, broad s), 9.48 (1H, d), 7.80 (2H, m), 7.65-7.50 (3H, m), 7.44 (2H, d), 7.32 (2H, d), 7.09-6.92 (3H, m), 4.96 (2H, s), 3.48 (1H, d), 2.78 (2H, t), 2.62-2.48 (1H, m), 2.42 (2H, t), 1.99 (3H, s), 1.90-1.78 (1H, m), 1.72-1.28 (6H, m), 1.05-0.91 (1H, m).<br>LC-MS (method 7): $R_t$ = 2.61 min; m/z = 540 (M + H)$^+$. |
| 31 | 3-{3-[(4-cyano-3-methyl-2-{4-[(5-oxo-2-phenyl-5,6-dihydro-4H-1,3,4-oxadiazin-4-yl)methyl]phenyl}butanoyl)amino]-2-methylphenyl}-propanoic acid (mixture of diastereomers)<br>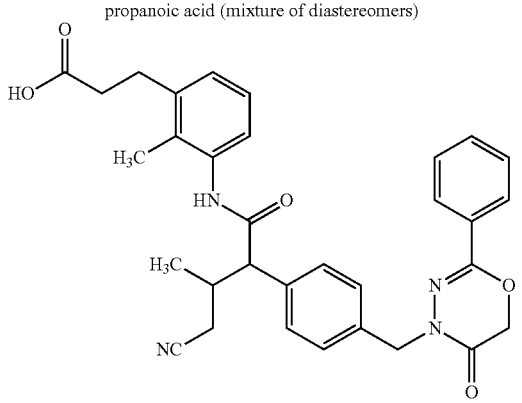<br>preparation method 3 (from Ex. 171A) | $^1$H-NMR (400 MHz, DMSO-$d_6$, δ/ppm): 12.14-(1H, s), 9.68 (1H, d), 7.76 (2H, d), 7.54-7.31 (7H, m), 7.08-6.92 (3H, m), 4.92 (2H, s), 4.89 (2H, s), 3.63 (1H, d), 2.76 (2H, t), 2.65-2.48 (1H, m), 2.48-2.35 (3H, m), 2.11-1.98 (1H, m), 1.92 (3H, s), 1.18 and 0.82 (tog. 3H, 2d).<br>LC-MS (method 11): $R_t$ = 1.18 min; m/z = 553 (M + H)$^+$. |

| Example | Name/Structure Preparation method/Starting material | Analytical data |
|---|---|---|
| 32 | 3-{3-[(4-cyano-3-methyl-2-{4-[(5-oxo-2-phenyl-5,6-dihydro-4H-1,3,4-oxadiazin-4-yl)methyl]-phenyl}butanoyl)amino]phenyl}propanoic acid (mixture of diastereomers)<br><br>preparation method 2 (from Ex. 172A) | LC-MS (method 7): $R_t$ = 2.35 min; m/z = 539 (M + H)$^+$. |
| 33 | 4-[(4-cyano-3-methyl-2-{4-[(5-oxo-2-phenyl-5,6-dihydro-4H-1,3,4-oxadiazin-4-yl)methyl]phenyl}-butanoyl)amino]-2,3-dihydro-1H-indene-2-carboxylic acid (mixture of diastereomers)<br><br>preparation method 2 (from Ex. 173A) | LC-MS (method 7): $R_t$ = 2.36 min; m/z = 551 (M + H)$^+$. |

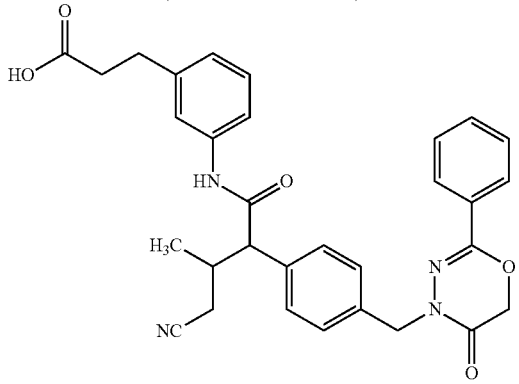 [SMILES: CC(CC#N)C(C(=O)Nc1cccc(CCC(=O)O)c1)c1ccc(CN2N=C(c3ccccc3)OCC2=O)cc1]

Example 34

3-{2-[(Cyclopentyl{4-[(5-oxo-2-phenyl-5,6-dihydro-4H-1,3,4-oxadiazin-4-yl)methyl]phenyl}acetyl)amino]-1,3-thiazol-4-yl}propanoic acid (racemate)

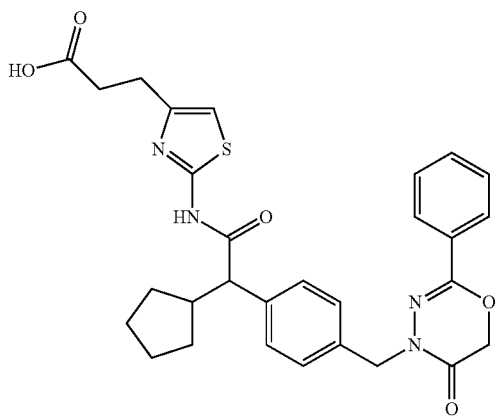 [SMILES: O=C(O)CCc1csc(NC(=O)C(c2ccc(CN3N=C(c4ccccc4)OCC3=O)cc2)C2CCCC2)n1]

Preparation Method 4

20 mg (0.1 mmol) of ethyl 3-(2-amino-1,3-thiazol-4-yl)propanoate [Beilstein Reg. No. 9762098], 41.7 mg (0.13 mmol) of TBTU and 25.8 mg of ethyldiisopropylamine were added to a solution of 39.2 mg (0.1 mmol) of cyclopentyl{4-[(5-oxo-2-phenyl-5,6-dihydro-4H-1,3,4-oxadiazin-4-yl)methyl]phenyl}acetic acid (Example 51A) in 0.5 ml DMSO. The mixture was stirred at room temperature overnight. 0.3 ml of 2 M aqueous sodium hydroxide solution was then added, and the mixture was once more stirred overnight. The solvent was then evaporated, and the residue obtained was purified directly by preparative HPLC/MS. This gave 7.1 mg (0.013 mmol, 13% of theory) of the title compound.

LC-MS (method 14): $R_t$=2.20 min; m/z=547 (M+H)$^+$.

The compound listed in the table below was obtained in an analogous manner:

| Example | Name/Structure Preparation method/Starting materials | Analytical data |
|---------|------------------------------------------------------|-----------------|
| 35 | {2-[(cyclopentyl{4-[(5-oxo-2-phenyl-5,6-dihydro-4H-1,3,4-oxadiazin-4-yl)methyl]phenyl}acetyl)amino]-1,3-thiazol-4-yl}acetic acid (racemare)<br>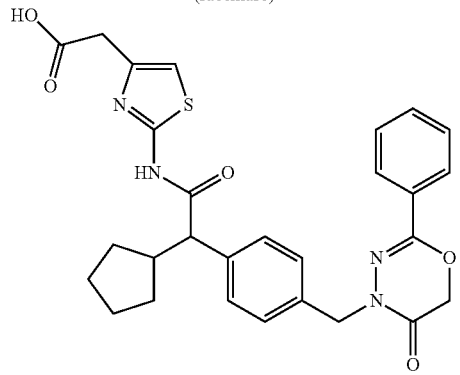<br>preparation method 4 (from Ex. 51A and methyl(2-amino-1,3-thiazol-4-yl)acetate[CAS Reg. No. 64987-16-2]) | LC-MS (method 14): $R_t$ = 2.23 min; m/z = 533 $(M + H)^+$. |

Example 36

4-{[(Cyclopentyl{4-[(5-oxo-2-phenyl-5,6-dihydro-4H-1,3,4-oxadiazin-4-yl)methyl]phenyl}-acetyl)amino]methyl}benzenecarboxylic acid (racemate)

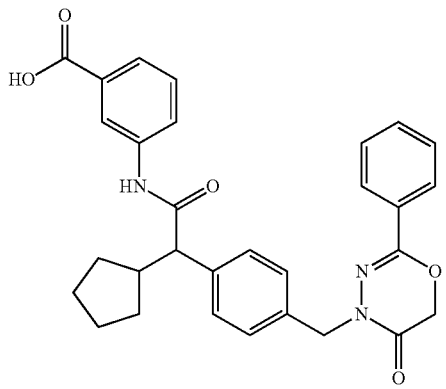 [SMILES: O=C(O)c1cccc(NC(=O)C(c2ccc(CN3N=C(c4ccccc4)OCC3=O)cc2)C2CCCC2)c1]

969 mg (1.757 mmol) of methyl 4-{[(cyclopentyl{4-[(5-oxo-2-phenyl-5,6-dihydro-4H-1,3,4-oxadiazin-4-yl)methyl]phenyl}acetyl)amino]methyl}benzenecarboxylate (Example 113A) were dissolved in 30 ml of dioxane/water (3:1 v/v), and 3.87 ml (3.865 mmol) of 1 N aqueous sodium hydroxide solution were added. The mixture was stirred at room temperature overnight. Saturated aqueous ammonium chloride solution was then added, and the mixture was extracted repeatedly with dichloromethane. The combined organic phases were dried over sodium sulfate and concentrated on a rotary evaporator. This gave 803 mg (1.53 mmol, 87% of theory) of the title compound.

Example 37 and Example 38 ent-4-{[(Cyclopentyl{4-[(5-oxo-2-phenyl-5,6-dihydro-4H-1,3,4-oxadiazin-4-yl)methyl]phenyl}acetyl)amino]methyl}benzenecarboxylic acid (enantiomers 1 and 2)

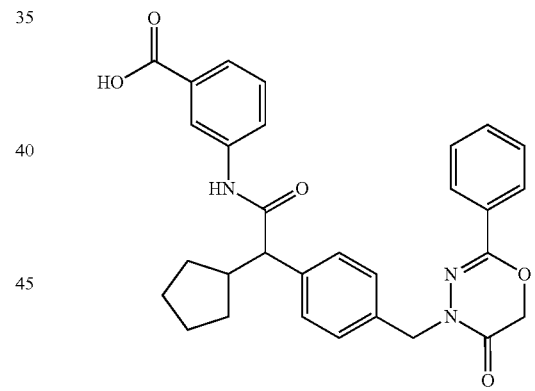

500 mg of the racemic 4-{[(cyclopentyl{4-[(5-oxo-2-phenyl-5,6-dihydro-4H-1,3,4-oxadiazin-4-yl)methyl]phenyl}acetyl)amino]methyl}benzenecarboxylic acid obtained (Example 36) were separated into the enantiomers by preparative HPLC on a chiral phase [column: Daicel Chiralpak OJ-H, 5 μm, 250 mm×20 mm; mobile phase: isohexane/(ethanol+0.2% trifluoroacetic acid+1% water) 60:40 (v/v); flow rate: 15 ml/min; UV detection: 220 nm; temperature: 40° C.]:

Example 37

Enantiomer 1

$R_t$ 5.84 min; purity >96%; >99% ee (column: see above)
Yield: 257 mg
LC-MS (method 2): $R_t$=2.38 min; MS (ESIpos): m/z=526 $(M+H)^+$.

Example 38

Enantiomer 2

$R_t$ 7.61 min; purity >97.5%; >98% ee (column: see above)
Yield: 214 mg
LC-MS (method 2): $R_t$=2.38 min; MS (ESIpos): m/z=526 (M+H)$^+$.

Example 39

4-[(3-Methyl-2-{4-[(5-oxo-2-phenyl-5,6-dihydro-4H-1,3,4-oxadiazin-4-yl)methyl]phenyl}-butanoyl)amino]-2,3-dihydro-1H-indene-2-carboxylic acid (mixture of isomers)

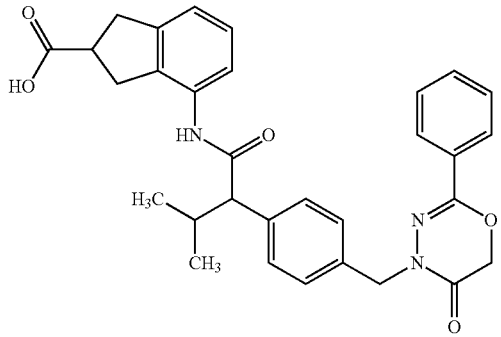 [SMILES: CC(C)C(C(=O)Nc1cccc2c1CC(C(=O)O)C2)c1ccc(CN2N=C(c3ccccc3)OCC2=O)cc1]

26 mg (0.63 mmol) of lithium hydroxide monohydrate were added to a solution of 170 mg (0.32 mmol) of methyl 4-[(3-methyl-2-{4-[(5-oxo-2-phenyl-5,6-dihydro-4H-1,3,4-oxadiazin-4-yl)methyl]phenyl}butanoyl)amino]-2,3-dihydro-1H-indene-2-carboxylate (Example 134A) in 11 ml of THF and 11 ml of water, and the mixture was stirred at 60° C. for 12 h. The reaction mixture was then adjusted to pH 2 with 1 M hydrochloric acid and extracted twice with ethyl acetate. The combined organic phases were dried over magnesium sulfate and then concentrated to dryness under reduced pressure. This gave 141 mg (content 98%, 0.26 mmol, 84% of theory) of the title compound as a mixture of isomers.
LC-MS (method 11): $R_t$=1.30 min; m/z=526 (M+H)$^+$.

Examples 40-43

4-[(3-Methyl-2-{4-[(5-oxo-2-phenyl-5,6-dihydro-4H-1,3,4-oxadiazin-4-yl)methyl]phenyl}-butanoyl)amino]-2,3-dihydro-1H-indene-2-carboxylic acid (isomers 1-4)

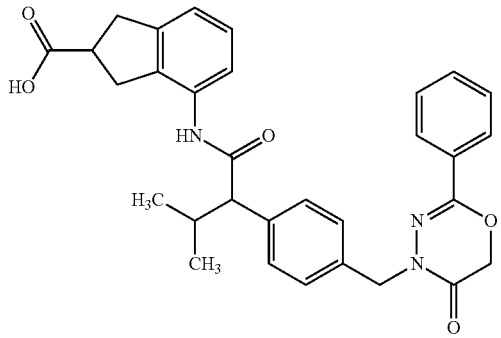 [SMILES: CC(C)C(C(=O)Nc1cccc2c1CC(C(=O)O)C2)c1ccc(CN2N=C(c3ccccc3)OCC2=O)cc1]

141 mg (content 98%, 0.26 mmol) of the mixture of isomers of 4-[(3-methyl-2-{4-[(5-oxo-2-phenyl-5,6-dihydro-4H-1,3,4-oxadiazin-4-yl)methyl]phenyl}butanoyl)amino]-2,3-dihydro-1H-indene-2-carboxylic acid obtained (Example 39) were separated into the individual isomers by preparative HPLC on a chiral phase [column: Daicel Chiralpak AD-H, 5 μm, 250 mm×20 mm; mobile phase: isohexane/(isopropanol+0.2% trifluoroacetic acid+1% water) 70:30 (v/v); flow rate: 15 ml/min; UV detection: 220 nm; temperature: 25° C.]:

Example 40

Isomer 1

$R_t$ 7.79 min; purity >99%; >99% ee (column: see above)
Yield: 36 mg
LC-MS (method 11): $R_t$=1.30 min; m/z=526 (M+H)$^+$.

Example 41

Isomer 2

$R_t$ 8.37 min; purity 93%; >99% ee (column: see above)
Yield: 13 mg
LC-MS (method 11): $R_t$=1.30 min; m/z=526 (M+H)$^+$.

Example 42

Isomer 3

$R_t$ 10.70 min; purity >99%; >98.5% ee (column: see above)
Yield: 41.4 mg
$^1$H-NMR (400 MHz, DMSO-d$_6$, δ/ppm): 12.5-12.1 (1H, broad s), 9.49 (1H, s), 7.76 (2H, d), 7.53-7.25 (8H, m), 7.04 (1H, t), 6.95 (1H, d), 4.91 (2H, s), 4.86 (2H, s), 3.38 (1H, d), 3.28-2.95 (6H, m), 2.35-2.21 (1H, m), 1.02 (3H, d), 0.66 (3H, d).
LC-MS (method 11): $R_t$=1.30 min; m/z=526 (M+H)$^+$.

Example 43

Isomer 4

$R_t$ 12.10 min; purity >94%; >99% ee (column: see above)
Yield: 14 mg
LC-MS (method 11): $R_t$=1.30 min; m/z=526 (M+H)$^+$.

Example 44

4-[(Cyclopentyl{4-[(5-oxo-2-phenyl-5,6-dihydro-4H-1,3,4-oxadiazin-4-yl)methyl]phenyl}-acetyl)amino]-2-methyl-2,3-dihydro-1H-indene-2-carboxylic acid (mixture of diastereomers)

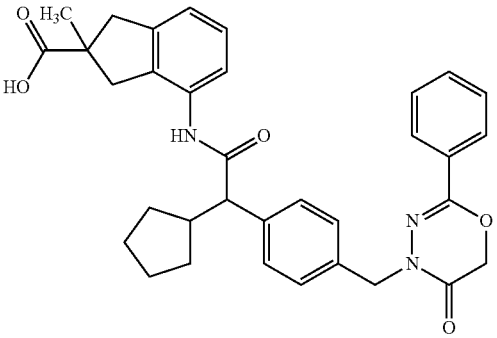 [SMILES: CC1(C(=O)O)Cc2cccc(NC(=O)C(c3ccc(CN4N=C(c5ccccc5)OCC4=O)cc3)C3CCCC3)c2C1]

333

11 mg (0.26 mmol) of lithium hydroxide monohydrate were added to a solution of 74 mg (0.13 mmol) of methyl 4-[(cyclopentyl{4-[(5-oxo-2-phenyl-5,6-dihydro-4H-1,3,4-oxadiazin-4-yl)methyl]phenyl}acetyl)amino]-2-methyl-2,3-dihydro-1H-indene-2-carboxylate (Example 131A) in 2 ml of THF and 1 ml of water, and the mixture was stirred at room temperature for 12 h. The reaction mixture was then adjusted to pH 2 with 1 M hydrochloric acid and extracted twice with ethyl acetate. The combined organic phases were dried over magnesium sulfate, filtered and then concentrated to dryness under reduced pressure. This gave 64 mg (0.11 mmol, 88% of theory) of the title compound as a mixture of diastereomers.

LC-MS (method 11): $R_t$=1.40 min; m/z=566 (M+H)$^+$.

Example 45 and Example 46

4-[(Cyclopentyl{4-[(5-oxo-2-phenyl-5,6-dihydro-4H-1,3,4-oxadiazin-4-yl)methyl]phenyl}-acetyl)amino]-2-methyl-2,3-dihydro-1H-indene-2-carboxylic acid (diastereomers 1 and 2)

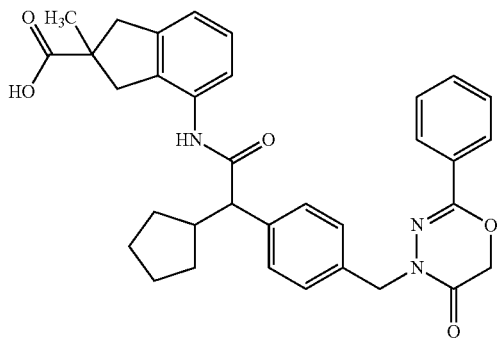 [SMILES: CC1(C(=O)O)Cc2cccc(NC(=O)C(c3ccc(CN4N=C(c5ccccc5)OCC4=O)cc3)C3CCCC3)c2C1]

60 mg (0.11 mmol) of the mixture of diastereomers of 4-[(cyclopentyl{4-[(5-oxo-2-phenyl-5,6-dihydro-4H-1,3,4-oxadiazin-4-yl)methyl]phenyl}acetyl)amino]-2-methyl-2,3-dihydro-1H-indene-2-carboxylic acid obtained (Example 44) were separated further by preparative HPLC on a chiral phase [column: Daicel Chiralpak AD-H, 5 μm, 250 mm×20 mm; mobile phase: isohexane/(ethanol+0.2% trifluoroacetic acid+1% water) 70:30 (v/v); flow rate: 15 ml/min; UV detection: 220 nm; temperature: 35° C.]:

Example 45

Diastereomer 1

$R_t$ 6.2 min; purity >99%; >99% ee (column: see above)
Yield: 19 mg
LC-MS (method 7): $R_t$=2.74 min; m/z=566 (M+H)$^+$.

Example 46

Diastereomer 2

$R_t$ 8.8 min; purity >95.5%; >99% ee (column: see above)
Yield: 37 mg
$^1$H-NMR (400 MHz, DMSO-d$_6$, δ/ppm): 12.33 (1H, s), 9.48 (1H, s), 7.76 (2H, d), 7.55-7.38 (5H, m), 7.30 (3H, t), 7.04 (1H, t), 6.94 (1H, d), 4.91 (2H, s), 4.85 (2H, s), 3.53 (1H, d), 3.38-3.28 (1H, m), 3.23 (1H, d), 2.78-2.61 (2H, m), 2.61-2.46 (1H, m), 1.87-1.72 (1H, m), 1.72-1.20 (6H, m), 1.24 (3H, s), 1.04-0.90 (1H, m).
LC-MS (method 7): $R_t$=2.76 min; m/z=566 (M+H)$^+$.

334

Example 47

4-{[{4-[(2-tert-Butyl-5-oxo-5,6-dihydro-4H-1,3,4-oxadiazin-4-yl)methyl]phenyl}-(cyclopentyl)acetyl]amino}-2,3-dihydro-1H-indene-2-carboxylic acid (mixture of diastereomers)

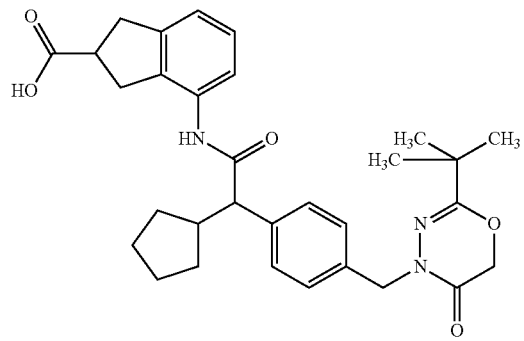 [SMILES: CC(C)(C)C1=NN(Cc2ccc(C(C(=O)Nc3cccc4c3CC(C(=O)O)C4)C3CCCC3)cc2)C(=O)CO1]

167 mg (0.306 mmol) of methyl 4-{[{4-[(2-tert-butyl-5-oxo-5,6-dihydro-4H-1,3,4-oxadiazin-4-yl)methyl]phenyl}(cyclopentyl)acetyl]amino}-2,3-dihydro-1H-indene-2-carboxylate (Example 108A) were dissolved in 14 ml of dioxane/water (3:1 v/v), and 0.46 ml of 1 N aqueous sodium hydroxide solution was added. The mixture was stirred at room temperature overnight. The mixture was then acidified with 1 N hydrochloric acid and extracted repeatedly with dichloromethane, and the combined organic phases were washed with saturated sodium chloride solution and dried over sodium sulfate. The solvent was removed under reduced pressure and the residue was purified by preparative HPLC. This gave 68 mg (42% of theory) of the title compound as a mixture of diastereomers.

LC-MS (method 10): $R_t$=2.28 min; m/z=532 (M+H)$^+$.

Example 48 and Example 49

4-{[{4-[(2-tert-Butyl-5-oxo-5,6-dihydro-4H-1,3,4-oxadiazin-4-yl)methyl]phenyl}-(cyclopentyl)acetyl]amino}-2,3-dihydro-1H-indene-2-carboxylic acid (diastereomers 1 and 2)

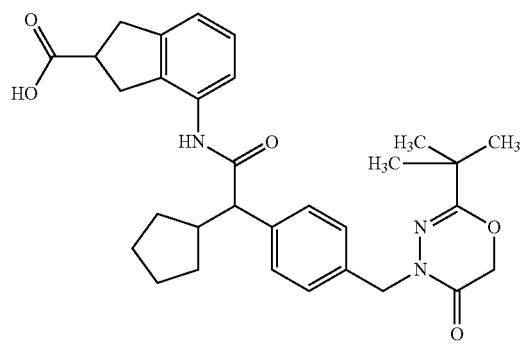 [SMILES: CC(C)(C)C1=NN(Cc2ccc(C(C(=O)Nc3cccc4c3CC(C(=O)O)C4)C3CCCC3)cc2)C(=O)CO1]

62 mg (0.117 mmol) of the mixture of diastereomers of 4-{[{4-[(2-tert-butyl-5-oxo-5,6-dihydro-4H-1,3,4-oxadiazin-4-yl)methyl]phenyl}(cyclopentyl)acetyl] amino}-2,3- dihydro-1H-indene-2-carboxylic acid obtained (Example 47) were separated further by preparative HPLC on a chiral phase [column: chiral silica gel phase based on the selector poly(N-methacryloyl-L-leucine-tert-butylamide, 670 mm×40 mm; mobile phase: ethyl acetate; flow rate: 80 ml/min; UV detection: 260 nm; temperature: 24° C.]:

Example 48

Diastereomer 1

$R_t$ 2.63 min; >97.5% ee (column: see above)
Yield: 23 mg

Example 49

Diastereomer 2

$R_t$ 4.04 min; >98% ee (column: see above)
Yield: 27 mg.

Example 50

4-[(5,5,5-Trifluoro-2-{4-[(5-oxo-2-phenyl-5,6-dihydro-4H-1,3,4-oxadiazin-4-yl)methyl]phenyl}pentanoyl)amino]-2,3-dihydro-1H-indene-2-carboxylic acid (mixture of diastereomers)

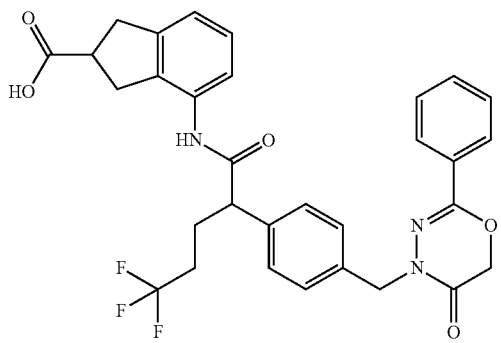 [SMILES: O=C(O)C1Cc2cccc(NC(=O)C(CCC(F)(F)F)c3ccc(CN4N=C(c5ccccc5)OCC4=O)cc3)c2C1]

32 mg (0.76 mmol) of lithium hydroxide monohydrate were added to a solution of 112 mg (0.19 mmol) of methyl 4-[(5,5,5-trifluoro-2-{4-[(5-oxo-2-phenyl-5,6-dihydro-4H-1,3,4-oxadiazin-4-yl)methyl]phenyl}pentanoyl)amino]-2,3-dihydro-1H-indene-2-carboxylate (Example 143A) in 2 ml of THF and 1 ml of water, and the mixture was stirred at room temperature overnight. The reaction mixture was then adjusted to pH 2 with 1 M hydrochloric acid and extracted twice with ethyl acetate. The combined organic phases were dried over magnesium sulfate, filtered and then concentrated to dryness under reduced pressure. The residue obtained was purified by preparative HPLC. This gave 74 mg (0.13 mmol, 68% of theory) of the title compound as a mixture of diastereomers.

LC-MS (method 10): $R_t$=2.19 min; m/z=580 (M+H)$^+$.

51 and Example 52

4-[(5,5,5-Trifluoro-2-{4-[(5-oxo-2-phenyl-5,6-dihydro-4H-1,3,4-oxadiazin-4-yl)methyl]phenyl}pentanoyl)amino]-2,3-dihydro-1H-indene-2-carboxylic acid (diastereomers 1 and 2)

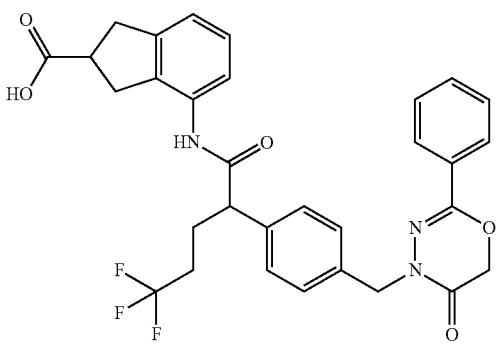 [SMILES: O=C(O)C1Cc2cccc(NC(=O)C(CCC(F)(F)F)c3ccc(CN4N=C(c5ccccc5)OCC4=O)cc3)c2C1]

74 mg (0.13 mmol) of the mixture of diastereomers of 4-[(5,5,5-trifluoro-2-{4-[(5-oxo-2-phenyl-5,6-dihydro-4H-1,3,4-oxadiazin-4-yl)methyl]phenyl}pentanoyl)amino]-2,3-dihydro-1H-indene-2-carboxylic acid obtained (Example 50) were separated further by preparative HPLC on a chiral phase [column: Daicel Chiralpak AD-H, 5 μm, 250 mm×20 mm; mobile phase: isohexane/(ethanol+0.2% trifluoroacetic acid+1% water) 50:50 (v/v); flow rate: 15 ml/min; UV detection: 220 nm; temperature: 30° C.]:

Example 51

Diastereomer 1

$R_t$ 5.61 min; purity >99%; >99% ee (column: see above)
Yield: 20 mg
LC-MS (method 11): $R_t$=1.34 min; m/z=580 (M+H)$^+$.

Example 52

Diastereomer 2

$R_t$ 9.21 min; purity >99%; >99% ee (column: see above)
Yield: 39 mg
$^1$H-NMR (400 MHz, DMSO-$d_6$, δ/ppm): 12.45-12.10 (1H, s), 9.57 (1H, s), 7.76 (2H, d), 7.53-7.31 (8H, m), 7.07 (1H, t), 6.97 (1H, d), 4.91 (2H, s), 4.86 (2H, s), 3.99 (1H, t), 3.24-3.12 (1H, m), 3.08 (2H, d), 2.98 (2H, t), 2.29-2.10 (3H, m), 1.97-1.82 (1H, m).

LC-MS (method 11): $R_t$=1.34 min; m/z=580 (M+H)$^+$.

Example 53

3-{3-[(3-Methyl-2-{4-[(5-oxo-2-phenyl-5,6-dihydro-4H-1,3,4-oxadiazin-4-yl)methyl]phenyl}butanoyl)amino]cyclohexyl}propanoic acid (mixture of isomers)

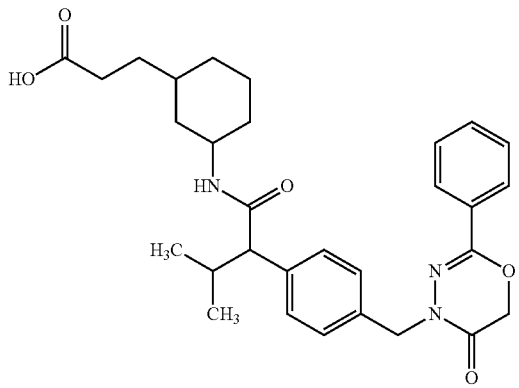 [SMILES: CC(C)C(C(=O)NC1CCCC(CCC(=O)O)C1)c1ccc(CN2N=C(c3ccccc3)OCC2=O)cc1]

94 mg (2.25 mmol) of lithium hydroxide monohydrate were added to a solution of 600 mg (1.12 mmol) of methyl 3-{3-[(3-methyl-2-{4-[(5-oxo-2-phenyl-5,6-dihydro-4H-1,3,4-oxadiazin-4-yl)methyl]phenyl}butanoyl)amino]cyclohexyl}propanoate (Example 142A) in 15 ml of THF and 15 ml of water, and the mixture was stirred at room temperature overnight. The reaction mixture was then adjusted to pH 2 with 1 M hydrochloric acid and extracted twice with ethyl acetate. The combined organic phases were dried over magnesium sulfate, filtered and then concentrated to dryness under reduced pressure. This gave 573 mg (1.10 mmol, 98% of theory) of the title compound as a mixture of isomers.

LC-MS (method 7): $R_t$=2.48 min, m/z=520 (M+H)$^+$ (diastereomer 1); $R_t$=2.52 min, m/z=520 (M+H)$^+$ (diastereomer 2).

Examples 54-57

3-{3-[(3-Methyl-2-{4-[(5-oxo-2-phenyl-5,6-dihydro-4H-1,3,4-oxadiazin-4-yl)methyl]phenyl}butanoyl)amino]cyclohexyl}propanoic acid (isomers 1-4)

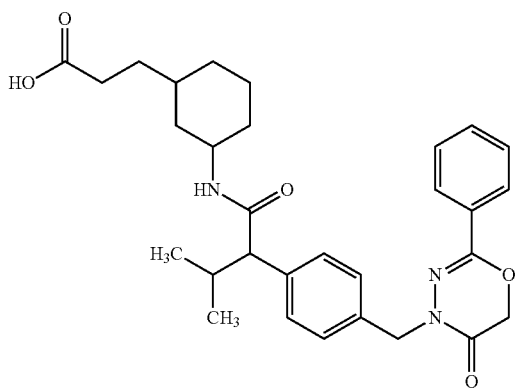 [SMILES: CC(C)C(C(=O)NC1CCCC(CCC(=O)O)C1)c1ccc(CN2N=C(c3ccccc3)OCC2=O)cc1]

573 mg (1.10 mmol) of the mixture of isomers of 3-{3-[(3-methyl-2-{4-[(5-oxo-2-phenyl-5,6-dihydro-4H-1,3,4-oxadiazin-4-yl)methyl]phenyl}butanoyl)amino]cyclohexyl}propanoic acid obtained (Example 53) were initially separated by preparative HPLC into the two diastereomers [column: Kromasil 100 C18, 5 µm, 250 mm×20 mm; mobile phase: water/acetonitrile/1% trifluoroacetic acid 40:50:10 (v/v); flow rate: 25 ml/min; UV detection: 210 nm; temperature: 40° C.; yield: 209 mg diastereomer 1 $R_t$=7.37 min, 243 mg diastereomer 2 $R_t$=7.77 min].

209 mg of the diastereomer 1 obtained in this manner were then separated further into the enantiomers by preparative HPLC on a chiral phase [Daicel Chiralpak AS-H, 5 µm, 250 mm×20 mm; mobile phase: isohexane/(ethanol+0.2% trifluoroacetic acid+1% water) 80:20 (v/v); flow rate: 15 ml/min; UV detection: 220 nm; temperature: 30° C.]:

Example 54

Diastereomer 1/Enantiomer 1

$R_t$ 6.24 min; purity >99%; >99% ee (Daicel column: see above)

Yield: 19 mg $^1$H-NMR (400 MHz, DMSO-d$_6$, δ/ppm): 11.98 (1H, s), 7.84 (1H, s), 7.76 (2H, d), 7.52-7.41 (3H, m), 7.33-7.22 (4H, m), 4.91 (2H, s), 4.84 (2H, s), 3.48-3.35 (1H, m), 2.93 (1H, d), 2.27-2.12 (3H, m), 1.82 (1H, d), 1.60 (2H, d), 1.52 (1H, d), 1.46-1.34 (2H, m), 1.31-1.05 (2H, m), 1.00-0.87 (1H, m), 0.92 (3H, d), 0.80-0.64 (2H, m), 0.59 (3H, d).

LC-MS (method 11): $R_t$=1.27 min; m/z=520 (M+H)$^+$.

Example 55

Diastereomer 1/Enantiomer 2

$R_t$ 14.28 min; purity >99%; >99% ee (Daicel column: see above)

Yield: 99 mg

LC-MS (method 11): $R_t$=1.27 min; m/z=520 (M+H)$^+$. 243 mg of the diastereomer 2 obtained above were also separated further into the enantiomers by preparative HPLC on a chiral phase [Daicel Chiralpak AD-H, 5 µm, 250 mm×20 mm; mobile phase: isohexane/(ethanol+0.2% trifluoroacetic acid+1% water) 80:20 (v/v); flow rate: 15 ml/min; UV detection: 220 nm; temperature: 30° C.]:

Example 56

Diastereomer 2/Enantiomer 1

$R_t$ 5.82 min; purity >99%; >99% ee (Daicel column: see above)

Yield: 17 mg $^1$H-NMR (400 MHz, DMSO-d$_6$, δ/ppm): 12.1-11.8 (1H, broad s), 7.85 (1H, s), 7.76 (2H, d), 7.53-7.41 (3H, m), 7.32-7.22 (4H, m), 4.91 (2H, s), 4.84 (2H, s), 3.48-3.35 (1H, m), 2.93 (1H, d), 2.25-2.15 (1H, m), 2.12 (2H, t), 1.79 (1H, d), 1.67 (1H, d), 1.57 (2H, t), 1.41-1.28 (2H, m), 1.28-1.11 (2H, m), 1.07-0.96 (1H, m), 0.91 (3H, d), 0.79-0.62 (2H, m), 0.59 (3H, d).

LC-MS (method 7): $R_t$=2.53 min; m/z=520 (M+H)$^+$.

Example 57

Diastereomer 2/Enantiomer 2

$R_t$ 9.89 min; purity >99%; >99% ee (Daicel column: see above)

Yield: 100 mg

LC-MS (method 7): $R_t$=2.53 min; m/z=520 (M+H)$^+$.

Example 58

3-{3-[(3-Methyl-2-{4-[(5-oxo-2-phenyl-5,6-dihydro-4H-1,3,4-oxadiazin-4-yl)methyl]-phenyl}pentanoyl)amino]phenyl}propanoic acid (mixture of isomers)

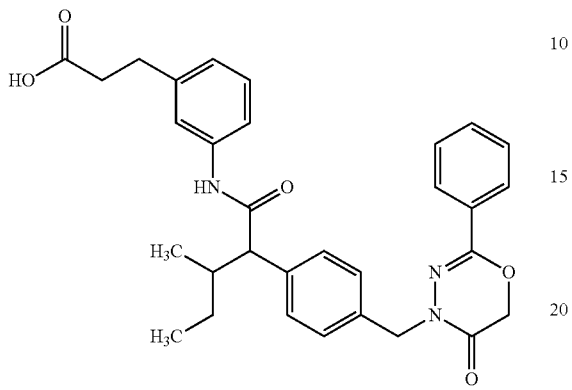

1.2 ml (1.20 mmol) of 1 N aqueous sodium hydroxide solution were added to a solution of 167 mg (0.30 mmol) of ethyl 3-{3-[(3-methyl-2-{4-[(5-oxo-2-phenyl-5,6-dihydro-4H-1,3,4-oxadiazin-4-yl)methyl]phenyl}pentanoyl)amino]phenyl}propanoate (Example 146A) in 4 ml of THF, and the mixture was stirred at room temperature overnight. After the reaction had gone to completion, the THF was removed under reduced pressure and the reaction solution was diluted with water and then adjusted to pH 2 with 1 M hydrochloric acid. The precipitated solid was filtered off, washed with water and dried under reduced pressure at 45° C. overnight. This gave 155 mg (0.29 mmol, 97% of theory) of the title compound as a mixture of isomers.

LC-MS (method 7): $R_t$=2.64 min; m/z=528 (M+H)$^+$.

Examples 59-62

3-{3-[(3-Methyl-2-{4-[(5-oxo-2-phenyl-5,6-dihydro-4H-1,3,4-oxadiazin-4-yl)methyl]-phenyl}pentanoyl)amino]phenyl}propanoic acid (isomers 1-4)

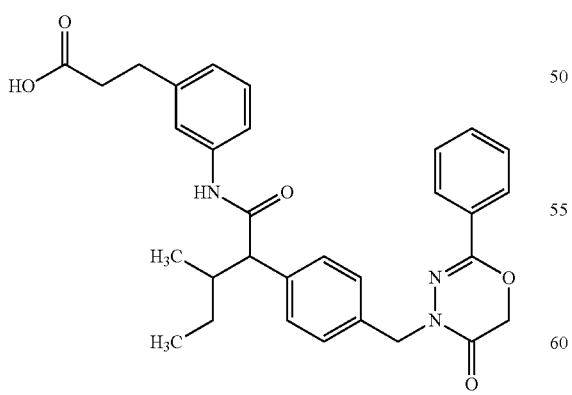

155 mg (0.29 mmol) of the mixture of isomers of 3-{3-[(3-methyl-2-{4-[(5-oxo-2-phenyl-5,6-dihydro-4H-1,3,4-oxadiazin-4-yl)methyl]phenyl}pentanoyl)amino]phenyl}propanoic acid obtained (Example 58) were separated further by preparative HPLC on a chiral phase [column: Daicel Chiralpak AS-H, 5 µm, 250 mm×20 mm; mobile phase: isohexane/(ethanol+0.2% trifluoroacetic acid+1% water) 75:25 (v/v); flow rate: 15 ml/min; UV detection: 220 nm; temperature: 25° C.]. This gave two fractions, each of which was re-separated by further HPLC chromatography on a chiral phase [column: Daicel Chiralpak AD-H, 5 µm, 250 mm×20 mm; mobile phase: isohexane/(ethanol+0.2% trifluoroacetic acid+1% water) 75:25 (v/v); flow rate: 15 ml/min; UV detection: 220 nm; temperature: 25° C.]:

Example 59

Isomer 1

$R_t$ 6.81 min; purity >99%; >99% ee (Daicel AD-H column: see above)

Yield: 49 mg

LC-MS (method 11): $R_t$=1.36 min; m/z=528 (M+H)$^+$.

Example 60

Isomer 2

$R_t$ 7.51 min; purity >99%; >99% ee (Daicel AD-H column: see above)

Yield: 24 mg $^1$H-NMR (400 MHz, DMSO-d$_6$, δ/ppm): 12.09 (1H, s), 10.02 (1H, s), 7.76 (2H, d), 7.52-7.35 (7H, m), 7.31 (2H, d), 7.14 (1H, t), 6.86 (1H, d), 4.90 (2H, s), 4.84 (2H, s), 3.36 (1H, d), 2.74 (2H, t), 2.47 (2H, t), 2.23-2.10 (1H, m), 1.21-1.07 (1H, m), 0.96 (3H, d), 0.94-0.79 (1H, m), 0.74 (3H, t).

LC-MS (method 11): $R_t$=1.35 min; m/z=528 (M+H)$^+$.

Example 61

Isomer 3

$R_t$ 8.20 min; purity >99%; >99% ee (Daicel AD-H column: see above)

Yield: 44 mg $^1$H-NMR (400 MHz, DMSO-d$_6$, δ/ppm): 12.09 (1H, s), 10.02 (1H, s), 7.76 (2H, d), 7.53-7.35 (7H, m), 7.31 (2H, d), 7.14 (1H, t), 6.86 (1H, d), 4.90 (2H, s), 4.84 (2H, s), 3.33 (1H, d), 2.73 (2H, t), 2.47 (2H, t), 2.24-2.10 (1H, m), 1.59-1.46 (1H, m), 1.27-1.10 (1H, m), 0.90 (3H, t), 0.61 (3H, d).

LC-MS (method 11): $R_t$=1.36 min; m/z=528 (M+H)$^+$.

Example 62

Isomer 4

$R_t$ 9.42 min; purity >99%; >99% ee (Daicel AD-H column: see above)

Yield: 17 mg

LC-MS (method 11): $R_t$=1.35 min; m/z=528 (M+H)$^+$.

Example 63

4-[(3-Methyl-2-{4-[(5-oxo-2-phenyl-5,6-dihydro-4H-1,3,4-oxadiazin-4-yl)methyl]phenyl}-pentanoyl)amino]-2,3-dihydro-1H-indene-2-carboxylic acid (mixture of isomers)

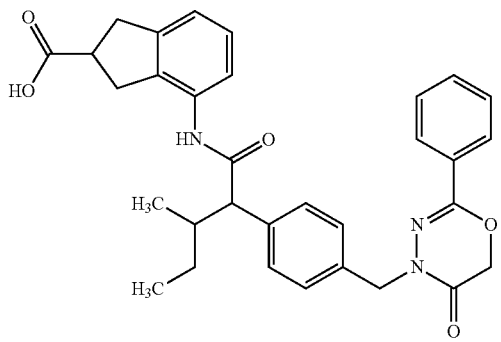 [SMILES: CCC(C)C(C(=O)Nc1cccc2c1CC(C(=O)O)C2)c1ccc(CN2N=C(c3ccccc3)OCC2=O)cc1]

A solution of 180 mg (0.31 mmol) of methyl 4-[(3-methyl-2-{4-[(5-oxo-2-phenyl-5,6-dihydro-4H-1,3,4-oxadiazin-4-yl)methyl]phenyl}pentanoyl)amino]-2,3-dihydro-1H-indene-2-carboxylate (Example 147A) in 3.6 ml of THF and 1.3 ml (1.3 mmol) of 1 N aqueous sodium hydroxide solution was stirred at room temperature overnight. After the reaction had gone to completion, the THF was removed under reduced pressure and the reaction solution was diluted with water and then adjusted to pH 2 with 1 M hydrochloric acid. The precipitated solid was filtered off, washed with water and dried under reduced pressure at 45° C. overnight. This gave 159 mg (0.29 mmol, 91% of theory) of the title compound as a mixture of isomers.

LC-MS (method 10): $R_t$=2.18 min; m/z=540 (M+H)$^+$.

Examples 64-67

4-[(3-Methyl-2-{4-[(5-oxo-2-phenyl-5,6-dihydro-4H-1,3,4-oxadiazin-4-yl)methyl]phenyl}-pentanoyl)amino]-2,3-dihydro-1H-indene-2-carboxylic acid (isomers 1-4)

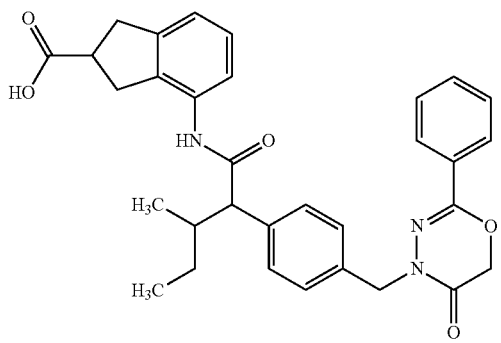 [SMILES: CCC(C)C(C(=O)Nc1cccc2c1CC(C(=O)O)C2)c1ccc(CN2N=C(c3ccccc3)OCC2=O)cc1]

159 mg (0.29 mmol) of the mixture of isomers of 4-[(3-methyl-2-{4-[(5-oxo-2-phenyl-5,6-dihydro-4H-1,3,4-oxadiazin-4-yl)methyl]phenyl}pentanoyl)amino]-2,3-dihydro-1H-indene-2-carboxylic acid obtained (Example 63) were separated further by preparative HPLC on a chiral phase [column: Daicel Chiralpak AD-H, 5 µm, 250 mm×20 mm; mobile phase: isohexane/(isopropanol+0.2% trifluoroacetic acid+1% water) 70:30 (v/v); flow rate: 15 ml/min; UV detection: 220 nm; temperature: 30° C.]:

Example 64

Isomer 1

$R_t$ 9.91 min; purity >99%; >97.5% ee (column: see above)
Yield: 17 mg
LC-MS (method 7): $R_t$=2.65 min; m/z=540 (M+H)$^+$.

Example 65

Isomer 2

$R_t$ 11.26 min; purity >99%; >98% ee (column: see above)
Yield: 14 mg
LC-MS (method 7): $R_t$=2.60 min; m/z=540 (M+H)$^+$.

Example 66

Isomer 3

$R_t$ 12.27 min; purity >99%; >98% ee (column: see above)
Yield: 34 mg
LC-MS (method 7): $R_t$=2.65 min; m/z=540 (M+H)$^+$.

Example 67

Isomer 4

$R_t$ 12.94 min; purity >99%; >98% ee (column: see above)
Yield: 35 mg
$^1$H-NMR (400 MHz, DMSO-d$_6$, δ/ppm): 12.28 (1H, s), 9.49 (1H, s), 7.76 (2H, d), 7.53-7.36 (5H, m), 7.35-7.25 (3H, m), 7.04 (1H, t), 6.95 (1H, d), 4.91 (2H, s), 4.86 (2H, s), 3.49 (1H, d), 3.25-3.18 (1H, m), 3.09 (2H, t), 3.00 (2H, d), 2.22-2.08 (1H, m), 1.62-1.48 (1H, m), 1.29-1.15 (1H, m), 0.92 (3H, t), 0.61 (3H, d).
LC-MS (method 7): $R_t$=2.66 min; m/z=540 (M+H)$^+$.

Example 68

4-{[(3-Methyl-2-{4-[(5-oxo-2-phenyl-5,6-dihydro-4H-1,3,4-oxadiazin-4-yl)methyl]phenyl}-pentanoyl)amino]methyl}cyclohexanecarboxylic acid (mixture of isomers)

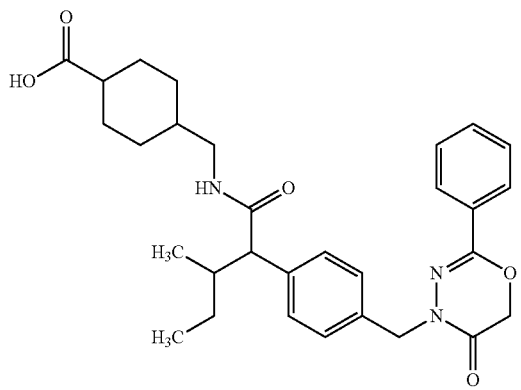 [SMILES: CCC(C)C(C(=O)NCC1CCC(C(=O)O)CC1)c1ccc(CN2N=C(c3ccccc3)OCC2=O)cc1]

A solution of 492 mg (0.90 mmol) of ethyl 4-{[(3-methyl-2-{4-[(5-oxo-2-phenyl-5,6-dihydro-4H-1,3,4-oxadiazin-4-yl)methyl]phenyl}pentanoyl)amino]methyl}cyclohexanecarboxylate (Example 150A) in 8 ml of THF and 4.6 ml (4.6 mmol) of 1 N aqueous sodium hydroxide solution was stirred at 60° C. for four days. After the reaction had gone to completion, the THF was removed under reduced pressure and the reaction solution was diluted with water and then adjusted to pH 2 with 1 M hydrochloric acid. The precipitated solid was filtered off, washed with water and dried under reduced pressure at 45° C. overnight. This gave 343 mg (0.66 mmol, 73% of theory) of the title compound as a mixture of isomers.

LC-MS (method 7): $R_t$=2.48 min and 2.52 min; m/z=520 (M+H)$^+$.

Examples 69-75

4-{[(3-Methyl-2-{4-[(5-oxo-2-phenyl-5,6-dihydro-4H-1,3,4-oxadiazin-4-yl)methyl]phenyl}-pentanoyl)amino]methyl}cyclohexanecarboxylic acid (isomers 1-7)

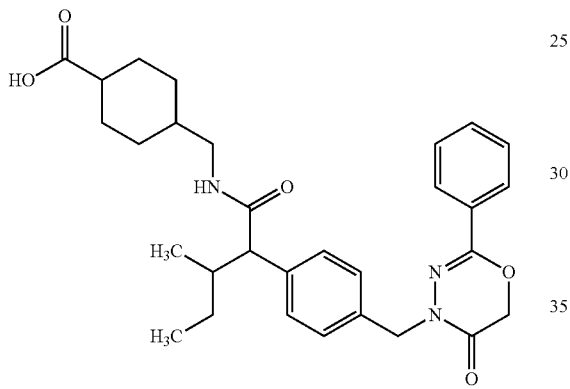

343 mg (0.66 mmol) of the mixture of isomers of 4-{[(3-methyl-2-{4-[(5-oxo-2-phenyl-5,6-dihydro-4H-1,3,4-oxadiazin-4-yl)methyl]phenyl}pentanoyl)amino]methyl}cyclohexanecarboxylic acid obtained (Example 68) were separated into the individual isomers by preparative HPLC on a chiral phase [column: Daicel Chiralpak AD-H, 5 μm, 250 mm×20 mm; mobile phase: isohexane/(ethanol+0.2% trifluoroacetic acid+1% water) 75:25 (v/v); flow rate: 15 ml/min; UV detection: 220 nm; temperature: 30° C.]. This gave 18 fractions which were re-chromatographed using a mobile phase composition of isohexane/(isopropanol+0.2% trifluoroacetic acid+1% water) 75:25 (v/v) under otherwise identical conditions.

Example 69

Isomer 1

$R_t$ 4.71 min; purity >95% (column: see above)
Yield: 19 mg
LC-MS (method 10): $R_t$=2.03 min; m/z=520 (M+H)$^+$.

Example 70

Isomer 2

$R_t$ 5.18 min; purity >88% (column: see above)
Yield: 5 mg
LC-MS (method 7): $R_t$=2.08 min; m/z=520 (M+H)$^+$.

Example 71

Isomer 3

$R_t$ 5.79 min; purity >93% (column: see above)
Yield: 5 mg
LC-MS (method 7): $R_t$=2.08 min; m/z=520 (M+H)$^+$.

Example 72

Isomer 4

$R_t$ 6.92 min; purity >99% (column: see above)
Yield: 55 mg
$^1$H-NMR (400 MHz, DMSO-d$_6$, δ/ppm): 12.4-11.6 (1H, broad s), 7.95 (1H, t), 7.76 (2H, d), 7.53-7.39 (3H, m), 7.32-7.21 (4H, m), 4.91 (2H, s), 4.84 (2H, s), 3.09 (1H, d), 3.04-2.91 (1H, m), 2.78-2.64 (1H, m), 2.40-2.28 (1H, m), 2.12-2.00 (1H, m), 1.82-1.69 (2H, m), 1.54-1.29 (6H, m), 1.18-0.98 (3H, m), 0.86 (3H, t), 0.55 (3H, d).
LC-MS (method 7): $R_t$=2.08 min; m/z=520 (M+H)$^+$.

Example 73

Isomer 5

$R_t$ 7.92 min; purity >97.5% (column: see above)
Yield: 41 mg
LC-MS (method 7): $R_t$=2.08 min; m/z=520 (M+H)$^+$.

Example 74

Isomer 6

$R_t$ 9.33 min; purity >99% (column: see above)
Yield: 88 mg
LC-MS (method 7): $R_t$=2.07 min; m/z=520 (M+H)$^+$.

Example 75

Isomer 7

$R_t$ 9.62 min; purity >93% (column: see above)
Yield: 14 mg
LC-MS (method 7): $R_t$=2.08 min; m/z=520 (M+H)$^+$.

Example 76

3-{2-Methyl-3-[(3-methyl-2-{4-[(5-oxo-2-phenyl-5,6-dihydro-4H-1,3,4-oxadiazin-4-yl)methyl]phenyl}pentanoyl)amino]phenyl}propanoic acid (mixture of isomers)

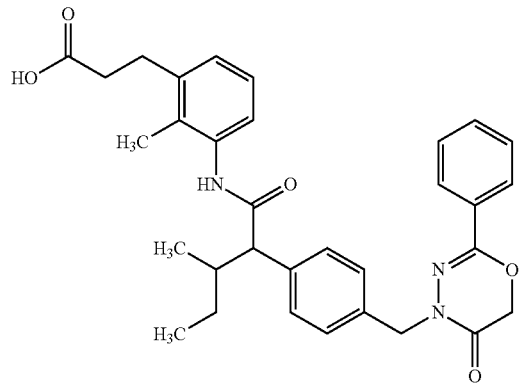 [SMILES: CCC(C)C(C(=O)Nc1cccc(CCC(=O)O)c1C)c1ccc(CN2N=C(c3ccccc3)OCC2=O)cc1]

A solution of 175 mg (0.31 mmol) of ethyl 3-{2-methyl-3-[(3-methyl-2-{4-[(5-oxo-2-phenyl-5,6-dihydro-4H-1,3,4-oxadiazin-4-yl)methyl]phenyl}pentanoyl)amino]phenyl}propanoate (Example 151A) in 5.5 ml of THF and 1.2 ml (1.2 mmol) of 1 N aqueous sodium hydroxide solution was stirred at 60° C. overnight. After the reaction had gone to completion, the THF was removed under reduced pressure and the reaction solution was diluted with water and then adjusted to pH 2 with 1 M hydrochloric acid. The precipitated solid was filtered off, washed with water and dried under reduced pressure at 45° C. overnight. This gave 165 mg (0.30 mmol, 99% of theory) of the title compound as a mixture of isomers.

LC-MS (method 10): $R_t$=2.13 min; m/z=542 (M+H)$^+$.

Examples 77-80

3-{2-Methyl-3-[(3-methyl-2-{4-[(5-oxo-2-phenyl-5,6-dihydro-4H-1,3,4-oxadiazin-4-yl)methyl]phenyl}pentanoyl)amino]phenyl}propanoic acid (isomers 1-4)

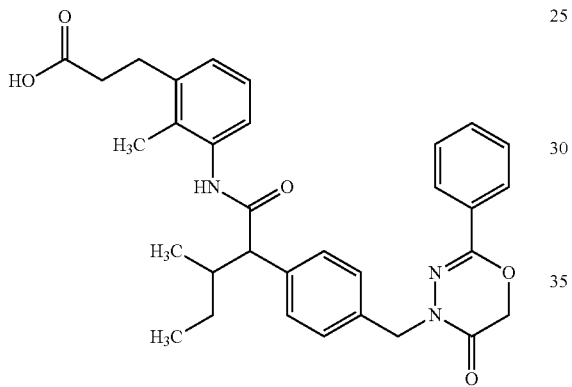

240 mg (0.44 mmol) of the mixture of isomers of 4-{[(3-methyl-2-{-4-[(5-oxo-2-phenyl-5,6-dihydro-4H-1,3,4-oxadiazin-4-yl)methyl]phenyl}pentanoyl)amino]methyl}cyclohexanecarboxylic acid obtained (Example 76) were separated further by preparative HPLC on a chiral phase [column: Daicel Chiralpak IC, 5 µm, 250 mm×20 mm; mobile phase: (tert-butyl methyl ether+0.2% glacial acetic acid)/methanol 90:10 (v/v); flow rate: 15 ml/min; UV detection: 220 nm; temperature: 25° C.]:

Example 77

Isomer 1

$R_t$ 7.72 min; purity >99%; >98% ee
[column: Daicel Chiralpak AD-H, 5 µm, 250 mm×4.6 mm; mobile phase: isohexane/(isopropanol+0.2% trifluoroacetic acid+1% water) 75:25 (v/v); flow rate: 2 ml/min; UV detection: 220 nm; temperature: 45° C.]
Yield: 69 mg
$^1$H-NMR (400 MHz, DMSO-d$_6$, δ/ppm): 12.4-11.8 (1H, broad s), 9.48 (1H, s), 7.76 (2H, d), 7.53-7.42 (3H, m), 7.39 (2H, d), 7.31 (2H, d), 7.06-6.91 (3H, m), 4.92 (2H, s), 4.87 (2H, s), 3.45 (1H, d), 2.76 (2H, t), 2.40 (2H, t), 2.22-2.09 (1H, m), 1.94 (3H, s), 1.30-1.09 (1H, m), 1.01 (3H, d), 0.96-0.81 (1H, m), 0.76 (3H, t).
LC-MS (method 7): $R_t$=2.62 min; m/z=542 (M+H)$^+$.

Example 78

Isomer 2

$R_t$ 8.53 min; purity >99%; >98% ee (analytical column: see above)
Yield: 66 mg
LC-MS (method 7): $R_t$=2.62 min; m/z=542 (M+H)$^+$.

Example 79

Isomer 3

$R_t$ 8.84 min; purity >99%; >98% ee (analytical column: see above)
Yield: 37 mg
LC-MS (method 7): $R_t$=2.62 min; m/z=542 (M+H)$^+$.

Example 80

Isomer 4

$R_t$ 8.43 min; purity >99%; >98% ee (analytical column: see above)
Yield: 37 mg
LC-MS (method 7): $R_t$=2.62 min; m/z=542 (M+H)$^+$.

Example 81

2-Methyl-4-[(3-methyl-2-{4-[(5-oxo-2-phenyl-5,6-dihydro-4H-1,3,4-oxadiazin-4-yl)methyl]phenyl}pentanoyl)amino]-2,3-dihydro-1H-indene-2-carboxylic acid (mixture of isomers)

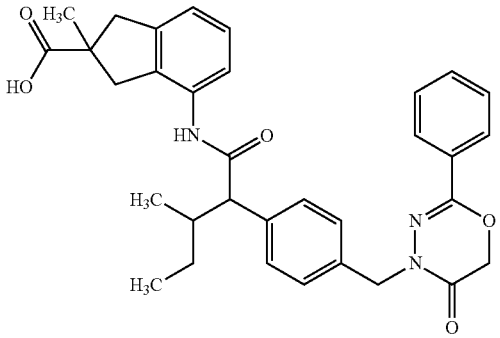 [SMILES: CCC(C)C(C(=O)Nc1cccc2c1CC(C)(C(=O)O)C2)c1ccc(CN2N=C(c3ccccc3)OCC2=O)cc1]

100 mg (2.39 mmol) of lithium hydroxide monohydrate were added to a solution of 339 mg (0.60 mmol) of methyl 2-methyl-4-[(3-methyl-2-{4-[(5-oxo-2-phenyl-5,6-dihydro-4H-1,3,4-oxadiazin-4-yl)methyl]phenyl}pentanoyl)amino]-2,3-dihydro-1H-indene-2-carboxylate (Example 160A) in 12 ml of THF and 6 ml of water, and the mixture was stirred at room temperature overnight. After the reaction had gone to completion, the THF was removed under reduced pressure and the reaction solution was diluted with water and then adjusted to pH 2 with 1 M hydrochloric acid. The precipitated solid was filtered off, washed with water and dried under reduced pressure at 45° C. overnight. This gave 305 mg (0.55 mmol, 92% of theory) of the title compound as a mixture of isomers.

LC-MS (method 10): $R_t$=2.13 min; m/z=542 (M+H)$^+$.

Examples 82-88

2-Methyl-4-[(3-methyl-2-{4-[(5-oxo-2-phenyl-5,6-dihydro-4H-1,3,4-oxadiazin-4-yl)methyl]-phenyl}pentanoyl)amino]-2,3-dihydro-1H-indene-2-carboxylic acid (isomers 1-7)

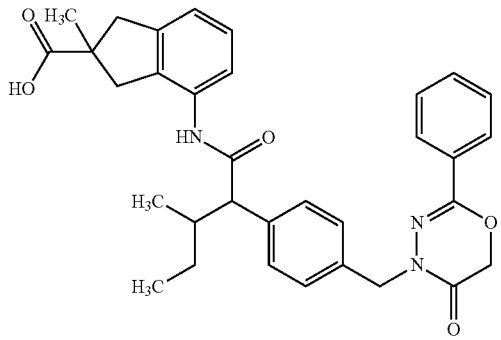 [SMILES: CCC(C)C(C(=O)Nc1cccc2c1CC(C)(C(=O)O)C2)c1ccc(CN2N=C(c3ccccc3)OCC2=O)cc1]

300 mg (0.54 mmol) of the mixture of isomers of 2-methyl-4-[(3-methyl-2-{4-[(5-oxo-2-phenyl-5,6-dihydro-4H-1,3,4-oxadiazin-4-yl)methyl]phenyl}pentanoyl)amino]-2,3-dihydro-1H-indene-2-carboxylic acid obtained (Example 81) were separated further by preparative HPLC on a chiral phase [column: Daicel Chiralpak AD-H, 5 μm, 250 mm×20 mm; mobile phase: isohexane/(isopropanol+0.2% trifluoroacetic acid+1% water) 70:30 (v/v); flow rate: 15 ml/min; UV detection: 220 nm; temperature: 30° C.]. This gave 7 fractions which were re-chromatographed under identical conditions.

Example 82

Isomer 1

$R_t$ 7.89 min; purity >94% (column: see above)
Yield: 16 mg
LC-MS (method 10): $R_t$=2.32 min; m/z=554 (M+H)$^+$.

Example 83

Isomer 2

$R_t$ 8.42 min; purity >98.5% (column: see above)
Yield: 84 mg
LC-MS (method 10): $R_t$=2.32 min; m/z=554 (M+H)$^+$.

Example 84

Isomer 3

$R_t$ 9.22 min; purity >98% (column: see above)
Yield: 14 mg
LC-MS (method 10): $R_t$=2.32 min; m/z=554 (M+H)$^+$.

Example 85

Isomer 4

$R_t$ 11.61 min; purity >96.5% (column: see above)
Yield: 25 mg
LC-MS (method 10): $R_t$=2.32 min; m/z=554 (M+H)$^+$.

Example 86

Isomer 5

$R_t$ 13.40 min; purity >97.3% (column: see above)
Yield: 66 mg
$^1$H-NMR (400 MHz, DMSO-d$_6$, δ/ppm): 12.6-11.9 (1H, broad s), 9.46 (1H, s), 7.76 (2H, d), 7.53-7.45 (3H, m), 7.39 (2H, d), 7.32 (3H, d), 7.04 (1H, m), 6.93 (1H, d), 4.91 (2H, s), 4.86 (2H, s), 3.49 (1H, d), 3.34-3.20 (2H, m), 2.75-2.61 (2H, m), 2.22-2.07 (1H, m), 1.63-1.49 (1H, m), 1.31-1.15 (1H, m), 1.23 (3H, s), 0.92 (3H, t), 0.62 (3H, d).
LC-MS (method 10): $R_t$=2.32 min; m/z=554 (M+H)$^+$.

Example 87

Isomer 6

$R_t$ 14.78 min; purity >97.2% (column: see above)
Yield: 14 mg
LC-MS (method 10): $R_t$=2.32 min; m/z=554 (M+H)$^+$.

Example 88

Isomer 7

$R_t$ 16.60 min; purity >95.5% (column: see above)
Yield: 52 mg
LC-MS (method 10): $R_t$=2.32 min; m/z=554 (M+H)$^+$.

Example 89

3-{2-Methyl-3-[(3-methyl-2-{4-[(5-oxo-2-phenyl-5,6-dihydro-4H-1,3,4-oxadiazin-4-yl)methyl]phenyl}hexanoyl)amino]phenyl}propanoic acid (mixture of isomers)

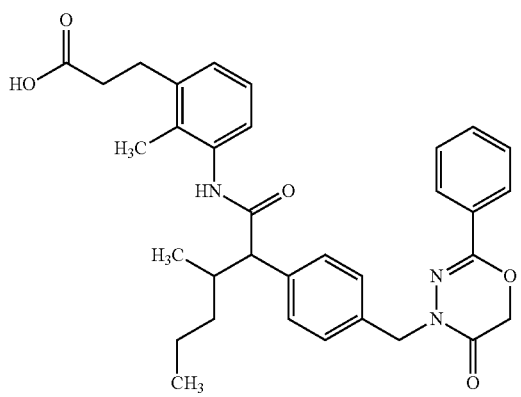

1.74 ml (22.56 mmol) of trifluoroacetic acid were added to a solution of 460 mg (0.75 mmol) of tert-butyl 3-{2-methyl-3-[(3-methyl-2-{4-[(5-oxo-2-phenyl-5,6-dihydro-4H-1,3,4-oxadiazin-4-yl)methyl]phenyl}hexanoyl)amino]phenyl}propanoate (Example 163A) in 10 ml of dichloromethane, and the mixture was stirred at room temperature for 2 h. The reaction mixture was then concentrated to dryness under reduced pressure. This gave 410 mg (0.74 mmol, 98% of theory) of the title compound as a mixture of isomers.
LC-MS (method 11): $R_t$=1.40 min; m/z=556 (M+H)$^+$.

Examples 90-93

3-{2-Methyl-3-[(3-methyl-2-{4-[(5-oxo-2-phenyl-5,6-dihydro-4H-1,3,4-oxadiazin-4-yl)methyl]phenyl}hexanoyl)amino]phenyl}propanoic acid (isomers 1-4)

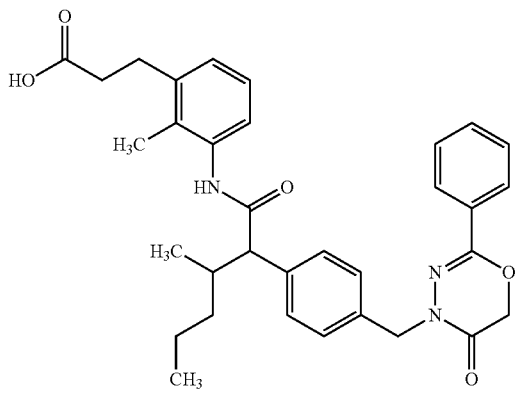 [SMILES: CCCC(C)C(C(=O)Nc1cccc(CCC(=O)O)c1C)c1ccc(CN2N=C(c3ccccc3)OCC2=O)cc1]

400 mg (0.72 mmol) of the mixture of isomers of 3-{2-methyl-3-[(3-methyl-2-{4-[(5-oxo-2-phenyl-5,6-dihydro-4H-1,3,4-oxadiazin-4-yl)methyl]phenyl}hexanoyl)amino]phenyl}propanoic acid obtained (Example 89) were separated further by preparative HPLC on a chiral phase [column: Daicel Chiralpak AD-H, 5 μm, 250 mm×20 mm; mobile phase: isohexane/(isopropanol+0.2% trifluoroacetic acid+1% water) 70:30 (v/v); flow rate: 15 ml/min; UV detection: 220 nm; temperature: 40° C.]. This gave four fractions which were re-purified by further HPLC chromatography on a chiral phase [conditions as above, or column: Daicel Chiralpak IA, 5 μm, 250 mm×20 mm; mobile phase: methanol/(tert-butyl methyl ether+0.2% glacial acetic acid) 7:93 (v/v); flow rate: 15 ml/min; UV detection: 220 nm; temperature: 40° C.].

Example 90

Isomer 1

$R_t$ 12.02 min; purity >99%; >99% ee
[column: Daicel Chiralpak AD-H, 5 μm, 250 mm×4.6 mm; mobile phase: isohexane/(isopropanol+0.2% trifluoroacetic acid+1% water) 80:20 (v/v); flow rate: 2 ml/min; UV detection: 220 nm; temperature: 30° C.]
Yield: 94 mg
$^1$H-NMR (400 MHz, DMSO-$d_6$, δ/ppm): 12.14 (1H, s), 9.48 (1H, s), 7.76 (2H, d), 7.53-7.41 (3H, m), 7.38 (2H, d), 7.31 (2H, d), 7.05-6.92 (3H, m), 4.92 (2H, s), 4.87 (2H, s), 3.40 (1H, d), 2.76 (2H, t), 2.41 (2H, t), 2.29-2.16 (1H, m), 1.94 (3H, s), 1.59-1.40 (2H, m), 1.34-1.18 (2H, m), 0.89 (3H, t), 0.63 (3H, d).
LC-MS (method 10): $R_t$=2.29 min; m/z=556 (M+H)$^+$.

Example 91

Isomer 2

$R_t$ 15.06 min; purity >99%; >99% ee (analytical column: see above)
Yield: 95 mg
LC-MS (method 10): $R_t$=2.29 min; m/z=556 (M+H)$^+$.

Example 92

Isomer 3

$R_t$ 16.42 min; purity >99%; >99% ee (analytical column: see above)
Yield: 32 mg
LC-MS (method 10): $R_t$=2.29 min; m/z=556 (M+H)$^+$.

Example 93

Isomer 4

$R_t$ 13.57 min; purity >99%; >99% ee (analytical column: see above)
Yield: 40 mg
LC-MS (method 10): $R_t$=2.29 min; m/z=556 (M+H)$^+$.

Example 94

2E)-3-{3-[(Cyclopentyl{4-[(5-oxo-2-phenyl-5,6-dihydro-4H-1,3,4-oxadiazin-4-yl)methyl]phenyl}acetyl)amino]phenyl}prop-2-enoic acid (enantiomer 1

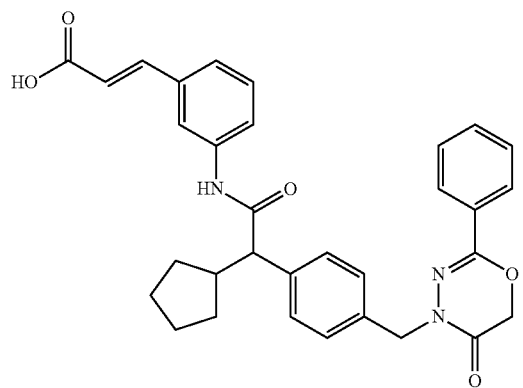 [SMILES: O=C(O)/C=C/c1cccc(NC(=O)C(c2ccc(CN3N=C(c4ccccc4)OCC3=O)cc2)C2CCCC2)c1]

Preparation Method 5

827 mg (1.461 mmol) of ethyl (2E)-3-{3-[(cyclopentyl{4-[(5-oxo-2-phenyl-5,6-dihydro-4H-1,3,4-oxadiazin-4-yl)methyl]phenyl}acetyl)amino]phenyl}prop-2-enoate (Example 174A) were dissolved in 28 ml of dioxane/water (3:1 v/v), and 2.2 ml of 1 N aqueous sodium hydroxide solution were added. The reaction mixture was stirred at room temperature overnight. The reaction mixture was then acidified to pH 1 with 1 N hydrochloric acid and extracted repeatedly with ethyl acetate. The combined organic phases were washed with saturated sodium chloride solution, dried over sodium sulfate and concentrated under reduced pressure. This gave 780 mg (95% of theory) of the target compound.

LC-MS (method 10): $R_t$=2.52 min; m/z=538 (M+H)$^+$.

The compounds listed in the table below were obtained in an analogous manner:

| Example | Name/Structure Preparation method/Starting material | Analytical data |
|---|---|---|
| 95 | (2E)-3-{2-[(cyclopentyl{4-((5-oxo-2-phenyl-5,6-dihydro-4H-1,3,4-oxadiazin-4-yl)methyl]phenyl}-acetyl)amino]phenyl}prop-2-enoic acid (enantiomer 1)<br><br>preparation method 5 (from Ex. 109A) | LC-MS (method 11): $R_t$ = 1.33 min; m/z = 538 $(M + H)^+$. |
| 96 | (2E)-3-{4-[(cyclopentyl{4-[(5-oxo-2-phenyl-5,6-dihydro-4H-1,3,4-oxadiazin-4-yl)methyl]phenyl}-acetyl)amino]phenyl}prop-2-enoic acid (enantiomer 1)<br><br>preparation method 5 (from Ex. 111A) | LC-MS (method 12): $R_t$ = 2.56 min; m/z = 538 $(M + H)^+$. |
| 97 | (2E)-3-{2-[(3-methyl-2-{4-[(5-oxo-2-phenyl-5,6-dihydro-4H-1,3,4-oxadiazin-4-yl)methyl]phenyl}-butanoyl)amino]phenyl}prop-2-enoic acid (enantiomer 1)<br><br>preparation method 5 (from Ex. 192A) | LC-MS (method 10): $R_t$ = 2.04 min; m/z = 512 $(M + H)^+$. |

| Example | Name/Structure Preparation method/Starting material | Analytical data |
|---|---|---|
| 98 | (2E)-3-{4-[(3-methyl-2-{4-[(5-oxo-2-phenyl-5,6-dihydro-4H-1,3,4-oxadiazin-4-yl)methyl]phenyl}-butanoyl)amino]phenyl}prop-2-enoic acid (enantiomer 1)<br>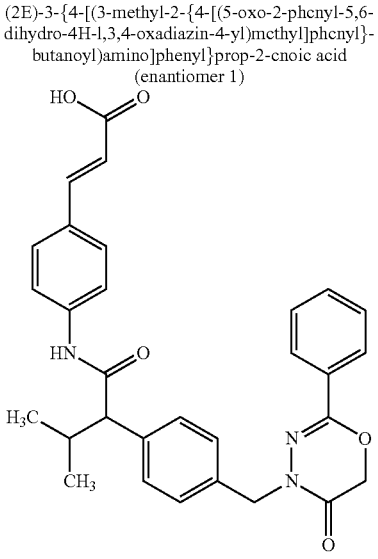<br>preparation method 5 (from Ex. 176A) | LC-MS (method 11):<br>$R_t$ = 1.29 min;<br>m/z = 512<br>$(M + H)^+$. |
| 99 | (2E)-3-{3-[(2-{4-[(2-tert-butyl-5-oxo-5,6-dihydro-4H-1,3,4-oxadiazin-4-yl)methyl]phenyl}-3-methyl-butanoyl)amino]phenyl}prop-2-enoic acid (racemate)<br>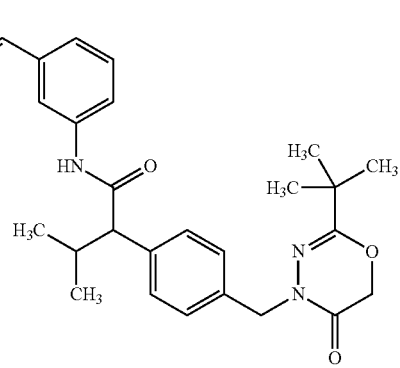<br>preparation method 5 (from Ex. 178A) | LC-MS (method 7):<br>$R_t$ = 2.65 min;<br>m/z = 492<br>$(M + H)^+$. |

Example 100

3-{4-[(Cyclopentyl{4-[(5-oxo-2-phenyl-5,6-dihydro-4H-1,3,4-oxadiazin-4-yl)methyl]phenyl}acetyl)amino]phenyl}propanoic acid (enantiomer 1)

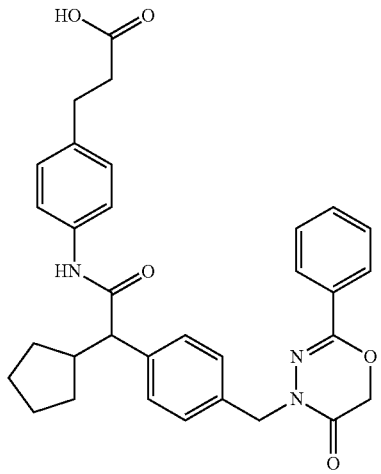 [SMILES: O=C(O)/C=C/c1ccc(NC(=O)C(c2ccc(CN3N=C(c4ccccc4)OCC3=O)cc2)C2CCCC2)cc1]

50 mg of palladium on carbon (10%) were added to a solution of 46 mg (0.085 mmol) of (2E)-3-{4-[(cyclopentyl{4-[(5-oxo-2-phenyl-5,6-dihydro-4H-1,3,4-oxadiazin-4-yl)methyl]phenyl}acetyl)amino]phenyl}prop-2-enoic acid (Example 96) in 10 ml of ethanol. Under an atmosphere of hydrogen, the mixture was hydrogenated at atmospheric pressure for 2 h. The reaction mixture was then filtered through Tonsil, the filter residue was washed with ethanol and the combined filtrates were concentrated on a rotary evaporator. The crude product was purified by preparative HPLC. This gave 29 mg (63% of theory) of the title compound.

LC-MS (method 11): $R_t$=1.35 min; m/z=540 $(M+H)^+$.

The compounds listed in the table below were obtained in an analogous manner:

| Example | Name/Structure/Starting material | Analytical data |
|---------|----------------------------------|-----------------|
| 101 | 3-{2-[(cyclopentyl{4-[(5-oxo-2-phenyl-5,6-dihydro-4H-1,3,4-oxadiazin-4-yl)methyl]phenyl}acetyl)amino]phenyl}propanoic acid (enantiomer 1)<br><br>(from Ex. 95) | LC-MS (method 11): $R_t$ = 1.33 min; m/z = 540 $(M + H)^+$. |
| 102 | 3-{3-[(2-{4-[(2-tert-butyl-5-oxo-5,6-dihydro-4H-1,3,4-oxadiazin-4-yl)methyl]phenyl}-3-methylbutanoyl)amino]phenyl}propanoic acid (racemate)<br><br>(from Ex. 99) | LC-MS (method 11): $R_t$ = 1.32 min; m/z = 494 $(M + H)^+$. |

Example 103

3-{3-[(Cyclopentyl{4-[(5-oxo-2-phenyl-5,6-dihydro-4H-1,3,4-oxadiazin-4-yl)methyl]phenyl}acetyl)amino]phenyl}propanoic acid (enantiomer 1)

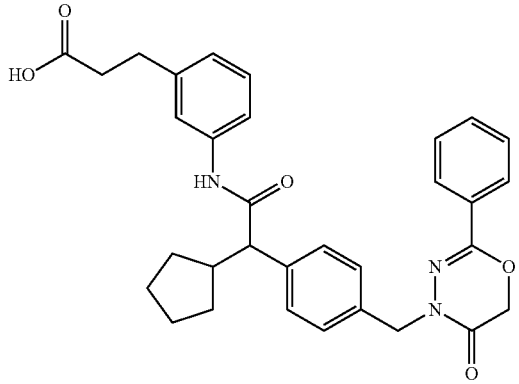 [SMILES: O=C(O)CCc1cccc(NC(=O)C(c2ccc(CN3N=C(c4ccccc4)OCC3=O)cc2)C2CCCC2)c1]

Preparation Method 6

11.05 ml of 1 N aqueous sodium hydroxide solution were added to a solution of 4.18 g (7.363 mmol) of ethyl 3-{3-[(cyclopentyl{4-[(5-oxo-2-phenyl-5,6-dihydro-4H-1,3,4-oxadiazin-4-yl)methyl]phenyl}acetyl)amino]phenyl}propanoate (Example 180A) in 195 ml of dioxane/water (4:1 v/v). The mixture was stirred at room temperature overnight and then acidified to pH 1 with 1 N hydrochloric acid and extracted repeatedly with ethyl acetate. The combined organic phases were washed with saturated sodium chloride solution, dried over sodium sulfate and concentrated on a rotary evaporator. The crude product was dissolved in ethyl acetate and filtered through silica gel. Activated carbon was added to the filtrate, and the mixture was heated at reflux and filtered through Tonsil. Concentration under reduced pressure gave 3.20 g (81% of theory) of the title compound.

LC-MS (method 11): $R_t$=1.36 min; m/z=540 (M+H)$^+$.

The compounds listed in the table below were obtained in an analogous manner:

| Example | Name/Structure Preparation method/Starting material | Analytical data |
|---|---|---|
| 104 | {3-[(cyclopentyl{4-[(5-oxo-2-pheny-1-5,6-dihydro-4H-1,3-4-oxadiazin-4-yl)methyl]phenyl}acetyl)amino]phenyl}acetic acid (enantiomer 1)<br><br>preparation method 6 (from Ex. 110A) | LC-MS (method 10): $R_t$ = 2.16 min; m/z = 526 (M + H)$^+$. |
| 105 | 3-{3-[(3-methyl-2-{4-[(5-oxo-2-phenyl-5,6-dihydro-4H-1,3,4-oxadiazin-4-yl)methyl]phenyl}butanoyl)amino]phenyl}propanoic acid (enantiomer 1)<br><br>preparation method 6 (from Ex. 193A) | $^1$H-NMR (400 MHz, DMSO-$d_6$, δ/ppm): 12.25-11.95 (1H, broad s), 10.01 (1H, s), 7.76 (2H, d), 7.53-7.35 (7H, m), 7.32 (2H, d), 7.14 (1H, t), 6.86 (1H, d), 4.90 (2H, s), 4.84 (2H, s), 3.22 (1H, d), 2.74 (2H, t), 2.48 (2H, t), 2.40-2.22 (1H, m), 1.03 (3H, d), 0.65 (3H, d). LC-MS (method 11): $R_t$ = 1.29 min; m/z = 514 (M + H)$^+$. |

| Example | Name/Structure Preparation method/Starting material | Analytical data |
|---|---|---|
| 106 | 3-{4-[(3-methyl-2-{4-[(5-oxo-2-phenyl-5,6-dihydro-4H-1,3,4-oxadiazin-4-yl)methyl]phenyl}butanoyl)-amino]phenyl}propanoic acid (enantiomer 1)<br />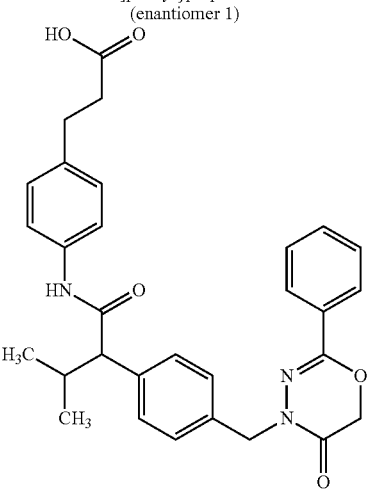<br />preparation method 6 (from Ex. 186A) | LC-MS (method 10): $R_t$ = 2.07 min; m/z = 514 (M + H)$^+$. |
| 107 | ({3-[(3-methyl-2-{4-[(5-oxo-2-phenyl-5,6-dihydro-4H-1,3,4-oxadiazin-4-yl)methyl]phenyl}butanoyl)-amino]phenyl}sulfanyl)acetic acid (enantiomer 1)<br />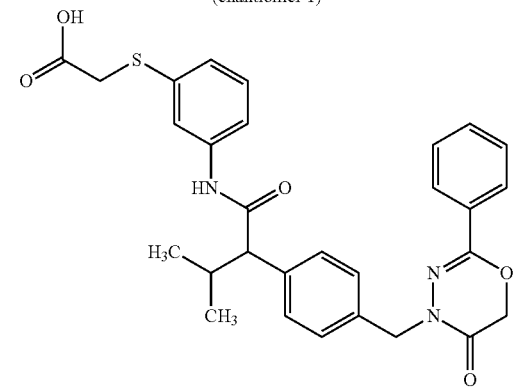<br />preparation method 6 (from Ex. 137A) | $^1$H-NMR (400 MHz, DMSO-d$_6$, δ/ppm): 12.85-12.65 (1H, broad s), 10.11 (1H, s), 7.77 (2H, d), 7.60 (1H, s), 7.53-7.40 (3H, m), 7.40-7.28 (5H, m), 7.19 (1H, t), 6.97 (1H, d), 4.90 (2H, s), 4.84 (2H, s), 3.74 (2H, s), 3.21 (1H, d), 2.39-2.25 (1H, m), 0.99 (3H, d), 0.66 (3H, d).<br />LC-MS (method 11): $R_t$ = 1.29 min; m/z = 532 (M + H)$^+$. |

| Example | Name/Structure Preparation method/Starting material | Analytical data |
|---|---|---|
| 108 | ({3-[(cyclopentyl{4-[(5-oxo-2-phenyl-5,6-dihydro-4H-1,3,4-oxadiazin-4-yl)methyl]phenyl}acetyl)-amino]phenyl}sulfanyl)acetic acid (enantiomer 1)<br><br>preparation method 2 (from Ex. 138A) | $^1$H-NMR (400 MHz, DMSO-d$_6$, δ/ppm): 12.85-12.60 (1H, broad s), 10.09 (1H, s), 7.76 (2H, d), 7.60 (1H, s), 7.53-7.28 (8H, m), 7.20 (1H, t), 6.97 (1H, d), 4.90 (2H, s), 4.84 (2H, s), 3.74 (2H, s), 3.36 (1H, d), 2.64-2.47 (1H, m), 1.86-1.71 (1H, m), 1.71-1.15 (6H, m), 1.03-0.90 (1H, m). LC-MS (method 11): R$_t$ = 1.36 min; m/z = 558 (M + H)$^+$. |
| 109 | 5-{[(cyclopentyl{4-[(5-oxo-2-phenyl-5,6-dihydro-4H-1,3,4-oxadiazin-4-yl)methyl]phenyl}acetyl)amino]methyl}isoxazol-3-carboxylic acid (enantiomer 1)<br><br>preparation method 2 (from Ex. 139A) | $^1$H-NMR (400 MHz, DMSO-d$_6$, δ/ppm): 14.2-13.8 (1H, broad s), 8.72 (1H, t), 7.77 (2H, d), 7.53-7.40 (3H, m), 7.38-7.22 (4H, m), 6.43 (1H, s), 4.91 (2H, s), 4.84 (2H, s), 4.54-4.40 (1H, m), 4.38-4.22 (1H, m), 3.21 (1H, d), 2.60-2.41 (1H, m), 1.79-1.11 (7H, m), 1.01-0.84 (1H, m), LC-MS (method 7): R$_t$ = 2.97 min; m/z = 517 (M + H)$^+$. |
| 110 | 4-{3-[(cyclopentyl{4-[(5-oxo-2-phenyl-5,6-dihydro-4H-1,3,4-oxadiazin-4-yl)methyl]phenyl}acetyl)amino]phenyl}butanoic acid (enantiomer 1)<br><br>preparation method 1 (from Ex. 179A) | LC-MS (method 11): R$_t$ = 1.39 min; m/z = 554 (M + H)$^+$. |

-continued

| Example | Name/Structure Preparation method/Starting material | Analytical data |
|---|---|---|
| 111 | 2-{3-[(cyclopentyl{4-[(5-oxo-2-phenyl-5,6-dihydro-4H-1,3,4-oxadiazin-4-yl)methyl]phenyl}acetyl)amino]-2-methylphenoxy}-2-methylpropanoic acid (enantiomer 1)<br>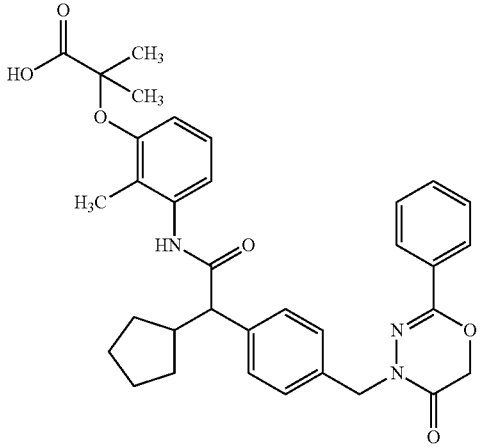 [SMILES: Cc1c(NC(=O)C(c2ccc(CN3N=C(c4ccccc4)OCC3=O)cc2)C2CCCC2)cccc1OC(C)(C)C(=O)O]<br>preparation method 1 (from Ex. 177A) | LC-MS (method 11):<br>$R_t$ = 1.40 min;<br>m/z = 584<br>$(M + H)^+$. |
| 112 | 2-methyl-2-({3-[(3-methyl-2-{4-[(5-oxo-2-phenyl-5,6-dihydro-4H-1,3,4-oxadiazin-4-yl)methyl]phenyl}-butanoyl)amino]phenyl}sulfanyl)propanoic acid (enantiomer 1)<br>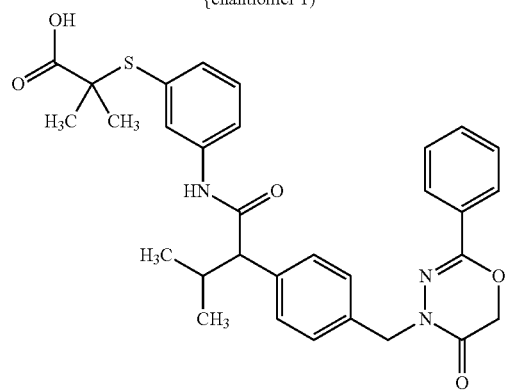<br>preparation method 2 (from Ex. 140A) | $^1$H-NMR (400 MHz, DMSO-$d_6$, δ/ppm):<br>12.70-12.45 (1H, broad s), 10.17 (1H, s), 7.81-7.71 (3H, m), 7.59 (1H, d), 7.53-7.41 (3H, m), 7.38 (2H, d), 7.31 (2H, d), 7.26 (1H, t), 7.09 (1H, d), 4.90 (2H, s), 4.85 (2H, s), 3.22 (1H, d), 2.39-2.25 (1H, m), 1.36 (6H, s), 1.00 (3H, d), 0.66 (3H, d).<br>LC-MS (method 10):<br>$R_t$ = 2.32 min; m/z = 560 $(M + H)^+$. |
| 113 | 2-({3-[(cyclopentyl{4-[(5-oxo-2-phenyl-5,6-dihydro-4H-1,3,4-oxadiazin-4-yl)methyl]phenyl}acetyl)amino]phenyl}sulfanyl)-2-methylpropanoic acid (enantiomer 1)<br>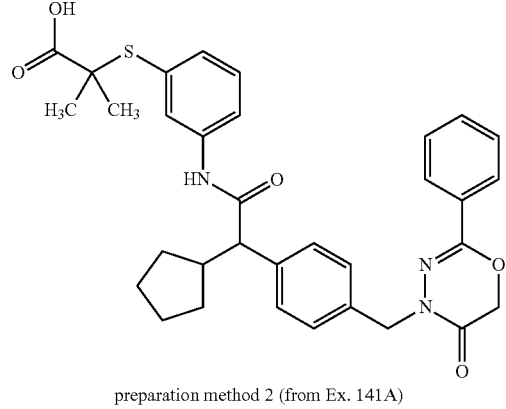<br>preparation method 2 (from Ex. 141A) | $^1$H-NMR (400 MHz, DMSO-$d_6$, δ/ppm): 12.70-12.45 (1H, broad s), 10.15 (1H, s), 7.75 (3H, t), 7.58 (1H, d), 7.53-7.40 (3H, m), 7.39 (2H, d), 7.32 (2H, d), 7.26 (1H, t), 7.09 (1H, d), 4.90 (2H, s), 4.84 (2H, s), 3.45-3.29 (1H, d), 2.65-2.47 (1H, m), 1.84-1.71 (1H, m), 1.69-1.41 (4H, m), 1.40-1.30 (1H, m), 1.36 (6H, s), 1.29-1.19 (1H, m), 1.06-0.89 (1H, m).<br>LC-MS (method 10):<br>$R_t$ = 2.43 min; m/z = 586 $(M + H)^+$. |

| Example | Name/Structure Preparation method/Starting material | Analytical data |
|---|---|---|
| 114 | 2-{3-[(cyclopentyl{4-[(5-oxo-2-phenyl-5,6-dihydro-4H-1,3,4-oxadiazin-4-yl)methyl]phenyl}acetyl)amino]phenyl}-2-methylpropanoic acid (enantiomer 1)<br>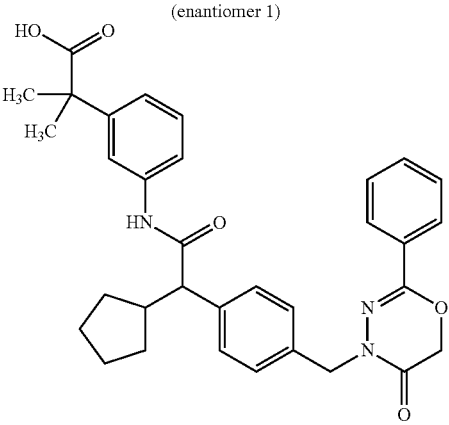<br>preparation method 1 (from Ex. 181A) | LC-MS (method 10): $R_t$ = 2.30 min; m/z = 554 $(M + H)^+$. |
| 115 | 3-{3-[(cyclopentyl{4-[(5-oxo-2-phenyl-5,6-dihydro-4H-1,3,4-oxadiazin-4-yl)methyl]phenyl}acetyl)amino]-2-methylphenyl}propanoic acid (enantiomer 1)<br>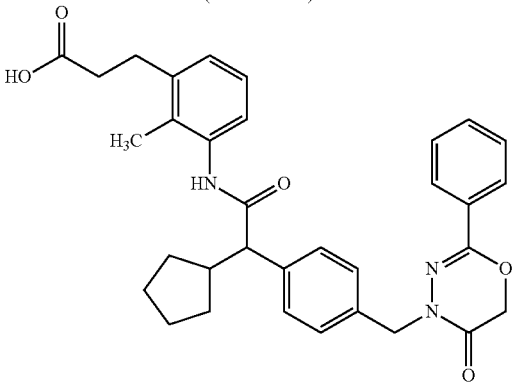<br>preparation method 3 (from Ex. 175A) | $^1$H-NMR (400 MHz, DMSO-$d_6$, δ/ppm): 12.14 (1H, s), 9.46 (1H, s), 7.77 (2H, d), 7.53-7.38 (5H, m), 7.31 (2H, d), 7.05-6.93 (3H, m), 4.92 (2H, s), 4.87 (2H, s), 3.45(1H, d), 2.77 (2H, t), 2.65-2.47 (1H, m), 2.41 (2H, t), 1.96 (3H, s), 1.89-1.77 (1H, m), 1.74-1.27 (6H, m), 1.05-0.91 (1H, m). LC-MS (method 11): $R_t$ = 1.36 min; m/z = 554 $(M + H)^+$. |
| 116 | 3-{trans-4-[(3-methyl-2-{4-[(5-oxo-2-phenyl-5,6-dihydro-4H-1,3,4-oxadiazin-4-yl)methyl]phenyl}-butanoyl)amino]cyclohexyl}propanoic acid (enantiomer 1)<br>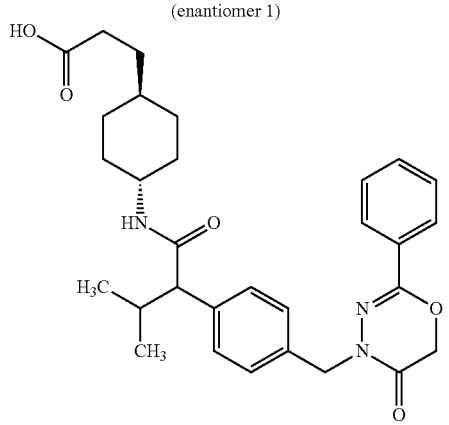<br>preparation method 2 (from Ex. 144A) | $^1$H-NMR (400 MHz, DMSO-$d_6$, δ/ppm): 12.05-11.87 (1H, broad s), 7.83 (1H, d), 7.76 (2H, d), 7.53-7.40 (3H, m), 7.32-7.22 (4H, m), 4.91 (2H, s), 4.84 (2H, s), 3.42-3.28 (1H, m), 2.93 (1H, d), 2.26-2.12 (3H, m), 1.87-1.76 (1H, m), 1.72-1.49 (3H, m), 1.41-1.32 (2H, m), 1.18-0.96 (3H, m), 0.96-0.77 (2H, m), 0.91 (3H, d), 0.59 (3H, d). LC-MS (method 10): $R_t$ = 2.03 min; m/z = 520 $(M + H)^+$. |

| Example | Name/Structure Preparation method/Starting material | Analytical data |
|---|---|---|
| 117 | 3-{cis-4-[(3-methy]-2-{4-[(5-oxo-2-phenyl-5,6-dihydro-4H-1,3,4-oxadiazin-4-yl)methyl]phenyl}-butanoyl)amino]cyclohexyl}propanoic acid (enantiomer 1)<br><br>preparation method 2 (from Ex. 145A) | ¹H-NMR (400 MHz, DMSO-d₆, δ/ppm): 12.05-11.90 (1H, broad s), 7.82-7.72 (3H, m), 7.53-7.41 (3H, m), 7.35-7.22 (4H, m), 4.91 (2H, s), 4.84 (2H, s), 3.73-3.62 (1H, m), 3.11 (1H, d), 2.27-2.12 (3H, m), 1.63-1.50 (1H, m), 1.50-1.20 (10H, m), 0.92 (3H, d), 0.61 (3H, d).<br>LC-MS (method 10):<br>R$_t$ = 2.04 min;<br>m/z = 520 (M + H)⁺. |
| 118 | 3-{trans-4-[(cyclopentyl{4-[(5-oxo-2-phenyl-5,6-dihydro-4H-1,3,4-oxadiazin-4-yl)methyl]phenyl}acetyl)-amino]cyclohexyl}propanoic acid (enantiomer 1)<br><br>preparation method 2 (from Ex. 148A) | ¹H-NMR (400 MHz, DMSO-d₆, δ/ppm): 12.2-11.8 (1H, broad s), 7.81 (1H, d), 7.77 (2H, d), 7.54-7.40 (3H, m), 7.28 (4H, q), 4.91 (2H, s), 4.83 (2H, s), 3.44-3.24 (1H, m), 3.08 (1H, d), 2.57-2.38 (1H, m), 2.17 (2H, t), 1.85-1.74 (1H, m), 1.74-0.96 (15H, m), 0.96-0.77 (3H, m),<br>LC-MS (method 7):<br>R$_t$ = 2.61 min;<br>m/z = 546 (M + H)⁺. |
| 119 | 3-{cis-4-[(cyclopentyl{4-[(5-oxo-2-phenyl-5,6-dihydro-4H-1,3,4-oxadiazin-4-yl)methyl]phenyl}-acetyl)amino]cyclohexyl}propanoic acid (enantiomer 1)<br><br>preparation method 2 (from Ex. 149A) | ¹H-NMR (400 MHz, DMSO-d₆, δ/ppm): 11.98 (1H, s), 7.77 (3H, d), 7.54-7.41 (3H, m), 7.33 (2H, d), 7.26 (2H, d), 4.91 (2H, s), 4.84 (2H, s), 3.74-3.62 (1H, m), 3.26 (1H, d), 2.57-2.39 (1H, m), 2.19 (2H, t), 1.72-1.20 (17H, m), 0.99-0.79 (2H, m).<br>LC-MS (method 7):<br>R$_t$ = 2.60 min;<br>m/z = 546 (M + H)⁺. |

-continued

| Example | Name/Structure Preparation method/Starting material | Analytical data |
|---|---|---|
| 120 | (1S, 3S)-3-[(cyclopentyl{4-[(5-oxo-2-phenyl-5,6-dihydro-4H-1,3,4-oxadiazin-4-yl)methyl]phenyl}acetyl)-amino]cyclopentanecarboxylic acid (enantiomer 1)<br />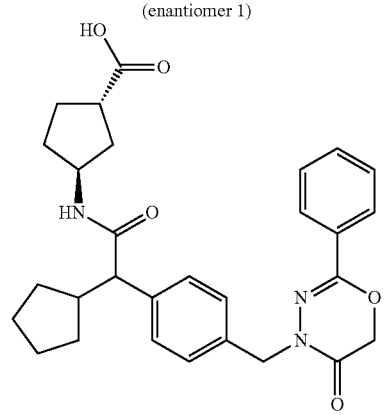<br />preparation method 2 (from Ex. 152A) | $^1$H-NMR (400 MHz, DMSO-$d_6$, δ/ppm): 12.05 (1H, s), 7.98 (1H, d), 7.77 (2H, d), 7.53-7.41 (3H, m), 7.29 (4H, q), 4.91 (2H, s), 4.84 (2H, s), 4.01-3.92 (1H, m), 3.09 (1H, d), 2.84-2.72 (1H, m), 2.58-2.39 (1H, m), 1.96-1.79 (3H, m), 1.74-1.11 (10H, m), 0.95-0.81 (1H, m). LC-MS (method 7): $R_t$ = 2.45 min; m/z = 504 (M + H)$^+$. |
| 121 | (1S, 3R)-3-[(cyclopentyl{4-[(5-oxo-2-phenyl-5,6-dihydro-4H-1,3,4-oxadiazin-4-yl)methyl]phenyl}-acetyl)amino]cyclopentanecarboxylic acid (enantiomer 1)<br />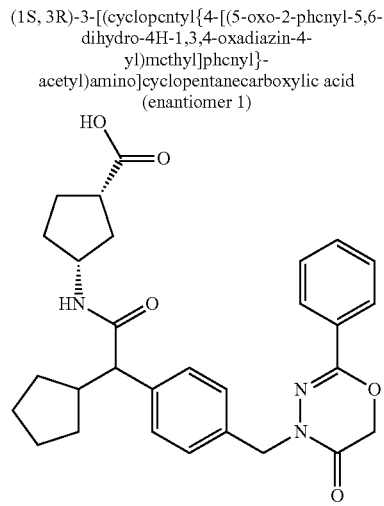<br />preparation method 2 (from Ex. 153A) | $^1$H-NMR (400 MHz, DMSO-$d_6$, δ/ppm): 12.06 (1H, s), 8.00 (1H, d), 7.77 (2H, d), 7.53-7.40 (3H, m), 7.28 (4H, q), 4.91 (2H, s), 4.84 (2H, s), 3.97-3.83 (1H, m), 3.10 (1H, d), 2.72-2.60 (1H, m), 2.57-2.38 (1H, m), 2.21-1.98 (1H, m), 1.82-1.25 (11H, m), 1.25-1.12 (1H, m), 0.96-0.81 (1H, m). LC-MS (method 7): $R_t$ = 2.42 min; m/z = 504 (M + H)$^+$. |
| 122 | (1R, 3R)-3-[(cyclopentyl{4-[(5-oxo-2-phenyl-5,6-dihydro-4H-1,3,4-oxadiazin-4-yl)methyl]-phenyl}acetyl)amino]cyclopentanecarboxylic acid (enantiomer 1)<br />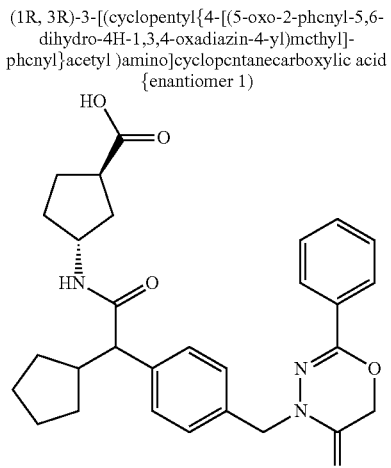<br />preparation method 2 (from Ex. 154A) | $^1$H-NMR (400 MHz, DMSO-$d_6$, δ/ppm): 12.06 (1H, s), 7.97 (1H, d), 7.77 (2H, d), 7.53-7.41 (3H, m), 7.28 (4H, q), 4.91 (2H, s), 4.84 (2H, s), 4.03-3.92 (1H, m), 3.09 (1H, d), 2.84-2.72 (1H, m), 2.58-2.39 (1H, m), 1.99-1.11 (13H, m), 0.95-0.81 (1H, m). LC-MS (method 7): $R_t$ = 2.42 min; m/z = 504 (M + H)$^+$. |

| Example | Name/Structure Preparation method/Starting material | Analytical data |
|---|---|---|
| 123 | (1R, 3S)-3-[(cyclopentyl{4-[(5-oxo-2-phenyl-5,6-dihydro-4H-1,3,4-oxadiazin-4-yl)methyl]phenyl}-acetyl)amino]cyclopentanecarboxylic acid (enantiomer 1)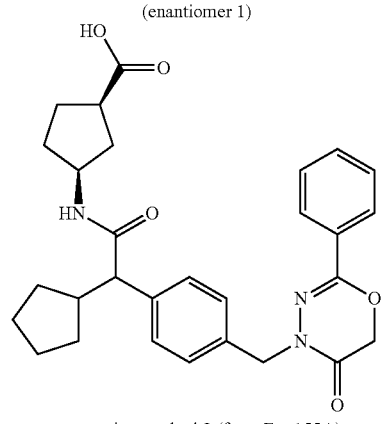preparation method 2 (from Ex. 155A) | $^1$H-NMR (400 MHz, DMSO-d$_6$, δ/ppm): 12.05 (1H, s), 8.00 (1H, d), 7.77 (2H, d), 7.53-7.40 (3H, m), 7.28 (4H, q), 4.91 (2H, s), 4.84 (2H, s), 3.97-3.83 (1H, m), 3.10 (1H, d), 2.72-2.60 (1H, m), 2.57-2.38 (1H, m), 2.21-1.98 (1H, m), 1.82-1.25 (11H, m), 1.25-1.12 (1H, m), 0.96-0.81 (1H, m), LC-MS (method 11): R$_t$ = 1.24 min; m/z = 504 (M + H)$^+$. |
| 124 | cis-4-[(cyclopentyl{4-[(5-oxo-2-phenyl-5,6-dihydro-4H-1,3,4-oxadiazin-4-yl)methyl]phenyl}acetyl)-amino]cyclohexanecarboxylic acid (enantiomer 1)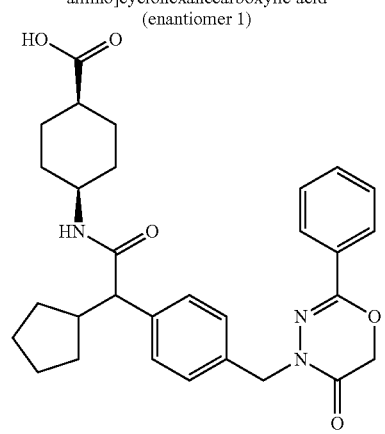preparation method 2 (from Ex. 159A) | $^1$H-NMR (400 MHz, DMSO-d$_6$, δ/ppm): 12.15-11.92 (1H, broad s), 7.85 (1H, d), 7.77 (2H, d), 7.53-7.40 (3H, m), 7.28 (4H, q), 4.91 (2H, s), 4.83 (2H, s), 3.45-3.29 (1H, m), 3.09 (1H, d), 2.56-2.39 (1H, m), 2.25-2.04 (1H, m), 1.92-1.77 (3H, m), 1.75-1.63 (1H, m), 1.63-1.01 (10H, m), 0.95-0.81 (1H, m). LC-MS (method 11): R$_t$ = 1.28 min; m/z = 518 (M + H)$^+$. |
| 125 | trans-4-[(cyclopentyl{4-[(5-oxo-2-phenyl-5,6-dihydro-4H-1,3,4-oxadiazin-4-yl)methyl]phenyl}-acetyl)amino]cyclohexanecarboxylic acid (enantiomer 1)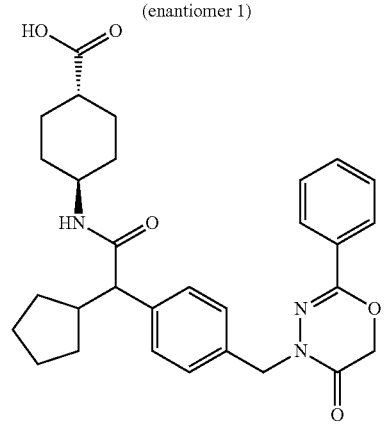preparation method 2 (from Ex. 158A) | $^1$H-NMR (400 MHz, DMSO-d$_6$, δ/ppm): 12.3-11.9 (1H, broad s), 7.85 (1H, d), 7.77 (2H, d), 7.53-7.40 (3H, m), 7.29 (4H, q), 4.91 (2H, s), 4.83 (2H, s), 3.67-3.53 (1H, m), 3.21 (1H, d), 2.57-2.39 (1H, m), 2.38-2.27 (1H, m), 1.87-1.72 (2H, m), 1.72-1.36 (10H, m), 1.36-1.24 (2H, m), 1.24-1.13 (1H, m), 0.95-0.81 (1H, m). LC-MS (method 11): R$_t$ = 1.27 min; m/z = 518 (M + H)$^+$. |

| Example | Name/Structure Preparation method/Starting material | Analytical data |
|---|---|---|
| 126 | 4-[(cyclopentyl{4-[(5-oxo-2-phenyl-5,6-dihydro-4H-1,3,4-oxadiazin-4-yl)methyl]phenyl}acetyl)amino]-2,3-dihydro-1H-indene-2-carboxylic acid (enantiomer 1)<br><br>preparation method 2 (from Ex. 105A) | $^1$H-NMR (400 MHz, DMSO-d$_6$, δ/ppm): 12.4-12.2 (1H, broad s), 9.48 (1H, s), 7.77 (2H, d), 7.53-7.38 (5H, m), 7.31 (2H, d), 7.27 (1H, d), 7.04 (1H, t), 6.96 (1H, d), 4.91 (2H, s), 4.85 (2H, s), 3.52 (1H, d), 3.28-3.19 (1H, m), 3.14-3.06 (2H, m), 3.06-2.98 (2H, m), 2.63-2.45 (1H, m), 1.85-1.72 (1H, m), 1.72-1.20 (6H, m), 1.02-0.90 (1H, m).<br>LC-MS (method 10):<br>R$_t$ = 2.23 min;<br>m/z = 552<br>(M + H)$^+$. |
| 127 | 3-{3-[(cyclopentyl{4-[(5-oxo-2-phenyl-5,6-dihydro-4H-1,3,4-oxadiazin-4-yl)methyl]phenyl}acetyl)-amino]cyclohexyl}propanoic acid (isomer 1)<br><br>preparation method 2 (from Ex. 188A) | $^1$H-NMR (400 MHz, DMSO-d$_6$, δ/ppm): 12.05-11.85 (1H, broad s), 7.81-7.71 (3H, m), 7.53-7.41 (3H, m), 7.33 (2H, d), 7.27 (2H, d), 4.91 (2H, s), 4.83 (2H, s), 3.82-3.72 (1H, m), 3.26 (1H, d), 2.57-2.39 (1H, m), 2.08 (2H, t), 1.72-1.57 (2H, m), 1.57-1.28 (12H, m), 1.28-1.17 (2H, m), 1.17-1.06 (1H, m), 1.02-0.82 (2H, m).<br>LC-MS (method 7):<br>R$_t$ = 2.66 min;<br>m/z = 546<br>(M + H)$^+$. |
| 128 | 3-{3-[(cyclopentyl{4-[(5-oxo-2-phenyl-5,6-dihydro-4H-1,3,4-oxadiazin-4-yl)methyl]phenyl}acetyl)-amino]cyclohexyl}propanoic acid (isomer 2)<br><br>preparation method 2 (from Ex. 189A) | LC-MS (method 7):<br>R$_t$ = 2.61 min;<br>m/z = 546<br>(M + H)$^+$. |

| Example | Name/Structure Preparation method/Starting material | Analytical data |
|---|---|---|
| 129 | 3-{3-[(cyclopentyl{4-[(5-oxo-2-phenyl-5,6-dihydro-4H-1,3,4-oxadiazin-4-yl)methyl]phenyl}acetyl)-amino]cyclohexyl}propanoic acid (isomer 3)<br>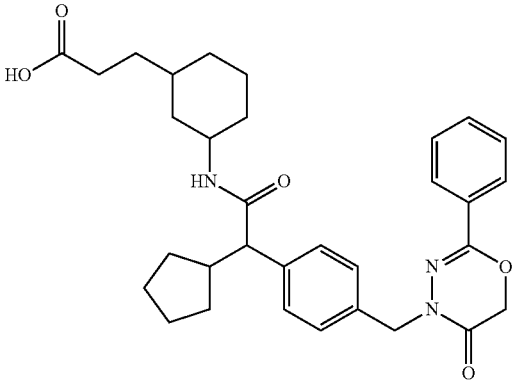 [SMILES: O=C(O)CCC1CCCC(NC(=O)C(c2ccc(CN3N=C(c4ccccc4)OCC3=O)cc2)C2CCCC2)C1]<br>preparation method 2 (from Ex. 190A) | LC-MS (method 7): $R_t$ = 2.61 min; m/z = 546 (M + H)⁺. |
| 130 | 3-{3-[(cyclopentyl{4-[(5-oxo-2-phenyl-5,6-dihydro-4H-1,3,4-oxadiazin-4-yl)methyl]phenyl}acetyl)-amino]cyclohexyl}propanoic acid (isomer 4)<br>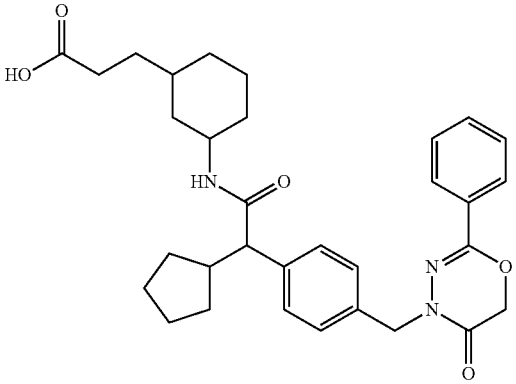 [SMILES: O=C(O)CCC1CCCC(NC(=O)C(c2ccc(CN3N=C(c4ccccc4)OCC3=O)cc2)C2CCCC2)C1]<br>preparation method 2 (from Ex. 191A) | ¹H-NMR (400 MHz, DMSO-$d_6$, δ/ppm): 11.94 (1H, s), 7.82 (1H, d), 7.77 (2H, d), 7.53-7.40 (3H, m), 7.29 (4H, q), 4.91 (2H, s), 4.84 (2H, s), 3.48-3.35 (1H, m), 3.07 (1H, d), 2.57-2.38 (1H, m), 2.13 (2H, t), 1.82-1.72 (1H, m), 1.72-1.11 (13H, m), 1.08-0.94 (2H, m), 0.94-0.79 (1H, m), 0.79-0.62 (2H, m). LC-MS (method 7): $R_t$ = 2.66 min; m/z = 546 (M + H)⁺. |

Example 131

4-{[(Cyclopentyl{4-[(5-oxo-2-phenyl-5,6-dihydro-4H-1,3,4-oxadiazin-4-yl)methyl]phenyl}-acetyl)amino]methyl}cyclohexanecarboxylic acid (isomer 1)

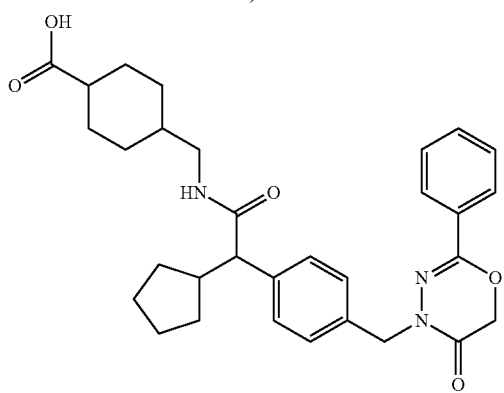

Preparation Method 7

0.55 ml (1.11 mmol) of 2 M aqueous sodium hydroxide solution was added to a solution of 31 mg (55 μmol) of ethyl 4-{[(cyclopentyl{4-[(5-oxo-2-phenyl-5,6-dihydro-4H-1,3,4-oxadiazin-4-yl)methyl]phenyl}acetyl)amino]methyl}cyclohexanecarboxylate (Example 127A) in 3 ml of dioxane, and the mixture was stirred at room temperature overnight. The reaction mixture was then extracted once with tert-butyl methyl ether. The aqueous phase was then adjusted to pH 2 with 1 M hydrochloric acid and extracted twice with ethyl acetate. The ethyl acetate phases were combined and dried over sodium sulfate. After filtration, the solvent was removed to dryness. This gave 25 mg (47 μmol, 85% of theory) of the title compound as a colorless solid.

¹H-NMR (400 MHz, DMSO-$d_6$, δ/ppm): 11.97 (1H, broad s), 7.93-7.90 (1H, t), 7.77-7.75 (2H, m), 7.52-7.43 (3H, m), 7.32-7.25 (4H, m), 4.90 (2H, s), 4.83 (2H, s), 3.62-3.59 (1H, m), 3.15-3.13 (1H, d), 2.97-2.90 (1H, m), 2.72-2.66 (1H, m), 2.08-2.02 (1H, m), 1.84-0.78 (17H, m).

LC-MS (method 10): $R_t$=2.09 min; m/z=531 (M+H)⁺.

The compounds listed in the table below were obtained in an analogous manner:

| Example | Name/Structure Preparation method/Starting material | Analytical data |
|---|---|---|
| 132 | 4-{[(cyclopentyl{4-[(5-oxo-2-phenyl-5,6-dihydro-4H-1,3,4-oxadiazin-4-yl)methyl]phenyl}acetyl)amino]-methyl}cyclohexanecarboxylic acid (isomer 2)<br><br>preparation method 7 (from Ex. 128A) | $^1$H-NMR (400 MHz, DMSO-d$_6$, δ/ppm): 11.97 (1H, broad s), 7.93-7.90 (1H, t), 7.77-7.75 (2H, m), 7.52-7.43 (3H, m), 7.32-7.25 (4H, m), 4.90 (2H, s), 4.83 (2H, s), 3.62-3.58 (1H, m), 3.15-3.13 (1H, d), 2.97-2.91 (1H, m), 2.72-2.63 (1H, m), 2.08-2.02 (1H, m), 1.84-0.78 (17H, m).<br>LC-MS (method 11): R$_t$ = 1.31 min; m/z = 532 (M + H)$^+$. |
| 133 | 4-{[(cyclopentyl{4-[(5-oxo-2-phenyl-5,6-dihydro-4H-1,3,4-oxadiazin-4-yl)methyl]phenyl}acetyl)amino]-methyl}cyclohexanecarboxylic acid (isomer 3)<br><br>preparation method 7 (from Ex. 129A) | $^1$H-NMR (400 MHz, DMSO-d$_6$, δ/ppm): 12.00 (1H, broad s), 7.93-7.90 (1H, t), 7.78-7.75 (2H, m), 7.52-7.43 (3H, m), 7.31-7.23 (4H, m), 4.90 (2H, s), 4.83 (2H, s), 3.13-3.11 (1H, d), 3.00-2.95 (1H, m), 2.73-2.67 (1H, m), 2.37-2.33 (1H, m), 1.76-0.86 (18H, m).<br>LC-MS (method 11): R$_t$ = 1.31 min; m/z = 532 (M + H)$^+$. |
| 134 | 4-{[(cyclopentyl{4-[(5-oxo-2-phenyl-5,6-dihydro-4H-1,3,4-oxadiazin-4-yl)methyl]phenyl}acetyl)amino]-methyl}cyclohexanecarboxylic acid (isomer 4)<br><br>preparation method 7 (from Ex. 130A) | $^1$H-NMR (400 MHz, DMSO-d$_6$, δ/ppm): 12.01 (1H, broad s), 7.93-7.90 (1H, t), 7.78-7.75 (2H, m), 7.51-7.43 (3H, m), 7.32-7.25 (4H, m), 4.90 (2H, s), 4.84 (2H, s), 3.14-3.11 (1H, d), 3.02-2.95 (1H, m), 2.73-2.69 (1H, m), 2.36-2.34 (1H, m), 1.80-0.80 (18H, m).<br>LC-MS (method 11): R$_t$ = 1.31 min; m/z = 532 (M + H)$^+$. |

The compounds listed in the table below were prepared analogously to Exemplary embodiments 1, 2 and 3:

| Example | Name/Structure/Starting material | Analytical data |
|---|---|---|
| 135 | 3-{2-methyl-3-[(3-methyl-2-{4-[(5-oxo-2-phenyl-5,6-dihydro-4H-1,3,4-oxadiazin-4-yl)methyl]-phenyl}butanoyl)amino]phenyl}propanoic acid<br>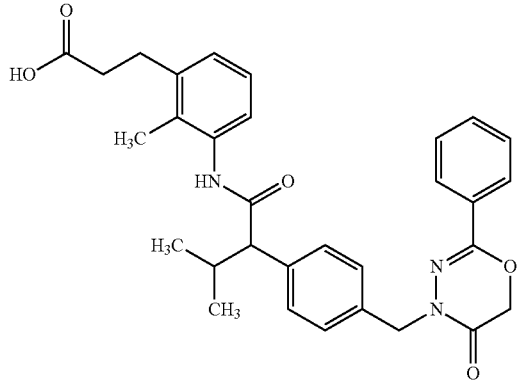 [SMILES: Cc1c(CCC(=O)O)cccc1NC(=O)C(c1ccc(CN2N=C(c3ccccc3)OCC2=O)cc1)C(C)C]<br>(from tert-butyl 3-{2-methyl-3-[(3-methyl-2-{4-[(5-oxo-2-phenyl-5,6-dihydro-4H-1,3,4-oxadiazin-4-yl)-methyl]phenyl}butanoyl)amino]phenyl}propanoate | LC-MS (method 10): $R_t$ = 2.08 min; m/z = 528 (M + H)$^+$.<br>$^1$H-NMR (400 MHz, DMSO-d$_6$): δ = 9.48 (s, 1H), 7.76 (d, 2H), 7.42-7.54 (m, 3H), 7.39 (d, 2H), 7.32 (d, 2H), 6.94-7.04 (m, 3H), 4.92 (s, 2H), 4.87 (s, 2H), 3.31 (d, 1H), 2.76 (t, 2H), 2.41 (t, 2H), 2.25-2.37 (m, 1H), 1.94 (s, 3H), 1.05 (d, 3H), 0.67 (d, 3H). |
| 136 | 3-{3-[(cyclopentyl{4-[(5-oxo-2-phenyl-5,6-dihydro-4H-1,3,4-oxadiazin-4-yl)methyl]phenyl}-acetyl)amino]phenyl}-2,2-dimethylpropanoic acid<br>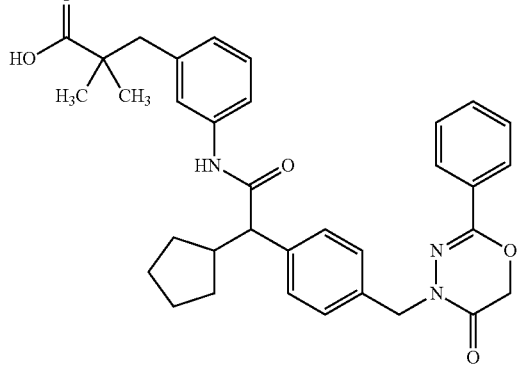<br>(from methyl 3-{3-[(cyclopentyl{4-[(5-oxo-2-phenyl-5,6-dihydro-4H-1,3,4-oxadiazin-4-yl)methyl]phenyl}acetyl)amino]phenyl}-2,2-dimethylpropanoate) | LC-MS (method 7): $R_t$ = 2.79 min; m/z = 568 (M + H)$^+$.<br>$^1$H-NMR (400 MHz, DMSO-d$_6$): δ = 12.01-12.37 (br. s, 1H), 9.98 (s, 1H), 7.76 (d, 2H), 7.36-7.55 (m, 6H), 7.28-7.37 (m, 3H), 7.13 (t, 1H), 6.79 (d, 1H), 4.90 (s, 2H), 4.84 (s, 2H), 3.31 (d, 1H), 2.67-2.75 (s, 2H), 2.47-2.64 (m, 1H), 1.71-1.85 (m, 1H), 1.18-1.71 (m, 6H), 1.04 (s, 6H), 0.89-0.99 (m, 1H). |

| Example | Name/Structure/Starting material | Analytical data |
|---|---|---|
| 137 | 3-{3-[(cyclopentyl{4-[(6-oxo-3-phenylpyridazin-1(6H)-yl)methyl]phenyl}acetyl)amino]phenyl}-2,2-dimethylpropanoic acid (enantiomer 1)<br>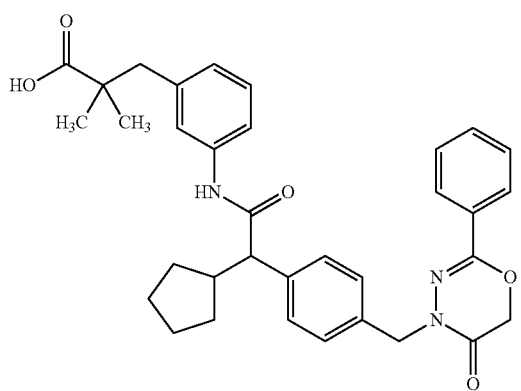<br>(from methyl 3-{3-[(cyclopentyl{4-[(6-oxo-3-phenylpyridazin-1(6H)-yl)methyl]phenyl}acetyl)-amino]phenyl}-2,2-dimethylpropanoate (enantiomer 1)) | LC-MS (method 7): $R_t$ = 2.74 min; m/z = 564 $(M + H)^+$.<br>$^1$H-NMR (400 MHz, DMSO-$d_6$): δ = 12.10 (br. s, 1H), 9.97 (s, 1H), 8.06 (d, 1H), 7.87 (d, 2H), 7.41-7.52 (m, 4H), 7.39 (d, 2H), 7.28-7.35 (m, 3H), 7.13 (t, 1H), 7.07 (d, 1H), 6.79 (d, 1H), 5.29 (s, 2H), 3.37 (d, 1H), 2.70 (s, 2H), 2.47-2.61 (m, 1H), 1.72-1.83 (m, 1H), 1.14-1.68 (m, 6H), 1.05 (s, 6H), 0.91-1.00 (m, 1H). |
| 138 | 3-{3-[(cyclopentyl{4-[(6-oxo-3-phenylpyridazin-1(6H)-yl)methyl]phenyl}acetyl)amino]phenyl}-2,2-dimethylpropanoic acid (enantiomer 2)<br>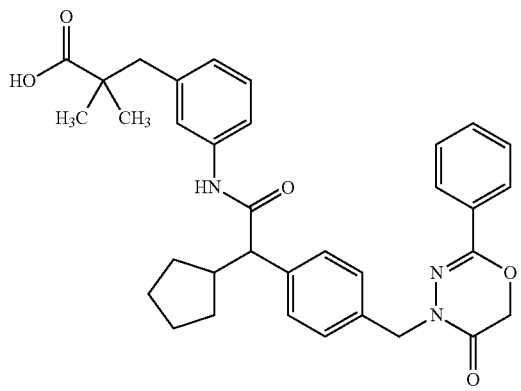<br>(from methyl 3-{3-[(cyclopentyl{4-[(6-oxo-3-phenylpyridazin-1(6H)-yl)methyl]phenyl}acetyl)amino]phenyl}-2,2-dimethylpropanoate (enantiomer 2)) | LC-MS (method 7): $R_t$ = 2.74 min; m/z = 564 $(M + H)^+$.<br>$^1$H-NMR (400 MHz, DMSO-$d_6$): δ = 12.10 (br. s, 1H), 9.97 (s, 1H), 8.06 (d, 1H), 7.87 (d, 2H), 7.41-7.52 (m, 4H), 7.39 (d, 2H), 7.28-7.35 (m, 3H), 7.13 (t, 1H), 7.07 (d, 1H), 6.79 (d, 1H), 5.29 (s, 2H), 3.37 (d, 1H), 2.70 (s, 2H), 2.47-2.61 (m, 1H), 1.72-1.83 (m, 1H), 1.14-1.68 (m, 6H), 1.05 (s, 6H), 0.91-1.00 (m, 1H). |

| Example | Name/Structure/Starting material | Analytical data |
|---|---|---|
| 139 | 2,2-dimethyl-3-{3-[(3-methyl-2-{4-[(5-oxo-2-phenyl-5,6-dihydro-4H-1,3,4-oxadiazin-4-yl)methyl]phenyl}-butanoyl)amino]phenyl}propanoic acid<br>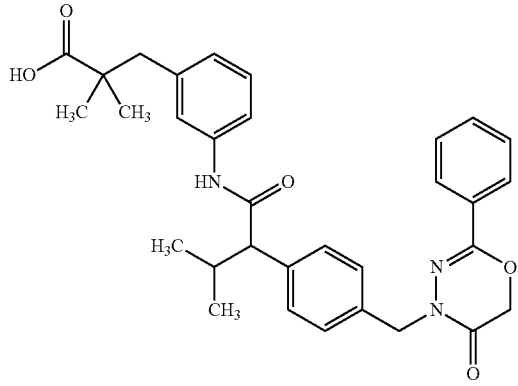 [SMILES: CC(C)C(C(=O)Nc1cccc(CC(C)(C)C(=O)O)c1)c1ccc(CN2N=C(c3ccccc3)OCC2=O)cc1]<br>(from methyl 2,2-dimethyl-3-{3-[(3-methyl-2-{4-[(5-oxo-2-phenyl-5,6-dihydro-4H-1,3,4-oxadiazin-4-yl)-methyl]phenyl}butanoyl)amino]phenyl}propanoate | LC-MS (method 10): $R_t$ = 2.31 min; m/z = 542 (M + H)$^+$.<br>$^1$H-NMR (400 MHz, DMOS-d$_6$): δ = 12.22 (br. s, 1H), 10.00 (s, 1H), 7.76 (d, 2H), 7.40-7.52 (m, 4H), 7.37 (d, 2H), 7.27-7.35 (m, 3H), 7.13 (t, 1H), 6.79 (d, 1H), 4.90 (s, 2H), 4.84 (s, 2H), 3.23 (d, 1H), 2.70 (s, 2H), 2.24-2.39 (m, 1H), 1.04 (s, 6H), 0.99 (d, 3H), 0.65 (d, 3H). |
| 140 | 3-{3-[(cyclopentyl{4-[(6-oxo-3-phenylpyridazin-1(6H)-yl)methyl]phenyl}acetyl)amino]-2-methyl-phenyl}propanoic acid (enantiomer 1)<br>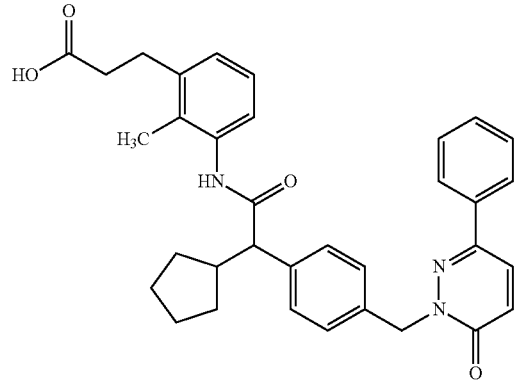 [SMILES: Cc1c(CCC(=O)O)cccc1NC(=O)C(c1ccc(Cn2nc(-c3ccccc3)ccc2=O)cc1)C1CCCC1]<br>(from tert-butyl 3-{3-[(cyclopentyl{4-[(6-oxo-3-phenylpyridazin-1(6H)-yl)methyl]phenyl}acetyl)-amino]-2-methylphenyl}propanoate (enantiomer 1)) | LC-MS (method 10): $R_t$ = 2.12 min; m/z = 550 (M + H)$^+$.<br>$^1$H-NMR (400 MHz, DMSO-d$_6$): δ = 11.83-12.43 (br. s, 1H), 9.46 (s, 1H), 8.08 (d, 1H), 7.88 (d, 2H), 7.44-7.53 (m, 3H), 7.40 (d, 2H), 7.32 (d, 2H), 7.09 (d, 1H), 6.92-7.05 (m, 3H), 5.32 (s, 2H), 3.45 (d, 1H), 2.78 (t, 2H), 2.55-2.63 (m, 1H), 2.42 (t, 2H), 1.97 (s, 3H), 1.29-1.88 (m, 7H), 0.96 (dd, 1H). |

| Example | Name/Structure/Starting material | Analytical data |
|---|---|---|
| 141 | 3-{3-[(cyclopentyl{4-[(6-oxo-3-phenylpyridazin-1(6H)-yl)methyl]phenyl}acetyl)amino]-2-methyl-phenyl}propanoic acid (enantiomer 2)<br>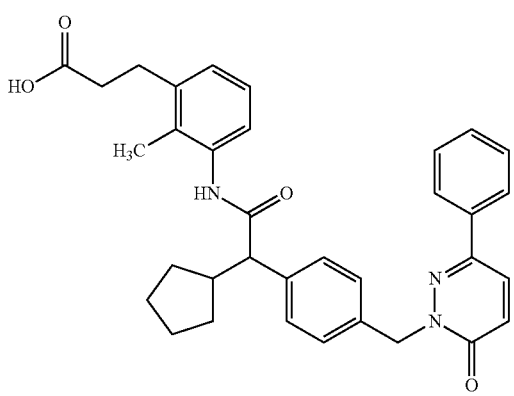 [SMILES: Cc1c(CCC(=O)O)cccc1NC(=O)C(c1ccc(Cn2nc(-c3ccccc3)ccc2=O)cc1)C1CCCC1]<br>(from tert-butyl 3-{3-[(cyclopentyl{4-[(6-oxo-3-phenylpyridazin-1(6H)-yl)methyl]phenyl}acetyl)-amino]-2-methylphenyl}propanoate (enantiomer 2)) | LC-MS (method 10): $R_t$ = 2.12 min; m/z = 550 $(M + H)^+$.<br>$^1$H-NMR (400 MHz, DMSO-$d_6$): δ = 11.83-12.43 (br. s, 1H), 9.46 (s, 1H), 8.08 (d, 1H), 7.88 (d, 2H), 7.44-7.53 (m, 3H), 7.40 (d, 2H), 7.32 (d, 2H), 7.09 (d, 1H), 6.92-7.05 (m, 3H), 5.32 (s, 2H), 3.45 (d, 1H), 2.78 (t, 2H), 2.55-2.63 (m, 1H), 2.42 (t, 2H), 1.97 (s, 3H), 1.29-1.88 (m, 7H), 0.96 (dd, 1H).<br>$[α]_D^{20}$ = +48.0°, c = 0.26, methanol. |
| 142 | 3-{2-methyl-3-[(6,6,6-trifluoro-4-methyl-2-{4-[(5-oxo-2-phenyl-5,6-dihydro-4H-1,3,4-oxadiazin-4-yl)methyl]-phenyl}hexanoyl)amino]phenyl}propanoic acid<br>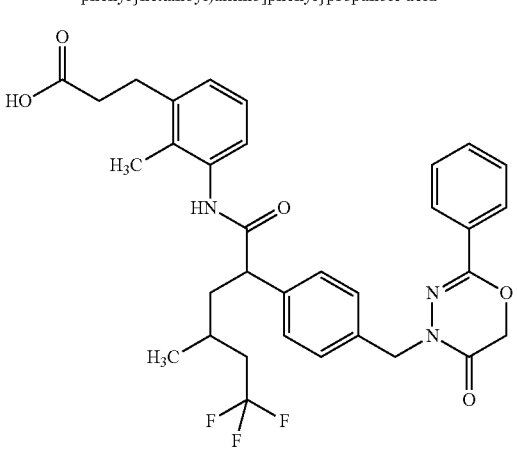<br>(from methyl 3-{2-methyl-3-[(6,6,6-trifluoro-4-methyl-2-{4-[(5-oxo-2-phenyl-5,6-dihydro-4H-1,3,4-oxadiazin-4-yl)methyl]phenyl}hexanoyl)amino]phenyl}-propanoate) | LC-MS (method 10): Rt = 2.25 min; m/z = 610 $(M + H)^+$.<br>$^1$H-NMR (400 MHz, DMSO-$d_6$): δ = 12.14 (s, 1H), 9.54 (d, 1H), 7.76 (d, 2H), 7.42-7.54 (m, 3H), 7.40 (d, 2H), 7.34 (d, 2H), 6.95-7.05 (m, 3H), 4.91 (s, 2H), 4.87 (s, 2H), 3.91 (m, 1H), 2.74-2.81 (m, 2H), 2.37-2.45 (m, 2H), 2.26-2.37 (m, 1H), 2.07-2.26 (m, 1H), 1.91-1.99 (m, 3H), 1.75-1.87 (m, 1H), 1.43-1.72 (m, 3H), 1.08 (d, 1H), 1.01 (d, 1H). |

| Example | Name/Structure/Starting material | Analytical data |
|---|---|---|
| 143 | 2,2-dimethyl-3-{3-[(3-methyl-2-{4-[(5-oxo-2-phenyl-5,6-dihydro-4H-1,3,4-oxadiazin-4-yl)methyl]phenyl}-pentanoyl)amino]phenyl}propanoic acid<br><br>(from methyl 2,2-dimethyl-3-{3-[(3-methyl-2-{4-[(5-oxo-2-phenyl-5,6-dihydro-4H-1,3,4-oxadiazin-4-yl)-methyl]phenyl}pentanoyl)amino]phenyl}propanoate) | LC-MS (method 11): $R_t$ = 1.44 min; m/z = 556 $(M + H)^+$.<br>$^1$H-NMR (400 MHz, DMSO-$d_6$): δ = 10.01 (s, 1H), 7.76 (d, 2H), 7.41-7.52 (m, 4H), 7.35-7.40 (m, 2H), 7.28-7.35 (m, 3H), 7.13 (t, 1H), 6.79 (d, 1H), 4.90 (s, 2H), 4.84 (s, 2H), 2.70 (br. s, 2H), 2.16 (d, 1H), 1.52 (d, 1H), 1.11-1.25 (m, 2H), 1.04 (br. s, 6H), 0.90 (t, 3H), 0.61 (d, 3H). |
| 144 | 3-{3-[(cyclopentyl{4-[(2-oxo-5-phenyl-1,3,4-oxa-diazol-3(2H)-yl)methyl]phenyl}acetyl)amino]-2-methylphenyl}propanoic acid (enantiomer 1)<br><br>(from tert-butyl 3-{3-[(cyclopentyl{4-[(2-oxo-5-phenyl-1,3,4-oxadiazol-3(2H)-yl)methyl]phenyl}-acetyl)amino]-2-methylphenyl}propanoate (enantiomer 1)) | LC-MS (method 10): $R_t$ = 2.22 min; m/z = 540 $(M + H)^+$.<br>$^1$H-NMR (400 MHz, DMSO-$d_6$): δ = 11.95-12.34 (br. s, 1H), 9.48 (s, 1H), 7.80 (d, 2H), 7.50-7.62 (m, 3H), 7.44 (d, 2H), 7.33 (d, 2H), 6.94-7.06 (m, 3H), 4.96 (s, 2H), 3.48 (d, 1H), 2.79 (t, 2H), 2.43 (t, 2H), 1.99 (s, 3H), 1.78-1.90 (m, 1H), 1.30-1.71 (m, 6H), 0.94-1.03 (m, 2H). |

| Example | Name/Structure/Starting material | Analytical data |
|---|---|---|
| 145 | 3-{3-[(cyclopentyl{4-[(2-oxo-5-phenyl-1,3,4-oxadiazol-3(2H)-yl)methyl]phenyl}acetyl)amino]-2-methylphenyl}propanoic acid (enantiomer 2)<br><br>(from tert-butyl 3-{3-[(cyclopentyl{4-[(2-oxo-5-phenyl-1,3,4-oxadiazol-3(2H)-yl)methyl]phenyl}-acetyl)amino]-2-methylphenyl}propanoate (enantiomer 2)) | LC-MS (method 10): $R_t$ = 2.22 min; m/z = 540 (M + H)$^+$.<br>$^1$H-NMR (400 MHz, DMSO-d$_6$): δ = 11.95-12.34 (br. s, 1H), 9.48 (s, 1H), 7.80 (d, 2H), 7.50-7.62 (m, 3H), 7.44 (d, 2H), 7.33 (d, 2H), 6.94-7.06 (m, 3H), 4.96 (s, 2H), 3.48 (d, 1H), 2.79 (t, 2H), 2.43 (t, 2H), 1.99 (s, 3H), 1.78-1.90 (m, 1H), 1.30-1.71 (m, 6H), 0.94-1.03 (m, 2H). |
| 146 | 4-[(cyclopentyl{4-[(6-oxo-3-phenylpyridazin-1(6H)-yl)methyl]phenyl}acetyl)amino]-2,3-dihydro-1H-indene-2-carboxylic acid<br><br>(from methyl 4-[(cyclopentyl{4-[(6-oxo-3-phenylpyridazin-1(6H)-yl)methyl]phenyl}acetyl)amino]-2,3-dihydro-1H-indene-2-carboxylate) | LC-MS (method 11): $R_t$ = 1.34 min; m/z = 548 (M + H)$^+$.<br>$^1$H-NMR (400 MHz, DMSO-d$_6$): δ = 12.01-12.32 (br. s, 1H), 9.47 (d, 1H), 8.07 (d, 1H), 7.88 (d, 2H), 7.45-7.51 (m, 3H), 7.40 (d, 2H), 7.32 (d, 2H), 7.26 (d, 1H), 7.08 (d, 1H), 7.04 (t, 1H), 6.95 (d, 1H), 5.31 (s, 2H), 3.46-3.57 (m, 4H), 3.07-3.13 (m, 1H), 3.02 (d, 1H), 1.71-1.85 (m, 1H), 1.21-1.71 (m, 6H), 1.04 (d, 1H), 0.91-0.99 (m, 1H). |
| 147 | 3-{2-methyl-3-[(4,4,4-trifluoro-3-methyl-2-{4-[(6-oxo-3-phenylpyridazin-1(6H)-yl)methyl]phenyl}-butanoyl)amino]phenyl}propanoic acid<br><br>(from tert-butyl 3-{2-methyl-3-[(4,4,4-trifluoro-3-methyl-2-{4-[(6-oxo-3-phenylpyridazin-1(6H)-yl)-methyl]phenyl}butanoyl)amino]phenyl}propanoate | LC-MS (method 11): $R_t$ = 1.27 min; m/z = 578 (M + H)$^+$.<br>$^1$H-NMR (400 MHz, DMSO-d$_6$): δ = 11.89-12.36 (br. s, 1H), 9.62 (s, 1H), 8.08 (d, 1H), 7.87 (d, 2H), 7.40-7.52 (m, 5H), 7.36 (d, 2H), 7.10 (d, 1H), 6.92-7.04 (m, 3H), 5.34 (s, 2H), 3.91 (d, 1H), 3.28-3.41 (m, 1H), 2.75 (t, 2H), 2.40 (t, 2H), 1.88 (s, 3H), 0.78 (d, 3H). |

| Example | Name/Structure/Starting material | Analytical data |
|---|---|---|
| 148 | 3-{3-[(cyclopentyl{4-[(2-oxo-3,4-dihydroquinolin-1(2H)-yl)methyl]phenyl}acetyl)amino]-2-methyl-phenyl}propanoic acid<br>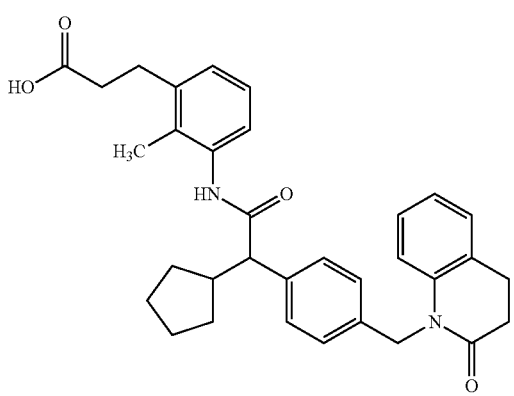 [SMILES: Cc1c(CCC(=O)O)cccc1NC(=O)C(c1ccc(CN2C(=O)CCc3ccccc32)cc1)C1CCCC1]<br>(from tert-butyl 3-{3-[(cyclopentyl{4-[(2-oxo-3,4-dihydroquinolin-1(2H)-yl)methyl]phenyl}-acetyl)amino]-2-methylphenyl}propanoate) | LC-MS (method 11): $R_t$ = 1.28 min; m/z = 525 (M + H)$^+$.<br>$^1$H-NMR (400 MHz, DMSO-$d_6$): δ = 12.01-12.29 (br. s, 1H), 9.42 (s, 1H), 7.35 (d, 2H), 7.22 (d, 1H), 7.16 (d, 2H), 7.10 (d, 1H), 6.86-7.04 (m, 5H), 5.11 (s, 2H), 2.92-2.98 (m, 2H), 2.79 (t, 2H), 2.65-2.72 (m, 2H), 2.42 (t, 2H), 1.92 (s, 3H), 1.79-1.87 (m, 1H), 1.29-1.72 (m, 7H), 1.23 (s, 2H). |
| 149 | 3-{3-[(cyclopentyl{4-[(1-oxoisoquinolin-2(1H)-yl)methyl]phenyl}acetyl)amino]-2-methyl-phenyl}propanoic acid<br>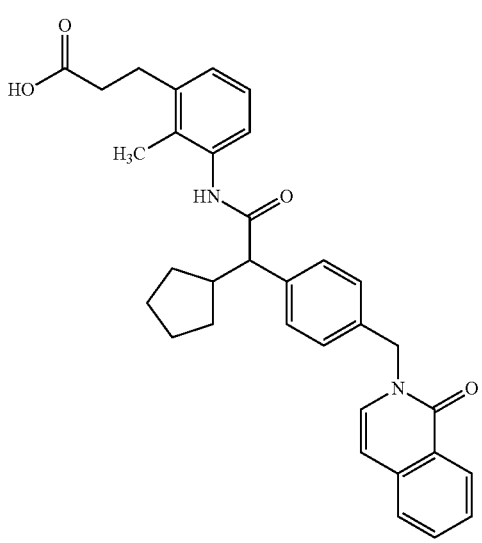 [SMILES: Cc1c(CCC(=O)O)cccc1NC(=O)C(c1ccc(Cn2ccc3ccccc3c2=O)cc1)C1CCCC1]<br>(from tert-butyl 3-{3-[(cyclopentyl{4-[(1-oxo-isoquinolin-2(1H)-yl)methyl]phenyl}acetyl)amino]-2-methylphenyl}propanoate) | LC-MS (method 10): $R_t$ = 2.06 min; m/z = 523 (M + H)$^+$. |

| Example | Name/Structure/Starting material | Analytical data |
|---|---|---|
| 150 | 3-{3-[(cyclopentyl{4-[(4-oxoquinazolin-3(4H)-yl)methyl]phenyl}acetyl)amino]-2-methylphenyl}propanoic acid 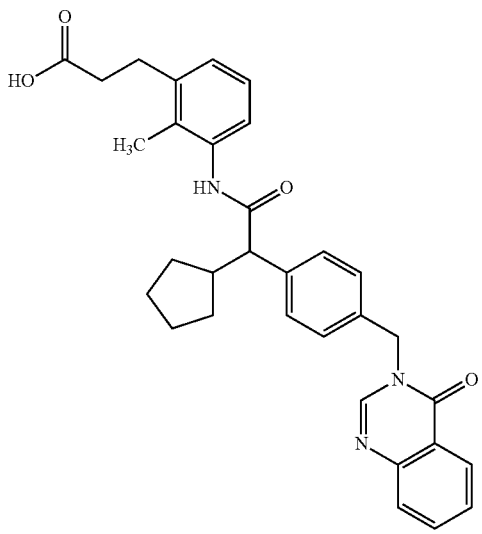 [SMILES: Cc1c(CCC(=O)O)cccc1NC(=O)C(c1ccc(Cn2cnc3ccccc3c2=O)cc1)C1CCCC1] (from tert-butyl 3-{3-[(cyclopentyl{4-[(4-oxo-quinazolin-3(4H)-yl)methyl]phenyl}acetyl)amino]-2-methylphenyl}propanoate) | LC-MS (method 7): $R_t$ = 2.42 min; m/z = 524 $(M + H)^+$. $^1$H-NMR (400 MHz, DMSO-$d_6$): δ = 12.03-12.24 (br. s, 1H), 9.45 (s, 1H), 8.47 (s, 1H), 8.28 (d, 1H), 7.82-7.99 (m, 3H), 7.38 (d, 2H), 7.27 (d, 2H), 6.89-7.04 (m, 3H), 5.32 (s, 2H), 3.44 (d, 1H), 2.78 (t, 2H), 2.42 (t, 2H), 1.98 (s, 3H), 1.82 (dd, 1H), 1.61-1.72 (m, 1H), 1.29-1.59 (m, 5H), 0.95 (dd, 1H). |
| 151 | 3-{3-[(cyclopentyl{4-[(1-oxophthalazin-2(1H)-yl)methyl]phenyl}acetyl)amino]-2-methylphenyl}propanoic acid 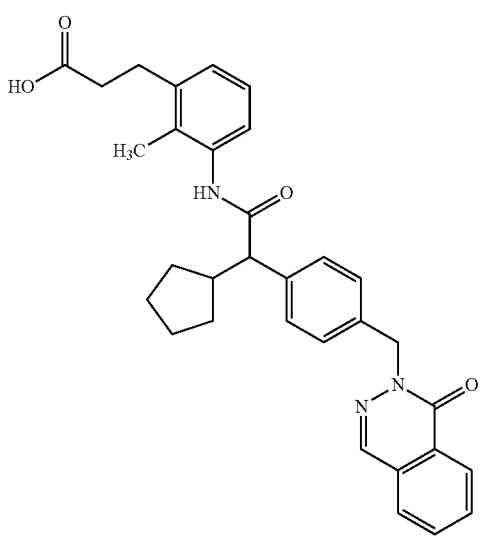 [SMILES: Cc1c(CCC(=O)O)cccc1NC(=O)C(c1ccc(Cn2ncc3ccccc3c2=O)cc1)C1CCCC1] (from tert-butyl 3-{3-[(cyclopentyl{4-[(1-oxo-phthalazin-2(1H)-yl)methyl]phenyl}acetyl)amino]-2-methylphenyl}propanoate) | LC-MS (method 7): $R_t$ = 2.30 min; m/z = 524 $(M + H)^+$. $^1$H-NMR (400 MHz, DMSO-$d_6$): δ = 12.13 (br. s, 1H), 9.45 (s, 1H), 8.57 (s, 1H), 8.16 (d, 1H), 7.84 (t, 1H), 7.70 (d, 1H), 7.56 (t, 1H), 7.40 (d, 2H), 7.31 (d, 2H), 6.90-7.08 (m, 3H), 5.19 (s, 2H), 3.45 (d, 1H), 2.78 (t, 2H), 2.42 (t, 2H), 1.97 (s, 3H), 1.78-1.90 (m, 1H), 1.29-1.71 (m, 6H), 0.88-1.01 (m, 1H). |

-continued

| Example | Name/Structure/Starting material | Analytical data |
|---|---|---|
| 152 | 3-(3-{[{4-[(6-chloro-2-oxo-3,4-dihydroquinolin-1(2H)-yl)methyl]phenyl}(cyclopentyl)acetyl]amino}-2-methylphenyl)propanoic acid 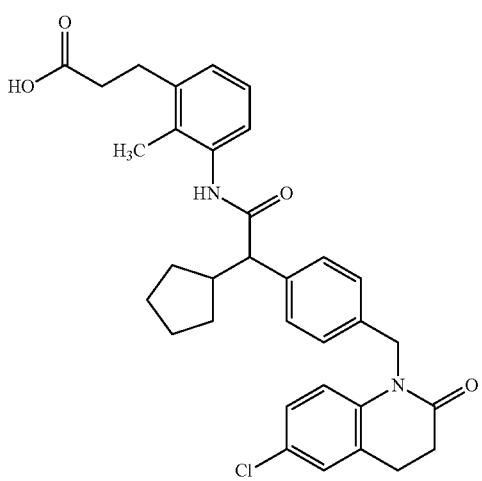 [SMILES: Cc1c(CCC(=O)O)cccc1NC(=O)C(c1ccc(CN2C(=O)CCc3cc(Cl)ccc32)cc1)C1CCCC1] (from tert-butyl 3-(3-{[{4-[(6-chloro-2-oxo-3,4-dihydroquinolin-1(2H)-yl)methyl]phenyl}(cyclopentyl)acetyl]amino}-2-methylphenyl)propanoate) | LC-MS (method 10): $R_t$ = 2.13 min; m/z = 560 (M + H)⁺. |
| 153 | 3-(3-{[{4-[(3-chloro-6-oxopyridazin-1(6H)-yl)methyl]phenyl}(cyclopentyl)acetyl]amino}-2-methylphenyl)propanoic acid 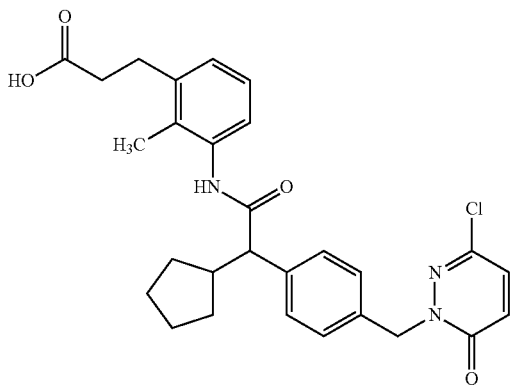 [SMILES: Cc1c(CCC(=O)O)cccc1NC(=O)C(c1ccc(Cn2nc(Cl)ccc2=O)cc1)C1CCCC1] (from tert-butyl 3-(3-{[{4-[(3-chloro-6-oxopyridazin-1(6H)-yl)methyl]phenyl}(cyclopentyl)acetyl]amino}-2-methylphenyl)propanoate) | LC-MS (method 7): $R_t$ = 2.30 min; m/z = 508 (M + H)⁺. ¹H-NMR (400 MHz, DMSO-d₆): δ = 12.13 (br. s, 1H), 9.46 (s, 1H), 7.57 (d, 1H), 7.40 (d, 2H), 7.24 (d, 2H), 7.09 (d, 1H), 6.95-7.04 (m, 3H), 5.18 (s, 2H), 3.57-3.64 (m, 1H), 3.46 (d, 1H), 2.79 (t, 2H), 2.43 (t, 2H), 1.99 (s, 3H), 1.80-1.88 (m, 1H), 1.76 (dt, 1H), 1.62-1.72 (m, 1H), 1.52-1.60 (m, 2H), 1.46 (d, 1H), 1.29-1.41 (m, 2H). |

| Example | Name/Structure/Starting material | Analytical data |
| --- | --- | --- |
| 154 | 3-{3-[(cyclopentyl{4-[(4-methyl-1-oxophthalazin-2(1H)-yl)methyl]phenyl}acetyl)amino]-2-methylphenyl}propanoic acid<br><br>(from tert-butyl 3-{3-[(cyclopentyl{4-[(4-methyl-1-oxophthalazin-2(1H)-yl)methyl]phenyl}acetyl)amino]-2-methylphenyl}propanoate) | LC-MS (method 7): $R_t$ = 2.47 min; m/z = 538 $(M + H)^+$.<br>$^1$H-NMR (400 MHz, DMSO-$d_6$): δ = 12.13 (s, 1H), 9.45 (s, 1H), 8.31 (d, 1H), 7.96 (d, 2H), 7.84-7.92 (m, 1H), 7.38 (d, 2H), 7.26 (d, 2H), 6.94-7.05 (m, 3H), 5.28 (s, 2H), 3.44 (d, 1H), 2.78 (t, 2H), 2.42 (t, 2H), 1.98 (s, 3H), 1.78-1.90 (m, 1H), 1.62-1.73 (m, 1H), 1.49-1.60 (m, 2H), 1.40-1.50 (m, 1H), 1.28-1.38 (m, 2H), 0.96 (dd, 1H). |
| 155 | 3-{3-[(cyclopentyl{4-[(1,1-dioxido-3-oxo-1,2-benzisothiazol-2(3H)-yl)methyl]phenyl}acetyl)amino]-2-methylphenyl}propanoic acid<br><br>(from tert-butyl 3-{3-[(cyclopentyl{4-[(1,1-dioxido-3-oxo-1,2-benzisothiazol-2(3H)-yl)methyl]phenyl}acetyl)amino]-2-methylphenyl}propanoate) | LC-MS (method 10): $R_t$ = 2.09 min; m/z = 561 $(M + H)^+$.<br>$^1$H-NMR (400 MHz, DMSO-$d_6$): δ = 11.93-12.29 (br. s, 1H), 9.48 (s, 1H), 8.33 (d, 1H), 8.13 (d, 1H), 7.96-8.10 (m, 2H), 7.32-7.45 (m, 4H), 6.92-7.06 (m, 3H), 4.90 (s, 2H), 3.46 (d, 1H), 2.79 (t, 2H), 2.43 (t, 2H), 1.99 (s, 3H), 1.77-1.89 (m, 1H), 1.63-1.70 (m, 1H), 1.51-1.62 (m, 2H), 1.41-1.49 (m, 1H), 1.29-1.39 (m, 2H), 1.24 (s, 1H), 0.92-1.05 (m, 1H). |
| 156 | 1-{3-[(cyclopentyl{4-[(6-oxo-3-phenylpyridazin-1(6H)-yl)methyl]phenyl}acetyl)amino]benzyl}-cyclopropanecarboxylic acid<br><br>(from tert-butyl 1-{3-[(cyclopentyl{4-[(6-oxo-3-phenylpyridazin-1(6H)-yl)methyl]phenyl}acetyl)amino]benzyl}cyclopropanecarboxylate) | LC-MS (method 10): $R_t$ = 2.29 min; m/z = 562 $(M + H)^+$.<br>$^1$H-NMR (400 MHz, DMSO-$d_6$): δ = 12.07 (s, 1H), 9.97 (s, 1H), 8.06 (d, 1H), 7.87 (d, 2H), 7.35-7.55 (m, 7H), 7.31 (d, 2H), 7.12 (t, 1H), 7.07 (d, 1H), 6.89 (d, 1H), 5.29 (s, 2H), 3.37 (d, 1H), 2.81 (s, 2H), 2.56-2.64 (m, 1H), 1.72-1.85 (m, 1H), 1.58-1.69 (m, 1H), 1.49-1.58 (m, 2H), 1.38-1.48 (m, 1H), 1.28-1.38 (m, 1H), 1.20-1.28 (m, 1H), 1.10 (d, 2H), 0.91-1.00 (m, 1H), 0.78 (d, 2H). |

| Example | Name/Structure/Starting material | Analytical data |
|---|---|---|
| 157 | 1-{3-[(4,4,4-trifluoro-3-methyl-2-{4-[(6-oxo-3-phenylpyridazin-1(6H)-yl)methyl]phenyl}butanoyl)amino]benzyl}cyclopropanecarboxylic acid (isomer 1)<br><br>(from tert-butyl 1-{3-[(4,4,4-trifluoro-3-methyl-2-{4-[(6-oxo-3-phenylpyridazin-1(6H)-yl)methyl]-phenyl}-butanoyl)amino]benzyl}cyclopropanecarboxylate (isomer 1)) | LC-MS (method 11): $R_t$ = 1.36 min; m/z = 590 $(M + H)^+$.<br>$^1$H-NMR (400 MHz, DMSO-$d_6$): δ = 12.07 (br. s, 1H), 10.15 (s, 1H), 8.06 (d, 1H), 7.87 (d, 2H), 7.42-7.51 (m, 3H), 7.40 (d, 3H), 7.35 (d, 3H), 7.13 (t, 1H), 7.07 (d, 1H), 6.90 (d, 1H), 5.31 (s, 2H), 3.81 (d, 1H), 2.80 (s, 2H), 1.17-1.23 (1H, m), 1.06-1.12 (m, 2H), 0.77 (d, 5H). |
| 158 | 1-{3-[(4,4,4-trifluoro-3-methyl-2-{4-[(6-oxo-3-phenylpyridazin-1(6H)-yl)methyl]phenyl}-butanoyl)amino]benzyl}cyclopropanecarboxylic acid (isomer 2)<br><br>(from tert-butyl 1-{3-[(4,4,4-trifluoro-3-methyl-2-{4-[(6-oxo-3-phenylpyridazin-1(6H)-yl)methyl]phenyl}-butanoyl)amino]benzyl}cyclopropanecarboxylate (isomer 2)) | LC-MS (method 11): $R_t$ = 1.36 min; m/z = 590 $(M + H)^+$.<br>$^1$H-NMR (400 MHz, DMSO-$d_6$): δ = 12.07 (br. s, 1H), 10.15 (s, 1H), 8.06 (d, 1H), 7.87 (d, 2H), 7.42-7.51 (m, 3H), 7.40 (d, 3H), 7.35 (d, 3H), 7.13 (t, 1H), 7.07 (d, 1H), 6.90 (d, 1H), 5.31 (s, 2H), 3.81 (d, 1H), 2.80 (s, 2H), 1.17-1.23 (1H, m), 1.06-1.12 (m, 2H), 0.77 (d, 5H). |

| Example | Name/Structure/Starting material | Analytical data |
|---|---|---|
| 159 | 3-{3-[(cyclopentyl{4-[(3-methyl-6-oxopyridazin-1(6H)-yl)methyl]phenyl}acetyl)amino]-2-methylphenyl}propanoic acid<br>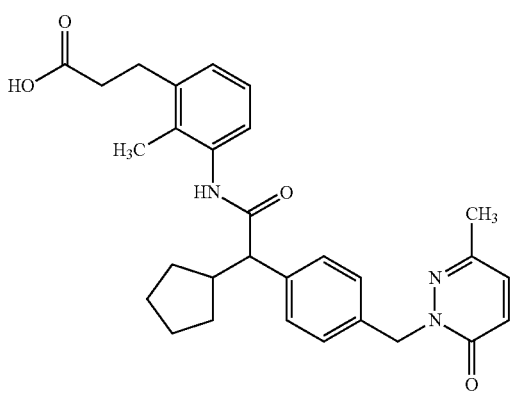 [SMILES: Cc1ccc(=O)n(Cc2ccc(C(C(=O)Nc3cccc(CCC(=O)O)c3C)C3CCCC3)cc2)n1]<br>(from tert-butyl 3-{3-[(cyclopentyl{4-[(3-methyl-6-oxopyridazin-1(6H)-yl)methyl]phenyl}acetyl)amino]-2-methylphenyl}propanoate) | LC-MS (method 15): $R_t$ = 1.01 min; m/z = 488 (M + H)$^+$.<br>$^1$H-NMR (400 MHz, DMSO-$d_6$): δ = 11.79-12.29 (br. s, 1H), 9.46 (s, 1H), 7.36 (dd, 3H), 7.22 (d, 2H), 6.95-7.04 (m, 3H), 6.91 (d, 1H), 5.16 (s, 2H), 3.45 (d, 1H), 2.79 (t, 2H), 2.52-2.61 (m, 1H), 2.43 (t, 2H), 2.26 (s, 3H), 1.99 (s, 3H), 1.77-1.89 (m, 1H), 1.62-1.71 (m, 1H), 1.51-1.61 (m, 2H), 1.42-1.50 (m, 1H), 1.30-1.41 (m, 2H), 0.92-1.02 (m, 1H). |
| 160 | 1-{3-[(5,5,5-trifluoro-3-methyl-2-{4-[(5-oxo-2-phenyl-5,6-dihydro-4H-1,3,4-oxadiazin-4-yl)methyl]phenyl}pentanoyl)amino]benzyl}cyclopropanecarboxylic acid<br>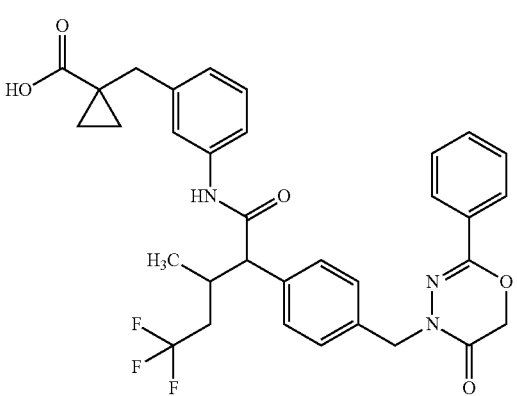 [SMILES: CC(CC(F)(F)F)C(C(=O)Nc1cccc(CC2(C(=O)O)CC2)c1)c1ccc(CN2N=C(c3ccccc3)OCC2=O)cc1]<br>(from tert-butyl 1-{3-[(5,5,5-trifluoro-3-methyl-2-{4-[(5-oxo-2-phenyl-5,6-dihydro-4H-1,3,4-oxadiazin-4-yl)methyl]phenyl}pentanoyl)amino]benzyl}-cyclopropanecarboxylate) | LC-MS (method 11): $R_t$ = 1.43 min; m/z = 608 (M + H)$^+$ (diastereomer 1); $R_t$ = 1.44 min; m/z = 608 (M + H)$^+$ (diastereomer 2).<br>$^1$H-NMR (400 MHz, DMSO-$d_6$): δ = 12.07 (br. s, 1H), 10.14 (s, 0.5H), 10.09 (s, 0.5H) 7.75 (d, 2H), 7.31-7.51 (m, 9H), 7.14 (t, 1H), 6.90 (d, 1H), 4.91 (s, 2H), 4.86 (s, 2H), 3.49 (d, 1H), 2.80 (s, 2H), 2.49-2.64 (m, 1H), 2.24-2.36 (m, 1H), 2.20-2.37 (m, 1H), 1.95-2.10 (m, 0.5H), 1.76-1.95 (m, 0.5H), 1.07-1.15 (m, 4H), 0.72-0.81 (m, 3H). |

| Example | Name/Structure/Starting material | Analytical data |
|---|---|---|
| 161 | 1-(3-{[{4-[(3-chloro-6-oxopyridazin-1(6H)-yl)-methyl]-phenyl}(cyclopentyl)acetyl]amino}benzyl)-cyclopropanecarboxylic acid<br>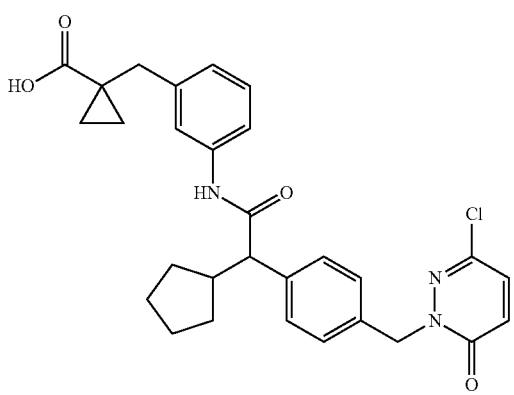 [SMILES: O=C(Nc1cccc(CC2(C(=O)O)CC2)c1)C(c1ccc(Cn2nc(Cl)ccc2=O)cc1)C1CCCC1]<br>(from tert-butyl 1-(3-{[{4-[(3-chloro-6-oxopyridazin-1(6H)-yl)methyl]phenyl}(cyclopentyl)acetyl]-amino}benzyl)cyclopropanecarboxylate) | LC-MS (method 11): $R_t$ = 1.29 min; m/z = 520 $(M + H)^+$.<br>$^1$H-NMR (400 MHz, DMSO-$d_6$): δ =12.08 (s, 1H), 9.97 (s, 1H), 7.40-7.45 (m, 2H), 7.36 (d, 2H), 7.32 (d, 1H), 7.21 (d, 2H), 7.13 (t, 1H), 6.89 (d, 2H), 5.16 (s, 2H), 3.36 (d, 1H), 2.81 (s, 2H), 2.49-2.63 (m, 1H), 1.72-1.83 (m, 1H), 1.41-1.71 (m, 3H), 1.29-1.40 (m, 1H), 1.19-1.30 (m, 1H), 1.10 (d, 2H), 0.89-1.02 (m, 1H), 0.78 (d, 2H). |
| 162 | 3-{3-[(cyclopentyl{4-[(5-methyl-2-oxopyridin-1(2H)-yl)methyl]phenyl}acetyl)amino]-2-methyl-phenyl}propanoic acid<br>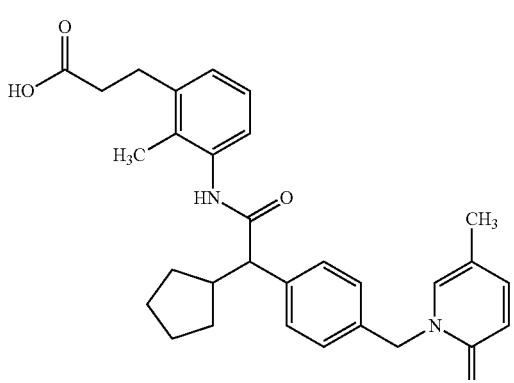<br>(from tert-butyl 3-{3-[(cyclopentyl{4-[(5-methyl-2-oxopyridin-1(2H)-yl)methyl]phenyl}acetyl)amino]-2-methylphenyl}propanoate) | LC-MS (method 15): $R_t$ = 1.00 min; m/z = 487 $(M + H)^+$.<br>$^1$H-NMR (500 MHz, DMSO-$d_6$): δ = 11.90-12.30 (br. s, 1H), 9.47 (s, 1H), 7.56 (s, 1H), 7.38 (d, 2H), 7.30 (d, 1H), 7.22 (d, 2H), 6.93-7.06 (m, 3H), 6.37 (d, 1H), 5.02 (s, 2H), 3.45 (d, 1H), 2.79 (t, 2H), 2.53-2.63 (m, 1H), 2.43 (t, 2H), 2.00 (s, 3H), 1.99 (s, 3H), 1.80-1.90 (m, 1H), 1.64-1.73 (m, 1H), 1.50-1.60 (m, 2H), 1.46 (d, 1H), 1.30-1.39 (m, 2H), 0.96 (dd, 1H). |

| Example | Name/Structure/Starting material | Analytical data |
|---|---|---|
| 163 | 3-{3-[(cyclopentyl{4-[(3-oxo-1,2-benzisoxazol-2(3H)-yl)methyl]phenyl}acetyl)amino]-2-methyl-phenyl}propanoic acid<br>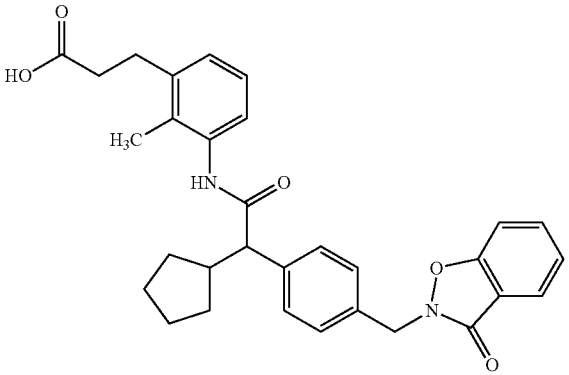 [SMILES: Cc1c(CCC(=O)O)cccc1NC(=O)C(c1ccc(Cn2oc3ccccc3c2=O)cc1)C1CCCC1]<br>(from tert-butyl 3-{3-[(cyclopentyl{4-[(3-oxo-1,2-benzisoxazol-2(3H)-yl)methyl]phenyl}acetyl)-amino]-2-methylphenyl}propanoate) | LC-MS (method 11): $R_t$ = 1.23 min; m/z = 513 $(M + H)^+$. |
| 164 | 1-{3-[(4,4,4-trifluoro-3-methyl-2-{4-[(5-oxo-2-phenyl-5,6-dihydro-4H-1,3,4-oxadiazin-4-yl)methyl]phenyl}-butanoyl)amino]benzyl}cyclopropanecarboxylic acid (isomer 1)<br>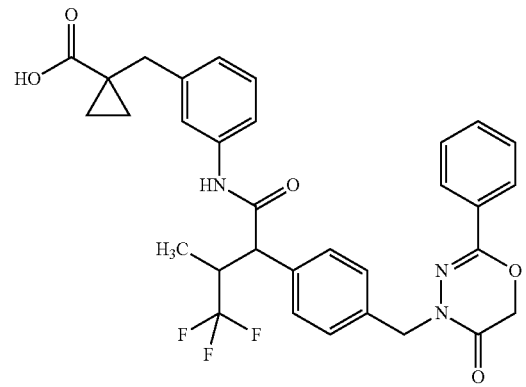 [SMILES: CC(C(C(=O)Nc1cccc(CC2(C(=O)O)CC2)c1)c1ccc(CN2N=C(c3ccccc3)OCC2=O)cc1)C(F)(F)F]<br>(from tert-butyl 1-{3-[(4,4,4-trifluoro-3-methyl-2-{4-[(5-oxo-2-phenyl-5,6-dihydro-4H-1,3,4-oxa-diazin-4-yl)methyl]phenyl}butanoyl)amino]benzyl}-cyclopropanecarboxylate (isomer 1)) | LC-MS (method 15): $R_t$ = 1.23 min; m/z = 594 $(M + H)^+$.<br>$^1$H-NMR (400 MHz, DMSO-$d_6$): δ = 12.08 (br. s, 1H), 10.24 (s, 1H), 7.75 (d, 2H), 7.36-7.51 (m, 7H), 7.32 (d, 2H), 7.12-7.18 (m, 1H), 6.91 (d, 1H), 4.90 (s, 2H), 4.83-4.87 (m, 2H), 3.87 (d, 1H), 3.15-3.29 (m, 1H), 2.80 (s, 2H), 1.20 (d, 3H), 1.07-1.12 (m, 2H), 0.75-0.81 (m, 2H). |

| Example | Name/Structure/Starting material | Analytical data |
|---|---|---|
| 165 | 1-{3-[(4,4,4-trifluoro-3-methyl-2-{4-[(5-oxo-2-phenyl-5,6-dihydro-4H-1,3,4-oxadiazin-4-yl)methyl]phenyl}-butanoyl)amino]benzyl}cyclopropanecarboxylic acid (isomer 2)<br>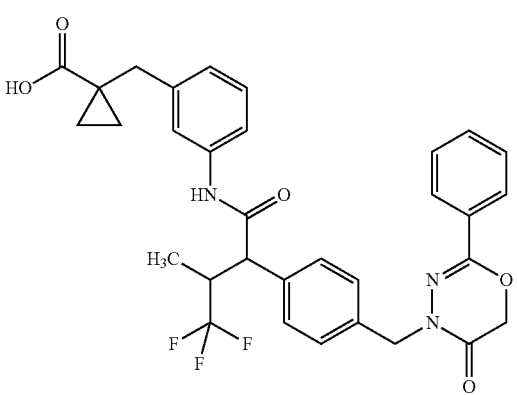 [SMILES: CC(C(C(=O)Nc1cccc(CC2(C(=O)O)CC2)c1)c1ccc(CN2N=C(c3ccccc3)OCC2=O)cc1)C(F)(F)F]<br>(from tert-butyl 1-{3-[(4,4,4-trifluoro-3-methyl-2-{4-[(5-oxo-2-phenyl-5,6-dihydro-4H-1,3,4-oxadiazin-4-yl)methyl]phenyl}butanoyl)amino]-benzyl}cyclopropanecarboxylate (isomer 2)) | LC-MS (method 15): $R_t$ = 1.23 min; m/z = 594 $(M + H)^+$.<br>$^1$H-NMR (400 MHz, DMSO-$d_6$): δ =12.08 (br. s, 1H), 10.24 (s, 1H), 7.75 (d, 2H), 7.36-7.51 (m, 7H), 7.32 (d, 2H), 7.12-7.18 (m, 1H), 6.91 (d, 1H), 4.90 (s, 2H), 4.83-4.87 (m, 2H), 3.87 (d, 1H), 3.15-3.29 (m, 1H), 2.80 (s, 2H), 1.20 (d, 3H), 1.07-1.12 (m, 2H), 0.75-0.81 (m, 2H). |
| 166 | 1-{3-[(4,4,4-trifluoro-3-methyl-2-{4-[(5-oxo-2-phenyl-5,6-dihydro-4H-1,3,4-oxadiazin-4-yl)methyl]phenyl}-butanoyl)amino]benzyl}cyclopropanecarboxylic acid (isomer 3)<br>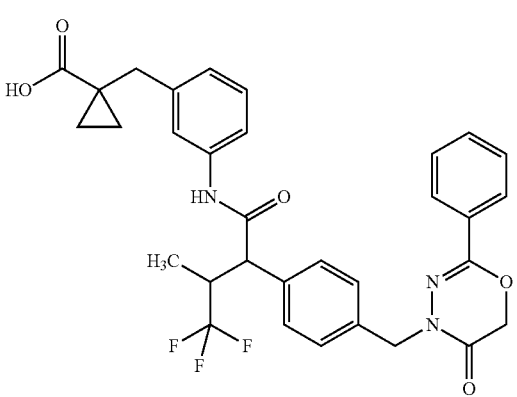 [SMILES: CC(C(C(=O)Nc1cccc(CC2(C(=O)O)CC2)c1)c1ccc(CN2N=C(c3ccccc3)OCC2=O)cc1)C(F)(F)F]<br>(from tert-butyl 1-{3-[(4,4,4-trifluoro-3-methyl-2-{4-[(5-oxo-2-phenyl-5,6-dihydro-4H-1,3,4-oxadiazin-4-yl)methyl]phenyl}butanoyl)amino]-benzyl}cyclopropanecarboxylate (isomer 3)) | LC-MS (method 15): $R_t$ = 1.22 min; m/z = 594 $(M + H)^+$.<br>$^1$H-NMR (400 MHz, DMSO-$d_6$): δ = 11.50-12.50 (br. s, 1H), 10.15 (s, 1H), 7.75 (d, 2H), 7.39-7.51 (m, 7H), 7.36 (d, 2H), 7.13 (t, 1H), 6.90 (d, 1H), 4.90 (s, 2H), 4.86 (s, 2H), 3.82 (d, 1H), 3.30-3.44 (m, 1H), 2.80 (s, 2H), 1.09 (d, 2H), 0.78 (d, 5H). |

| Example | Name/Structure/Starting material | Analytical data |
|---|---|---|
| 167 | 1-{3-[(4,4,4-trifluoro-3-methyl-2-{4-[(5-oxo-2-phenyl-5,6-dihydro-4H-1,3,4-oxadiazin-4-yl)methyl]phenyl}-butanoyl)amino]benzyl}cyclopropanecarboxylic acid (isomer 4)<br>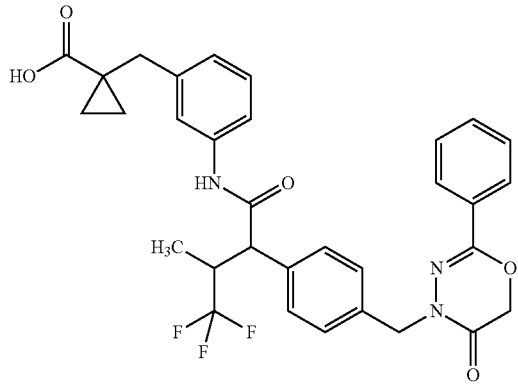 [SMILES: CC(C(C(=O)Nc1cccc(CC2(C(=O)O)CC2)c1)c1ccc(CN2N=C(c3ccccc3)OCC2=O)cc1)C(F)(F)F]<br>(from tert-butyl 1-{3-[(4,4,4-trifluoro-3-methyl-2-{4-[(5-oxo-2-phenyl-5,6-dihydro-4H-1,3,4-oxadiazin-4-yl)methyl]phenyl}butanoyl)amino]-benzyl}cyclopropanecarboxylate (isomer 4)) | LC-MS (method 15): $R_t$ = 1.23 min; m/z = 594 $(M + H)^+$.<br>$^1$H-NMR (400 MHz, DMSO-$d_6$): δ = 11.50-12.50 (br. s, 1H), 10.15 (s, 1H), 7.75 (d, 2H), 7.39-7.51 (m, 7H), 7.36 (d, 2H), 7.13 (t, 1H), 6.90 (d, 1H), 4.90 (s, 2H), 4.86 (s, 2H), 3.82 (d, 1H), 3.30-3.44 (m, 1H), 2.80 (s, 2H), 1.09 (d, 2H), 0.78 (d, 5H). |
| 168 | 3-{2-methyl-3-[(4,4,4-trifluoro-3-methyl-2-{4-[(5-oxo-2-phenyl-5,6-dihydro-4H-1,3,4-oxadiazin-4-yl)methyl]-phenyl}butanoyl)amino]phenyl}propanoic acid<br>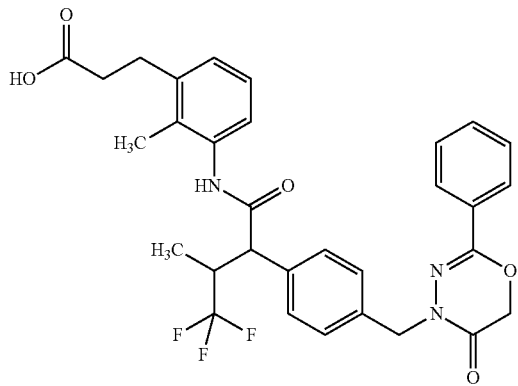 [SMILES: Cc1c(CCC(=O)O)cccc1NC(=O)C(c1ccc(CN2N=C(c3ccccc3)OCC2=O)cc1)C(C)C(F)(F)F]<br>(from tert-butyl 3-{2-methyl-3-[(4,4,4-trifluoro-3-methyl-2-{4-[(5-oxo-2-phenyl-5,6-dihydro-4H-1,3,4-oxadiazin-4-yl)methyl]phenyl}butanoyl)-amino]phenyl}propanoate) | LC-MS (method 15): $R_t$ = 1.14 min; m/z = 582 $(M + H)^+$. |

| Example | Name/Structure/Starting material | Analytical data |
|---|---|---|
| 169 | 3-{3-[(4,4,4-trifluoro-3-methyl-2-{4-[(5-oxo-2-phenyl-5,6-dihydro-4H-1,3,4-oxadiazin-4-yl)methyl]phenyl}-butanoyl)amino]phenyl}-propanoic acid<br>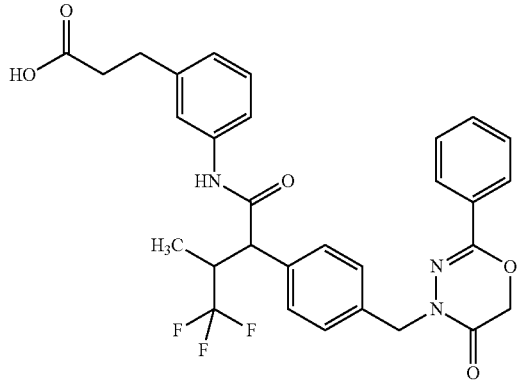 [SMILES: CC(C(C(=O)Nc1cccc(CCC(=O)O)c1)c1ccc(CN2N=C(c3ccccc3)OCC2=O)cc1)C(F)(F)F]<br>(from tert-butyl 3-{3-[(4,4,4-trifluoro-3-methyl-2-{4-[(5-oxo-2-phenyl-5,6-dihydro-4H-1,3,4-oxadiazin-4-yl)-methyl]phenyl}butanoyl)amino]phenyl}-propanoate) | LC-MS (method 15): $R_t$ = 1.17 min; m/z = 568 $(M + H)^+$. |
| 170 | 1-(3-{[2-{4-[(5-oxo-2-phenyl-5,6-dihydro-4H-1,3,4-oxadiazin-4-yl)methyl]phenyl}-3-(trifluoromethyl)-pentanoyl]amino}benzyl)cyclopropanecarboxylic acid<br>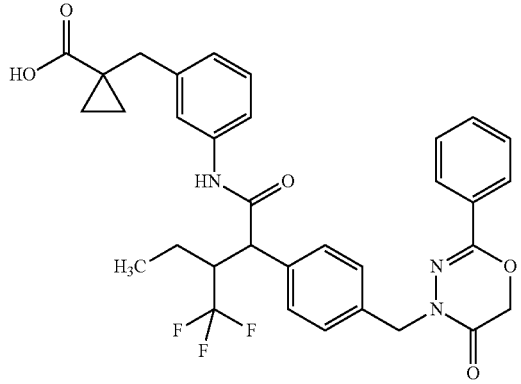 [SMILES: CCC(C(C(=O)Nc1cccc(CC2(C(=O)O)CC2)c1)c1ccc(CN2N=C(c3ccccc3)OCC2=O)cc1)C(F)(F)F]<br>(from tert-butyl 1-(3-{[2-{4-[(5-oxo-2-phenyl-5,6-dihydro-4H-1,3,4-oxadiazin-4-yl)methyl]phenyl}-3-(trifluoromethyl)pentanoyl]amino}benzyl)-cyclopropanecarboxylate) | LC-MS (method 15): $R_t$ = 1.26 min; m/z = 608 $(M + H)^+$.<br>$^1$H-NMR (400 MHz, DMSO-$d_6$): δ = 12.10 (br. s, 1H), 10.16 (s, 1H), 7.75 (d, 2H), 7.28-7.60 (m, 9H), 7.13 (t, 1H), 6.89 (d, 1H), 4.90 (s, 2H), 4.86 (s, 2H), 3.94 (d, 1H), 3.20-3.31 (m, 1H), 2.80 (s, 2H), 1.20-1.43 (m, 2H), 1.09 (d, 2H), 0.71-0.81 (m, 5H). |

| Example | Name/Structure/Starting material | Analytical data |
|---|---|---|
| 171 | 1-{3-[(cyclopentyl{4-[(3-methyl-6-oxopyridazin-1(6H)-yl)methyl]phenyl}acetyl)amino]benzyl}-cyclopropanecarboxylic acid<br><br>(from tert-butyl 1-{3-[(cyclopentyl{4-[(3-methyl-6-oxopyridazin-1(6H)-yl)methyl]phenyl}acetyl)-amino]benzyl}cyclopropanecarboxylate) | LC-MS (method 11): $R_t$ = 1.23 min; m/z = 500 (M + H)$^+$. |
| 172 | 3-(3-{[cyclopentyl(4-{[6-oxo-3-(trifluoromethyl)-pyridazin-1(6H)-yl]methyl}phenyl)acetyl]amino}-2-methylphenyl)propanoic acid<br><br>(from tert-butyl 3-(3-{[cyclopentyl(4-{[6-oxo-3-(trifluoromethyl)pyridazin-1(6H)-yl]methyl}-phenyl)acetyl]amino}-2-methylphenyl)propanoate) | LC-MS (method 15): $R_t$ = 1.13 min; m/z = 542 (M + H)$^+$.<br>$^1$H-NMR (400 MHz, DMSO-d$_6$): δ = 12.13 (s, 1H), 9.47 (s, 1H), 7.87 (d, 1H), 7.41 (d, 2H), 7.26 (d, 2H), 7.21 (d, 1H), 6.95-7.06 (m, 3H), 5.29 (s, 2H), 3.46 (d, 1H), 2.79 (t, 2H), 2.56-2.63 (m, 1H), 2.43 (t, 2H), 1.98 (s, 3H), 1.77-1.88 (m, 1H), 1.30-1.72 (m, 6H), 0.96 (dd, 1H). |

| Example | Name/Structure/Starting material | Analytical data |
|---|---|---|
| 173 | 1-(3-{[cyclopentyl(4-{[6-oxo-3-(trifluoromethyl)-pyridazin-1(6H)-yl]methyl}phenyl)acetyl]amino}-benzyl)cyclopropanecarboxylic acid<br>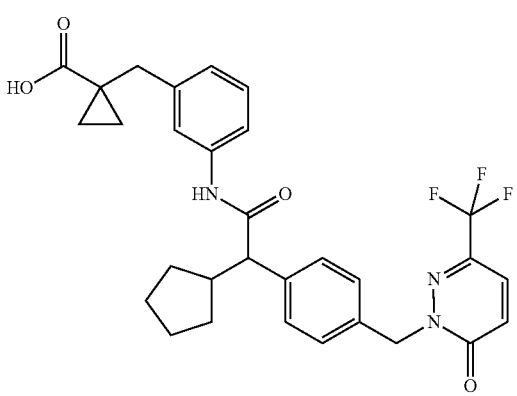 [SMILES: O=C(Nc1cccc(CC2(C(=O)O)CC2)c1)C(c1ccc(Cn2nc(C(F)(F)F)ccc2=O)cc1)C1CCCC1]<br>(from tert-butyl 1-(3-{[cyclopentyl(4-{[6-oxo-3-(trifluoromethyl)pyridazin-1(6H)-yl]methyl}-phenyl)-acetyl]amino}benzyl)cyclopropanecarboxylate) | LC-MS (method 15): $R_t$ = 1.20 min; m/z = 554 $(M + H)^+$.<br>$^1$H-NMR (400 MHz, DMSO-$d_6$): δ = 12.08 (br. s, 1H), 9.98 (s, 1H), 7.85 (d, 1H), 7.35-7.46 (m, 4H), 7.26 (d, 2H), 7.09-7.21 (m, 2H), 6.89 (d, 1H), 5.27 (s, 2H), 3.38 (d, 1H), 2.81 (s, 2H), 2.56-2.64 (m, 1H), 1.73-1.84 (m, 1H), 1.18-1.70 (m, 6H), 1.07-1.13 (m, 2H), 0.85-1.02 (m, 1H), 0.78 (d, 2H). |
| 174 | 3-(3-{[cyclopentyl(4-{[6-oxo-3-(trifluoromethyl)-pyridazin-1(6H)-yl]methyl}phenyl)acetyl]amino}-phenyl)propanoic acid<br>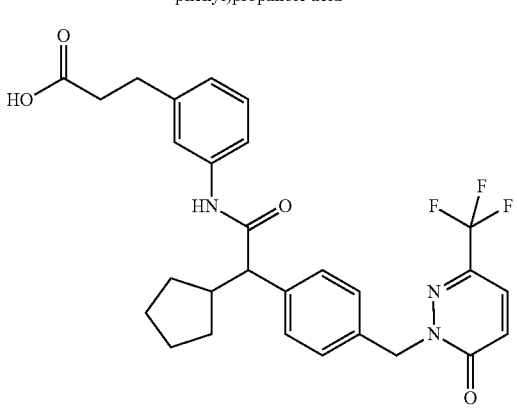<br>(from methyl 3-(3-{[cyclopentyl(4-{[6-oxo-3-(trifluoromethyl)pyridazin-1(6H)-yl]methyl}phenyl)acetyl]-amino}phenyl)propanoate) | LC-MS (method 11): $R_t$ = 1.31 min; m/z = 528 $(M + H)^+$.<br>$^1$H-NMR (400 MHz, DMSO-$d_6$): δ = 12.07 (br. s, 1H), 9.99 (s, 1H), 7.85 (d, 1H), 7.39 (d, 4H), 7.26 (d, 2H), 7.07-7.20 (m, 2H), 6.87 (d, 1H), 5.27 (s, 2H), 3.37 (d, 1H), 2.75 (t, 2H), 2.57-2.64 (m, 1H), 2.48 (t, 2H), 1.78 (dd, 1H), 1.59-1.71 (m, 1H), 1.41-1.59 (m, 3H), 1.34 (dd, 1H), 1.25 (dd, 1H), 0.95 (dd, 1H). |

| Example | Name/Structure/Starting material | Analytical data |
|---|---|---|
| 175 | 1-{3-[(cyclopentyl{4-[(3-methyl-2-oxopyridin-1(2H)-yl)methyl]phenyl}acetyl)amino]benzyl}-cyclopropanecarboxylic acid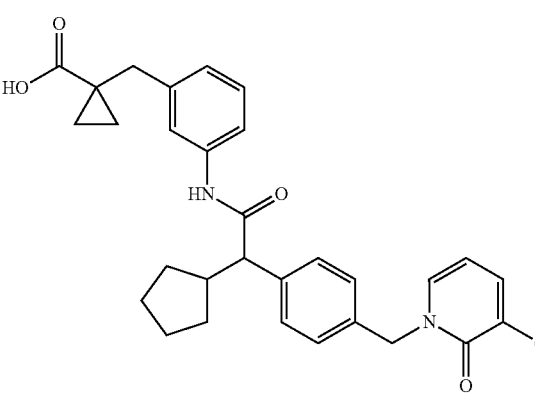(from tert-butyl 1-{3-[(cyclopentyl{4-[(3-methyl-2-oxopyridin-1(2H)-yl)methyl]phenyl}acetyl)-amino]benzyl}cyclopropanecarboxylate) | LC-MS (method 15): $R_t$ = 1.11 min; m/z = 499 $(M + H)^+$. $^1$H-NMR (400 MHz, DMSO-$d_6$): δ = 11.5-12.5 (br. s, 1H), 9.97 (s, 1H), 7.62 (d, 1H), 7.39-7.47 (m, 2H), 7.36 (d, 2H), 7.28 (d, 1H), 7.22 (d, 2H), 7.13 (t, 1H), 6.89 (d, 1H), 6.13 (t, 1H), 5.06 (s, 2H), 3.38 (d, 1H), 2.81 (s, 2H), 2.58-2.64 (m, 1H), 1.99 (s, 3H), 1.70-1.82 (m, 1H), 1.58-1.68 (m, 1H), 1.49-1.58 (m, 2H), 1.40-1.49 (m, 1H), 1.29-1.38 (m, 1H), 1.24 (dd, 1H), 1.06-1.13 (m, 2H), 0.94 (dd, 1H), 0.74-0.82 (m, 2H). |
| 176 | 1-(3-{[cyclopentyl(4-{[2-oxo-4-(trifluoromethyl)-pyridin-1(2H)-yl]methyl}phenyl)acetyl]amino}-benzyl)cyclopropanecarboxylic acid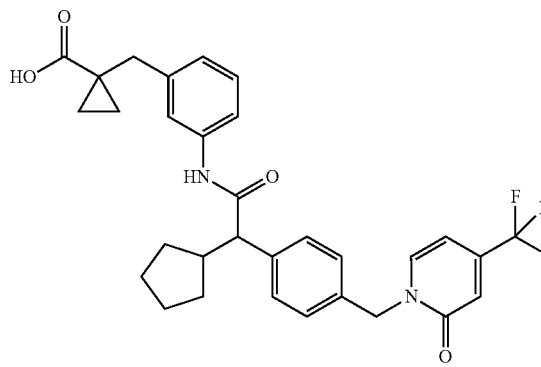(from tert-butyl 1-(3-{[cyclopentyl(4-{[2-oxo-4-(trifluoromethyl)pyridin-1(2H)-yl]methyl}phenyl)acetyl]-amino}benzyl)cyclopropanecarboxylate) | LC-MS (method 15): $R_t$ = 1.17 min; m/z = 553 $(M + H)^+$. $^1$H-NMR (400 MHz, DMSO-$d_6$): δ = 12.08 (s, 1H), 9.97 (s, 1H), 8.06 (d, 1H), 7.36-7.46 (m, 4H), 7.25 (d, 2H), 7.13 (t, 1H), 6.89 (d, 1H), 6.80 (s, 1H), 6.49 (dd, 1H), 5.12 (s, 2H), 3.38 (d, 1H), 2.81 (s, 2H), 2.56-2.64 (m, 1H), 1.72-1.83 (m, 1H), 1.59-1.70 (m, 1H), 1.49-1.58 (m, 2H), 1.40-1.49 (m, 1H), 1.28-1.39 (m, 1H), 1.20-1.29 (m, 1H), 1.07-1.12 (m, 2H), 0.89-1.01 (m, 1H), 0.74-0.80 (m, 2H). |

| Example | Name/Structure/Starting material | Analytical data |
|---|---|---|
| 177 | 3-(3-{[(3,3-difluorocyclopentyl){4-[(5-oxo-2-phenyl-5,6-dihydro-4H-1,3,4-oxadiazin-4-yl)methyl]phenyl}acetyl]amino}phenyl)propanoic acid<br>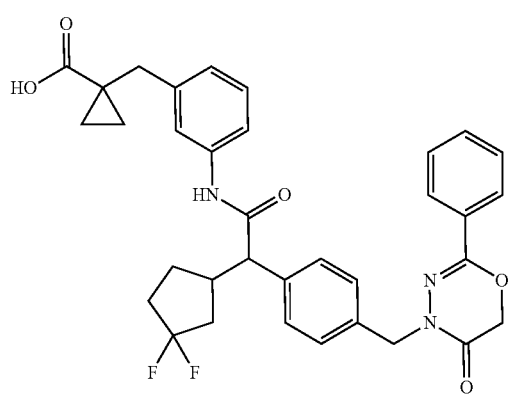 [SMILES: O=C(Nc1cccc(CC2(C(=O)O)CC2)c1)C(c1ccc(CN2N=C(c3ccccc3)OCC2=O)cc1)C1CCC(F)(F)C1]<br>(from methyl 3-(3-{[(3,3-difluorocyclopentyl){4-[(5-oxo-2-phenyl-5,6-dihydro-4H-1,3,4-oxadiazin-4-yl)-methyl]phenyl}acetyl]amino}phenyl)propanoate) | LC-MS (method 11): $R_t$ = 1.33 min; m/z = 576 $(M + H)^+$.<br>$^1$H-NMR (400 MHz, DMSO-$d_6$): δ = 12.08 (br. s, 1H), 10.06 (d, 1H), 7.76 (d, 2H), 7.38-7.54 (m, 7H), 7.34 (d, 2H), 7.15 (t, 1H), 6.88 (d, 1H), 4.90 (s, 2H), 4.85 (s, 2H), 3.52 (d, 1H), 2.82-2.96 (m, 1H), 2.74 (t, 2H), 2.47 (t, 2H), 1.95-2.38 (m, 3H), 1.79-1.92 (m, 1H), 1.44-1.70 (m, 2H). |
| 178 | 1-(3-{[(3,3-difluorocyclopentyl){4-[(5-oxo-2-phenyl-5,6-dihydro-4H-1,3,4-oxadiazin-4-yl)methyl]phenyl}-acetyl]amino}benzyl)cyclopropanecarboxylic acid<br>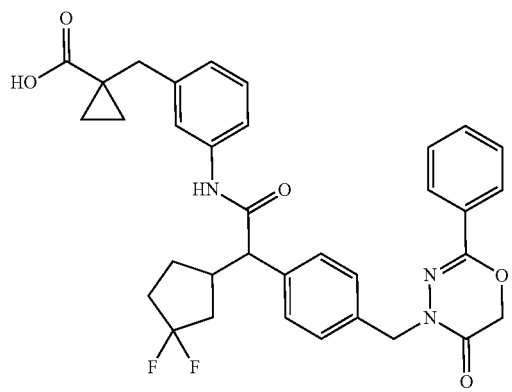 [SMILES: O=C(Nc1cccc(CC2(C(=O)O)CC2)c1)C(c1ccc(CN2N=C(c3ccccc3)OCC2=O)cc1)C1CCC(F)(F)C1]<br>(from tert-butyl 1-(3-{[(3,3-difluorocyclopentyl){4-[(5-oxo-2-phenyl-5,6-dihydro-4H-1,3,4-oxadiazin-4-yl)-methyl]phenyl}acetyl]amino}benzyl)-cyclopropanecarboxylate) | LC-MS (method 11): $R_t$ = 1.39 min; m/z = 602 $(M + H)^+$.<br>$^1$H-NMR (400 MHz, DMSO-$d_6$): δ = 12.07 (br. s, 1H), 10.05 (d, 1H), 7.76 (d, 2H), 7.38-7.53 (m, 7H), 7.34 (d, 2H), 7.14 (t, 1H), 6.90 (d, 1H), 4.90 (s, 2H), 4.85 (s, 2H), 3.49-3.55 (m, 1H), 2.88 (dd, 1H), 2.80 (s, 2H), 1.79-2.39 (m, 4H), 1.46-1.65 (m, 1H), 1.21-1.37 (m, 1H), 1.09 (d, 2H), 0.78 (d, 2H). |

| Example | Name/Structure/Starting material | Analytical data |
|---|---|---|
| 179 | 1-{3-[(cyclopentyl{4-[(4-methyl-2-oxopyridin-1(2H)-yl)methyl]phenyl}acetyl)amino]benzyl}-cyclopropanecarboxylic acid<br>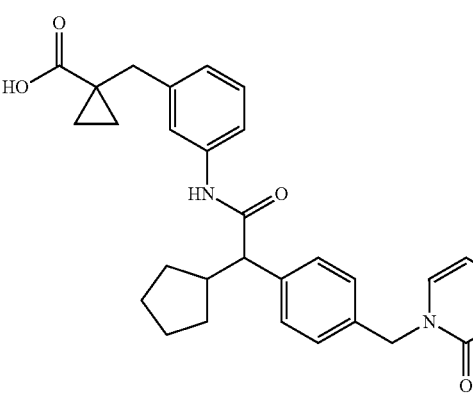<br>(from tert-butyl 1-{3-[(cyclopentyl{4-[(4-methyl-2-oxopyridin-1(2H)-yl)methyl]phenyl}acetyl)-amino]benzyl}cyclopropanecarboxylate) | LC-MS (method 15): $R_t$ = 1.06 min; m/z = 499 (M + H)$^+$.<br>$^1$H-NMR (400 MHz, DMSO-d$_6$): δ = 12.10 (br. s, 1H), 9.96 (s, 1H), 7.62 (d, 1H), 7.39-7.47 (m, 2H), 7.36 (d, 2H), 7.20 (d, 2H), 7.13 (t, 1H), 6.89 (d, 1H), 6.21 (br. s, 1H), 6.07 (d, 1H), 5.01 (s, 2H), 3.38 (d, 1H), 2.81 (s, 2H), 2.10 (s, 3H), 1.71-1.83 (m, 2H), 1.19-1.68 (m, 6H), 1.10 (br. s, 2H), 0.90-1.01 (m, 1H), 0.78 (br. s, 2H). |
| 180 | 3-(3-{[4,4,4-trifluoro-3-methyl-2-(4-{[6-oxo-3-(trifluoromethyl)pyridazin-1(6H)-yl]methyl}-phenyl)butanoyl]amino}phenyl)propanoic acid<br>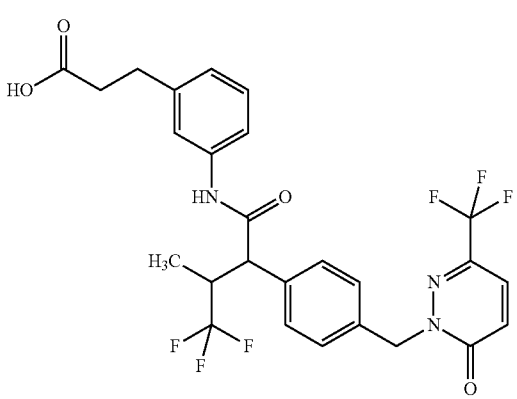 [SMILES: CC(C(C(=O)Nc1cccc(CCC(=O)O)c1)c1ccc(Cn2nc(C(F)(F)F)ccc2=O)cc1)C(F)(F)F]<br>(from methyl 3-(3-{[4,4,4-trifluoro-3-methyl-2-(4-{[6-oxo-3-(trifluoromethyl)pyridazin-1(6H)-yl]-methyl}-phenyl)butanoyl]amino}phenyl)propanoate) | LC-MS (method 15): $R_t$ = 1.11 min; m/z = 556 (M + H)$^+$. |

| Example | Name/Structure/Starting material | Analytical data |
|---|---|---|
| 181 | 1-(3-{[4,4,4-trifluoro-3-methyl-2-(4-{[6-oxo-3-(trifluoromethyl)pyridazin-1(6H)-yl]methyl}-phenyl)-butanoyl]amino}benzyl)cyclopropanecarboxylic acid (enantiomer 1)<br>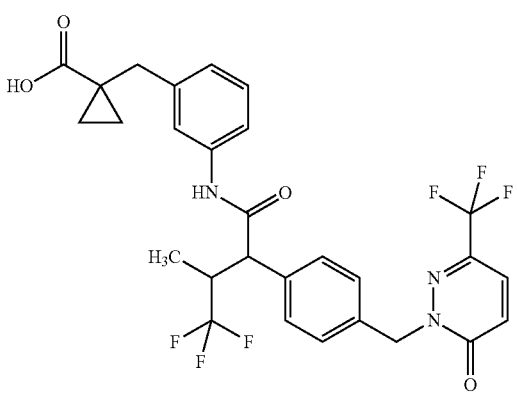 [SMILES: CC(C(C(=O)Nc1cccc(CC2(C(=O)O)CC2)c1)c1ccc(Cn2nc(C(F)(F)F)ccc2=O)cc1)C(F)(F)F]<br>(from tert-butyl 1-(3-{[4,4,4-trifluoro-3-methyl-2-(4-{[6-oxo-3-(trifluoromethyl)pyridazin-1(6H)-yl]methyl}phenyl)butanoyl]amino}benzyl)-cyclopropanecarboxylate (enantiomer 1)) | LC-MS (method 15): $R_t$ = 1.14 min; m/z = 582 $(M + H)^+$.<br>$^1$H-NMR (400 MHz, DMSO-$d_6$): δ = 11.85-12.25 (br. s, 1H), 10.15 (s, 1H), 7.84 (d, 1H), 7.41 (d, 3H), 7.36 (s, 1H), 7.30 (d, 2H), 7.19 (d, 1H), 7.14 (t, 1H), 6.91 (d, 1H), 5.29 (s, 2H), 3.82 (d, 1H), 3.28-3.44 (m, 1H), 1.06-1.14 (m, 2H), 0.79 (d, 5H). |
| 182 | 1-(3-{[4,4,4-trifluoro-3-methyl-2-(4-{[6-oxo-3-(trifluoromethyl)pyridazin-1(6H)-yl]methyl}phenyl)-butanoyl]amino}benzyl)cyclopropanecarboxylic acid (enantiomer 2)<br>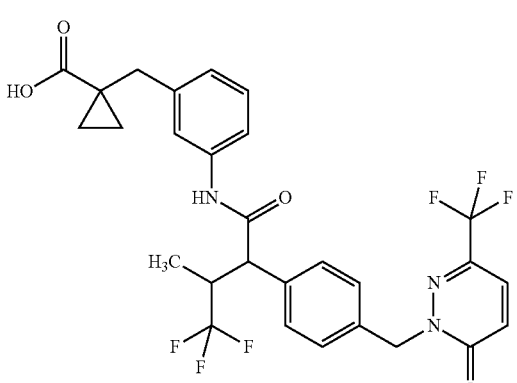<br>(from tert-butyl 1-(3-{[4,4,4-trifluoro-3-methyl-2-(4-{[6-oxo-3-(trifluoromethyl)pyridazin-1(6H)-yl]methyl}phenyl)butanoyl]amino}benzyl)-cyclopropanecarboxylate (enantiomer 2)) | LC-MS (method 15): $R_t$ = 1.14 min; m/z = 582 $(M + H)^+$.<br>$^1$H-NMR (400 MHz, DMSO-$d_6$): δ = 11.85-12.25 (br. s, 1H), 10.15 (s, 1H), 7.84 (d, 1H), 7.41 (d, 3H), 7.36 (s, 1H), 7.30 (d, 2H), 7.19 (d, 1H), 7.14 (t, 1H), 6.91 (d, 1H), 5.29 (s, 2H), 3.82 (d, 1H), 3.28-3.44 (m, 1H), 1.06-1.14 (m, 2H), 0.79 (d, 5H). |

| Example | Name/Structure/Starting material | Analytical data |
|---|---|---|
| 183 | 1-(3-{[cyclopentyl(4-{[2-oxo-3-(trifluoromethyl)-pyridin-1(2H)-yl]methyl}phenyl)acetyl]amino}-benzyl)cyclopropanecarboxylic acid<br>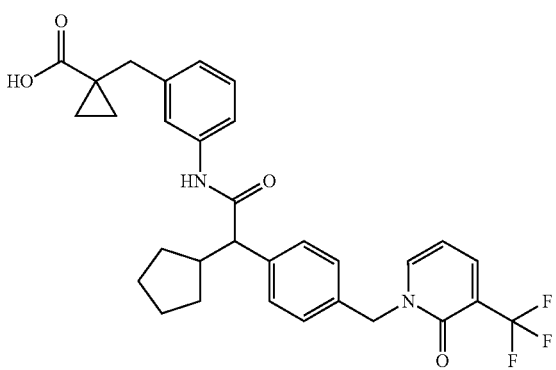 [SMILES: O=C(Nc1cccc(CC2(C(=O)O)CC2)c1)C(c1ccc(Cn2cccc(C(F)(F)F)c2=O)cc1)C1CCCC1]<br>(from tert-butyl 1-(3-{[cyclopentyl(4-{[2-oxo-3-(trifluoromethyl)pyridin-1(2H)-yl]methyl}phenyl)-acetyl]amino}benzyl)cyclopropanecarboxylate) | LC-MS (method 15): $R_t$ = 1.16 min; m/z = 553 $(M + H)^+$.<br>$^1$H-NMR (400 MHz, DMSO-$d_6$): δ = 12.07 (s, 1H), 9.97 (s, 1H), 8.14 (d, 1H), 7.93 (d, 1H), 7.36-7.46 (m, 4H), 7.26 (d, 2H), 7.13 (t, 1H), 6.89 (d, 1H), 6.38 (t, 1H), 5.13 (s, 2H), 3.38 (d, 1H), 2.81 (s, 2H), 2.56-2.64 (m, 1H), 1.77 (dd, 1H), 1.41-1.68 (m, 4H), 1.28-1.38 (m, 1H), 1.23-1.29 (m, 1H), 1.10 (d, 2H), 0.95 (dd, 1H), 0.78 (d, 2H). |
| 184 | 3-{2-chloro-3-[(4,4,4-trifluoro-3-methyl-2-{4-[(5-oxo-2-phenyl-5,6-dihydro-4H-1,3,4-oxadiazin-4-yl)methyl]-phenyl}butanoyl)amino]phenyl}propanoic acid<br>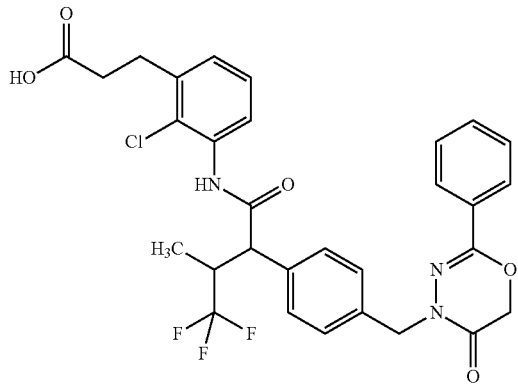 [SMILES: CC(C(C(=O)Nc1cccc(CCC(=O)O)c1Cl)c1ccc(CN2N=C(c3ccccc3)OCC2=O)cc1)C(F)(F)F]<br>(from tert-butyl 3-{2-chloro-3-[(4,4,4-trifluoro-3-methyl-2-{4-[(5-oxo-2-phenyl-5,6-dihydro-4H-1,3,4-oxadiazin-4-yl)methyl]phenyl}butanoyl)-amino]phenyl}propanoate) | LC-MS (method 15): $R_t$ = 1.21 min; m/z = 602 $(M + H)^+$.<br>$^1$H-NMR (400 MHz, DMSO-$d_6$): δ = 12.21 (br. s, 1H), 9.78 (s, 1H), 7.76 (d, 2H), 7.41-7.55 (m, 5H), 7.32-7.39 (m, 3H), 7.19 (t, 1H), 7.12 (d, 1H), 4.92 (s, 2H), 4.88 (s, 2H), 4.10 (d, 1H), 3.36-3.43 (m, 1H), 2.87 (t, 2H), 2.46 (t, 2H), 0.79 (d, 3H). |

-continued

| Example | Name/Structure/Starting material | Analytical data |
|---------|----------------------------------|-----------------|
| 185 | 3-{4-fluoro-3-[(4,4,4-trifluoro-3-methyl-2-{4-[(5-oxo-2-phenyl-5,6-dihydro-4H-1,3,4-oxadiazin-4-yl)methyl]-phenyl}butanoyl)amino]phenyl}propanoic acid<br><br>(from tert-butyl 3-{4-fluoro-3-[(4,4,4-trifluoro-3-methyl-2-{4-[(5-oxo-2-phenyl-5,6-dihydro-4H-1,3,4-oxadiazin-4-yl)methyl]phenyl}butanoyl)amino]phenyl}-propanoate) | LC-MS (method 15): $R_t$ = 1.15 min; m/z = 586 $(M + H)^+$.<br>$^1$H-NMR (400 MHz, DMSO-$d_6$): δ = 12.09 (br. s, 1H), 9.99 (s, 1H), 7.76 (d, 2H), 7.66 (d, 1H), 7.40-7.53 (m, 5H), 7.36 (d, 2H), 7.09 (dd, 1H), 6.92-7.00 (m, 1H), 4.91 (s, 2H), 4.87 (s, 2H), 4.08 (d, 1H), 3.36-3.42 (m, 1H), 2.73 (t, 2H), 2.41-2.48 (m, 2H), 0.77 (d, 3H). |
| 186 | 1-{4-fluoro-3-[(4,4,4-trifluoro-3-methyl-2-{4-[(5-oxo-2-phenyl-5,6-dihydro-4H-1,3,4-oxadiazin-4-yl)methyl]phenyl}butanoyl)amino]benzyl}-cyclopropanecarboxylic acid<br><br>(from tert-butyl 1-{4-fluoro-3-[(4,4,4-trifluoro-3-methyl-2-{4-[(5-oxo-2-phenyl-5,6-dihydro-4H-1,3,4-oxadiazin-4-yl)methyl]phenyl}butanoyl)-amino]benzyl}cyclopropanecarboxylate) | LC-MS (method 15): $R_t$ = 1.21 min; m/z = 612 $(M + H)^+$.<br>$^1$H-NMR (400 MHz, DMSO-$d_6$): δ = 12.11 (br. s, 1H), 9.97 (s, 1H), 7.76 (d, 2H), 7.67 (d, 1H), 7.40-7.53 (m, 5H), 7.36 (d, 2H), 7.08 (t, 1H), 6.95-7.02 (m, 1H), 4.91 (s, 2H), 4.87 (s, 2H), 4.07 (d, 1H), 3.29-3.40 (m, 1H), 2.79 (s, 2H), 1.07 (d, 2H), 0.77 (d, 5H). |

-continued

| Example | Name/Structure/Starting material | Analytical data |
|---|---|---|
| 187 | 3-{4-chloro-3-[(cyclopentyl{4-[(5-oxo-2-phenyl-5,6-dihydro-4H-1,3,4-oxadiazin-4-yl)methyl]-phenyl}acetyl)amino]phenyl}propanoic acid<br>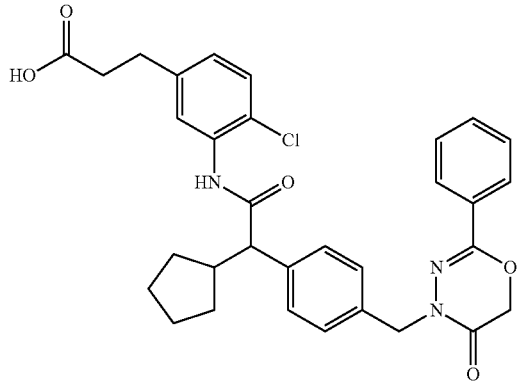 [SMILES: O=C(O)CCc1ccc(Cl)c(NC(=O)C(c2ccc(CN3N=C(c4ccccc4)OCC3=O)cc2)C2CCCC2)c1]<br>(from tert-butyl 3-{4-chloro-3-[(cyclopentyl{4-[(5-oxo-2-phenyl-5,6-dihydro-4H-1,3,4-oxadiazin-4-yl)methyl]-phenyl}acetyl)amino]phenyl}propanoate) | LC-MS (method 15): $R_t$ = 1.25 min; m/z = 574 (M + H)$^+$.<br>$^1$H-NMR (400 MHz, DMSO-$d_6$): δ = 12.01-12.25 (br. s, 1H), 9.60 (s, 1H), 7.79 (d, 2H), 7.38-7.55 (m, 6H), 7.33 (t, 3H), 7.02 (dd, 1H), 4.91 (s, 2H), 4.85 (s, 2H), 3.59 (d, 1H), 2.75 (t, 2H), 2.49-2.62 (m, 1H), 2.47 (t, 2H), 1.76-1.89 (m, 1H), 1.61-1.75 (m, 1H), 1.49-1.61 (m, 2H), 1.41-1.49 (m, 1H), 1.29-1.41 (m, 2H), 0.89-1.04 (m, 1H). |

Example 188 and Example 189

1-(3-{[{4-[(3-Chloro-6-oxopyridazin-1(6H)-yl)methyl]phenyl}(cyclopentyl)acetyl]amino}-benzyl)cyclopropanecarboxylic acid (enantiomers 1 and 2)

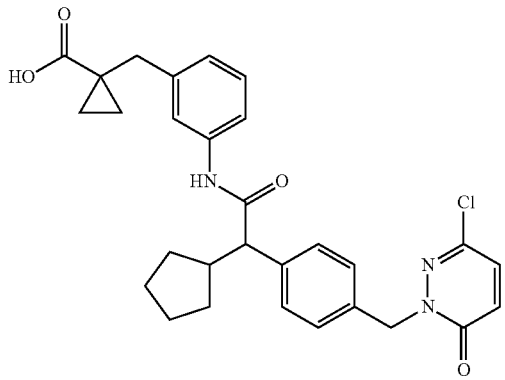 [SMILES: O=C(Nc1cccc(CC2(C(=O)O)CC2)c1)C(c1ccc(Cn2nc(Cl)ccc2=O)cc1)C1CCCC1]

170 mg (0.33 mmol) of racemic 1-(3-{[{4-[(3-chloro-6-oxopyridazin-1(6H)-yl)methyl]-phenyl}(cyclopentyl)acetyl]amino}benzyl)cyclopropanecarboxylic acid were separated into the enantiomers by preparative HPLC on a chiral phase [column: Daicel Chiralpak AD-H, 5 μm, 250 mm×20 mm; mobile phase: isohexane/(isopropanol+0.2% trifluoroacetic acid+1% water) 70:30 (v/v); flow rate: 15 ml/min; UV detection: 220 nm; temperature: 30° C.]:

Example 188

Enantiomer 1

Yield: 93 mg $R_t$ 7.83 min; purity >99%; >99% ee

[column: Daicel Chiralpak AD-H, 5 μm, 250 mm×4.6 mm; mobile phase: isohexane/(isopropanol+0.2% trifluoroacetic acid+1% water) 65:35 (v/v); flow rate: 1 ml/min; UV detection: 220 nm; temperature: 25° C.].

LC-MS (method 15): $R_t$=1.15 min; m/z=520 (M+H)$^+$.

$^1$H-NMR (400 MHz, DMSO-$d_6$): δ=9.98 (s, 1H), 7.55 (d, 1H), 7.35-7.46 (m, 4H), 7.25 (d, 2H), 7.14 (t, 1H), 7.07 (d, 1H), 6.89 (d, 1H), 5.15 (s, 2H), 3.38 (d, 1H), 2.81 (s, 2H), 2.55-2.62 (m, 1H), 1.77 (dd, 1H), 1.41-1.68 (m, 4H), 1.20-1.40 (m, 2H), 1.07-1.14 (m, 2H), 0.91-1.00 (m, 1H), 0.78 (d, 2H).

Example 189

Enantiomer 2

Yield: 85 mg $R_t$ 9.17 min; purity >99%; >97% ee

[column: Daicel Chiralpak AD-H, 5 μm, 250 mm×4.6 mm; mobile phase: isohexane/(isopropanol+0.2% trifluoroacetic acid+1% water) 65:35 (v/v); flow rate: 1 ml/min; UV detection: 220 nm; temperature: 25° C.].

LC-MS (method 15): $R_t$=1.15 min; m/z=520 (M+H)$^+$.

$^1$H-NMR (400 MHz, DMSO-$d_6$): δ=9.98 (s, 1H), 7.55 (d, 1H), 7.35-7.47 (m, 4H), 7.25 (d, 2H), 7.14 (t, 1H), 7.07 (d, 1H), 6.89 (d, 1H), 5.15 (s, 2H), 3.38 (d, 1H), 2.81 (s, 2H), 2.56-2.64 (m, 1H), 1.69-1.84 (m, 1H), 1.40-1.67 (m, 4H), 1.19-1.38 (m, 2H), 1.10 (d, 2H), 0.90-1.01 (m, 1H), 0.78 (d, 2H).

Example 190 and Example 191

3-{2-Methyl-3-[(4,4,4-trifluoro-3-methyl-2-{4-[(5-oxo-2-phenyl-5,6-dihydro-4H-1,3,4-oxadiazin-4-yl)methyl]phenyl}butanoyl)amino]phenyl}propanoic acid (isomers 1 and 2)

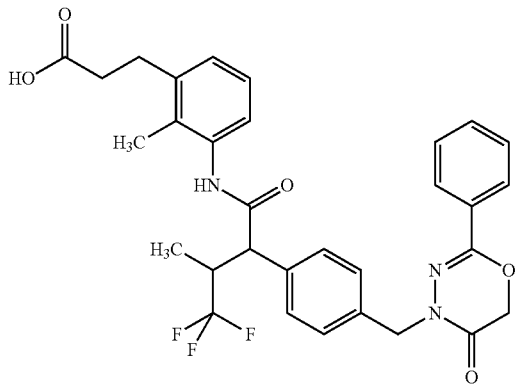 [SMILES: Cc1c(CCC(=O)O)cccc1NC(=O)C(c1ccc(CN2N=C(c3ccccc3)OCC2=O)cc1)C(C)C(F)(F)F]

120 mg (0.21 mmol) of the mixture of isomers of 3-{2-methyl-3-[(4,4,4-trifluoro-3-methyl-2-{4-[(5-oxo-2-phenyl-5,6-dihydro-4H-1,3,4-oxadiazin-4-yl)methyl]phenyl}butanoyl)amino]-phenyl}propanoic acid were separated further by preparative HPLC on a chiral phase [column: Daicel Chiralpak AD-H, 5 μm, 250 mm×20 mm; mobile phase: isohexane/(isopropanol+0.2% trifluoroacetic acid+1% water) 70:30 (v/v); flow rate: 15 ml/min; UV detection: 220 nm; temperature: 30° C.]:

Example 190

Isomer 1

Yield: 37 mg
$R_t$ 6.59 min; purity >99%; >99% ee
[column: Daicel Chiralpak AD-H, 5 μm, 250 mm×4.6 mm; mobile phase: isohexane/(isopropanol+0.2% trifluoroacetic acid+1% water) 65:35 (v/v); flow rate: 1 ml/min; UV detection: 220 nm; temperature: 25° C.].
LC-MS (method 15): $R_t$=1.16 min; m/z=582 (M+H)$^+$.
$^1$H-NMR (400 MHz, DMSO-d$_6$): δ=12.13 (br. s, 1H), 9.62 (s, 1H), 7.76 (d, 2H), 7.40-7.55 (m, 5H), 7.36 (d, 2H), 6.92-7.07 (m, 3H), 4.92 (s, 2H), 4.89 (s, 2H), 3.91 (d, 1H), 3.36-3.44 (m, 1H), 2.73 (t, 2H), 2.39 (t, 2H), 1.87 (s, 3H), 0.79 (d, 3H).
$[α]_D^{20}$=+64.0°, c=0.420, methanol.

Example 191

Isomer 2

Yield: 35 mg
$R_t$ 7.25 min; purity >99%; >96% ee
[column: Daicel Chiralpak AD-H, 5 μm, 250 mm×4.6 mm; mobile phase: isohexane/(isopropanol+0.2% trifluoroacetic acid+1% water) 65:35 (v/v); flow rate: 1 ml/min; UV detection: 220 nm; temperature: 25° C.].
LC-MS (method 15): $R_t$=1.16 min; m/z=582 (M+H)$^+$.
$^1$H-NMR (400 MHz, DMSO-d$_6$): δ=12.13 (br. s, 1H), 9.62 (s, 1H), 7.76 (d, 2H), 7.40-7.55 (m, 5H), 7.36 (d, 2H), 6.92-7.07 (m, 3H), 4.92 (s, 2H), 4.89 (s, 2H), 3.91 (d, 1H), 3.36-3.44 (m, 1H), 2.73 (t, 2H), 2.39 (t, 2H), 1.87 (s, 3H), 0.79 (d, 3H).
$[α]_D^{20}$=−62.6°, c=0.420, methanol.

Examples 192-195

3-{3-[(4,4,4-Trifluoro-3-methyl-2-{4-[(5-oxo-2-phenyl-5,6-dihydro-4H-1,3,4-oxadiazin-4-yl)methyl]phenyl}butanoyl)amino]phenyl}propanoic acid (isomers 1-4)

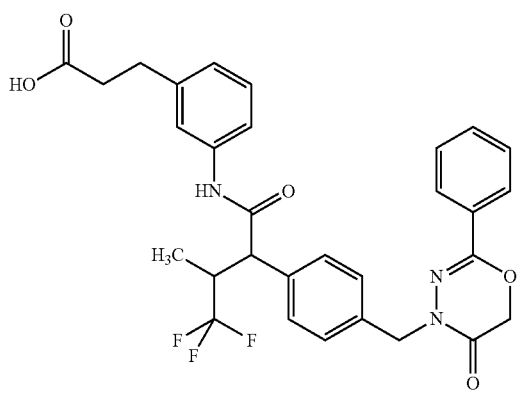 [SMILES: CC(C(C(=O)Nc1cccc(CCC(=O)O)c1)c1ccc(CN2N=C(c3ccccc3)OCC2=O)cc1)C(F)(F)F]

125 mg (0.22 mmol) of the mixture of isomers of 3-{3-[(4,4,4-trifluoro-3-methyl-2-{4-[(5-oxo-2-phenyl-5,6-dihydro-4H-1,3,4-oxadiazin-4-yl)methyl]phenyl}butanoyl)amino]phenyl}propanoic acid were separated further by preparative HPLC on a chiral phase [column: Daicel Chiralpak AD-H, 5 μm, 250 mm×20 mm; mobile phase: isohexane/(isopropanol+0.2% trifluoroacetic acid+1% water) 70:30 (v/v); flow rate: 15 ml/min; UV detection: 220 nm; temperature: 30° C.]. Initially, 22 mg of isomer 4 were isolated. The mixture of isomers 1 to 3 obtained at the same time was separated by further preparative HPLC on a chiral phase [column: Daicel Chiralpak AS-H, 5 μm, 250 mm×20 mm; mobile phase: isohexane/(ethanol+0.2% trifluoroacetic acid+1% water) 75:25 (v/v); flow rate: 15 ml/min; UV detection: 220 nm; temperature: 30° C.]. This gave 26 mg of isomer 1. The remaining mixture of isomers 2 and 3 was separated by further preparative HPLC on a chiral phase [column: Daicel Chiralpak AD-H, 5 μm, 250 mm×20 mm; mobile phase: isohexane/(ethanol+0.2% trifluoroacetic acid+1% water) 75:25 (v/v); flow rate: 15 ml/min; UV detection: 220 nm; temperature: 30° C.]. This gave 11 mg of isomer 2 and 19 mg of isomer 3.

Example 192

Isomer 1

Yield: 26 mg
$R_t$ 6.63 min; purity >98.5%; >97% ee
[column: Daicel Chiralpak AS-H, 5 μm, 250 mm×4.6 mm; mobile phase: isohexane/(ethanol+0.2% trifluoroacetic acid+1% water) 75:25 (v/v); flow rate: 1 ml/min; UV detection: 220 nm; temperature: 25° C.].
LC-MS (method 15): $R_t$=1.16 min; m/z=568 (M+H)$^+$.
$^1$H-NMR (400 MHz, DMSO-d$_6$): δ=10.18 (s, 1H), 7.75 (d, 2H), 7.32-7.54 (m, 10H), 7.15 (t, 1H), 6.88 (d, 1H), 4.90 (s, 2H), 4.86 (s, 2H), 3.82 (d, 1H), 2.73 (t, 2H), 2.46 (t, 2H), 0.78 (d, 3H).

Example 193

Isomer 2

Yield: 11 mg
$R_t$ 6.36 min; purity >95%; >97% ee
[column: Daicel Chiralpak AD-H, 5 µm, 250 mm×4.6 mm; mobile phase: isohexane/(ethanol+0.2% trifluoroacetic acid+1% water) 75:25 (v/v); flow rate: 1 ml/min; UV detection: 220 nm; temperature: 25° C.].
LC-MS (method 11): $R_t$=1.34 min; m/z=568 (M+H)$^+$.

Example 194

Isomer 3

Yield: 19 mg
$R_t$ 7.06 min; purity >96%; >96% ee
[column: Daicel Chiralpak AD-H, 5 µm, 250 mm×4.6 mm; mobile phase: isohexane/(ethanol+0.2% trifluoroacetic acid+1% water) 75:25 (v/v); flow rate: 1 ml/min; UV detection: 220 nm; temperature: 25° C.].
LC-MS (method 11): $R_t$=1.34 min; m/z=568 (M+H)$^+$.

Example 195

Isomer 4

Yield: 22 mg
$R_t$ 7.82 min; purity >90%; >98% ee
[column: Daicel Chiralpak AD-H, 5 µm, 250 mm×4.6 mm; mobile phase: isohexane/(ethanol+0.2% trifluoroacetic acid+1% water) 75:25 (v/v); flow rate: 1 ml/min; UV detection: 220 nm; temperature: 25° C.].

Example 196 and Example 197

1-{3-[(Cyclopentyl{4-[(3-methyl-6-oxopyridazin-1(6H)-yl)methyl]phenyl}acetyl)amino]-benzyl}cyclopropanecarboxylic acid (enantiomers 1 and 2)

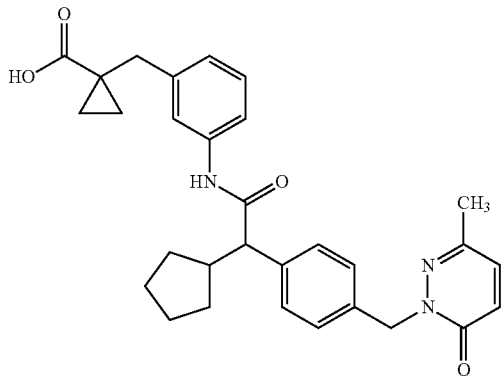

180 mg (0.36 mmol) of the racemic 1-{3-[(cyclopentyl{4-[(3-methyl-6-oxopyridazin-1(6H)-yl)methyl]phenyl}acetyl)amino]benzyl}cyclopropanecarboxylic acid were separated into the enantiomers by preparative HPLC on a chiral phase [column: Daicel Chiralpak AD-H, 5 µm, 250 mm×20 mm; mobile phase: isohexane/(isopropanol+0.2% trifluoroacetic acid+1% water) 70:30 (v/v); flow rate: 15 ml/min; UV detection: 220 nm; temperature: 30° C.]:

Example 196

Enantiomer 1

Yield: 94 mg
$R_t$ 8.74 min; purity >99%; >99% ee
[column: Daicel Chiralpak AD-H, 5 µm, 250 mm×4.6 mm; mobile phase: isohexane/(isopropanol+0.2% trifluoroacetic acid+1% water) 65:35 (v/v); flow rate: 1 ml/min; UV detection: 220 nm; temperature: 25° C.].
LC-MS (method 15): $R_t$=1.09 min; m/z=500 (M+H)$^+$.

Example 197

Enantiomer 2

Yield: 84 mg
$R_t$ 10.46 min; purity >99%; >98% ee
[column: Daicel Chiralpak AD-H, 5 µm, 250 mm×4.6 mm; mobile phase: isohexane/(isopropanol+0.2% trifluoroacetic acid+1% water) 65:35 (v/v); flow rate: 1 ml/min; UV detection: 220 nm; temperature: 25° C.].
LC-MS (method 15): $R_t$=1.09 min; m/z=500 (M+H)$^+$.

Example 198 and Example 199

3-(3-{[Cyclopentyl(4-{[6-oxo-3-(trifluoromethyl)pyridazin-1(6H)-yl]methyl}phenyl)acetyl]-amino}-2-methylphenyl)propanoic acid (enantiomers 1 and 2)

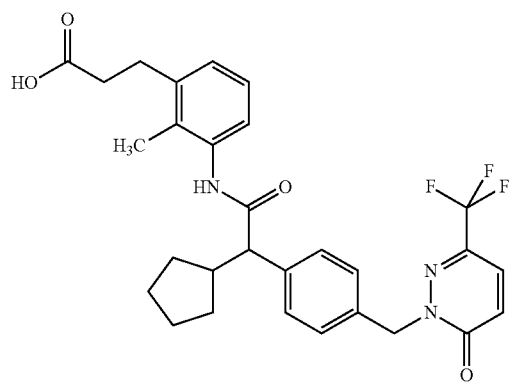 [SMILES: Cc1c(CCC(=O)O)cccc1NC(=O)C(c1ccc(Cn2nc(C(F)(F)F)ccc2=O)cc1)C1CCCC1]

110 mg (0.20 mmol) of the racemic 3-(3-{[cyclopentyl(4-{[6-oxo-3-(trifluoromethyl)pyridazin-1(6H)-yl]methyl}phenyl)acetyl]amino}-2-methylphenyl)propanoic acid were separated into the enantiomers by preparative HPLC on a chiral phase [column: Daicel Chiralpak AD-H, 5 µm, 250 mm×20 mm; mobile phase: isohexane/(isopropanol+0.2% trifluoroacetic acid+1% water) 70:30 (v/v); flow rate: 15 ml/min; UV detection: 220 nm; temperature: 30° C.]:

Example 198

Enantiomer 1

Yield: 94 mg
$R_t$ 9.32 min; purity >92.5%; >99% ee
[column: Chiralcel OD-H, 5 µm, 250 mm×4.6 mm; mobile phase: isohexane/(isopropanol+0.2% trifluoroacetic acid+1% water) 70:30 (v/v); flow rate: 1 ml/min; UV detection: 220 nm; temperature: 25° C.].
LC-MS (method 11): $R_t$=1.29 min; m/z=542 (M+H)$^+$.

Example 199

Enantiomer 2

Yield: 84 mg
$R_t$ 7.84 min; purity >98%; >96% ee
[column: Chiralcel OD-H, 5 μm, 250 mm×4.6 mm; mobile phase: isohexane/(isopropanol+0.2% trifluoroacetic acid+1% water) 70:30 (v/v); flow rate: 1 ml/min; UV detection: 220 nm; temperature: 25° C.].
LC-MS (method 11): $R_t$=1.29 min; m/z=542 (M+H)$^+$.

Example 200 and Example 201

1-(3-{[Cyclopentyl(4-{[6-oxo-3-(trifluoromethyl)pyridazin-1(6H)-yl]methyl}phenyl)acetyl]-amino}benzyl)cyclopropanecarboxylic acid (enantiomers 1 and 2)

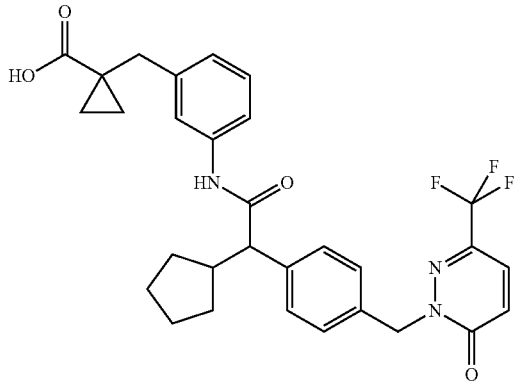 [SMILES: O=C(Nc1cccc(CC2(C(=O)O)CC2)c1)C(c1ccc(Cn2nc(C(F)(F)F)ccc2=O)cc1)C1CCCC1]

130 mg (0.24 mmol) of the racemic 1-(3-{[cyclopentyl(4-{[6-oxo-3-(trifluoromethyl)pyridazin-1(6H)-yl]methyl}phenyl)acetyl]amino}benzyl)cyclopropanecarboxylic acid were separated into the enantiomers by preparative HPLC on a chiral phase [column: Daicel Chiralpak AD-H, 5 μm, 250 mm×20 mm; mobile phase: isohexane/(isopropanol+0.2% trifluoroacetic acid+1% water) 70:30 (v/v); flow rate: 15 ml/min; UV detection: 220 nm; temperature: 30° C.]:

Example 200

Enantiomer 1

Yield: 67 mg
$R_t$ 6.58 min; purity >99%; >99% ee
[column: Daicel Chiralpak AD-H, 5 μm, 250 mm×4.6 mm; mobile phase: isohexane/(isopropanol+0.2% trifluoroacetic acid+1% water) 70:30 (v/v); flow rate: 1 ml/min; UV detection: 220 nm; temperature: 25° C.].
LC-MS (method 11): $R_t$=1.38 min; m/z=554 (M+H)$^+$.

Example 201

Enantiomer 2

Yield: 60 mg
$R_t$ 8.10 min; purity >99%; >97.5% ee
[column: Daicel Chiralpak AD-H, 5 μm, 250 mm×4.6 mm; mobile phase: isohexane/(isopropanol+0.2% trifluoroacetic acid+1% water) 70:30 (v/v); flow rate: 1 ml/min; UV detection: 220 nm; temperature: 25° C.].
LC-MS (method 11): $R_t$=1.38 min; m/z=554 (M+H)$^+$.

General Procedure 8: Cleavage of Tert-Butyl Esters to the Corresponding Carboxylic Acids Using Hydrogen Chloride At RT, the tert-butyl ester in question was dissolved in a 4 N solution of hydrogen chloride gas in 1,4-dioxane (about 0.05 to 0.2 mol/l) and stirred at RT for 2-6 h. The reaction mixture was then frozen (about −76° C.) and lyophilized under high vacuum. If required, the product was purified by preparative RP-HPLC (mobile phase: acetonitrile/water gradient).

The following examples were prepared according to General procedure 8:

| Example | Name/Structure | Analytical data |
|---|---|---|
| 202 | 1-{3-[(cyclopentyl{4-[(1-oxo-1,3-dihydro-2H-isoindol-2-yl)methyl]phenyl}acetyl)amino]-benzyl}cyclopropanecarboxylic acid | LC-MS (method 12): $R_t$ = 2.38 min; m/z = 523 (M + H)$^+$.<br>$^1$H-NMR (400 MHz, DMSO-d$_6$): δ = 9.98 (s, 1H), 7.72 (d, 1H), 7.61-7.36 (m, 8H), 7.22 (d, 2H), 7.13 (t, 1H), 6.89 (d, 1H), 4.69 (s, 2H), 4.35 (s, 2H), 3.57 (s, 2H), 3.37 (d, 1H), 2.62-2.55 (m, 1H), 1.82-1.72 (m, 1H), 1.69-1.18 (m, 6H), 1.10 (q, 2H), 0.86-1.00 (m, 1H), 0.78 (q, 2H). |

| Example | Name/Structure | Analytical data |
|---|---|---|
| 203 | 1-(3-{[(2S)-2-cyclopentyl-2-{4-[(1-oxo-1,3-dihydro-2H-isoindol-2-yl)methyl]phenyl}acetyl]-amino}benzyl)cyclopropanecarboxylic acid | LC-MS (method 11): $R_t$ = 1.29 min; m/z = 523 (M + H)$^+$. $^1$H-NMR (400 MHz, DMSO-$d_6$): δ = 12.07 (br. s, 1H), 9.98 (s, 1H), 7.72 (d, 2H), 7.62-7.36 (m, 7H), 7.22 (d, 2H), 7.13 (t, 1H), 6.89 (d, 1H), 4.69 (s, 2H), 4.35 (s, 2H), 2.81 (s, 2H), 2.65-2.59 (m, 1H), 1.85-1.72 (m, 1H), 1.69-1.42 (m, 4H), 1.40-1.30 (m, 1H), 1.28-1.18 (m, 1H), 1.13-1.07 (m, 2H), 1.02-0.89 (m, 1H), 0.83-0.75 (m, 2H). |

Example 204

(+)-1-(3-{[(2S)-2-Cyclopentyl-2-{4-[(5-oxo-2-phenyl-5,6-dihydro-4H-1,3,4-oxadiazin-4-yl)-methyl]phenyl}acetyl]amino}benzyl)cyclopropane carboxylic acid

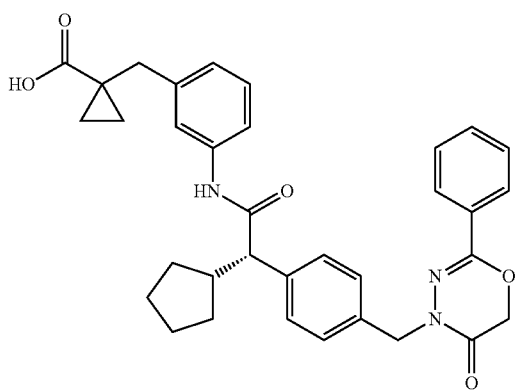 [SMILES: O=C(Nc1cccc(CC2(C(=O)O)CC2)c1)[C@H](c1ccc(CN2N=C(c3ccccc3)OCC2=O)cc1)C1CCCC1]

4.24 g (0.6.82 mmol) of tert-butyl 1-(3-{[(2S)-2-cyclopentyl-2-{4-[(5-oxo-2-phenyl-5,6-dihydro-4H-1,3,4-oxadiazin-4-yl)methyl]phenyl}acetyl]amino}benzyl)cyclopropanecarboxylate were initially charged in 20 ml of dichloromethane, and 5.25 ml of trifluoroacetic acid were added. The mixture was stirred at RT for 2.5 h. The reaction mixture was then concentrated under reduced pressure, the residue was added to water and the mixture was extracted three times with ethyl acetate. The combined organic phases were dried over magnesium sulfate and concentrated under reduced pressure. The product was purified by chromatography on silica gel (mobile phase cyclohexane/ethyl acetate 2:1+0.1% acetic acid). This gave 3.6 g (89% of theory) of the title compound.

LC-MS (method 15): $R_t$=1.27 min; m/z=566 (M+H)$^+$.

$^1$H-NMR (400 MHz, DMSO-$d_6$): δ=12.05 (br. s, 1H), 9.97 (s, 1H), 7.76 (d, 2H), 7.54-7.35 (m, 7H), 7.31 (d, 2H), 7.13 (t, 1H), 6.88 (d, 1H), 4.89 (s, 2H), 4.84 (s, 2H), 3.38 (d, 1H), 2.80 (s, 2H), 2.66-2.56 (m, 1H), 1.85-1.21 (m, 6H), 1.09 (q, 3H), 1.02-0.93 (m, 1H), 0.81-0.74 (m, 2H).

$[α]_D^{20}$=+28.0°, c=0.570, chloroform.

General Procedure 9A: Cleavage of Tert-Butyl Esters to the Corresponding Carboxylic Acids Using Trifluoroacetic Acid At 0° C. to RT, trifluoroacetic acid (TFA) was added dropwise to a solution of the tert-butyl ester in question in dichloromethane (concentration 0.1 to 1.0 mol/l; additionally, optionally a drop of water) until a dichloromethane/TFA ratio of about 2:1 to 1:2 (v/v) had been reached. The mixture was stirred at RT for 1-18 h (if appropriate warming to up to 40° C. until complete conversion was achieved) and then concentrated under reduced pressure. The crude product was, if required, purified by crystallization from water/acetonitrile mixtures or by preparative RP-HPLC (mobile phase: acetonitrile/water gradient).

The following examples were prepared according to General procedure 9A:

| Example | Name/Structure | Analytical data |
|---|---|---|
| 205 | (+)-1-(3-{[(2S)-2-cyclopentyl-2-{4-[(5-oxo-2-phenyl-5,6-dihydro-4H-1,3,4-oxadiazin-4-yl)-methyl]phenyl}acetyl]amino}-2-methylbenzyl)-cyclopropanecarboxylic acid | LC-MS (method 7): $R_t$ = 2.71 min; m/z = 580 $(M + H)^+$. $^1$H-NMR (400 MHz, DMSO-$d_6$): δ = 12.28-12.06 (m, 1H), 9.48 (s, 1H), 7.77 (d, 2H), 7.55-7.35 (m, 5H), 7.31 (d, 2H), 7.06-6.91 (m, 3H), 4.92 (s, 2H), 4.87 (s, 2H), 3.49-3.41 (m, 1H), 2.89 (s, 2H), 2.65-2.57 (m, 1H), 1.89 (s, 3H), 1.87-1.78 (m, 1H), 1.73-1.61 (m, 1H), 1.62-1.52 (m, 2H), 1.50-1.42 (m, 1H), 1.40-1.29 (m, 2H), 1.13 (d, 2H), 1.03-0.91 (m, 1H), 0.59 (d, 2H). $[α]_D^{20}$ = +21.0°, c = 0.500, chloroform. |
| 206 | 1-{3-[(cyclopentyl{4-[(3-oxo-1,3-dihydro-2H-indazol-2-yl)methyl]phenyl}acetyl)amino]-benzyl}cyclopropanecarboxylic acid | LC-MS (method 11): $R_t$ = 1.27 min; m/z = 524 $(M + H)^+$. |
| 207 | 1-(3-{[(2S,3R)-4,4,4-trifluoro-3-methyl-2-{4-[(1-oxo-1,3-dihydro-2H-isoindol-2-yl)methyl]-phenyl}butanoyl]-amino}benzyl)cyclopropanecarboxylic acid | LC-MS (method 15): $R_t$ = 1.11 min; m/z = 551 $(M + H)^+$. $^1$H-NMR (400 MHz, DMSO-$d_6$): δ = 10.15 (s, 1H), 7.72 (d, 1H), 7.61-7.46 (m, 3H), 7.44-7.39 (m, 3H), 7.36 (s, 1H), 7.27 (d, 2H), 7.14 (t, 1H), 6.90 (d, 1H), 4.71 (s, 2H), 4.36 (s, 2H), 3.82 (d, 1H), 2.81 (s, 2H), 1.09 (d, 2H), 0.81-0.73 (m, 5H). |

| Example | Name/Structure | Analytical data |
|---|---|---|
| 208 | 1-(3-{[(2R,3S)-4,4,4-trifluoro-3-methyl-2-{4-[(1-oxo-1,3-dihydro-2H-isoindol-2-yl)methyl]phenyl}butanoyl]-amino}benzyl)cyclopropanecarboxylic acid | LC-MS (method 15): $R_t$ = 1.11 min; m/z = 551 $(M + H)^+$. $^1$H-NMR (400 MHz, DMSO-$d_6$): δ = 10.15 (s, 1H), 7.72 (d, 1H), 7.62-7.46 (m, 3H), 7.45-7.39 (m, 3H), 7.36 (s, 1H), 7.27 (d, 2H), 7.14 (t, 1H), 6.90 (d, 1H), 4.71 (s, 2H), 4.36 (s, 2H), 3.82 (d, 1H), 2.81 (s, 2H), 1.13-1.07 (m, 2H), 0.77 (d, 5H). |
| 209 | 1-{3-[(cyclopentyl{4-[(5,6-difluoro-1-oxo-1,3-dihydro-2H-isoindol-2-yl)methyl]phenyl}acetyl)-amino]benzyl}cyclopropanecarboxylic acid | LC-MS (method 11): $R_t$ = 1.35 min; m/z = 559 $(M + H)^+$. $^1$H-NMR (400 MHz, DMSO-$d_6$): δ = 9.98 (s, 1H), 7.76 (t, 1H), 7.65 (dd, 1H), 7.47-7.36 (m, 4H), 7.22 (d, 2H), 7.14 (t, 1H), 6.89 (d, 1H), 4.68 (s, 2H), 4.33 (s, 2H), 3.38 (d, 1H), 3.17 (d, 1H), 2.81 (s, 2H), 2.64-2.56 (m, 1H), 1.38-1.18 (m, 6H), 1.14-1.07 (m, 2H), 0.99-0.91 (m, 1H), 0.81-0.74 (m, 2H). |
| 210 | 1-{3-[(cyclopenyl{4-[(4,7-difluoro-1-oxo-1,3-dihydro-2H-isoindol-2-yl)methyl]phenyl}acetyl)-amino]benzyl}cyclopropanecarboxylic acid | LC-MS (method 11): $R_t$ = 1.34 min; m/z = 559 $(M + H)^+$. $^1$H-NMR (400 MHz, DMSO-$d_6$): δ = 9.98 (s, 1H), 7.51-7.37 (m, 5H), 7.33 (dt, 1H), 7.25 (d, 2H), 7.13 (t, 1H), 6.89 (d, 1H), 4.65 (s, 2H), 4.47 (s, 2H), 3.38 (d, 1H), 2.81 (s, 2H), 2.63-2.56 (m, 1H), 1.84-1.20 (m, 8H), 1.13-1.08 (m, 2H), 1.02-0.91 (m, 1H), 0.81-0.74 (m, 2H). |

-continued

| Example | Name/Structure | Analytical data |
|---|---|---|
| 211 | 1-(3-{[{4-[(5-chloro-2-oxopyridin-1(2H)-yl)-methyl]phenyl}(cyclopentyl)acetyl]amino}-benzyl)cyclopropanecarboxylic acid | LC-MS (method 15): $R_t$ = 1.12 min; m/z = 519 $(M + H)^+$. $^1$H-NMR (400 MHz, DMSO-$d_6$): δ = 9.97 (s, 1H), 8.09 (s, 1H), 7.48 (dd, 1H), 7.42 (s, 2H), 7.38 (d, 2H), 7.25 (d, 2H), 7.13 (t, 1H), 6.89 (d, 1H), 6.45 (d, 1H), 5.03 (s, 2H), 3.39 (d, 1H), 2.81 (s, 2H), 2.63-2.56 (m, 1H), 1.84-1.72 (m, 1H), 1.69-1.19 (m, 6H), 1.10 (q, 2H), 1.00-0.89 (m, 1H), 0.81-0.75 (m, 2H). |
| 212 | 1-(3-{[cyclopentyl(4-{[2-oxo-5-(trifluoromethyl)-pyridin-1(2H)-yl]methyl}phenyl)acetyl]amino}-benzyl)cyclopropanecarboxylic acid | LC-MS (method 15): $R_t$ = 1.17 min; m/z = 553 $(M + H)^+$. $^1$H-NMR (400 MHz, DMSO-$d_6$): δ = 9.97 (s, 1H), 8.54 (s, 1H), 7.67 (dd, 1H), 7.47-7.35 (m, 4H), 7.25 (d, 2H), 7.13 (t, 1H), 6.89 (d, 1H), 6.55 (d, 1H), 5.12 (s, 2H), 3.57 (s, 3H), 3.37 (d, 1H), 2.81 (s, 2H), 2.65-2.56 (m, 1H), 1.84-1.19 (m, 4H), 1.13-1.07 (m, 2H), 1.03-0.88 (m, 1H), 0.81-0.74 (m, 2H). |
| 213 | 1-{3-[(cyclopentyl{4-[(4-fluoro-1-oxo-1,3-dihydro-2H-isoindol-2-yl)methyl]phenyl}acetyl)-amino]benzyl}cyclopropanecarboxylic acid | LC-MS (method 15): $R_t$ = 1.18 min; m/z = 541 $(M + H)^+$. $^1$H-NMR (400 MHz, DMSO-$d_6$): δ = 9.98 (s, 1H), 7.61-7.53 (m, 2H), 7.46-7.36 (m, 5H), 7.24 (d, 2H), 7.13 (t, 1H), 6.89 (d, 1H), 4.69 (s, 2H), 4.48 (s, 2H), 3.38 (d, 1H), 2.81 (s, 2H), 2.63-2.55 (m, 1H), 1.83-1.21 (m, 7H), 1.10 (q, 2H), 1.00-0.91 (m, 1H), 0.78 (q, 2H). |

| Example | Name/Structure | Analytical data |
|---|---|---|
| 214 | (+)-1-(3-{[(2S)-2-cyclopentyl-2-{4-[(4-fluoro-1-oxo-1,3-dihydro-2H-isoindol-2-yl)methyl]-phenyl}acetyl]-amino}benzyl)cyclopropanecarboxylic acid | LC-MS (method 15): $R_t$ = 1.16 min; m/z = 541 (M + H)$^+$. $^1$H-NMR (400 MHz, DMSO-$d_6$): δ = 12.08 (br. s, 1H), 9.98 (s, 1H), 7.61-7.51 (m, 2H), 7.47-7.36 (m, 5H), 7.24 (d, 2H), 7.13 (t, 1H), 6.89 (d, 1H), 4.69 (s, 2H), 4.48 (s, 2H), 3.38 (d, 1H), 2.81 (s, 2H), 2.63-2.55 (m, 1H), 1.85-1.20 (m, 7H), 1.10 (q, 2H), 1.01-0.91 (m, 1H), 0.78 (q, 2H). $[a]_D^{20}$ = +45°, c = 0.112, chloroform. |
| 215 | (−)-1-(3-{[(2R)-2-cyclopentyl-2-{4-[(4-fluoro-1-oxo-1,3-dihydro-2H-isoindol-2-yl)methyl]-phenyl}acetyl]-amino}benzyl)cyclopropanecarboxylic acid | LC-MS (method 15): $R_t$ = 1.16 min; m/z = 541 (M + H)$^+$. $^1$H-NMR (400 MHz, DMSO-$d_6$): δ = 12.08 (br. s, 1H), 9.98 (s, 1H), 7.63-7.52 (m, 2H), 7.47-7.36 (m, 5H), 7.24 (d, 2H), 7.13 (t, 1H), 6.89 (d, 1H), 4.69 (s, 2H), 4.47 (s, 2H), 3.38 (d, 1H), 2.81 (s, 2H), 2.63-2.55 (m, 1H), 1.83-1.18 (m, 7H), 1.10 (q, 2H), 1.01-0.92 (m, 1H), 0.78 (q, 2H). $[a]_D^{20}$ = −34°, c = 0.210, chloroform. |
| 216 | (+)-1-(3-{[(2S)-2-{4-[(5-chloro-2-oxopyridin-1(2H)-yl)methyl]phenyl}-2-cyclopentylacetyl]-amino}benzyl)cyclopropanecarboxylic acid | LC-MS (method 15): $R_t$ = 1.12 min; m/z = 519 (M + H)$^+$. $^1$H-NMR (400 MHz, DMSO-$d_6$): δ = 9.97 (s, 1H), 8.09 (d, 1H), 7.48 (dd, 1H), 7.44-7.33 (m, 4H), 7.25 (d, 2H), 7.13 (t, 1H), 6.89 (d, 1H), 6.45 (d, 1H), 5.03 (s, 2H), 3.37 (d, 1H), 2.81 (s, 2H), 2.66-2.55 (m, 1H), 1.85-1.18 (m, 7H), 1.13-1.08 (m, 2H), 0.94 (dd, 1H), 0.77 (q, 2H). $[a]_D^{20}$ = +40°, c = 0.550, chloroform. |

| Example | Name/Structure | Analytical data |
|---|---|---|
| 217 | (+)-3-(3-{[(2S)-2-{4-[(5-chloro-2-oxopyridin-1(2H)-yl)methyl]phenyl}-2-cyclopentylacetyl]-amino}phenyl)propanoic acid | LC-MS (method 15): $R_t$ = 1.06 min; m/z = 493 $(M + H)^+$.<br>$^1$H-NMR (400 MHz, DMSO-$d_6$): δ = 9.98 (s, 1H), 8.10 (d, 1H), 7.48 (dd, 1H), 7.42-7.35 (m, 4H), 7.25 (d, 2H), 7.15 (t, 1H), 6.87 (d, 1H), 6.45 (d, 1H), 5.03 (s, 2H), 4.03 (q, 1H), 3.37 (d, 1H), 2.79-2.70 (m, 2H), 2.67-2.55 (m, 1H), 1.84-1.20 (m, 7H), 1.21-1.14 (m, 1H), 1.17 (t, 1H).<br>$[α]_D^{20}$ = +27.6°, c = 0.485, chloroform. |
| 218 | 3-(3-{[(2S)-2-cyclopentyl-2-(4-{[2-oxo-5-(trifluoromethyl)pyridin-1(2H)-yl]methyl}-phenyl)acetyl]amino}phenyl)propanoic acid | LC-MS (method 15): $R_t$ = 1.10 min; m/z = 527 $(M + H)^+$.<br>$^1$H-NMR (400 MHz, DMSO-$d_6$): δ = 12.09 (s, 1H), 9.98 (s, 1H), 8.54 (s, 1H), 7.67 (dd, 1H), 7.45-7.36 (m, 4H), 7.26 (d, 2H), 7.15 (t, 1H), 6.87 (d, 1H), 6.55 (d, 1H), 5.12 (s, 2H), 3.37 (d, 1H), 2.80-2.71 (m, 2H), 2.64-2.55 (m, 1H), 1.84-1.18 (m, 7H), 0.94 (dd, 1H). |
| 219 | (+)-1-(3-{[(2S,3R)-4,4,4-trifluoro-2-{4-[(4-fluoro-1-oxo-1,3-dihydro-2H-isoindol-2-yl)methyl]phenyl}-3-methylbutanoyl]amino}-benzyl)cyclopropanecarboxylic acid | LC-MS (method 11): $R_t$ = 1.29 min; m/z = 569 $(M + H)^+$.<br>$^1$H-NMR (400 MHz, DMSO-$d_6$): δ = 10.14 (s, 1H), 7.52-7.61 (m, 2H), 7.38-7.47 (m, 4H), 7.36 (s, 1H), 7.29 (d, 2H), 7.14 (t, 1H), 6.90 (d, 1H), 4.71 (s, 2H), 4.48 (s, 2H), 3.82 (d, 1H), 3.37-3.48 (m, 1H), 2.81 (s, 2H), 1.04-1.13 (m, 2H), 0.78 (d, 5H).<br>$[α]_D^{20}$ = +45.1°, c = 0.575, chloroform. |

| Example | Name/Structure | Analytical data |
|---|---|---|
| 220 | (-)-1-(3-{[(2R,3S)-4,4,4-trifluoro-2-{4-[(4-fluoro-1-oxo-1,3-dihydro-2H-isoindol-2-yl)methyl]phenyl}-3-methylbutanoyl]amino}-benzyl)cyclopropanecarboxylic acid | LC-MS (method 11): $R_t$ = 1.29 min; m/z = 569 $(M + H)^+$. $^1$H-NMR (400 MHz, DMSO-$d_6$): δ = 12.00 (br. s, 1H), 10.14 (s, 1H), 7.62-7.51 (m, 2H), 7.49-7.38 (m, 4H), 7.36 (s, 1H), 7.29 (d, 2H), 7.14 (t, 2H), 6.90 (d, 1H), 4.71 (s, 2H), 4.51-4.46 (m, 2H), 3.82 (d, 1H), 2.81 (s, 2H), 1.10 (d, 2H), 0.78 (d, 5H). $[α]_D^{20}$ = -32.9°, c = 0.555, chloroform. |
| 221 | 1-(3-{[(2S)-2-cyclopentyl-2-(4-{[2-oxo-5-(trifluoromethyl)pyridin-1(2H)-yl]methyl}phenyl)acetyl]amino}-benzyl)cyclopropanecarboxylic acid | LC-MS (method 15): $R_t$ = 1.15 min; m/z = 553 $(M + H)^+$. $^1$H-NMR (400 MHz, DMSO-$d_6$): δ = 12.07 (s, 1H), 9.97 (s, 1H), 8.54 (s, 1H), 7.67 (dd, 1H), 7.45-7.36 (m, 4H), 7.25 (d, 2H), 7.13 (t, 1H), 6.89 (d, 1H), 6.55 (d, 1H), 5.12 (s, 2H), 3.37 (d, 1H), 2.81 (s, 2H), 2.67-2.55 (m, 1H), 1.84-1.19 (m, 7H), 1.10 (q, 2H), 1.02-0.88 (m, 1H), 0.78 (q, 2H). |
| 222 | (-)-3-(3-{[(2R,3S)-4,4,4-trifluoro-3-methyl-2-(4-{[2-oxo-5-(trifluoromethyl)pyridin-1(2H)-yl]methyl}phenyl)-butanoyl]amino}phenyl)propanoic acid | LC-MS (method 11): $R_t$ = 1.23 min; m/z = 555 $(M + H)^+$. $^1$H-NMR (400 MHz, DMSO-$d_6$): δ = 10.15 (s, 1H), 8.54 (br. s, 1H), 7.67 (dd, 1H), 7.42-7.33 (m, 4H), 7.29 (d, 2H), 7.16 (t, 1H), 6.89 (d, 1H), 6.55 (d, 1H), 5.13 (s, 2H), 3.81 (d, 1H), 3.57 (s, 4H), 2.74 (t, 2H), 0.77 (d, 3H). $[α]_D^{20}$ = -45.4°, c = 0.545, chloroform. |

| Example | Name/Structure | Analytical data |
|---|---|---|
| 223 | (+)-3-(3-{[(2S,3R)-4,4,4-trifluoro-3-methyl-2-(4-{[2-oxo-5-(trifluoromethyl)pyridin-1(2H)-yl]methyl}phenyl)-butanoyl]amino}phenyl)propanoic acid | LC-MS (method 11): $R_t$ = 1.23 min; m/z = 555 (M + H)$^+$. $^1$H-NMR (400 MHz, DMSO-$d_6$): δ = 10.15 (s, 1H), 8.54 (br. s, 1H), 7.67 (dd, 1H), 7.43-7.33 (m, 4H), 7.29 (d, 2H), 7.15 (t, 1H), 6.88 (d, 1H), 6.55 (d, 1H), 5.13 (s, 2H), 3.81 (d, 1H), 3.57 (s, 3H), 2.77-2.72 (m, 2H), 1.35 (s, 1H), 0.77 (d, 3H). $[α]_D^{20}$ = +66°, c = 0.205, chloroform. |
| 224 | (+)-3-(3-{[(2S)-2-cyclopentyl-2-{4-[(5-oxo-2-phenyl-5,6-dihydro-4H-1,3,4-oxadiazin-4-yl)methyl]phenyl}acetyl]amino}-4-fluorophenyl)propanoic acid | LC-MS (method 15): $R_t$ = 1.22 min; m/z = 558 (M + H)$^+$. $^1$H-NMR (400 MHz, DMSO-$d_6$): δ = 9.78 (s, 1H), 7.81-7.74 (m, 2H), 7.64 (dd, 1H), 7.50-7.42 (m, 3H), 7.40 (d, 2H), 7.35-7.27 (m, 3H), 7.09 (dd, 1H), 7.00-6.92 (m, 1H), 4.91 (s, 2H), 4.85 (s, 2H), 3.59 (d, 1H), 2.73 (t, 2H), 2.46 (t, 2H), 0.86-1.87 (m, 9H). $[α]_D^{20}$ = +52.6°, c = 0.515, chloroform. |
| 225 | (+)-3-(3-{[(2S)-2-cyclopentyl-2-{4-[(5-oxo-2-phenyl-5,6-dihydro-4H-1,3,4-oxadiazin-4-yl)methyl]phenyl}acetyl]amino}-2-fluorophenyl)propanoic acid | LC-MS (method 7): $R_t$ = 2.70 min; m/z = 558 (M + H)$^+$. $^1$H-NMR (400 MHz, DMSO-$d_6$): δ = 12.19 (br. s, 1H), 9.78 (s, 1H), 7.78 (d, 1H), 7.62 (m, 1H), 7.52-7.48 (m, 5H), 7.31 (d, 2H), 7.03-6.98 (m, 2H), 4.91 (s, 2H), 4.85 (s, 2H), 3.61 (d, 1H), 2.81 (t, 2H), 1.83-1.75 (m, 1H), 1.70-1.25 (m, 5H), 1.01-0.92 (m, 1H). $[α]_D^{20}$ = +9.5°, c = 0.455, chloroform. |

| Example | Name/Structure | Analytical data |
|---|---|---|
| 226 | (+)-3-(3-{[(2S,3R)-4,4,4-trifluoro-2-{4-[(4-fluoro-1-oxo-1,3-dihydro-2H-isoindol-2-yl)methyl]phenyl}-3-methylbutanoyl]amino}phenyl)propanoic acid 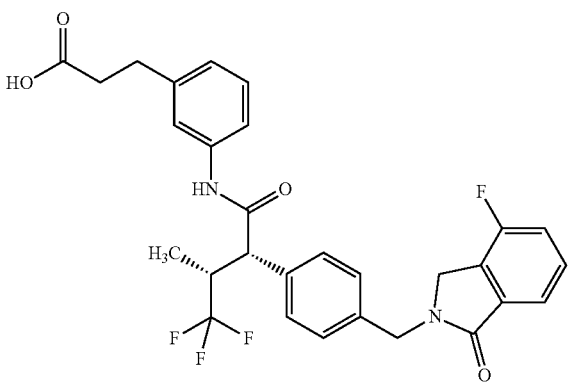 | LC-MS (method 15): $R_t$ = 1.09 min; m/z = 543 $(M + H)^+$. $^1$H-NMR (400 MHz, DMSO-$d_6$): δ = 12.11 (s, 1H), 10.18 (s, 1H), 7.60-7.53 (m, 1H), 7.48-7.35 (m, 5H), 7.30 (d, 2H), 7.17 (t, 1H), 6.89 (d, 1H), 4.72 (s, 2H), 4.49 (s, 2H), 3.72 (d, 1H), 3.42-3.30 (m, 1H), 2.79-2.70 (m, about 2H), 0.78 (d, 3H). $[a]_D^{20}$ = +85°, c = 0.300, chloroform. |
| 227 | (−)-3-(3-{[(2R,3S)-4,4,4-trifluoro-2-{4-[(4-fluoro-1-oxo-1,3-dihydro-2H-isoindol-2-yl)methyl]phenyl}-3-methylbutanoyl]amino}phenyl)propanoic acid 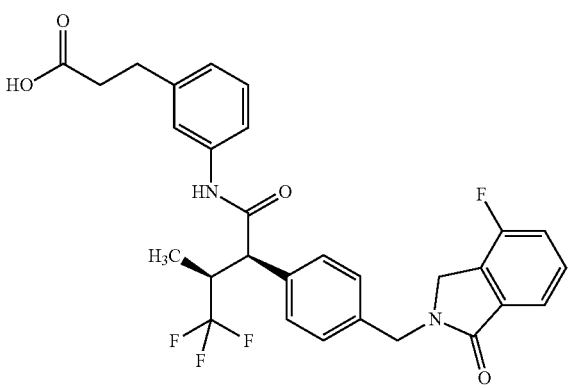 | LC-MS (method 15): $R_t$ = 1.08 min; m/z = 543 $(M + H)^+$. $^1$H-NMR (400 MHz, DMSO-$d_6$): δ = 12.12 (br. s, 1H), 10.18 (s, 1H), 7.60-7.53 (m, 1H), 7.48-7.35 (m, 5H), 7.30 (d, 2H), 7.17 (t, 1H), 6.89 (d, 1H), 4.72 (s, 2H), 4.49 (s, 2H), 3.72 (d, 1H), 3.40-3.30 (m, 1H), 2.72 (t, 2H), 2.49 (m, about 2H), 0.78 (d, 3H). $[a]_D^{20}$ = −73.6°, c = 0.375, chloroform. |

General Procedure 9B: Cleavage of Tert-Butyl Esters to the Corresponding Carboxylic Acids Using Trifluoroacetic Acid 20 eq. of trifluoroacetic acid were added to a solution of the tert-butyl ester in question in dichloromethane (about 0.1 mol/l). The reaction solution was stirred at room temperature overnight and then added to a mixture of water and ethyl acetate (1:1 v/v). The organic phase was washed three times with water and once with saturated sodium chloride solution, dried over magnesium sulfate and concentrated. If appropriate, the product obtained was purified by preparative RP-HPLC.

The following compounds were prepared according to General procedure 9B:

| Example | Name/Structure | Analytical data |
|---|---|---|
| 228 | (+/-)-3-{3-[(cyclopentyl{4-[(1,3-dioxo-1,3-dihydro-2H-isoindol-2-yl)methyl]phenyl}acetyl)amino]-2-methylphenyl}propanoic acid | LC-MS (method 7): $R_t$ = 2.50 min; m/z = 525 $[M + H]^+$. $^1$H-NMR (400 MHz, DMSO-$d_6$): δ = 12.18 (s, 1H), 9.45 (s, 1H), 7.91-7.85 (m, 4H), 7.38 (d, 2H), 7.26 (d, 2H), 7.04-6.96 (m, 3H), 4.75 (s, 2H), 3.44 (d, 1H), 2.78 (t, 2H), 2.42 (t, 2H), 1.98 (s, 3H), 1.87-1.29 (m, 8H), 1.0-0.9 (m, 1H). |
| 229 | (+/-)-3-{3-[(cyclopentyl{4-[(1-oxo-1,3-dihydro-2H-isoindol-2-yl)methyl]phenyl}acetyl)amino]-2-methylphenyl}propanoic acid | LC-MS (method 11): $R_t$ = 2.50 min; m/z = 511 $[M + H]^+$. $^1$H-NMR (400 MHz, DMSO-$d_6$): δ = 9.46 (s, 1H), 7.73 (d, 1H), 7.54-7.63 (m, 2H), 7.46-7.53 (m, 1H), 7.41 (d, 2H), 7.23 (d, 2H), 6.94-7.07 (m, 3H), 4.71 (s, 2H), 4.37 (s, 2H), 3.45 (d, 1H), 2.79 (t, 2H), 2.43 (t, 2H), 1.98 (d, 4H), 1.26-1.90 (m, 7H), 0.97 (dq, 1H). |
| 230 | (+/-)-3-{3-[(cyclopentyl{4-[(5-oxo-2-phenyl-5,6-dihydro-4H-1,3,4-oxadiazin-4-yl)methyl]phenyl}-acetyl)amino]-5-fluorophenyl}propanoic acid | LC-MS (method 11): $R_t$ = 1.43 min; m/z = 558 $[M + H]^+$. $^1$H-NMR (400 MHz, DMSO-$d_6$): δ = 12.13 (br. s, 1H), 10.20 (s, 1H), 7.66-7.83 (m, 2H), 7.41-7.53 (m, 3H), 7.38 (d, 2H), 7.28-7.35 (m, 2H), 7.11 (s, 1H), 6.73 (d, 1H), 4.76-4.95 (m, 4H), 3.27-3.43 (m, 3H), 2.70-2.79 (m, 2H), 1.70-1.85 (m, 1H), 1.17-1.69 (m, 6H), 1.09 (t, 1H), 0.90-1.02 (m, 1H). |

| Example | Name/Structure | Analytical data |
|---|---|---|
| 231 | (+/-)-1-{3-[(cyclopentyl{4-[(5-oxo-2-phenyl-5,6-dihydro-4H-1,3,4-oxadiazin-4-yl)methyl]phenyl}-acetyl)amino]-4-fluorobenzyl}cyclopropanecarboxylic acid 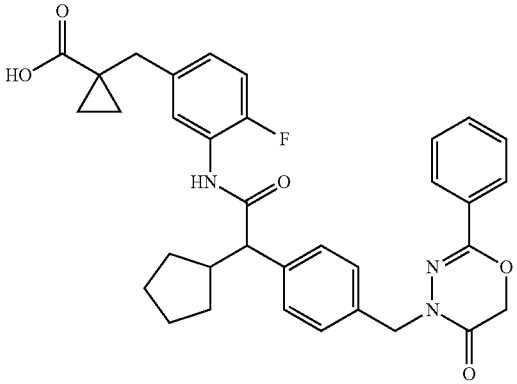 | LC-MS (method 11): $R_t$ = 1.45 min; m/z = 584 [M + H]$^+$. $^1$H-NMR (400 MHz, DMSO-d$_6$): δ = 12.10 (s, 1H), 9.76 (s, 1H), 7.73-7.82 (m, 2H), 7.65 (dd, 1H), 7.42-7.53 (m, 3H), 7.37-7.42 (m, 2H), 7.28-7.34 (m, 2H), 7.08 (dd, 1H), 6.96-7.03 (m, 1H), 4.81-4.95 (m 4H), 3.58 (d, 1H), 2.79 (s, 2H), 1.20-1.86 (m, 8H), 1.07 (q, 2H), 0.91-1.02 (m, 1H), 0.73-0.82 (m, 2H). |
| 232 | (+/-)-3-(5-{2-cyclopentyl-2-{4-[(5-oxo-2-phenyl-5,6-dihydro-4H-1,3,4-oxadiazin-4-yl)methyl]-phenyl}acetyl]amino}-2-fluorophenyl)propanoic acid 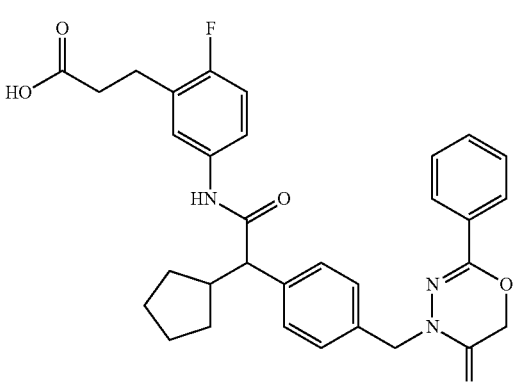 | LC-MS (method 11): $R_t$ = 1.41 min; m/z = 558 [M + H]$^+$. $^1$H-NMR (400 MHz, DMSO-d$_6$): δ = 12.05-12.34 (m, 1H), 10.04 (s, 1H), 7.69-7.83 (m, 2H), 7.40-7.56 (m, 5H), 7.35--7.40 (m, 2H), 7.27-7.34 (m, 2H), 7.02 (t, 1H), 4.69-4.96 (m, 4H), 3.17 (d, 1H), 2.72-2.81 (m, 2H), 2.42-2.48 (m, 2H), 1.72-1.87 (m, 1H), 1.16-1.72 (m, 7H), 0.90-1.04 (m, 1H). |
| 233 | 1-{3-[(cyclopentyl{4-[(5-oxo-2-phenyl-5,6-dihydro-4H-1,3,4-oxadiazin-4-yl)methyl]phenyl}-acetyl)amino]-2-fluorobenzyl}cyclopropanecarboxylic acid 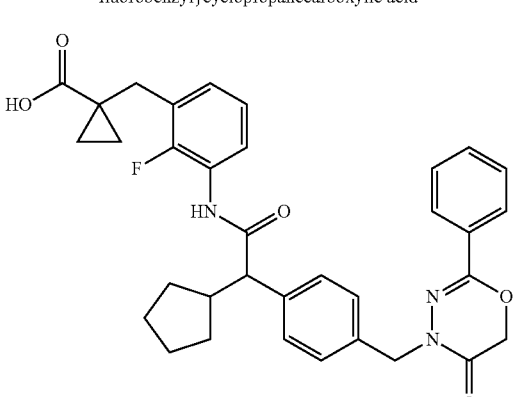 | LC-MS (method 11): $R_t$ = 1.45 min; m/z = 584 [M + H]$^+$. $^1$H-NMR (400 MHz, DMSO-d$_6$): δ = 12.19 (br. s, 1H), 9.77 (s, 1H), 7.73-7.82 (m, 2H), 7.55-7.65 (m, 1H), 7.36-7.53 (m, 5H), 7.29-7.35 (m, 2H), 7.05-7.13 (m, 1H), 6.96-7.05 (m, 1H), 4.77-4.97 (m, 4H), 3.60 (d, 1H), 2.90 (s, 2H), 1.72-1.86 (m, 1H), 1.21-1.72 (m, 6H), 1.09-1.16 (m, 2H), 0.90-1.02 (m, 1H), 0.70-0.83 (m, 2H). |

| Example | Name/Structure | Analytical data |
|---|---|---|
| 234 | (+/-)-1-{5-[(cyclopentyl{4-[(5-oxo-2-phenyl-5,6-dihydro-4H-1,3,4-oxadiazin-4-yl)methyl]phenyl}-acetyl)amino]-2-fluorobenzyl}cyclopropanecarboxylic acid | LC-MS (method 15): $R_t$ = 1.29 min; m/z = 584 [M +H]$^+$.<br>$^1$H-NMR (400 MHz, DMSO-d$_6$): δ = 12.16 (br. s, 1H), 10.05 (s, 1H), 7.71-7.82 (m, 2H), 7.41-7.56 (m, 5H), 7.36-7.41 (m, 2H), 7.28-7.36 (m, 2H), 6.95-7.06 (m, 1H), 4.79-4.96 (m, 4H), 2.85 (s, 2H), 1.71-1.83 (m, 1H), 1.18-1.68 (m, 6H), 1.09-1.15 (m, 2H), 0.91-1.02 (m, 1H), 0.71-0.81 (m, 2H). |
| 235 | (+/-)-1-{3-[(cyclopentyl{4-[(5-oxo-2-phenyl-5,6-dihydro-4H-1,3,4-oxadiazin-4-yl)methyl]phenyl}-acetyl)amino]-5-fluorobenzyl}cyclopropanecarboxylic acid | LC-MS (method 15): $R_t$ = 1.30 min; m/z = 584 [M + H]$^+$.<br>$^1$H-NMR (400 MHz, DMSO-d$_6$): δ = 12.13 (br. s, 1H), 10.20 (s, 1H), 7.67-7.83 (m, 2H), 7.41-7.54 (m, 5H), 7.36-7.40 (m, 2H), 7.28-7.35 (m, 2H), 7.14 (s, 1H), 6.71 (d, 1H), 4.78-4.94 (m, 4H), 2.80 (s, 2H), 1.71-1.84 (m, 1H), 1.17-1.70 (m, 6H), 1.09-1.16 (m, 2H), 0.96 (dd, 1H), 0.77-0.87 (m, 2H). |

Example 236 and Example 237

1-{3-[(Cyclopentyl{4-[(5-oxo-2-phenyl-5,6-dihydro-4H-1,3,4-oxadiazin-4-yl)methyl]phenyl}acetyl)amino]-5-fluorobenzyl}cyclopropanecarboxylic acid (enantiomers 1 and 2)

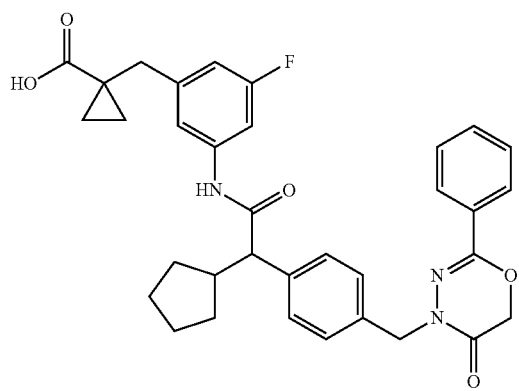 [SMILES: O=C(Nc1cc(F)cc(CC2(C(=O)O)CC2)c1)C(c1ccc(CN2N=C(c3ccccc3)OCC2=O)cc1)C1CCCC1]

57 mg of the racemic 1-{3-[(cyclopentyl{4-[(5-oxo-2-phenyl-5,6-dihydro-4H-1,3,4-oxadiazin-4-yl)methyl]phenyl}acetyl)amino]-5-fluorobenzyl}cyclopropanecarboxylic acid were separated into the enantiomers by preparative HPLC on a chiral phase [column: Daicel Chiralpak AD-H, 5 μm, 250 mm×20 mm; flow rate: 15 ml/min; UV detection: 220 nm; injection volume: 0.2 ml; temperature: 40° C.; mobile phase: 30% isopropanol/70% isohexane]:

Example 236

Enantiomer 1

Yield: 30 mg

LC-MS (method 15): $R_t$=1.30 min; m/z=584 [M+H]$^+$.

$^1$H-NMR (400 MHz, DMSO-d$_6$): δ=12.13 (br. s, 1H), 10.20 (s, 1H), 7.67-7.83 (m, 2H), 7.41-7.54 (m, 5H), 7.36-7.40 (m, 2H), 7.28-7.35 (m, 2H), 7.14 (s, 1H), 6.71 (d, 1H), 4.78-4.94 (m, 4H), 2.80 (s, 2H), 1.71-1.84 (m, 1H), 1.17-1.70 (m, 6H), 1.09-1.16 (m, 2H), 0.96 (dd, 1H), 0.77-0.87 (m, 2H).

$[α]_D^{20}$=−26°, c=0.28, chloroform.

Example 237

Enantiomer 2

Yield: 32 mg (slightly contaminated)
LC-MS (method 15): $R_t$=1.30 min; m/z=584 [M+H]$^+$.
$^1$H-NMR (400 MHz, DMSO-$d_6$): δ=12.13 (br. s, 1H), 10.20 (s, 1H), 7.67-7.83 (m, 2H), 7.41-7.54 (m, 5H), 7.36-7.40 (m, 2H), 7.28-7.35 (m, 2H), 7.14 (s, 1H), 6.71 (d, 1H), 4.78-4.94 (m, 4H), 2.80 (s, 2H), 1.71-1.84 (m, 1H), 1.17-1.70 (m, 6H), 1.09-1.16 (m, 2H), 0.96 (dd, 1H), 0.77-0.87 (m, 2H).
$[α]_D^{20}$=+23°, c=0.26, chloroform.

Examples 238-241

1-(3-{[(3,3-Difluorocyclopentyl) {4-[(5-oxo-2-phenyl-5,6-dihydro-4H-1,3,4-oxadiazin-4-yl)-methyl]phenyl}acetyl]amino}benzyl)cyclopropanecarboxylic acid (isomers 1-4)

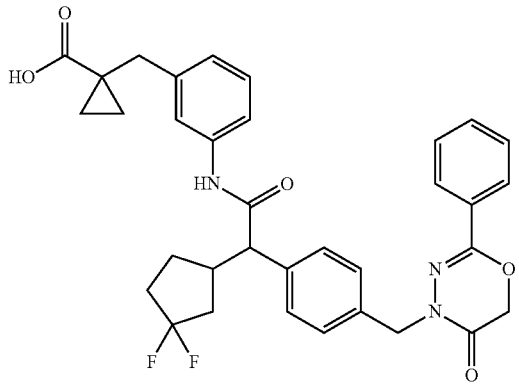

90 mg (0.15 mmol) of the mixture of isomers of 1-(3-{[(3,3-difluorocyclopentyl){4-[(5-oxo-2-phenyl-5,6-dihydro-4H-1,3,4-oxadiazin-4-yl)methyl]phenyl}acetyl]amino}-benzyl)cyclopropanecarboxylic acid were separated further by preparative HPLC on a chiral phase [column: Daicel Chiralcel OD-H, 5 μm, 250 mm×20 mm; mobile phase: isohexane/(ethanol+0.2% trifluoroacetic acid+1% water) 75:25 (v/v); flow rate: 15 ml/min; UV detection: 220 nm; temperature: 40° C.]. Three fractions were isolated, fraction 2 consisting of 2 isomers. This mixed fraction was separated again by further preparative HPLC on a chiral phase [column: Daicel Chiralpak AD-H, 5 μm, 250 mm×20 mm; mobile phase: isohexane/(ethanol+0.2% trifluoroacetic acid+1% water) 70:30 (v/v); flow rate: 15 ml/min; UV detection: 220 nm; temperature: 30° C.].

Example 238

Isomer 1

Yield: 15 mg
$R_t$ 9.61 min; chem. purity >99%; isomeric purity: contaminated with 1.2% isomer 2
[column: Daicel Chiralpak AD-H, 5 μm, 250 mm×4.6 mm; mobile phase: isohexane/(ethanol+0.2% trifluoroacetic acid+1% water) 70:30 (v/v); flow rate: 1 ml/min; UV detection: 220 nm; temperature: 40° C.].
LC-MS (method 15): $R_t$=1.22 min; m/z=602 (M+H)$^+$.

Example 239

Isomer 2

Yield: 12 mg
$R_t$ 8.68 min; purity >99%; >99% ee
[column: Daicel Chiralpak AD-H, 5 μm, 250 mm×4.6 mm; mobile phase: isohexane/(ethanol+0.2% trifluoroacetic acid+1% water) 70:30 (v/v); flow rate: 1 ml/min; UV detection: 220 nm; temperature: 40° C.].
LC-MS (method 15): $R_t$=1.22 min; m/z=602 (M+H)$^+$.

Example 240

Isomer 3

Yield: 15 mg
$R_t$ 10.28 min; chem. purity >99%; isomeric purity: contaminated with 10.9% isomer 1 and 3.8% isomer 2
[column: Daicel Chiralpak AD-H, 5 μm, 250 mm×4.6 mm; mobile phase: isohexane/(ethanol+0.2% trifluoroacetic acid+1% water) 70:30 (v/v); flow rate: 1 ml/min; UV detection: 220 nm; temperature: 40° C.].
LC-MS (method 15): $R_t$=1.22 min; m/z=602 (M+H)$^+$.

Example 241

Isomer 4

Yield: 19 mg
$R_t$ 7.96 min; purity >99%; >99% ee
[column: Daicel Chiralpak AD-H, 5 μm, 250 mm×4.6 mm; mobile phase: isohexane/(ethanol+0.2% trifluoroacetic acid+1% water) 70:30 (v/v); flow rate: 1 ml/min; UV detection: 220 nm; temperature: 40° C.].
LC-MS (method 15): $R_t$=1.22 min; m/z=602 (M+H)$^+$.

B. ASSESSMENT OF THE PHARMACOLOGICAL ACTIVITY

The pharmacological effect of the compounds according to the invention can be shown in the following assays:

B-1. Vasorelaxant Effect In Vitro:

Rabbits are anesthetized and sacrificed by intravenous injection of thiopental sodium (about 50 mg/kg) and exsanguinated. The saphenous artery is removed and divided into rings 3 mm wide. The rings are mounted singly on in each case a pair of triangular hooks open at the end and made of 0.3 mm-thick special wire (Remanium®). Each ring is placed under an initial tension in 5 ml organ baths with Krebs-Henseleit solution which is at 37° C., is gassed with carbogen and has the following composition: NaCl 119 mM; KCl 4.8 mM; $CaCl_2 \times 2H_2O$ 1 mM; $MgSO_4 \times 7H_2O$ 1.4 mM; $KH_2PO_4$ 1.2 mM; $NaHCO_3$ 25 mM; glucose 10 mM; bovine serum albumin 0.001%. The force of contraction is detected with Statham UC2 cells, amplified and digitized via A/D converters (DAS-1802 HC, Keithley Instruments, Munich) and recorded in parallel on chart recorders. Contractions are induced by addition of phenylephrine.

After several (generally 4) control cycles, the substance to be investigated is added in each further run in increasing dosage, and the level of the contraction achieved under the influence of the test substance is compared with the level of the contraction reached in the last preceding run. The concentration necessary to reduce the contraction reached in the preceding control by 50% is calculated from this ($IC_{50}$). The standard application volume is 5 μl. The proportion of DMSO in the bath solution corresponds to 0.1%.

Representative results for the compounds according to the invention are listed in Table 1:

TABLE 1

Vasorelaxant effect in vitro

| Example No. | IC$_{50}$ [nM] |
|---|---|
| 46 | 110 |
| 77 | 625 |
| 86 | 180 |
| 103 | 120 |
| 115 | 163 |
| 126 | 145 |
| 138 | 52 |
| 143 | 345 |
| 156 | 45 |
| 164 | 26 |
| 166 | 4.9 |
| 185 | 64 |
| 186 | 37 |
| 192 | 356 |
| 204 | 86 |
| 214 | 11 |
| 224 | 490 |
| 237 | 158 |

B-2. Stimulation of Recombinant Soluble Guanylate Cyclase (sGC) In Vitro:

Investigations on the stimulation of recombinant soluble guanylate cyclase (sGC) by the compounds according to the invention with and without sodium nitroprusside, and with and without the heme-dependent sGC inhibitor 1H-1,2,4-oxadiazolo-(4,3a)-quinoxalin-1-one (ODQ) are carried out by the method described in detail in the following reference: M. Hoenicka, E. M. Becker, H. Apeler, T. Sirichoke, H. Schroeder, R. Gerzer and J.-P. Stasch, "Purified soluble guanylyl cyclase expressed in a baculovirus/Sf9 system: Stimulation by YC-1, nitric oxide, and carbon oxide", *J. Mol. Med.* 77 (1999), 14-23. The heme-free guanylate cyclase is obtained by adding Tween 20 to the sample buffer (0.5% in the final concentration).

The activation of sGC by a test substance is reported as n-fold stimulation of the basal activity. The result for Example 103 is shown in Table 2:

TABLE 2

Stimulation (n-fold) of recombinant soluble guanylate cyclase (sGC) in vitro by Example 103

| Concentration | Heme-containing sGC | | | Heme-free sGC |
|---|---|---|---|---|
| Example 103 [μM] | Basal | +0.1 μM DEA/NO | +10 μM ODQ | Basal |
| 0 | 1.0 | 6.5 | 5.7 | 1.0 |
| 0.1 | 1.2 | 6.9 | 5.8 | 1.1 |
| 1 | 1.4 | 7.8 | 8.5 | 2.4 |
| 10 | 6.2 | 13.5 | 36.8 | 13.9 |
| 100 | 22.3 | 35.6 | 91.8 | 56.1 |

[DEA/NO = 2-(N,N-diethylamino)diazenolate 2-oxide; ODQ = 1H-1,2,4-oxadiazolo-(4,3a)-quinoxalin-1-one].

It is evident from Table 2 that stimulation both of the heme-containing and of the heme-free enzyme is achieved. Furthermore, combination of Example 103 and 2-(N,N-diethylamino)-diazenolate 2-oxide (DEA/NO), an NO donor, shows no synergistic effect, i.e. the effect of DEA/NO is not potentiated as would be expected with an sGC activator acting via a heme-dependent mechanism. In addition, the effect of the sGC activator according to the invention is not blocked by the heme-dependent inhibitor of soluble guanylate cyclase ODQ, but is in fact increased. The results in Table 2 thus confirm the mechanism of action of the compounds according to the invention as activators of soluble guanylate cyclase.

B-3. Action at Recombinant Guanylate Cyclase Reporter Cell Lines

The cellular action of the compounds according to the invention is determined at a recombinant guanylate cyclase reporter cell line, as described in F. Wunder et al., *Anal. Biochem.* 339, 104-112 (2005).

Representative results for the compounds according to the invention are listed in Table 3:

TABLE 3 sGC-activating activity in the CHO reporter cell in vitro

| Example No. | MEC [nM] |
|---|---|
| 1 | 10 |
| 3 | 300 |
| 11 | 300 |
| 21 | 30 |
| 22 | 300 |
| 26 | 300 |
| 29 | 30 |
| 30 | 30 |
| 38 | 30 |
| 46 | 3 |
| 62 | 3 |
| 77 | 1 |
| 86 | 1 |
| 103 | 10 |
| 105 | 10 |
| 106 | 10 |
| 115 | 3 |
| 118 | 30 |
| 126 | 30 |
| 138 | 10 |
| 143 | 3 |
| 156 | 3 |
| 160 | 30 |
| 164 | 0.3 |
| 166 | 0.3 |
| 170 | 3 |
| 171 | 30 |
| 176 | 30 |
| 181 | 0.7 |
| 184 | 3 |
| 185 | 0.3 |
| 186 | 0.2 |
| 187 | 1 |
| 192 | 3 |
| 204 | 1 |
| 207 | 3 |
| 213 | 3 |
| 214 | 0.1 |
| 219 | 0.2 |
| 220 | 0.3 |
| 224 | 1 |
| 230 | 30 |
| 231 | 0.2 |
| 232 | 20 |
| 233 | 0.3 |
| 234 | 1 |
| 237 | 1 |
| 241 | 3 |

(MEC = minimum effective concentration).

B-4. Stimulation of sGC Enzyme Activity

Soluble guanylate cyclase (sGC) converts on stimulation GTP into cGMP and pyrophosphate (PPi). PPi is detected with the aid of the assay described below. The signal produced in the assay increases as the reaction progresses and serves as a measure of the sGC enzyme activity under the given stimulation.

To carry out the assay, 29 μl of enzyme solution [0-10 nM soluble guanylate cyclase (prepared according to Honicka et al., *J. Mol. Med.* 77, 14-23 (1999)) in 50 mM TEA, 2 mM MgCl$_2$, 0.1% BSA (fraction V), 0.005% Brij®, pH 7.5] are initially introduced into a microplate, and 1 μl of the substance to be tested (as a serially diluted solution in DMSO) is added. The mixture is incubated at room temperature for 10 min. Then 20 μl of detection mix [1.2 nM Firefly Luciferase (*Photinus pyralis* luciferase, Promega), 29 μM dehydroluciferin (prepared according to Bitler & McElroy, *Arch. Biochem. Biophys.* 72, 358 (1957)), 122 μM luciferin (Promega), 153 μM ATP (Sigma) and 0.4 mM DTT (Sigma) in 50 mM TEA, 2 mM MgCl$_2$, 0.1% BSA (fraction V), 0.005% Brij®, pH 7.5] are added. The enzyme reaction is started by adding 20 μl of substrate solution [1.25 mM guanosine 5'-triphosphate (Sigma) in 50 mM TEA, 2 mM MgCl$_2$, 0.1% BSA (fraction V), 0.005% Brij®, pH 7.5] and measured continuously in a luminometer. The extent of the stimulation by the substance to be tested can be determined relative to the signal of the unstimulated reaction.

The activation of heme-free guanylate cyclase is examined by addition of 25 μM of 1H-1,2,4-oxadiazolo[4,3-a]quinoxalin-1-one (ODQ) to the enzyme solution and subsequent incubation for 30 minutes and compared to the stimulation of the native enzyme.

Representative results for the compounds according to the invention are listed in Table 4:

TABLE 4

Activating action at the sGC enzyme in vitro

| Example No. | MEC [nM] | EC$_{50}$ [nM] |
|---|---|---|
| 46 | 4.1 | 130 |
| 77 | 0.4 | 24 |
| 86 | 1.4 | 73 |
| 103 | 20 | 381 |
| 115 | 1.6 | 40 |
| 126 | 10 | 320 |
| 138 | 5.1 | 330 |
| 156 | 0.2 | 5.4 |
| 160 | 3.4 | 35 |
| 164 | 0.5 | 6.1 |
| 166 | 0.4 | 2.4 |
| 170 | 1 | 11 |
| 171 | 3.7 | 59 |
| 176 | 10 | 320 |
| 181 | 1.4 | 69 |
| 184 | 7 | 240 |
| 186 | 0.1 | 1.5 |
| 192 | 2.5 | 30 |
| 204 | 0.5 | 18 |
| 207 | 0.5 | 11 |
| 213 | 1.2 | 24 |
| 214 | 0.4 | 19 |
| 219 | 0.2 | 3.6 |
| 220 | 2 | 75 |
| 224 | 1 | 20 |
| 230 | 8.1 | 420 |
| 231 | 0.4 | 5.2 |
| 232 | 93 | 1100 |
| 233 | 3.3 | 78 |
| 234 | 4.1 | 220 |
| 237 | 0.9 | 21 |
| 241 | 1.2 | 17 |

(MEC = minimum effective concentration; EC$_{50}$ = concentration at 50% of maximum efficacy).

B-5. Radiotelemetric Measurement of Blood Pressure and Heart Rate on Conscious SH Rats A commercially available telemetry system from Data Sciences International DSI, USA, is employed for the measurements on conscious SH rats described below.

The system consists of 3 main components: (1) implantable transmitters, (2) receivers, which are linked via a multiplexer to a (3) data acquisition computer. The telemetry system makes it possible to continuously record the blood pressure and heart rate of conscious animals in their usual habitat.

The investigations are carried out on adult female spontaneously hypertensive rats (SH rats) with a body weight of >200 g. After transmitter implantation, the experimental animals are housed singly in type 3 Makrolon cages. They have free access to standard feed and water. The day/night rhythm in the experimental laboratory is changed by the room lighting at 6.00 am and at 7.00 μm.

The telemetry transmitters (TAM PA-C40, DSI) as employed are surgically implanted under aseptic conditions in the experimental animals at least 14 days before the first experimental use. The animals instrumented in this way can be employed repeatedly after the wound has healed and the implant has settled.

For the implantation, the fasted animals are anesthetized with pentobarbital (Nembutal, Sanofi, 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and layered closure of the wound is performed. An antibiotic (Tardomyocel COMP, Bayer, 1 ml/kg s.c.) is administered postoperatively for prophylaxis of infection.

Outline of Experiment:

The substances to be investigated are administered orally by gavage in each case to a group of animals (n=6). The test substances are dissolved in suitable solvent mixtures, or suspended in 0.5% strength Tylose, appropriate for an administration volume of 5 ml/kg of body weight. A solvent-treated group of animals is employed as control.

The telemetry measuring unit is configured for 24 animals. Each experiment is recorded under an experiment number.

Each of the instrumented rats living in the system is assigned a separate receiving antenna (1010 Receiver, DSI). The implanted transmitters can be activated externally by means of an incorporated magnetic switch and are switched to transmission in the run-up to the experiment. The emitted signals can be detected online by a data acquisition system (Dataquest™ A.R.T. for Windows, DSI) and be appropriately processed. The data are stored in each case in a file created for this purpose and bearing the experiment number.

In the standard procedure, the following are measured for 10-second periods in each case: (1) systolic blood pressure (SBP), (2) diastolic blood pressure (DBP), (3) mean arterial pressure (MAP) and (4) heart rate (HR).

The acquisition of measured values is repeated under computer control at 5-minute intervals. The source data obtained as absolute value are corrected in the diagram with the currently measured barometric pressure and stored as individual data. Further technical details are given in the documentation from the manufacturing company (DSI).

The test substances are administered at 9.00 am on the day of the experiment. Following the administration, the parameters described above are measured over 24 hours. After the end of the experiment, the acquired individual data are sorted using the analysis software (Dataquest™ A.R.T. Analysis). The void value is assumed to be the time 2 hours before administration of the substance, so that the selected data set includes the period from 7.00 am on the day of the experiment to 9.00 am on the following day.

The data are smoothed over a presettable time by determination of the average (15-minute average, 30-minute average) and transferred as a text file to a storage medium. The measured values presorted and compressed in this way are transferred into Excel templates and tabulated.

C. EXEMPLARY EMBODIMENTS OF PHARMACEUTICAL COMPOSITIONS

The compounds according to the invention can be converted into pharmaceutical preparations in the following ways:

Tablet:

Composition:

100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:

The mixture of compound according to the invention, lactose and starch is granulated with a 5% strength solution (m/m) of the PVP in water. The granules are dried and then mixed with the magnesium stearate for 5 minutes. This mixture is compressed in a conventional tablet press (see above for format of the tablet). A guideline compressive force for the compression is 15 kN.

Suspension which can be Administered Orally:

Composition:

1000 mg of the compound according to the invention, 1000 mg of ethanol (96%), 400 mg of Rhodigel (xanthan gum from FMC, Pennsylvania, USA) and 99 g of water. 10 ml of oral suspension correspond to a single dose of 100 mg of the compound according to the invention.

Production:

The Rhodigel is suspended in ethanol, and the compound according to the invention is added to the suspension. The water is added while stirring. The mixture is stirred for about 6 h until the swelling of the Rhodigel is complete.

Solution which can be Administered Orally:

Composition:

500 mg of the compound according to the invention, 2.5 g of polysorbate and 97 g of polyethylene glycol 400.20 g of oral solution correspond to a single dose of 100 mg of the compound according to the invention.

Production:

The compound according to the invention is suspended in the mixture of polyethylene glycol and polysorbate with stirring. The stirring process is continued until the compound according to the invention has completely dissolved.

I.V. Solution:

The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:

1. A compound of formula (I)

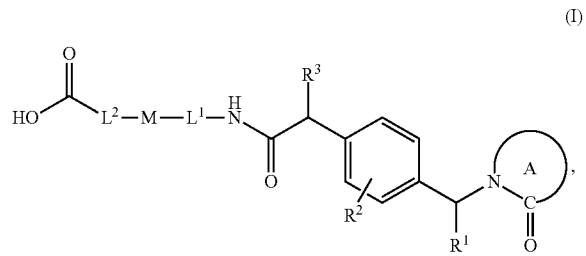

wherein, ring A represents an oxo-substituted azaheterocycle of the formula

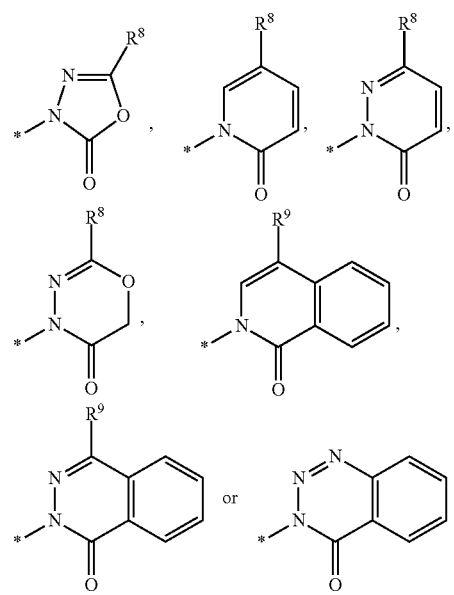

in which

* denotes the point of attachment to the remainder of the molecule, $R^8$ represents trifluoromethyl, $(C_3-C_6)$-cycloalkyl or phenyl, where phenyl for its part may be substituted up to two times by identical or different radicals selected from the group consisting of fluorine, chlorine, cyano, methyl, trifluoromethyl, methoxy and trifluoromethoxy, and $R^9$ represents hydrogen or has the meaning of $R^8$ given above, $R^1$ represents hydrogen or methyl, $R^2$ represents hydrogen, fluorine or chlorine, $R^3$ represents $(C_3-C_6)$-alkyl or $(C_3-C_6)$-alkenyl, each of which may be substituted up to six times by fluorine, or represents $(C_3-C_6)$-cycloalkyl, cyclopentenyl or cyclohexenyl, each of which may be substituted up to two times by identical or different radicals from the group consisting of methyl, ethyl and trifluoromethyl and also up to four times by fluorine, $L^1$ represents a bond or represents methylene or ethane-1,2-diyl, L² represents a bond or represents methylene, ethane-1,2-diyl, propane-1,3-diyl or ethene-1,2-diyl, each of which may be substituted up to two times by methyl,
or
represents a group of the formula

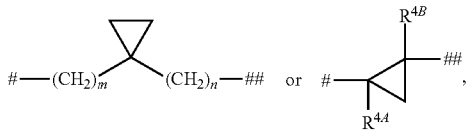

in which
# denotes the point of attachment to the carboxylic acid grouping,
## denotes the point of attachment to group M,
m represents the number 0 or 1,
n represents the number 1 or 2,
and
$R^{4A}$ and $R^{4B}$ independently of one another represent hydrogen or methyl,
M represents phenylene, which may be substituted up to two times by identical or different radicals selected from the group consisting of fluorine, chlorine, methyl and trifluoromethyl,
or
represents cyclopentane-1,3-diyl, cyclohexane-1,3-diyl or cyclohexane-1,4-diyl, each of which may be substituted up to two times by identical or different radicals from the group consisting of fluorine and methyl,
or
L² and M are attached to one another and together form a group of the formula

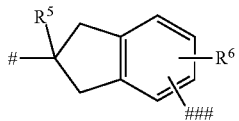

in which
# denotes the point of attachment to the carboxylic acid grouping,
### denotes the point of attachment to group L¹,
$R^5$ represents hydrogen, methyl or trifluoromethyl
and
$R^6$ represents hydrogen, fluorine or chlorine.

2. A compound of the formula (I)

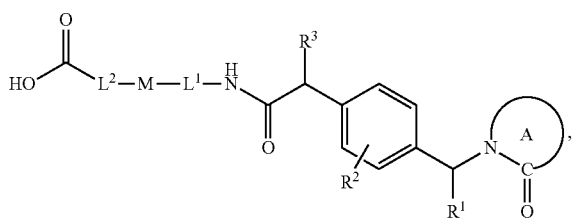

(I)

wherein
ring A represents an oxo-substituted azaheterocycle of the formula

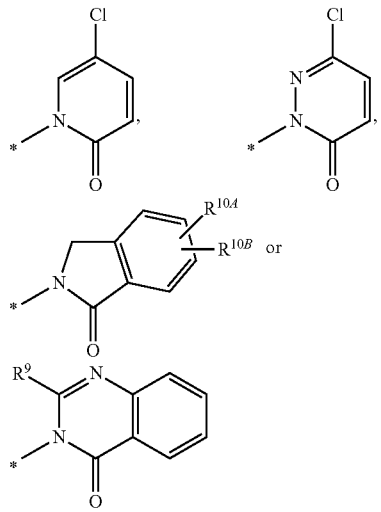

in which
* denotes the point of attachment to the remainder of the molecule,
$R^9$ represents hydrogen, methyl or trifluoromethyl
and
$R^{10A}$ and $R^{10B}$ independently of one another represent hydrogen or fluorine,
$R^1$ represents hydrogen or methyl,
$R^2$ represents hydrogen, fluorine or chlorine,
$R^3$ represents $(C_3-C_6)$-alkyl or $(C_3-C_6)$-alkenyl, each of which may be substituted up to six times by fluorine,
or
represents $(C_3-C_6)$-cycloalkyl, cyclopentenyl or cyclohexenyl, each of which may be substituted up to two times by identical or different radicals from the group consisting of methyl, ethyl and trifluoromethyl and also up to four times by fluorine,
$L^1$ represents a bond or represents methylene or ethane-1,2-diyl,
$L^2$ represents a bond or represents methylene, ethane-1,2-diyl, propane-1,3-diyl or ethene-1,2-diyl, each of which may be substituted up to two times by methyl,
or
represents a group of the formula

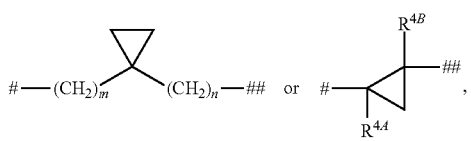

in which
# denotes the point of attachment to the carboxylic acid grouping,
## denotes the point of attachment to group M,
m represents the number 0 or 1,
n represents the number 1 or 2,
and
$R^{4A}$ and $R^{4B}$ independently of one another represent hydrogen or methyl,
M represents phenylene, which may be substituted up to two times by identical or different radicals selected from the group consisting of fluorine, chlorine, methyl and trifluoromethyl, or
represents cyclopentane-1,3-diyl, cyclohexane-1,3-diyl or cyclohexane-1,4-diyl, each of which may be substituted up to two times by identical or different radicals from the group consisting of fluorine and methyl,
or
L² and M are attached to one another and together form a group of the formula

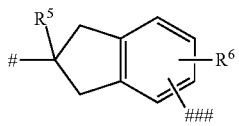

in which
# denotes the point of attachment to the carboxylic acid grouping,
### denotes the point of attachment to group L¹,
R⁵ represents hydrogen, methyl or trifluoromethyl
and
R⁶ represents hydrogen, fluorine or chlorine.

3. The compound of claim 1 in which
ring A represents an oxo-substituted azaheterocycle of the formula

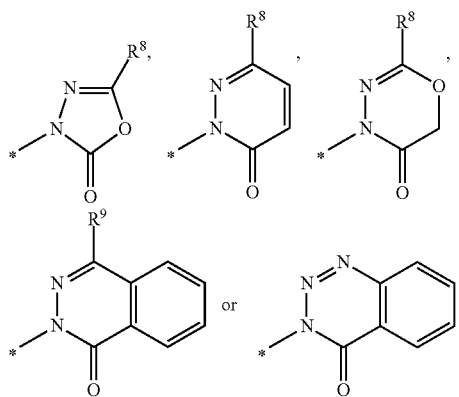

in which
* denotes the point of attachment to the remainder of the molecule,
R⁸ represents trifluoromethyl or phenyl which may be substituted up to two times by identical or different radicals selected from the group consisting of fluorine, chlorine, methyl and trifluoromethyl
and
R⁹ represents hydrogen or has the meaning of R⁸ given above,
R¹ represents hydrogen,
R² represents hydrogen,
R³ represents propan-2-yl, butan-2-yl, pentan-2-yl, 1,1,1-trifluoropropan-2-yl, 1,1,1-trifluorobutan-2-yl, 4,4,4-trifluorobutan-2-yl, 4,4,4-trifluoro-2-methylbutan-1-yl, cyclopentyl or 3,3-difluorocyclopentyl,
L¹ represents a bond or represents methylene,
L² represents a bond, represents methylene or ethane-1,2-diyl, each of which may be substituted up to two times by methyl, or represents ethene-1,2-diyl or
represents a group of the formula

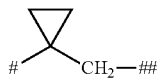

in which
# denotes the point of attachment to the carboxylic acid grouping
and
## denotes the point of attachment to group M,
M represents 1,3-phenylene or 1,4-phenylene, each of which may be substituted up to two times by identical or different radicals from the group consisting of fluorine, chlorine, methyl and trifluoromethyl, or represents cyclohexane-1,3-diyl or cyclohexane-1,4-diyl,
or
L² and M are attached to one another and together form a group of the formula

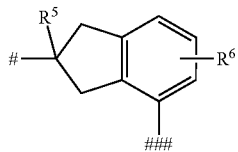

in which
# denotes the point of attachment to the carboxylic acid grouping,
### denotes the point of attachment to group L¹,
R⁵ represents hydrogen or methyl
and
R⁶ represents hydrogen or fluorine.

4. The compound of claim 2 in which
ring A represents an oxo-substituted azaheterocycle of the formula

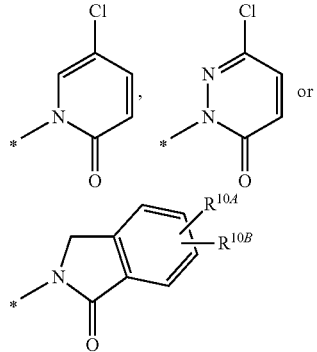

in which
* denotes the point of attachment to the remainder of the molecule
and
R¹⁰ᴬ and R¹⁰ᴮ independently of one another represent hydrogen or fluorine,
R¹ represents hydrogen,
R² represents hydrogen,
R³ represents propan-2-yl, butan-2-yl, pentan-2-yl, 1,1,1-trifluoropropan-2-yl, 1,1,1-trifluorobutan-2-yl, 4,4,4- trifluorobutan-2-yl, 4,4,4-trifluoro-2-methylbutan-1-yl, cyclopentyl or 3,3-difluorocyclopentyl, L¹ represents a bond, L² represents methylene or ethane-1,2-diyl, each of which may be substituted up to two times by methyl, or represents ethene-1,2-diyl or represents a group of the formula

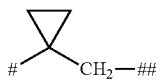

in which

\# denotes the point of attachment to the carboxylic acid grouping and

\#\# denotes the point of attachment to group M,

M represents 1,3-phenylene or 1,4-phenylene, each of which may be substituted up to two times by identical or different radicals from the group consisting of fluorine, chlorine, methyl and trifluoromethyl, or L² and M are attached to one another and together form a group of the formula

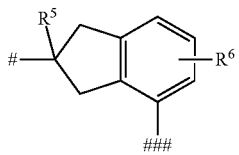

in which

\# denotes the point of attachment to the carboxylic acid grouping,

\#\#\# denotes the point of attachment to group L¹,

R⁵ represents hydrogen or methyl and

R⁶ represents hydrogen or fluorine.

5. A process for preparing the compound of the formula (I) as defined in claim 1, comprising converting a compound of the formula (II)

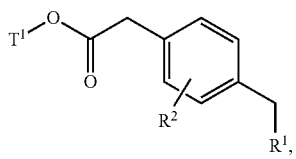

(II)

in which R¹ and R² have the meanings given in claim 1 and

T¹ represents (C₁-C₄)-alkyl, in an inert solvent in the presence of a base with a compound of the formula (III)

R³—X           (III), in which R³ has the meaning given in claim 1 and

X represents a leaving group, into a compound of the formula (IV)

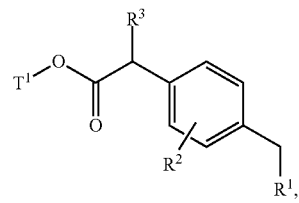

(IV)

brominating the compound of the formula (IV) in an inert solvent with elemental bromine or with N-bromosuccinimide to give a compound of the formula (V)

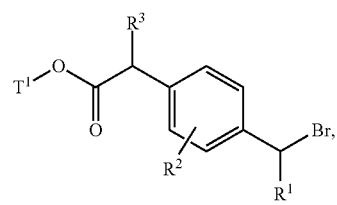

(V)

reacting the compound of the formula (V) in an inert solvent in the presence of a base with a compound of the formula (VI)

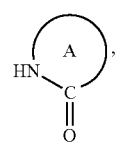

(VI)

in which ring A represents an oxo-substituted azaheterocycle, as defined in claim 1, to give a compound of the formula (VII)

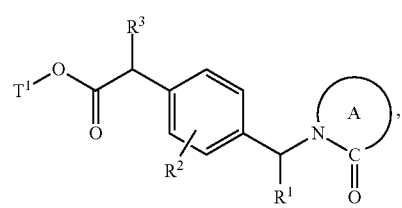

(VII)

removing the ester radical T¹ in (VII) under basic or acidic conditions, to give a carboxylic acid of the formula (VIII)

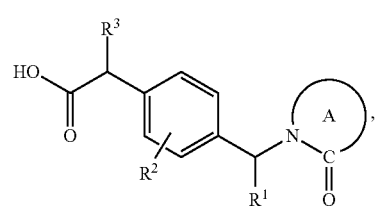

(VIII)

coupling the carboxylic acid of the formula (VIII) in an inert solvent in the presence of a condensing agent or via the intermediate of the corresponding carbonyl chloride in the presence of a base with an amine of the formula (IX)

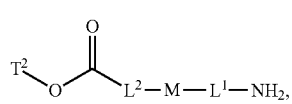
(IX)

in which $L^1$, $L^2$ and M have the meanings given in claim 1 and
$T^2$ represents $(C_1-C_4)$-alkyl,
to give a compound of the formula (X)

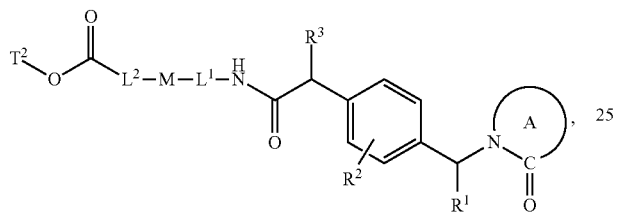
(X)

and removing the ester radical $T^2$ in (X) by further basic or acidic solvolysis to give the carboxylic acid of the formula (I)
and the compounds of the formula (I) are separated where appropriate by methods known to the skilled person into their enantiomers and/or diastereomers, and/or where appropriate reacted with the appropriate (i) solvents and/or (ii) bases or acids to give salts thereof.

6. A pharmaceutical composition comprising the compound of claim 1 and at least one inert, non-toxic, pharmaceutically suitable excipient.

7. A pharmaceutical composition comprising the compound of claim 1 and at least one active ingredient selected from the group consisting of an organic nitrate, an NO donor, a cGMP-PDE inhibitor, a stimulator of guanylate cyclase, an agent having antithrombotic activity, an agent for lowering blood pressure, and an agent for altering lipid metabolism.

8. A process for preparing the compound of the formula (I) as defined in claim 2, comprising converting a compound of the formula (II)

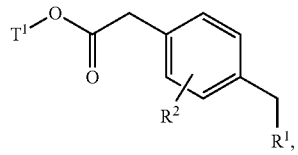
(II)

in which $R^1$ and $R^2$ have the meanings given in claim 2 and
$T^1$ represents $(C_1-C_4)$-alkyl,
in an inert solvent in the presence of a base with a compound of the formula (III)

$R^3$—X (III), in which $R^3$ has the meaning given in claim 7
and
X represents a leaving group,
into a compound of the formula (IV)

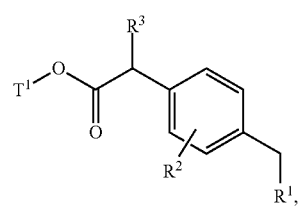
(IV)

brominating the compound of the formula (IV) in an inert solvent with elemental bromine or with N-bromosuccinimide to give a compound of the formula (V)

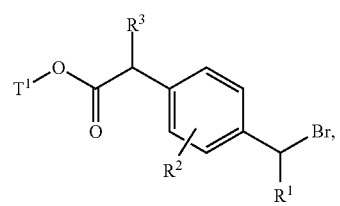
(V)

reacting the compound of the formula (V) in an inert solvent in the presence of a base with a compound of the formula (VI)

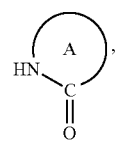
(VI)

in which ring A represents an oxo-substituted azaheterocycle, as defined in claim 2,
to give a compound of the formula (VII)

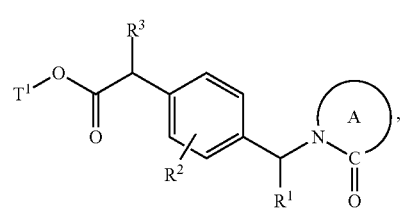
(VII)

removing the ester radical $T^1$ in (VII) under basic or acidic conditions, to give a carboxylic acid of the formula (VIII)

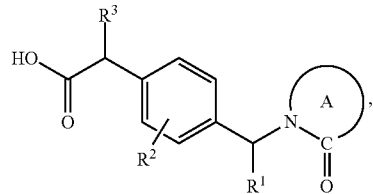

(VIII)

coupling the carboxylic acid of the formula (VIII) in an inert solvent in the presence of a condensing agent or via the intermediate of the corresponding carbonyl chloride in the presence of a base with an amine of the formula (IX)

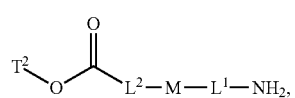

(IX)

in which $L^1$, $L^2$ and M have the meanings given in claim 2 and $T^2$ represents $(C_1-C_4)$-alkyl, to give a compound of the formula (X)

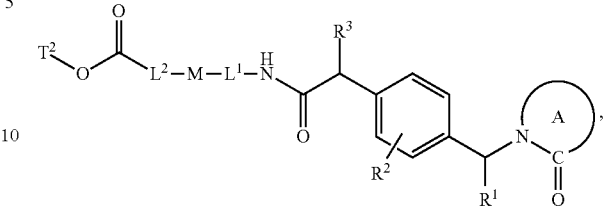

(X)

and removing the ester radical $T^2$ in (X) by further basic or acidic solvolysis to give the carboxylic acid of the formula (I)

and the compounds of the formula (I) are separated where appropriate by methods known to the skilled person into their enantiomers and/or diastereomers, and/or where appropriate reacted with the appropriate (i) solvents and/or (ii) bases or acids to give salts thereof.

9. A pharmaceutical composition comprising a compound as defined in claim 2 and at least one inert, non-toxic, pharmaceutically suitable excipient.

10. A pharmaceutical composition comprising a compound as defined in claim 2 and at least one active ingredient selected from the group consisting of an organic nitrate, an NO donor, a cGMP-PDE inhibitor, a stimulator of guanylate cyclase, an agent having antithrombotic activity, an agent for lowering blood pressure, and an agent for altering lipid metabolism.

* * * * *